United States Patent
De Wildt et al.

(10) Patent No.: US 9,629,909 B2
(45) Date of Patent: Apr. 25, 2017

(54) METHODS FOR TARGETING PULMONARY DISEASES WITH AGENTS THAT BIND A TARGET IN PULMONARY TISSUE

(71) Applicant: Domantis Limited, Brentford, Middlesex (GB)

(72) Inventors: Rudolf M. T. De Wildt, Cambridge (GB); Steve Holmes, Cambridge (GB); Ian M. Tomlinson, Cambridge (GB); Gregory P. Winter, Cambridge (GB); Mary F. Fitzgerald, Harlow (GB); Justian Craig Fox, Harlow (GB); Armin Sepp, Cambridge (GB); Jennifer Luckett, Cambridge (GB); Benjamin P. Woolven, Cambridge (GB)

(73) Assignee: Domantis Limited, Brentford, Middlesex (GB)

( * ) Notice: Subject to any disclaimer, the term of this patent is extended or adjusted under 35 U.S.C. 154(b) by 698 days.

(21) Appl. No.: 13/920,371

(22) Filed: Jun. 18, 2013

(65) Prior Publication Data

US 2013/0309227 A1 Nov. 21, 2013

Related U.S. Application Data

(60) Continuation of application No. 13/356,228, filed on Jan. 23, 2012, now Pat. No. 8,497,244, which is a division of application No. 12/084,084, filed as application No. PCT/GB2006/003935 on Oct. 23, 2006, now Pat. No. 8,129,503.

(30) Foreign Application Priority Data

Oct. 24, 2005 (GB) .................. 0521621.3

(51) Int. Cl.
*A61K 39/395* (2006.01)
*C07K 16/28* (2006.01)
*A61K 9/00* (2006.01)

(52) U.S. Cl.
CPC .......... *A61K 39/3955* (2013.01); *A61K 9/007* (2013.01); *C07K 16/28* (2013.01); *C07K 16/2878* (2013.01); *C07K 2317/31* (2013.01); *C07K 2317/569* (2013.01); *C07K 2317/76* (2013.01)

(58) Field of Classification Search
None
See application file for complete search history.

(56) References Cited

U.S. PATENT DOCUMENTS 5,055,289 A 10/1991 Frincke et al.
8,497,244 B2 * 7/2013 de Wildt ............... C07K 16/28
514/13.5

FOREIGN PATENT DOCUMENTS

| EP | 1948694 | 7/2008 |
|---|---|---|
| WO | WO90/05144 | 5/1990 |
| WO | WO90/14430 | 11/1990 |
| WO | WO92/01047 | 1/1992 |
| WO | WO92/20791 | 11/1992 |
| WO | WO93/11236 | 6/1993 |
| WO | WO02/43660 | 6/2002 |
| WO | WO2004/003019 | 1/2004 |
| WO | WO2004/022096 | 3/2004 |
| WO | WO2004/022718 | 3/2004 |
| WO | WO2004/058821 | 7/2004 |
| WO | WO2005/035572 | 4/2005 |
| WO | WO 2006/003388 A2 | 1/2006 |
| WO | WO 2006/030220 A1 | 3/2006 |
| WO | WO2006/038027 | 4/2006 |
| WO | WO2006/059108 | 6/2006 |
| WO | WO 2007/049017 A2 | 5/2007 |
| WO | WO 2007/049017 A3 | 5/2007 |
| WO | WO2008/021237 | 2/2008 |
| WO | WO 2008/021237 | 2/2008 |

OTHER PUBLICATIONS

Mehrad et al. (J Immunol 1999; 162:1633-1640).*
Paulussen et al. (J Clin Oncol. Sep. 1998;16(9):3044-52).*
Rube et al. (Int. J. Radiation Oncology Biol. Phys., vol. 56, No. 5, pp. 1414-1425, 2003).*
Visser et al. (Lung (2012) 190:579-581).*
Moore et al., Clinical Infectious Diseases 2005; 41:S213-7.*
Edwards et al., Chest; Nov. 2003; 124: 1916-1923.*
Freeburn et al., Eur. Cytokine Netw., vol. 16, No. 1, Mar. 2005, 5-16.*
Parsons et al., Am J Physiol Lung Cell Mol Physiol 288: L426-L431, 2005.*
Chen et al., Sarcoidosis Vasc Diffuse Lung Dis 2004; 21: 199-203.*
Lucas et al., Biochemical Pharmacology 77 (2009) 1763-1772.*
Geiser et al., Swiss Med Wkly 2 0 0 3 ; 1 3 3 : 5 8 6-5 9 0.*
Van Wasterloo et al., Crit Care Med 2005; 33:1770-1778.*

(Continued)

*Primary Examiner* — Zachary Skelding
(74) *Attorney, Agent, or Firm* — Leah M. Octavio; Andrea V. Lockenour

(57) ABSTRACT

Disclosed is the use of an agent (e.g., antibody fragment, antagonist, ligand, dAb monomer) that binds a target in pulmonary tissue for the manufacture of a long action or long therapeutic window formulation for local delivery to pulmonary tissue, and methods for administering an agent that binds a target in pulmonary tissue to a subject to produce a long therapeutic window in pulmonary tissue. The formulation is for, and the method comprises, administering locally to pulmonary tissue. Also disclosed is the use of antagonists of TNFR1 for the manufacture of a formulation or medicament for treating, preventing or suppressing lung inflammation or a respiratory disease, and methods of treating such diseases. Also disclosed are the use of agents a for the manufacture of a delivery device (e.g., inhaler, intranasal delivery device) for the treatment or prevention of lung inflammation or a respiratory disease, and a delivery device for the treatment or prevention of lung inflammation or a respiratory disease that contains an agent as described herein.

70 Claims, 87 Drawing Sheets

(56) References Cited

OTHER PUBLICATIONS

Chmiel et al., Clinical Reviews in Allergy and Immunology, vol. 23, 2002: 5-27.*
Thannickall et al., Expert Opinion on Pharmacotherapy, 5:8, 1671-1686.*
Ward, et al., Nature: International Weekly Journal of Science, Jan. 1, 1989, pp. 544-548.
EP Application No. 06794871 file history.
Saerens et al.,. J Mol Biol. Sep. 23, 2005;352(3):597-607.
Vajdos et al., J Mol Biol. Jul. 5, 2002;320(2):415-28.
Rudikoff et al., Proc. Natl. Acad. Sci. USA, 79: 1979-1983, Mar. 1982.
Colman P. M., Research in Immunology, 145:33-36, 1994.
Brown et al., J Immunol. May 1, 1996;156(9):3285-91.
Muyldermans et al., Reviews in Molecular Biotechnology 74 (2001), 277-302.
P.M. Colman, Research in Immunology, 145:33-36, 1994.
Kontermann, et al., "*A Humanized Tumor Necrosis Factor Receptor 1 (TNFR1)-specific Antagonistic Antibody for Selective Inhibition of Tumor Necrosis Factor (TNF) Action*," J Immunother, Apr. 2008, pp. 225-234, vol. 31(3).
Woo, et al., "*VCAM-1 Upregulation Via PKCdelta-p38 Kinase-Linked Cascade Mediates the TNF-alpha-induced Leukocyte Adhesion and Emigration in the Lung Airway Epithelium.*" Am. J. Physiol. Lung Cell Mol. Physiol. 2005, pp. L307-L316, vol. 288.
Qin, et al., "In Vivo *Evaluation of a Morpholino Antisense Oligomer Directed Against Tumor Necrosis Factor-alpha*," Antisense & Nucleic Acid Drug Development 2000, pp. 11-16, vol. 10.
Stenton, et al., "*Inhibition of Allergic Inflammation in the Airways using Aerosolized Antisense to Syk Kinase*," The Journal of Immunology, 2002, pp. 1028-1036, vol. 169.
Bolon, et al., "*Impact of Systemic Antagonism of Interleukin-1 (IL-1) or Tumor Necrosis Factor (TNF) on Arthritis Induced by Intra-Articular Instillation of IL-1 beta, TNF-alpha or Lipopolysaccharide (LPS)*," Annals of Rheumatic Diseases, Jul. 2003, p. 123, vol. 62: No. Suppl 1 (abstract only).
Domain antibody products treat respirator disease, Retrieved from Internet: http//www.laboratorytalk.com/news/arg/arg109.html, 2007.
Neumann, D., et al., The membrane form of the type II IL-1 receptor accounts for inhibitory function, Journal of Immunology, vol. 165, No. 6, , pp. 3350-3357, Sep. 15, 2000.
Chung K.F., New asthma treatments: recent advances and current objectives, Revuew Francaise D'Allergologie Et D'Immunologie Clinique, vol. 378, No. 7, pp. S214-S221, 1998.
DeBoer, W.I., Perspectives for cytokine antagonist therapy in COPD, Drug Discovery Today, Elsevier, Rahway, vol. 10, No. 2, pp. 93-106, Jan. 2005.
Holt L.J., et al., Domain antibodies proteins for therapy, Trends in Biotechnology, Elsevier Publications, vol. 21, No. 11, pp. 484-490Nov. 2003.
International Search Report for Related PCT Application No. PCT/GB2006/003935.
Angrill, et al., *Am. J. Resp. and Critical Care Med.*, 164:1628-1632 (2001).
Chmiel, et al., *Clinical Reviews in allergy and Immunology*, Abstract, 23:5-27 (2002).
Kafoury, et al., *Int. J. Environ. Res. Public Health*, 2(1):107-113 (2005).
Miyazaki, et al., *J. Clin. Invest.*, 96:250-259 (1995).
Mohr, Lawrence, *Curr. Opin. Pulm. Med.*, 10:401-411 (2004).
Rimal, et al., *Curr. Opin. Pulm. Med.*, 11:169-173 (2005).
Schwarz, M.A., *Ped. Resp. Reviews*, 2:3-9 (2001).
Thomas, Paul S., *Immunology and Cell Biology*, 79:132:140 (2001).

* cited by examiner

\>TAR2h-12 (SEQ ID NO:1)
EVQLLESGGGLVQPGGSLRLSCAASGFTFV~AYNMG~WVRQAPGKGLEWVS~~FIDMYGAKTYYADSV
KG~~RFTISRDNSKNTLYLQMNSLRAEDTAVYYCAK~~~LCLMDCSGDIFDY~~~WGQGTLVTVSS

\>TAR2h-13 (SEQ ID NO:2)
EVQLLESGGGLVQPGGSLRLSCAASGFTFP~ADEMY~WVRQAPGKGLEWVS~~SIGWPGGATYYADSV
KG~~RFTISRDNSKNTLYLQMNSLRAEDTAVYYCAK~~~YGRNFDY~~~WGQGTLVTVSS

\>TAR2h-14 (SEQ ID NO:3)
EVQLLESGGGLVQPGGSLRLSCAASGFTFD~QYDMS~WVRQAPGKGLEWVS~~LIDPSGGHTYYADSV
KG~~RFTISRNNSKNTLYLQMNSLRAEDTAVYYCAK~~~PVFSDWPAVEFDY~~~WGQGTLVTVSS

\>TAR2h-16 (SEQ ID NO:4)
EVQLLESGGGLVQPGGSLRLSCAASGFTFG~NYDMQ~WVRQAPGKGLEWVS~~SIDGTGGTTYYADSV
KG~~RFTISRDNSKNTLYLQMNSLRAEDTAVYYCAQ~~~ETNAFDY~~~WGQGTLVTVSS

\>TAR2h-17 (SEQ ID NO:5)
EVQLLESGGGLVQPGGSLRLSCAASGFTFG~GYQMG~WVRQAPGKGLEWVS~~FIDFTGAHTYYADSV
KG~~RFTISRDNSKNTLYLQMNSLRAEDTAVYYCAK~~~LSDDLTLPERFPFDY~~~WGQGTLVTVSS

\>TAR2h-18 (SEQ ID NO:6)
EVQLLESGGGLVQPGGSLRLSCAASGFTFA~DYNMT~WVRQAPGKGLEWVS~~WIDQEGVFTYYADSV
KG~~RFTISRDNSKNTLYLQMNSLRAEDTAVYYCAK~~~DFSAAVMLRTSFDY~~~WGQGTLVTVSS

\>TAR2h-19  (SEQ ID NO:7)
EVQLLESGGGLVQPGGSLRLSCAVSGFTFH~DYGMV~WVRQAPGKGLEWVS~~QISIDGRTTYYADSV
KG~~RFTISRDNSKNTLYLQMNSLRAEDTAVYYCAK~~~RIFEFDY~~~WGQGTLVTVSS

\>TAR2h-20 (SEQ ID NO:8)
EVQLLESGGGLVQPGGSLRLSCAASGFTFS~AYNMS~WVRQAPGKGLEWVS~~AISPSGNETYYADSV
KG~~RFTISRDNSKNTLYLQMNSLRAEDTAVYYCAK~~~GAGEAFDY~~~WGQGTLVTVSS

\>TAR2h-21 (SEQ ID NO:9)
EVQLLESGGGLVQPGGSLRLSCAASGFTFT~EYNMG~WVRQAPGKGLEWVS~~FIGHSGQHTYYADSV
KG~~RFTISRDNSKNTLYLQMNSLRAEDTAVYYCAE~~~LNNLMFDY~~~WGQGTLVTVSS

\>TAR2h-22  (SEQ ID NO:10)
EVQLLESGGGLVQPGGSLRLSCAASGFTFG~EYNMA~WVRQAPGKGQEWVS~~FISTGGHVTYYADSV
KG~~RFTISRDNSKNTLYLQMNSLRAEDTAVYYCAK~~~FSVRFRSSIFDY~~~WGQGTLVTVSS

FIG. 6A

```
>TAR2h-23 (SEQ ID NO:11)
EVQLLESGGGLVQPGGSLRLSCAASGYTFT~EYTMG~WVRQAPGKGLEWVS~~WIAVDGIHTYYADSV
KG~~RFTISRDNSKNTLYLQMNSLRAEDTAVYYCAK~~~LDWTATDFSIFDY~~~WGQGTLVTVSS

>TAR2h-24 (SEQ ID NO:12)
EVQLLESGGGLVQPGGSLRLSCAASGFTFA~NYTML~WVRQAPGKGLEWVS~~VISAEGRTTYYADSV
KG~~RFTISRDNSKNTLYLQMNSLRAEDTAVYYCAK~~~LNMKATNFKDFDY~~~WGQGTLVTVSS

>TAR2h-25 (SEQ ID NO:13)
EVQLLESGGGLVQPGGSLRLSCAASGFTFS~EYAML~WVRQAPGKGLEWVS~~LIDRTGVITYYADSV
KG~~RFTISRDNSKNTLYLQMNSLRAEDTAVYYCAK~~~RDYQYHLYQDFDY~~~RGQGTLVTVSS

>TAR2h-26 (SEQ ID NO:14)
EVQLLESGGGLVQPGGSLRLSCAASGFTFA~TYSMG~WVRQAPGKGLEWVS~~MIDPEGYHTYYADSV
KG~~RFTISRDNSKNTLYLQMNSLRAEDTAVYYCAE~~~TNRPLTYKPWFDY~~~WGQGTLVTVSS

>TAR2h-27  (SEQ ID NO:15)
EVQLLESGGGLVQPGGSLRLSCAASGFTFT~DYNMA~WVRQAPGKGLEWVS~~FISQEGHHTYYADSV
KG~~RFTISRDNSKNTLYLQMNSLRAEDTAVYYCAK~~~FSTIATLSLFDY~~~WGQGTLVTVSS

>TAR2h-29 (SEQ ID NO:16)
EVQLLESGGGLVQPGGSLRLSCAASGFTFA~TYNMG~WVRQAPGKGLEWVS~~SIAWLGSETYYADSV
KG~~RFTISRDNSKNTLYLQMNSLRAEDTAVYYCAK~~~HCKAECTGDLFDY~~~WGQGTLVTVSS

>TAR2h-30 (SEQ ID NO:17)
EVQLLESGGGLVQPGGALRLSCAASGFTFG~IYSMG~WVRQAPGKGLEWVS~~SISGVGMETYYADSV
KG~~RFTISRDNSENTLYLQMNSLRAEDTAVYYCAK~~~HSYPTRGRHLFDY~~~WGQGTLVTVSS

>TAR2h-32 (SEQ ID NO:18)
EVQLLESGGGLVQPGGSLRLSCAASGFTFE~WYWMG~WVRQAPGKGLEWVS~~AISGSGGSTYYADSV
KG~~RFTISRDNSKNTLYLQMNSLRAEDTAVYYCAK~~~VKLGGGPNFDY~~~RGQGTLVTVSS

>TAR2h-33 (SEQ ID NO:19)
EVQLLESGGGLVQPGGSLRLSCAASGFTFH~RYSMG~WVRQAPGKGLEWVS~~AISSSGGITYYADSV
KG~~RFTISRDNSKNTLYLQMNSLRAEDTAVYYCAK~~~STQAQGLELDY~~~WGQGTLVTVSS
```

FIG. 6B

```
>TAR2h-10-1(SEQ ID NO:20)
EVQLLESGGGLVQPGGSLRLSCAASGFTFE~WYWMG~WVRQAPGKGLEWVS~~AISGSGGSTYYADSV
KG~~RFTISRDNSKNTLYLQMNNLRAEDTAVYYCAK~~~VKLGGGPNFDY~~~RGQGTLVTVSS

>TAR2h-10-2     (SEQ ID NO:21)
EVQLLESGGGLVQPGGSLRLSCAASGFTFE~WYWMG~WVRQAPGKGLEWVS~~AISGSGGSTYYADSV
KG~~RFTISRDNSKNTLYLQMNSLRAEDTAVYYCAK~~~VKLGGGPNFDY~~~RGQGTLVTVSS

>TAR2h-10-3     (SEQ ID NO:22)
EVQLLESGGGLVQPGGSLRLTCAASGFTFE~WYWMG~WVRQAPGKGLEWVS~~AISGSGGSTYYADSV
KG~~RFTISRDNSKNTLYLQMNSLRAEDTAVYYCAK~~~VKLGGGPNFDY~~~WGQGTLVTVSS

>TAR2h-10-4     (SEQ ID NO:23)
EVQLLESGGGLVQPGGSLRLSCAASGFTFE~WYWMG~WIRQAPGKGLEWVS~~AISGSGGSTYYADSV
KG~~RFTISRDNSKNTLYLQMNSLRAEDTAVYYCAK~~~VKLGGGPNFDY~~~WGQGTLVTVSS

>TAR2h-10-5     (SEQ ID NO:24)
EVQLLESGGGLVQPGGSLRLSCAASGFTFE~WYWMG~WVRQAPGKGLEWVS~~AISGSGGSTYYADSV
KG~~RFTISRDNSKNTLYLQMNSLRAEDTAVYYCAK~~~VKLGGGPNFDY~~~RGQGTLVTVSS

>TAR2h-10-6     (SEQ ID NO:25)
EVQLLESGGGLVQPGGSLRLSCAASGFTFE~WYWMG~WVRQAPGKGPEWVS~~AISGSGGSTYYADSV
KG~~RFTISRDNSKNTLYLQMNSLRAEDTAVYYCAK~~~VKLGGGPNFDY~~~RGQGTLVTVSS

>TAR2h-10-7     (SEQ ID NO:26)
EVQLLESGGGLVQPGGSLRLSCAASGFTFE~WYWMG~WVRQAPGKGLEWVS~~AISGSGGSTYYADSV
KG~~RFTISRDNSKNTLYLQMNSLRAKDTAVYYCAK~~~VKLGGGPNFDY~~~RGQGTLVTVSS

>TAR2h-10-8     (SEQ ID NO:27)
EVQLLESGGGLVQPGGSLRLSCAASGFTFE~WYWMG~WVRQAPGKGLEWVS~~AISGSGGSTYYADSV
KG~~RFTISRDNSKNTLYLQMNSLRAGDTAVYYCAK~~~VKLGGGPNFDY~~~RGQGTLVTVSS

>TAR2h-10-9     (SEQ ID NO:28)
EVQLLESGGGLVQPGGSLRLSCAASGFTFE~WYWMG~WVRQAPGKGLEWVS~~AISGSGGRTYYADSV
KG~~RFTISRDNSKNTLYLQMNSLRAEDTAVYYCAK~~~VKLGGGPNFDY~~~WGQGTLVTVSS
```

FIG. 6C

```
>TAR2h-10-10 (SEQ ID NO:29)
EVQLLESGGGLVQPGGSLRLSCAASGFTFE~WYWMG~WVRQAPGKGLEWVS~~AISGSGGSTYYADSV
KG~~RFTISRDNSKNTLYLQMNSLRAEDTAVYYCAK~~~VKLGGGPNFDD~~~RGQGTLVTVSS

>TAR2h-10-11 (SEQ ID NO:30)
EVQLLESGGGLVQPGGSLRLSCAASGFTFE~WYWMG~WVRQAPGKGLEWVS~~AISGSGGSKYYADSV
KG~~RFTISRDNSKNTLYLQMNSLRAEDTAVYYCAK~~~VKLGGGPNFDY~~~RGQGTLVTVSS

>TAR2h-10-12 (SEQ ID NO:31)
EVQLLESGGGLVQPGGSLRLSCAASGFTFG~WYWMG~WVRQAPGKGLEWAS~~AISGSGGNTYYADSV
KG~~RFTISRDNSKNTLYLQMNSLRAEDTAVYYCAK~~~VKLGGGPNFDY~~~WGQGTLVTVSS

>TAR2h-10-13 (SEQ ID NO:32)
EVQLLESGGGLVQPGGSLRLSCAASGFTFE~WYWMG~WVRQAPGKGLGWVS~~AISGSGGSTYYADSV
RG~~RFTISRDNSKNTLYLQMNSLRAEDTAVYYCAK~~~VKLGGGPNFDY~~~RGQGTLVTVSS

>TAR2h-10-14 (SEQ ID NO:33)
EVQLLESGGGLVQPGGSLRXSCAASGFTFE~WYWMG~WVRQAPGKGPEWVS~~AISGSGGSTYYADSV
KG~~RFTISRDNSKNTLYLQMNSLRAEDTAVYYCAK~~~VKLGGGPNFDY~~~WGQGTLVTVSS

>TAR2h-10-15 (SEQ ID NO:34)
EVQLLESGGGLVQPGGSLRLSCAASGFTFE~WYWMG~WVRQAPGKGLEWVS~~AISGSGGSTYYADSV
KG~~RFTISRDNSKNTLYLQMNSLRAEDTAVYYCAK~~~VKLGGGPNFDY~~~RGRGTLVTVSS

>TAR2h-10-16 (SEQ ID NO:35)
EVQLLESGGGLVQPGGSLRLSCAASGFTFE~WYWMG~WIRQAPGKGLEWVS~~AISGSGGSTYYADSV
KG~~RFTISRDNSKNTLYLQMNSLRAKDTAVYYCAK~~~VKLGGGPNFDY~~~RGQGTLVTVSS

>TAR2h-10-17 (SEQ ID NO:36)
EVQLLESGGGLVQPGGSLRLSCAASGFTFE~WYWMG~WIRQAPGKGLGWVS~~AISGSGGSTYYADSV
RG~~RFTISRDNSKNTLYLQMNSLRAEDTAVYYCAK~~~VKLGGGPNFDY~~~RGQGTLVTVSS

>TAR2h-10-18 (SEQ ID NO:37)
EVQLLESGGGLVQPGGSLRLSCAASGFTFG~WYWMG~WVRQAPGKGLEWAS~~AISGSGGNTYYADSV
KG~~RFTISRDNSKNTLYLQMNSLRAEDTAVYYCAK~~~VKLGGGPNFDY~~~WGQGTLVTVSS
```

FIG. 6D

>TAR2h-10-19 (SEQ ID NO:38)
EVQLLESGGGLVQPGGSLRLSCAASGFTFE~WYWMG~WVRQAPGKGLGWVS~~AISGSGGSTYYADSV
RG~~RFTISRDNSKNTLYLQMNSLRAKDTAVYYCAK~~~VKLGGGPNFDY~~~RGQGTLVTVSS

>TAR2h-10-20 (SEQ ID NO:39)
EVQLLESGGGLVQPGGSLRLSCAASGFTFG~WYWMG~WVRQAPGKGLEWAS~~AISGSGGNTYYADSV
KG~~RFTISRDNSKNTLYLQMNSLRAKDTAVYYCAK~~~VKLGGGPNFDY~~~WGQGTLVTVSS

>TAR2h-10-21 (SEQ ID NO:40)
EVQLLESGGGLVQPGGSLRLSCAASGFTFG~WYWMG~WVRQAPGKGLEWVS~~AISGSGGSTYYADSV
KG~~RFTISRDNSKNTLYLQMNSLRAKDTAVYYCAK~~~VKLGGGPNFDY~~~RGQGTLVTVSS

>TAR2h-10-22 (SEQ ID NO:41)
EVQLLESGGGLVQPGGSLRLSCAASGFTFG~WYWMG~WVRQAPGKGLGWVS~~AISGSGGSTYYADSV
RG~~RFTISRDNSKNTLYLQMNSLRAEDTAVYYCAK~~~VKLGGGPNFDY~~~RGQGTLVTVSS

>TAR2h-10-27 (SEQ ID NO:42)
EVQLLESGGGLVQPGGSLRLSCAASGFTFE~WYWMG~WVRQAPGKGLEWVS~~AISGSGGSTYYADSV
KG~~RFTISRDNSKNTLYLQMNSLRAEDAAVYYCAK~~~VKLGGGPNFGY~~~RGQGTLVTVSS

>TAR2h-10-29 (SEQ ID NO:43)
EVQLLESGGGLVQPGGSLRLSCAASGFDFE~WYWMG~WVRQAPGKGLEWVS~~AISGSGGSTYYADSV
KG~~RFTISRDNSKNTLYLQMNSLRAEDAAVYYCAK~~~VKLGGGPNFGY~~~RGQGTLVTVSS

>TAR2h-10-31 (SEQ ID NO:44)
EVQLLESGGGLVQPGGSLRLSCAASGFTFE~WYWMG~WVRQAPGKGLEWVS~~AISGSGGSTYYADSV
KG~~RFTISRDNSKSTLYLQMNSLRAEDAAVYYCAK~~~VKLGGGPNFGY~~~RGQGTLVTVSS

>TAR2h-10-35 (SEQ ID NO:45)
EVQLLESGGGLVQPGGSLRLSCAASGFDFE~WYWMG~WVRQAPGKGLEWVS~~AISGSGGSTYYADSV
KG~~RFTISRDNSKNTLYLQMNSLHAEDAAVYYCAK~~~VKLGGGPNFGY~~~RGQGTLVTVSS

>TAR2h-10-36 (SEQ ID NO:46)
EVQLLESGGGLVQPGGSLRLSCAVSGLTFE~WYWMG~WVRQAPGKGLEWVS~~AISGSGGSTYYADSV
KG~~RFTISRDNSKNTLYLQMNSLRAEDAAVYYCAK~~~VKLGGGPNFGY~~~RGQGTLVTVSS

FIG. 6E

>TAR2h-10-37 (SEQ ID NO:47)
EVQLLGSGGGLVQPGGSLRLSCAASGFTFA~WYWMG~WVRQAPGKGLEWVS~~AISGSGGSTYYADSV
KG~~RFTISRDNSKNTLYLQMNSLRAEDAAVYYCAK~~~VKLGGGPNFGY~~~RGQGTLVTVSS

>TAR2h-10-38 (SEQ ID NO:48)
EVQLLESGGGLVQPGGSLRLSCAASGFTFE~WYWMG~WVRQAPGKGLEWVS~~AISGSGGSTYYADSV
KG~~RFTISRDNSKNTLYLQMNSLRAKDAAVYYCAK~~~VKLGGGPNFGY~~~RGQGTLVTVSS

>TAR2h-10-45 (SEQ ID NO:49)
EVQLLESGGGLVQPGGSLRLSCAASGFTFE~PYWMG~WVRQAPGKGLEWVS~~AISGSGGSTYYADSV
KG~~RFTISRDNSKNTLYLQMNSLRAEDAAVYYCAK~~~VKLGGGPNFGY~~~RGQGTLVTVSS

>TAR2h-10-47 (SEQ ID NO:50)
EVQLLESGGGFVQPGGSLRLSCAASGFTFE~WYWMS~WVRQAPGKGLEWVS~~AISGSGGSTYYADSV
KG~~RFTISRDNSKNTLYLQMNSLRAEDASVYYCAK~~~VKLGGGPNFGY~~~RGQGTLVTVSS

>TAR2h-10-48 (SEQ ID NO:51)
EVQLLESGGGLVQPGGSLRLPCAASGFTFE~WYWMT~WVRQAPGKGLEWVS~~AISGSGGSTYYADSV
KG~~RFTISRDNSKNTLYLQMNSLRAEDAAVYYCAK~~~VKLGGGPNFGY~~~RGQGTLVTVSS

>TAR2h-10-57 (SEQ ID NO:52)
EVQLLESGGGLVQPGGSLRLSCAASGLTFE~WYWMG~WVRQAPGKGLEWVS~~AISGSGGSTYYADSV
KG~~RFTISRDNSKNTLYLQMNSLRAEDAAVYYCAK~~~VKLGGGPNFGY~~~RGQGTLVTVSS

>TAR2h-10-56 (SEQ ID NO:53)
EVQLLESGGGLVQPGGSLRLSCAASGLTFE~WYWMG~WVRQAPGKGLEWVS~~AVSGSGGSTYYADSV
KG~~RFTISRDNSKNTLYLQMNSLRAEDAAVYYCAK~~~VKLGGGPNFGY~~~RGQGTLVTVSS

>TAR2h-10-58 (SEQ ID NO:54)
EVQLLESGGGLVQPGGSLRLSCAASGLTFE~WYWMG~WVRQAPGKGLEWVS~~AISGSGDSTYYADSV
KG~~RFTISRDNSKNTLYLQMNSLRAEDAAVYYCAK~~~VKLGGGPNFGY~~~RGQGTLVTVSS

>TAR2h-10-66 (SEQ ID NO:55)
EVQLLESGGGLVQPGGSLRLSCAASGFTFE~WYWMG~WVRQAPGKGLEWVS~~AMSGSGGSTYYADSV
KG~~RFTISRDNSKNTLYLQMNSLRAEDAAVYYCAK~~~VKLGGGPNFGN~~~RGLGTLVTVSS

FIG. 6F

>TAR2h-10-64 (SEQ ID NO:56)
EVQLLESGGGSVQPGGSLRLSCAASGFTFD~WYWMG~WVRQAPGKGLEWAS~~AISGSGGSTYYADSV
KD~~RFTISRDNSKNTLYLQMNSLRAEDAAVYYCAK~~~VKLGGGPDFGY~~~RGQGTLVTVSS

>TAR2h-10-65 (SEQ ID NO:57)
EVQLLESGGGLVQPGGSLRLSCAASGFTFE~WYWMG~WVRQAPGKGLEWVS~~AISGSGGSTYYADSV
KG~~RFTISRDNSKNTLYLQMNSLRAEDGAVYYCAK~~~VKLGGELNFGY~~~RGQGTLVTVSS

>TAR2h-10-68 (SEQ ID NO:58)
EVQLLESGGGLVQPGGSLRLSCAASGFTFE~WYWMG~WVRQAPGKGLEWVS~~AISGSGGSTYYADSV
KG~~RFTISRDNSKNTLYLQMNSLRAEDAAVYYCAK~~~VKLGGGPNFGN~~~RGQGTPVTVSS

>TAR2h-10-69 (SEQ ID NO:59)
EVQLLESGGGLVQPGGSLRLSCAASGFTFE~WYWMG~WVRQAPGKGLEWVS~~AISGSGGSTYYADSV
KG~~RFTISRDNSKNTLYLQMNSLRPEDAAVYYCAK~~~VKLGGGPNFGP~~~RGQGTLVTVSS

>TAR2h-10-67 (SEQ ID NO:60)
EVQLLESGGGLVQPGGSLRLSCAASGFTFE~WYWMG~WVRQAPGKGLEWVS~~AISGSGGSTYYADSV
KG~~RFTISRDNSKNTLYLQMNSLRAEDAAVYYCAK~~~VKLGGGPNFGN~~~RGQGTLVTVSS

>TAR2h-10-61 (SEQ ID NO:61)
EVQLLESGGGLVQPGGSLRLSCAASGFTIE~WYWMG~WVRQAPGKGLEWVS~~AISGSGGSTYYADSV
KG~~RFTISRDNSKNTLYLQMNSLRAEDAAVYYCAK~~~VKLGGGPNFGY~~~RGQGTLVTVSS

>TAR2h-10-62 (SEQ ID NO:62)
EVQLLESGGGLVQPGGSLRLSCAASGFTFE~WYWMG~WVRQAPGKGLEWVS~~AISGSGGSTFYADSV
KG~~RFTISRDNSKNTLYLQMNSLRAEDAAVYYCAK~~~VKLGGGPNFGY~~~RGQGTLVTVSS

>TAR2h-10-63 (SEQ ID NO:63)
EVQLLESGGGLVQPGGSLRLSCAASGFTFE~WYWMG~WVRQAPGKGLEWVT~~AISGSGGSTFYADSV
KG~~RFTISRDNSKNTLYLQMNSLRAEDAAVYYCAK~~~VKLGGGPNFGY~~~RGQGTLVTVSS

>TAR2h-10-60 (SEQ ID NO:64)
EVQLLESGGGLVQPGGSLRLSCAASGFSFE~WYWMG~WVRQAPGKGLEWVS~~AISGSGDSTYYADSV
KG~~RFTISRDNSKNTLYLQMNSLRAEDAAVYYCAK~~~VKLGGGPNFGY~~~RGQGTLVTVSS

FIG. 6G

\>TAR2h-10-55 (SEQ ID NO:65)
EVQLLESGGGLVQPGGSLRLSCAASGFPFE~WYWMG~WVRQAPGKGLEWVS~~AISGSGDSTYYADSV
KG~~RFTISRDNSKNTLYQQMNSLRAEDAAVYYCAK~~~VKLGGGPNFGY~~~RGQGTLVTVSS

\>TAR2h-10-59 (SEQ ID NO:66)
EVQLLESGGGLVQPGGSLRLSCAASGFSFE~WYWMG~WVRQAPGKGLEWVS~~AISGSGGSTYYADSV
KG~~RFTISRDNSKNTLYLQMNSLRAEDAAVYYCAK~~~VKLGGGPNFGY~~~RGQGTLVTVSS

\>TAR2h-10-70 (SEQ ID NO:67)
EVQLLESGGGLVQPGGSLRLSCAASGFTFE~WYWMG~WVRQAPGKGLEWVS~~AISGSGGSTYYADSV
KG~~RFTISRDNSKNTLYLQMNSLRAEDAAVYYCAK~~~VKLGGGPNYGY~~~RGQGTLVTVSS

\>TAR2h-34  (SEQ ID NO:68)
EVQLLESGGGLVQPGGSLRLSCAASGFTFP~EYGMA~WVRQAPGKGLEWVS~~TISHGGEHTYYADSV
KG~~RFTISRDNSKNTLYLQMNSLRAEDTAVYYCAQ~~~HPVSHPKFDY~~~WGQGTLVTVSS

\>TAR2h-35 (SEQ ID NO:69)
EVQLLESGGGLVQPGGSLRLSCAASGFTFD~AYNMF~WVRQAPGKGLEWVS~~AISPSGRETYYADSV
KG~~RFTISRDNSKNTLYLQMNSLRAEDTAVYYCAK~~~RYPDFDY~~~WGQGTLVTVSS

\>TAR2h-36 (SEQ ID NO:70)
EVQLLESGGGLVQPGGSLRLSCAASGFTFS~DYTMG~WVRQAPGKGLEWVS~~LIDRPGNHTYYADSV
KG~~RFTISRDNSKNTLYLQMNSLRAEDTAVYYCAK~~~WGLNVEDFDY~~~WGQGTLVTVSS

\>TAR2h-37 (SEQ ID NO:71)
EVQLLESGGGLVQPGGSLRLSCAASGFTFI~EYDMG~WVRQAPGKGLEWVS~~MISSDGRLTYYADSV
KG--RFTISRDNSKNTLYLQMNSLRAEDTAVYYCAK~~~TWDGLNRNFDY~~~WGQGTLVTVSS

\>TAR2h-38 (SEQ ID NO:72)
EVQLLESGGGLVQPGGSLRLSCAASGFTFI~GYNMY~WVRQAPGKGLEWVS~~FISPSGRETYYADSV
KG--RFTISRDNSKNTLYLQMNSLRAEDTAVYYCAK~~~TLSADGRFDY~~~WGQGTLVTVSS

\>TAR2h-39 (SEQ ID NO:73)
EVQLLESGGGLVQPGGSLRLSCAASGFTFG~SYDMG~WVRQAPGKGLEWVS~~FIDVSGTLTYYADSV
KG~~RFTISRDNSKNTLYLQMNSLRAEDTAVYYCAK~~~TVELDGLDFDY~~~WGQGTLVTVSS

FIG. 6H

>TAR2h-40 (SEQ ID NO:74)
EVQLLESGGGLVQPGGSLRLSCAASGFTFA~DYDMG~WVRQAPGKGLEWVS~~FIDSSGSRTYYADSV
KG~~RFTISRDNSKNTLYLQMNSLRAEDTAVYYCAK~~~TAEIVNSRFDY~~~WGQGTLVTVSS

>TAR2h-41 (SEQ ID NO:75)
EVQLLESGGGLVQPGGSLRLSCAASGFTFD~KYQMG~WVRQAPGKGLEWVS~~FIDSNGHHTYYADSV
KG~~RFTISRDNSKNTLYLQMNSLRAEDTAVYYCAE~~~LDNLSITPFDY~~~WGQGTLVTVSS

>TAR2h-42 (SEQ ID NO:76)
EVQLLESGGGLVQPGGSLRLSCAASGFTFA~KYNMY~WVRQAPGKGLEWVS~~AISPKGQHTYYADSV
KG~~RFTISRDNSKNTLYLQMNSLRAEDTAVYYCAE~~~GMGSDAITFDY~~~WGQGTLVTVSS

>TAR2h-43 (SEQ ID NO:77)
EVQLLESGGGLVQPGGSLRLSCAASGFTFS~DYTMG~WARQAPGKGLEWVS~~FIDSDGLHTYYADSV
KG~~RFTISRDNSKNTLYLQMNSLRAEDTAVYYCAQ~~~NPQYAYESSRFDY~~~WGQGTLVTVSS

>TAR2h-44 (SEQ ID NO:78)
EVQLLESGGGLVQPGGSLRLSCAASGFTFL~QYPMV~WVRQAPGKGLEWVS~~SILAPGGPTYYADSV
KG~~RFTISRDNSKNSLYLQMNSLRAEDTAVYYCAK~~~HPTHTPHPNFDY~~~WGQGTLVTVSS

>TAR2h-45 (SEQ ID NO:79)
EVQLLESGGGLVQPGGSLRLSCAASGFTFG~GYRMA~WVRQAPGKGLEWVS~~FIDSEGVLTYYADSV
KG~~RFTISRDNSKNTLYLQMNSLRAEDTAVYYCAK~~~LCSSNCNMRNFDY~~~WGQGTLVTVSS

>TAR2h-47 (SEQ ID NO:80)
EVQLLESGGGLVQPGGSLRLSCAASGFTFP~VYNMA~WVRQAPGKGLEWVS~~FIAGNGQQTYYADSV
KG~~RFTISRDNSKNTLYLQMNSLRAEDTAVYYCAK~~~FASKVSPMSLTDFDY~~~WGQGTLVTVSS

>TAR2h-48 (SEQ ID NO:81)
EVQLLESGGGLVQPGGSLRLSCAASGFTFH~KYGMA~WVRQAPGKGLEWVS~~FIDLAGLHTYYADSV
RG~~RFTISRDNSKNTLYLQMNSLRAEDTAVYYCAK~~~FATYSSGNEEQPFDY~~~WGQGTLVTVSS

>TAR2h-50 (SEQ ID NO:82)
EVQLLESGGGLVQPGGSLRLSCAASGFTFS~AYNMA~WVRQAPGKGLEWVS~~FIAQSGGHTYYADSV
KG~~RFTISRDNSKNTLYLQMNSLRAEDTAVYYCAK~~~FSHPDEEGTQMFDY~~~WGQGTLVTVSS

FIG. 6I

>TAR2h-51 (SEQ ID NO:83)
EVQLLESGGGLVQPGGSLRLSCAASGFTFA~TYNMS~WVRQAPGKGLEWVS~~AIDAGGMHTYYADSV
KG~~RFTISRDNSKNTLYLQMNSLRAEDTAVYYCAK~~~GTEPFDY~~~WGQGTLVTVSS

>TAR2h-66 (SEQ ID NO:84)
EVQLLESGGGLVQPGGSLRLSCAASGFTFD~EYXMG~WVRQAPGKGLEWVS~~LISPRGSKTYYADSV
KG~~RFTISRDNSKNTLYLQMNSLRAEDTAVYYCAK~~~YKPPFDY~~~WGQGTLVTVSS

>TAR2h-67 (SEQ ID NO:85)
EVQLLESGGGLVQPGGSLRLSCAASGFTFE~DYPMA~WVRQAPGKGLEWVS~~FIGLKGIHTYYADSV
KG~~RFTISRDNSKNTLYLQMNSLRAEDTAVYYCAK~~~DLNNFDY~~~WGQGTLVTVSS

>TAR2h-68 (SEQ ID NO:86)
EVQLLESGGGLVQPGGSLRLSCAASGFTFG~NGNMV~WVRQAPGKGLEWVS~~HIDEYGTNTYYADSV
KG~~RFTISRDNSKNTLYLQMNSLRAEDTAVYYCAK~~~PRNDRPGFDY~~~WGQGTLVTVSS

>TAR2h-70 (SEQ ID NO:87)
EVQLLESGGGLVQPGGSLRLSCAASGFTFP~TEHMY~WVRQAPGKGLEWVS~~GIDTGGSHTYYADSV
KG~~RFTISRDNSKNTLYLQMNSLRAEDTAVYYCAK~~~GLHWSSDSGPVHFDY~~~WGQGTLVTVSS

>TAR2h-71 (SEQ ID NO:88)
EVQLLESGGGLVQPGGSLRLSCAASGFTFG~NVDMH~WVRQAPGKGLEWVS~~AISSAGGETYYADSV
KG~~RFTISRDNSKNTLYLQMNSLRAEDTAVYYCAK~~~RMLANSPLAFDY~~~WGQGTLVTVSS

>TAR2h-72 (SEQ ID NO:89)
EVQLLESGGGLVQPGGSLRLSCAASGFTFG~YEPMA~WVRQAPGKGLEWVS~~TISHTGRDTYYADSV
KG~~RFTISRDNSKNTLYLQMNSLRAEDTAVYYCAK~~~RWSSFDY~~~WGQGTLVTVSS

>TAR2h-73 (SEQ ID NO:90)
EVQLLESGGGLVQPGGSLRLSCAASGFTFP~SEKMA~WVRQAPGKGLEWVS~~SIDERGIMTYYADSV
KG~~RFTISRDNSKNTLYLQMNSLRAEDTAVYYCAK~~~RWTFNTAFDY~~~WGQGTLVTVSS

>TAR2h-74 (SEQ ID NO:91)
EVQLLESGGGLVQPGGSLRLSCAASGFTFS~RENMH~WVRQAPGKGLEWVS~~GIGPRGMPTYYADSV
KG~~RFTISRDNSKNTLYLQMNSLRAEDTAVYYCAK~~~GMNSHDGFDY~~~WGQGTLVTVSS

>TAR2h-75 (SEQ ID NO:92)
EVQLLESGGGLVQPGGSLRLSCAASGFTFN~AYTMI~WVRQAPGKGLEWVS~~YIDPHGTITYYADSV
KG~~RFTISRDNSKNTLYLQMNSLRAEDTAVYYCAK~~~LPRAAPRFDY~~~WGQGTLVTVSS

FIG. 6J

```
>TAR2h-76 (SEQ ID NO:93)
EVQLLESGGGLVQPGGSLRLSCAASGFTFD~ASEMD~WVRQAPGKGLEWVS~~AISPSGSATYYADSV
KG~~RFTISRDNSKNTLYLQMNSLRAEDTAVYYCAK~~~WTPGRTTFDY~~~WGQGTLVTVSS

>TAR2h-77 (SEQ ID NO:94)
EVQLLESGGGLVQPGGSLRLSCAASGFTFP~TEHMY~WVRQAPGKGLEWVS~~GIDTGGSHTYYADSV
KG~~RFTISRDNSKNTLYLQMNSLRAEDTAVYYCAK~~~GLHWSSDSGPVHFDY~~~WGQGTLVTVSS

>TAR2h-78 (SEQ ID NO:95)
EVQLLESGGGLVQPGGSLRLSCAASGFTFK~LYNMA~WVRQAPGKGLEWVS~~FIAAAGPETYYADSV
KG~~RFTISRDNSKNTLYLQMNSLRAEDTAVYYCAK~~~LGDISSIPQHPFDY~~~WGQGTLVTVSS

>TAR2h-79 (SEQ ID NO:96)
EVQLLESGGGLVQPGGSLRLSCAASGFTFG~NVDMH~WVRQAPGKGLEWVS~~AISSAGGETYYADSV
KG~~RFTISRDNSKNTLYLQMNSLRAEDTAVYYCAK~~~SADITKGFDY~~~WGQGTLVTVSS

TAR2h-15 (SEQ ID NO:97)
EVRLLESGGGLVQPGGSLRLSCAASGFTF~GKYTMT~WVRQAPGKGLEWVS~~HISDDGNSTYYADSV
KG~~RFTISRDNSKNTLYLQMNSLRAEDTAVYYCAK~~~VPILAPRNLFDY~~~WGQGTLVTVSS

TAR2h-131-8      (SEQ ID NO:98)
EVQLLESGGGLIQPGGSLRLSCAASGFTFA~HETMV~WVRQAPGKGLEWVS~~HIDRVGQDTYYADSV
KG~~RFTISRDNSKNTLYLQMNSLRAEDTAVYYCAK~~~LPKRGPWFDY~~~RGQGTLVTVSS

TAR2h-131-24     (SEQ ID NO:99)
EVQLLESGGGLIQPGGSLRLSCAASGFTFA~HETMV~WVRQAPGKGLEWVS~~HIDRVGQDTYYADSV
KG--RFTISRDNSKNTLYLQMNSLRAEDTAVYYCAR~~~LPKRGPWFDY~~~RGQGTLVTVSS

TAR2h-15-8 (SEQ ID NO:100)
EVRLLESGGGLVQPGGSLRLSCVASGFTFG~KSTMT~WVRQAPGKGLEWVS~~HISDDGNSTYYADSV
KG~~RFTISRDNSKNTLYLQMNSLRAEDTAVYYCAK~~~VPILAPRNLFDY~~~WGQGTLVTVSS

TAR2h-15-8-1     (SEQ ID NO:101)
EVRLLESGGGLVQPGGSLRLSCVASGFNFG~KSTMT~WVRQAPGKGLEWVS~~HISDDGNSTYYADSV
KG~~RFTISRDNSKNTLYLQMNSLRAEDTAVYYCAK~~~VPILAPRNLFDY~~~WGQGTLVTVSS
```

FIG. 6K

```
TAR2h-15-8-2      (SEQ ID NO:102)
EVRLLESGGGLVQPGGSLRLSCVASGFTFG~KGTMT~WVRQAPGKGLEWVS~~HISDDGNSTYYADSV
KG~~RFTISRDNSKNTLYLQMNSLRAEDTAVYYCAK~~~VPILAPRNLFDY~~~WGQGTLVTVSS

TAR2h-185-23      (SEQ ID NO:103)
EVQLLESGGGLVQPGGSLRLSCAASGFTFA~RYNMG~WVRQAPGKGLEWVS~~LIDPSGGHTYYAXSV
KG~~RSTISRNNSKNTLYLQMNSLRAEDTAVYYCGK~~~PVFSDWPAVEFDY~~~WGQGTLVTVSS

TAR2h-154-10-5   (SEQ ID NO:104)
EVQLLESGGGMVQPGGSLRLSCAAPGFTFE~HEGMV~WVRQAPGKGLEWVS~~HIGEDGQSTYYADSV
KG~~RFTISRDNSKNTLYLQMNSLRAEDTAVYYCAS~~~IPKAGPSFDY~~~WGQGTLVTVSS

TAR2h-14-2 (SEQ ID NO:105)
EVQLLESGGGLVQPGGSLRLSCAASGSTFD~QYDMS~WVRRAPGKGLEWVS~~LIDPSGGHTYYADSV
KG~~RFTISRNNTKNTLYLQMNSLRAEDTAVYYCAK~~~PVFSDWPAVEFDY~~~WGQGTLVTVSS

TAR2h-151-8      (SEQ ID NO:106)
EVQLLESGGGLVQPGGSLRLSCAASGFTFD~YGNMF~WVRQAPGKGLEWIS~~AISGSGGSTYYADSV
KG~~RFTISRDNSKNTLYLQMNSLRAEDTAVYYCAK~~~DMTTDSPPGFDY~~~WGQGTLVTVSS

TAR2h-152-7      (SEQ ID NO:107)
EVQLLESGGGLVQPGGSLRLSCAASGFTFA~KETMS~WVRQAPGKGLEWVS~~WISPHGAHTFYADSV
KG~~RFTISRDNSKNTLYLQMNSLRAEDTAVYYCAK~~~PRFSYYPRVSFDY~~~RGQGTLVTVSS

TAR2h-35-4 (SEQ ID NO:108)
EVQLLESGGGLVQPGGSLRLSCAASGFTFD~AYNMF~WFRQAPGKGPEWVS~~AIGPSGRETYYADSV
KG~~RFTITRDNSKNTLYLQMNSLRAEDTAVYYCAK~~~RYPDFDY~~~WGQGTLVTVSS

TAR2h-154-7      (SEQ ID NO:109)
EVQLLESGGGLVQPGGSLRLSCAASGFTFE~HEGMV~WVRQAPGKGLEWVS~~HIGEDGQSTYYADSV
KG~~RFTISRDNSRNTLYLQMNSLRAEDTAVYYCAN~~~IPKAGPSFDY~~~WGQGTLVTVSS

TAR2h-80      (SEQ ID NO:110)
EVQLLESGGGLVQPGGSLRLSCAASGFTFK~LYNMA~WVRQAPGKGLEWVS~~FIAAAGPETYYADSV
KG~~~RFTISRDNSKNTLYLQMNSLRAEDTAVYYCAK~~~~LGDISSIPQHPFDY~~~WGQGTLVTVSS
```

FIG. 6L

```
TAR2h-81   (SEQ ID NO:111)
EVQLLESGGGLVQPGGSLRLSCAASGFTFS-RENMH-WVRQAPGKGLEWVS--GIGPRGMPTYYADSV
KG--RFTISRDNSKNTLYLQMNSLRAEDTAVYYCAK---GMNSHDGFDY---WGQGTLVTVSS

TAR2h-82   (SEQ ID NO:112)
EVQLLESGGGLVQPGGSLRLSCAASGFTFD-ASEMD-WVRQAPGKGLEWVS--AISPSGSATYYADSV
KG--RFTISRDNSKNTLYLQMNSLRAEDTAVYYCAK---RMLANSPLAFDY---WGQGTLVTVSS

TAR2h-83   (SEQ ID NO:113)
EVQLLESGGGLVQPGGSLRLSCAASGFTFS-AYNMA-WVRQAPGKGLEWVS--FIAQSGGHTYYADSV
KG--RFTISRDNSKNTLYLQMNSLRAEDTAVYYCAK---FSHPDEEGTQMFDY---WGQGTLVTVSS

TAR2h-84   (SEQ ID NO:114)
EVQLLESGGGLVQPGGSLRLSCAASGFTFA-DYQMA-WVRQAPGKGLEWVS--RIDRGGFTYYADSVK
G--RFTISRDNSKNTLYLQMNSLRAEDTAVYYCAK---PSWHADQYFDY---WGQGTLVTVSS

TAR2h-85   (SEQ ID NO:115)
EVQLLESGGGLVQPGGSLRLSCAASGFTFK-DYNMM-WVRQAPGKGLEWVS--AIATSGRETYYADSV
KG--RFTISRDNSKNTLYLQMNSLRAEDTAVYYCAK---FTFGGNQDFDY---WGQGTLVTVSS

TAR2h-86   (SEQ ID NO:116)
EVQLLESGGGLVQPGGSLRLSCAASGFTFA-KYNMY-WVRQAPGKGLEWVS--AISPKGQHTYYADSV
KG--RFTISRDNSKNTLYLQMNSLRAEDTAVYYCAE---GMGSDAITFDY---WGQGTLVTVSS

TAR2h-87   (SEQ ID NO:117)
EVQLLESGGGLVQPGGSLRLSCAASGFTFS-AYNMA-WVRQAPGKGLEWVS--FIAQSGGHTYYADSV
KG--RFTISRDNSKNTLYLQMNSLRAEDTAVYYCAK---FSHPDEEGTQMFDY---WGQGTLVTVSS

TAR2h-88   (SEQ ID NO:118)
EVQLLESGGGLVQPGGSLRLSCAASGFTFE-RYDMF-WVRQAPGKGLEWVS--GISPRGRETYYADSV
KG--RFTISRDNSKNTLYLQMNSLRAEDTAVYYCAK---DMINYHGTPSFDY---WGQGTLVTVSS

TAR2h-89   (SEQ ID NO:119)
EVQLLESGGGLVQPGGSLRLSCAASGFTFX-NYNMV-WVRQAPGKGLEWVS--WISGAGHSTYYADSV
KG--RFTISRDNSKNTLYLQMNSLRAEDTAVYYCAK---DVDMAGKLNVFDY---WGQGTLVTVSS

FIG. 6M
```

TAR2h-90    (SEQ ID NO:120)
EVQLLESGGGLVQPGGSLRLSCAASGFTFK~QYNMY~WVRQAPGKGLEWVS~~FISPSGGETYYADSV
KG~~RFTTSRDNSKNTLYLQMNSLRAEDTAVYYCAK~~~DVDMAGKLNVFDY~~~WGQGTLVTVSS

TAR2h-91    (SEQ ID NO:121)
EVQLLESGGGLVQPGGSLRLSCAASGFTFA~DYQMA~WVRQAPGKGLEWVS~~RIDRGGFHTYYADSV
KG~~RFTISRDNSKNTLYLQMNSLRAEDTAVYYCAK~~~PSWHADQYFDY~~~WGQGTLVTVSS

TAR2h-92    (SEQ ID NO:122)
EVQLLESGGGLVQPGGSLRLTCAASGFTFD~DVNMT~WVRQAPGKGLEWVS~~AIGPSGTETYYADSV
KG~~RFTISRDNSKNTLYLQMNSLRAEDTAVYYCAK~~~HSKTGSAMFDY~~~WGQGTLVTVSS

TAR2h-93    (SEQ ID NO:123)
EVQLLESGGGLVQPGGSLRLSCAASGFTFG~NGNMV~WVRQAPGKGLEWVS~~HIDEYGTNTYYADSV
KG~~RFTISRDNSKNTLYLQMNSLRAEDTAVYYCAK~~~PRNDRPGFDY~~~WGQGTLVTVSS

TAR2h-94    (SEQ ID NO:124)
EVQLLESGGGLVQPGGSLRLSCAASGFTFS~RENMH~WVRQAPGKGLEWVS~~GIGPRGMPTYYADSV
KG~~RFTISRDNSKNTLYLQMNSLRAEDTAVYYCAK~~~GMNSHDGFDY~~~WGQGTLVTVSS

TAR2h-95    (SEQ ID NO:125)
EVQLLESGGGLRLSCAASGFTFK~GSNMG~WVRQAPGKGLEWVS~~LIDGRGQHTYYADSV
KG~~RFTISRDNSKNTLYLQMNSLRAEDTAVYYCAK~~~PSVREFDY~~~RGQGTLVTVSS

TAR2h-96    (SEQ ID NO:126)
EVQLLESGGGLVQPGGSLRLSCAASGFTFS~RENMH~WVRQAPGKGLEWVS~~GIGPRGMPTYYADSV
KG~~RFTISRDNSKNTLYLQMNSLRAEDTAVYYCAK~~~RMLANSPLAFDY~~~WGQGTLVTVSS

TAR2h-97    (SEQ ID NO:127)
EVQLLESGGGLVQPGGSLRLSCTASGFTFS~ESTMN~WVRQAPGKGLEWVS~~VITAQGGDTYYADSV
KG~~RFTISRDNSKNTLYLQMNSLRAEDTAVYYCAK~~~PDVLFDY~~~WGQGTLVTVSS

TAR2h-99    (SEQ ID NO:128)
EVQLLESGGGLVQPGGSLRLSCAASGFTFE~EYNML~WVRQAPGKGLEWVS~~GIGPSGRETYYADSV
KG~~RFTISRDNSKNTLYLQMNSLRAEDTAVYYCAK~~~GSITLFDY~~~WGQGTLVTVSS

FIG. 6N

TAR2h-100 (SEQ ID NO:129)
EVQLLESGGGLVQPGGSLRLSCAASGFTFS~GYNMY~WVRQAPGKGLEWVS~~AIDAYGTHTYYADSV
KG~~RFTISRDNSKNTLYLQMNSLRAEDTAVYYCAE~~~GLQTSDHGERISFDY~~~WGQGTLVTVSS

TAR2h-101 (SEQ ID NO:130)
EVQLLESGGGLVQPGGSLRLSCAASGFTFD~QYDMS~WVRQAPGKGLEWVS~~LIDPSGGHTYYADSV
KG~~RFTISRNNSKNTLYLQMNSLRAEDTAVYYCAK~~~PVFSDWPAVEFDY~~~WGQGTLVTVSS

TAR2h-102 (SEQ ID NO:131)
EVQLLESGGGLVQPGGSLRLSCAASGFTFD~QYDMS~WVRQAPGKGLEWVS~~LIDPSGGHTYYADSV
KG~~RFTISRNNSKNTLYLQMNSLRAEDTAVYYCAK~~~PVFSDWPAVEFDY~~~WGQGTLVTVSS

TAR2h-103 (SEQ ID NO:132)
EVQLLESGGGLVQPGGSLRLSCAASGFTFT~RYSMG~WVRQAPGKGLEWVS~~MIDVPGLHTYYADSV
KG~~RFTISRDNSKNTLYLQMNSLRAEDTAVYYCAK~~~ISQFGSNAFDY~~~WGQGTLVTVSS

TAR2h-104 (SEQ ID NO:133)
EVQLLESGGGLVQPGGSLRLSCAASGFTFE~WYWMG~WVRQAPGKGLEWVS~~AISGSGGSTYYAXSV
KG~~RFTISRDNSKNTLYLQMNSLRAEDAAVYYCAK~~~VKLGGXPNFGY~~~RGQGTLVTVSS

TAR2h-105 (SEQ ID NO:134)
EVQLLESGGGLVQPGGSLRLSCAASGFTFT~RYSMG~WVRQAPGKGLEWVS~~FIDPPSVHTYYADSV
KG~~RFTISRDNSKNTLYLQMNSLRAEDTAVYYCAK~~~ISQFGSNAFDY~~~WGQGTLVTVSS

TAR2h-106 (SEQ ID NO:135)
EVQLLESGGGLVQPGGSLRLSCAASGFTFT~RYSMG~WVRQAPGKGLEWVS~~MIDVGGSHTYYAXSV
KG~~RFTISRDNSKNTLYLQMNSLRAEDTAVYYCAK~~~ISQFGSNAFDY~~~WGQGTLVTVSS

TAR2h-107 (SEQ ID NO:136)
EVQLLESGGGLVQPGGSLRLSCAASGFTFT~RYSMG~WVRQAPGKGLEWVS~~MIDTGGVHTYYAXSV
KG~~RFTISRDNSKNTLYLQMNSLRAEDTAVYYCAK~~~ISQFGSNAFDY~~~WGQGTLVTVSS

TAR2h-108 (SEQ ID NO:137)
EVQLLESGGGLVQPGGSLRLSCAASGFTFT~RYSMG~WVRQAPGKGLEWVS~~MIDVPGRHTYYADSV
KG~~RFTISRDNSKNTLYLQMNSLRAEDTAVYYCAK~~~ISQFGSNAFDY~~~WGQGTLVTVSS

FIG. 60

TAR2h-109 (SEQ ID NO:138)
EVQLLESGGGLVQPGGSLRLSCAASGFTFT~RYSMG~WVRQAPGKGLEWVS~~MIAHAGPETYYADSV
KG~~RFTISRDNSKNTLYLQMNSLRAEDTAVYYCAK~~~ISQFGSNAFDY~~~WGQGTLVTVSS

TAR2h-110 (SEQ ID NO:139)
EVQLLESGGGLVQPGGSLRLSCAASGFTFT~RYSMG~WVRQAPGKGLEWVS~~MIDTRGVRTYYADSV
KG~~RFTISRDNSKNTLYLQMNSLRAEDTAVYYCAK~~~ISQFGSNAFDY~~~WGQGTLVTVSS

TAR2h-111 (SEQ ID NO:140)
EVQLLESGGGLVQPGGSLRLSCAASGFTFT~RYSMG~WVRQAPGKGLEWVS~~MIDVPGNHTYYADSV
KG~~RFTISRDNSKNTLYLQMNSLRAEDTAVYYCAK~~~ISQFGSNAFDY~~~WGQGTLVTVSS

TAR2h-112 (SEQ ID NO:141)
EVQLLESGGGLVQPGGSLRLSCAASGFTFT~RYSMG~WVRQAPGKGLEWVS~~MIDVGGRHTYYADSV
KG~~RFTISRDNSKNTLYLQMNSLRAEDTAVYYCAK~~~ISQFGPNAFDY~~~WGQGTLVTVSS

TAR2h-113 (SEQ ID NO:142)
EVQLLESGGGSVQPGGSLRLSCAASGFTFT~RYSMG~WVRQAPGKGLEWVS~~RIDSYGRGTYYADSV
KG~~RFTISRDNSKNTLYLQMNSLRAEDTAVYYCAK~~~VRSPYTFDY~~~WGQGTLVTVSS

TAR2h-114 (SEQ ID NO:143)
EVQLLESGGGLVQPGGSLRLSCAASGFTFS~GYNMG~WVRQAPGKGLEWVS~~TISTQGYHTYYADSV
KG~~RFTISRDNSKNTLYLQMNSLRAEDTAVYYCAK~~~AFTSDFDY~~~WGQGTLVTVSS

TAR2h-115 (SEQ ID NO:144)
EVQLLESGGGLVQPGGSLRLSCAASGFTFS~GYNMY~WVRQAPGKGLEWVS~~GISGPGLETYYADSV
KG~~RFTISRDNSKNTLYLQMNSLRAEDTAVYYCAQ~~~GMSKTSTFDY~~~WGQGTLVTVSS

TAR2h-116 (SEQ ID NO:145)
EVQLLESGGGLVQPGGSLRLSCAASGFTFT~EYYME~WVRQAPGKGLEWVS~~SIDPDGSLTYYADSV
KG~~RFTISRDNSKNTLYLQMNSLRAEDTAVYYCAK~~~YPREKFDY~~~WGQGTLVTVSS

TAR2h-117 (SEQ ID NO:146)
EVQLLESGGGLVQPGGSLRLSCAASGFTFD~KYQMG~WVRQAPGKGLEWVS~~FIDSNGHHTYYADSV
KG~~RFTISRDNSKNTLYLQMNSLRAEDTAVYYCAQ~~~LSVQGSNLFDY~~~WGQGTLVTVSS

FIG. 6P

TAR2h-118 (SEQ ID NO:147)
EVQLLESGGGLVQPGGSLRLSCAASGFTFV~HYTMG~WVRQAPGKGLEWVS~~WIHSDGVHTYYADSV
KG~~RFTISRDNSKNTLYLQMNSLRAEDTAVYYCAK~~~FTWGEKKTFDY~~~WGQGTLVTVSS

TAR2h-119 (SEQ ID NO:148)
EVQLLESGGGLVQPGGSLRLSCAASGFTFM~GYDMH~WVRQAPGKGLEWVS~~GISAKGTETYYADSV
KG~~RFTISRDNSKNTLYLQMNSLRAEDTAVYYCAK~~~GSSGSDGLFDY~~~WGQGTLVTVSS

TAR2h-120 (SEQ ID NO:149)
EVQLLESGGGLVQPGGSLRLSCAASGFTFP~VYNMA~WVRQAPGKGLEWVS~~FIAGNGQQTYYADSV
KG~~RFTISRDNSKNTLYLQMNSLRAEDTAVYYCAK~~~FASKVSPMSLTDFDY~~~WGQGTLVTVSS

TAR2h-121 (SEQ ID NO:150)
EVQLLESGGGLVQPGGSLRLSCAASGFTFV~QYNMH~WVRQAPGKGLEWVS~~GISSGGMRTYYADSV
KG~~RFTISRDNSKNTLYLQMNSLRAEDTAVYYCAK~~~GIRDSTLPRGTLFDY~~~WGQGTLVTVSS

TAR2h-122 (SEQ ID NO:151)
EVQLLESGGGLVQPGGSLRLSCAASGFTFE~TYSMH~WVRQAPGKGLEWVS~~SISLPGSRTYYADSV
KG~~RFTISRDNSKNTLYLQMNSLRAEDTAVYYCAK~~~HSKSSHRQSFDY~~~WGQGTLVTVSS

TAR2h-123 (SEQ ID NO:152)
EVQLLESGGGLVQPGGSLRLSCAASGFTFN~QYDMH~WVRQAPGKGLEWVS~~GISFSGYETYYADSV
KG~~RFTISRDNSKNTLYLQMNSLRAEDTAVYYCAK~~~GRGPAPMRSLFDY~~~WGQGTLVTVSS

TAR2h-124 (SEQ ID NO:153)
EVQLLESGGGLVQPGGSLRLSCAASGFTFV~DYPMV~WVRQAPGKGLEWVS~~HITSMGESTYYADSV
KG~~RFTISRDNSKNMLYLQMNSLRAEDTAVYYCAK~~~LPTHFPIRFDY~~~WGQGTLVTVSS

TAR2h-125 (SEQ ID NO:154)
EVQLLESGGGLVQPGGSLRLSCAASGFTFK~QYNMY~WVRQAPGKGLEWVS~~FISPSGGETYYADSV
KG~~RFTISRDNSKNTLYLQMNSLRAEDTAVYYCAK~~~SIKPFDY~~~WGQGTLVTVSS

TAR2h-126 (SEQ ID NO:155)
EVQLLESGGGLVQPGGSLRLSCAASGFTFS~MYSMA~WVRQAPGKGLEWVS~~FIDFDGLHTYYADSV
KG~~RFTISRDNSKNTLYLQMNSLRAEDTAVYYCAK~~~FSTSTMALFDY~~~WGQGTLVTVSS

FIG. 6Q

TAR2h-127 (SEQ ID NO:156)
EVQLLESGGGLVRPGGSLRLSCAASGFTFP~EYNMH~WVRQAPGKGLEWVS~~AIGTAGGSTYYADSV
KG~~RFTISRDNSKNMLYLQMNSLRAEDTAVYYCAK~~~GYRPRTGSMLFDY~~~WGQGTLVTVSS

TAR2h-128 (SEQ ID NO:157)
EVQLLESGGGLVQPGGSLRLSCAASGFTFA~KYNMY~WVRQAPGKGLEWVS~~AISPKGQQTYYADSV
KG~~RFTISRDNSKNTLYLQMNSLRAEDTAVYYCAE~~~GMGSDAITFDY~~~WGQGTLVTVSS

TAR2h-129 (SEQ ID NO:158)
EVQLLESGGGLVQPGGSLRLSCAASGFTFA~DYDMA~WVRQAPGKGLEWVS~~FIDRKGHHTYYADSV
KG~~RFTISRDNSKNTLYLQMNSLRAEDTAVYYCAK~~~TTDIQRLNSAFDY~~~WGQGTLVTVSS

TAR2h-130 (SEQ ID NO:159)
EVQLLESGGGLVQPGGSLRLSCAASGFTFG~NGVMA~WVRQAPGKGLEWVS~~HINENGGATYYADSV
KG~~RFTISRDNSKNTLYLQMNSLRAEDTAVYYCAK~~~PSIESPIFDY~~~WGQGTLVTVSS

TAR2h-131 (SEQ ID NO:160)
EVQLLESGGGLVQPGGSLRLSCAASGFTFA~HEPMV~WVRQAPGKGLEWVS~~HIDRVGQDTYYADSV
KG~~RFTISRDNSKNTLYLQMNSLRAEDTAVYYCAK~~~LPKRGPRFDY~~~WGQGTLVTVSS

TAR2h-132 (SEQ ID NO:161)
EVQLLESGGGLVQPGGSLRLSCAASGFTFE~ESVMG~WVRQAPGKGLEWVS~~AISPGGSETYYADSV
KG~~RFTISRDNSKNTLYLQMNSLRAEDAAVYYCAK~~~RTGPPGSTVFDY~~~WGQGTLVTVSS

TAR2h-133 (SEQ ID NO:162)
EVQLLESGGGLVQPGGSLRLSCAASGFTFG~DEPMH~WVRQAPGKGLEWVS~~GIGKEGQPTYYADSV
KG~~RFTISRDNSKNTLYLQMNSLRAEDTAVYYCAK~~~LGGPFDY~~~WGQGTLVTVSS

TAR2h-151 (SEQ ID NO:163)
EVQLLESGGGLVQPGGSLRLSCAASGFTFD~YGNMF~WVRQAPGKGLEWVS~~AISGSGGSTYYADSV
KG~~RFTISRDNSKNTLYLQMNSLRAEDTAVYYCAK~~~DMTTDSPPGFDY~~~WGQGTLVTVSS

TAR2h-152 (SEQ ID NO:164)
EVQLLESGGGLVQPGGSLRLSCAASGFTFA~KETMS~WVRQAPGKGLEWVS~~WISPHGALTYYADSV
KG~~RFTISRDNSKNTLYLQMNSLRAEDTAVYYCAK~~~PRFSYYPRVSFDY~~~WGQGTLVTVSS

FIG. 6R

TAR2h-153  (SEQ ID NO:165)
EVQLLESGGGLVQPGGSLRLSCAASGFTFG~NGNMV~WVRQAPGKGLEWVS~~HIDEYGTNTYYADSV
KG~~RFTISRDNSKNTLYLQMNSLRAEDTAVYYCAK~~~PRNDRPGFDY~~~WGQGTLVTVSS

TAR2h-154  (SEQ ID NO:166)
EVQLLESGGGLVQPGGSLRLSCAASGFTFG~NGNMV~WVRQAPGKGLEWVS~~HIDXYGTNTYYADSV
KG~~RFTISRDNSKNTLYLQMNSLRAGDTAVYYCAK~~~PRNDRPGFDY~~~WGQGTLVTVSS

TAR2h-159  (SEQ ID NO:167)
EVQLLESGGGLVQPGGSLRLSCAASGFTFA~GQDMR~WVRQAPGKGLEWVS~~SIPSSGFNTYYADSV
KG~~RFTISRDNSKNTLYLQMNSLRAEDTAVYYCAK~~~RAKDRSVSQMPYFDY~~~WGQGTLVTVSS

TAR2h-165  (SEQ ID NO:168)
EVQLLESGGGLVQPGGSLRLSCAASGFTFM~RPDMV~WVRQAPGKGLEWVS~~TIKDWGDQTYYADSV
KG~~RFTISRDNSKNTLYLQMNSLRAEDAAVYYCAK~~~ADSRAQLDFDY~~~WGQGTLVTVSS

TAR2h-166  (SEQ ID NO:169)
EVQLLESGGGLVQPGGSLRLSCAASGFTFS~SYAMS~WVRQAPGKGLEWVS~~AISGSGGSTYYADSV
KG~~RFTISRDNSKNTLYLQMNSLRAEDTAVYYCAK~~~PYFLFRATSFDY~~~WGQGTLVTVSS

TAR2h-168  (SEQ ID NO:170)
EVQLLESGGGLVQPGGSLRLSCAASGFTFH~DDDMV~WVRQAPGKGLEWVS~~SIPGNGYVTYYADSV
KG~~RFTISRDNSKNTLYLQMNSLRAEDTAVYYCAK~~~RPDPTSVFFDY~~~WGQGTLVTVSS

TAR2h-171  (SEQ ID NO:171)
EVQLLESGGGLVQPGGSLRLSCAASGFTFG~DDWMT~WVRQAPGKGLEWVS~~GIAAYGISTYYADSV
KG~~RFTISRDNSKNTLYLQMNSLRAEDAAVYYCAE~~~SGKVFDY~~~WGQGTLVTVSS

TAR2h-172  (SEQ ID NO:172)
EVQLLESGGGLVQPGGSLRLSCAASGFTFV~ERPMD~WVRQAPGKGLEWVS~~LIGADGLSTYYADSV
KG~~RFTISRDNSKNTLYLQMNSLRAEDTAVYYCAK~~~LFRPGLLWFDY~~~WGQGTLVTVSS

TAR2h-173  (SEQ ID NO:173)
EVQLLESGGGLVQPGGSLRLSCAASGFTFT~GQDMQ~WVRQAPGKGLEWVS~~GINADGMATYYADSV
KG~~RFTISRDNSKNTLYLQMNSLRAEDTAVYYCAK~~~TSPTMRSFDY~~~WGQGTLVTVSS

FIG. 6S

TAR2h-174 (SEQ ID NO:174)
EVQLLESGGGLVQPGGSLRLSCAASGFTFG~EEYMQ~WVRQAPGKGLEWVS~~LIPHTGNPTYYADSV
KG~~RFTISRDNSKNTLYLQMNSLRAEDTAVYYCAK~~~LANSLLFDY~~~WGQGTLVTVSS

TAR2h-176 (SEQ ID NO:175)
EVQLLESGGGLVQPGGSLRLSCAASGFTFH~RCKMG~WVRQAPGKGLEWVS~~FIEYDGRDTYYADSV
KG~~RFTISRDNSKNTLYLQMNSLRAEDTAVYYCAK~~~ECTRPYGMFDY~~~WGQGTLVTVSS

TAR2h-178 (SEQ ID NO:176)
EVQLLESGGGLVQPGGSLRLSCAASGFTFN~RYSMG~WLRQAPGKGLEWVS~~FIDKVGHHTWYEDPV
KG~~RFTISRDNSKNTLYLQMNSLRAEDTAVYYCAK~~~ISQFGPNAFDY~~~WGQGTQVTVSS

TAR2h-201 (SEQ ID NO:177)
EVQLLESGGGLVQPGGSLRLSCAASGFTFT~RYSMG~WVRQAPGKGLEWVS~~MIAHAGPERYYADSV
KG~~RFTISRDNSKNTLYLQMNSLRAEDTAVYYCAK~~~ISXFGSNAFDY~~~WGQGTLVTVSS

TAR2h-202 (SEQ ID NO:178)
EVQLLESGGGLVQPGGSLRLSCAASGFTFT~RYNMG~WVRQAPGKGLEWVS~~FIDPPSVHTYYADSV
KG~~RFTISRDNSKNTLYLQMNSLRAEDTAVYYCAN~~~ISQFGSNAFDY~~~WGQGTLVTVSS

TAR2h-203 (SEQ ID NO:179)
EVQLLESGGGLVQPGGSLRLSCAASGFTFT~RYSMG~WVRQAPGKGLEWVS~~FIDPPSVHTYYADSV
KG~~RFTISRDNSKNTLYLQMNSLRAEDTAVYYXAE~~~ISQFGSNAFDY~~~WGQGTLVTVSS

TAR2h-204 (SEQ ID NO:180)
EVQLFESGGGLVQPGGSLRLSCAASGFTFT~RYSMG~WVRQAPGKGLEWVS~~MIAHAGPETYYADSV
KG~~RFTISRDNSKNTLYLQMNSLRAEDTAVYYCAK~~~ISQFGSNALDY~~~WGRGTLVTVSS

TAR2h-185-25 (SEQ ID NO:181)
EVQLLESGGGLVQPGGSLRLSCAASGFTFA~RYNMG~WVRQAPGKGLEWVS~~LIDPSGGHTYYADSV
KG~~RFTISRNNSKNTLYLQMNSLRAEDTAVYYCGK~~~PVFSDWPAVEFDY~~~WGQGTVVTVSS

TAR2h-154-10 (SEQ ID NO:182)
EVQLLESGGGMVQPGGSLRLSCAASGFTFE~HEGMV~WVRQAPGKGLEWVS~~HIGEDGQSTYYADSV
KG~~RFTISRDNSKNTLYLQMNSLRAEDTAVYYCAN~~~IPKAGPSFDY~~~WGQGTLVTVSS

FIG. 6T

TAR2h-205 (SEQ ID NO:183)
EVQLLESGGGLVQPGGSLRLSCAASGFTFV~KYSMG~WVRQAPGKGLEWVS~~QISNTGGHTYYADSV
KG~~RFTISRDNSKNTLYLQMNSLRAEDTAVYYCAK~~~YTGRWEPFDY~~~WGQGTLVTVSS

>TAR2h-10 (SEQ ID NO:184)
EVQLLESGGGLVQPGGSLRLSCAASGFTFE~WYWMG~WVRQAPGKGLEWVS~~AISGSGGSTYYADSV
KG~~RFTISRDNSKNTLYLQMNSLRAEDTAVYYCAK~~~VKLGGGPNFDY~~~WGQGTLVTVSS

TAR2h-5 (SEQ ID NO:185)
EVQLLESGGGLVQPGGSLRLSCAASGFTFDLYNMFWVRQAPGKGLEWVSFISQTGR
LTWYADSVKGRFTISRDNSKNTLYLQMNSLRAEDTAVYYCAKTLEDFDYWGQGTLVTVS

TAR2h-5d1 (SEQ ID NO:186)
EVQLLESGGGLVQPGGSLRLSCAASGFTFPVYMMGWVRQAPGKGLEWVSSIDALGGR
TGYADSVKGRFTISRDNSKNTLYLQMNSLRAEDTAVYYCAKTMSNKTHTFDYWGQGTLVTS

TAR2h-5d2 (SEQ ID NO:187)
EVQLLESGGGLVQPGGSLRLSCAASGFTFVAYNMTWVRQAPGKGLEWVSSINTFGNX
TRYADSVKGRFTISRDNSKNTLYLQMNSLRAEDTAVYYCAKGSRPFDYWGQGTLVTVS

TAR2h-5d3 (SEQ ID NO:188)
EVQLLESGGGLVQPGGSLRLSCAASGFTFXGYRMGWVRQAPGKGLEWVSWITRTGGT
TQYADSVKGRFTISRDNSKNTLYLQMNSLRAEDTAVYYCAKPAKLVGVGFDYWGQGT
LVTVS

TAR2h-5d4 (SEQ ID NO:189)
EVQLLESGGGLVQPGGSLRLSCAASGFTFRKYXMGWVRQAPGKGLEWVSQIGAKGQS
TDYADSVKGRFTISRDNSKNTLYLQMNSLRAEDTAVYYCAKKKRGENYFFDYWGQGT
LVTVS

TAR2h-5d5 (SEQ ID NO:190)
EVQLLESGGGLVQPGGSLRLSCAASGFTFRRYSMSWVRQAPGKGLEWVSDISRSGRY
THYADSVKGRFTISRDNSKNTLYLQMNSLRAEDTAVYYCAKRIDSSQNGFDYWGQGT
LVTVS

TAR2h-5d6 (SEQ ID NO:191)
EVQLLESGGGLVQPGGSLRLSCAASGFTFXGYKMFWVRQAPGKGLEWVSAISGSGGS
TYYADSVKGRFTISRDNSKNTLYLQMNSLRAEDTAVYYCAKQKENFDYWGQGTLVTVS

TAR2h-5d7 (SEQ ID NO:192)
EVQLLESGGGLVQPGGSLRLSCAASGFTFGDYAMWWVRQAPGKGLEWVSVISSNGGS
TFYADSVKGRFTISRDNSKNTLYLQMNSLRAEDTAVYYCAKRVRKRTPEFDYWGQGT
LVTVS

FIG. 6U

TAR2h-5d8  (SEQ ID NO:193)
EVQLLESGGGLVQPGGSLRLSCAASGFTFRRYKMGWVRQAPGKGLEWVSAIGRNGTK
TNYADSVKGRFTISRDNSKNTLYLQMNSLRAEDTAVYYCAKIYTGKPAAFDYWGQGT
LVTVS

TAR2h-5d9   (SEQ ID NO:194)
EVQLLESGGGLVQPGGSLRLSCAASGFTFKKYXMSWVRQAPGKGLEWVSAISGSGGS
TYYADSVKGRFTISRDNSKNTLYLQMNSLRAEDTAVYYCAKMLRTKNKVFDYWGQGT
LVTVS

TAR2h-5d10  (SEQ ID NO:195)
EVQLLESGGGLVQPGGSLRLSCAASGFTFRRYKMGWVRQAPGKGLEWVSAIGRNGTK
TNYADSVKGRFTISRDNSKNTLYLQMNSLRAEDTAVYYCAKIYTGKPAAFDYWGQGT
LVTVS

TAR2h-5d11  (SEQ ID NO:196)
EVQLLESGGGLVQPGGSLRLSCAASGFTFXSYRMGWVRQAPGKGLEWVSSISSRGRH
TSYADSVKGRFTISRDNSKNTLYLQMNSLRAEDTAVYYCAKRVPGRGRSFDYWGQGT
LVTVS

TAR2h-5d12  (SEQ ID NO:197)
EVQLLESGGGLVQPGGSLRLSCAASGFPFRRYRMRWVRQAPGKGLEWVSGISPGGKH
TTYADSVKGRFTISRDNSKNTLYLQMNSLRAEDTAVYYCAKGEGGASSAFDYWGQGT
LVTVS

TAR2h-5d13  (SEQ ID NO:198)
EVQLLESGGGLVQPGGSLRLSCAASGFTFXRYGMVWVRQAPGKGLEWVSAISGSGGS
TYYADSVKGRFTISRDNSKNTLYLQMNSLRAEDTAVYYCAKRHSSEARQFDYWGQGT
LVTVS

FIG. 6V

TAR2m-14 (SEQ ID NO:199)
DIQMTQSPSSLSASVGDRVTITC~RASQPIGVALN~WYQQKPGKAPKLLIY~~GGSYLQS~~GVPSRY
SGSGSGTDFTLTISSLQPGDFATYYC~~~QQDWRYPGT~~~FGQGTKVEIKR

TAR2m-15 (SEQ ID NO:200)
DIQMTQSPSSLSASVGDRVTITC~RASQYIHTSLQ~WYQQKPGKAPKLLIY~~GSSRLQS~~GVPSRF
SGSGSGTDFTLTISSLQPEDFATYYC~~~QQNHHSPFT~~~FGQGTKVEIKR

TAR2m-19 (SEQ ID NO:201)
EVQLLESGGGLVQPGGSLRLSCAASGFTFRKYDMHWVRQAPGKGLEWVSTISPSGRRTYYADSVKGRF
TISRDNSKNTLYLQMNSLRAEDTAVYYCAENLDQVLSFDYWGQGTLVTVSS

TAR2m-20 (SEQ ID NO:202)
EVQLLESGGGLVQPGGSLRLSCAASGFTFGSYSMSWVRQAPGKGLEWVSGIDNGGHSTYYADSVKGRF
TISRDNSKNTLYLQMNSLRAEDTAVYYCAKRSSGLPFPFDYWGQGTLVTVSS

TAR2m-21 (SEQ ID NO:203)
EVQLLESGGGLVQPGGSLRLSCAASGFTFTRYSMGWVRQAPGKGLEWVSRIDSYGRGTYYADSVKGRF
TISRDNSKNTLYLQMNSLRAEDTAVYYCAKISQFGSNAFDYWGQGTLVTVSS

TAR2m-24 (SEQ ID NO:204)
DIQMTQSPSSLSASVGDRVTITCRASQYIHSSLQWYQQKPGKAPKLLIYSSSRLHSGVPPRFSGSGSG
TDFTLTISSLQPEDFATYYCQQNHFRPHTFGQGTKVEIKR

TAR2m-21-23 (SEQ ID NO:205)
EVQLLESGGGLVQPGGSLRLSCAASGFTFN~RYSMG~WLRQAPGKGLEWVS~~RIDSYGRGTYYEDPV
KG~~RFSISRDNSKNTLYLQMNSLRAEDTAVYYCAK~~~ISQFGSNAFDY~~~WGQGTQVTVSS

TAR2m-21-07 (SEQ ID NO:206)
EVQLLESGGGLVQPGGSLRLSCAASGFTFSRCSMGWLRQAPGKGLEWVSRIDSYGRGTYYADSVKGRF
TISRDNSKNTLYLQMNSLRAEDTAVYYCAKISKFGSNAFDYWGQGTLVTVSS

TAR2m-21-43 (SEQ ID NO:207)
EVQLLESGGGLVQPGGSLRLSCAASGFTFTRYSMGWLRQAPGKGLEWVSRIDSYGRGTYDADSVKGRF
TISRDNSKNTLYLQMNSLRAEDTAVYYCAKISQFGSNAFDYWGQGTLVTVSS

TAR2m-21-48 (SEQ ID NO:208)
EVQLLESGGGLIQPGGSLRLSCAASGFTFTRYSMGWLRQAPGKGLEWVSRIDSYGRGTYDTDSVKGRF
TISRDNSRNTLYLQMNSLRAEDTAVYYCAKISQFGSNAFDYWGQGTLVTVSS

TAR2m-21-10 (SEQ ID NO:209)
EVQLLESGGGLVQPGGSLRLSCAASGFTFTRYSMGWLRQAPGKGLEWVSRIDSYGRGTYYADSVKGRF
TISRDNSKNTLYLQMNSLRAEDTAVYYCAKISQFGSNAFDYWGQGTLVTVSS

FIG. 7A

TAR2m-21-06 (SEQ ID NO:210)
EVQLLESGGGLVQPGGSLRLSCAASGFTFTRYSMGWIRQAPGKGLEWVSRIDSYGRGTYYADSVKGRF
TISRDNSKNTLYLQMNSLRAEDTAVYYCAKISQFGSNAFDYWGQGTLVTVSS

TAR2m-21-17 (SEQ ID NO:211)
EVQLLESGGGLVQPGGSLRLSCAASGFTFTRYSMGWVRQAPGKGLEWVSRIDSYGRGTYYADSVKGRF
TISRDNSKNTLYLQMNSLRAEDTAVYYCAKISQFGSNAFDYWGQGTVVTVSS

Human (*Homo sapiens*) TNFR1 (extracellular region Genbank accession 33991418)
CTGGTCCCTCACCTAGGGGACAGGGAGAAGAGAGATAGTGTGTGTCCCCAAGGAAAATA
TATCCACCCTCAAAATAATTCGATTTGCTGTACCAAGTGCCACAAAGGAACCTACTTGTA
CAATGACTGTCCAGGCCCGGGGCAGGATACGGACTGCAGGGAGTGTGAGAGCGGCTCCT
TCACCGCTTCAGAAAACCACCTCAGACACTGCCTCAGCTGCTCCAAATGCCGAAAGGAA
ATGGGTCAGGTGGAGATCTCTTCTTGCACAGTGGACCGGGACACCGTGTGTGGCTGCAG
GAAGAACCAGTACCGGCATTATTGGAGTGAAAACCTTTTCCAGTGCTTCAATTGCAGCCT
CTGCCTCAATGGGACCGTGCACCTCTCCTGCCAGGAGAAACAGAACACCGTGTGCACCT
GCCATGCAGGTTTCTTTCTAAGAGAAAACGAGTGTGTCTCCTGTAGTAACTGTAAGAAAA
GCCTGGAGTGCACGAAGTTGTGCCTACCCCAGATTGAGAATGTTAAGGGCACTGAGGAC
TCAGGCACCACA (SEQ ID NO:212)

FIG. 8B

LVPHLGDREKRDSVCPQGKYIHPQNNSICCTKCHKGTYLYNDCPGPGQDTDCRECESGSFTA
SENHLRHCLSCSKCRKEMGQVEISSCTVDRDTVCGCRKNQYRHYWSENLFQCFNCSLCLNG
TVHLSCQEKQNTVCTCHAGFFLRENECVSCSNCKKSLECTKLCLPQIENVKGTEDSGTT
(SEQ ID NO:213)

FIG. 9A

Murine (*Mus musculus*) TNFR1 (extracellular region Genbank accession 31560798)
CTAGTCCCTTCTCTTGGTGACCGGGAGAAGAGGGATAGCTTGTGTCCCCAAGGAAAGTA
TGTCCATTCTAAGAACAATTCCATCTGCTGCACCAAGTGCCACAAAGGAACCTACTTGGT
GAGTGACTGTCCGAGCCCAGGGCGGGATACAGTCTGCAGGGAGTGTGAAAAGGGCACCT
TTACGGCTTCCCAGAATTACCTCAGGCAGTGTCTCAGTTGCAAGACATGTCGGAAAGAA
ATGTCCCAGGTGGAGATCTCTCCTTGCCAAGCTGACAAGGACACGGTGTGTGGCTGTAA
GGAGAACCAGTTCCAACGCTACCTGAGTGAGACACACTTCCAGTGCGTGGACTGCAGCC
CCTGCTTCAACGGCACCGTGACAATCCCCTGTAAGGAGACTCAGAACACCGTGTGTAAC
TGCCATGCAGGGTTCTTTCTGAGAGAAAGTGAGTGCGTCCCTTGCAGCCACTGCAAGAA
AAATGAGGAGTGTATGAAGTTGTGCCTACCTCCTCCGCTTGCAAATGTCACAAACCCCCA
GGACTCAGGTACTGCG (SEQ ID NO:214)

FIG. 9B

LVPSLGDREKRDSLCPQGKYVHSKNNSICCTKCHKGTYLVSDCPSPGRDTVCRECEKGTFTA
SQNYLRQCLSCKTCRKEMSQVEISPCQADKDTVCGCKENQFQRYLSETHFQCVDCSPCFNGT
VTIPCKETQNTVCNCHAGFFLRESECVPCSHCKKNEECMKLCLPPPLANVTNPQDSGTA
(SEQ ID NO:215)

>TAR2m-15-8 (SEQ ID NO:216)
DIQMTQSPSSLSASVGDRVTITC~RASQYIHTSVQ~WYQQKPGKAPKLLIY~~GSSRLHS~~GVPSRF
SGSGSGTDFTLTISSLQPEDFATYYC~~~QQNHYSPFT~~~FGQGTKVEIKR

>TAR2m-15-12 (SEQ ID NO:217)
DIQMTQSPSSLSASVGDRVTITC~RASQYIHTSVQ~WYQQKPGKAPKLLIY~~GSSRLHS~~GVPSRF
SGSGSGTDFTLTISSLQPEDFATYYC~~~QQNHYSPFT~~~YGQGTKVEIKR

>TAR2m-15-2 (SEQ ID NO:218)
DIQMTQSPSSLSASVGDRVTITC~RASQYIHTSLQ~WYQQKPGKAPKLLIY~~GSSRLHS~~GVPSRF
SGSGSGTDFTLTISSLQPEDFATYYC~~~QQNHYSPFT~~~FGQGTKVEIKR

>TAR2m-15-5 (SEQ ID NO:219)
DIQMTQSPSSLSASVGDRVTITC~RASQYIHTSLQ~WYQQKPGKALKLLIY~~GSSRLQS~~GVPSRF
SGSGSGTDFTFTISSLQPEDFATYYC~~~QQNHHSPFT~~~YGQGTKVEIKR

>TAR2m-15-6 (SEQ ID NO:220)
DIQMTQSPSSLSASVGDRVTITC~RASQYIHTSLQ~WYQQKPGKAPKLLIY~~GSSRLHS~~GVPSRF
SGSGSGTDFTLTIRSLQPEDLATYYC~~~QQNHYSPFT---FGQGTKVEING

>TAR2m-15-9 (SEQ ID NO:221)
DIQMTQSPSSLSASVGDRVTITC~RASQYIHTSLQ~WYQQKPGKAPKLLIY~~GSSRLHS~~GVPSRF
SGSGSGTDFTLTISSLQPEDFATYYC~~~QQNHYSPFT---YGQGTKVEIKR

>Tar2h-131-1 (SEQ ID NO:222)
EVQLLESGGGLVQPGGSLRLSCAASGFTFA~HEPMV~WVRQAPGKGLEWVS~~HIDRVGQDTYYADSV
KG~~RFIISRDNSKNTLYLQMYSLRAEDTAVYYCAI~~~LPKRGPRFDY~~~WGQGTLVTVSS

>Tar2h-131-2 (SEQ ID NO:223)
EVQLLESGGGLVQPGGSLRLSCAASGFTFA~HEPMV~WVRQAPGKGLEWVS~~HIDRVGQDTYYADSV
KG~~RFTISRDNSKNTLYLQMNSLRAEDTAVYYCAR~~~LPKRGPRFDY~~~WGHGTLVTVSS

>Tar2h-131-3 (SEQ ID NO:224)
EVQLLESGGGLVQPGGSLRLSCAASGFTFA~HEPMV~WVRQAPGKGLEWVS~~HIDRVGQDTYYADSV
KG~~RFTISRDNSKNTLYLQMNSLRAEDTAVYYCAI~~~LPKRGPRFDY~~~WGQGTLVTVSS

>Tar2h-131-4 (SEQ ID NO:225)
EVQLLESGGGLVQPGGSLRLSCTASGFTFA~HEPMV~WVRQAPGKGLEWVS~~HIDRVGQDTYYADSV
KG~~RFTISRDNSKNTLYLQMNSLRAEDTAVYYCAR~~~LPKRGPRFDY~~~WGLGTLVTVSS

>Tar2h-131-5 (SEQ ID NO:226)
EVKLLESGGGLVQPGGSLRLSCAASGFTFA~HEPMV~WIRQAPGKGLEWVS~~HIDRVGQDTYYADSV
KG~~RYTISRDNSKNTLYLQMNSLRAEDTAVYYCAR~~~LPKRGPRFDY~~~WGQGTLVTVSS

>Tar2h-131-6 (SEQ ID NO:227)
EVQLLESGGGLVQPGGSLRLSCAASGFTFA~HEPMV~WVRQAPGKGLEWVS~~HIDRVGQDTYYADSV
KG~~RFTISRDNSKNTLYLQMNSLRAEDTAVYYCAR---LPKRGPRFDY---WGLGTLVTVSS

>Tar2h-131-7 (SEQ ID NO:228)
EVQLLESGGGLVQPGGSLRLSCAASGFTFA~HEPMV~WVRQAPGKGLEWVS~~HIDRAGQDTYYADSV
KG~~RFTISRDNSKNTLYLQMNSLRAEDTAVYYCAR~~~LPKRGPRFDY~~~WGLGTLVTVSS

FIG. 10A

>Tar2h-131-8 (SEQ ID NO:229)
EVQLLESGGGLIQPGGSLRLSCAASGFTFA~HETMV~WVRQAPGKGLEWVS~~HIDRVGQDTYYADSV
KG~~RFTISRDNSKNTLYLQMNSLRAEDTAVYYCAK~~~LPKRGPWFDY~~~RGQGTLVTVSS

>Tar2h-131-9 (SEQ ID NO:230)
EVQLLESGGGLVRPGGSLRLSCAASGFTFA~HEPMV~WVRQAPGKGLEWVS~~HIDRVGQDTYYADSV
KG~~RFTISRDNSKNTLYLQMNSLRAEDTAVYYCAR~~~LPKRGPRFDY~~~WGLGTLVTVSS

>Tar2h-131-10 (SEQ ID NO:231)
EVQLLESGGGLVQPGGSLRLSCAASGFTFA~HEPMV~WVRQAPGKGLEWVS~~HIDRVGQDTYYADSV
KG~~RFTISRDNSKNTLYLQMNSLRAEDTAIYYCAR~~~LPKRGPRFDY~~~WGLGTLVTVSS

>Tar2h-131-11 (SEQ ID NO:232)
EVQLLESGGGLVQPGGSLRLSCAASGFTFA~HEPMV~WVRQAPGKGLEWVS~~HIDRVGQDPYYADSV
KG~~RFTISRDNSKNTLYLQMNSLRAEDTAVYYCAR~~~LPKRGPRFDY~~~WGQGTLVTVSS

>Tar2h-131-12 (SEQ ID NO:233)
EVQLLESGGGLVQPGGSLRLSCAASGFTFA~HEPMV~WIRQAPGKGLEWVS~~HIDRVGQDTYYADSV
KG~~RFTISRDNSKNTLYLQMNSLRAEDTAVYYCAI~~~LPKRGPRFDY~~~WGQGTLVTVSS

>Tar2h-131-13 (SEQ ID NO:234)
EVQLLESGGGLVQPGGSLRLSCAASGFTFA~HEPMV~WVRQAPGKGLEWVS~~HIDRVGQDPYYADSV
KG~~RFTISRDNSKNTLYLQMNSLRAEDTAVYYCAR~~~LPKRGPRFDY~~~WGLGTLVTVSS

>Tar2h-131-14 (SEQ ID NO:235)
EVQLLESGGGLVQPGGSLRLSCAASGFTFA~HEPMV~WVRQAPGKGLEWVS~~HIDRVGQDAYYADSV
KG~~RFTISRDNSKNTLYLQMNSLRAEDTAVYYCAI~~~LPKRGPRFDY~~~WGQGTLVTVSS

>Tar2h-131-15 (SEQ ID NO:236)
EVQLLESGGGLVQPGGSLRLSCAASGFTFA~HEPMV~WVRQAPGKGLEWVS~~HIDRVGQDTYYADSV
KG~~RSTISRDNSKNTLYLQMNSLRAEDTAIYYCAR~~~LPKRGPRFDY~~~WGLGTLVTVSS

>Tar2h-131-16 (SEQ ID NO:237)
EVQLLESGGGLVQPGGSLRLSCAASGFTFA~HEPMV~WVRQAPGKGLEWVS~~HIDRVGQDTYYADSV
KG~~RFTISRDNSKNTLYLQMNSLRAEDTAIYYCAR~~~PPKRGPRFDY~~~WGLGTLVTVSS

>Tar2h-131-17 (SEQ ID NO:238)
EVQLLESGGGLVQPGGSLRLSCAASGFTFA~HEPMV~WVRQAPGKGLEWVS~~HIDRVGQDTYYADSV
KG~~RFTISRDNSKNTLYLQMNSLRAKDTAIYYCAR~~~LPKRGPRFDY~~~WGLGTLVTVSS

>Tar2h-131-18 (SEQ ID NO:239)
EVQLLESGGGLVQPGGSLRLSCAASGFTFA~HEPMV~WVRQAPGKGLEWVS~~HIDRVGQDTYYADSA
KG~~RFTISRDNSKNTLYLQMNSLRAEDTAIYYCAR~~~LPKRGPRFDY~~~WGLGTLVTVSS

>Tar2h-131-19 (SEQ ID NO:240)
EVQLLESGGGLVQPGGSLRLSCAASGFTFA~HEPMV~WVRQAPGKGLEWVS~~HIDRVGQDTYYADSV
KG~~RFTISRDNSKNTLYPQMNSLRAEDTAIYYCAR~~~LPKRGPRFDY~~~WGLGTLVTVSS

>Tar2h-131-20 (SEQ ID NO:241)
EVQLLESGGGLVQPGGSLRLSCAASGFTFA~HEPMV~WVRQAPGKGLEWVS~~HIDRVGQDTYYADSV
KG~~RFTVSRDNSKNTLYLQMNSLRAEDTAIYYCAR~~~LPKRGPRFDY~~~WGLGTLVTVSS

FIG. 10B

>Tar2h-131-21 (SEQ ID NO:242)
EVQLLESGGGLVQPGGSLRLSCAASGFTFA~HEPMV~WVRQAPGKGLEWVS~~HIDRVGQDTYYADSV
KG~~RFIISRDNSKNTLYLQMYSLRAEDTAVYYCAM~~~LPKRGPRFGY~~~WGQGTLVTVSS

>Tar2h-131-22 (SEQ ID NO:243)
EVQLLESGGGLVQPGGSLRLSCAASGFTFA~HEPMV~WVRQAPGKGLEWVS~~HIDRVGQDTYYADSV
KG~~RFTISRDNSKNTLYLQMNSLCAEDTAIYYCAR~~~LPKRGPRFDY~~~WGLGTLVTVSS

>Tar2h-131-23 (SEQ ID NO:244)
EVQLLESGGGLIQPGGSLRLSCAASGFTFA~HETMV~WVRQAPGKGLEWVS~~HIDRVGQDTYYADSV
KG~~RFTISRDNSKNTLYLQMNSLRAEDTAVYYCAG~~~LPKRGPWFDY~~~RGQGTLVTVSS

>Tar2h-131-24 (SEQ ID NO:245)
EVQLLESGGGLIQPGGSLRLSCAASGFTFA~HETMV~WVRQAPGKGLEWVS~~HIDRVGQDTYYADSV
KG~~RFTISRDNSKNTLYLQMNSLRAEDTAVYYCAR~~~LPKRGPWFDY~~~RGQGTLVTVSS

>Tar2h-131-25 (SEQ ID NO:246)
EVQLLESGGGLIQPGGSLRLSCAASGFTFA~HETMV~WVRQAPGKGLEWVS~~HIDRVGQDTYYADSV
KG~~RFTISRDNSKNTLYLQMNSLRAEDTAVYYCAQ~~~LPKRGPWFDY~~~RGQGTLVTVSS

>Tar2h-131-26 (SEQ ID NO:247)
EVQLLESGGGLIQPGGSLRLSCAASGFTFA~HETMV~WVRQAPGKGLEWVS~~HIDRVGQDTYYADSV
KG~~RFTISRDNSKNTLYLQMNSLRVEDTAVYYCAS~~~LPKRGPWFDY~~~RGQGTLVTVSS

>Tar2h131-27 (SEQ ID NO:248)
EVQLLESGGGLYQPGGSLRLSCAASGFTFA~HETMV~WVRQAPGKGLEWVS~~HIDRVGQDTYYADSV
KG~~RFTISRDNSKNTLYLQMNSLRAEDTAVYYCAK~~~LPKRGPWFDY~~~RGQGTLVTVSS

>Tar2h131-28 (SEQ ID NO:249)
EVQLLESGGGLGQPGGSLRLSCAASGFTFA~HETMV~WVRQAPGKGLEWVS~~HIDRVGQDTYYADSV
KG~~RFTISRDNSKNTLYLQMNSLRAEDTAVYYCAK~~~LPKRGPWFDY~~~RGQGTLVTVSS

>Tar2h131-29 (SEQ ID NO:250)
EGQLLESGGGLXQPGGSLLLSCAASGFTFA~HETMV~WVRQAPGKGLEWVS~~HIDRVGQDTYYADSV
KG~~RFTISRDNSKNTLYLQMNSLRAEDTAVYYCAK~~~LPKRGPWFDY~~~RGQGTLVTVSS

>Tar2h131-30 (SEQ ID NO:251)
EVQLLESGGGLVQPGGSLRLSCAASGFTFA~HETMV~WVRQAPGKGLEWVS~~HIDRVGQDTYYADSV
KG~~RFTISRDNSKNTLYLQMNSLRAEDTAVYYCAK~~~LPKRGPWFDY~~~RGQGTLVTVSS

>Tar2h131-31 (SEQ ID NO:252)
EVQLLESGGGLIQPGGSLRLSCAASGFTFA~HETMV~WVRQAPGKGLEWVS~~HIDRVGQDPYYADSV
KG~~RFTISRDNSKNTLYLQMNSLRAEDTAVYYCAK~~~LPKRGPWFDY~~~RGQGTLVTVSS

>Tar2h131-32 (SEQ ID NO:253)
EGQLLESGGGLIQPGGSLRLSCGASGFTFA~HETMV~WVRQAPGKGLEWVS~~HIDRVGQDPYYADSV
KG~~RFTISRDNSKNTLYLQMNSLRAEDTAVYYCAK~~~LPKRGPWFDY~~~RGQGTLVTVSS

>Tar2h131-33 (SEQ ID NO:254)
EVQLLESGGGLIQPGGSLRLSCAASGFTFA~HETMV~WVRQAPGKGLEWVS~~HIDRVGQDNYYADSV
KG~~RFTISRDNSKNTLYLQMNSLRAEDTAVYYCAK~~~LPKRGPWFDY~~~RGQGTLVTVSS

FIG. 10C

```
>Tar2h131-34 (SEQ ID NO:255)
EVQLLESGGGLIQPGGSLRLSCAASGFTFA~HETMV~WVRQAPGKGLEWVS~~HIDRVGQDTYYADSV
KG~~RFTISRDNSKNTLYLQMNSLRAEDTAVYYCAK~~~LPKRGPGFDY~~~RGQGTLVTVSS

>Tar2h131-35 (SEQ ID NO:256)
EVQLLESGGGLIQPGGSLRLSCAASGFTFA~HETMV~WVRQAPGKGLEWVS~~HIDRVGQDTYYADSV
KG~~RFTISRDNSKNTLYLQMNSLRAEDTAVYYCAK~~~LPKRGPVFDY~~~RGQGTLVTVSS

>Tar2h131-36 (SEQ ID NO:257)
EVQLLESGGGLIQPGGSLRLSCAASGFTFA~HETMV~WVRQAPGKGLEWVS~~HIDRVGQDTYYADSV
KG~~RFTISRDNSKNTLYLQMNSLRAEDTAVYYCAK~~~LPKRGPWFDY~~~YGQGTLVTVSS

>Tar2h131-37 (SEQ ID NO:258)
EGQLLESGGGLIQPGGSLLLSCAPSGFTFA~HETMV~WVRQAPGKGLEWVS~~HIDRVGQDTYYADSV
KG~~RFTISRDNSKNTLYLQMNSLRAEDTAVYYCAK~~~LPKRGPWFDY~~~KGQGTLVTVSS

>Tar2h131-38 (SEQ ID NO:259)
EVQLLESGGGLIQPGGSLRLSCAASGFTFA~HETMV~WVRQAPGKGLEWVS~~HIDRVGQDTYYADSV
KG~~RFTISRDNSKNTLYLQMNSLRAEDTAVYYCAK~~~LPKRGPWFDY~~~VGQGTLVTVSS

>Tar2h131-39 (SEQ ID NO:260)
EVQLLESGGGLIQPGGSLRLSCAASGFTFA~HETMV~WVRQAPGKGLEWVS~~HIDRVGQDTYYADSV
KG~~RFTISRDNSKNTLYLQMNSLRAEDTAVYYCAK~~~LPKRGPWFDY~~~LGQGTLVTVSS

>Tar2h131-40 (SEQ ID NO:261)
EVQLLESGGGLVQPGGSLRLSCAASGFTFA~HEPMV~WVRQAPGKGLEWVS~~HIDRVGQDTYYADSV
KG~~RFTISRDNSKNTLYLQMNSLRAEDTAVYYCAS~~~LPKRGPRFDY~~~WGQGTLVTVSS

>Tar2h131-41 (SEQ ID NO:262)
EVQLLESGGGLVQPGGSLRLSCAASGFTFA~HEPMV~WVRQAPGKGLEWVS~~HIDRVGQDTYYADSV
KG~~RFTISRDNSKNTLYLQMNSLRAEDTAVYYCAG~~~LPKRGPRFDY~~~WGQGTLVTVSS

>Tar2h131-42 (SEQ ID NO:263)
EVQLLESGGGLVQPGGSLRLSCAASGFTFA~HEPMV~WVRQAPGKGLEWVS~~HIDRVGQDTYYADSV
KG~~RFTISRDNSKNTLYLQMNSLRAEDTAVYYCAR~~~LPKRGPRFDY~~~WGQGTLVTVSS

>Tar2h131-43 (SEQ ID NO:264)
EVQLLESGGGLVQPGGSLRLSCAASGFTFA~HEPMV~WVRQAPGKGLGWVS~~HIDRVGQDTYYADSV
KG~~RFTISRDNSKNTLYLQMNSLRAEDTAVYYCAP~~~LPKRGPRFDY~~~WGQGTLVTVSS

>Tar2h131-44 (SEQ ID NO:265)
EVQLLESGGGLVQPGGSLRLSCAASGFTFA~HEPMV~WVRQAPGKGLEWVS~~HIDRVGQDTYYADSV
KG~~RFTISRDNSKNTLYLQMNSLRAEDTAVYYCAI~~~LPKRGPRFDY~~~WGQGTLVTVSS

>Tar2h131-45 (SEQ ID NO:266)
EVQLLESGGGLVQPGGSLRLSCAASGFTFA~HEPMV~WIRQAPGKGLEWVS~~HIDRVGQDTYYADSV
KG~~RFTISRDNSKNTLYLQMNSLRAEDTAVYYCAM~~~LPKRGPRFDY~~~WGQGTLVTVSS

>Tar2h131-46 (SEQ ID NO:267)
EVQLLESGGGLVQPGGSLRLSCAASGFTFA~HEPMV~WVRQAPGKGLEWVS~~HIDRVGQDTYYADSV
KG~~RFTISRDNSKNTLYLQMNSLRAEDTAVYYCAL~~~LPKRGPRFDY~~~WGQGTLVTVSS
```

FIG. 10D

>Tar2h131-47 (SEQ ID NO:268)
EVQLLESGGGLIQPGGSLRLSCAASGFTFA~HXTMV~WVRQAPGKGLEWVS~~HIDRVGQDKYYADSV
KG~~RFTISRDNSKNTLYLQMNSLRAEDTAVYYCAK~~~LPKRGPWFDY~~~RGQGTLVTVSS

>Tar2h131-48 (SEQ ID NO:269)
EVQLLESGGGLIQPGGSLRLSCAASGFTFA~HXTMV~WVRQAPGKGLEWVS~~HIDRVGQDTYYADSV
KG~~RFTISRDNSKNTLYLQMNSLRAEDTAVYYCAK~~~LPKRGPWFDY~~~IGQGTLVTVSS

>Tar2h131-49 (SEQ ID NO:270)
EVQLLESGGGLIQPGGSLRLSCAASGFTFA~HETMV~WVRQAPGKGLEWVS~~HIDRVGQDTYYADSV
KG~~RFTISRDNSKNTLYLQMNSLRAEDTAVYYCAK~~~LPKRGPWFDY~~~NGQGTLVTVSS

>Tar2h-131-50 (SEQ ID NO:271)
EVQLLESGGGLIQPGGSLRLSCAASGFTFA~HEVMV~WVRQAPGKGLEWVS~~HIDRVGQDTYYADSV
KG~~RFTISRDNSKNTLYLQMNSLRAEDTAVYYCAK~~~LPKRGPWFDY~~~RGQGTLVTVSS

>Tar2h-131-51 (SEQ ID NO:272)
EVQLLESGGGLIQPGGSLRLSCAASGFTFA~HELMV~WVRQAPGKGLEWVS~~HIDRVGQDTYYADSV
KG~~RFTISRDNSKNTLYLQMNSLRAEDTAVYYCAK~~~LPKRGPWFDY~~~RGQGTLVTVSS

>Tar2h-131-52 (SEQ ID NO:273)
EVQLLESGGNLVQPGGSLRLSCAASGFTFA~HETMV~WVRQAPGKGLEWVS~~HIDRVGQDTYYADSV
KG~~RFTISRDNSKNTLYLQMNSLRAEDTAVYYCAK~~~LPKRGPWFDY~~~RGQGTLVTVSS

>Tar2h-131-53 (SEQ ID NO:274)
EVQLLESGGGLVQPGGSLRLSCAASGFTFA~HETMV~WVRQAPGKGLEWVS~~HIDRVGQDTYYADSV
KG~~RFTISRDNSKNTLYLQMNSLRAEDTAVYYCAK~~~LPKRGPWFDY~~~RGQGTLVTVSS

>Tar2h-131-54 (SEQ ID NO:275)
EVQLLESGGGLIQPGGSLRLSCAASGFTFA~HKTMV~WVRQAPGKGLEWVS~~HIDRVGQDTYYADSV
KG~~RFTISRDNSKNTLYLQMNSLRAEDTAVYYCAL~~~LPKRGPWFDY~~~RGQGTLVTVSS

>Tar2h-131-55 (SEQ ID NO:276)
EVQLLESGGGLIQPGGSLRLSCAASGFTFA~HETMV~WVRQAPGKGLEWVS~~HIDRVGQDTYYADPV
KG~~RFTISRDNSKNTLYLQMNSLRAEDTAVYYCAR~~~LPKRGPWFDY~~~RGQGTLATVSS

>Tar2h-131-56 (SEQ ID NO:277)
EVQLLESGGGLIQPGGSLRLSCAASGFTFA~HETMV~WVRQAPGKGLEWVS~~HIDRVGQDTYYADSV
KG~~RFTISRDNSKNSLYLQMNSLRAEDTAVYYCAV~~~LPKRGPWFDY~~~RGQGTLVTVSS

>Tar2h-131-57 (SEQ ID NO:278)
EVQLLESGGGLIQPGGSLRLSCAASGFTFA~HETMV~WVRQAPGKGLEWVS~~HIDRVGQDTYYADSV
KG~~RFTISRDNPKNTLYLQMNSLRAEDTAVYYCAR~~~LPKRGPWFDY~~~RGQGTLVTVSS

>Tar2h-131-58 (SEQ ID NO:279)
EVQLLESGGGLIQPGGSLRLSCAASGFTFA~HDTMV~WVRQAPGKGLEWVS~~HIDRVGQDTYYADSV
KG~~RFTISRDNSKNTLYLQMNSLRAEDTAVYYCAR~~~LPKRGPWFDY~~~QGQGTLVTVSS

>Tar2h-131-59 (SEQ ID NO:280)
EVQLLESGGGLIQPGGSLRLSCAASGFTFA~HDTMV~WVRQAPGKGLEWVS~~HIDRVGQDTYYADSV
KD~~RFTISRDNSKNTLYLQMNSLRAEDTAVYYCAV~~~LPKRGPWFDY~~~RGQGTLVTVSS

FIG. 10E

>Tar2h-131-60 (SEQ ID NO:281)
EVQLLESGGGLIQPGGSLRLSCAASGFTFA~HETMV~WVRQAPGKGLEWVS~~HIDRVGQDTYYADSV
KG~~RFTISRDNSKNTLFLQMNSLRAEDTAVYYCAR~~~LPKRGPWFDY~~~RGRGTLVTVSS

>Tar2h-131-61 (SEQ ID NO:282)
EVQLLESGGGLIQPGGSLRLSCAASGFTFA~HETMV~WVRQAPGKGLEWVS~~HIDRVGQDTYYADSV
EG~~RFTISRDNSKNTLYLQMNSLRAEDTAVYYCAV~~~LPKRGPWFDY~~~RGQGTLVTVSS

>Tar2h-131-62 (SEQ ID NO:283)
EVQLLESGGGLIQPGGSLRLSCAASGFTFA~HETMV~WVRQAPGKGLEWVS~~HIDRVGQDTYYADSV
EG~~RFTISRDNSKNTLYLQMNSLRAEDTAVYYCAL~~~LPKRGPWFDY~~~RGQGTLVTVSS

>Tar2h-131-63 (SEQ ID NO:284)
EVQLLESGGGLIQPGGSLRLSCAASGFTFA~HETMV~WVRQAPGKGQEWVS~~HIDRVGQDTYYADSV
KG~~RFTISRDNSKNSLYLQMNSLRAEDTAVYYCAV~~~LPKRGPWFDY~~~RGQGTLVTVSS

>Tar2h-131-64 (SEQ ID NO:285)
EVQLSESGGGLIQPGGSLRLSCVASGFTFA~HETMV~WVRQAPGKGLEWVS~~HIDRVGQDTYYADSV
KG~~RFTISRDNSKNTLYLQMNSLRAEDTAVYYCAI~~~LPKRGPWFDY~~~RGQGTLVTVSS

>Tar2h-131-65 (SEQ ID NO:286)
EVQLLESGGGLIQPGGSLRLTCAASGFTFA~HETMV~WVRQAPGKGLEWVS~~HIDRVGQDTYYADSV
KG~~RFTISRDNSKNTLYLQMNSLRAEDTAVYYCAV~~~LPKRGPWFDY~~~RGQGTLVTVSS

>Tar2h-131-66 (SEQ ID NO:287)
EVQLLESGGGLIQPGGSLRLSCAASGFTFA~HETMV~WVRQAPGKGLEWVS~~HIDRVGQDTYYADSV
KG~~RFTISRDNSMNTLYLQMNSLRAEDTAVYYCAL~~~LPKRGPWFDY~~~RGQGTLVTVSS

>Tar2h-131-67 (SEQ ID NO:288)
EVQLLESGGGSIQPGGSLRLSCAASGFTFA~HETMV~WVRQAPGKGLEWVS~~HIDRVGQDTYYADSV
KG~~RFTISRDNSKNTLYLQMNSLRAEDTAVYYCAV~~~LPKRGPWFDY~~~RGQGTLVTVSS

>Tar2h-131-68 (SEQ ID NO:289)
EVQLLESGGGLIQPGGSLRLSCAASGFTFA~HETMV~WVRQAPGKGLEWVS~~HIDRVGQDTYYADSV
KG~~RFTISRNNSMNTLYLQMNSLRAEDTAVYYCAI~~~LPKRGPWFDY~~~RGQGTLVTVSS

>Tar2h-131-69 (SEQ ID NO:290)
EVQLLESGGGLIQPGGSLRLSCAASGFTFA~HETMV~WVRQAPGRGLEWVS~~HIDRVGQDTYYADSV
KG~~RFTISRDNSKNTLYLQMNSLRAEDTAVYYCAV~~~LPKRGPWFDY~~~RGQGTLVTVSS

>Tar2h-131-70 (SEQ ID NO:291)
EVQLLESGGGLIQPGGSLRLSCAASGFTFA~HETMV~WVRQAPGKGLEWVS~~HIDRVGQDPYYADSV
KG~~RFTISRDNSKNTLYLQMNSLRAEDTAVYYCAL~~~LPKRGPWFDY~~~RGQGTLVTVSS

>Tar2h-131-71 (SEQ ID NO:292)
EVQLLESGGGLIQPGGSLRLSCAASGFTFA~HETMV~WVRQAPGKGLEWVS~~HIDRVGQDTYYADSV
KG~~RFTISRDNSKNTLYLQMNSLRAEDTAVYYCAM~~~LPKRGPWFDY~~~RGQGTLVTVSS

>Tar2h-131-72 (SEQ ID NO:293)
EVQLLESGGGLIQPGGSLRLSCAASGFTFA~HDTMV~WVRQAPGKGLEWVS~~HIDRVGQDTYYADSV
KG~~RFTISRDNTKNTLYLQMNSLRAEDTAVYYCAL~~~LPKRGPWFDY~~~RGQGTLVTVSS

FIG. 10F

>Tar2h-131-73 (SEQ ID NO:294)
EVQLLESGGGLIEPGGSLRLSCAASGFTFA~HETMV~WVRQAPGKGLEWVS~~HIDRVGQDTYYADSV
KG~~RFTISRDNSKNTLYLQMNSLRAEDSAVYYCAR~~~LPKRGPWFDY~~~RGQGTLVTVSS

>Tar2h-131-74 (SEQ ID NO:295)
DVQLLESGGGLIQPGGSLRLSCAASGFTFA~HETMV~WVRQAPGKGLEWVS~~HIDRVGQDTYYADSV
KG~~RFTISRDNSKNTLYLQMNSLRAEDTAAYYCAV~~~LPKRGPWFDY~~~RGQGTLVTVSS

>Tar2h-131-75 (SEQ ID NO:296)
EVQLMESGGGLIQPGGSLRLSCAASGFTFA~HETMV~WVRQAPGKGLEWVS~~HIDRVGQDTYYADSV
KG~~RFTISRDNSKNTLYLQMNSLRAEDTAVYYCAE~~~LPKRGPWFDH~~~RGQGTLVTVSS

>Tar2h-131-76 (SEQ ID NO:297)
EVQLLESGGGLIQPGGSLRLSCAASGFTFA~HETMV~WVRQAPGKGLEWVS~~HIDRVGQDTYYADSV
KG~~RFAISRDNSKNTLYLQMNSLRAEDTAVYYCAM~~~LPKRGPWFDY~~~RGQGTLVTVSS

>Tar2h-131-77 (SEQ ID NO:298)
EVQLLESGGGLIQPGGSLRLSCAASGFTFA~HETMV~WVRQAPGKGLEWVS~~HIDRVGQDTYYTDSV
KG~~RFTISRDNSKNTLYLQMNSLRAEDTAVYYCAL~~~LPKRGPWFDY~~~RGQGTMVTVSS

>Tar2h-131-78 (SEQ ID NO:299)
EVQLLESGGGLMQPGGSLRLSCAASGFTFA~HETMV~WVRQAPGKGLEWVS~~HIDLVGQDTYYADSV
KG~~RFTISRDNSKNTLYLQMNSLRAEDTAVYHCAR~~~LPKRGPWFDY~~~RGQGTLVTVSS

>Tar2h-131-79 (SEQ ID NO:300)
EVQLLESGGGLIQPGGSLRLSCATSGFTFA~HETMV~WVRQAPGKGLEWVS~~HIDRVGQDTYYADSV
KG~~RFTISRDNSKNTLYMQMNSLRAEDTAVYYCAV~~~LPKRGPWFDY~~~QGQGTLVTVSS

>Tar2h-131-80 (SEQ ID NO:301)
EVQLLESGGGLIQPGGSLRLSCAASGFTFA~HETMV~WVRQAPGKGLEWVS~~HIDRVGQDTYYADPV
KG~~RFTISRDNSRNTLYLQMNSLRSEDTAVYYCAV~~~LPKRGPWFDY~~~RGQGTLVTVSS

>Tar2h-131-81 (SEQ ID NO:302)
EVQLLESGGGLIQPGGSLRLSCAASGFTFA~HETMV~WVRQAPGKGLEWVS~~HIDRVGQDTYYADSV
KG~~RFTISRDNSKNTLYLQMNSLRAEDTAVYSCAL~~~LPKRGPWFDY~~~RGQGTLVTVSS

>Tar2h-131-82 (SEQ ID NO:303)
EVQLLESGGGLIQPGGSLRLSCAASGFTFA~HETMV~WVRQAPGKGLEWVS~~HIDRVGQDTYYADSV
KG~~RFTISRDNSKNALYLQMNSLRAEDTAVYYCAV~~~LPKRGPWFDY~~~RGQGTLVTVSS

>Tar2h-131-83 (SEQ ID NO:304)
EVQLLESGGGLVQPGGSLRLSCAASGFTFA~HETMV~WVRQAPGKGLEWVS~~HIDRVGQDTYYADSV
KG~~RFTISRDNSKNTLYLQMNSLRAEDTAVYYCAL~~~LPKRGPWFDY~~~WGQGTLVTVSS

>Tar2h-131-86 (SEQ ID NO:305)
EVQLLESGGGLIQPGGSLRLSCAASGFTFA~HETMV~WVREAPGKGLEWVS~~HIDRVGQDTYYADSV
KG~~RFTISRDNSKNTLYLQMNSLRAEDTAVYYCAI~~~LPKRGPWFDY~~~RGQGTLVTVSS

>Tar2h-131-87 (SEQ ID NO:306)
EVQLLESGGGLIQPGGSLRLSCAASGFTFA~HETMV~WVRQAPGKGLEWVS~~HIDRVGQDTYYADSV
EG~~RFTISRDNSKNTLYLQMNSLRAEDTAVYYCAV~~~LPKRGPWFDY~~~RGQGTLVTVSS

FIG. 10G

>Tar2h-131-88 (SEQ ID NO:307)
EVQLLESGGGLIQPGGSLRLSCAASGFTFA~HETMV~WVRQAPGKGLEWVS~~HIDRVGQDTYYADPV
KG~~RFTISRDNSRNTLYLQMNSLRAEDTAVYYCAV~~~LPKRGPWFDY~~~RGQGTLVTVSS

>Tar2h-131-89 (SEQ ID NO:308)
EVQLLESGGDLIQPGGSLRLSCAASGFTFA~HETMV~WVRQAPGKGLEWVS~~HIDRVGQDTYYADSV
KG~~RFTISRDNSKNTLYLQMNSLRAEDTAVYYCAV~~~LPKRGPWFDY~~~RGQGTLVTVSS

>Tar2h-131-90 (SEQ ID NO:309)
EVQLLESGGGSIQPGGSLRLSCAASGFTFA~HETMV~WVRQAPGKGLEWVS~~HIDRVGQDTYYADSV
KG~~RFTISRDNSKNTLYLQMNSLRAEDTAVYYCAV~~~LPKRGPWFDY~~~RGQGTLVTVSS

>Tar2h-131-91 (SEQ ID NO:310)
EVQLLESGGGLIQPGGSLHLSCAASGFTFE~HETMV~WVRQAPGKGLEWVS~~HIDRVGQDPYYADSV
KG~~RFTISRDNSKNTLYLQMNSLRAEDTAVYYCAR~~~LPKRGPWFDY~~~RGQGTLVTVSS

>Tar2h-131-92 (SEQ ID NO:311)
EVQLLESGGGLIQPGGSLRLSCAASGFTFA~HDTMV~WVRQAPGKGLEWVS~~HIDRVGQDTYYADSV
KG~~RFTISRDNSKNTLYLQMNSLRAEDTAVYYCAR~~~LPKRGPWFDY~~~RGQGTLVTVSS

>Tar2h-131-93 (SEQ ID NO:312)
EVQLLESGGGLIQPGGSLRLSCAASGFTFA~HETMV~WVRQAPGKGLEWVS~~HIDRVGQDPYYADSV
KG~~RFTISRDNSKNTLYLQMNSLRAEDTAVYYCAR~~~LPKRGPWFDY~~~RGQGTLVTVSS

>Tar2h-131-94 (SEQ ID NO:313)
EVQLLESGGGLIQPGGSLRLSCAASGFTFA~HETMV~WVRQAPGKDLEWVS~~HIDRVGQDTYYADSV
KG~~RFTISRDNSKNTLYLQMNSLRAEDTAVYYCAV~~~LPKRGPWFDY~~~RGQGTLVTVSS

>Tar2h-131-95 (SEQ ID NO:314)
EVQLLESGGGLIQPGGSLRLSCAASGFTFA~HDTMV~WVRQAPGKGLEWVS~~HIDRVGQDTYYADSV
KG~~RFTISRDNSKNTLYLQMNSLRAEDTAVYYCAR~~~LPKRGPWFDY~~~RGQGTLVTVSS

>Tar2h-131-96 (SEQ ID NO:315)
EVQLLESGGGLIQPGGSLRLSCAASGFTFA~HETMV~WVRQAPGKGLEWVS~~HIDRVGQDTYYADSV
KG~~RFTISRDNSKNTLYLQMNSLRAEDTAVYHCAV~~~LPKRGPWFDY~~~RGQGTLVTVSS

>Tar2h-131-97 (SEQ ID NO:316)
EVQLLESGGGLIQPGGSLRLSCAASGFTFA~HETMV~WVREAPGKGLEWVS~~HIDRVGQDTYYADSV
KG~~RFTISRDNSKNTLYLQMNSLRAEDTAVYYCAV~~~LPKRGPWFDY~~~RGQGTLVTVSS

>Tar2h-131-99 (SEQ ID NO:317)
EVQLLESGGGLIHPGGTLRLSCAASGFTFA~HETMV~WVRQAPGKGLEWVS~~HIDRVGQDPYYADSV
KG~~RFTISRDNSKNTLYLQMNSLRAEDTAVYYCAR~~~LPKRGPWFDY~~~RGQGTLVTVSS

>Tar2h-131-100 (SEQ ID NO:318)
EVQLLESGGGLIQPGGSLRLSCAASGFTFA~HETMV~WVRQAPGKGLEWVS~~HIDRVGQDPYYADSV
KG~~RFTISRDNSKNTLYLQMNSLRAEDTAVYYCAR~~~LPKRGPWFDY~~~RGQGTQVTVSS

>Tar2h-131-101 (SEQ ID NO:319)
EVQLLESGGGLVQPGGSLRLSCAASGFTFA~HETMV~WVRQAPGKGLEWVS~~HIDRVGQDTYYADSV
KG~~RFTISRDNSKNTLYLQMNSLRAEDTAVYYCAL~~~LPKRGPWFDY~~~WGQGTLVTVSS

FIG. 10H

>Tar2h-131-102 (SEQ ID NO:320)
EVQLLESGGGLVQPGGSLRLSCAASGFTFA~HETMV~WVRQAPGKGLEWVS~~HIDRVGQDTYYADSV
EG~~RFTISRDNSKNTLYLQMNSLRAEDTAVYYCAV~~~LPKRGPWFDY~~~WGQGTLVTVSS

>Tar2h-131-103 (SEQ ID NO:321)
EVQLLESGGGLVQPGGSLRLSCAASGFTFA~HETMV~WVRQAPGKGLEWVS~~HIDRVGQDPYYADSV
KG~~RFTISRDNSKNTLYLQMNSLRAEDTAVYYCAL~~~LPKRGPWFDY~~~WGQGTLVTVSS

>Tar2h-131-104 (SEQ ID NO:322)
EVQLLESGGGLIQPGGSLRLSCAASGFTFA~HETMV~WVRQAPGKDLEWVS~~HIDRDGQDTYYADSV
KG~~RFSISRDNSKNTLYLQMNSLRAEDTAVYYCAR~~~LPKRGPWFDY~~~RGQGTLVTVSS

>Tar2h-131-105 (SEQ ID NO:323)
EVQLLESGGGLIQPGGSLRLSCAASGFTFA~HETMV~WVRQAPGKGLEWVS~~HIDRVGQDTYYADSV
KG~~RFTTSRDNSKNTLYLQMNSLRAEDTAVYYCAR~~~LPKRGPWFDY~~~RGQGTLVTVSS

>Tar2h-131-106 (SEQ ID NO:324)
EVQLLESGGGLIQPGGSLRLSCAASGFTFA~HETMV~WVRQAPGKGLEWVS~~HIDRDGQDTYYADSV
MG~~RFTVSRDNSKNTLYLQMNSLRAEDTAVYYCAI~~~IPKRGPWFDY~~~RGQGTLVTVSS

>Tar2h-131-107 (SEQ ID NO:325)
EVQLLESGGGLIQPGGSLRLSCAASGFTFA~HETMV~WVRQAPGKDLEWVS~~HIDRVGQDTYYADSV
EG~~RFTISRDNSKNTLYLQMNSLRAEDTAVYYCAV~~~LPKRGPWFDY~~~RGQGTLVTVSS

>Tar2h-131-108 (SEQ ID NO:326)
EVQLLESGGGLIQPGGSLRLSCAASGFTFA~HETMV~WVRQAPGKGLEWVS~~HTDRVGQDTYYADSV
KG~~RFTISRDNSRNTLYLQMNSLRAEDTAVYYCAV~~~LPKRGPWFDY~~~RGQGTLVTVSS

>Tar2h-131-109 (SEQ ID NO:327)
EVQLLESGGGLIQPGGTLRLSCAASGFTFA~LETMV~WVRQAPGKGLEWVS~~HIDRVGQDTYYADSV
KG~~RFTTSRDNSRNTLYLQMNSLRAEDTAVYYCAR~~~LPKRGPWFDY~~~RGQGTLVTVSS

>Tar2h-131-110 (SEQ ID NO:328)
EVQLLESGGGLIQPGGSLRLSCAASGFTFA~HETMV~WVRQAPGKGLEWVS~~HIDRVGQDTYYADSV
KG~~RFTISRDNSKNTLYLQMNSLRAEDTAVYYCAV~~~IPKRGPWFDY~~~RGQGTLVTVSS

>Tar2h-131-111 (SEQ ID NO:329)
EVQLLESGGGLIQPGGSLRLSCAASGFTFA~HETMV~WVRQAPGKGLEWVS~~HIDRVGQDTYYADSV
KG~~RFTISRDNSKNTLYLQMNSLRAEDTAVYYCAV~~~LPKRGPWFDY~~~RGQGTQVTVSS

>Tar2h-131-112 (SEQ ID NO:330)
EVQLLESGGGLIQPGGSLRLSCAASGFTFA~HETMV~WVRQAPGKGIEWVS~~HIDRVGQDTYYADSV
KG~~RFTISRDNSKNTLYLQMNSLRAEDTAVYYCAV~~~LPKRGPWFDY~~~RGQGTLVTVSS

>Tar2h-131-113 (SEQ ID NO:331)
EVQLLESGGGLVQPGGSLRLSCAASGFTFA~HDTMV~WVRQAPGKGLEWVS~~HIDRVGQDTYYADSV
EG~~RFTISRDNSKNTLYLQMNSLRAEDTAVYYCAV~~~LPKRGPWFDY~~~WGQGTLVTVSS

>Tar2h-131-114 (SEQ ID NO:332)
EVQLLESGGGLVQPGGSLRLSCAASGFTFA~HDVMV~WVRQAPGKGLEWVS~~HIDRVGQDTYYADSV
EG~~RFTISRDNSKNTLYLQMNSLRAEDTAVYYCAV~~~LPKRGPWFDY~~~WGQGTLVTVSS

FIG. 10I

>Tar2h-131-115 (SEQ ID NO:333)
EVQLLESGGGLVQPGGSLRLSCAASGFTFA~HETMV~WVRQAPGKGLEWVS~~HIDRVGQDPYYTDSV
ED~~RFTISRDNSKNTLYLQMNSLRAEDTAVYYCAV~~~LPKRGPWFDY~~~WGQGTLVTVSS

>Tar2h-131-116 (SEQ ID NO:334)
EVQLLESGGGLVQPGGSLRLSCAASGFTFA~HETMV~WVRQAPGKGLEWVS~~HIDRVGQDTYYADSV
EG~~RFTISRDNSKNTLYLQMNSLRAEDTAVYYCAL~~~LPKRGPWFDY~~~WGQGTLVTVSS

>Tar2h-131-117 (SEQ ID NO:335)
EVQLLESGGGLVQPGGSLRLSCAASGFTFA~HETMV~WVRQAPGKGLEWVS~~HIDRVGQDPYYADSV
EG~~RFTISRDNSKNTLYLQMNSLRAEDTAVYYCAV~~~LPKRGPWFDY~~~WGQGTLVTVSS

>Tar2h-131-120 (SEQ ID NO:336)
EVQLLESGGGLIQPGGSLRLSCAASGFTFN~KETMV~WVRQAPGKGLEWVS~~HIDRVGQDTYYADSV
KG~~RFTISRDNSKNTLYLQMNSLRAEDTAVYYCAL~~~LPKRGPWFDY~~~RGQGTLVTVSS

>Tar2h-131-121 (SEQ ID NO:337)
EVQLLESGGGLIQPGGSLRLSCAASGFTFN~TETMV~WVRRAPGKGLEWVS~~HIDRVGQDTYYADSV
KG~~RFTISRDNSKNTLYLQMNSLRAEDTAVYYCAL~~~LPKRGPWFDY~~~RGQGTLVTVSS

>Tar2h-131-122 (SEQ ID NO:338)
EVQLLESGGGLIQPGGSLRLSCAASGFTFT~KETMV~WVRQAPGKGLEWVS~~HIDRVGQDTYYADSV
KG~~RFTISRDNSKNTLYLQMNSLRAEDTAVYYCAL~~~LPKRGPWFDY~~~RGQGTLVTVSS

>Tar2h-131-123 (SEQ ID NO:339)
EVQLLESGGGLIQPGGSLRLSCAASGFTFA~HETMV~WVRQAPGKGLEWVS~~HIDGGGVDTYYADPV
KG~~RFTISRDNSKNTLYLQMNSLRAEDTAVYYCAL~~~LPKRGPWFDY~~~RGQGTLVTVSS

>Tar2h-131-124 (SEQ ID NO:340)
EVQLLESGGGLIQPGGSLRLSCAASGFTFA~HETMV~WVRQAPGKGLEWVS~~HIDGGGRDTYYADPV
KG~~RFTISRDNSKNTLYLQMNSLRAEDTAVYYCAL~~~LPKRGPWFDY~~~RGQGTLVTVSS

>Tar2h-131-125 (SEQ ID NO:341)
EVQLLESGGGLIQPGGSLRLSCAASGFTFA~HETMV~WVRQAPGKGLEWVS~~HIDGGGVDTYYADPV
KG~~RFTISRDNSKNTLYLQMNSLRAEDTAVYYCAL~~~LPKRGPWFDY~~~RGQGTLVTVSS

>Tar2h-131-126 (SEQ ID NO:342)
EVQLLESGGGLIQPGGSLRLSCAASGFTFN~NQVMV~WVRQAPGKGLEWVS~~HIDRVGQDTYYADSV
KG~~RFTISRDNSKNTLYLQMNSLRAEDTAVYYCAL~~~LPKRGPWFDY~~~RGQGTLVTVSS

>Tar2h-131-127 (SEQ ID NO:343)
EVQLLESGGGLIQPGGSLRLSCAASGFTFA~HETMV~WVRQAPGKGLEWVS~~HIDGGGLDTYYADPV
KG~~RFTISRDNSKNTLYLQMNSLRAEDTAVYYCAL~~~LPKRGPWFDY~~~RGQGTLVTVSS

>Tar2h-131-128 (SEQ ID NO:344)
EVQLLESGGGLIQPGGSLRLSCAASGFTFA~HETMV~WVRQAPGKGLEWVS~~HIDAVGSDTYYADPV
KG~~RFTISRDNSKNTLYLQMNSLRAEDTAVYYCAL~~~LPKRGPWFDY~~~RGQGTLVTVSS

>Tar2h-131-129 (SEQ ID NO:345)
EVQLLESGGGLIQPGGSLRLSCAASGFTFA~HETMV~WVRQAPGKGLEWVS~~HIDRVGQDTYYADSV
KG~~RFTISRDNSKNTLYLQMNSLRAEDTAVYYCAL~~~LPKRGPWFDY~~~RGQGTLVTVSS

FIG. 10J

>Tar2h-131-130 (SEQ ID NO:346)
EVQLLESGGGLIQPGGSLRLSCAASGFTFG~NEVMV~WVRQAPGKGLEWVS~~HIDRVGQDTYYADSV
KG~~RFTISRDNSKNTLYLQMNSLRAEDTAVYYCAL~~~LPKRGPWFDY~~~RGQGTLVTVSG

>Tar2h-131-131 (SEQ ID NO:347)
EVQLLESGGGLIQPGGSLRLSCAASGFTFN~NQTMV~WVRQAPGKGLEWVS~~HIDRVGQDTYYADSV
KG~~RFTISRDNSKNTLYLQMNSLRAEDTAVYYCAL~~~LPKRGPWFDY~~~RGQGTLVTVSS

>Tar2h-131-132 (SEQ ID NO:348)
EVQLLESGGGLIQPGGSLRLSCAASGFTFD~NTTMV~WVRQAPGKGLEWVS~~HIDRVGQDTYYADSV
KG~~RFTISRDNSKNTLYLQMNSLRAEDTAVYYCAL~~~LPKRGPWFDY~~~RGQGTLVTVSS

>Tar2h-131-136 (SEQ ID NO:349)
EVQLLESGGGLVQPGGSLRLSCAASGFTFA~HETMV~WVRQAPGKGLEWVS~~HIDRVGQDPYYADSV
EG~~RFTISRDNSKNTLYLQMNSLRAEDTAVYYCAL~~~LPKRGPWFDY~~~WGQGTLVTVSS

>Tar2h-131-151 (SEQ ID NO:350)
EVQLLESGGGLIQPGGSLRLSCAASGFTFA~HETMV~WVRQAPGKGLEWVS~~HIDGGVDTYYADPV
KG~~RFTISRDNSKNTLYLQMNSLRAEDTAVYYCAL~~~LPKRGPWFDY~~~RGQGTLVTVSS

>Tar2h-131-180 (SEQ ID NO:351)
EVQLLESGGGLIQPGGSLRLSCAASGFTFA~HETMV~WVRQAPGKGLEWVS~~HIDRVGQDPYYADSV
EG~~RFTISRDNSKNTLYLQMNSLRAEDTAVYYCAV~~~LPKRGPWFDY~~~RGQGTLVTVSS

>Tar2h-131-181 (SEQ ID NO:352)
EVQLLESGGGLIQPGGSLRLSCAASGFTFA~HETMV~WVRQAPGKGLEWVS~~HIDRVGQDPYYADSV
EG~~RFTISRDNSKNTLYLQMNSLRAEDTAVYYCAL~~~LPKRGPWFDY~~~RGQGTLVTVSS

>Tar2h-131-182 (SEQ ID NO:353)
EVQLLESGGGLIQPGGSLRLSCAASGFTFA~HETMV~WVRQAPGKGLEWVS~~HIDRVGQDPYYADSV
EG~~RFTISRDNSKNTLYLQMNSLRAEDTAVYYCAV~~~LPKRGPWFDY~~~WGQGTLVTVSS

>Tar2h-131-183 (SEQ ID NO:354)
EVQLLESGGGLIQPGGSLRLSCAASGFTFA~HETMV~WVRQAPGKGLEWVS~~HIDRVGQDPYYADSV
EG~~RFTISRDNSKNTLYLQMNSLRAEDTAVYYCAV~~~LPKRGPWFDY~~~WGQGTLVTVSS

>Tar2h-131-184 (SEQ ID NO:355)
EVQLLESGGGLIQPGGSLRLSCAASGFTFA~HETMV~WVRQAPGKGLEWVS~~HIDRVGQDPYYADSV
EG~~RFTISRDNSKNTLYLQMNSLRAEDTAVYYCAL~~~LPKRGPWFDY~~~WGQGTLVTVSS

>Tar2h-131-185 (SEQ ID NO:356)
EVQLLESGGGLVQPGGSLRLSCAASGFTFA~HETMV~WVRQAPGKGLEWVS~~HIDRVGQDPYYADSV
EG~~RFTISRDNSKNTLYLQMNSLRAEDTAVYYCAL~~~LPKRGPWFDY~~~RGQGTLVTVSS

>Tar2h-131-188 (SEQ ID NO:357)
EVQLLESGGGLIQPGGSLRLSCAASGFTFA~HETMV~WVRQAPGKGLEWVS~~HIDGGVDTYYADPV
KG~~RFTISRDNSKNTLYLQMNSLRAEDTAVYYCAL~~~LPKRGPWFDY~~~WGQGTLVTVSS

>Tar2h-131-189 (SEQ ID NO:358)
EVQLLESGGGLVQPGGSLRLSCAASGFTFA~HETMV~WVRQAPGKGLEWVS~~HIDGGVDTYYADPV
KG~~RFTISRDNSKNTLYLQMNSLRAEDTAVYYCAL~~~LPKRGPWFDY~~~WGQGTLVTVSS

FIG. 10K

>Tar2h-131-190 (SEQ ID NO:359)
EVQLLESGGGLIQPGGSLRLSCAASGFTFA~HETMV~WVRQAPGKGLEWVS~~HIDGGGVDTYYADPV
KG~~RFTISRDNSKNTLYLQMNSLRAEDTAVYYCAV~~~LPKRGPWFDY~~~RGQGTLVTVSS

>Tar2h-131-191 (SEQ ID NO:360)
EVQLLESGGGLVQPGGSLRLSCAASGFTFA~HETMV~WVRQAPGKGLEWVS~~HIDGGGVDTYYADPV
KG~~RFTISRDNSKNTLYLQMNSLRAEDTAVYYCAV~~~LPKRGPWFDY~~~RGQGTLVTVSS

>Tar2h-131-192 (SEQ ID NO:361)
EVQLLESGGGLIQPGGSLRLSCAASGFTFA~HETMV~WVRQAPGKGLEWVS~~HIDGGGVDTYYADPV
KG~~RFTISRDNSKNTLYLQMNSLRAEDTAVYYCAV~~~LPKRGPWFDY~~~WGQGTLVTVSS

>Tar2h-131-193 (SEQ ID NO:362)
EVQLLESGGGLVQPGGSLRLSCAASGFTFA~HETMV~WVRQAPGKGLEWVS~~HIDGGGVDTYYADPV
KG~~RFTISRDNSKNTLYLQMNSLRAEDTAVYYCAV~~~LPKRGPWFDY~~~WGQGTLVTVSS

>Tar2h-131-194 (SEQ ID NO:363)
EVQLLESGGGLVQPGGSLRLSCAASGFTFA~HETMV~WVRQAPGKGLEWVS~~HIPPVGQDPFYADSV
KG~~RFTISRDNSKNTLYLQMNSLRAEDTAVYYCAV~~~LPKRGPWFDY~~~WGQGTLVTVSS

>Tar2h-131-195 (SEQ ID NO:364)
EVQLLESGGGLIQPGGSLRLSCAASGFTFA~HETMV~WVRQAPGKGLEWVS~~HIPPVGQDPFYADSV
KG~~RFTISRDNSKNTLYLQMNSLRAEDTAVYYCAL~~~LPKRGPWFDY~~~WGQGTLVTVSS

>Tar2h-131-196 (SEQ ID NO:365)
EVQLLESGGGLIQPGGSLRLSCAASGFTFA~HETMV~WVRQAPGKGLEWVS~~HIPPVGQDPFYADSV
KG~~RFTISRDNSKNTLYLQMNSLRAEDTAVYYCAV~~~LPKRGPWFDY~~~WGQGTLVTVSS

>Tar2h-131-197 (SEQ ID NO:366)
EVQLLESGGGLIQPGGSLRLSCAASGFTFA~HETMV~WVRQAPGKGLEWVS~~HIDGGGVDTYYADPV
KG~~RFTISRDNSKNSLYLQMNSLRAEDTAVYYCAL~~~LPKRGPWFDY~~~WGQGTLVTVSS

>Tar2h-131-198 (SEQ ID NO:367)
EVQLLESGGGLVQPGGSLRLSCAASGFTFA~HETMV~WVRQAPGKGLEWVS~~HIPPVGQDPFYADSV
KG~~RFTISRDNSKNSLYLQMNSLRAEDTAVYYCAL~~~LPKRGPWFDY~~~WGQGTLVTVSS

>Tar2h-131-500 (SEQ ID NO:368)
EVQLLESGGGLVQPGGSLRLSCAASGFTFH~DQHMV~WVRQAPGKGLEWVS~~HIDRVGQDTYYADSV
KG~~RFTISRDNSKNTLYLQMNSLRAEDTAVYYCAL~~~LPKRGPWFDY~~~WGQGTLVTVSS

>Tar2h-131-501 (SEQ ID NO:369)
EVQLLESGGGLVQPGGSLRLSCAASGFTFA~NNIMV~WVRQAPGKGLEWVS~~HIDRVGQDTYYADSV
KG~~RFTISRDNSKNTLYLQMNNLRAEDTAVYYCAL~~~LPKRGPWFDY~~~WGQGTLVTVSS

>Tar2h-131-502 (SEQ ID NO:370)
EVQLLESGGGLVQPGGSLRLSCAASGFSFK~NKTMV~WVRQAQGKGLEWVS~~HIDRVGQDTYYADSV
KG~~RFTISRDNSKNTLYLQMNSLRAEDTAVYYCAL~~~LPKRGPWFDY~~~WGQGTLVTVSS

>Tar2h-131-503 (SEQ ID NO:371)
EVQLLESGGGLVQPGGSLRLSCAASGFTFN~KHTMV~WVRQAPGKGLEWVS~~HIDRVGQDTYYADSV
KG~~RFTISRDNSKNTLYLQMNSLRAEDTAVYYCAL~~~LPKRGPWFDY~~~WGQGTLVTVSS

FIG. 10L

>Tar2h-131-504 (SEQ ID NO:372)
EVQLLESGGGLVQPGGSLRLSCAASGFTFN~NETMV~WVRQAPGKGLEWVS~~HIDRVGQDTYYADSV
KG~~RFTISRDNSKNTLYLQMNSLRAEDTAVYYCAL~~~LPKRGPWFDY~~~WGQGTLVTVSS

>Tar2h-131-505 (SEQ ID NO:373)
EVQLLESGGGLVQPGGSLRLSCAASGFTFA~HETMV~WVRQAPGKGLEWVS~~HIDGRGGGTYYTDSV
KG~~RFTTSRDNSKNTLYLQMNSLRAEDTAVYYCAL~~~LPKRGPWFDY~~~WGQGTLVTVSS

>Tar2h-131-506 (SEQ ID NO:374)
EVQLLESGGGLVQPGGSLRLSCAASGFTFA~HETMV~WVRQAPGKGLEWVS~~HIDQQGEGTYYTDSV
KG~~RFTISRDNSKNTLYLQMNSLRAEDTAVYYCAL~~~LPKRGPWFDY~~~WGQGTLVTVSS

>Tar2h-131-507 (SEQ ID NO:375)
EVQLLESGGGLVQPGGSLRLSCAASGFTFA~HETMV~WVRQAPGKGLEWVS~~HIDGGGGTYYADSV
KG~~RFTISRDNSKNTLYLQMNSLRAEDTAVYYCAL~~~LPKRGPWFDY~~~WGQGTLVTVSS

>Tar2h-131-508 (SEQ ID NO:376)
EVQLLESGGGLVQPGGSLRLSCAASGFTFA~HETMV~WVRQAPGKGLEWVS~~HIDGGGLGTYYADSV
KG~~RFTISRDNSKNTLYLQMNSLRAEDTAVYYCAL~~~LPKRGPWFDY~~~WGQGTLVTVSS

>Tar2h-131-509 (SEQ ID NO:377)
EVQLLESGGGLVQPGGSLRLSCAASGFTFA~HETMV~WVRQAPGKGLEWVS~~HIDRVGQDTYYADSV
KG~~RFTISRDNSKNTLYLQMNSLRAEDTAVYYCAR~~~LPKRGPWFDY~~~WGQGTLVTVSS

>Tar2h-131-510 (SEQ ID NO:378)
EVQLLESGGGLVQPGGSLRLSCAASGFTFN~NKTMV~WVRQAPGKGLEWVS~~HIDGRGERTYYADSV
KG~~RFTISRDNSKNTLYLQMNSLRAEDTAVYYCAL~~~LPKRGPWFDY~~~WGQGTLVTVSS

>Tar2h-131-511 (SEQ ID NO:379)
EVQLLESGGGLVQPGGSLRLSCAASGFTFA~HETMV~WVRQAPGKGLEWVS~~HIPPVGQDPFYADSV
KG~~RFTISRDNSKNTLYLQMNSLRAEDTAVYYCAL~~~LPKRGPWFDY~~~WGQGTLVTVSS

>Tar2h-131-512 (SEQ ID NO:380)
EVQLLESGGGLVQPGGSLRLSCAASGFTFA~HETMV~WVRQAPGRGLEWVS~~HIDRVGQDTYYADSV
KG~~RFTISRDNSKNTLYLQMNSLRAEDTAVYYCAL~~~LPKRGPWFDY~~~WGQGTLVTVSS

>Tar2h-131-513 (SEQ ID NO:381)
EVQLLESGGGLVQPGGSLRLSCAASGFTFA~HETMV~WVRQAPGKGLEWVS~~HIDRVGQDTYYADSV
KG~~RFTISRDNSKNTLYLQMNSLRAEDTAVYYCAR~~~LPRRGPWFDY~~~WGQGTLVTVSS

>Tar2h-131-514 (SEQ ID NO:382)
EVQXLESGGGLVQPGGSLRLSCAASGFTFA~HETMV~WVRQAPGKGLEWVS~~HIDRVGQDTYYADSV
RG~~RFTISRDNSKNTLYLQMNSLRAEDTAVYYCAL~~~LPKRGPWFDY~~~WGQGTLVTVSS

>Tar2h-131-515 (SEQ ID NO:383)
EVQLLESGGGLVQPGGSLRLSCAASGFTFA~HETMV~WVRQAPGKGLEWVS~~HISDDGNSTYYADSV
KG~~RFTISRDNSKNTLYLQMNSLRAEDTAVYYCAR~~~LPKRGPWFDY~~~WGQGTLVTVSS

>Tar2h-131-516 (SEQ ID NO:384)
EVQLLESGGGLVQPGGSLRLSCAASGFTFA~HEAMV~WVRQAPGKGLEWVS~~HIDGGGESTYYADSV
KG~~RFTISRDNSKNTLYLQMNSLRAEDTAVYYCAR~~~LPPPGPWFDY~~~WGQGTLVTVSS

FIG. 10M

\>Tar2h-131-517 (SEQ ID NO:385)
EVQLLESGGGLVQPGGSLRLSCAASGFTFH~NKDMV~WVRQAPGKGLEWVS~~HIDGGGESTYYADSV
KG~~RFTISRDNSKNTLYLQMNSLRAEDTAVYYCAR~~~LPLLLPWFDY~~~WGQGTLVTVSS

\>Tar2h-131-518 (SEQ ID NO:386)
EVQLLESGGGLVQPGGSLRLSCAASGFTFA~MRTMV~WVRQAPGKGLEWVS~~HIDGGGESTYYADSV
KG~~RFTISRDNSKNTLYLQMNSLRAEDTAVYYCAR~~~LPKRGPWFDY~~~WGQGTLVTVSS

\>Tar2h-131-519 (SEQ ID NO:387)
EVQLLESGGGLVQPGGSLRLSCAASGFTFA~HETMV~WVRQAPGKGLEWVS~~HIDGGGESTYYADSV
KG~~RFTISRDNSKNTLYLQMNSLRAEDTAVYYCAR~~~LPKRGPWFDY~~~WGQGTLVTVSS

\>Tar2h-131-520 (SEQ ID NO:388)
EVQLLESGGGLVQPGGSLRLSCAASGFTFA~HETMV~WVRQAPGKGLEWVS~~HIDGGGLVTYYTDSV
KG~~RFTISRDNSKNTLYLQMNSLRAEDTAVYYCAL~~~LPKRGPWFDY~~~WGQGTLVTVSS

\>Tar2h-131-521 (SEQ ID NO:389)
EVQLLESGGGLVQPGGSLRLSCAASGFTFN~NTTMV~WVRQAPGKGLEWVS~~HIDGVGGDTYYADPV
KG~~RFTISRDNSKNTLYLQMNSLRAEDTAVYYCAL~~~LPKRGPWFDY~~~WGQGTLVTVSS

\>Tar2h-131-522 (SEQ ID NO:390)
EVQLLESGGGLVQPGGSLRLSCAASGFTFA~NKTMV~WVRQAPGKGLEWVS~~HIDGLGLVTYYADSV
EG~~RFTISRDNSKNTLYLQMNSLRAEDTAVYYCAL~~~LPKRGPWFDY~~~WGQGTLVTVSS

\>Tar2h-131-523 (SEQ ID NO:391)
EVQLLESGGGLVQPGGSLRLSCAASGFTFN~TTNMV~WVRQAPGKGLEWVS~~EIRVGGGDTYYADSV
KG~~RFTISRDNSKNTLYLQMNSLRAEDTAVYYCAL~~~LPKRGPWFDY~~~WGQGTLVTVSS

\>Tar2h-131-524 (SEQ ID NO:392)
EVQLLESGGGLVQPGGSLRLSCAASGFTFK~NKTMV~WVRQAPGKGLEWVS~~HIDQEGEGTYYADSV
KG~~RFTISRDNSKNTLYLQMNSLRAEDTAVYYCAL~~~LPKRGPWFDY~~~RGQGTLVTVSS

\>Tar2h-131-525 (SEQ ID NO:393)
EVQLLESGGGLVQPGGSLRLSCAASGFTFN~NTTMV~WVRQAPGKGLEWVS~~HIDGEGSVTYYADSV
KG~~RFTISRDNSKNTLYLQMNSLRAEDTAVYYCAL~~~LPKRGPWFDY~~~WGQGTLVTVSS

\>Tar2h-131-526 (SEQ ID NO:394)
EVQLLESGGGLVQPGGSLRLSCAASGFTFE~NKTMV~WVRQAPGKGLEWVS~~HIDATGTITYYADSV
KG~~RFTISRDNSKNTLYLQMNSLRAEDTAVYYCAL~~~LPKRGPWFDY~~~RGQGTLVTVSS

\>Tar2h-131-527 (SEQ ID NO:395)
EVQLLESGGGLVQPGGSLRLSCAASGFTFN~KKTMV~WVRQAPGKGLEWVS~~HIDGKGQATYYADSV
KG~~RFTISRDNSKNTLYLQMNSLRAEDTAVYYCAL~~~LPKRGPWFDY~~~WGQGTLVTVSS

\>Tar2h-131-528 (SEQ ID NO:396)
EVQXLESGGGLVQPGGSLRLSCAASGFTFA~HETMV~WVRQAPGKGLEWVS~~HIDRVGQDTYYADSV
EG~~RFTISRDNSKNTLYLQMNSLRAEDTAVYYCAL~~~LPKRGPWFDY~~~WGQGTLVTVSS

FIG. 10N

>Tar2h-131-529 (SEQ ID NO:397)
EVQLLESGGGLVQPGGSLRLSCAASGFTFA~HETMV~WVRQAPGKGLEWVS~~HIDGGGESTYYADSV
EG~~RFTISRDNSKNTLYLQMNSLRAEDTAVYYCAR~~~LPKRGPWFDY~~~WGQGTLVTVSS

>Tar2h-131-530 (SEQ ID NO:398)
EVQLLESGGGLVQPGGSLRLSCAASGFTFA~HETMV~WVRQAPGKGLEWVS~~HIDGGGESTYYADPV
EG~~RFTISRDNSKNTLYLQMNSLRAEDTAVYYCAR~~~LPKRGPWFDY~~~WGQGTLVTVSS

>Tar2h-131-531 (SEQ ID NO:399)
EVQLLESGGGLVQPGGSLRLSCAASGFTFE~NKTMV~WVRQAPGKGLEWVS~~HIDATGTITYYADSV
EG~~RFTISRDNSKNTLYLQMNSLRAEDTAVYYCAL~~~LPKRGPWFDY~~~RGQGTLVTVSS

>Tar2h-131-532 (SEQ ID NO:400)
EVQLLESGGGLVQPGGSLRLSCAASGFTFN~KKTMV~WVRQAPGKGLEWVS~~HIDGKGQATYYADSV
EG~~RFTISRDNSKNTLYLQMNSLRAEDTAVYYCAL~~~LPKRGPWFDY~~~WGQGTLVTVSS

>Tar2h-131-533 (SEQ ID NO:401)
EVQLLESGGGLVQPGGSLRLSCAASGFTFN~KKTMV~WVRQAPGKGLEWVS~~HIDGKGQDPFYTDSV
KG~~RFTISRDNSKNTLYLQMNSLRAEDTAVYYCAL~~~LPKRGPWFDY~~~WGQGTLVTVSS

>Tar2h-131-534 (SEQ ID NO:402)
EVQLLESGGGLVQPGGSLRLSCAASGFTFA~HETMV~WVRQAPGKGLEWVS~~HIDGGGLVTYYTDPV
KG~~RFTISRDNSKNTLYLQMNSLRAEDTAVYYCAL~~~LPKRGPWFDY~~~WGQGTLVTVSS

>Tar2h-131-535 (SEQ ID NO:403)
EVQLLESGGGLVQPGGSLRLSCAASGFTFA~HETMV~WVRQAPGKGLEWVS~~HIDGGGLVTYYTDSV
EG~~RFTISRDNSKNTLYLQMNSLRAEDTAVYYCAL~~~LPKRGPWFDY~~~WGQGTLVTVSS

>Tar2h-131-536 (SEQ ID NO:404)
EVQLLESGGGLVQPGGSLRLSCAASGFTFA~HETMV~WVRQAPGKGLEWVS~~HIDGGGLVTYYTDPV
EG~~RFTISRDNSKNTLYLQMNSLRAEDTAVYYCAL~~~LPKRGPWFDY~~~WGQGTLVTVSS

>Tar2h-131-537 (SEQ ID NO:405)
EVQLLESGGGLVQPGGSLRLSCAASGFTFA~HETMV~WVRQAPGKGLEWVS~~HIPPVGQDPFYADSV
EG~~RFTISRDNSKNTLYLQMNSLRAEDTAVYYCAL~~~LPKRGPWFDY~~~WGQGTLVTVSS

>Tar2h-131-538 (SEQ ID NO:406)
EVQLLESGGGLVQPGGSLRLSCAASGFTFA~HETMV~WVRQAPGKGLEWVS~~HIPPVGQDPFYADPV
KG~~RFTISRDNSKNTLYLQMNSLRAEDTAVYYCAL~~~LPKRGPWFDY~~~WGQGTLVTVSS

>Tar2h-131-539 (SEQ ID NO:407)
EVQLLESGGGLVQPGGSLRLSCAASGFTFA~HETMV~WVRQAPGKGLEWVS~~HIPPVGQDPFYTDSV
KG~~RFTISRDNSKNTLYLQMNSLRAEDTAVYYCAL~~~LPKRGPWFDY~~~WGQGTLVTVSS

>Tar2h-131-539 (SEQ ID NO:408)
EVQLLESGGGLVQPGGSLRLSCAASGFTFA~HETMV~WVRQAPGKGLEWVS~~HIPPVGQDPFYTDSV
KG~~RFTISRDNSKNTLYLQMNSLRAEDTAVYYCAL~~~LPKRGPWFDY~~~WGQGTLVTVSS

>Tar2h-131-539 (SEQ ID NO:409)
EVQLLESGGGLVQPGGSLRLSCAASGFTFA~HETMV~WVRQAPGKGLEWVS~~HIPPVGQDPFYTDSV
KG~~RFTISRDNSKNTLYLQMNSLRAEDTAVYYCAL~~~LPKRGPWFDY~~~WGQGTLVTVSS

FIG. 100

```
>Tar2h-131-540 (SEQ ID NO:410)
EVQLLESGGGLVQPGGSLRLSCAASGFTFA~HETMV~WVRQAPGKGLEWVS~~HIPPVGQDPFYTDSV
EG~~RFTISRDNSKNTLYLQMNSLRAEDTAVYYCAL~~~LPKRGPWFDY~~~WGQGTLVTVSS

>Tar2h-131-541 (SEQ ID NO:411)
EVQLLESGGGLVQPGGSLRLSCAASGFTFA~HETMV~WVRQAPGKGLEWVS~~HIDGGGESTYYTDPV
KG~~RFTISRDNSKNTLYLQMNSLRAEDTAVYYCAR~~~LPKRGPWFDY~~~WGQGTLVTVSS

>Tar2h-131-542 (SEQ ID NO:412)
EVQLLESGGGLVQPGGSLRLSCAASGFTFA~HETMV~WVRQAPGKGLEWVS~~HIDGGGESTYYTDSV
EG~~RFTISRDNSKNTLYLQMNSLRAEDTAVYYCAR~~~LPKRGPWFDY~~~WGQGTLVTVSS

>Tar2h-131-543 (SEQ ID NO:413)
EVQLLESGGGLVQPGGSLRLSCAASGFTFA~HETMV~WVRQAPGKGLEWVS~~HIDGGGESTYYTDPV
EG~~RFTISRDNSKNTLYLQMNSLRAEDTAVYYCAR~~~LPKRGPWFDY~~~WGQGTLVTVSS

>Tar2h-131-544 (SEQ ID NO:414)
EVQLLESGGGLVQPGGSLRLSCAASGFTFN~KKTMV~WVRQAPGKGLEWVS~~HIDGKGQATYYTDPV
KG~~RFTISRDNSKNTLYLQMNSLRAEDTAVYYCAL~~~LPKRGPWFDY~~~WGQGTLVTVSS

>Tar2h-131-545 (SEQ ID NO:415)
EVQLLESGGGLVQPGGSLRLSCAASGFTFN~KKTMV~WVRQAPGKGLEWVS~~HIDGKGQATYYTDSV
EG~~RFTISRDNSKNTLYLQMNSLRAEDTAVYYCAL~~~LPKRGPWFDY~~~WGQGTLVTVSS

>Tar2h-131-546 (SEQ ID NO:416)
EVQLLESGGGLVQPGGSLRLSCAASGFTFN~KKTMV~WVRQAPGKGLEWVS~~HIDGKGQATYYTDPV
EG~~RFTISRDNSKNTLYLQMNSLRAEDTAVYYCAL~~~LPKRGPWFDY~~~WGQGTLVTVSS

>Tar2h-131-547 (SEQ ID NO:417)
EVQLLESGGGLVQPGGSLRLSCAASGFTFA~HETMV~WVRQAPGKGLEWVS~~HIPPVGQDPFYTDPV
KG~~RFTISRDNSKNTLYLQMNSLRAEDTAVYYCAL~~~LPKRGPWFDY~~~WGQGTLVTVSS

>Tar2h-131-548 (SEQ ID NO:418)
EVQLLESGGGLVQPGGSLRLSCAASGFTFA~HETMV~WVRQAPGKGLEWVS~~HIPPVGQDPFYADPV
EG~~RFTISRDNSKNTLYLQMNSLRAEDTAVYYCAL~~~LPKRGPWFDY~~~WGQGTLVTVSS

>Tar2h-131-549 (SEQ ID NO:419)
EVQLLESGGGLVQPGGSLRLSCAASGFTFN~KKTMV~WVRQAPGKGLEWVS~~HIDGKGQDPFYTDSV
EG~~RFTISRDNSKNTLYLQMNSLRAEDTAVYYCAL~~~LPKRGPWFDY~~~WGQGTLVTVSS

>Tar2h-131-550 (SEQ ID NO:420)
EVQLLESGGGLVQPGGSLRLSCAASGFTFN~KKTMV~WVRQAPGKGLEWVS~~HIDGKGQDPFYADPV
KG~~RFTISRDNSKNTLYLQMNSLRAEDTAVYYCAL~~~LPKRGPWFDY~~~WGQGTLVTVSS

>Tar2h-131-551 (SEQ ID NO:421)
EVQLLESGGGLVQPGGSLRLSCAASGFTFN~KKTMV~WVRQAPGKGLEWVS~~HIDGKGQDPFYTDPV
KG~~RFTISRDNSKNTLYLQMNSLRAEDTAVYYCAL~~~LPKRGPWFDY~~~WGQGTLVTVSS

>Tar2h-131-552 (SEQ ID NO:422)
EVQLLESGGGLVQPGGSLRLSCAASGFTFN~KKTMV~WVRQAPGKGLEWVS~~HIDGKGQDPFYTDSV
EG~~RFTISRDNSKNTLYLQMNSLRAEDTAVYYCAL~~~LPKRGPWFDY~~~WGQGTLVTVSS
```

FIG. 10P

>Tar2h-131-553 (SEQ ID NO:423)
EVQLLESGGGLVQPGGSLRLSCAASGFTFN~KKTMV~WVRQAPGKGLEWVS~~HIDGKGQDPFYTDPV
EG~~RFTISRDNSKNTLYLQMNSLRAEDTAVYYCAL~~~LPKRGPWFDY~~~WGQGTLVTVSS

>Tar2h-131-554 (SEQ ID NO:424)
EVQLLESGGGLVQPGGSLRLSCAASGFTFA~HETMV~WVRQAPGKGLEWVS~~HIPPVGQDPFYTDPV
EG~~RFTISRDNSKNTLYLQMNSLRAEDTAVYYCAL~~~LPKRGPWFDY~~~WGQGTLVTVSS

>Tar2h-131-555 (SEQ ID NO:425)
EVQLLESGGGLVQPGGSLRLSCAASGFTFA~HETMV~WVRQAPGKGLEWVS~~HIDGGGESPYYADSV
KG~~RFTISRDNSKNTLYLQMNSLRAEDTAVYYCAR~~~LPKRGPWFDY~~~WGQGTLVTVSS

>Tar2h-131-556 (SEQ ID NO:426)
EVQLLESGGGLIQPGGSLRLSCAASGFTFA~HETMV~WVRQAPGKGLEWVS~~HIPPVGQDPFYADSV
KG~~RFTISRDNSKNTLYLQMNSLRAEDTAVYYCAL~~~LPKRGPWFDY~~~WGQGTLVTVSS

>Tar2h-131-557 (SEQ ID NO:427)
EVQLLESGGGLIQPGGSLRLSCAASGFTFA~HETMV~WVRQAPGKGLEWVS~~HIPPVGQDPFYADPV
KG~~RFTISRDNSKNTLYLQMNSLRAEDTAVYYCAL~~~LPKRGPWFDY~~~WGQGTLVTVSS

>Tar2h-131-558 (SEQ ID NO:428)
EVQLLESGGGLIQPGGSLRLSCAASGFTFA~HETMV~WVRQAPGKGLEWVS~~HIPPVGQDPFYTDSV
KG~~RFTISRDNSKNTLYLQMNSLRAEDTAVYYCAL~~~LPKRGPWFDY~~~WGQGTLVTVSS

>Tar2h-131-559 (SEQ ID NO:429)
EVQLLESGGGLIQPGGSLRLSCAASGFTFA~HETMV~WVRQAPGKGLEWVS~~HIPPVGQDPFYTDSV
EG~~RFTISRDNSKNTLYLQMNSLRAEDTAVYYCAL~~~LPKRGPWFDY~~~WGQGTLVTVSS

>Tar2h-131-560 (SEQ ID NO:430)
EVQLLESGGGLIQPGGSLRLSCAASGFTFA~HETMV~WVRQAPGKGLEWVS~~HIDGGGESTYYADSV
EG~~RFTISRDNSKNTLYLQMNSLRAEDTAVYYCAR~~~LPKRGPWFDY~~~WGQGTLVTVSS

>Tar2h-131-561 (SEQ ID NO:431)
EVQLLESGGGLIQPGGSLRLSCAASGFTFA~HETMV~WVRQAPGKGLEWVS~~HIDGGGESTYYTDPV
KG~~RFTISRDNSKNTLYLQMNSLRAEDTAVYYCAR~~~LPKRGPWFDY~~~WGQGTLVTVSS

>Tar2h-131-562 (SEQ ID NO:432)
EVQLLESGGGLIQPGGSLRLSCAASGFTFA~HETMV~WVRQAPGKGLEWVS~~HIDGGGESTYYTDSV
EG~~RFTISRDNSKNTLYLQMNSLRAEDTAVYYCAR~~~LPKRGPWFDY~~~WGQGTLVTVSS

>Tar2h-131-563 (SEQ ID NO:433)
EVQLLESGGGLIQPGGSLRLSCAASGFTFA~HETMV~WVRQAPGKGLEWVS~~HIDGGGESTYYTDPV
EG~~RFTISRDNSKNTLYLQMNSLRAEDTAVYYCAR~~~LPKRGPWFDY~~~WGQGTLVTVSS

FIG. 10Q

\>Tar2h-131 (SEQ ID NO:434)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGCCGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACCGCGGTATATTACTGTGCGAAA~~~CTTCCTAAGAGGGGGCCTAGGTTTGACTAC~~~TGGG
GTCAGGGAACCCTGGTCACCGTCTCGAGC

\>Tar2h-131-1(SEQ ID NO:435)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGCCGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCATCATCTCCCGCGACAATTCCAAGAACACGCTGTATCTGCAAATGTACAGCCTGCGTGCCGA
GGACACCGCGGTATATTACTGTGCGATA~~~CTTCCTAAGAGGGGGCCTAGGTTTGACTAC~~~TGGG
GTCAGGGAACCCTGGTCACCGTCTCGAGC

\>Tar2h-131-2(SEQ ID NO:436)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGCCGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTACAAATGAACAGCCTGCGTGCCGA
GGACACCGCGGTATATTACTGTGCGAGA~~~CTTCCTAAGAGGGGGCCTAGGTTTGACTAC~~~TGGG
GTCATGGAACCCTGGTCACCGTCTCGAGC

\>Tar2h-131-3(SEQ ID NO:437)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGCCGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACCGCGGTATATTACTGTGCGATA~~~CTTCCTAAGAGGGGGCCTAGGTTTGACTAC~~~TGGG
GTCAGGGAACCCTGGTCACCGTCTCGAGC

\>Tar2h-131-4(SEQ ID NO:438)
GAGGTGCAGCTGTTGGAGTCTGGGGGAGGCTTGGTACAGCCTGGGGGGTCCCTGCGTCTCTCCTGTAC
AGCCTCCGGATTCACTTTTGCG~CATGAGCCGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACCGCGGTATATTACTGTGCGAGA~~~CTTCCTAAGAGGGGGCCTAGGTTTGACTAC~~~TGGG
GTCTGGGAACCCTGGTCACCGTCTCGAGC

\>Tar2h-131-5(SEQ ID NO:439)
GAGGTGAAGCTGTTGGAGTCTGGGGGAGGCTTGGTACAGCCTGGGGGGTCCCTGCGTCTCTCCTGTGC
AGCCTCCGGATTCACCTTTGCG~CATGAGCCGATGGTG~TGGATCCGCCAGGCTCCAGGGAAGGGTCT
AGAGTGGGTCTCA~~CATATTGATCGTGTTGGTCAGGATACATACTACGCAGACTCCGTGAAGGGC~~
CGGTACACCATCTCCCGCGACAATTCCAAGAATACGCTGTATCTGCAAATGAACAGCCTGCGTGCCGA
GGACACCGCGGTATATTACTGTGCGAGA~~~CTTCCTAAGAGGGGGCCTAGGTTTGACTAC~~~TGGG
GTCAGGGAACCCTGGTCACCGTCTCGAGC

FIG. 14A

\>Tar2h-131-6(SEQ ID NO:440)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGCCGATGGTG~TGGGTCCGCCAGGCTCCAGGGAAGGGTCT
AGAGTGGGTCTCA~~CATATTGATCGTGTTGGTCAGGATACATACTACGCAGACTCGGTGAAGGGC~~
CGGTTCACCATCTCCCGCGACAATTCCAAGAACACGCTGTATCTGCAAATGAACAGCCTGCGTGCCGA
GGACACCGCGGTATATTACTGTGCGAGA~~~CTTCCTAAGAGGGGGCCTAGGTTTGACTAC~~~TGGG
GTCTGGGAACCCTGGTCACCGTCTCGAGC

\>Tar2h-131-7(SEQ ID NO:441)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGCCGATGGTG~TGGGTCCGCCAGGCTCCAGGGAAGGGTCT
AGAGTGGGTCTCA~~CATATTGATCGTGCTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACCGCGGTATATTACTGTGCGAGA~~~CTTCCTAAGAGGGGGCCTAGGTTTGACTAC~~~TGGG
GTCTGGGAACCCTGGTCACCGTATCGAGC

\>Tar2h-131-8(SEQ ID NO:442)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGAAA~~~CTTCCTAAGAGGGGGCCTTGGTTTGACTAC~~~CGGG
GTCAGGGAACCCTGGTCACCGTCTCGAGC

\>Tar2h-131-9(SEQ ID NO:443)
GAAGTGCAGCTGTTGGAGTCTGGGGGAGGCTTGGTACGGCCTGGGGGGTCCCTGCGTCTCTCCTGTGC
AGCCTCCGGATTCACCTTTGCG~CATGAGCCGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACCGCGGTATATTACTGTGCGAGA~~~CTTCCTAAGAGGGGGCCTAGGTTTGACTAC~~~TGGG
GTCTGGGAACCCTGGTCACCGTCTCGAGC

\>Tar2h-131-10(SEQ ID NO:444)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGCCGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAGATGAACAGCCTGCGTGCCGA
GGACACCGCGATATATTACTGTGCGAGA~~~CTTCCTAAGAGGGGGCCTAGGTTTGACTAC~~~TGGG
GTCTGGGAACCCTGGTCACCGTCTCGAGC

\>Tar2h-131-11(SEQ ID NO:445)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGCCGATGGTG~TGGGTCCGCCAGGCTCCAGGGAAGGGTCT
AGAGTGGGTCTCA~~CATATTGATCGTGTTGGTCAGGATCCATACTACGCAGACTCCGTGAAGGGC~~
CGGTTCACCATCTCCCGCGACAATTCCAAGAACACGCTGTATCTGCAAATGAACAGCCTGCGTGCCGA
GGACACCGCGGTATATTACTGTGCGAGA~~~CTTCCTAAGAGGGGGCCTAGGTTTGACTAC~~~TGGG
GTCAGGGAACCCTGGTCACCGTCTCGAGC

FIG. 14B

>Tar2h-131-12(SEQ ID NO:446)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGCCGATGGTG~TGGATCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACCGCGGTATATTACTGTGCGATA~~~CTTCCTAAGAGGGGGCCTAGGTTTGACTAC~~~TGGG
GTCAGGGAACCCTGGTCACCGTCTCGAGC

>Tar2h-131-13(SEQ ID NO:447)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGCCGATGGTG~TGGGTCCGCCAGGCTCCAGGGAAGGGTCT
AGAGTGGGTCTCA~~CATATTGATCGTGTTGGTCAAGATCCATACTACGCAGACTCCGTGAAGGGC~~
CGGTTCACCATCTCCCGCGACAATTCCAAGAACACGCTGTATCTGCAAATGAACAGCCTGCGTGCCGA
GGACACCGCGGTATATTACTGTGCGAGA~~~CTTCCTAAGAGGGGGCCTAGGTTTGACTAC~~~TGGG
GTCTGGGAACCCTGGTCACCGTCTCGAGC

>Tar2h-131-14(SEQ ID NO:448)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGCCGATGGTG~TGGGTCCGCCAGGCTCCAGGGAAGGGTCT
AGAGTGGGTCTCA~~CATATTGATCGTGTTGGTCAGGATGCATACTACGCAGACTCCGTGAAGGGC~~
CGGTTCACCATCTCCCGCGACAATTCCAAGAACACGCTGTATCTGCAAATGAACAGCCTGCGTGCCGA
GGACACCGCGGTATATTACTGTGCGATA~~~CTTCCTAAGAGGGGGCCTAGGTTTGACTAC~~~TGGG
GTCAGGGAACCCTGGTCACCGTCTCGAGC

>Tar2h-131-15(SEQ ID NO:449)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGCCGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTCCACCATCTCCCGCGACAATTCCAAGAACACGCTGTATCTGCAGATGAACAGCCTGCGTGCCGA
GGACACCGCGATATATTACTGTGCGAGA~~~CTTCCTAAGAGGGGGCCTAGGTTTGACTAC~~~TGGG
GTCTGGGAACCCTGGTCACCGTCTCGAGC

>Tar2h-131-16(SEQ ID NO:450)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGCCGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAGATGAACAGCCTGCGTGCCGA
GGACACCGCGATATATTACTGTGCGAGA~~~CCTCCTAAGAGGGGGCCTAGGTTTGACTAC~~~TGGG
GTCTGGGAACCCTGGTCACCGTCTCGAGC

>Tar2h-131-17(SEQ ID NO:451)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGCCGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAGATGAACAGCCTGCGTGCCAA
GGACACCGCGATATATTACTGTGCGAGA~~~CTTCCTAAGAGGGGGCCTAGGTTTGACTAC~~~TGGG
GTCTGGGAACCCTGGTCACCGTCTCGAGC

FIG. 14C

\>Tar2h-131-18(SEQ ID NO:452)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGCCGATGGTG~TGGGTCCGCCAGGCTCCAGGGAAGGGTCT
AGAGTGGGTCTCA~~CATATTGATCGTGTTGGTCAGGATACATACTACGCAGACTCCGCGAAGGGC~~
CGGTTCACCATCTCCCGCGACAATTCCAAGAACACGCTGTATCTGCAGATGAACAGCCTGCGTGCCGA
GGACACCGCGATATATTACTGTGCGAGA~~~CTTCCTAAGAGGGGGCCTAGGTTTGACTAC~~~TGGG
GTCTGGGAACCCTGGTCACCGTCTCGAGC

\>Tar2h-131-19(SEQ ID NO:453)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGCCGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCCGCAGATGAACAGCCTGCGTGCCGA
GGACACCGCGATATATTACTGTGCGAGA~~~CTTCCTAAGAGGGGGCCTAGGTTTGACTAC~~~TGGG
GTCTGGGAACCCTGGTCACCGTCTCGAGC

\>Tar2h-131-20(SEQ ID NO:454)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGCCGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCGTCTCCCGCGACAATTCCAAGAACACGCTGTATCTGCAGATGAACAGCCTGCGTGCCGA
GGACACCGCGATATATTACTGTGCGAGA~~~CTTCCTAAGAGGGGGCCTAGGTTCGACTAC~~~TGGG
GTCTGGGAACCCTGGTCACCGTCTCGAGC

\>Tar2h-131-21(SEQ ID NO:455)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGCCGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCATCATCTCCCGCGACAATTCCAAGAACACGCTGTATCTGCAAATGTACAGCCTGCGTGCCGA
GGACACCGCGGTATATTACTGTGCGATG~~~CTTCCTAAGAGGGGGCCTAGGTTTGGCTAC~~~TGGG
GTCAGGGAACCCTGGTCACCGTCTCGAGC

\>Tar2h-131-22(SEQ ID NO:456)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGCCGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAGATGAACAGCCTGTGTGCCGA
GGACACCGCGATATATTACTGTGCGAGA~~~CTTCCTAAGAGGGGGCCTAGGTTTGACTAC~~~TGGG
GTCTGGGAACCCTGGTCACCGTCTCGAGC

\>Tar2h-131-23(SEQ ID NO:457)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGGGG~~~CTTCCTAAGAGGGGGCCTTGGTTTGACTAC~~~CGGG
GTCAGGGAACCCTGGTCACCGTCTCGAGC

FIG. 14D

>Tar2h-131-24(SEQ ID NO:458)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCGC~~~CTTCCTAAGAGGGGGCCTTGGTTTGACTAC~~~CGGG
GTCAGGGAACCCTGGTCACCGTCTCGAGC

>Tar2h-131-25(SEQ ID NO:459)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCCGTATATTACTGTGCGCAG~~~CTTCCTAAGAGGGGGCCTTGGTTTGACTAC~~~CGGG
GTCAGGGAACCCTGGTCACCGTCTCGAGC

>Tar2h-131-26(SEQ ID NO:460)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGTCGA
GGACACAGCGGTATATTACTGTGCGTCC~~~CTTCCTAAGAGGGGGCCTTGGTTTGACTAC~~~CGGG
GTCAGGGAACCCTGGTCACCGTCTCGAGC

>Tar2h131-27(SEQ ID NO:461)
GAGGTGCAGCTGTTGGAGTCTGGGGGAGGCTTGTACCAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGAAA~~~CTTCCTAAGAGGGGGCCTTGGTTTGACTAC~~~CGGG
GTCAGGGAACCCTGGTCACCGTCTCGAGC

>Tar2h131-28(SEQ ID NO:462)
GAGGTGCAGCTGTTGGAGTCTGGGGGAGGCTTGGGGCAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGAAA~~~CTTCCTAAGAGGGGGCCTTGGTTTGACTAC~~~CGGG
GTCAGGGAACCCTGGTCACCGTCTCGAGC

>Tar2h131-29(SEQ ID NO:463)
GAGGGGCAGCTGTTGGAGTCTGGGGGAGGCTTGGTTCAACCTGGGGGGTCCCTGCTTCTATCCTGTGC
AGCCTCCGGATTCACCTTTGCG~CATGAGACAATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGAAA~~~CTTCCTAAGAGGGGGCCTTGGTTTGACTAC~~~CGGG
GTCAGGGAACCCTGGTCACCGTCTCGAGC

FIG. 14E

\>Tar2h131-30(SEQ ID NO:464)
GAGGTGCAGCTGTTGGAGTCTGGGGGAGGCTTGGTTCAGCCTGGGGGGTCCCTGCGTCTCTCCTGTGC
AGCCTCCGGATTCACCTTTGCG~CATGAAACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGAAA~~~CTTCCTAAGAGGGGGCCTTGGTTTGACTAC~~~CGGG
GTCAGGGAACCCTGGTCACCGTCTCGAGC

\>Tar2h131-31(SEQ ID NO:465)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATCCCTACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGAAA~~~CTTCCTAAGAGGGGGCCTTGGTTTGACTAC~~~CGGG
GTCAGGGAACCCTGGTCACCGTCTCGAGC

\>Tar2h131-32(SEQ ID NO:466)
GAGGGGCAGCTGTTGGAGTCTGGGGGAGGCTTGATACAGCCTGGGGGGTCCCTGCGTCTATCCTGTGG
AGCCTCCGGATTCACCTTTGCG~CATGAGACAATGGTG~TGGGTCCGCCAGGCTCCAGGGAAGGGTCT
AGAGTGGGTCTCA~~CATATTGATCGTGTTGGTCAGGATCCCTACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGAAA~~~CTTCCTAAGAGGGGGCCTTGGTTTGACTAC~~~CGGG
GTCAGGGAACCCTGGTCACCGTCTCGAGC

\>Tar2h131-33(SEQ ID NO:467)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATAACTACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGAAA~~~CTTCCTAAGAGGGGGCCTTGGTTTGACTAC~~~CGGG
GTCAGGGAACCCTGGTCACCGTCTCGAGC

\>Tar2h131-34(SEQ ID NO:468)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGAAA~~~CTTCCTAAGAGGGGGCCTGGGTTTGACTAC~~~CGGG
GTCAGGGAACCCTGGTCACCGTCTCGAGC

\>Tar2h131-35(SEQ ID NO:469)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAAACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGAAA~~~CTTCCTAAGAGGGGGCCTGTGTTTGACTAC~~~CGGG
GTCAGGGAACCCTGGTCACCGTCTCGAGC

FIG. 14F

\>Tar2h131-36(SEQ ID NO:470)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGAAA~~~CTTCCTAAGAGGGGGCCTTGGTTTGACTAC~~~TACG
GTCAGGGAACCCTGGTCACCGTCTCGAGC

\>Tar2h131-37(SEQ ID NO:471)
GAGGGGCAGCTGTTGGAGTCTGGGGGAGGCTTGATACAGCCTGGGGGGTCCCTGCTTCTATCCTGTGC
ACCCTCCGGATTCACCTTTGCG~CATGAGACAATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGAAA~~~CTTCCTAAGAGGGGGCCTTGGTTTGACTAC~~~AAGG
GTCAGGGAACCCTGGTCACCGTCTCGAGC

\>Tar2h131-38(SEQ ID NO:472)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGAAA~~~CTTCCTAAGAGGGGGCCTTGGTTTGACTAC~~~GTGG
GTCAGGGAACCCTGGTCACCGTCTCGAGC

\>Tar2h131-39(SEQ ID NO:473)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGAAA~~~CTTCCTAAGAGGGGGCCTTGGTTTGACTAC~~~TTGG
GTCAGGGAACCCTGGTCACCGTCTCGAGC

\>Tar2h131-40(SEQ ID NO:474)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGCCGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACCGCGGTATATTACTGTGCGAGC~~~CTTCCTAAGAGGGGGCCTAGGTTTGACTAC~~~TGGG
GTCAGGGAACCCTGGTCACCGTCTCGAGC

\>Tar2h131-41(SEQ ID NO:475)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGCCGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACCGCGGTATATTACTGTGCGGGG~~~CTTCCTAAGAGGGGGCCTAGGTTTGACTAC~~~TGGG
GTCAGGGAACCCTGGTCACCGTCTCGAGC

FIG. 14G

>Tar2h131-42(SEQ ID NO:476)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGCCGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACCGCGGTATATTACTGTGCGAGG~~~CTTCCTAAGAGGGGGCCTAGGTTTGACTAC~~~TGGG
GTCAGGGAACCCTGGTCACCGTCTCGAGC

>Tar2h131-43(SEQ ID NO:477)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGCCGATGGTG~TGGGTCCGCCAGGCTCCAGGGAAGGGTCT
AGGGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACCGCCGTATATTACTGTGCGCCC~~~CTTCCTAAGAGGGGGCCTAGGTTTGACTAC~~~TGGG
GTCAGGGAACCCTGGTCACCGTCTCGAGC

>Tar2h131-44(SEQ ID NO:478)
GAGGTGCAGCTGTTGGAGTCTGGGGGAGGCTTGGTACAGCCTGGGGGGTCCCTGCGCCTCTCCTGTGC
AGCCTCCGGATTCACCTTTGCG~CATGAGCCGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAgAACACGCTGTATCTGCAAATGAACAGCCTGCGTGCCGA
GGACACCGCCGTATATTACTGTGCGATC~~~CTTCCTAAGAGGGGGCCTAGGTTTGACTAC~~~TGGG
GTCAGGGAACCCTGGTCACCGTCTCGAGC

>Tar2h131-45(SEQ ID NO:479)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGCCGATGGTG~TGGATCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACCGCGGTATATTACTGTGCGATG~~~CTTCCTAAGAGGGGGCCTAGGTTTGACTAC~~~TGGG
GTCAGGGAACCCTGGTCACCGTCTCGAGC

>Tar2h131-46(SEQ ID NO:480)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGCCGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACCGCGGTATATTACTGTGCGCTG~~~CTTCCTAAGAGGGGGCCTAGGTTTGACTAC~~~TGGG
GTCAGGGAACCCTGGTCACCGTCTCGAGC

>Tar2h131-47(SEQ ID NO:481)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATAAGTACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGAAA~~~CTTCCTAAGAGGGGGCCTTGGTTTGACTAC~~~CGGG
GTCAGGGAACCCTGGTCACCGTCTCGAGC

FIG. 14H

\>Tar2h131-48(SEQ ID NO:482)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGAAA~~~CTTCCTAAGAGGGGGCCTTGGTTTGACTAC~~~ATCG
GTCAGGGAACCCTGGTCACCGTCTCGAGC

\>Tar2h131-49(SEQ ID NO:483)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGAAA~~~CTTCCTAAGAGGGGGCCTTGGTTTGACTAC~~~AACG
GTCAGGGAACCCTGGTCACCGTCTCGAGC

\>Tar2h-131-50(SEQ ID NO:484)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGGTGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGAAA~~~CTTCCTAAGAGGGGGCCTTGGTTTGACTAC~~~CGGG
GTCAGGGAACCCTGGTCACCGTCTCGAGC

\>Tar2h-131-51(SEQ ID NO:485)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGTTGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGAAA~~~CTTCCTAAGAGGGGGCCTTGGTTTGACTAC~~~CGGG
GTCAGGGAACCCTGGTCACCGTCTCGAGC

\>Tar2h-131-52(SEQ ID NO:486)
GAGGTGCAGCTGTTGGAGTCTGGGGGAAACTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGAAA~~~CTTCCTAAGAGGGGGCCTTGGTTTGACTAC~~~CGGG
GTCAGGGAACCCTGGTCACCGTCTCGAGC

\>Tar2h-131-53(SEQ ID NO:487)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGAAA~~~CTTCCTAAGAGGGGGCCTTGGTTTGACTAC~~~CGGG
GTCAGGGAACCCTGGTCACCGTCTCGAGC

FIG. 14I

>Tar2h-131-54 (SEQ ID NO:488)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATAAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGTTG~~~CTTCCTAAGAGGGGGCCTTGGTTTGACTAC~~~CGGG
GTCAGGGAACCCTGGTCACCGTCTCGAGC

>Tar2h-131-55 (SEQ ID NO:489)
GAGGTGCAGcTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACCCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCGC~~~CTACCTAAGAGGGGGCCTTGGTTTGACTAC~~~CGGG
GTCAGGGAACCCTGGcCACCGTCTCGAGC

>Tar2h-131-56 (SEQ ID NO:490)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACTCGCTGTATCTGCAAATGAACAGCCTGCGTGCCGA
GGACACAGCCGTATATTACTGTGCGGTC~~~CTTCCTAAGAGGGGGCCTTGGTTTGACTAT~~~CGGG
GTCAGGGAACCCTGGTCACCGTCTCGAGC

>Tar2h-131-57 (SEQ ID NO:491)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATCCCAAGAACACGCTGTATCTGCAAATGAACAGCCTGCGTGCCGA
GGACACAGCGGTATATTACTGTGCGCGC~~~CTTCCTAAGAGGGGCCTTGGTTTGACTAC~~~CGGG
GTCAGGGAACCCTGGTCACCGTCTCGAGC

>Tar2h-131-58 (SEQ ID NO:492)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGATACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCGC~~~CTTCCTAAGAGGGGGCCTTGGTTTGACTAC~~~CAGG
GTCAGGGAACCCTGGTCACCGTCTCGAGC

>Tar2h-131-59 (SEQ ID NO:493)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGATACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGAC~~
CGGTTCACCATCTCCCGCGACAATTCCAAGAACACGCTGTATCTGCAAATGAATAGCCTGCGTGCCGA
GGACACAGCCGTATATTACTGTGCGGTG~~~CTTCCTAAGAGGGGGCCTTGGTTTGACTAC~~~CGGG
GTCAGGGAACCCTGGTCACCGTCTCGAGC

FIG. 14J

>Tar2h-131-60 (SEQ ID NO:494)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTTTCTGCAAATGAACAGCCTGCGTGCCGA
GGACACAGCGGTATATTACTGTGCGCGC~~~CTTCCTAAGAGGGGGCCTTGGTTTGACTAC~~~CGGG
GTCGGGGAACCCTGGTCACCGTCTCGAGC

>Tar2h-131-61 (SEQ ID NO:495)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGGAGGGC~~
CGGTTCACCATCTCCCGCGACAATTCCAAGAACACGCTGTATCTGCAAATGAACAGCCTGCGTGCCGA
GGACACAGCGGTATATTACTGTGCGGTC~~~CTTCCTAAGAGGGGGCCTTGGTTTGACTAC~~~CGGG
GTCAGGGAACCCTGGTCACCGTCTCGAGC

>Tar2h-131-62 (SEQ ID NO:496)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGGAGGGC~~
CGGTTCACCATCTCCCGCGACAATTCCAAGAACACGCTGTATCTGCAAATGAACAGCCTGCGTGCCGA
GGACACAGCCGTATATTACTGTGCGCTG~~~CTCCCTAAGAGGGGGCCTTGGTTTGACTAC~~~CGGG
GTCAGGGAACCCTGGTCACCGTCTCGAGC

>Tar2h-131-63 (SEQ ID NO:497)
GAGGTGCAGCTGTTAGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCA
AGAGTGGGTCTCA~~CATATTGATCGTGTTGGTCAGGATACATACTACGCAGACTCCGTGAAGGGC~~
CGGTTCACCATCTCCCGCGACAATTCCAAGAACTCGCTGTATCTGCAAATGAACAGCCTGCGTGCCGA
GGACACAGCCGTATATTACTGTGCGGTC~~~CTTCCTAAGAGGGGGCCTTGGTTTGACTAC~~~CGGG
GTCAGGGAACCCTGGTCACCGTCTCGAGC

>Tar2h-131-64 (SEQ ID NO:498)
GAGGTGCAGCTGTCGGAGTCTGGGGGAGGCTTGATACAGCCTGGGGGGTCCCTGCGTCTCTCCTGTGT
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCCGTATATTACTGTGCGATC~~~CTTCCTAAGAGGGGGCCTTGGTTTGACTAC~~~CGGG
GTCAGGGAACCCTGGTCACCGTCTCGAGC

>Tar2h-131-65 (SEQ ID NO:499)
GAGGTGCAGCTGTTGGAGTCTGGGGGAGGCTTGATACAGCCTGGGGGGTCCCTGCGTCTCACCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGGTG~~~CTTCCTAAGAGGGGGCCTTGGTTTGACTAC~~~CGGG
GTCAGGGAACCCTGGTCACCGTCTCGAGC

FIG. 14K

\>Tar2h-131-66 (SEQ ID NO:500)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCATGAACACGCTGTATCTGCAAATGAACAGCCTGCGTGCCGA
GGACACAGCGGTATATTACTGTGCGTTG~~~CTTCCTAAGAGGGGGCCTTGGTTTGACTAC~~~CGGG
GTCAGGGAACCCTGGTCACCGTCTCGAGC

\>Tar2h-131-67 (SEQ ID NO:501)
GAGGTGCAGCTGTTGGAGTCTGGGGGAGGCTCGATACAGCCAGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACGGCGGTATATTACTGTGCGGTC~~~CTTCCTAAGAGGGGGCCTTGGTTTGACTAC~~~CGGG
GTCAGGGAACCCTGGTCACCGTCTCGAGC

\>Tar2h-131-68 (SEQ ID NO:502)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCAACAATTCCATGAACACGCTGTATCTGCAAATGAACAGCCTGCGTGCCGA
GGACACAGCGGTATATTACTGTGCGATC~~~CTTCCTAAGAGGGGGCCTTGGTTTGACTAC~~~CGGG
GTCAGGGAACCCTGGTCACCGTCTCGAGC

\>Tar2h-131-69 (SEQ ID NO:503)
GAGGTGCAGCTGTTGGAGTCTGGGGGAGGCTTGATACAGCCTGGGGGGTCCCTGCGTCTCTCCTGCGC
AGCCTCCGGATTCACCTTTGCG~CATGAGACGATGGTG~TGGGTCCGCCAGGCTCCAGGGAGGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCCGTATATTACTGTGCGGTG~~~CTTCCTAAGAGGGGGCCTTGGTTTGACTAC~~~CGGG
GTCAGGGAACCCTGGTCACCGTCTCGAGC

\>Tar2h-131-70 (SEQ ID NO:504)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATCCATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCCGTATATTACTGTGCGCTC~~~CTTCCTAAGAGGGGGCCTTGGTTTGACTAC~~~CGGG
GTCAGGGAACCCTGGTCACCGTCTCGAGC

\>Tar2h-131-71 (SEQ ID NO:505)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCCGTATATTACTGTGCGATG~~~CTTCCTAAGAGGGGGCCTTGGTTTGACTAC~~~CGGG
GTCAGGGAACCCTGGTCACCGTCTCGAGC

FIG. 14L

>Tar2h-131-72 (SEQ ID NO:506)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGATACGATGGTG~TGGGTCCGCCAGGCTCCAGGGAAGGGTCT
AGAGTGGGTCTCT~~CATATTGATCGTGTTGGTCAGGATACATACTACGCAGACTCCGTGAAGGGC~~
CGGTTCACCATCTCCCGCGACAATACCAAGAACACGCTGTATCTGCAAATGAACAGCCTGCGTGCCGA
GGACACAGCCGTATATTACTGTGCGCTC~~~CTTCCTAAGAGGGGGCCTTGGTTTGACTAC~~~CGGG
GTCAGGGAACCCTGGTCACCGTCTCGAGC

>Tar2h-131-73 (SEQ ID NO:507)
GAGGTGCAGCTGTTGGAGTCTGGGGGAGGCTTGATAGAGCCTGGGGGGTCCCTGCGTCTATCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACTCAGCGGTATATTACTGTGCGCGC~~~CTTCCTAAGAGGGGGCCATGGTTTGACTAC~~~CGGG
GTCAGGGAACCCTGGTCACCGTCTCGAGC

>Tar2h-131-74 (SEQ ID NO:508)
GATGTGCAGCTGCTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGCATATTACTGTGCGGTC~~~CTTCCTAAGAGGGGGCCTTGGTTTGACTAC~~~CGGG
GTCAGGGAACCCTGGTCACCGTCTCGAGC

>Tar2h-131-75 (SEQ ID NO:509)
GAGGTGCAGCTGATGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGGAG~~~CTTCCTAAGAGGGGGCCTTGGTTTGACCAC~~~CGGG
GTCAGGGAACACTGGTCACCGTCTCGAGC

>Tar2h-131-76 (SEQ ID NO:510)
GAGGTGCAGCTGCTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCGCCATCTCCCGCGACAATTCCAAGAACACGCTGTATCTGCAAATGAACAGCCTGCGTGCCGA
GGACACAGCCGTATATTACTGTGCGATG~~~CTTCCTAAGAGGGGGCCTTGGTTTGACTAC~~~CGGG
GCCAGGGAACCCTGGTCACCGTCTCGAGC

>Tar2h-131-77 (SEQ ID NO:511)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACACAGACTCCGTGAAGGGC~~
CGGTTCACCATCTCCCGCGACAATTCCAAGAACACGCTGTATCTGCAAATGAACAGCCTGCGTGCCGA
GGACACAGCCGTATATTACTGTGCGTTG~~~CTTCCTAAGAGGGGGCCTTGGTTTGACTAC~~~CGGG
GTCAGGGAACCATGGTCACCGTCTCGAGC

FIG. 14M

>Tar2h-131-78 (SEQ ID NO:512)
GAGGTGCAGCTGTTGGAGTCTGGGGGAGGCTTGATGCAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCTTGTTGGTCAGGATACATACTATGCAGACTCCGTGAAGGGC~~
CGGTTCACCATCTCCCGCGACAATTCCAAGAACACGCTGTATCTACAAATGAACAGCCTGCGTGCCGA
GGACACAGCAGTATATCACTGCGCGCGC~~~CTTCCTAAGAGGGGGCCTTGGTTTGACTAC~~~CGGG
GTCAGGGAACCCTGGTCACCGTCTCGAGC

>Tar2h-131-79 (SEQ ID NO:513)
GAGGTGCAACTGTTGGAGTCTGGGGGAGGCTTGATACAGCCTGGGGGGTCCCTGCGTCTCTCCTGTGC
AACCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATATGCAAATGAACAGCCTGCGTGCCGA
GGACACAGCGGTATATTACTGTGCGGTC~~~CTTCCTAAGAGGGGGCCTTGGTTTGACTAC~~~CAGG
GTCAGGGAACCCTGGTCACCGTCTCGAGC

>Tar2h-131-80 (SEQ ID NO:514)
GAGGTGCAGCTGTTGGAGTCTGGGGGAGGCTTGATACAGCCTGGGGGGTCCCTGCGTCTCTCCTGTGC
AGCCTCCGGGTTCACCTTTGCG~CATGAGACGATGGTG~TGGGTCCGCCAGGCTCCAGGGAAGGGTCT
AGAGTGGGTCTCA~~CATATTGATCGTGTAGGTCAGGATACATACTACGCAGACCCGTGAAGGGC~~
CGGTTCACCATCTCCCGCGACAATTCCAGGAACACGCTGTATCTGCAAATGAACAGCCTGCGTTCCGA
GGATACAGCGGTATATTACTGTGCGGTC~~~CTTCCTAAGAGGGGGCCTTGGTTTGACTAC~~~CGGG
GTCAGGGAACCCTGGTCACCGTCTCGAGC

>Tar2h-131-81 (SEQ ID NO:515)
GAGGTGCAGCTGTTGGAGTCTGGGGGGGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCCGTATATAGCTGTGCGTTG~~~CTTCCTAAGAGGGGGCCTTGGTTTGACTAC~~~CGGG
GTCAGGGAACCCTGGTCACCGTCTCGAGC

>Tar2h-131-82 (SEQ ID NO:516)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCAGTGAAGGGC~~
CGGTTCACCATCTCCCGCGACAATTCCAAGAACGCGCTGTATCTGCAAATGAACAGCCTGCGTGCCGA
GGACACAGCGGTATATTACTGTGCGGTC~~~CTTCCTAAGAGGGGGCCTTGGTTTGACTAC~~~CGGG
GTCAGGGAACCCTGGTCACCGTCTCGAGC

>Tar2h-131-83 (SEQ ID NO:517)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCGAGC

FIG. 14N

>Tar2h-131-86 (SEQ ID NO:518)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCGAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCCGTATATTACTGTGCGATC~~~CTTCCTAAGAGGGGGCCTTGGTTTGACTAC~~~AGGG
GTCAGGGAACCCTGGTCACCGTCTCGAGC

>Tar2h-131-87 (SEQ ID NO:519)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGGAGGGC~~
CGGTTCACCATCTCCCGCGACAATTCCAAGAACACGCTGTATCTGCAAATGAACAGCCTGCGTGCCGA
GGACACAGCGGTATATTACTGTGCGGTG~~~CTTCCTAAGAGGGGGCCTTGGTTTGACTAC~~~CGGG
GTCAGGGAACCCTGGTCACCGTCTCGAGC

>Tar2h-131-88 (SEQ ID NO:520)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACCCCGTGAAGGGC~~
CGGTTCACCATCTCCCGCGACAATTCCAGGAACACGCTGTATCTGCAAATGAACAGCCTGCGTGCCGA
GGACACAGCGGTATATTACTGTGCGGTG~~~CTTCCTAAGAGGGGGCCTTGGTTTGACTAC~~~CGGG
GTCAGGGAACCCTGGTCACCGTCTCGAGC

>Tar2h-131-89 (SEQ ID NO:521)
GAGGTGCAACTTTTGGAGTCTGGGGGAGACTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCCGTATATTACTGTGCGGTG~~~CTTCCTAAGAGGGGGCCTTGGTTTGACTAC~~~CGGG
GTCAGGGAACCCTGGTCACCGTCTCGAGC

>Tar2h-131-90 (SEQ ID NO:522)
GAGGTGCAGCTGTTGGAGTCTGGGGGAGGCTCGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTTAAGGGC~~
CGGTTCACCATCTCCCGCGACAATTCCAAGAACACGCTGTATCTGCAAATGAACAGCCTGCGTGCCGA
GGACACAGCGGTATATTACTGTGCGGTG~~~CTTCCTAAGAGGGGGCCTTGGTTTGACTAC~~~CGGG
GTCAGGGAACCCTGGTCACCGTCTCGAGC

>Tar2h-131-91 (SEQ ID NO:523)
GAGGTGCAGCTGTTGGAGTCTGGGGGAGGCTTGATACAGCCTGGGGGGTCCCTGCATCTCTCCTGTGC
AGCCTCCGGATTCACCTTTGAG~CATGAGACGATGGTG~TGGGTCCGTCAGGCTCCAGGGAAGGGTCT
AGAGTGGGTCTCA~~CATATTGATCGAGTTGGTCAGGATCCATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCGC~~~CTTCCTAAGAGGGGGCCTTGGTTTGACTAC~~~CGGG
GTCAGGGAACCCTGGTCACCGTCTCGAGC

FIG. 140

>Tar2h-131-92 (SEQ ID NO:524)
GAGGTGCAGCTGTTGGAGTCTGGGGGAGGCTTGATACAGCCTGGGGGGTCCCTGCGTCTCTCCTGTGC
GGCCTCCGGATTCACCTTTGCG~CATGATACGATGGTG~TGGGTCCGCCAGGCTCCAGGGAAGGGTCT
AGAGTGGGTCTCA~~CATATTGATCGTGTTGGTCAGGATACATACTACGCAGATTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCGC~~~CTTCCTAAGAGGGGGCCTTGGTTTGACTAC~~~CGGG
GTCAGGGGACCCTGGTCACCGTCTCGAGC

>Tar2h-131-93 (SEQ ID NO:525)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATCCATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCGC~~~CTTCCTAAGAGGGGGCCTTGGTTTGACTAC~~~CGGG
GTCAGGGAACCCTGGTCACCGTCTCGAGC

>Tar2h-131-94 (SEQ ID NO:526)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGATCT
AGAGTGGGTCTCA~~CATATTGATCGTGTTGGTCAGGATACATACTACGCAGACTCCGTGAAGGGC~~
CGGTTTACCATCTCCCGCGACAATTCCAAGAACACGCTGTATCTGCAAATGAACAGCCTGCGTGCCGA
GGACACAGCGGTATATTACTGTGCGGTG~~~CTTCCTAAGAGGGGGCCTTGGTTTGACTAC~~~CGGG
GTCAGGGAACCCTGGTCACCGTCTCGAGC

>Tar2h-131-95 (SEQ ID NO:527)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGATACGATGGTG~TGGGTCCGCCAGGCTCCAGGGAAGGGTCT
AGAGTGGGTCTCA~~CATATTGATCGTGTTGGTCAGGATACGTACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCGC~~~CTTCCTAAGAGGGGGCCTTGGTTTGACTAC~~~CGGG
GTCAGGGAACCCTGGTCACCGTCTCGAGC

>Tar2h-131-96 (SEQ ID NO:528)
GAGGTGCAGCTGTTGGAGTCCGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCCGTATACCACTGTGCGGTG~~~CTTCCTAAGAGGGGGCCTTGGTTTGACTAC~~~CGGG
GTCAGGGAACCCTGGTCACCGTCTCGAGC

>Tar2h-131-97 (SEQ ID NO:529)
GAGGTGCAGCTGTTGGAGTCTGGGGGAGGCCTGATACAGCCTGGGGGGTCCCTGCGTCTCTCCTGTGC
AGCCTCCGGATTCACCTTTGCG~CATGAGACGATGGTG~TGGGTCCGCGAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCCGTATATTACTGTGCGGTC~~~CTTCCTAAGAGGGGGCCTTGGTTTGACTAC~~~CGGG
GTCAGGGAACCCTGGTCACCGTCTCGAGC

FIG. 14P

>Tar2h-131-99 (SEQ ID NO:530)
GAGGTGCAGCTGTTGGAGTCTGGGGGAGGCTTGATACATCCTGGGGGGACCCTGCGTCTCTCCTGTGC
AGCCTCCGGATTCACCTTTGCG~CATGAGACGATGGTG~TGGGTCCGCCAGGCTCCGGGGAAGGGTCT
AGAGTGGGTCTCA~~CATATTGATCGTGTTGGTCAGGATCCATACTATGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCGC~~~CTCCCTAAGAGGGGGCCTTGGTTTGACTAC~~~CGGG
GTCAGGGAACCCTGGTCACCGTCTCGAGC

>Tar2h-131-100(SEQ ID NO:531)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATCCATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCGC~~~CTTCCTAAGAGGGGGCCTTGGTTTGACTAC~~~CGGG
GTCAGGGAACCCAGGTCACCGTCTCGAGC

>Tar2h-131-101 (SEQ ID NO:532)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCGAGC

>Tar2h-131-102 (SEQ ID NO:533)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGGAGGGC~~
CGGTTCACCATCTCCCGCGACAATTCCAAGAACACGCTGTATCTGCAAATGAACAGCCTGCGTGCCGA
GGACACAGCGGTATATTACTGTGCGGTC~~~CTTCCTAAGAGGGGGCCTTGGTTTGACTAC~~~TGGG
GTCAGGGAACCCTGGTCACCGTCTCGAGC

>Tar2h-131-103 (SEQ ID NO:534)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATCCATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCCGTATATTACTGTGCGCTC~~~CTTCCTAAGAGGGGGCCTTGGTTTGACTAC~~~TGGG
GTCAGGGAACCCTGGTCACCGTCTCGAGC

>Tar2h-131-104 (SEQ ID NO:535)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGATCT
AGAGTGGGTATCA~~CATATTGATCGTGATGGTCAGGATACATACTACGCAGACTCCGTGAAGGGC~~
CGGTTCTCCATCTCCCGCGACAATTCCAAAAACACGCTGTATCTGCAAATGAACAGCCTGCGTGCCGA
GGACACAGCGGTATATTACTGTGCGCGC~~~CTTCCTAAGAGGGGGCCTTGGTTTGACTAC~~~CGGG
GTCAGGGAACCCTGGTCACCGTCTCGAGC

FIG. 14Q

\>Tar2h-131-105 (SEQ ID NO:536)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCACCTCCCGCGACAATTCCAAGAACACGCTGTATCTGCAAATGAACAGCCTGCGTGCCGA
GGACACAGCGGTATATTACTGTGCGCGC~~~CTCCCTAAGAGGGGCCTTGGTTTGACTAC~~~CGGG
GTCAGGGAACCCTGGTCACCGTCTCGAGT

\>Tar2h-131-106 (SEQ ID NO:537)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGATGGTCAGGATACATACTACGCAGACTCCGTGATGGGC~~
CGGTTCACCGTCTCCCGCGACAATTCCAAGAACACGCTGTATCTGCAAATGAACAGCCTGCGTGCCGA
GGACACAGCCGTATATTACTGTGCGATC~~~ATTCCTAAGAGGGGCCTTGGTTTGACTAC~~~CGGG
GTCAGGGAACCCTGGTCACCGTCTCGAGC

\>Tar2h-131-107 (SEQ ID NO:538)
GAGGTGCAGCTGTTGGAGTCTGGGGGAGGCTTGATACAGCCTGGGGGGTCTCTGCGTCTCTCCTGTGC
AGCCTCCGGATTCACCTTTGCG~CATGAGACGATGGTG~TGGGTCCGCCAGGCTCCAGGGAAGGATCT
AGAGTGGGTCTCA~~CATATTGATCGTGTTGGTCAGGATACATACTACGCAGACTCCGTGGAGGGC~~
CGGTTCACCATCTCCCGCGACAATTCCAAGAACACGCTGTATCTGCAAATGAACAGCCTGCGTGCCGA
GGACACAGCCGTATATTACTGTGCGGTG~~~CTTCCTAAGAGGGGCCTTGGTTTGACTAC~~~CGGG
GTCAGGGAACCCTGGTCACCGTCTCGAGC

\>Tar2h-131-108 (SEQ ID NO:539)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATACTGATCGTGTTGGTCAGGATACATACTACGCAGACTCCGTGAAGGGC~~
CGGTTCACCATCTCCCGCGACAATTCCAGGAACACGCTGTATCTGCAAATGAACAGCCTGCGTGCCGA
GGACACAGCGGTATATTACTGTGCGGTG~~~CTTCCTAAGAGGGGCCATGGTTTGACTAC~~~CGGG
GTCAGGGAACCCTGGTCACCGTCTCGAGC

\>Tar2h-131-109 (SEQ ID NO:540)
GAGGTGCAGCTGTTGGAGTCTGGGGGAGGCTTGATACAGCCTGGGGGGACCCTGCGTCTCTCCTGTGC
AGCCTCCGGATTCACCTTTGCG~CTTGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCACCTCCCGCGACAATTCCAGGAACACGCTGTATCTGCAAATGAACAGCCTGCGTGCCGA
GGACACAGCGGTATATTACTGTGCGCGC~~~CTTCCTAAGAGGGGCCTTGGTTTGACTAC~~~CGGG
GTCAGGGAACCCTGGTCACCGTCTCGAGC

\>Tar2h-131-110 (SEQ ID NO:541)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTACGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGGTG~~~ATTCCTAAGAGGGGCCTTGGTTTGACTAC~~~CGGG
GTCAGGGAACCCTGGTCACCGTCTCGAGC

FIG. 14R

>Tar2h-131-111 (SEQ ID NO:542)
GAGGTGCAGCTGTTGGAGTCTGGGGGAGGCTTGATACAGCCTGGGGGGTCCCTGCGTCTCTCCTGTGC
AGCCTCCGGATTCACATTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGGTG~~~CTTCCTAAGAGGGGGCCTTGGTTTGACTAC~~~CGGG
GTCAGGGAACCCAGGTCACCGTCTCGAGC

>Tar2h-131-112 (SEQ ID NO:543)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACAATGGTG~TGGGTCCGCCAGGCTCCTGGGAAGGGTAT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGGTG~~~CTTCCTAAGAGGGGGCCTTGGTTTGACTAC~~~CGGG
GTCAGGGAACCCTGGTCACCGTCTCGAGC

>Tar2h-131-113 (SEQ ID NO:544)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGATACGATGGTG~TGGGTCCGCCAGGCTCCAGGGAAGGGTCT
AGAGTGGGTCTCA~~CATATTGATCGTGTTGGTCAGGATACATACTACGCAGACTCCGTGGAGGGC~~
CGGTTCACCATCTCCCGCGACAATTCCAAGAACACGCTGTATCTGCAAATGAACAGCCTGCGTGCCGA
GGACACAGCGGTATATTACTGTGCGGTC~~~CTTCCTAAGAGGGGGCCTTGGTTTGACTAC~~~TGGG
GTCAGGGAACCCTGGTCACCGTCTCGAGC

>Tar2h-131-114 (SEQ ID NO:545)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGATGTGATGGTG~TGGGTCCGCCAGGCTCCAGGGAAGGGTCT
AGAGTGGGTCTCA~~CATATTGATCGTGTTGGTCAGGATACATACTACGCAGACTCCGTGGAGGGC~~
CGGTTCACCATCTCCCGCGACAATTCCAAGAACACGCTGTATCTGCAAATGAACAGCCTGCGTGCCGA
GGACACAGCGGTATATTACTGTGCGGTC~~~CTTCCTAAGAGGGGGCCTTGGTTTGACTAC~--TGGG
GTCAGGGAACCCTGGTCACCGTCTCGAGC

>Tar2h-131-115 (SEQ ID NO:546)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATCCATACTACACAGATTCCGTGGAGGAC~~
CGGTTCACCATCTCCCGCGACAATTCCAAGAACACGCTGTATCTGCAAATGAACAGCCTGCGTGCCGA
GGACACAGCGGTATATTACTGTGCGGTC~~~CTTCCTAAGAGGGGGCCTTGGTTTGACTAC~~~TGGG
GTCAGGGAACCCTGGTCACCGTCTCGAGC

>Tar2h-131-116 (SEQ ID NO:547)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGGAGGGC~~
CGGTTCACCATCTCCCGCGACAATTCCAAGAACACGCTGTATCTGCAAATGAACAGCCTGCGTGCCGA
GGACACAGCGGTATATTACTGTGCGTTG~~~CTTCCTAAGAGGGGGCCTTGGTTTGACTAC~~~TGGG
GTCAGGGAACCCTGGTCACCGTCTCGAGC

FIG. 14S

\>Tar2h-131-117 (SEQ ID NO:548)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATCCATACTACGCAGATTCCGTGGAGGGC~~
CGGTTCACCATCTCCCGCGACAATTCCAAGAACACGCTGTATCTGCAAATGAACAGCCTGCGTGCCGA
GGACACAGCGGTATATTACTGTGCGGTC~~~CTTCCTAAGAGGGGCCTTGGTTTGACTAC~~~TGGG
GTCAGGGAACCCTGGTCACCGTCTCGAGC

\>Tar2h-131-120 (SEQ ID NO:549)
GAGGTGCAGCTGTTGGAGTCTGGGGGAGGCTTGATACAGCCTGGGGGGTCCCTGCGTCTCTCCTGTGC
AGCCTCCGGATTCACCTTTAAC~AAGGAGACCATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACTGCGGTATATTACTGTGCGCTG~~~CTTCCTAAGAGGGGCCTTGGTTTGACTAC~~~CGGG
GTCAGGGAACCCTGGTCACCGTCTCGAGC

\>Tar2h-131-121 (SEQ ID NO:550)
GAGGTGCAGCTGTTGGAGTCTGGGGGAGGCTTGATACAGCCTGGGGGGTCCCTGCGTCTCTCCTGTGC
AGCCTCCGGATTCACCTTTAAC~ACGGAGACCATGGTG~TGGGTCCGCCGGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGCCTTGGTTTGACTAC~~~CGGG
GTCAGGGAACCCTGGTCACCGTCTCGAGC

\>Tar2h-131-122 (SEQ ID NO:551)
GAGGTGCAGCTGTTGGAGTCTGGGGGAGGCTTGATACAGCCTGGGGGGTCCCTGCGTCTCTCCTGTGC
AGCCTCCGGATTCACCTTTACG~AAGGAGACCATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGTGACAATTCCAAGAACACGCTGTATCTGCAAATGAACAGCCTGCGTGCCGA
GGACACAGCGGTATATTACTGTGCGCTG~~~CTTCCTAAGAGGGGCCTTGGTTTGACTAC~~~CGGG
GTCAGGGAACCCTGGTCACCGTCTCGAGC

\>Tar2h-131-123 (SEQ ID NO:552)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATGGGGGGGGGGTGGATACATACTACGCAGACCCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGCCTTGGTTTGACTAC~~~CGGG
GTCAGGGAACCCTGGTCACCGTCTCGAGC

\>Tar2h-131-124 (SEQ ID NO:553)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATGGGGGGGGCGGGATACATACTACGCAGACCCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGCCTTGGTTTGACTAC~~~CGGG
GTCAGGGAACCCTGGTCACCGTCTCGAGC

FIG. 14T

>Tar2h-131-125 (SEQ ID NO:554)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATGGGGGGGGGTGGATACATACTACGCAGACCCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~CGGG
GTCAGGGAACCCTGGTCACCGTCTCGAGC

>Tar2h-131-126 (SEQ ID NO:555)
GAGGTGCAGCTGTTGGAGTCTGGGGGAGGCTTGATACAGCCTGGGGGGTCCCTGCGTCTCTCCTGTGC
AGCCTCCGGATTCACCTTTAAC~AACCAGGTCATGGTG~TGGGTCCGCCAGGCTCCAGGGAAGGGACT
AGAGTGGGTCTCA~~CATATTGATCGTGTTGGTCAGGATACATACTACGCAGACTCCGTGAAGGGC~~
CGGTTCACCATCTCCCGCGATAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~CGGG
GTCAGGGAACCCTGGTCACCGTCTCGAGC

>Tar2h-131-127 (SEQ ID NO:556)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATGGGGGGGGGTTGGATACATACTACGCAGACCCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~CGGG
GTCAGGGAACCCTGGTCACCGTCTCGAGC

>Tar2h-131-128 (SEQ ID NO:557)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATGCGGTGGGGTCCGATACATACTACGCAGACCCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~CGGG
GTCAGGGAACCCTGGTCACCGTCTCGAGC

>Tar2h-131-129 (SEQ ID NO:558)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~CGGG
GTCAGGGAACCCTGGTCACCGTCTCGAGC

>Tar2h-131-130 (SEQ ID NO:559)
GAGGTGCAGCTGTTGGAGTCTGGGGGAGGCTTGATACAGCCTGGGGGGTCCCTGCGTCTCTCCTGTGC
AGCCTCCGGATTCACCTTTGGC~AACGAGGTCATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~CGGG
GTCAGGGAACCCTGGTCACCGTCTCGGGC

FIG. 14U

>Tar2h-131-131 (SEQ ID NO:560)
GAGGTGCAGCTGTTGGAGTCTGGGGGAGGCTTGATACAGCCTGGGGGGTCCCTGCGTCTCTCCTGTGC
AGCCTCCGGATTCACCTTTAAC~AACCAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~CGGG
GTCAGGGAACCCTGGTCACCGTCTCGAGC

>Tar2h-131-132 (SEQ ID NO:561)
GAGGTGCAGCTGTTGGAGTCTGGGGGAGGCTTGATACAGCCTGGGGGGTCCCTGCGTCTCTCCTGTGC
AGCCTCCGGATTCACCTTTGAC~AACACGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~CGGG
GTCAGGGAACCCTGGTCACCGTCTCGAGC

>Tar2h-131-136 (SEQ ID NO:562)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATCCATACTACGCAGATTCCGTGGAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTC~~~CTTCCTAAGAGGGGGCCTTGGTTTGACTAC~~~TGGG
GTCAGGGAACCCTGGTCACCGTCTCGAGC

>Tar2h-131-151 (SEQ ID NO:563)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATGGGGGGGGGTGGATACATACTACGCAGACCCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~CGGG
GTCAGGGAACCCTGGTCACCGTCTCTAGC

>Tar2h-131-180 (SEQ ID NO:564)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATCCATACTACGCAGATTCCGTGGAGGGC~~
CGGTTCACCATCTCCCGCGACAATTCCAAGAACACGCTGTATCTGCAAATGAACAGCCTGCGTGCCGA
GGACACAGCGGTATATTACTGTGCGGTC~~~CTTCCTAAGAGGGGGCCTTGGTTTGACTAC~~~CGGG
GTCAGGGAACCCTGGTCACCGTCTCGAGC

>Tar2h-131-181 (SEQ ID NO:565)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATCCATACTACGCAGATTCCGTGGAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTC~~~CTTCCTAAGAGGGGGCCTTGGTTTGACTAC~~~CGGG
GTCAGGGAACCCTGGTCACCGTCTCGAGC

FIG. 14V

>Tar2h-131-182 (SEQ ID NO:566)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATCCATACTACGCAGATTCCGTGGAGGGC~~
CGGTTCACCATCTCCCGCGACAATTCCAAGAACACGCTGTATCTGCAAATGAACAGCCTGCGTGCCGA
GGACACAGCGGTATATTACTGTGCGGTC~~~CTTCCTAAGAGGGGGCCTTGGTTTGACTAC~~~TGGG
GTCAGGGAACCCTGGTCACCGTCTCGAGC

>Tar2h-131-183 (SEQ ID NO:567)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATCCATACTACGCAGATTCCGTGGAGGGC~~
CGGTTCACCATCTCCCGCGACAATTCCAAGAACACGCTGTATCTGCAAATGAACAGCCTGCGTGCCGA
GGACACAGCGGTATATTACTGTGCGGTC~~~CTTCCTAAGAGGGGGCCTTGGTTTGACTAC~~~TGGG
GTCAGGGAACCCTGGTCACCGTCTCGAGC

>Tar2h-131-184 (SEQ ID NO:568)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATCCATACTACGCAGATTCCGTGGAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTC~~~CTTCCTAAGAGGGGGCCTTGGTTTGACTAC~~~TGGG
GTCAGGGAACCCTGGTCACCGTCTCGAGC

>Tar2h-131-185 (SEQ ID NO:469)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATCCATACTACGCAGATTCCGTGGAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTC~~~CTTCCTAAGAGGGGGCCTTGGTTTGACTAC~~~AGGG
GTCAGGGAACCCTGGTCACCGTCTCGAGC

>Tar2h-131-188 (SEQ ID NO:570)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATGGGGGGGGGTGGATACATACTACGCAGACCCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCGAGC

>Tar2h-131-189 (SEQ ID NO:571)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATGGGGGGGGGTGGATACATACTACGCAGACCCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCTAGC

FIG. 14W

```
>Tar2h-131-190 (SEQ ID NO:572)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATGGGGGGGGGGTGGATACATACTACGCAGACCCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGGTA~~~CTTCCTAAGAGGGGGCCTTGGTTTGACTAC~~~CGGG
GTCAGGGAACCCTGGTCACCGTCTCTAGC

>Tar2h-131-191 (SEQ ID NO:573)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATGGGGGGGGGGTGGATACATACTACGCAGACCCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGGTA~~~CTTCCTAAGAGGGGGCCTTGGTTTGACTAC~~~CGGG
GTCAGGGAACCCTGGTCACCGTCTCTAGC

>Tar2h-131-192 (SEQ ID NO:574)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATGGGGGGGGGGTGGATACATACTACGCAGACCCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGGTA~~~CTTCCTAAGAGGGGGCCTTGGTTTGACTAC~~~TGGG
GTCAGGGAACCCTGGTCACCGTCTCTAGC

>Tar2h-131-193 (SEQ ID NO:575)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATGGGGGGGGGGTGGATACATACTACGCAGACCCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGGTA~~~CTTCCTAAGAGGGGGCCTTGGTTTGACTAC~~~TGGG
GTCAGGGAACCCTGGTCACCGTCTCTAGC

>Tar2h-131-194 (SEQ ID NO:576)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTCCCCGGTTGGTCAGGATCCCTTCTACGCAGACTCCGTGAAGGGC~~
CGGTTCACCATCTCCCGCGACAATTCCAAGAACACGCTATATCTGCAAATGAACAGCCTGCGTGCCGA
GGACACAGCGGTATATTACTGTGCGGTA~~~CTTCCTAAGAGGGGGCCTTGGTTTGACTAC~~~TGGG
GTCAGGGAACCCTGGTCACCGTCTCGAGC

>Tar2h-131-195 (SEQ ID NO:577)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTCCCCGGTTGGTCAGGATCCCTTCTACGCAGACTCCGTGAAGGGC~~
CGGTTCACCATCTCCCGCGACAATTCCAAGAACACGCTATATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCGAGC
```

FIG. 14X

>Tar2h-131-196 (SEQ ID NO:578)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTCCCCGGTTGGTCAGGATCCCTTCTACGCAGACTCCGTGAAGGGC~~
CGGTTCACCATCTCCCGCGACAATTCCAAGAACACGCTATATCTGCAAATGAACAGCCTGCGTGCCGA
GGACACAGCGGTATATTACTGTGCGGTA~~~CTTCCTAAGAGGGGGCCTTGGTTTGACTAC~~~TGGG
GTCAGGGAACCCTGGTCACCGTCTCGAGC

>Tar2h-131-197 (SEQ ID NO:579)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATGGGGGGGGGTGGATACATACTACGCAGACCCCGTGAAGGGC~~
CGGTTCACCATCTCCCGCGACAATTCCAAGAACTCCCTGTATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCGAGC

>Tar2h-131-198 (SEQ ID NO:580)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTCCCCGGTTGGTCAGGATCCCTTCTACGCAGACTCCGTGAAGGGC~~
CGGTTCACCATCTCCCGCGACAATTCCAAGAACTCCCTATATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCGAGC

>Tar2h-131-500 (SEQ ID NO:581)
GAGGTGCAGCTGTTGGAGTCTGGGGGAGGCTTGGTACAGCCTGGGGGGTCCCTGCGTCTCTCCTGTGC
AGCCTCCGGATTCACCTTTCAC~GACCAGCACATGGTG~TGGGTCCGCCAGGCTCCGGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCGAGC

>Tar2h-131-501 (SEQ ID NO:582)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~AACAACATCATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAACCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCGAGC

>Tar2h-131-502 (SEQ ID NO:583)
GAGGTGCAGCTGTTGGAGTCTGGGGGAGGCCTGGTACAGCCTGGGGGGTCCCTGCGTCTCTCCTGTGC
AGCCTCCGGATTCTCCTTTAAG~AACAAGACGATGGTG~TGGGTCCGCCAGGCTCAGGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCGAGC

FIG. 14Y

>Tar2h-131-503 (SEQ ID NO:584)
GAGGTGCAGCTGTTGGAGTCTGGGGGAGGCTTGGTACAGCCTGGGGGGTCCCTGCGTCTCTCCTGTGC
AGCCTCCGGATTCACCTTTAAC~AAGCACACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGTTG~~~CTTCCTAAGAGGGGGCCTTGGTTTGACTAC~~~TGGG
GTCAGGGAACCCTGGTCACCGTCTCGAGT

>Tar2h-131-504 (SEQ ID NO:585)
GAGGTGCAGCTGTTGGAGTCTGGGGGAGGCTTGGTACAGCCTGGGGGGTCCCTGCGTCTCTCCTGTGC
AGCCTCCGGATTCACCTTTAAC~AACGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCGAGC

>Tar2h-131-505 (SEQ ID NO:586)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGACT
AGAGTGGGTCTCA~~CATATTGATGGGAGGGGTGGGGGGACATACTACACAGACTCCGTGAAGGGC~~
CGGTTCACCACCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCGAGC

>Tar2h-131-506 (SEQ ID NO:587)
GAGGTGCAGCTGTTGGAGTCTGGCGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCAGCAGGGTGAGGGGACATACTACACAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCGAGC

>Tar2h-131-507 (SEQ ID NO:488)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCCCCAGGGAAGGGTCT
AGAGTGGGTCTCA~~CATATTGATGGGGGGGTGGGGGACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCGAGC

>Tar2h-131-508 (SEQ ID NO:489)
GAGGTGCAGCTGTTGGAGTCTGGGGGAGGCCTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATGGGGGGGTTTGGGGACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCGAGC

FIG. 14Z

>Tar2h-131-509 (SEQ ID NO:590)
GAGGTGCAGCTGTTGGAGTCTGGAGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCGC~~~CTACCTAAGAGGGGCCCTTGGTTTGACTAC~~~TGGG
GTCAGGGAACCCTGGTCACCGTCTCGAGC

>Tar2h-131-510 (SEQ ID NO:591)
GAGGTGCAGCTGTTGGAGTCTGGGGGAGGCTTGGTACAGCCTGGGGGGTCCCTGCGTCTCTCCTGTGC
AGCCTCCGGATTCACCTTTAAC~AACAAGACCATGGTG~TGGGTCCGCCAGGCTCCAGGGAAGGGTCT
AGAGTGGGTCTCA~~CATATTGATGGGCGGGGTGAGCGGACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGCCTTGGTTTGACTAC~~~TGGG
GTCAGGGAACCCTGGTCACCGTCTCGAGC

>Tar2h-131-511 (SEQ ID NO:592)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTCCCCGGTTGGTCAGGATCCCTTCTACGCAGACTCCGTGAAGGGC~~
CGGTTCACCATCTCCCGCGACAATTCCAAGAACACGCTATATCTGCAAATGAACAGCCTGCGTGCCGA
GGACACAGCGGTATATTACTGTGCGCTG~~~CTTCCTAAGAGGGGCCTTGGTTTGACTAC~~~TGGG
GTCAGGGAACCCTGGTCACCGTCTCGAGC

>Tar2h-131-512 (SEQ ID NO:593)
GAGGTGCAGCTGTTGGAGTCTGGGGGAGGCTTGGTACAGCCTGGGGGATCCCTGCGTCTCTCCTGTGC
AGCCTCCGGATTCACCTTTGCG~CATGAGACGATGGTG~TGGGTCCGCCAGGCTCCAGGGAGGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACCGCGGTATATTACTGTGCGCTG~~~CTTCCTAAGAGGGGCCTTGGTTTGACTAC~~~TGGG
GTCAGGGAACCCTGGTCACCGTCTCGAGC

>Tar2h-131-513 (SEQ ID NO:594)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATCGTGTTGGTCAGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACCGCGGTATATTACTGTGCGCGC~~~CTACCTAGGAGGGGCCTTGGTTTGACTAC~~~TGGG
GTCAGGGAACCCTGGTAACCGTCTCGAGC

>Tar2h-131-514 (SEQ ID NO:595)
GAGGTGCAGCGTTGGAGTCTGGGGGAGGCTTGGTACAGCCTGGGGGGTCCCTGCGTCTCTCCTGTGCA
GCCTCCGGATTCACCTTTGCG~CATGAGACGATGGTG~TGGGTCCGCCAGGCTCCAGGGAAGGGTCTA
GAGTGGGTCTCA~~CATATTGATCGTGTTGGTCAGGATACATACTACGCAGACTCCGTGAGGGC~~C
GGTTCACCATCTCCCGCGACAATTCCAAGAACACGCTGTATCTGCAAATGAACAGCCTGCGTGCCGAG
GACACAGCGGTATATTACTGTGCGCTG~~~CTTCCTAAGAGGGGCCTTGGTTTGACTAC~~~TGGGG
TCAGGGAACCCTGGTCACCGTCTCGAGC

FIG. 14A2

>Tar2h-131-515(SEQ ID NO:596)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTTCGGATGATGGTAATTCTACATACTACGCAGACTCCGTGAAGGGC~~
CGGTTCACCATCTCCCGCGACAATTCCAAGAACACGCTGTATCTGCAAATGAACAGCCTGCGTGCCGA
GGACACCGCGGTATATTACTGTGCGCGG~~~CTCCCGAAGAGGGGGCCTTGGTTTGACTAC~~~TGGG
GTCAGGGAACCCTGGTCACCGTCTCGAGC

>Tar2h-131-516(SEQ ID NO:597)
GAGGTGCAGCTGTTGGAGTCTGGGGGAGGCTTGGTACAGCCTGGGGGGTCCCTGCGTCTCTCCTGTGC
AGCCTCCGGATTCACCTTTGCC~CATGAGGCCATGGTG~TGGGTCCGCCAGGCTCCAGGGAAGGGTCT
AGAGTGGGTCTCA~~CATATTGATGGGGGGGGTGAGAGCACATACTACGCAGACTCCGTGAAGGGC~~
CGGTTCACCATCTCCCGCGACAATTCCAAGAACACGCTGTATCTGCAAATGAACAGCCTGCGTGCCGA
GGACACCGCGGTATATTACTGTGCGCGC~~~CTACCTCCGCCGGGGCCTTGGTTTGACTAC~~~TGGG
GTCAGGGAACCCTGGTCACCGTCTCGAGC

>Tar2h-131-517 (SEQ ID NO:598)
GAGGTGCAGCTGTTGGAGTCTGGGGGAGGCTTGGTACAGCCTGGGGGGTCCCTGCGTCTCTCCTGTGC
AGCCTCCGGATTCACCTTTCAC~AACAAGGACATGGTG~TGGGTCCGCCAGGCTCCAGGGAAGGGTCT
AGAGTGGGTCTCA~~CATATTGATGGGGGGGGTGAGAGCACATACTACGCAGACTCCGTGAAGGGC~~
CGGTTCACCATCTCCCGCGACAATTCCAAGAACACGCTGTATCTGCAAATGAACAGCCTGCGTGCCGA
GGACACCGCGGTATATTACTGTGCGCGC~~~CTACCTTTGTTGTTGCCTTGGTTTGACTAC~~~TGGG
GTCAGGGAACCCTGGTCACCGTCTCGAGC

>Tar2h-131-518 (SEQ ID NO:599)
GAGGTGCAGCTGTTGGAGTCTGGGGGAGGCTTGGTACAGCCTGGGGGGTCCCTGCGTCTCTCCTGTGC
AGCCTCCGGATTCACCTTTGCC~ATGAGGACGATGGTG~TGGGTCCGCCAGGCTCCAGGGAAGGGTCT
AGAGTGGGTCTCA~~CATATTGATGGGGGGGGTGAGAGCACATACTACGCAGACTCCGTGAAGGGC~~
CGGTTCACCATCTCCCGCGACAATTCCAAGAACACGCTGTATCTGCAAATGAACAGCCTGCGTGCCGA
GGACACCGCGGTATATTACTGTGCGCGC~~~CTACCTAAGCGGGGGCCTTGGTTTGACTAC~~~TGGG
GTCAGGGAACCCTGGTCACCGTCTCGAGC

>Tar2h-131-519 (SEQ ID NO:600)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATGGGGGGGGTGAGAGCACATACTACGCAGACTCCGTGAAGGGC~~
CGGTTCACCATCTCCCGCGACAATTCCAAGAACACGCTGTATCTGCAAATGAACAGCCTGCGTGCCGA
GGACACCGCGGTATATTACTGTGCGCGC~~~CTACCTAAGCGGGGGCCTTGGTTTGACTAC~~~TGGG
GTCAGGGAACCCTGGTCACCGTCTCGAGC

>Tar2h-131-520 (SEQ ID NO:601)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATGGGGGGGGGTTGGTGACATACTACACAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGCCTTGGTTTGACTAC~~~TGGG
GTCAGGGAACCCTGGTCACCGTCTCGAGC

FIG. 14B2

>Tar2h-131-521 (SEQ ID NO:602)
GAGGTGCAGCTGTTGGAGTCTGGGGGAGGCTTGGTACAGCCTGGGGGGTCCCTGCGTCTCTCCTGTGC
AGCCTCCGGATTCACCTTTAAC~AACACGACCATGGTG~TGGGTCCGCCAGGCTCCAGGGAAGGGTCT
AGAGTGGGTCTCG~~CATATTGATGGCGTGGGGGGGGATACATACTACGCAGACCCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCGAGC

>Tar2h-131-522 (SEQ ID NO:603)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~AACAAGACCATGGTG~TGGGTCCGCCAGGCTCCAGGGAAGGGTCT
AGAGTGGGTCTCA~~CATATTGATGGGTTGGGTTTAGTGACATACTACGCAGACTCCGTGGAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCGAGC

>Tar2h-131-523 (SEQ ID NO:604)
GAGGTGCAGCTGTTGGAGTCTGGGGGAGGCTTGGTACAGCCTGGGGGGTCCCTGCGTCTCTCCTGTGC
AGCCTCCGGATTCACCTTTAAC~ACGACGAACATGGTG~TGGGTCCGCCAGGCTCCAGGGAAGGGTCT
AGAGTGGGTCTCA~~GAGATTAGGGTTGGGGGTGGGGATACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCAAGC

>Tar2h-131-524 (SEQ ID NO:605)
GAGGTGCAGCTGTTGGAGTCTGGGGGAGGTTTGGTACAGCCTGGGGGGTCCCTGCGTCTCTCCTGTGC
AGCCTCCGGATTCACCTTTAAG~AACAAGACCATGGTG~TGGGTCCGCCAGGCTCCAGGGAAGGGTCT
AGAGTGGGTCTCA~~CATATTGATCAGGAGGGTGAGGGCACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~CGGG
GTCAGGGAACCCTGGTCACCGTCTCGAGC

>Tar2h-131-525 (SEQ ID NO:606)
GAGGTGCAGCTGTTGGAGTCTGGGGGAGGCTTGGTACAGCCTGGGGGGTCCCTGCGTCTCTCCTGTGC
AGCCTCCGGATTCACCTTTAAC~AACACCACGATGGTG~TGGGTCCGCCAGGCTCCAGGGAAGGGTCT
AGAGTGGGTCTCA~~CATATTGATGGGGAGGGTTCGGTGACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCGAGC

>Tar2h-131-526 (SEQ ID NO:607)
GAGGTGCAGCTGTTGGAGTCTGGGGGAGGCTTGGTACAGCCTGGGGGGTCCCTGCGTCTCTCCTGTGC
AGCCTCCGGATTCACCTTTGAG~AACAAGACCATGGTG~TGGGTCCGCCAGGCTCCAGGGAAGGGTCT
AGAGTGGGTCTCA~~CATATTGATGCCACCGGTACCATCACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~CGGG
GTCAGGGAACCCTGGTCACCGTCTCGAGC

FIG. 14C2

>Tar2h-131-527 (SEQ ID NO:608)
GAGGTGCAGCTGTTGGAGTCTGGGGGAGGCTTGGTACAGCCTGGGGGGTCCCTGCGTCTCTCCTGTGC
AGCCTCCGGATTCACCTTTAAC~AAGAAGACCATGGTG~TGGGTCCGCCAGGCTCCAGGGAAGGGTCT
AGAGTGGGTCTCA~~CATATTGATGGGAAGGGTCAGGCGACATACTACGCAGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGGACCCTGGTCACCGTCTCGAGC

>Tar2h-131-528 (SEQ ID NO:609)
GAGGTGCAGCGTTGGAGTCTGGGGGAGGCTTGGTACAGCCTGGGGGGTCCCTGCGTCTCTCCTGTGCA
GCCTCCGGATTCACCTTTGCG~CATGAGACGATGGTG~TGGGTCCGCCAGGCTCCAGGGAAGGGTCTA
GAGTGGGTCTCA~~CATATTGATCGTGTTGGTCAGGATACATACTACGCAGACTCCGTGGAGGGC~~C
GGTTCACCATCTCCCGCGACAATTCCAAGAACACGCTGTATCTGCAAATGAACAGCCTGCGTGCCGAG
GACACAGCGGTATATTACTGTGCGCTG~~~CTTCCTAAGAGGGGGCCTTGGTTTGACTAC~~~TGGGG
TCAGGGAACCCTGGTCACCGTCTCGAGC

>Tar2h-131-529 (SEQ ID NO:610)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATGGGGGGGGTGAGAGCACATACTACGCAGACTCCGTGGAGGGC~~
CGGTTCACCATCTCCCGCGACAATTCCAAGAACACGCTGTATCTGCAAATGAACAGCCTGCGTGCCGA
GGACACCGCGGTATATTACTGTGCGCGC~~~CTACCTAAGCGGGGGCCTTGGTTTGACTAC~~~TGGG
GTCAGGGAACCCTGGTCACCGTCTCGAGC

>Tar2h-131-530 (SEQ ID NO:611)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATGGGGGGGGTGAGAGCACATACTACGCAGACCCGGTGGAGGGC~~
CGGTTCACCATCTCCCGCGACAATTCCAAGAACACGCTGTATCTGCAAATGAACAGCCTGCGTGCCGA
GGACACCGCGGTATATTACTGTGCGCGC~~~CTACCTAAGCGGGGGCCTTGGTTTGACTAC~~~TGGG
GTCAGGGAACCCTGGTCACCGTCTCGAGC

>Tar2h-131-531 (SEQ ID NO:612)
GAGGTGCAGCTGTTGGAGTCTGGGGGAGGCTTGGTACAGCCTGGGGGGTCCCTGCGTCTCTCCTGTGC
AGCCTCCGGATTCACCTTTGAG~AACAAGACCATGGTG~TGGGTCCGCCAGGCTCCAGGGAAGGGTCT
AGAGTGGGTCTCA~~CATATTGATGCCACCGGTACCATCACATACTACGCAGACTCCGTGGAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~CGGG
GTCAGGGAACCCTGGTCACCGTCTCGAGC

>Tar2h-131-532 (SEQ ID NO:613)
GAGGTGCAGCTGTTGGAGTCTGGGGGAGGCTTGGTACAGCCTGGGGGGTCCCTGCGTCTCTCCTGTGC
AGCCTCCGGATTCACCTTTAAC~AAGAAGACCATGGTG~TGGGTCCGCCAGGCTCCAGGGAAGGGTCT
AGAGTGGGTCTCA~~CATATTGATGGGAAGGGTCAGGCGACATACTACGCAGACTCCGTGGAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGGACCCTGGTCACCGTCTCGAGC

FIG. 14D2

>Tar2h-131-533 (SEQ ID NO:614)
GAGGTGCAGCTGTTGGAGTCTGGGGGAGGCTTGGTACAGCCTGGGGGGTCCCTGCGTCTCTCCTGTGC
AGCCTCCGGATTCACCTTTAAC~AAGAAGACCATGGTG~TGGGTCCGCCAGGCTCCAGGGAAGGGTCT
AGAGTGGGTCTCA~~CATATTGATGGGAAGGGTCAGGATCCCTTCTACACCGACTCCGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGGACCCTGGTCACCGTCTCGAGC

>Tar2h-131-534 (SEQ ID NO:615)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATGGGGGGGGGTTGGTGACATACTACACCGACCCGGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCGAGC

>Tar2h-131-535 (SEQ ID NO:616)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATGGGGGGGGGTTGGTGACATACTACACCGACTCCGTGGAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCGAGC

>Tar2h-131-536 (SEQ ID NO:617)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATGGGGGGGGGTTGGTGACATACTACACCGACCCGGTGGAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCGAGC

>Tar2h-131-537 (SEQ ID NO:618)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTCCCCGGTTGGTCAGGATCCCTTCTACGCAGACTCCGTGGAGGGC~~
CGGTTCACCATCTCCCGCGACAATTCCAAGAACACGCTATATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCGAGC

>Tar2h-131-538 (SEQ ID NO:619)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTCCCCGGTTGGTCAGGATCCCTTCTACGCAGACCCGGTGAAGGGC~~
CGGTTCACCATCTCCCGCGACAATTCCAAGAACACGCTATATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCGAGC

FIG. 14E2

\>Tar2h-131-539 (SEQ ID NO:620)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTCCCCCGGTTGGTCAGGATCCCTTCTACACCGACTCCGTGAAGGGC~~
CGGTTCACCATCTCCCGCGACAATTCCAAGAACACGCTATATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCGAGC

\>Tar2h-131-540 (SEQ ID NO:621)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTCCCCCGGTTGGTCAGGATCCCTTCTACACCGACTCCGTGGAGGGC~~
CGGTTCACCATCTCCCGCGACAATTCCAAGAACACGCTATATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCGAGC

\>Tar2h-131-541 (SEQ ID NO:622)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCACGGAAGGGTCT
AGAGTGGGTCTCA~~CATATTGATGGGGGGGTGAGAGCACATACTACACCGACCCGGTGAAGGGC~~
CGGTTCACCATCTCCCGCGACAATTCCAAGAACACGCTGTATCTGCAAATGAACAGCCTGCGTGCCGA
GGACACCGCGGTATATTACTGTGCGCGC~~~CTACCTAAGCGGGGCCTTGGTTTGACTAC~~~TGGG
GTCAGGGAACCCTGGTCACCGTCTCGAGC

\>Tar2h-131-542 (SEQ ID NO:623)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATGGGGGGGTGAGAGCACATACTACACCGACTCCGTGGAGGGC~~
CGGTTCACCATCTCCCGCGACAATTCCAAGAACACGCTGTATCTGCAAATGAACAGCCTGCGTGCCGA
GGACACCGCGGTATATTACTGTGCGCGC~~~CTACCTAAGCGGGGCCTTGGTTTGACTAC~~~TGGG
GTCAGGGAACCCTGGTCACCGTCTCGAGC

\>Tar2h-131-543 (SEQ ID NO:624)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATGGGGGGGTGAGAGCACATACTACACCGACCCGGTGGAGGGC~~
CGGTTCACCATCTCCCGCGACAATTCCAAGAACACGCTGTATCTGCAAATGAACAGCCTGCGTGCCGA
GGACACCGCGGTATATTACTGTGCGCGC~~~CTACCTAAGCGGGGCCTTGGTTTGACTAC~~~TGGG
GTCAGGGAACCCTGGTCACCGTCTCGAGC

\>Tar2h-131-544 (SEQ ID NO:625)
GAGGTGCAGCTGTTGGAGTCTGGGGGAGGCTTGGTACAGCCTGGGGGGTCCCTGCGTCTCTCCTGTGC
AGCCTCCGGATTCACCTTTAAC~AAGAAGACCATGGTG~TGGGTCCGCCAGGCTCCAGGGAAGGGTCT
AGAGTGGGTCTCA~~CATATTGATGGGAAGGGTCAGGCGACATACTACACCGACCCGGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGGACCCTGGTCACCGTCTCGAGC

FIG. 14F2

>Tar2h-131-545 (SEQ ID NO:626)
GAGGTGCAGCTGTTGGAGTCTGGGGGAGGCTTGGTACAGCCTGGGGGGTCCCTGCGTCTCTCCTGTGC
AGCCTCCGGATTCACCTTTAAC~AAGAAGACCATGGTG~TGGGTCCGCCAGGCTCCAGGGAAGGGTCT
AGAGTGGGTCTCA~~CATATTGATGGGAAGGGTCAGGCGACATACTACACCGACTCCGTGGAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGGACCCTGGTCACCGTCTCGAGC

>Tar2h-131-546 (SEQ ID NO:627)
GAGGTGCAGCTGTTGGAGTCTGGGGGAGGCTTGGTACAGCCTGGGGGGTCCCTGCGTCTCTCCTGTGC
AGCCTCCGGATTCACCTTTAAC~AAGAAGACCATGGTG~TGGGTCCGCCAGGCTCCAGGGAAGGGTCT
AGAGTGGGTCTCA~~CATATTGATGGGAAGGGTCAGGCGACATACTACACCGACCCGGTGGAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGGACCCTGGTCACCGTCTCGAGC

>Tar2h-131-547 (SEQ ID NO:628)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTCCCCGGTTGGTCAGGATCCCTTCTACACCGACCCGGTGAAGGGC~~
CGGTTCACCATCTCCCGCGACAATTCCAAGAACACGCTATATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCGAGC

>Tar2h-131-548 (SEQ ID NO:629)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTCCCCGGTTGGTCAGGATCCCTTCTACGCAGACCCGGTGGAGGGC~~
CGGTTCACCATCTCCCGCGACAATTCCAAGAACACGCTATATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCGAGC

>Tar2h-131-549 (SEQ ID NO:630)
GAGGTGCAGCTGTTGGAGTCTGGGGGAGGCTTGGTACAGCCTGGGGGGTCCCTGCGTCTCTCCTGTGC
AGCCTCCGGATTCACCTTTAAC~AAGAAGACCATGGTG~TGGGTCCGCCAGGCTCCAGGGAAGGGTCT
AGAGTGGGTCTCA~~CATATTGATGGGAAGGGTCAGGATCCCTTCTACACCGACTCCGTGGAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGGACCCTGGTCACCGTCTCGAGC

>Tar2h-131-550 (SEQ ID NO:631)
GAGGTGCAGCTGTTGGAGTCTGGGGGAGGCTTGGTACAGCCTGGGGGGTCCCTGCGTCTCTCCTGTGC
AGCCTCCGGATTCACCTTTAAC~AAGAAGACCATGGTG~TGGGTCCGCCAGGCTCCAGGGAAGGGTCT
AGAGTGGGTCTCA~~CATATTGATGGGAAGGGTCAGGATCCCTTCTACGCAGACCCGGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGGACCCTGGTCACCGTCTCGAGC

FIG. 14G2

>Tar2h-131-551 (SEQ ID NO:632)
GAGGTGCAGCTGTTGGAGTCTGGGGGAGGCTTGGTACAGCCTGGGGGGTCCCTGCGTCTCTCCTGTGC
AGCCTCCGGATTCACCTTTAAC~AAGAAGACCATGGTG~TGGGTCCGCCAGGCTCCAGGGAAGGGTCT
AGAGTGGGTCTCA~~CATATTGATGGGAAGGGTCAGGATCCCTTCTACACCGACCCGGTGAAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGGACCCTGGTCACCGTCTCGAGC

>Tar2h-131-552 (SEQ ID NO:633)
GAGGTGCAGCTGTTGGAGTCTGGGGGAGGCTTGGTACAGCCTGGGGGGTCCCTGCGTCTCTCCTGTGC
AGCCTCCGGATTCACCTTTAAC~AAGAAGACCATGGTG~TGGGTCCGCCAGGCTCCAGGGAAGGGTCT
AGAGTGGGTCTCA~~CATATTGATGGGAAGGGTCAGGATCCCTTCTACACCGACTCCGTGGAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGGACCCTGGTCACCGTCTCGAGC

>Tar2h-131-553 (SEQ ID NO:634)
GAGGTGCAGCTGTTGGAGTCTGGGGGAGGCTTGGTACAGCCTGGGGGGTCCCTGCGTCTCTCCTGTGC
AGCCTCCGGATTCACCTTTAAC~AAGAAGACCATGGTG~TGGGTCCGCCAGGCTCCAGGGAAGGGTCT
AGAGTGGGTCTCA~~CATATTGATGGGAAGGGTCAGGATCCCTTCTACACCGACCCGGTGGAGGGC~~
CGGTTCACCATCTCCCGCGACAATTCCAAGAACACGCTGTATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGGACCCTGGTCACCGTCTCGAGC

>Tar2h-131-554 (SEQ ID NO:635)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTCCCCCGGTTGGTCAGGATCCCTTCTACACCGACCCGGTGGAGGGC~~
CGGTTCACCATCTCCCGCGACAATTCCAAGAACACGCTATATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCGAGC

>Tar2h-131-555 (SEQ ID NO:636)
GAGGTGCAGCTGTTGGAGTCTGGGGGAGGCTTGGTACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATGGGGGGGTGAGAGCCCCTACTACGCAGACTCCGTGAAGGGC~~
CGGTTCACCATCTCCCGCGACAATTCCAAGAACACGCTGTATCTGCAAATGAACAGCCTGCGTGCCGA
GGACACCGCGGTATATTACTGTGCGCGC~~~CTACCTAAGCGGGGGCCTTGGTTTGACTAC~~~TGGG
GTCAGGGAACCCTGGTCACCGTCTCGAGC

>Tar2h-131-556 (SEQ ID NO:637)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTCCCCCGGTTGGTCAGGATCCCTTCTACGCAGACTCCGTGAAGGGC~~
CGGTTCACCATCTCCCGCGACAATTCCAAGAACACGCTATATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCGAGC

FIG. 14H2

>Tar2h-131-557 (SEQ ID NO:638)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTCCCCCGGTTGGTCAGGATCCCTTCTACGCAGACCCGGTGAAGGGC~~
CGGTTCACCATCTCCCGCGACAATTCCAAGAACACGCTATATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCGAGC

>Tar2h-131-558 (SEQ ID NO:639)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTCCCCCGGTTGGTCAGGATCCCTTCTACACCGACTCCGTGAAGGGC~~
CGGTTCACCATCTCCCGCGACAATTCCAAGAACACGCTATATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCGAGC

>Tar2h-131-559 (SEQ ID NO:640)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTCCCCCGGTTGGTCAGGATCCCTTCTACACCGACTCCGTGGAGGGC~~
CGGTTCACCATCTCCCGCGACAATTCCAAGAACACGCTATATCTGCAAATGAACAGCCTGCGTGCCGA
GGACACAGCGGTATATTACTGTGCGCTG~~~CTTCCTAAGAGGGGGCCTTGGTTTGACTAC~~~TGGG
GTCAGGGAACCCTGGTCACCGTCTCGAGC

>Tar2h-131-560 (SEQ ID NO:641)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATGGGGGGGTGAGAGCACATACTACGCAGACTCCGTGGAGGGC~~
CGGTTCACCATCTCCCGCGACAATTCCAAGAACACGCTGTATCTGCAAATGAACAGCCTGCGTGCCGA
GGACACCGCGGTATATTACTGTGCGCGC~~~CTACCTAAGCGGGGGCCTTGGTTTGACTAC~~~TGGG
GTCAGGGAACCCTGGTCACCGTCTCGAGC

>Tar2h-131-561 (SEQ ID NO:642)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATGGGGGGGTGAGAGCACATACTACACCGACCCGGTGAAGGGC~~
CGGTTCACCATCTCCCGCGACAATTCCAAGAACACGCTGTATCTGCAAATGAACAGCCTGCGTGCCGA
GGACACCGCGGTATATTACTGTGCGCGC~~~CTACCTAAGCGGGGCCTTGGTTTGACTAC~~~TGGG
GTCAGGGAACCCTGGTCACCGTCTCGAGC

>Tar2h-131-562 (SEQ ID NO:643)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATGGGGGGGTGAGAGCACATACTACACCGACTCCGTGGAGGGC~~
CGGTTCACCATCTCCCGCGACAATTCCAAGAACACGCTGTATCTGCAAATGAACAGCCTGCGTGCCGA
GGACACCGCGGTATATTACTGTGCGCGC~~~CTACCTAAGCGGGGCCTTGGTTTGACTAC~~~TGGG
GTCAGGGAACCCTGGTCACCGTCTCGAGC

FIG. 14I2

>Tar2h-131-563 (SEQ ID NO:644)
GAGGTGCAGCTGTTGGAGTCTGGGGGAGGCTTGATACAGCCTGGGGGGTCCCTGCGTCTCTCCTGTGC
AGCCTCCGGATTCACCTTTGCG~CATGAGACGATGGTG~TGGGTCCGCCAGGCTCCAGGGAAGGGTCT
AGAGTGGGTCTCA~~CATATTGATGGGGGGGGTGAGAGCACATACTACACCGACCCGGTGGAGGGC~~
CGGTTCACCATCTCCCGCGACAATTCCAAGAACACGCTGTATCTGCAAATGAACAGCCTGCGTGCCGA
GGACACCGCGGTATATTACTGTGCGCGC~~~CTACCTAAGCGGGGGCCTTGGTTTGACTAC~~~TGGG
GTCAGGGAACCCTGGTCACCGTCTCGAGC

>Tar2m-15-2 (SEQ ID NO:645)
GACATCCAGATGACCCAGTCTCCATCCTCCCTGTCTGCATCTGTAGGAGACCGTGTCACCATCACTTG
C~CGGGCAAGTCAGTATATTCATACGAGTTTACAG~TGGTACCAGCAGAAACCAGGGAAAGCCCCTAA
ACTCCTGATC~~TATGGGTCGTCCAGGTTGCATAGT~~GGGGTCCCATCACGTTTCAGTGGCAGTGGA
TCTGGGACAGATTTCACTCTCACCATCAGCAGTCTGCAACCTGAAGATTTTGCTACGTACTACTGT~~
~CAACAGAATCATTATAGTCCTTTTACG~~~TTCGGCCAAGGGACCAAGGTGGAAATCAAACGG

>Tar2m-15-5 (SEQ ID NO:646)
GACATCCAGATGACCCAGTCTCCATCCTCCCTGTCTGCATCTGTAGGAGACCGTGTCACCATCACTTG
C~CGGGCAAGTCAGTATATTCATACGAGTTTACAG~TGGTACCAGCAGAAACCAGGGAAAGCCCTTAA
GCTCCTGATC~~TATGGGTCGTCCAGGTTGCAAAGT~~GGGGTCCCATCACGTTTCAGTGGCAGTGGA
TCTGGGACAGATTTCACTTTCACCATCAGCAGTCTGCAACCTGAAGATTTTGCTACGTACTACTGT~~
~CAACAGAATCATCATAGTCCCTTTACG~~~TACGGCCAAGGGACCAAGGTGGAAATCAAACGG

>Tar2m-15-6 (SEQ ID NO:647)
GACATCCAGATGACCCAGTCTCCATCCTCCCTGTCTGCATCTGTAGGAGACCGTGTCACCATCACTTG
C~CGGGCAAGTCAGTATATTCATACGAGTTTACAG~TGGTACCAGCAGAAACCAGGGAAAGCCCCTAA
ACTCCTGATC~~TATGGGTCGTCCAGGTTGCATAGT~~GGGGTCCCATCACGTTTCAGTGGCAGTGGA
TCTGGGACAGATTTCACTCTCACCATCAGGAGTCTGCAACCTGAAGATCTTGCTACGTACTACTGT~~
~CAACAGAATCATTACAGTCCTTTTACG~~~TTCGGCCAAGGGACCAAGGTGGAAATCAACGGG

>Tar2m-15-8 (SEQ ID NO:648)
GACATCCAGATGACCCAGTCTCCATCCTCCCTGTCTGCATCTGTAGGAGACCGTGTCACCATCACTTG
C~CGGGCAAGTCAGTATATTCATACGAGTGTACAG~TGGTACCAGCAGAAACCAGGGAAAGCCCCTAA
ACTCCTGATC~~TATGGGTCGTCCAGGTTGCATAGT~~GGGGTCCCATCACGTTTCAGTGGCAGTGGA
TCTGGGACAGATTTCACTCTCACCATCAGCAGTCTGCAACCTGAAGATTTTGCTACGTACTACTGT~~
~CAACAGAATCATTATAGTCCTTTTACG~~~TTCGGCCAAGGGACCAAGGTGGAAATCAAACGG

>Tar2m-15-9 (SEQ ID NO:649)
GACATCCAGATGACCCAGTCTCCATCCTCCCTGTCTGCATCTGTAGGAGACCGTGTCACCATCACTTG
C~CGGGCAAGTCAGTATATTCATACGAGTTTACAA~TGGTACCAGCAGAAACCAGGGAAAGCCCCTAA
ACTCCTGATC~~TATGGGTCGTCCAGGTTGCATAGT~~GGGGTCCCATCACGTTTCAGTGGCAGTGGA
TCTGGGACAGATTTCACTCTCACCATCAGCAGTCTGCAACCTGAAGATTTTGCTACGTACTACTGT~~
~CAACAGAATCATTATAGTCCTTTTACG~~~TACGGCCAAGGGACCAAGGTGGAAATCAAACGG

>Tar2m-15-12 (SEQ ID NO:650)
GACATCCAGATGACCCAGTCTCCATCCTCCCTGTCTGCATCTGTAGGAGACCGTGTCACCATCACTTG
C~CGGGCAAGTCAGTATATTCATACGAGTGTACAG~TGGTACCAGCAGAAACCAGGGAAAGCCCCTAA
ACTCCTGATC~~TATGGGTCGTCCAGGTTGCATAGT~~GGGGTCCCATCACGTTTCAGTGGCAGTGGA
TCTGGGACAGATTTCACTCTCACCATCAGCAGTCTGCAACCTGAAGATTTTGCTACGTACTACTGT~~
~CAACAGAATCATTATAGTCCTTTTACG~~~TACGGCCAAGGGACCAAGGTGGAAATCAAACGG

FIG. 14J2

METHODS FOR TARGETING PULMONARY DISEASES WITH AGENTS THAT BIND A TARGET IN PULMONARY TISSUE

RELATED APPLICATIONS

This application is a continuation of U.S. application Ser. No. 13/356,228 which is a divisional of U.S. application Ser. No. 12/084,084 which is in turn the U.S. National Stage application of International Application No. PCT/GB2006/003935, filed Oct. 23, 2006 and published in English which claims priority under 35 U.S.C. §119 or 365 to United Kingdom, Application No. GB 0521621.3, filed Oct. 24, 2005. The entire teachings of the above applications are incorporated herein by reference.

BACKGROUND OF THE INVENTION

The in vivo use of many agents with therapeutic or diagnostic potential is not possible. Larger agents that have in vivo serum half-lives that are sufficiently long to allow for therapeutic or diagnostic efficacy often are unable to penetrate tissues or organs to produces a desired therapeutic or diagnostic effect at a desired location. Smaller agents are able to enter tissues and organs, but frequently have short in vivo serum half-lives, and are rapidly cleared from the systemic circulation. For example, the in vivo serum half-life of dAb monomers is about 30 minutes. (See, Examples 9 and 13 of WO 2004/081026 A2.) Similarly, the in vivo serum half-life of antigen-binding fragments of antibodies, particularly Fv fragments, is also short and makes them unsuitable for many in vivo therapeutic and diagnostic applications. (Peters et al., *Science* 286(5439):434 (1999).) Further, altering or modifying such agents to increase the in vivo serum half-life can reduce the activity of the agent.

A need exists for methods for administering agents (e.g., to pulmonary tissue) to produce a long therapeutic window for the agent.

Agents that bind TNF and neutralize its activity have proven to be effective therapeutic agents for certain inflammatory conditions, such as arthritis. However, agents that bind TNF have not been demonstrated to be effective in treating lung inflammation or respiratory diseases, such as chronic obstructive pulmonary disease (COPD). (See, e.g., van der Vaart et al., *Am. Respir. Crit. Care Med.*, 172(4): 465-9 (2005), Rennard et al., *Proc. Amer. Thorac. Soc.*, 2(Abstract Issue):A133, A541 (2005), Abdelhady et al., *Proc. Amer. Thorac. Soc.*, 2(Abstract Issue):A133 (2005).) Moreover, therapeutic agents that target TNF alpha, such as ENBREL® (etanercept; Immunex Corporation) antagonize TNFR1 and TNFR2, and administering such agents can produce immunosuppression and related side effects (e.g., serious infections). These side effects can limit the use of such agents, particularly for chronic diseases where the agent is administered over a long period. (Kollias G. and Kontoyiannis D., *Cytokine Growth Factor Rev.*, 13(4-5): 315-321 (2002).) In contrast, agents that specifically antagonize TNFR1 would have reduced side effects. However, targeting TNFR1 is difficult because agents that cause the receptor to cluster can activate signaling through the receptor, which can lead to the elaboration of inflammatory mediators such as TNF. In fact, multivalent agents that bind TNFR1, such as anti-TNFR1 antibodies, can induce TNFR1 clustering and signal transduction in the absence of TNF and are commonly used as TNFR1 agonists. (See, e.g., Belka et al., *EMBO*, 14(6):1156-1165 (1995); Mandik-Nayak et al., *J. Immunol*, 167:1920-1928 (2001).) Accordingly, multivalent agents that bind TNFR1, are generally not effective antagonists of TNFR1 even if they block the binding of TNFα to TNFR1.

A need exists for improved agents that antagonize TNF and method for administering such agents to treat lung inflammation and lung disease.

SUMMARY OF THE INVENTION

The invention relates to use of an agent that binds a target in pulmonary tissue (e.g., antibody fragment, antagonist, ligand, dAb monomer) for the manufacture of a long action or long therapeutic window formulation for local administration to pulmonary tissue, or for the manufacture of a medicament for local administration to pulmonary tissue of a low dose effective amount of said agent, wherein at least 50% of the pulmonary tissue level of agent is maintained for a period of at least about 4 hours. Preferably, the formulation or medicament is for local administration to the lung. Preferably, a lung level of at least about 1% of the amount of agent in the formulation or medicament is maintained for at least 4 hours after local administration. More preferably, the agent does not substantially enter the systemic circulation. In some embodiments, the agent has an in vivo serum half life of about 1 second to about 12 hours. In other embodiments, the formulation or medicament is for administering a dose of no more than about 10 mg/kg/day.

The invention relates to use of a domain antibody (dAb) that binds a target in pulmonary tissue for the manufacture of a daily dose formulation for local administration to pulmonary tissue, wherein at least 50% of the lung level of agent is maintained for a period of at least about 4 hours.

The invention relates to use of a domain antibody (dAb) that binds a target in pulmonary tissue for the manufacture of a formulation for treatment or prevention of a respiratory disease, wherein the formulation is for local administration to pulmonary tissue, and does not substantially enter the systemic circulation. In one embodiment, up to about 10 mg of a dAb that binds a target in pulmonary tissue is used. Preferably, the target in pulmonary tissue mediates lung inflammation or a pulmonary disease.

The invention relates to an inhaler or intranasal delivery device for providing a metered dose of a domain antibody (dAb) formulation to a subject for the treatment or prevention of a respiratory disease or condition, wherein the inhaler or intranasal delivery device comprises a dAb formulation and provides a metered daily close containing up to 10 mg of dAb. The invention also relates to use of a domain antibody (dAb) formulation in the manufacture of an inhaler or intranasal delivery device, for the purpose of providing a long-acting inhaled dAb formulation for local delivery to the lung.

The invention also relates to a method for administering an agent that binds a target in pulmonary tissue to a subject to produce a long therapeutic window in pulmonary tissue, comprising administering locally to pulmonary tissue of said subject an effective amount of said agent.

The invention also relates to a method for administering an agent that binds a target in pulmonary tissue to a subject to produce a long therapeutic window in pulmonary tissue, comprising selecting an agent that has an in vivo serum half-life of about 1 second to about 12 hours and binds a target in pulmonary tissue, and administering locally to pulmonary tissue of said subject an effective amount of said agent.

Suitable agents for use in the invention can bind a target in pulmonary tissue selected from the group consisting of TNFR1, IL-1, IL-1R, IL-4, IL-4R, IL-5, IL-6, IL-6R, IL-8, IL-8R, IL-9, IL-9R, IL-10, IL-12 IL-12R, IL-13, IL-13Rα1, IL-13Ra2, IL-15, IL-15R, IL-16, IL-17R, IL-17, IL-18, IL-18R, IL-23 IL-23R, IL-25, CD2, CD4, CD11a, CD23, CD25, CD27, CD28, CD30, CD40, CD40L, CD56, CD138, ALK5, EGFR, FcER1, TGFb, CCL2, CCL18, CEA, CR8, CTGF, CXCL12 (SDF-1), chymase, FGF, Furin, Endothelin-1, Eotaxins (e.g., Eotaxin, Eotaxin-2, Eotaxin-3), GM-CSF, ICAM-1, ICOS, IgE, IFNa, I-309, integrins, L-selectin, MIF, MIP4, MDC, MCP-1, MMPs, neutrophil elastase, osteopontin, OX-40, PARC, PD-1, RANTES, SCF, SDF-1, siglec8, TARC, TGFb, Thrombin, Tim-1, TNF, TNFR1, TRANCE, Tryptase, VEGF, VLA-4, VCAM, α4β7, CCR2, CCR3, CCR4, CCR5, CCR7, CCR8, alphavbeta6, alphavbeta 8, cMET, and CD8.

In an embodiment, an agent for use in the invention can bind a target selected from the group consisting of a protein in the TNF signalling cascade. Preferably, this Protein target is selected from the group comprising TNF alpha, TNF beta, TNFR2, TRADD, FADD, Caspase-8, TNF receptor-associated factor (TRAF), TRAF2, receptor-interacting protein (RIP), Hsp90, Cdc37, IKK alpha, IKK beta, NEMO, inhibitor of kB (IkB), NF-kB, NF-kB essential modulator, apoptosis signal-regulated kinase-1 (aSMase), neutral sphingomyelinase (nSMase), ASK1, Cathepsin-B, germinal center kinase (GSK), GSK-3, factor-associated death domain protein (FADD), factor associated with neutral sphingomyelinase activation (FAN), FLIP, JunD, inhibitor of NF-kB kinase (IKK), MKK3, MKK4, MKK7, IKK gamma, mitogen-activated protein kinase/Erk kinase kinase (MEKK), MEKK1, MEKK3, NIK, poly(ADP-ribose) polymerase (PARD), PKC-zeta, RelA, T2K, TRAF1, TRAF5, death effector domain (DED), death domain (DD), death inducing signalling complex (DISC), inhibitor of apoptosis protein (IAP), c-Jun N-terminal kinase (JNK), mitogen-activated protein kinase (MAPK), phosphoinositide-3OH kinase (PI3K), protein kinase A (PKA), PKB, PKC, PLAD, PTEN, rel homology domain (RHD), really interesting new gene (RING), stress-activated protein kinase (SAPK), TNF alpha-converting enzyme (TACE), silencer of death domain protein (SODD), and TRAF-associated NF-kB activator (TANK). With regard to these preferred targets, reference is made to WO04046189, WO04046186 and WO04046185 (incorporated herein by reference) which provide guidance on the selection of antibody single variable domains for targeting intracellular targets.

The invention relates to use of an antagonist of TNFR1 (e.g., ligand, dAb monomer) for use in the manufacture of a medicament for treating, suppressing or preventing lung inflammation and/or a respiratory disease.

The invention also relates to methods for beating, suppressing or preventing lung inflammation and/or a respiratory disease comprising, selecting an antagonist of Tumor Necrosis Factor Receptor 1 (TNFR1) that has efficacy in a suitable animal model of respiratory disease when administered in an amount that does not exceed about 10 mg/kg/day, wherein efficacy in said animal model exists when cellular infiltration of the lungs, as assessed by total cell count in bronchoalveolar lavage, is inhibited relative to untreated control with $p \leq 0.05$; and administering (e.g., locally administering to pulmonary tissue) an effective amount of said antagonist of TNFR1 to a subject in need thereof.

Respiratory diseases that can be treated, suppressed or prevented using the medicaments, formulations and methods of the invention include lung inflammation, chronic obstructive pulmonary disease, asthma, pneumonia, hypersensitivity pneumonitis, pulmonary infiltrate with eosinophilia, environmental lung disease, pneumonia, bronchiectasis, cystic fibrosis, interstitial lung disease, primary pulmonary hypertension, pulmonary thromboembolism, disorders of the pleura, disorders of the mediastinum, disorders of the diaphragm, hypoventilation, hyperventilation, sleep apnea, acute respiratory distress syndrome, mesothelioma, sarcoma, graft rejection, graft versus host disease, lung cancer, allergic rhinitis, allergy, asbestosis, aspergilloma, aspergillosis, bronchiectasis, chronic bronchitis, emphysema, eosinophilic pneumonia, idiopathic pulmonary fibrosis, invasive pneumococcal disease, influenza, nontuberculous mycobacteria, pleural effusion, pneumoconiosis, pneumocytosis, pneumonia, pulmonary actinomycosis, pulmonary alveolar proteinosis, pulmonary anthrax, pulmonary edema, pulmonary embolus, pulmonary inflammation, pulmonary histiocytosis X, pulmonary hypertension, pulmonary nocardiosis, pulmonary tuberculosis, pulmonary veno-occlusive disease, rheumatoid lung disease, sarcoidosis, Wegener's granulomatosis, and non-small cell lung carcinoma.

The invention also relates to the ligands and dAbs described herein.

The invention also relates to a ligand comprising a protein moiety that has a binding site with binding specificity for TNFR1, wherein said protein moiety comprises an amino acid sequence that is the same as the amino acid sequence of CDR3 of an anti-TNFR1 dAb disclosed herein.

In some embodiments, the ligand comprising a protein moiety that has a binding site with binding specificity for TNFR1, wherein the protein moiety has an amino acid sequence that is the same as the amino acid sequence of CDR3 of an anti-TNFR1 dAb disclosed herein, and also comprises an amino acid sequence that is the same as the amino acid sequence of CDR1 and/or CDR2 of an anti-TNFR1 dAb disclosed herein.

In other embodiments, the ligand comprises a immunoglobulin single variable domain that binds TNFR1, wherein the immunoglobulin single variable domain that binds TNFR1 differs from the amino acid sequence of an anti-TNFR1 dAb disclosed herein at no more than 25 amino acid positions and has a CDR1 sequence that has at least 50% identity to the CDR1 sequence of the anti-TNFR1 dAbs disclosed herein.

In other embodiments, the ligand comprises an immunoglobulin single variable domain that binds TNFR1, wherein the amino acid sequence of the immunoglobulin single variable domain that binds TNFR1 differs from the amino acid sequence of an anti-TNFR1 dAb disclosed herein at no more than 25 amino acid positions and has a CDR2 sequence that has at least 50% identity to the CDR2 sequence of the anti-TNFR1 dAbs disclosed herein.

In other embodiments, the ligand comprises an immunoglobulin single variable domain that binds TNFR1, wherein the amino acid sequence of the immunoglobulin single variable domain that binds TNFR1 differs from the amino acid sequence of an anti-TNFR1 dAb disclosed herein at no more than 25 amino acid positions and has a CDR3 sequence that has at least 50% identity to the CDR3 sequence of the anti-TNFR1 dAbs disclosed herein.

In other embodiments, the ligand comprises an immunoglobulin single variable domain that binds TNFR1, wherein the amino acid sequence of the immunoglobulin single variable domain that binds TNFR1 differs from the amino acid sequence of an anti-TNFR1 dAb disclosed herein at no more than 25 amino acid positions and has a CDR1 sequence and a CDR2 sequence that has at least 50% identity to the CDR1 or CDR2 sequences, respectively, of the anti-TNFR1 dAbs disclosed herein.

In other embodiments, the ligand comprises an immunoglobulin single variable domain that binds TNFR1, wherein the amino acid sequence of the immunoglobulin single variable domain that binds TNFR1 differs from the amino acid sequence of an anti-TNFR1 dAb disclosed herein at no more than 25 amino acid positions and has a CDR2 sequence and a CDR3 sequence that has at least 50% identity to the CDR2 or CDR3 sequences, respectively, of the anti-TNFR1 dAbs disclosed herein.

In other embodiments, the ligand comprises an immunoglobulin single variable domain that binds TNFR1, wherein the amino acid sequence of the immunoglobulin single variable domain that binds TNFR1 differs from the amino acid sequence of an anti-TNFR1 dAb disclosed herein at no more than 25 amino acid positions and has a CDR1 sequence and a CDR3 sequence that has at least 50% identity to the CDR1 or CDR3 sequences, respectively, of the anti-TNFR1 dAbs disclosed herein.

In other embodiments, the ligand comprises an immunoglobulin single variable domain that binds TNFR1, wherein the amino acid sequence of the immunoglobulin single variable domain that binds TNFR1 differs from the amino acid sequence of an anti-TNFR1 dAb disclosed herein at no more than 25 amino acid positions and has a CDR1 sequence, a CDR2 sequence and a CDR3 sequence that has at least 50% identity to the CDR1, CDR2 or CDR3 sequences, respectively, of the anti-TNFR1 dAbs disclosed herein.

In another embodiment, the invention is a ligand comprising an immunoglobulin single variable domain that binds TNFR1, wherein the immunoglobulin single variable domain that binds TNFR1 has a CDR1 sequence that has at least 50% identity to the CDR1 sequences of an anti-TNFR1 dAb disclosed herein.

In another embodiment, the invention is a ligand comprising an immunoglobulin single variable domain that binds TNFR1, wherein the immunoglobulin single variable domain that binds TNFR1 has a CDR2 sequence that has at least 50% identity to the CDR2 sequences of an anti-TNFR1 dAb disclosed herein.

In another embodiment, the invention is a ligand comprising an immunoglobulin single variable domain that binds TNFR1, wherein the immunoglobulin single variable domain that binds TNFR1 has a CDR3 sequence that has at least 50% identity to the CDR3 sequences of an anti-TNFR1 dAb disclosed herein.

In another embodiment, the invention is a ligand comprising an immunoglobulin single variable domain that binds TNFR1, wherein the immunoglobulin single variable domain that binds TNFR1 has a CDR1 and a CDR2 sequence that has at least 50% identity to the CDR1 and CDR2 sequences, respectively, of an anti-TNFR1 dAb disclosed herein.

In another embodiment, the invention is a ligand comprising an immunoglobulin single variable domain that binds TNFR1, wherein the immunoglobulin single variable domain that binds TNFR1 has a CDR2 and a CDR3 sequence that has at least 50% identity to the CDR2 and CDR3 sequences, respectively, of an anti-TNFR1 dAb disclosed herein.

In another embodiment, the invention is a ligand comprising an immunoglobulin single variable domain that binds TNFR1, wherein the immunoglobulin single variable domain that binds TNFR1 has a CDR1 and a CDR3 sequence that has at least 50% identity to the CDR1 and CDR3 sequences, respectively, of an anti-TNFR1 dAb disclosed herein.

In another embodiment, the invention is a ligand comprising an immunoglobulin single variable domain that binds TNFR1, wherein the immunoglobulin single variable domain that binds TNFR1 has a CDR1, CDR2, and a CDR3 sequence that has at least 50% identity to the CDR1, CDR2 and CDR3 sequences, respectively, of an anti-TNFR1 dAb disclosed herein.

The invention also relates to an isolated or recombinant nucleic acid encoding any of the ligands of the invention. In other embodiments, the invention relates to a vector comprising the recombinant nucleic acid of the invention.

The invention also relates to a host cell comprising the recombinant nucleic acid of the invention or the vector of the invention.

The invention also relates to a method for producing a ligand, comprising maintaining a host cell of the invention under conditions suitable for expression of a nucleic acid or vector of the invention, whereby as ligand is produced. In other embodiments, the method of producing a ligand further comprises isolating the ligand.

BRIEF DESCRIPTION OF THE DRAWINGS

FIG. 4A shows that local administration of anti-TNFR1 dAb monomer (DOM/ADS101-native (Dom1 in FIG. 1)) to the lung by intranasal administration (1 mg/kg administered once each day (q.d.)), and systemic administration of PEGylated anti-TNFR1 dAb monomer (DOM/ADS101-pegylated (TNFR1 in FIG. 2)) by intraperitoneal administration (10 mg/kg administered once every two days (q.a.d.)) were more efficacious in reducing the number of macrophages in BAL than phosphodiesterase 4 inhibitor (PDE4I) that was administered at a high dose (10 mg/kg administered orally twice a day (b.i.d.)). Similarly, FIG. 4B shows that local administration of anti-TNFR1 dAb monomer (DOM/ADS101-native (Dom1 in FIG. 1)) to the lung by intranasal administration (1 mg/kg administered once each day (q.d.)), and systemic administration of PEGylated anti-TNFR1 dAb monomer (DOM/ADS 101-pegylated (TNFR1 in FIG. 2)) by intraperitoneal administration (10 mg/kg administered once every two days (q.a.d.)) were more efficacious in reducing the number of neutrophils in BAL than phosphodiesterase 4 inhibitor (PDE4I) that was administered at a high dose (10 mg/kg administered orally twice a day (b.i.d.)).

FIG. 6A-6V shows the amino acid sequences (SEQ ID NOS:1-198) of several human immunoglobulin variable domains that have binding specificity for human TNFR1. The presented amino acid sequences are continuous with no gaps; the symbol has been inserted into the sequences to indicate the locations of the complementarity determining regions (CDRs). CDR1 is flanked by ~, CDR2 is flanked by ~~, and CDR3 is flanked by ——.

FIG. 7A-7B shows the amino acid sequences (SEQ ID NOS:199-211) of several human immunoglobulin variable domains that have binding specificity for mouse TNFR1. The presented amino acid sequences are continuous with no gaps; the symbol has been inserted into the sequences to indicate the locations of the complementarity determining regions (CDRs). CDR1 is flanked by ~, CDR2 is flanked by ~~, and CDR3 is flanked by ——.

FIG. 8A shows a nucleotide sequence (SEQ ID NO:212) encoding the extracellular domain of human (*homo sapiens*) TNFR1.

FIG. 8B shows the amino acid sequence (SEQ ID NO:213) of the extracellular domain of human (*homo sapiens*) TNFR1.

FIG. 9A shows a nucleotide sequence (SEQ ID NO:214) encoding the extracellular domain of mouse (*Mus musculus*) TNFR1.

FIG. 9B shows the amino acid sequence (SEQ ID NO:215) of the extracellular domain of mouse (*Mus musculus*) TNFR1.

FIG. 10A-10Q shows the amino acid sequences (SEQ ID NOS:216-221) of several human immunoglobulin variable domains that have binding specificity for mouse TNFR1, and the amino acid sequence (SEQ ID NOS:222-433) of several human immunoglobulin variable domains that have binding specificity for human TNFR1. The presented amino acid sequences are continuous with no gaps; the symbol ~ has been inserted into the sequences to indicate the locations of the complementarity determining regions (CDRs). CDR1 is flanked by ~, CDR2 is flanked by ~~, and CDR3 is flanked by ——.

FIGS. 14A-14Z and 14A2-14J2 show the nucleotide sequences of several nucleic acids that encode human immunoglobulin variable domains that have binding specificity for human TNFR1 (SEQ ID NOS:434-644), and the nucleotide sequences of several nucleic acids that encode human immunoglobulin variable domains that have binding specificity for mouse TNFR1 (SEQ ID NOS:645-650). The presented sequences are continuous with no gaps; the symbol has been inserted into the sequences to indicate the locations that encode the complementarity determining regions (CDRs). CDR1 is flanked by ~, CDR2 is flanked by ~~, and CDR3 is flanked by ——.

DETAILED DESCRIPTION OF THE INVENTION

Figure 1:
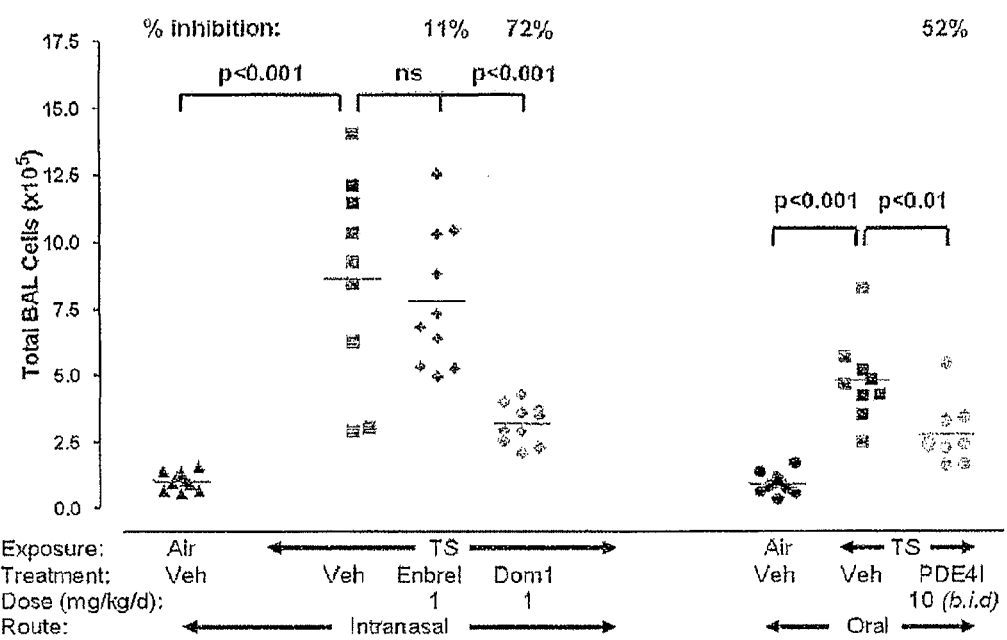
FIG. 1 is a plot showing that an antagonist of TNFR1 has superior efficacy in comparison to other therapeutic agents when administered locally to pulmonary tissue in a subchronic model of tobacco smoke-induced (TS) chronic obstructive pulmonary disease (COPD) in C57BL/6 mice. The plot shows the number of cells present in bronchoalveolar lavage (BAL) of mice at completion of the study described in Example 1. The individual data points for each mouse in the study and the group averages (means; horizontal lines) are shown. The results show that anti-TNFR1 dAb monomer (Dom1) locally administered to the lung by intranasal administration reduced the number of cells in BAL by 72% compared to the untreated group. The results also show that local administration to the lung of a therapeutic agent that targets TNF (ENBREL® (etanercept; Immunex Corporation)) did not have a statistically significant effect on the number of cells in BAL. The results further show that anti-TNFR1 dAb monomer (Dom1) locally administered to the lung by intranasal administration was more effective in reducing the number of cells in BAL that a phosphodiesterase 4 inhibitor (PDE4I, BAY 19-8004) that was administered at a high dose of 10 mg/kg orally twice a day (b.i.d.). TS, tobacco smoke-induced; Veh, vehicle; ns, not statistically significant.

As used herein, the term "antagonist" refers to an agent (e.g., a molecule, a compound) which binds a target (e.g., a receptor protein) and can inhibit a (i.e., one or more) function of the target. For example, an antagonist of a receptor protein can bind the receptor protein and inhibit the binding of a natural or cognate ligand to the receptor protein and/or inhibit signal transduction mediated through receptor protein. For example, antagonists of Tumor Necrosis Factor Receptor 1 "TNFR1" can bind TNFR1 and inhibit binding of TNFα to TNFR1 and/or inhibit signal transduction mediated through TNFR1. Antagonists can be identified, for example, by screening libraries or collections of molecules, such as, the Chemical Repository of the National Cancer Institute, or using other suitable methods. Preferred antagonists are "ligands" as described herein.

As used herein, the term "antagonist of Tumor Necrosis Factor Receptor 1 (TNFR1)" refers to an agent (e.g., a molecule, a compound) which binds TNFR1 and can inhibit a (i.e., one or more) function of TNFR1. For example, an antagonist of TNFR1 can inhibit the binding of TNFα to TNFR1 and/or inhibit signal transduction mediated through TNFR1. Accordingly, TNFR1-mediated processes and cellular responses (e.g., TNFα-induced cell death in a standard L929 cytotoxicity assay) can be inhibited with an antagonist of TNFR1. An antagonist of TNFR1 can be, for example, a small organic molecule, natural product, protein, peptide or peptidomimetic. Antagonists of TNFR1 can be identified, for example, by screening libraries or collections of molecules, such as, the Chemical Repository of the National Cancer Institute, as described herein or using other suitable methods. Preferred antagonists of TNFR1 are antibodies, antigen-binding fragments of antibodies, ligands and dAb monomers described herein.

As used herein, the term "ligand" refers to a polypeptide that comprises a domain that has binding specificity for a desired target. Preferably the binding domain is an immunoglobulin single variable domain (e.g., $V_H$, $V_L$, $V_{HH}$) that has binding specificity for a desired target antigen (e.g., a receptor protein). The binding domain can also comprises one or more complementarity determining regions (CDRs) of an immunoglobulin single variable domain that has binding specificity for a desired target antigen in a suitable format, such that the binding domain has binding specificity for the target antigen. For example, the CDRs can be grafted onto a suitable protein scaffold or skeleton, such as an affibody, an SpA scaffold, an LDL receptor class A domain or an EGF domain. Further, the ligand can be monovalent (e.g., a dAb monomer), bivalent (homobivalent, heterobivalent) or multivalent (homomultivalent, heteromultivalent) as described herein. Thus, "ligands" include polypeptides that consist of a dAb, include polypeptides that consist essentially of such a dAb, polypeptides that comprise a dAb (or the CDRs of a dAb) in a suitable format, such as an antibody format (e.g., IgG-like format, scFv, Fab, Fab', F(ab')$_2$) or a suitable protein scaffold or skeleton, such as an affibody, an SpA scaffold, an LDL receptor class A domain or an EGF domain, dual specific ligands that comprise a dAb that binds a first target protein, antigen or epitope (e.g., TNFR1) and a second dAb that binds another target protein, antigen or epitope (e.g., serum albumin), and multispecific ligands as described herein. The binding domain can also be a protein domain comprising a binding site for a desired target, e.g., a protein domain is selected from an affibody, an SpA domain, an LDL receptor class A domain an EGF domain, an avimer (see, e.g., U.S. Patent Application Publication Nos. 2005/0053973, 2005/0089932, 2005/0164301).

The phrase "immunoglobulin single variable domain" refers to an antibody variable region ($V_H$, $V_{HH}$, $V_L$) that specifically binds an antigen or epitope independently of other V regions or domains; however, as the term is used herein, an immunoglobulin single variable domain can be present in a format (e.g., homo- or hetero-multimer) with other variable regions or variable domains where the other regions or domains are not required for antigen binding by the single immunoglobulin variable domain (i.e., where the immunoglobulin single variable domain binds antigen independently of the additional variable domains). "Immunoglobulin single variable domain" encompasses not only an isolated antibody single variable domain polypeptide, but also larger polypeptides that comprise one or more monomers of an antibody single variable domain polypeptide sequence. A "domain antibody" or "dAb" is the same as an "immunoglobulin single variable domain" polypeptide as the term is used herein. An immunoglobulin single variable domain polypeptide, as used herein refers to a mammalian immunoglobulin single variable domain polypeptide, preferably human, but also includes rodent (for example, as disclosed in WO 00/29004, the contents of which are incorporated herein by reference in their entirety) or camelid $V_{HH}$ dAbs. Camelid dAbs are immunoglobulin single variable domain polypeptides which are derived from species including camel, llama, alpaca, dromedary, and guanaco, and comprise heavy chain antibodies naturally devoid of light chain: $V_{HH}$. $V_{HH}$ molecules are about ten times smaller than IgG molecules, and as single polypeptides, they are very stable, resisting extreme pH and temperature conditions.

As used herein, the term "dose" refers to the quantity of agent (e.g., antagonist of TNFR1) administered to a subject all at one time (unit dose), or in two or more administrations over a defined time interval. For example, dose can refer to the quantity of agent (e.g., antagonist of TNFR1) administered to a subject over the course of one day (24 hours) (daily dose), two days, one week, two weeks, three weeks or one or more months (e.g., by a single administration, or by two or more administrations). The interval between doses can be any desired amount of time.

As use herein, the term "therapeutic window" refers to the range of drug (e.g., antagonist, ligand, dAb monomer) concentrations in the plasma, or in a tissue or organ (e.g., pulmonary tissue, lung) to which a drug is locally administered, that result in a high probability of therapeutic efficacy.

"Complementary" Two immunoglobulin domains are "complementary" where they belong to families of structures which form cognate pairs or groups or are derived from such families and retain this feature. For example, a $V_H$ domain and a $V_L$ domain of an antibody are complementary; two $V_H$ domains are not complementary, and two $V_L$ domains are not complementary. Complementary domains may be found in other members of the immunoglobulin superfamily, such as the $V_\alpha$ and $V_\beta$ (or γ and δ) domains of the T-cell receptor. Domains which are artificial, such as domains based on protein scaffolds which do not bind epitopes unless engineered to do so, are non-complementary. Likewise, two domains based on (for example) an immunoglobulin domain and a fibronectin domain are not complementary.

"Immunoglobulin" This refers to a family of polypeptides which retain the immunoglobulin fold characteristic of antibody molecules, which contains two β sheets and, usually, a conserved disulphide bond. Members of the immunoglobulin superfamily are involved in many aspects of cellular and non-cellular interactions in vivo, including widespread roles in the immune system (for example, antibodies, T-cell receptor molecules and the like), involvement in cell adhesion (for example the ICAM molecules) and intracellular signalling (for example, receptor molecules, such as the PDGF receptor). The present invention is applicable to all immunoglobulin superfamily molecules which possess binding domains. Preferably, the present invention relates to antibodies.

"Domain" A domain is a folded protein structure which retains its tertiary structure independently of the rest of the protein. Generally, domains are responsible for discrete functional properties of proteins, and in many cases may be added, removed or transferred to other proteins without loss of function of the remainder of the protein and/or of the domain. By single antibody variable domain is meant a folded polypeptide domain comprising sequences characteristic of antibody variable domains. It therefore includes complete antibody variable domains and modified variable domains, for example in which one or more loops have been replaced by sequences which are not characteristic of antibody variable domains, or antibody variable domains which have been truncated or comprise N- or C-terminal extensions, as well as folded fragments of variable domains which retain at least in part the binding activity and specificity of the full-length domain.

"Repertoire" A collection of diverse variants, for example polypeptide variants which differ in their primary sequence. A library used in the present invention will encompass a repertoire of polypeptides comprising at least 1000 members.

"Library" The term library refers to a mixture of heterogeneous polypeptides or nucleic acids. The library is composed of members, each of which have a single polypeptide or nucleic acid sequence. To this extent, library is synonymous with repertoire. Sequence differences between library members are responsible for the diversity present in the library. The library may take the form of a simple mixture of polypeptides or nucleic acids, or may be in the form of organisms or cells, for example bacteria, viruses, animal or plant cells and the like, transformed with a library of nucleic acids. Preferably, each individual organism or cell contains only one or a limited number of library members. Advantageously, the nucleic acids are incorporated into expression vectors, in order to allow expression of the polypeptides encoded by the nucleic acids. In a preferred aspect, therefore, a library may take the form of a population of host organisms, each organism containing one or more copies of an expression vector containing a single member of the library in nucleic acid form which can be expressed to produce its corresponding polypeptide member. Thus, the population of host organisms has the potential to encode a large repertoire of genetically diverse polypeptide variants.

"Antibody" An antibody (for example IgG, IgM, IgA, IgD or IgE) or fragment (such as a Fab, F(ab')$_2$, Fv, disulphide linked Fv, scFv, closed conformation multispecific antibody, disulphide-linked scFv, diabody) whether derived from any species naturally producing an antibody, or created by recombinant DNA technology; whether isolated from serum, B-cells, hybridomas, transfectomas, yeast or bacteria).

"Dual-specific ligand" A ligand comprising a first immunoglobulin single variable domain and a second immunoglobulin single variable domain as herein defined, wherein the variable regions are capable of binding to two different antigens or two epitopes on the same antigen which are not normally bound by a monospecific immunoglobulin. For example, the two epitopes may be on the same hapten, but are not the same epitope or sufficiently adjacent to be bound by a monospecific ligand. The dual specific ligands according to the invention are composed of variable domains which have different specificities, and do not contain mutually complementary variable domain pairs which have the same specificity. Dual-specific ligands and suitable methods for preparing dual-specific ligands are disclosed in WO 2004/058821, WO 2004/003019, and WO 03/002609, the entire teachings of each of these published international applications are incorporated herein by reference.

"Antigen" A molecule that is bound by a ligand according to the present invention. Typically, antigens are bound by antibody ligands and are capable of raising an antibody response in vivo. It may be a polypeptide, protein, nucleic acid or other molecule. Generally, the dual specific ligands according to the invention are selected for target specificity against a particular antigen. In the case of conventional antibodies and fragments thereof, the antibody binding site defined by the variable loops (L1, L2, L3 and H1, H2, H3) is capable of binding to the antigen.

"Epitope" A unit of structure conventionally bound by an immunoglobulin $V_H/V_L$ pair. Epitopes define the minimum binding site for an antibody, and thus represent the target of specificity of an antibody. In the case of a single domain antibody, an epitope represents the unit of structure bound by a variable domain in isolation.

"Universal framework" A single antibody framework sequence corresponding to the regions of an antibody conserved in sequence as defined by Kabat ("Sequences of Proteins of Immunological Interest", US Department of Health and Human Services) or corresponding to the human germline immunoglobulin repertoire or structure as defined by Chothia and Lesk, (1987) J. Mol. Biol. 196:910-917. The invention provides for the use of a single framework, or a set of such frameworks, which has been found to permit the derivation of virtually any binding specificity though variation in the hypervariable regions alone.

"Half-life" The time taken for the serum concentration of the ligand to reduce by 50%, in vivo, for example due to degradation of the ligand and/or clearance or sequestration of the ligand by natural mechanisms. The ligands of the invention are stabilised in vivo and their half-life increased by binding to molecules which resist degradation and/or clearance or sequestration. Typically, such molecules are naturally occurring proteins which themselves have a long half-life in vivo. The half-life of a ligand is increased if its functional activity persists, in vivo, for a longer period than a similar ligand which is not specific for the half-life increasing molecule. Thus, a ligand specific for HSA and a target molecule is compared with the same ligand wherein the specificity for HSA is not present, that it does not bind HSA but binds another molecule. For example, it may bind a second epitope on the target molecule. Typically, the half life is increased by 10%, 20%, 30%, 40%, 50% or more. Increases in the range of 2×, 3×, 4×, 5×, 10×, 20×, 30×, 40×, 50× or more of the half life are possible. Alternatively, or in addition, increases in the range of up to 30×, 40×, 50×, 60×, 70×, 80×, 90×, 100×, 150× of the half life are possible.

"Substantially identical (or "substantially homologous")" A first amino acid or nucleotide sequence that contains a sufficient number of identical or equivalent (e.g., with a similar side chain, e.g., conserved amino acid substitutions) amino acid residues or nucleotides to a second amino acid or nucleotide sequence such that the first and second amino acid or nucleotide sequences have similar activities. In the case of antibodies, the second antibody has the same binding specificity and has at least 50% of the affinity of the same.

As used herein, the terms "low stringency," "medium stringency," "high stringency," or "very high stringency conditions" describe conditions for nucleic acid hybridization and washing. Guidance for performing hybridization reactions can be found in *Current Protocols in Molecular Biology*, John Wiley & Sons, N.Y. (1989), 6.3.1-6.3.6, which is incorporated herein by reference in its entirety. Aqueous and nonaqueous methods are described in that reference and either can be used. Specific hybridization conditions referred to herein are as follows: (1) low stringency hybridization conditions in 6×sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C., followed by one or more washes in 0.2×SSC, 0.1% SDS at 65° C.; and preferably (4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

As referred to herein, the term "competes" means that the binding of a first epitope to its cognate epitope binding domain is inhibited when a second epitope is bound to its cognate epitope binding domain. For example, binding may be inhibited sterically, for example by physical blocking of a binding domain or by alteration of the structure or environment of a binding domain such that its affinity or avidity for an epitope is reduced.

Sequences similar or homologous (e.g., at least about 70% sequence identity) to the sequences disclosed herein are also part of the invention. In some embodiments, the sequence identity at the amino acid level can be about 80%, 85%, 90%, 91%, 92%, 93%, 94%, 95%, 96%, 97%, 98%, 99% or higher. At the nucleic acid level, the sequence identity can be about 70%, 75%, 80%, 85%, 90%, 91%, 92%, 93%, 94%, 95%, 96%, 97%, 98%, 99% or higher. Alternatively, substantial identity exists when the nucleic acid segments will hybridize under selective hybridization conditions (e.g., very high stringency hybridization conditions), to the complement of the strand. The nucleic acids may be present in whole cells, in a cell lysate, or in a partially purified or substantially pure form.

Calculations of "homology" or "sequence identity" or "similarity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "homology" is equivalent to amino acid or nucleic acid "identity"). The percent identity between the two sequences is a function of the number of identical positions shared by the sequences, taking into account the number of gaps, and the length of each gap, which need to be introduced for optimal alignment of the two sequences.

Amino acid and nucleotide sequence alignments and homology, similarity or identity, as defined herein are preferably prepared and determined using the algorithm BLAST 2 Sequences, using default parameters (Tatusova, T. A. et al., *FEMS Microbiol Lett*, 174:187-188 (1999)). Alternatively, advantageously, the BLAST algorithm (version 2.0) is employed for sequence alignment, with parameters set to default values. The BLAST algorithm is described in detail at the world wide web site ("www") of the National Center for Biotechnology Information (".ncbi") of the National Institutes of Health ("nih") of the U.S. government (".gov"), in the "/Blast/" directory, in the "blast_help.html" file. The search parameters are defined as follows, and are advantageously set to the defined default parameters.

BLAST (Basic Local Alignment Search Tool) is the heuristic search algorithm employed by the programs blastp, blastn, blastx, tblastn, and tblastx; these programs ascribe significance to their findings using the Statistical methods of Karlin and Altschul, 1990, Proc. Natl. Acad. Sci. USA 87(6):2264-8 (see the "blast_help.html" file, as described above) with a few enhancements. The BLAST programs were tailored for sequence similarity searching, for example to identify homologues to a query sequence. The programs are not generally useful for motif-style searching. For a discussion of basic issues in similarity searching of sequence databases, see Altschul et al. (1994).

The five BLAST programs available at the National Center for Biotechnology Information web site perform the following tasks:

"blastp" compares an amino acid query sequence against a protein sequence database;

"blastn" compares a nucleotide query sequence against a nucleotide sequence database;

"blastx" compares the six-frame conceptual translation products of a nucleotide query sequence (both strands) against a protein sequence database;

"tblastn" compares a protein query sequence against a nucleotide sequence database dynamically translated in all six reading frames (both strands).

"tblastx" compares the six-frame translations of a nucleotide query sequence against the six-frame translations of a nucleotide sequence database.

BLAST uses the following search parameters:

HISTOGRAM Display a histogram of scores for each search; default is yes. (See parameter H in the BLAST Manual).

DESCRIPTIONS Restricts the number of short descriptions of matching sequences reported to the number specified; default limit is 100 descriptions. (See parameter V in the manual page). See also EXPECT and CUTOFF.

ALIGNMENTS Restricts database sequences to the number specified for which high-scoring segment pairs (HSPs) are reported; the default limit is 50. If more database sequences than this happen to satisfy the statistical significance threshold for reporting (see EXPECT and CUTOFF below), only the matches ascribed the greatest statistical significance are reported. (See parameter B in the BLAST Manual).

EXPECT The statistical significance threshold for reporting matches against database sequences; the default value is 10, such that 10 matches are expected to be found merely by chance, according to the stochastic model of Karlin and Altschul (1990). If the statistical significance ascribed to a match is greater than the EXPECT threshold, the match will not be reported. Lower EXPECT thresholds are more stringent, leading to fewer chance matches being reported. Fractional values are acceptable. (see parameter E in the BLAST Manual).

CUTOFF Cutoff score for reporting high-scoring segment pairs. The default value is calculated from the EXPECT value (see above). HSPs are reported for a database sequence only if the statistical significance ascribed to them is at least as high as would be ascribed to a lone HSP having a score equal to the CUTOFF value. Higher CUTOFF values are more stringent, leading to fewer chance matches being reported. (See parameter S in the BLAST Manual). Typically, significance thresholds can be more intuitively managed using EXPECT.

MATRIX Specify an alternate scoring matrix for BLASTP, BLASTX, TBLASTN and TBLASTX. The default matrix is BLOSUM62 (Henikoff & Henikoff, 1992, Proc. Natl. Acad. Sci. USA 89(22):10915-9). The valid alternative choices include: PAM40, PAM120, PAM250 and IDENTITY. No alternate scoring matrices are available for BLASTN; specifying the MATRIX directive in BLASTN requests returns an error response.

STRAND Restrict a TBLASTN search to just the top or bottom strand of the database sequences; or restrict a. BLASTN, BLASTX or TBLASTX search to just reading frames on the top or bottom strand of the query sequence.

FILTER Mask off segments of the query sequence that have low compositional complexity, as determined by the SEG program of Wootton & Federhen (1993) Computers and Chemistry 17:149-163, or segments consisting of short-periodicity internal repeats, as determined by the XNU program of Claverie & States, 1993, Computers and Chemistry 17:191-201, or, for BLASTN, by the DUST program of Tatusov and Lipman (see the world wide web site of the NCBI). Filtering can eliminate statistically significant but biologically uninteresting reports from the blast output (e.g., hits against common acidic-, basic- or proline-rich regions), leaving the more biologically interesting regions of the query sequence available for specific matching against database sequences.

Low complexity sequence found by a filter program is substituted using the letter "N" in nucleotide sequence (e.g., "N" repeated 13 times) and the letter "X" in protein sequences (e.g., "X" repeated 9 times).

Filtering is only applied to the query sequence (or its translation products), not to database sequences. Default filtering is DUST for BLASTN, SEG for other programs.

It is not unusual for nothing at all to be masked by SEG, XNU, or both, when applied to sequences in SWISS-PROT, so filtering should not be expected to always yield an effect. Furthermore, in some cases, sequences are masked in their entirety, indicating that the statistical significance of any matches reported against the unfiltered query sequence should be suspect. NCBI-gi Causes NCBI gi identifiers to be shown in the output, in addition to the accession and/or locus name. Most preferably, sequence comparisons are conducted using the simple BLAST search algorithm provided at the NCBI world wide web site described above, in the "/BLAST" directory.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) $4^{th}$ Ed, John Wiley & Sons, Inc. which are incorporated herein by reference) and chemical methods.

As described herein, a study in which an antagonist of TNFR1 consisting essentially of a dAb monomer that binds TNFR1 was administered in a mouse subchronic model of tobacco smoke-induced chronic obstructive pulmonary disease (COPD) was conducted. The study results revealed that antagonists of TNFR1 (e.g., that comprise a domain antibody (dAb) that binds TNFR1) are effective therapeutic agents for treating respiratory diseases (e.g., inflammation in the lung, acute lung disease, chronic lung disease (e.g., COPD)). In fact, the antagonists tested in the study were more efficacious than high dose phosphodiesterase 4 inhibitor or soluble TNFR1 (ENBREL® (etanercept; Immunex Corporation)) which binds and neutralizes TNFα. The antagonists of TNFR1 studied were efficacious in the model when administered systemically (intraperitoneal injection) or locally to the pulmonary tissue by intra-nasal administration.

Surprisingly, the study results show that local administration of an antagonists that binds a target in pulmonary tissue (e.g., TNFR1) was more effective at inhibiting cellular infiltration of the lungs in the model than was systemic administration of an extended half-life antagonist (PEGylated dAb monomer, PEGylated to increase the hydrodynamic size and the in vivo serum half-life of the dAb monomer), even though five times more antagonist was administered systemically. In molar terms 2.5 times more extended half-life antagonist (PEGylated dAb monomer, PEGylated to increase the hydrodynamic size and the in vivo serum half-life of the dAb monomer) was administered systemically compared to the locally administered dAb monomer.

As described herein, a further study in which the pharmacokinetics of a dAb monomer that binds TNFR1 after local administration to the pulmonary tissue by intranasal administration was conducted. The results of that study revealed that, following local administration to the pulmonary tissue, the dAb monomer had a long residence time in the lung, and that the amount of dAb monomer in the lung was substantially constant over an eight hour period. In addition, local delivery of the dAb monomer to the lung resulted in the brief presence of only a low concentration of dAb monomer in the serum. Specifically, a maximum level of about 150 ng/ml was detected in the serum 1 hour after administration, and no dAb monomer was detectable in the serum after 5 hours.

This results of the pharmacokinetic study are surprising and demonstrate that an agent that binds a target in pulmonary tissue, such as an antibody or antibody fragment that binds a target in pulmonary tissue (e.g, Fab fragment, Fab' fragment, Fv fragment (e.g., scFv, disulfide bonded Fv), $F(ab')_2$ fragment, dAb) or an antagonist of a target in pulmonary tissue (e.g., ligand, dAb monomer), can be locally administered to pulmonary tissue to provide a long therapeutic window (for treating, suppressing, preventing, or diagnosing respiratory conditions) in pulmonary tissue due to the long residence time of such agents in the pulmonary tissue. The results of the pharmacokinetic study, and the long therapeutic window provided by local administration to the pulmonary tissue, also explain the observed superior efficacy of locally administered antagonist of TNFR1 in the mouse model of COPD. Additionally, the observed superior efficacy of dAb monomer when administered locally at a lower dose, the low concentration of dAb monomer that enters into the serum, and the rapid clearance of dAb monomer from the serum, indicate that agents that bind a target in pulmonary tissue (e.g., antibody fragment that binds a target in pulmonary tissue (e.g, Fab fragment, Fab' fragment, Fv fragment (e.g., scFv, disulfide bonded Fv), F(ab')$_2$ fragment, dAb) are much less likely to produce side effects (e.g., immunosuppression, toxicity) than other types of therapeutic agents.

In further studies lung inflammation was induced by the inflammatory stimulator TNFα. The results of these studies demonstrate that antagonists of TNFR1 (anti-TNFR1 dAb that inhibit binding of TNFα to the receptor, or that do not inhibit binding of TNFα to the receptor) significantly inhibit TNFα-induced increases of other inflammatory mediators, such as the early acting neutrophil chemoattractants KC and MIP-1, and the later acting chemokine MCP-1 and adhesion molecule E-selectin, and inhibited cellular infiltration of the lungs.

The studies described herein demonstrate that agents that bind targets in the pulmonary tissue (e.g., antibody fragments (e.g, Fab fragment, Fab' fragment, Fv fragment (e.g., scFv, disulfide bonded Fv), F(ab')$_2$ fragment, dAb), antagonists, ligands, dAb monomers) are superior therapeutics for treating, suppressing or preventing lung inflammation and/or respiratory disease, or for diagnostic purposes, such as imaging. The results also demonstrate that even though dAb monomers have a short in vivo serum half-life, dAbs that bind a target in pulmonary tissue and antagonists that contain such a dAb, can be locally administered to pulmonary tissue to provide a long therapeutic window in pulmonary tissue due to the long residence time of such a dAb in the pulmonary tissue. Accordingly, other agents that bind a target in pulmonary tissue and have short in vivo half-lives (e.g., antibody fragments such as Fab fragments, Fab' fragments, Fv fragments (e.g., scFvs, disulfide bonded Fv)s, F(ab')$_2$ fragments) can be locally administered to pulmonary tissue to provide a long therapeutic window (e.g., for treating, suppressing, preventing, or diagnosing respiratory conditions) in pulmonary tissue.

Generally, agents that bind targets in the pulmonary tissue (e.g., antibody fragments (e.g, Fab fragment, Fab' fragment, Fv fragment (e.g., scFv, disulfide bonded Fv), F(ab')$_2$ fragment, dAb), antagonists, ligands, dAb monomers) can be locally administered to pulmonary tissue to provide a therapeutic window in pulmonary tissue of at least about 4 hours, at least about 5 hours, at least about 6 hours, at least about 7 hours, at least about 8 hours, at least about 9 hours, at least about 10 hours, at least about 11 hours, or at least about 12 hours.

Local Administration of Agents that Bind Targets in Pulmonary Tissue to Pulmonary Tissue.

In a first aspect, the invention relates to methods for administering an agent (e.g., antibody fragment, antagonist, ligand, dAb monomer) that binds a target in pulmonary tissue to a subject to produce a long therapeutic window (e.g., for treating, suppressing, preventing, or diagnosing respiratory conditions) in pulmonary tissue. For example, a therapeutic window in pulmonary tissue of at least about 4 hours, at least about 5 hours, at least about 6 hours, at least about 7 hours, at least about 8 hours, at least about 9 hours, at least about 10 hours, at least about 11 hours, or at least about 12 hours. In accordance with the first aspect of the invention, the agent is administered locally to pulmonary tissue of a subject (e.g., a human).

An agent that binds a target in pulmonary tissue (e.g., antibody fragments (e.g, Fab fragment, Fab' fragment, Fv fragment (e.g., scFv, disulfide bonded Fv), F(ab')$_2$ fragment, dAb), antagonists, ligands, dAb monomers) can be locally administered to pulmonary tissue (e.g., lung) of a subject using any suitable method. For example, an agent can be locally administered to pulmonary tissue via inhalation or intranasal administration. For inhalation or intranasal administration, the agent (antagonist of TNFR1, ligand, dAb monomer) can be administered using a nebulizer, inhaler, atomizer, aerosolizer, mister, dry powder inhaler, metered dose inhaler, metered dose sprayer, metered dose mister, metered dose atomizer, or other suitable delivery device.

In some embodiments, the method comprises administering locally to the pulmonary tissue of a subject an effective amount of an agent (e.g., antibody fragment, antagonist, ligand, dAb monomer) that has a short in vivo serum half-life and binds a target in pulmonary tissue. In accordance with the invention, such agents (e.g., antibody fragment, antagonist, ligand, dAb monomer) can be locally administered to pulmonary tissue to produce a long therapeutic window in pulmonary tissue but will not substantially accumulate in the serum. Due to the short in vivo half-life of such agents (e.g., antibody fragment, antagonist, ligand, dAb monomer), agents that cross the pulmonary epithelium and enter the serum will be quickly eliminated from the serum, and thus will not accumulate to levels that could produce unwanted effects (e.g., systemic side effects). For example, suitable agents (e.g., antibody fragment, antagonist, ligand, dAb monomer) that bind a target in pulmonary tissue for use in the first aspect of the invention can have an in vivo serum half-life of about one second to about 12 hours, about 12 hours or less, about 11 hours or less, about 10 hours or less, about 9 hours or less, about 8 hours or less, about 7 hours or less, about 6 hours or less, about 5 hours or less, about 4 hours or less, about 3 hours or less, about 2 hours or less, about 1 hour or less, or about 30 minutes or less. Preferred antagonists for administration in accordance with the first aspect of the invention comprise a dAb that binds a target in pulmonary tissue.

Particularly preferred agents (e.g., antagonists) for use in the first aspect of the invention are dAb monomers or antigen-binding fragments of antibodies that bind a target in pulmonary tissue (e.g., Fab fragments, Fab' fragments, Fv fragments (e.g., scFvs, disulfide bonded Fvs, F(ab')$_2$ fragments). The in vivo serum half-life of dAb monomers is about 30 minutes. (See, Examples 9 and 13 of WO 2004/081026 A2.) However, as described herein, local delivery of a dAb monomer that binds a target in pulmonary tissue (e.g., TNFR1) resulted in a therapeutic window in the pulmonary tissue of at least 8 hours. Similarly, the in vivo serum half-life of antigen-binding fragments of antibodies, particularly Fv fragments, is also short and makes them unsuitable for many in vivo therapeutic and diagnostic applications. (Peters et al., *Science* 286(5439):434 (1999).) However, as shown by the study results described herein, antigen-binding fragments of antibodies that bind a target in pulmonary tissue can be locally administered to pulmonary tissue to provide a long therapeutic window (e.g., for treating, suppressing, preventing, or diagnosing respiratory conditions) in pulmonary tissue, for example, a therapeutic window of at least 8 hours.

As described herein, locally administering an agent that binds a target in pulmonary tissue (e.g., antibody fragment, antagonist, ligand, dAb monomer) to pulmonary tissue produces a long therapeutic window in the pulmonary tissue (lung). In some embodiments, locally administering an agent that binds a target in pulmonary tissue (e.g., antibody fragment, antagonist, ligand, dAb monomer) to pulmonary tissue produces a long therapeutic window in pulmonary tissue (lung) that is characterized by the presence in the lung of at least about 1%, at least about 1.25%, at least about 1.5%, at least about 1.75%, at least about 2%, at least about 2.25%, at least about 2.5%, at least about 2.75%, or at least about 3% of the total amount of agent that was administered 4 hours, 5 hours, 6 hours, 7 hours, 8 hours, 9 hours, 10 hours, 11 hours, or 12 hours after administration. In some embodiments, locally administering an agent that binds a target in pulmonary tissue (e.g., antibody fragment, antagonist, ligand, dAb monomer) to pulmonary tissue produces a long therapeutic window in lung that is characterized by the presence in the lung as a whole (BAL and lung tissue) of at least about 40%, at least about 35%, at least about 30%, at least about 25%, at least about 20%, at least about 15%, at least about 10%, or at least about 5% of the total amount of agent that was administered 4 hours, 5 hours, 6 hours, 7 hours, 8 hours, 9 hours, 10 hours, 11 hours, or 12 hours after administration.

In other embodiments, locally administering an agent that binds a target in pulmonary tissue produces a long therapeutic window in pulmonary tissue (lung) wherein at least 50%, at least 60%, at least 70%, at least 75%, at least 80%, at least 85%, at least 90%, at least 95%, at least 96%, at lest 97%, at least 98%, at least 99% or more of the lung level of agent (e.g., level achieved following administration (e.g., the lung level achieved 1 hour after local administration to lung)) is maintained for a period of at least about 4 hours, at least about 5 hours, at least about 6 hours, at least about 7 hours, at least about 8 hours, at least about 9 hours, at least about 10 hours, at least about 11 hours, or at least about 12 hours.

As described herein, locally administering an agent that binds a target in pulmonary tissue (e.g., antibody fragment, antagonist, ligand, dAb monomer) to pulmonary tissue produces a long therapeutic window in the pulmonary tissue (lung), but the agent does not substantially enter the systemic circulation. An agent does not substantially enter the circulation when no more than about 2%, no more than about 1.75%, no more than about 1.5%, no more than about 1.25%, no more that about 1%, no more than about 0.75%, no more than about 0.5%, or no more than about 0.25% of the total amount of agent administered, or substantially no agent, is present in the serum 5 hours after the agent is administered. In some circumstances, an agent administered as described herein may enter the systemic circulation but not accumulate to a significant level because, for example, the agent is rapidly cleared from the systemic circulation. Accordingly, the invention provides method for locally administering an agent that binds a target in pulmonary tissue to pulmonary tissue, wherein no significant level of agent accumulates in the systemic circulation. The level of an agent in the systemic circulation is not significant when no more than about 2%, no more than about 1.75%, no more than about 1.5%, no more than about 1.25%, no more that about 1%, no more than about 0.75%, no more than about 0.5%, or no more than about 0.25% of the total amount of agent administered, or substantially no agent, is present in the serum 5 hours after the agent is administered.

Generally, only a "low dose effective amount of an agent" (e.g., antibody fragment, antagonist, ligand, dAb monomer) that binds a target in pulmonary tissue need be administered locally to the pulmonary tissue of a subject. A low dose effective amount is an amount of agent that is less than the amount of the same agent that would need to be administered systemically (i.e., effective systemic dose) to achieve the same effect. In certain embodiments, the low dose effective amount is about 80% or less of the effective systemic dose, about 70% or less of the effective systemic dose, about 60% or less of the effective systemic close, about 50% or less of the effective systemic dose, about 40% or less of the effective systemic dose, about 30% or less of the effective systemic dose, about 20% or less of the effective systemic dose, about 10% or less of the effective systemic dose, or about 5% or less of the effective systemic dose.

Suitable agents that can be locally administered to pulmonary tissue in accordance with the first aspect of the invention include agents, such as an antibody or antigen-binding fragments of antibodies (e.g, Fab fragment, Fab' fragment, Fv fragment (e.g., scFv, disulfide bonded Fv), F(ab')$_2$ fragment, dAb) and antagonists (e.g., ligand, dAb monomer) that bind a target in pulmonary tissue, such as TNFR1, IL-1, IL-1R, IL-4, IL-4R, IL-5, IL-6, IL-6R, IL-8, IL-8R, IL-9, IL-9R, IL-10, IL-12 IL-12R, IL-13, IL-13Rα1, IL-13Ra2, IL-15, IL-15R, IL-16, IL-17R, IL-17, IL-18, IL-18R, IL-23 IL-23R, IL-25, CD2, CD4, CD11a, CD23, CD25, CD27, CD28, CD30, CD40, CD40L, CD56, CD138, ALK5, EGFR, FcER1, TGFb, CCL2, CCL18, CEA, CR8, CTGF, CXCL12 (SDF-1), chymase, FGF, Furin, Endothelin-1, Eotaxins (e.g., Eotaxin, Eotaxin-2, Eotaxin-3), GM-CSF, ICAM-1, ICOS, IgE, IFNa, I-309, integrins, L-selectin, MIF, MIP4, MDC, MCP-1, MMPs, neutrophil elastase, osteopontin, OX-40, PARC, PD-1, RANTES, SCF, SDF-1, siglec8, TARC, TGFb, Thrombin, Tim-1, TNF, TNFR1, TRANCE, Tryptase, VEGF, VLA-4, VCAM, α4β7, CCR2, CCR3, CCR4, CCR5, CCR7, CCR8, alphavbeta6, alphavbeta 8, Cmet, or CD8.

In an embodiment, the target is selected from a protein in the TNF signalling cascade. Preferably, this protein target is selected from the group comprising TNF alpha, TNF beta, TNFR2, TRADD, FADD, Caspase-8, TNF receptor-associated factor (TRAF), TRAF2, receptor-interacting protein (RIP), Hsp90, Cdc37, IKK alpha, IKK beta, NEMO, inhibitor of kB (IkB), NF-kB, NF-kB essential modulator, apoptosis signal-regulated kinase-1 (aSMase), neutral sphingomyelinase (nSMase), ASK1, Cathepsin-B, germinal center kinase (GSK), GSK-3, factor-associated death domain protein (FADD), factor associated with neutral sphingomyelinase activation (FAN), FLIP, JunD, inhibitor of NF-kB kinase (IKK), MKK3, MKK4, MKK7, IKK gamma, mitogen-activated protein kinase/Erk kinase kinase (MEKK), MEKK1, MEKK3, NIK, poly(ADP-ribose) polymerase (PARP), PKC-zeta, RelA, T2K, TRAF1, TRAF5, death effector domain (DED), death domain (DD), death inducing signalling complex (DISC), inhibitor of apoptosis protein (IAP), c-Jun N-terminal kinase (JNK), mitogen-activated protein kinase (MAPK), phosphoinositide-3OH kinase (PI3K), protein kinase A (PKA), PKB, PKC, PLAD, PTEN, rel homology domain (RHD), really interesting new gene (RING), stress-activated protein kinase (SAPK), TNF alpha-converting enzyme (TACE), silencer of death domain protein (SODD), and TRAF-associated NF-kB activator (TANK). With regard to these preferred targets, reference is made to WO04046189, WO04046186 and WO04046185 (incorporated herein by reference) which provide guidance on the selection of antibody single variable domains for targeting intracellular targets.

Agents that bind targets in pulmonary tissue (e.g., antibody fragments (e.g, Fab fragment, Fab' fragment, Fv fragment (e.g., scFv, disulfide bonded Fv), F(ab')$_2$ fragment, dAb), antagonists, ligands, dAb monomers) can be prepared using any suitable method, such as the methods described herein in detail with respect to antagonists (e.g., ligands, dAb monomers) that bind TNFR1.

In some embodiments, the invention is a method for providing a long therapeutic window in pulmonary tissue of a subject (e.g., a human) for an agent (e.g., antibody fragment, antagonist, ligand, dAb monomer) that binds a target (e.g., TNFR1) in pulmonary tissue, comprising selecting an agent that has a short in vivo serum half-life (e.g., less than about 12 hours) and binds a target in pulmonary tissue, and administering locally to pulmonary tissue of the subject an effective amount or low dose effective amount of the agent that was selected.

In particular embodiments, the first aspect of the invention is a method for providing a long therapeutic window in pulmonary tissue of a subject (e.g., a human) for an agent (e.g., antibody fragment, antagonist, ligand, dAb monomer) that binds a target (e.g., TNFR1) in pulmonary tissue, comprising administering locally to pulmonary tissue of the subject an effective amount or low dose effective amount of said agent. Preferably, no more than about 10 mg/kg/day of agent is administered. For example, about 1 mg/kg/day to about 10 mg/kg/day, e.g., about 1 mg/kg/day, about 2 mg/kg/day, about 3 mg/kg/day, about 4 mg/kg/day, about 5 mg/kg/day, about 6 mg/kg/day, about 7 mg/kg/day, about 8 mg/kg/day, about 9 mg/kg/day, or about 10 mg/kg/day of agent is administered. In other preferred embodiments, such as when the agent is being administered locally to the pulmonary tissue (lung) of a human, no more than about 10 mg/day are administered. For example, in such embodiments the agent can be locally administered to pulmonary tissue at a dose of about 1 mg/day to about 10 mg/day (e.g., 10 mg/day, 9 mg/day, 8 mg/day, 7 mg/day, 6 mg/day, 5 mg/day, 4 mg/day, 3 mg/day, 2 mg/day, or 1 mg/day). Accordingly, the agent can be locally administered to pulmonary tissue at a dose of about 1 µg/kg/day to about 200 µg/kg/day (e.g., about 10 µg/kg/day, about 20 µg/kg/day, about 30 µg/kg/day, about 40 µg/kg/day, about 50 µg/kg/day, about 60 µg/kg/day, about 70 µg/kg/day, about 80 µg/kg/day, about 90 µg/kg/day, about 100 µg/kg/day, about 110 µg/kg/day, about 120 µg/kg/day, about 130 µg/kg/day, about 140 µg/kg/day, about 150 µg/kg/day, about 160 µg/kg/day, about 170 µg/kg/day, about 180 µg/kg/day, or about 190 µg/kg/day). In particular embodiments, about 5 µg/kg/day to about 3 mg/kg/day or preferably, about 50 µg/kg/day to about 500 µg/kg/day are administered.

Use of Agents that Bind Targets in Pulmonary Tissue to Pulmonary Tissue for Manufacture of Formulations and Medicaments.

The first aspect of the invention also relates to use of an agent (e.g., antibody fragment, antagonist, ligand, dAb monomer) that binds a target (e.g., TNFR1) in pulmonary tissue, as described herein, in the manufacture of long acting or long therapeutic window formulation for local administration to pulmonary tissue. The long therapeutic window or long action period in pulmonary tissue can be a period of at least about 4 hours, at least about 5 hours, at least about 6 hours, at least about 7 hours, at least about 8 hours, at least about 9 hours, at least about 10 hours, at least about 11 hours, or at least about 12 hours.

In some embodiments, the agent (e.g., antibody fragment, antagonist, ligand, dAb monomer) used has a short in vivo serum half-life and binds a target in pulmonary tissue. In accordance with the invention, such agents (e.g., antibody fragment, antagonist, ligand, dAb monomer) can be locally administered to pulmonary tissue to produce a long therapeutic window in pulmonary tissue but will not substantially accumulate in the serum. For example, suitable agents (e.g., antibody fragment, antagonist, ligand, dAb monomer) that bind a target in pulmonary tissue for use in the first aspect of the invention can have an in vivo serum half-life of about one second to about 12 hours, about 12 hours or less, about 11 hours or less, about 10 hours or less, about 9 hours or less, about 8 hours or less, about 7 hours or less, about 6 hours or less, about 5 hours or less, about 4 hours or less, about 3 hours or less, about 2 hours or less, about 1 hour or less, or about 30 minutes or less.

Particularly preferred agents (e.g., antagonists) for use in the first aspect of the invention are dAb monomers or antigen-binding fragments of antibodies that bind a target in pulmonary tissue (e.g., Fab fragments, Fab' fragments, Fv fragments (e.g., scFvs, disulfide bonded Fv)s, F(ab')$_2$ fragments).

In some embodiments, the invention relates to use of an agent (e.g., antibody fragment, antagonist, ligand, dAb monomer) that binds a target (e.g., TNFR1) in pulmonary tissue, as described herein, in the manufacture of long acting or long therapeutic window formulation for local administration to pulmonary tissue (lung) wherein at least 50%, at least 60%, at least 70%, at least 75%, at least 80%, at least 85%, at least 90%, at least 95%, at least 96%, at least 97%, at least 98%, at least 99% or more of the lung level of agent (e.g., level achieved following administration (e.g., the lung level achieved 1 hour after local administration to lung)) is maintained for a period of at least about 4 hours, at least about 5 hours, at least about 6 hours, at least about 7 hours, at least about 8 hours, at least about 9 hours, at least about 10 hours, at least about 11 hours, or at least about 12 hours. In some embodiments, the invention relates to use of an agent (e.g., antibody fragment, antagonist, ligand, dAb monomer) that binds a target (e.g., TNFR1) in pulmonary tissue, as described herein, in the manufacture of long acting or long therapeutic window formulation for local administration to pulmonary tissue (lung) wherein the long action period or long therapeutic window in lung that is characterized by the presence in the lung as a whole (BAL and lung tissue) of at least about 40%, at least about 35%, at least about 30%, at least about 25%, at least about 20%, at least about 15%, at least about 10%, or at least about 5% of the total amount of agent that was administered 4 hours, 5 hours, 6 hours, 7 hours, 8 hours, 9 hours, 10 hours, 11 hours, or 12 hours after administration.

In some embodiments, the invention relates to use of an agent (e.g., antibody fragment, antagonist, ligand, dAb monomer) that binds a target (e.g., TNFR1) in pulmonary tissue, as described herein, in the manufacture of long acting or long therapeutic window formulation for local administration to pulmonary tissue (lung) wherein a lung level of at least about 1%, at least about 1.25%, at least about 1.5%, at least about 1.75%, at least about 2%, at least about 2.25%, at least about 2.5%, at least about 2.75%, or at least about 3% of the amount of agent in the formulation (e.g., that is administered in a dose of the formulation) is present in pulmonary tissue for at least 4 hours, at least 5 hours, at least 6 hours, at least 7 hours, at least 8 hours, at least 9 hours, at least 10 hours, at least 11 hours, or at least 12 hours (e.g., after the formulation is administered).

Preferably the agent for use in the invention does not substantially enter the systemic circulation (e.g., when in a long acting or long therapeutic window formulation). As described herein, an agent does not substantially enter the circulation when no more than about 2%, no more than about 1.75%, no more than about 1.5%, no more than about 1.25%, no more that about 1%, no more than about 0.75%, no more than about 0.5%, or no more than about 0.25% of the total amount of agent administered (e.g, in a dose of the formulation), or substantially no agent, is present in the serum 5 hours after the agent (e.g, in a dose of the formulation) is administered. In some circumstances, an agent administered as described herein may enter the systemic circulation but not accumulate to a significant level because, for example, the agent is rapidly cleared from the systemic circulation. Accordingly, the invention provides for use of an agent that binds a target in pulmonary tissue to pulmonary tissue, wherein no significant level of agent accumulates in the systemic circulation. The level of an agent in the systemic circulation is not significant when no more than about 2%, no more than about 1.75%, no more than about 1.5%, no more than about 1.25%, no more that about 1%, no more than about 0.75%, no more than about 0.5%, or no more than about 0.25% of the total amount of agent administered (e.g, in a dose of the formulation), or substantially no agent, is present in the serum 5 hours after the agent (e.g, in a dose of the formulation) is administered.

The invention also relates to use of an agent (e.g., antibody fragment, antagonist, ligand, dAb monomer) that binds a target (e.g., TNFR1) in pulmonary tissue, as described herein, in the manufacture of a medicament for local administration to pulmonary tissue of a low dose effective amount of agent. As described herein, a low dose effective amount is generally about 80% or less of the effective systemic dose, about 70% or less of the effective systemic dose, about 60% or less of the effective systemic dose, about 50% or less of the effective systemic dose, about 40% or less of the effective systemic dose, about 30% or less of the effective systemic dose, about 20% or less of the effective systemic dose, about 10% or less of the effective systemic dose, or about 5% or less of the effective systemic dose.

In some embodiments, the invention is a method for producing a long acting or long therapeutic window formulation for local administration to pulmonary tissue comprising an agent (e.g., antibody fragment, antagonist, ligand, dAb monomer) that binds a target in pulmonary tissue, or a method for producing a medicament for local administration to pulmonary tissue of a low dose effective amount of agent (e.g., antibody fragment, antagonist, ligand, dAb monomer) that binds a target in pulmonary tissue. The methods comprise (1) selecting an agent that binds a target in pulmonary tissue and has a short in vivo serum half-life (e.g., less than about 12 hours), and (2) using the selected agent for the manufacture of a long acting or long therapeutic window formulation for local administration to pulmonary tissue, or for the manufacture of medicament for local administration to pulmonary tissue of a low dose effective amount of agent.

The invention also relates to use of an agent that binds a target in pulmonary tissue (e.g., antibody fragment, antagonist, ligand, dAb monomer), as described herein, for use in the manufacture of a long action or long therapeutic window formulation for local administration to pulmonary tissue (lung), as described herein, or in the manufacture of a medicament for local administration to pulmonary tissue of a low dose effective amount of agent, as described herein, wherein the formulation or medicament is for administering no more agent than about 10 mg/kg/day. For example, the formulation or medicament can be for administering about 1 mg/kg/day to about 10 mg/kg/day, e.g., about 1 mg/kg/day, about 2 mg/kg/day, about 3 mg/kg/day, about 4 mg/kg/day, about 5 mg/kg/day, about 6 mg/kg/day, about 7 mg/kg/day, about 8 mg/kg/day, about 9 mg/kg/day, or about 10 mg/kg/day. In some embodiments, the formulation or medicament is for local administration to the pulmonary tissue (lung) of a human, and the formulation or medicament is for administering no more than about 10 mg/day. For example, the formulation or medicament can be for administering agent at a dose of about 1 mg/day to about 10 mg/day (e.g., 10 mg/day, 9 mg/day, 8 mg/day, 7 mg/day, 6 mg/day, 5 mg/day, 4 mg/day, 3 mg/day, 2 mg/day, or 1 mg/day). Accordingly, the formulation or medicament can be for administering agent at a dose of about 1 µg/kg/day to about 200 µg/kg/day (e.g., about 10 µg/kg/day, about 20 µg/kg/day, about 30 µg/kg/day, about 40 µg/kg/day, about 50 µg/kg/day, about 60 µg/kg/day, about 70 µg/kg/day, about 80 µg/kg/day, about 90 µg/kg/day, about 100 µg/kg/day, about 110 µg/kg/day, about 120 µg/kg/day, about 130 µg/kg/day, about 140 µg/kg/day, about 150 µg/kg/day, about 160 µg/kg/day, about 170 µg/kg/day; about 180 µg/kg/day, or about 190 µg/kg/day). In particular embodiments, about 5 µg/kg/day to about 3 mg/kg/day or preferably, about 50 µg/kg/day to about 500 µg/kg/day are administered.

The formulations and medicaments produced using an agent that binds a target in pulmonary tissue, as described herein, can be locally administered to pulmonary tissue (e.g., lung) of a subject using any suitable method. For example, an agent can be locally administered to pulmonary tissue via inhalation or intranasal administration. For inhalation or intranasal administration, the agent (antagonist of TNFR1, ligand, dAb monomer) can be administered using a nebulizer, inhaler, atomizer, aerosolizes, mister, dry powder inhaler, metered dose inhaler, metered dose sprayer, metered dose mister, metered dose atomizer, or other suitable delivery device.

If desired, for example for diagnostic purposes (e.g. imaging), the agent that binds a target in pulmonary tissue (e.g., antibody fragment, antagonist, ligand, dAb monomer) can comprise a detectable label. Suitable detectable labels and methods for labeling an agent are well known in the art. Suitable detectable labels include, for example, a radioisotope (e.g., as Indium-111, Technetium-99m or Iodine-131), positron emitting labels (e.g., Fluorine-19), paramagnetic ions (e.g., Gadlinium (III), Manganese (II)), an epitope label (tag), an affinity label (e.g., biotin, avidin), a spin label, an enzyme, a fluorescent group or a chemiluminescent group. When labels are not employed, complex formation can be determined by surface plasmon resonance or other suitable methods.

Antagonists of TNFR1 for Treating, Suppressing or Preventing Lung Inflammation and Respiratory Diseases.

In a second aspect, the invention relates to methods for treating, suppressing or preventing lung inflammation and/or a respiratory disease comprising administering to a subject (e.g., a mammal, a human) in need thereof an effective amount of an antagonist of TNFR1 (e.g., a ligand, a dAb monomer). The invention also relates to the use of an antagonist of TNFR1 (e.g., a ligand, a dAb monomer) for the manufacture of a medicament for treating, suppressing or preventing lung inflammation and/or respiratory disease, and to a pharmaceutical composition for treating, suppressing or preventing lung inflammation and/or respiratory disease comprising an antagonist of TNFR1 (e.g., a ligand, a dAb monomer) as an active ingredient. Antagonists of TNFR1 suitable for use in the invention are described in detail herein and include small molecules, new chemical entities, ligands, dAb monomers, and the like.

The invention provides compositions comprising an antagonist of TNFR1 (e.g. ligand, dual-specific ligand, multi-specific ligand, dAb monomer) and a pharmaceutically acceptable carrier, diluent or excipient, and therapeutic and diagnostic methods that employ the ligands or compositions of the invention. Antagonists and ligands (e.g., dual-specific ligands, multispecific ligands, dAb monomers) according to the method of the present invention may be employed in in vivo therapeutic and prophylactic applications, in vivo diagnostic applications and the like.

Therapeutic and prophylactic uses of antagonists of TNFR1 (e.g., ligands, multispecific ligands, dual-specific ligands, dAb monomers) comprise administering an effective amount of antagonists of TNFR1 (e.g., ligands, multispecific ligands, dual-specific ligands, dAb monomers) to a recipient mammal or subject, such as a human.

For example, the antagonists of TNFR1 (e.g., ligands, multispecific ligands, dual-specific ligands, dAb monomers) will typically find use in preventing, suppressing or treating lung inflammation and/or respiratory diseases, such as a condition in which lung inflammation is a symptom or part of the pathology, acute respiratory diseases, chronic respiratory diseases, acute inflammatory respiratory diseases and chronic inflammatory respiratory diseases. For example, the antagonists of TNFR1 (e.g., ligands, multispecific ligands, dual-specific ligands, dAb monomers) can be administered to treat, suppress or prevent lung inflammation, chronic obstructive pulmonary disease (e.g., chronic bronchitis, chronic obstructive bronchitis, emphysema), asthma (e.g., steroid resistant asthma), pneumonia (e.g., bacterial pneumonia, such as Staphylococcal pneumonia), hypersensitivity pneumonitis, pulmonary infiltrate with eosinophilia, environmental lung disease, pneumonia, bronchiectasis, cystic fibrosis, interstitial lung disease, primary pulmonary hypertension, pulmonary thromboembolism, disorders of the pleura, disorders of the mediastinum, disorders of the diaphragm, hypoventilation, hyperventilation, sleep apnea, acute respiratory distress syndrome, mesothelioma, sarcoma, graft rejection, graft versus host disease, lung cancer, allergic rhinitis, allergy, asbestosis, aspergilloma, aspergillosis, bronchiectasis, chronic bronchitis, emphysema, eosinophilic pneumonia, idiopathic pulmonary fibrosis, invasive pneumococcal disease (IPD), influenza, nontuberculous mycobacteria, pleural effusion, pneumoconiosis, pneumocytosis, pneumonia, pulmonary actinomycosis, pulmonary alveolar proteinosis, pulmonary anthrax, pulmonary edema, pulmonary embolus, pulmonary inflammation, pulmonary histiocytosis X (eosinophilic granuloma), pulmonary hypertension, pulmonary nocardiosis, pulmonary tuberculosis, pulmonary veno-occlusive disease, rheumatoid lung disease, sarcoidosis, Wegener's granulomatosis, and non-small cell lung carcinoma.

In the instant application, the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Advantageously, dual- or multi-specific ligands may be used to target cytokines and other molecules which cooperate synergistically in therapeutic situations in the body of an organism. The invention therefore provides a method for synergising the activity of two or more binding domains (e.g., dAbs) wherein one domain binds TNFR1 or other target in pulmonary tissue, and the other domain binds a cytokine or other molecules, comprising administering a dual- or multi-specific ligand capable of binding to said two or more molecules (e.g., TNFR1 and a cytokine). For example, this aspect of the invention relates to combinations of $V_H$ domains and $V_L$ domains, $V_H$ domains only and $V_L$ domains only.

Synergy in a therapeutic context may be achieved in a number of ways. For example, target combinations may be therapeutically active only if both targets are targeted by the ligand, whereas targeting one target alone is not therapeutically effective. In another embodiment, one target alone may provide some low or minimal therapeutic effect, but together with a second target the combination provides a synergistic increase in therapeutic effect.

Animal model systems which can be used to screen the effectiveness of the antagonists of TNFR1 (e.g, ligands, antibodies or binding proteins thereof, dAb monomer) in preventing, suppressing or treating respiratory disease are available. For example, suitable animal models of respiratory disease include models of chronic obstructive pulmonary disease (see, Groneberg, D A et al., Respiratory Research 5:18 (2004)), and models of asthma (see, Coffman et al., *J. Exp. Med.* 201(12):1875-1879 (2001). Preferably, the antagonist of TNFR1 (e.g., ligand or dAb monomer) is efficacious in a mouse tobacco smoke-induced model of chronic obstructive pulmonary disease (e.g., the subchronic model disclosed herein) or a suitable primate model of asthma or chronic obstructive pulmonary disease. More preferably, the antagonist of TNFR1 (e.g., ligand or dAb monomer) is efficacious in a mouse tobacco smoke-induced model of chronic obstructive pulmonary disease (e.g., the subchronic model disclosed herein) (See, also, Wright and Churg, *Chest*, 122:301-306 (2002)). For example, administering an effective amount of the ligand can reduce, delay or prevent onset of the symptoms of COPD in the model, as compared to a suitable control. The prior art does not suggest using antagonists of TNFR1 (e.g., ligands or dAb monomers) in these models, or that they would be efficacious.

Generally, the present antagonists (e.g., ligands) will be utilised in purified form together with pharmacologically appropriate carriers. Typically, these carriers include aqueous or alcoholic/aqueous solutions, emulsions or suspensions, any including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) *Remington's Pharmaceutical Sciences*, 16th Edition). A variety of suitable formulations can be used, including extended release formulations.

The antagonists (e.g., ligands) of the present invention may be used as separately administered compositions or in conjunction with other agents. These can include various drugs, such as phosphodiesterase inhibitors (e.g., inhibitors of phosphodiesterase 4), bronchodilators (e.g., beta2-agonists, anticholinergics, theophylline), short-acting beta-agonists (e.g., albuterol, salbutamol, bambuterol, fenoterol, isoetherine, isoproterenol, levalbuterol, metaproterenol, pirbuterol, terbutaline and tornlate), long-acting beta-agonists (e.g., formoterol and salmeterol), short acting anticholinergics ipratropium bromide and oxitropium bromide), long-acting anticholinergics (e.g., tiotropium), theophylline (e.g. short acting formulation, long acting formulation), inhaled steroids (e.g., beclomethasone, beclometasone, budesonide, flunisolide, fluticasone propionate and triamcinolone), oral steroids (e.g., methylprednisolone, prednisolone, prednisolon and prednisone), combined short-acting beta-agonists with anticholinergics (e.g., albuterol/salbutamol/ipratropium, and fenoterol/ipratropium), combined long-acting beta-agonists with inhaled steroids (e.g., salmeterol/fluticasone, and formoterol/budesonide) and mucolytic agents (e.g., erdosteine, acetylcysteine, bromheksin, carbocysteine, guiafenesin and iodinated glycerol), cylcosporine, antibiotics, antivirals, methotrexate, adriamycin, cisplatinum, and immunotoxins.

Pharmaceutical compositions can include "cocktails" of various cytotoxic or other agents in conjunction with the antagonists (e.g., ligands) of the present invention, or even combinations of ligands according to the present invention having different specificities, such as ligands selected using different target antigens or epitopes, whether or not they are pooled prior to administration.

The antagonists of TNFR1 (e.g., ligands, dAb monomers) can be administered and or formulated together with one or more additional therapeutic or active agents. When an antagonist of TNFR1 (e.g ligand, dAb monomer) is administered with an additional therapeutic agent, the antagonist of TNFR1 can be administered before, simultaneously with or subsequent to administration of the additional agent. Generally, the antagonist of TNFR1 (e.g., ligand, dAb monomer) and additional agent are administered in a manner that provides an overlap of therapeutic effect.

The compositions containing the present antagonists (e.g., ligands) or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". For example, for treating lung inflammation and/or a respiratory disease, a sputum-inhibiting amount, a bronchial biopsy inflammation-inhibiting amount, a dyspnoea-inhibiting amount, a forced expiratory volume in one second (FEV (1)) increasing amount, an improvement in health status increasing amount, as quantified in a suitable questionnaire such as the St. George's Respiratory Questionnaire (e.g., an improvement score of 4 points).

Amounts needed to achieve these effects will depend upon the severity of the disease and the general state of the patient's own immune system, but generally range from 0.005 to 10.0 mg of agent, antagonist (e.g., ligand, dAb monomer) or binding protein thereof per kilogram of body weight, with doses of 0.05 to 2.0 mg/kg/dose being more commonly used. In particular embodiments, the amount administered will be about 5 µg/kg/dose to about 3 mg/kg/dose or preferably, about 50 µg/kg/dose to about 500 µg/kg/dose.

For prophylactic applications, compositions containing the present ligands or cocktails thereof may also be administered in similar or slightly lower dosages, to prevent, inhibit or delay onset of disease (e.g., to sustain remission or quiescence, or to prevent acute phase). The skilled clinician will be able to determine the appropriate dosing interval to treat, suppress or prevent disease. When an antagonist of TNFR1 (e.g., ligand) is administered to treat, suppress or prevent lung inflammation or a respiratory disease, it can be administered up to four times per day, twice weekly, once weekly, once every two weeks, once a month, or once every two months, at a dose of, for example, about 10 µg/kg to about 80 mg/kg, about 100 µg/kg to about 80 mg/kg, about 1 mg/kg to about 80 mg/kg, about 1 mg/kg to about 70 mg/kg, about 1 mg/kg to about 60 mg/kg, about 1 mg/kg to about 50 mg/kg, about 1 mg/kg to about 40 mg/kg, about 1 mg/kg to about 30 mg/kg, about 1 mg/kg to about 20 mg/kg, about 1 mg/kg to about 10 mg/kg, about 10 µg/kg to about 10 mg/kg, about 10 µg/kg to about 5 mg/kg, about 10 µg/kg to about 2.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg or about 10 mg/kg. In particular embodiments, the antagonist of TNFR1 (e.g., ligand) is administered to treat, suppress or prevent lung inflammation or a respiratory disease each day, every two days, once a week, once every two weeks or once a month at a dose of about 10 µg/kg to about 10 mg/kg (e.g., about 10 µg/kg, about 100 µg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg or about 10 mg/kg). In particular embodiments, about 5 µg/kg to about 3 mg/kg or preferably, about 50 µg/kg to about 500 µg/kg are administered.

The antagonist of TNFR1 (e.g., ligand) can also be administered to treat, suppress or prevent lung inflammation or a respiratory disease at a daily dose or unit dose of about 10 mg, about 9 mg, about 8 mg, about 7 mg, about 6 mg, about 5 mg, about 4 mg, about 3 mg, about 2 mg or about 1 mg.

Treatment or therapy performed using the compositions described herein is considered "effective" if one or more symptoms are reduced (e.g., by at least 10% or at least one point on a clinical assessment scale), relative to such symptoms present before treatment, or relative to such symptoms in an individual (human or model animal) not treated with such composition or other suitable control. Symptoms will vary depending upon the disease or disorder targeted, but can be measured by an ordinarily skilled clinician or technician. Such symptoms can be measured, for example, by monitoring one or more physical indicators of the disease or disorder (e.g., cellular infiltrate in lung tissue, production of sputum, cellular infiltrate in sputum, dyspnoea, exercise tolerance, spirometry (e.g., forced vital capacity (FVC), force expiratory volume in one second (FEY (1), FEV (1)/FVC), rate or severity of disease exacerbation, or by an accepted clinical assessment scale, for example, the St. George's Respiratory Questionnaire. Suitable clinical assessment scales include, for example, the severity of air flow obstruction according to FEV (1) (*Clinical Guideline 12, Chronic Obstructive Pulmonary Disease, Management of Chronic Obstructive Pulmonary Disease in Adults in Primary and Secondary Care*, National Institute for Clinical Excellence, London (2004)), Peak Expiratory Flow (PEF) (*British Guideline on the Management of Asthma*, British Thoracic Society, Scottish Intercollegiate Guidelines Network, Revised Edition (2004)), COPD stage according to the American Thoracic Society (ATS) standard (*Am. J. Respir. Crit. Care Med.*, 152:S77-S120 (1995), asthma impairment class according to the ATS standard (*Am. Rev. Respir. Dis.*, 147:1056-1061 (1993), or other accepted clinical assessment scale as known in the field. A sustained (e.g., one day or more, preferably longer) reduction in disease or disorder symptoms by at least 10% or by one or more points on a given clinical scale is indicative of "effective" treatment. Similarly, prophylaxis performed using a composition as described herein is "effective" if the onset or severity of one or more symptoms is delayed, reduced or abolished relative to such symptoms in a similar individual (human or animal model) not treated with the composition.

A composition containing an antagonist (e.g., ligand) according to the present invention may be utilised in prophylactic and therapeutic settings to aid in the alteration, inactivation, killing or removal of a select target cell population in a mammal. For example, such compositions can be used to reduce levels of inflammatory cells in lung and/or inhibit cell infiltration of the lung.

Composition containing an antagonist (e.g., ligand) according to the present invention can also be used to reduce levels of inflammatory mediators such as cytokines, chemokines, cellular adhesion molecules, that are induced by inflammatory stimuli in lung. For example, dAb monomer antagonists of TNFR1 can inhibit (i) inflammatory stimulus-induced (e.g., TNFalpha-induced) increases in the levels of the early acting mediators, such as the neutrophil chemoattractants KC and MIP-1, and/or (ii) inhibit inflammatory stimulus-induced (e.g., TNFalpha-induced) increases in the levels of later acting mediators, such as chemokine MCP-1 and adhesion molecule E-selectin. Other mediators such as LTB4, GRO-a, IP-10, GM-CSF, reactive oxygen species (ROS), NO and the like can be effected.

The ligands of this invention can be lyophilised for storage and reconstituted in a suitable carrier prior to use. This technique has been shown to be effective with conventional immunoglobulins and art-known lyophilisation and reconstitution techniques can be employed. It will be appreciated by those skilled in the art that lyophilisation and reconstitution can lead to varying degrees of antibody activity loss (e.g. with conventional immunoglobulins, IgM antibodies tend to have greater activity loss than IgG antibodies) and that use levels may have to be adjusted upward to compensate. The ligands of this invention can be lyophilised to form a dry powder for inhalation, and administered in that form.

The route of administration of pharmaceutical compositions according to the invention may be any of those commonly known to those of ordinary skill in the art. The administration can be by any appropriate mode, including parenterally, intravenously, intramuscularly, intraperitoneally, transdermally, via the pulmonary route, or by direct infusion with a catheter. The dosage and frequency of administration will depend on the age, sex and condition of the patient, concurrent administration of other drugs, counterindications and other parameters to be taken into account by the clinician. Administration can be local (e.g., local delivery to the lung by pulmonary administration, e.g., intranasal administration) or systemic as indicated.

In particular embodiments, an antagonist of TNFR1 is administered via pulmonary delivery, such as by inhalation (e.g., intrabronchial, intranasal or oral inhalation, intranasal drops) or by systemic delivery (e.g., parenteral, intravenous, intramuscular, intraperitoneal, subcutaneous). In preferred embodiments, the antagonist of TNFR1 (e.g., ligand, dAb monomer) is administered to a subject via pulmonary administration, such as inhalation or intranasal administration (e.g., intrabronchial, intranasal or oral inhalation, intranasal drops). For inhalation, the antagonist of TNFR1 (e.g., ligand, dAb monomer) can be administered with the use of a nebulizer, inhaler, atomizer, aerosolizer, mister, dry powder inhaler, metered dose inhaler, metered dose sprayer, metered dose mister, metered dose atomizer, or other suitable delivery device.

The invention relates to a method for treating, suppressing or preventing lung inflammation or a respiratory disease, comprising administering to a subject in need thereof an effective amount of an antagonist of TNFR1, wherein said effective amount does not exceed about 10 mg/kg/day, and wherein preferably the level of inflammatory cells in the lung is reduced relative to pretreatment levels with $p \leq 0.05$, or recruitment of inflammatory cells into the lung is inhibited relative to pretreatment levels with $p \leq 0.05$. The level of inflammatory cells in the lung or recruitment of inflammatory cells into the lung can be reduced or inhibited relative to pretreatment levels by at least about 30%, at least about 40%, at least about 50%, at least about 60%, at least about 70%, at least about 80%, at least about 90%, or at least about 95%.

Preferably, statistical analysis is performed using the methods described in the Examples herein. The level of inflammatory cells in the lung or recruitment of inflammatory cells into the lung can be reduced or inhibited relative to pretreatment levels with $p<0.001$ in some embodiments.

Levels of cells (e.g., inflammatory cells) in the lung can be assessed using any suitable method, such as total or differential cell counts (e.g., macrophage cell count, neutrophil cell count, eosinophil cell count, lymphocyte cell count, epithelial cell count) in BAL, sputum or biopsy (e.g., bronchial biopsy, lung biopsy).

The invention also relates to a method for treating a respiratory disease comprising (1) selecting an antagonist of Tumor Necrosis Factor Receptor 1 (TNFR1) that has efficacy in a suitable animal model of respiratory disease when administered in an amount that does not exceed about 10 mg/kg once per day, wherein efficacy in said animal model exists when cellular infiltration of the lungs as assessed by total cell count in bronchoalveolar lavage is inhibited relative to untreated control with $p \leq 0.05$; and (2) administering (e.g., locally to pulmonary tissue) an effective amount of said antagonist of TNFR1 to a subject in need thereof.

In some embodiments, the methods described herein are employed for treating, suppressing or preventing chronic obstructive pulmonary disease (e.g., chronic bronchitis, chronic obstructive bronchitis, emphysema), asthma (e.g., steroid resistant asthma), pneumonia (e.g., bacterial pneumonia, such as Staphylococcal pneumonia), or lung inflammation.

The invention also relates to the use of an antagonist of TNFR1, as described herein, for the manufacture of a medicament or formulation for treating lung inflammation or a respiratory disease described herein. The medicament can be for systemic administration and/or local administration to pulmonary tissue.

Antagonists of TNFR1

TNFR1 is a transmembrane receptor containing an extracellular region that binds ligand and an intracellular domain that lacks intrinsic signal transduction activity but can associate with signal transduction molecules. The complex of TNFR1 with bound TNF contains three TNFR1 chains and three TNF chains. (Banner et al., *Cell,* 73(3) 431-445 (1993).) The TNF ligand is present as a trimer, which is bound by three TNFR1 chains. (Id.) The three TNFR1 chains are clustered closely together in the receptor-ligand complex, and this clustering is a prerequisite to TNFR1-mediated signal transduction. In fact, multivalent agents that bind TNFR1, such as anti-TNFR1 antibodies, can induce TNFR1 clustering and signal transduction in the absence of TNF and are commonly used as TNFR1 agonists. (See, e.g., Belka et al., *EMBO,* 14(6):1156-1165 (1995); Mandik-Nayak at al., *J. Immunol,* 167:1920-1928 (2001).) Accordingly, multivalent agents that bind TNFR1, are generally not effective antagonists of TNFR1 even if they block the binding of TNFα to TNFR1.

The extracellular region of TNFR1 comprises a thirteen amino acid amino-terminal segment (amino acids 1-13 of SEQ ID NO:213 (human); amino acids 1-13 of SEQ ID NO:215 (mouse)), Domain 1 (amino acids 14-53 of SEQ ID NO:213 (human); amino acids 14-53 of SEQ ID NO:215 (mouse)), Domain 2 (amino acids 54-97 of SEQ ID NO:213 (human); amino acids 54-97 of SEQ ID NO:215 (mouse)), Domain 3 (amino acids 98-138 of SEQ ID NO:213 (human); amino acid 98-138 of SEQ ID NO:215 (mouse)), and Domain 4 (amino acids 139-167 of SEQ ID NO:213 (human); amino acids 139-167 of SEQ ID NO:215 (mouse)) which is followed by a membrane-proximal region (amino acids 168-182 of SEQ ID NO:213 (human); amino acids 168-183 SEQ ID NO:215 (mouse)). (See, Banner et al., *Cell* 73(3) 431-445 (1993) and Loetscher et al., *Cell* 61(2) 351-359 (1990).) Domains 2 and 3 make contact with bound ligand (TNFβ, TNFα). (Banner et al., *Cell*, 73(3) 431-445 (1993).) The extracellular region of TNFR1 also contains a region referred to as the pre-ligand binding assembly domain or PLAD domain (amino acids 1-53 of SEQ ID NO:213 (human); amino acids 1-53 of SEQ ID NO:215 (mouse)) (The Government of the USA, WO 01/58953; Deng et al., *Nature Medicine, doi:* 10.1038/nm1304 (2005)).

TNFR1 is shed from the surface of cells in vivo through a process that includes proteolysis of TNFR1 in Domain 4 or in the membrane-proximal region (amino acids 168-182 of SEQ ID NO:213; amino acids 168-183 of SEQ ID NO:215), to produce a soluble form of TNFR1. Soluble TNFR1 retains the capacity to bind TNFα, and thereby functions as an endogenous inhibitor of the activity of TNFα.

Antagonists of TNFR1 suitable for use in the invention (e.g., ligands described herein) that have binding specificity for Tumor Necrosis Factor Receptor 1 (TNFR1; p55; CD120a). Preferably the antagonists of TNFR1 do not have binding specificity for Tumor Necrosis Factor 2 (TNFR2), or do not substantially antagonize TNFR2. An antagonist of TNFR1 does not substantially antagonize TNFR2 when the antagonist (1 nM, 10 nM, 100 nM, 1 µM, 10 µM or 100 µM) results in no more than about 5% inhibition of TNFR2-mediated activity induced by TNFα (100 pg/ml) in a standard cell assay.

Antagonists of TNFR1 that are suitable for use in the invention are effective therapeutics (are efficacious, have therapeutic efficacy) for treating respiratory disease (e.g., acute respiratory disease, chronic respiratory disease, acute inflammatory respiratory disease, chronic inflammatory respiratory disease). For example, antagonists of TNFR1 that suitable for use in the invention are efficacious in models of respiratory diseases, when an effective amount is administered. Generally an effective amount is about 1 µg/kg to about 10 mg/kg or about 1 mg/kg to about 10 mg/kg (e.g., about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 10 mg/kg). Several suitable animal models of respiratory disease are known in the art, and are recognized by those skilled in the art as being predictive of therapeutic efficacy in humans. For example, suitable animal models of respiratory disease include models of chronic obstructive pulmonary disease (see, Groneberg, D A et al., *Respiratory Research* 5:18 (2004)), models of asthma (see, Coffman R L et al., *J. Exp. Med.* 201(12):1875-1879 (2001); Van Scott, M R et al., *J. App. Physiol.* 96:1433-1444 (2004)), and models of pulmonary fibrosis (e.g., Venkatesan, N et al., *Lung* 287:1342-1347 (2004). Preferably, the antagonist of TNFR1 (e.g., ligand or dAb monomer) is efficacious in a mouse tobacco-induced smoke model of chronic obstructive pulmonary disease (e.g., the subchronic model disclosed herein) or a suitable primate model of asthma or chronic obstructive pulmonary disease (see, e.g., Coffman R L et al., *J. Exp. Med.* 201(12):1875-1879 (2001); Van Scott, M R et al., *J. App. Physiol.* 96:1433-1444 (2004)). More preferably, the antagonist of TNFR1 (e.g., ligand or dAb monomer) is efficacious in a mouse tobacco smoke model of chronic obstructive pulmonary disease (e.g., the subchronic model disclosed herein) (See, also, Wright and Churg, *Chest*, 122:301-306 (2002)). For example, administering an effective amount of the ligand can reduce, delay or prevent onset of the symptoms of COPD in the model, as compared to a suitable control. The prior art does not suggest using antagonists of TNFR1 (e.g., ligands or dAb monomers) in these models, or that they would be efficacious.

Suitable antagonists of TNFR1 can be monovalent or multivalent. In some embodiments, the antagonist is monovalent and contains one binding site that interacts with TNFR1. Monovalent antagonists bind one TNFR1 and do not induce cross-linking or clustering of TNFR1 on the surface of cells which can lead to activation of the receptor and signal transduction. In particular embodiments, the monovalent antagonist of TNFR1 competes with TAR2m-21-23 for binding to mouse TNFR1 or competes with TAR2h-205 for binding to human TNFR1.

Multivalent antagonists of TNFR1 can contain two or more copies of a particular binding site for TNFR1 or contain two or more different binding sites that bind TNFR1. For example, the antagonist of TNFR1 can be a dimer, trimer or multimer comprising two or more copies of a particular dAb that binds TNFR1, or two or more different dAbs that bind TNFR1. Preferably, a multivalent antagonist of TNFR1 does not substantially agonize TNFR1 (act as an agonist of TNFR1) in a standard cell assay (i.e., when present at a concentration of 1 nM, 10 nM, 100 nM, 1 µM, 10 µM, 100 µM, 1000 µM or 5,000 µM, results in no more than about 5% of the TNFR1-mediated activity induced by TNFα (100 pg/ml) in the assay).

Suitable multivalent antagonists of TNFR1 can contain two or more binding sites for a desired epitope or domain of TNFR1. For example, a multivalent antagonist of TNFR1 can comprise two or more binding sites that bind the same epitope of TNFR1, or two or more binding sites that bind different epitopes or domains of TNFR1. In one example, the multivalent antagonist of TNFR1 comprises a first binding site that binds a first epitope of TNFR1, and a second binding site that binds a second different epitope of TNFR1. Preferably, such multivalent antagonists do not agonize TNFR1 when present at a concentration of about 1 nM, or about 10 nM, or about 100 nM, or about 1 µM, or about 10 µM, in a standard L929 cytotoxicity assay or a standard HeLa IL-8 assay as described herein.

Some antagonists of TNFR1 suitable for use in the invention bind TNFR1 and inhibit binding of TNFα to TNFR1. In particular embodiments, such an antagonist of TNFR1 competes with TAR2h-10-27, TAR2h-131-8, TAR2h-15-8, TAR2h-35-4, TAR2h-154-7, TAR2h-154-10 or TAR2h-185-25 for binding to TNFR1.

Some antagonist of TNFR1 suitable for use in the invention do not inhibit binding of TNFα to TNFR1, but do inhibit signal transduction mediated through TNFR1. For example, an antagonist of TNFR1 can inhibit TNFα-induced clustering of TNFR1, which precedes signal transduction through TNFR1. Such antagonists provide several advantages. For example, in the presence of such an antagonist, TNFα can bind TNFR1 expressed on the surface of cells and be removed from the cellular environment, but TNFR1 mediated signal transduction will not be activated. Thus, TNFR1 signal-induced production of additional TNFα and other mediators of inflammation will be inhibited. Similarly, antagonists of TNFR1 that bind TNFR1 and inhibit signal transduction mediated through TNFR1, but do no inhibit binding of TNFα to TNFR1, will not inhibit the TNFα-binding and inhibiting activity of endogenously produced soluble TNFR1. Accordingly, administering such an antagonist to a mammal in need thereof can complement the endogenous regulatory pathways that inhibit the activity TNFα and the activity of TNFR1 in vivo.

In a particular embodiment, the antagonist of TNFR1 suitable for use in the invention (e.g., a dAb monomer or ligand) binds TNFR1 and inhibits signal transduction mediated through TNFR1 upon binding of TNFα. Such an antagonist can inhibit signal transduction through TNFR1, but not inhibit TNFα binding to TNFR1 and/or shedding of TNFR1 to produce soluble TNFR1. Accordingly, administering such an antagonist to a mammal in need thereof can complement the endogenous regulatory pathways that inhibit the activity TNFα and the activity of TNFR1 in vivo.

Certain antagonists of TNFR1 suitable for use in the invention (e.g., chemical compound, new chemical entity, dAb monomer, ligand) bind TNFR1 and compete with TAR2m-21-23 for binding to mouse TNFR1 or competes with TAR2h-205 for binding to human TNFR1. Other antagonists of TNFR1 suitable for use in the invention (e.g., chemical compound, new chemical entity, dAb monomer, ligand) bind TNFR1 and compete with TAR2h-131-8, TAR2h-15-8, TAR2h-35-4, TAR2h-154-7, TAR2h-154-10, TAR2h-185-25, or TAR2h-27-10 for binding to TNFR1 (e.g., human and/or mouse TNFR1).

Some antagonists (e.g., ligands, dAb monomers) are cross reactive and bind human TNFR1 and TNFR1 from another species such as an animal amenable to use in medical research. For example, a dAb monomer that binds human TNFR1 and mouse TNFR1. Such antagonists (e.g., ligands, dAb monomers) provide the advantage of allowing preclinical and clinical studies using the same antagonist (e.g., dAb monomer) and obviate the need to conduct preclinical studies with a suitable surrogate antagonist. Preferred examples of cross reactive antagonists bind human TNFR1 and TNFR1 from a rodent, such as mouse, rat or guinea pig, rabbit, dog, sheep, pig, or a non-human primate such as, cynomolgus monkey or rhesus macaque.

Generally, a cross reactive antagonist of the invention binds human TNFR1 and TNFR1 from another species with similar affinities ($K_d$). Preferably, the cross reactive antagonists, such as a dAb monomer, binds human TNFR1 and TNFR1 from another species with affinities that differ by no more than about a factor of 100, a factor of 10 or a factor of 5. For example, a cross reactive dAb monomer can bind human TNFR1 with an affinity of 1 nM and also bind to mouse, cynomolgus monkey or rhesus macaque TNFR1 with an affinity from about 10 pM to about 100 nM, about 100 pM to about 10 nM, or about 200 pM to about 5 nM.

The cross reactive antagonists, such as a dAb monomer, can bind human TNFR1 and TNFR1 from another species (e.g., one of the non-human species mentioned in the preceding two paragraphs) with on rates ($K_{on}$) that differ by no more than about a factor of 100, a factor of 10, or a factor of 5, and/or with off rates ($K_{off}$) that differ by no more than about a factor of 100, a factor 10, or a factor or 5. For example, the antagonists can be a dAb monomer that binds both human TNFR1 and TNFR1 from another species with a $K_{on}$ of about $10^4$ M/s to about $10^5$ M/s, and/or a $K_{off}$ of about $10^{-3}$ s$^{-1}$ to about $10^{-5}$ s$^{-1}$.

Antagonists of TNFR1 suitable for use in the invention also include, an antibody that has binding specificity for TNFR1 or an antigen-binding fragment thereof, such as Fab fragment, Fab' fragment, F(ab')$_2$ fragment or Fv fragment (e.g., scFV). In some embodiments, the antagonist is monovalent, such as a dAb or a monovalent antigen-binding fragment of an antibody, such as a Fab fragment, Fab' fragment, or Fv fragment.

Preferably, the antagonist of TNFR1 is a ligand (e.g., a dAb monomer) as described herein. As described herein preferred antagonists of TNFR1 suitable for use in the invention comprise a dAb that binds TNFR1 and inhibits a function of TNFR1. However, instead of comprising a "dAb," an antagonist of TNFR1(e.g., ligand) suitable for use in the invention can comprise a domain that comprises the CDRs of a dAb that binds TNFR1 (e.g., CDRs grafted onto a suitable protein scaffold or skeleton, eg an affibody, an SpA scaffold, an LDL receptor class A domain or an EGF domain) or a protein domain comprising a binding site for TNFR1, e.g., wherein the domain is selected from an affibody, an SpA domain, an LDL receptor class A domain, an EGF domain, an avimer. The disclosure as a whole is to be construed accordingly to provide disclosure of antagonists, ligands and methods using such domains in place of a dAb.

Antagonists of TNFR1, including ligands according to any aspect of the present invention, as well as dAb monomers useful in constructing such ligands, preferably bind from their target(s) with a $K_d$ of 300 nM to 5 pM (ie, $3\times10^{-7}$ to $5\times10^{-12}$M), preferably 50 nM to 20 pM, or 5 nM to 200 pM or 1 nM to 100 pM, $1\times10^{-7}$ M or less, $1\times10^{-8}$ M or less, $1\times10^{-9}$ M or less, $1\times10^{-10}$ M or less, $1\times10^{-11}$ M or less; and/or a $K_{off}$ rate constant of $5\times10^{-1}$ s$^{-1}$ to $1\times10^{-7}$ s$^{-1}$, preferably $1\times10^{-2}$ s$^{-1}$ to $1\times10^{-6}$ s$^{-1}$, or $5\times10^{-3}$ s$^{-1}$ to $1\times10^{-5}$ s$^{-1}$, or $5\times10^{-1}$ s$^{-1}$ or less, or $1\times10^{-2}$ s$^{-1}$ or less, or $1\times10^{-3}$ s$^{-1}$ or less, or $1\times10^{-4}$ s$^{-1}$ or less, or $1\times10^{-5}$ s$^{-1}$ or less, or $1\times10^{-6}$ s$^{-1}$ or less as determined by surface plasmon resonance. The $K_d$ rate constant is defined as $K_{off}/K_{on}$. Additionally or alternatively, the ligand (e.g, dAb monomer) binds TNFR1 with a moderate or fast $K_{on}$, and a slow $K_{off}$. Preferably, a $K_{on}$ of about $10^4$ M/s to about $10^5$ M/s, and/or a $K_{off}$ of about $10^{-3}$ s$^{-1}$ to about $10^{-5}$ s$^{-1}$.

Ligands and dAb Monomers that Bind TNFR1

Preferred antagonists of TNFR1 that are suitable for use in the invention are ligands or dAb monomers that are efficacious in models of respiratory diseases when an effective amount is administered. Generally an effective amount is about 1 mg/kg to about 10 mg/kg (e.g., about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 10 mg/kg). In particular embodiments, about 5 μg/kg to about 3 mg/kg or preferably, about 50 μg/kg to about 500 μg/kg are administered.

Several suitable animal models of respiratory disease are known in the art, and are recognized by those skilled in the art as being predictive of therapeutic efficacy in humans. For example, suitable animal models of respiratory disease include models of chronic obstructive pulmonary disease (see, Groneberg, D A et al., Respiratory Research 5:18 (2004)), and models of asthma (see, Coffman et al., J. Exp. Med. 201(12):1875-1879 (2001). Preferably, the ligand or dAb monomer is efficacious in the mouse subchronic model of tobacco smoke-induced chronic obstructive pulmonary disease described herein. (See, also, Wright and Churg, Chest, 122:301-306 (2002).) For example, administering an effective amount of the ligand can reduce, delay or prevent onset of the symptoms of COPD in the model, as compared to a suitable control. The prior art does not suggest using antagonists of TNFR1 (e.g., ligands or dAb monomers) in these models, or that they would be efficacious.

Generally, suitable ligands (e.g., dAb monomer) comprise an anti-TNFR1 dAb monomer (e.g., dual specific ligand comprising such a dAb) that binds TNFR1 with a $K_d$ of 300 nM to 5 pM (ie, $3\times10^{-7}$ to $5\times10^{-12}$M), preferably 50 nM to 20 pM, more preferably 5 nM to 200 pM and most preferably 1 nM to 100 pM, for example $1\times10^{-7}$ M or less, preferably $1\times10^{-8}$ M or less, more preferably $1\times10^{-9}$ M or less, advantageously $1\times10^{-10}$ M or less and most preferably $1\times10^{-11}$ M or less; and/or a $K_{off}$ rate constant of $5\times10^{-1}$ s$^{-1}$ to $1\times10^{-7}$ s$^{-1}$, preferably $1\times10^{-2}$ s$^{-1}$ to $1\times10^{-6}$ s$^{-1}$, more preferably $5\times10^{-3}$ s$^{-1}$ to $1\times10^{-5}$ s$^{-1}$, for example $5\times10^{-1}$ s$^{-1}$ or less, preferably $1\times10^{-2}$ s$^{-1}$ or less, advantageously $1\times10^{-3}$ s$^{-1}$ or less, more preferably $1\times10^{-4}$ s$^{-1}$ or less, still more preferably $1\times10^{-5}$ s$^{-1}$ or less, and most preferably $1\times10^{-6}$ s$^{-1}$ or less as determined by surface plasmon resonance. (The $K_d = K_{off}/K_{on}$). Certain ligands or dAb monomers suitable for use in the invention specifically bind human TNFR1 with a $K_d$ of 50 nM to 20 pM, and a $K_{off}$ rate constant of $5\times10^{-1}$ s$^{-1}$ to $1\times10^{-7}$ s$^{-1}$, as determined by surface plasmon resonance.

Some ligands or dAb monomers inhibit binding of TNFα to TNFR1. For example, some ligands or dAb monomers inhibit binding of TNFα to TNFR1 with an inhibitory concentration 50 (IC50) of 500 nM to 50 pM, preferably 100 nM to 50 pM, more preferably 10 nM to 100 pM, advantageously 1 nM to 100 pM; for example 50 nM or less, preferably 5 nM or less, more preferably 500 pM or less, advantageously 200 pM or less, and most preferably 100 pM or less. Preferably, the TNFR1 is human TNFR1.

Other ligands and dAb monomers do not inhibit binding of TNFα to TNFR1, but are antagonists because they inhibit signal transduction mediated through TNFR1. For example, a ligand or dAb monomer can inhibit TNFα-induced clustering of TNFR1, which precedes signal transduction through TNFR1. For example, in certain embodiments, a ligand or dAb monomer can bind TNFR1 and inhibit TNFR1-mediated signaling, but does not substantially inhibit binding of TNFα to TNFR1. In some embodiments, the ligand or dAb monomer inhibits TNFα-induced crosslinking or clustering of TNFR1 on the surface of a cell. Such ligands or dAbs (e.g., TAR2m-21-23 described herein) are advantageous because they can antagonize cell surface TNFR1 but do not substantially reduce the inhibitory activity of endogenous soluble TNFR1. For example, the ligand or dAb can bind TNFR1, but inhibit binding of TNFα to TNFR1 in a receptor binding assay by no more that about 10%, no more that about 5%, no more than about 4%, no more than about 3%, no more than about 2%, or no more than about 1%. Also, in these embodiments, the ligand or dAb inhibits TNFα-induced crosslinking of TNFR1 and/or TNFR1-mediated signaling in a standard cell assay by at least about 10%, at least about 20%, at least about 30%, at least about 40%, at least about 50%, at least about 60%, at least about 70%, at least about 80%, at least about 90%, at least about 95%, or at least about 99%. Such ligands or dAb monomers provide several advantages, as discussed herein with respect to antagonists that have these properties. Accordingly, administering such ligand or dAb monomer to a mammal in need thereof can complement the endogenous regulatory pathways that inhibit the activity TNFα and the activity of TNFR1 in vivo.

The ligand can be monovalent (e.g., a dAb monomer) or multivalent (e.g., dual specific, multi-specific) as described herein. In particular embodiments, the ligand is a dAb monomer that binds TNFR1. Domain antibody monomers that bind TNFR1 have a small footprint, relative to other binding formats, such as a monoclonal antibody, for example. Thus, such a dAb monomer can selectively block a function of TNFR1, but not interfere with other functions of TNFR1. For example, a dAb monomer that binds TNFR1 can antagonize TNFR1 (e.g., inhibit TNFR1 mediated signal transduction) but not inhibit binding of TNFα to TNFR1 or shedding of TNFR1.

In more particular embodiments, the ligand is a dAb monomer that binds TNFR1 and competes with TAR2m-21-23 for binding to mouse TNFR1 or competes with TAR2h-205 for binding to human TNFR1.

In other embodiments, the ligand is multivalent and comprises two or more dAb monomers that bind TNFR1. Multivalent ligands can contain two or more copies of a particular dAb that binds TNFR1 or contain two or more dAbs that bind TNFR1. For example, the ligand can be a dimer, trimer or multimer comprising two or more copies of a particular dAb that binds TNFR1, or two or more different dAbs that bind TNFR1. In some examples, the ligand is a homo dimer or homo trimer that comprises two or three copies of a particular dAb that binds TNFR1, respectively. Preferably, a multivalent ligand does not substantially agonize TNFR1 (act as an agonist of TNFR1) in a standard cell assay (i.e., when present at a concentration of 1 nM, 10 nM, 100 nM, 1 μM, 10 μM, 100 μM, 1000 μM or 5,000 μM, results in no more than about 5% of the TNFR1-mediated activity induced by TNFα (100 pg/ml) in the assay).

In certain embodiments, the multivalent ligand contains two or more dAbs that bind desired epitopes or domains of TNFR1, or two or more copies of a dAb that binds a desired epitope of TNFR1. Ligands of this type can bind TNFR1 with high aviditiy, and be more selective for binding to cells that over express TNFR1 or express TNFR1 on their surface at high density than other ligand formats, such as dAb monomers.

In other particular embodiments, the multivalent ligand comprises two or more dAbs, or two or more copies of a particular dAb, that binds TNFR1. Multivalent ligands of this type can bind TNFR1 monomers with low affinity, but bind receptor multimers (e.g., trimers see in the receptor ligand complex) with high avidity. Thus, ligands of this format can be administered to effectively target receptors that have clustered or associated with each other and/or ligand TNFα) which is required for TNFR1-mediated signal transduction.

Preferably, the ligand or dAb monomer neutralizes (inhibits the activity of) TNFR1 in a standard assay (e.g., the standard L929 or standard HeLa IL-8 assays described herein) with a neutralizing dose 50 (ND50) of 500 nM to 50 pM, preferably 100 nM to 50 pM, more preferably 10 nM to 100 pM, advantageously 1 nM to 100 pM; for example 50 nM or less, preferably 5 nM or less, more preferably 500 pM or less, advantageously 200 pM or less, and most preferably 100 pM or less. In other embodiments, the ligand or dAb monomer binds TNFR1 and antagonizes the activity of the TNFR1 in a standard cell assay (e.g., the standard L929 or standard HeLa IL-8 assays described herein) with an ND$_{50}$ of ≤100 nM, and at a concentration of ≤10 μM the dAb agonizes the activity of the TNFR1 by ≤5% in the assay.

In other embodiments, the ligand or dAb monomer specifically binds TNFR1 with a $K_d$ described herein and inhibits lethality in a standard mouse LPS/D-galactosamine-induced septic shock model (i.e., prevents lethality or reduces lethality by at least about 10%, as compared with a suitable control). Preferably, the dAb monomer inhibits lethality by at least about 25%, or by at least about 50%, as compared to a suitable control in a standard mouse LPS/D-galactosamine-induced septic shock model when administered at about 5 mg/kg or more preferably about 1 mg/kg.

In particular embodiments, ligand or dAb monomer does not substantially agonize TNFR1 (act as an agonist of TNFR1) in a standard cell assay, such as assay the standard L929 or standard HeLa IL-8 assays described herein (i.e., when present at a concentration of 1 nM, 10 nM, 100 nM, 1 μM, 10 μM, 100 μM, 1000 μM or 5,000 μM, results in no more than about 5% of the TNFR1-mediated activity induced by TNFα (100 pg/ml) in the assay).

In other embodiments, the ligand comprises a domain antibody (dAb) monomer that specifically binds Tumor Necrosis Factor Receptor 1 (TNFR1, p55, CD120a) with a $K_d$ of 300 nM to 5 pM, and comprises an amino acid sequence that is at least about 80%, at least about 85%, at least about 90%, at least about 91%, at least about 92%, at least about 93%, at least about 94%, at least about 95%, at least about 96%, at least about 97%, at least about 98%, or at least about 99% homologous to the amino acid sequence or a dAb selected from the group consisting of TAR2h-12 (SEQ ID NO:1), TAR2h-13 (SEQ ID NO:2), TAR2h-14 (SEQ ID NO:3), TAR2h-16 (SEQ ID NO:4), TAR2h-17 (SEQ ID NO:5), TAR2h-18 (SEQ ID NO:6), TAR2h-19 (SEQ ID NO:7), TAR2h-20 (SEQ ID NO:8), TAR2h-21 (SEQ ID NO:9), TAR2h-22 (SEQ ID NO:10), TAR2h-23 (SEQ ID NO:11), TAR2h-24 (SEQ ID NO:12), TAR2h-25 (SEQ ID NO:13), TAR2h-26 (SEQ ID NO:14), TAR2h-27 (SEQ ID NO:15), TAR2h-29 (SEQ ID NO:16), TAR2h-30 (SEQ ID NO:17), TAR2h-32 (SEQ ID NO:18), TAR2h-33 (SEQ ID NO:19), TAR2h-10-1 (SEQ ID NO:20), TAR2h-10-2 (SEQ ID NO:21), TAR2h-10-3 (SEQ ID NO:22), TAR2h-10-4 (SEQ ID NO:23), TAR2h-10-5 (SEQ ID NO:24), TAR2h-10-6 (SEQ ID NO:25), TAR2h-10-7 (SEQ ID NO:26), TAR2h-10-8 (SEQ ID NO:27), TAR2h-10-9 (SEQ ID NO:28), TAR2h-10-10 (SEQ ID NO:29), TAR2h-10-11 (SEQ ID NO:30), TAR2h-10-12 (SEQ ID NO:31), TAR2h-10-13 (SEQ ID NO:32), TAR2h-10-14 (SEQ ID NO:33), TAR2h-10-15 (SEQ ID NO:34), TAR2h-10-16 (SEQ ID NO:35), TAR2h-10-17 (SEQ ID NO:36), TAR2h-10-18 (SEQ ID NO:37), TAR2h-10-19 (SEQ ID NO:38), TAR2h-10-20 (SEQ ID NO:39), TAR2h-10-21 (SEQ ID NO:40), TAR2h-10-22 (SEQ ID NO:41), TAR2h-10-27 (SEQ ID NO:42), TAR2h-10-29 (SEQ ID NO:43), TAR2h-10-31 (SEQ ID NO:44), TAR2h-10-35 (SEQ ID NO:45), TAR2h-10-36 (SEQ ID NO:46), TAR2h-10-37 (SEQ ID NO:47), TAR2h-10-38 (SEQ ID NO:48), TAR2h-10-45 (SEQ ID NO:49), TAR2h-10-47 (SEQ ID NO:50), TAR2h-10-48 (SEQ ID NO:51), TAR2h-10-57 (SEQ ID NO:52), TAR2h-10-56 (SEQ ID NO:53), TAR2h-10-58 (SEQ ID NO:54), TAR2h-10-66 (SEQ ID NO:55), TAR2h-10-64 (SEQ ID NO:56), TAR2h-10-65 (SEQ ID NO:57), TAR2h-10-68 (SEQ ID NO:58), TAR2h-10-69 (SEQ ID NO:59), TAR2h-10-67 (SEQ ID NO:60), TAR2h-10-61 (SEQ ID NO:61), TAR2h-10-62 (SEQ ID NO:62), TAR2h-10-63 (SEQ ID NO:63), TAR2h-10-60 (SEQ ID NO:64), TAR2h-10-55 (SEQ ID NO:65), TAR2h-10-59 (SEQ ID NO:66), TAR2h-10-70 (SEQ ID NO:67), TAR2h-34 (SEQ ID NO:68), TAR2h-35 (SEQ ID NO:69), TAR2h-36 (SEQ ID NO:70), TAR2h-37 (SEQ ID NO:71), TAR2h-38 (SEQ ID NO:72), TAR2h-39 (SEQ ID NO:73), TAR2h-40 (SEQ ID NO:74), TAR2h-41 (SEQ ID NO:75), TAR2h-42 (SEQ ID NO:76), TAR2h-43 (SEQ ID NO:77), TAR2h-44 (SEQ ID NO:78), TAR2h-45 (SEQ ID NO:79), TAR2h-47 (SEQ ID NO:80), TAR2h-48 (SEQ ID NO:81), TAR2h-50 (SEQ ID NO:82), TAR2h-51 (SEQ ID NO:83), TAR2h-66 (SEQ ID NO:84), TAR2h-67 (SEQ ID NO:85), TAR2h-68 (SEQ ID NO:86), TAR2h-70 (SEQ ID NO:87), TAR2h-71 (SEQ ID NO:88), TAR2h-72 (SEQ ID NO:89), TAR2h-73 (SEQ ID NO:90), TAR2h-74 (SEQ ID NO:91), TAR2h-75 (SEQ ID NO:92), TAR2h-76 (SEQ ID NO:93), TAR2h-77 (SEQ ID NO:94), TAR2h-78 (SEQ ID NO:95), TAR2h-79 (SEQ ID NO:96), TAR2h-15 (SEQ ID NO:97), TAR2h-131-8 (SEQ ID NO:98), TAR2h-131-24 (SEQ ID NO:99), TAR2h-15-8 (SEQ ID NO:100), TAR2h-15-8-1 SEQ ID NO:101), TAR2h-15-8-2 (SEQ ID NO:102), TAR2h-185-23 (SEQ ID NO:103), TAR2h-154-10-5 (SEQ ID NO:104), TAR2h-14-2 (SEQ ID NO:105), TAR2b-151-8 (SEQ ID NO:106), TAR2h-152-7 (SEQ ID NO:107), TAR2h-35-4 (SEQ ID NO:108), TAR2h-154-7 (SEQ ID NO:109), TAR2h-80 (SEQ ID NO:110), TAR2h-81 (SEQ ID NO:111), TAR2h-82 (SEQ ID NO:112), TAR2h-83 (SEQ ID NO:113), TAR2h-84 (SEQ ID NO:114), TAR2h-85 (SEQ ID NO:115), TAR2h-86 (SEQ ID NO:116), TAR2h-87 (SEQ ID NO:117), TAR2h-88 (SEQ ID NO:118), TAR2h-89 (SEQ ID NO: 119), TAR2h-90 (SEQ ID NO:120), TAR2h-91 (SEQ ID NO:121), TAR2h-92 (SEQ ID NO:122), TAR2h-93 (SEQ ID NO:123), TAR2h-94 (SEQ ID NO:124), TAR2h-95 (SEQ ID NO:125), TAR2h-96 (SEQ ID NO:126), TAR2h-97 (SEQ ID NO:127), TAR2h-99 (SEQ ID NO: 128), TAR2h-100 (SEQ ID NO:129), TAR2h-101 (SEQ ID NO:130), TAR2h-102 (SEQ ID NO:131), TAR2h-103 (SEQ ID NO:132), TAR2h-104 (SEQ ID NO:133), TAR2h-105 (SEQ ID NO:134), TAR2h-106 (SEQ ID NO:135), TAR2h-107 (SEQ ID NO:136), TAR2h-108 (SEQ ID NO:137), TAR2h-109 (SEQ ID NO: 138), TAR2h-110 (SEQ ID NO:139), TAR2h-111 (SEQ ID NO:140), TAR2h-112 (SEQ ID NO:141), TAR2h-113 (SEQ ID NO: 142), TAR2h-114 (SEQ ID NO: 143), TAR2h-115 (SEQ ID NO:144), TAR2h-116 (SEQ ID NO:145), TAR2h-117 (SEQ ID NO:146), TAR2h-118 (SEQ ID NO:147), TAR2h-119 (SEQ ID NO:148), TAR2h-120 (SEQ ID NO:149), TAR2h-121 (SEQ ID NO:150), TAR2h-122 (SEQ ID NO:151), TAR2h-123 (SEQ ID NO:152), TAR2h-124 (SEQ ID NO:153), TAR2h-125 (SEQ ID NO:154), TAR2h-126 (SEQ ID NO:155), TAR2h-127 (SEQ ID NO:156), TAR2h-128 (SEQ ID NO:157), TAR2h-129 (SEQ ID NO:158), TAR2h-130 (SEQ ID NO:159), TAR2h-131 (SEQ ID NO:160), TAR2h-132 (SEQ ID NO:161), TAR2h-133 (SEQ ID NO:162), TAR2h-151 (SEQ ID NO:163), TAR2h-152 (SEQ ID NO:164), TAR2h-153 (SEQ ID NO:165), TAR2h-154 (SEQ ID NO:166), TAR2h-159 (SEQ ID NO:167), TAR2h-165 (SEQ ID NO:168), TAR2h-166 (SEQ ID NO:169), TAR2h-168 (SEQ ID NO:170), TAR2h-171 (SEQ ID NO:171), TAR2h-172 (SEQ ID NO:172), TAR2h-173 (SEQ ID NO:173), TAR2h-174 (SEQ ID NO:174), TAR2h-176 (SEQ ID NO:175), TAR2h-178 (SEQ ID NO:176), TAR2h-201 (SEQ ID NO:177), TAR2h-202 (SEQ ID NO:178), TAR2h-203 (SEQ ID NO:179), TAR2h-204 (SEQ ID NO:180), TAR2h-185-25 (SEQ ID NO:181), TAR2h-154-10 (SEQ ID NO:182), TAR2h-205 (SEQ ID NO:183), TAR2h-10 (SEQ ID NO:184), TAR2h-5 (SEQ ID NO:185), TAR2h-5d1 (SEQ ID NO:186), TAR2h-5d2 (SEQ ID NO:187), TAR2h-5d3 (SEQ ID NO:188), TAR2h-5d4 (SEQ ID NO:189), TAR2h-5d5 (SEQ ID NO:190), TAR2h-5d6 (SEQ ID NO:191), TAR2h-5d7 (SEQ ID NO:192), TAR2h-5d8 (SEQ ID NO:193), TAR2h-5d9 (SEQ ID NO:194), TAR2h-5d10 (SEQ ID NO:195), TAR2h-5d11 (SEQ ID NO:196), TAR2h-5d2 (SEQ ID NO:197), and TAR2h-5d13 (SEQ ID NO:198).

In other embodiments, the ligand comprises a domain antibody (dAb) monomer that specifically binds Tumor Necrosis Factor Receptor 1 (TNFR1, p55, CD120a) with a $K_d$ of 300 nM to 5 pM, and comprises an amino acid sequence that is at least about 80%, at least about 85%, at least about 90%, at least about 91%, at least about 92%, at least about 93%, at least about 94%, at least about 95%, at least about 96%, at least about 97%, at least about 98%, or at least about 99% homologous to the amino acid sequence of a dAb that has the amino acid sequence of any of SEQ ID NO:216 through SEQ ID NO:433.

In other embodiments, the ligand comprises a domain antibody (dAb) monomer that specifically binds Tumor Necrosis Factor Receptor 1 (TNFR1, p55, CD120a) with a $K_d$ of 300 nM to 5 pM, and comprises an amino acid sequence that is at least about 80%, at least about 85%, at least about 90%, at least about 91%, at least about 92%, at least about 93%, at least about 94%, at least about 95%, at least about 96%, at least about 97%, at least about 98%, or at least about 99% homologous to the amino acid sequence or a dAb selected from the group consisting of TAR2m-14 (SEQ ID NO:199), TAR2m-15 (SEQ ID NO:200), TAR2m-19 (SEQ ID NO:201), TAR2m-20 (SEQ ID NO:202), TAR2m-21 (SEQ ID NO:203), TAR2m-24 (SEQ ID NO:204), TAR2m-21-23 (SEQ ID NO:205), TAR2m-21-07 (SEQ ID NO:206), TAR2m-21-43 (SEQ ID NO:207), TAR2m-21-48 (SEQ ID NO:208), TAR2m-21-10 (SEQ ID NO:209), TAR2m-21-06 (SEQ ID NO:210), and TAR2m-21-17 (SEQ ID NO:211).

In some embodiments, the ligand comprises a dAb monomer that binds TNFR1 and competes with any of the dAbs disclosed herein for binding to TNFR1 (e.g., mouse and/or human TNFR1).

The ligand of the invention can comprises a non-immunoglobulin binding moiety that has binding specificity for TNFR1 and preferably inhibits a function of TNFR1 (e.g., binding TNFα, signaling upon binding TNFα), wherein the non-immunoglobulin binding moiety comprises one, two or three of the CDRs of a $V_H$, $V_L$ or $V_{HH}$ that binds TNFR1 and a suitable scaffold. In certain embodiments, the non-immunoglobulin binding moiety comprises CDR3 but not CDR1 or CDR2 of a $V_H$, $V_L$, or $V_{HH}$ that binds TNFR1 and a suitable scaffold. In other embodiments, the non-immunoglobulin binding moiety comprises CDR1 and CDR2, but not CDR3 of a $V_H$, $V_L$ or $V_{HH}$ that binds TNFR1 and a suitable scaffold. In other embodiments, the non-immunoglobulin binding moiety comprises CDR1, CDR2 and CDR3 of a $V_H$, $V_L$ or $V_{HH}$ that binds TNFR1 and a suitable scaffold. Preferably, the CDR or CDRs of the ligand of these embodiments is a CDR or CDRs of an anti-TNFR1 dAb described herein. Preferably, the non-immunoglobulin binding moiety comprises one, two, or three of the CDRs of one the anti-TNFR1 dAbs disclosed herein. In other embodiments, the ligand comprises only CDR3 of a $V_H$, $V_L$ or $V_{HH}$ that binds TNFR1. The non-immunoglobulin domain can comprise an amino acid sequence that one or more regions that have sequence identity to one, two or three of the CDRs of an anti-TNFR1 dAb described herein. For example, the non-immunoglobulin domain can have an amino acid sequence that contains at least about 50%, at least about 60%, at least about 70%, at least about 80%, or at least about 90% sequence identity with CDR1, CDR2 and/or CDR3 of an anti-TNFR1 dAb disclosed herein. Even more preferably, the non-immunoglobulin binding moiety comprises one, two, or three of the CDRs of TAR2h-131-511, TAR2h-131-193 and TAR2h-131-194.

The invention also relates to a ligand comprising a protein moiety that has a binding site with binding specificity for TNFR1, wherein said protein moiety comprises an amino acid sequence that is the same as the amino acid sequence of CDR3 of an anti-TNFR1 dAb disclosed herein, such as TAR2h-131-511, TAR2h-131-193 and TAR2h-131-194.

In some embodiments, the ligand comprising a protein moiety that has a binding site with binding specificity for TNFR1, wherein the protein moiety has an amino acid sequence that is the same as the amino acid sequence of CDR3 of an anti-TNFR1 dAb disclosed herein, and also comprises an amino acid sequence that is the same as the amino acid sequence of CDR1 and/or CDR2 of an anti-TNFR1 dAb disclosed herein, such as TAR2h-131-511, TAR2h-131-193 and TAR2h-131-194.

In other embodiments, the ligand comprises a immunoglobulin single variable domain that binds TNFR1, wherein the immunoglobulin single variable domain that binds IL-4 differs from the amino acid sequence of an anti-TNFR1 dAb disclosed herein at no more than 25 amino acid positions and has a CDR1 sequence that has at least 50% identity to the CDR1 sequence of the anti-TNFR1 dAbs disclosed herein, such as TAR2h-131-511, TAR2h-131-193 and TAR2h-131-194.

In other embodiments, the ligand comprises an immunoglobulin single variable domain that binds TNFR1, wherein the amino acid sequence of the immunoglobulin single variable domain that binds TNFR1 differs from the amino acid sequence of an anti-TNFR1 dAb disclosed herein at no more than 25 amino acid positions and has a CDR2 sequence that has at least 50% identity to the CDR2 sequence of the anti-TNFR1 dAbs disclosed herein, such as TAR2h-131-511, TAR2h-131-193 and TAR2h-131-194.

In other embodiments, the ligand comprises an immunoglobulin single variable domain that binds TNFR1, wherein the amino acid sequence of the immunoglobulin single variable domain that binds TNFR1 differs from the amino acid sequence of an anti-TNFR1 dAb disclosed herein at no more than 25 amino acid positions and has a CDR3 sequence that has at least 50% identity to the CDR3 sequence of the anti-TNFR1 dAbs disclosed herein, such as TAR2h-131-511, TAR2h-131-193 and TAR2h-131-194.

In other embodiments, the ligand comprises an immunoglobulin single variable domain that binds TNFR1, wherein the amino acid sequence of the immunoglobulin single variable domain that binds TNFR1 differs from the amino acid sequence of an anti-TNFR1 dAb disclosed herein at no more than 25 amino acid positions and has a CDR1 sequence and a CDR2 sequence that has at least 50% identity to the CDR1 or CDR2 sequences, respectively, of the anti-TNFR1 dAbs disclosed herein, such as TAR2h-131-511, TAR2h-131-193 and TAR2h-131-194.

In other embodiments, the ligand comprises an immunoglobulin single variable domain that binds TNFR1, wherein the amino acid sequence of the immunoglobulin single variable domain that binds TNFR1 differs from the amino acid sequence of an anti-TNFR1 dAb disclosed herein at no more than 25 amino acid positions and has a CDR2 sequence and a CDR3 sequence that has at least 50% identity to the CDR2 or CDR3 sequences, respectively, of the anti-TNFR1 dAbs disclosed herein, such as TAR2h-131-511, TAR2h-131-193 and TAR2h-131-194.

In other embodiments, the ligand comprises an immunoglobulin single variable domain that binds TNFR1, wherein the amino acid sequence of the immunoglobulin single variable domain that binds TNFR1 differs from the amino acid sequence of an anti-TNFR1 dAb disclosed herein at no more than 25 amino acid positions and has a CDR1 sequence and a CDR3 sequence that has at least 50% identity to the CDR1 or CDR3 sequences, respectively, of the anti-TNFR1 dAbs disclosed herein, such as TAR2h-131-511, TAR2h-131-193 and TAR2h-131-194.

In other embodiments, the ligand comprises an immunoglobulin single variable domain that binds TNFR1, wherein the amino acid sequence of the immunoglobulin single variable domain that binds TNFR1 differs from the amino acid sequence of an anti-TNFR1 dAb disclosed herein at no more than 25 amino acid positions and has a CDR1 sequence, a CDR2 sequence and a CDR3 sequence that has at least 50% identity to the CDR1, CDR2 or CDR3 sequences, respectively, of the anti-TNFR1 dAbs disclosed herein; such as TAR2h-131-511, TAR2h-131-193 and TAR2h-131-194.

In another embodiment, the invention is a ligand comprising an immunoglobulin single variable domain that binds TNFR1, wherein the immunoglobulin single variable domain that binds TNFR1 has a CDR2 sequence that has at least 50% identity to the CDR2 sequences of an anti-TNFR1 dAb disclosed herein, such as TAR2h-131-511, TAR2h-131-193 and TAR2h-131-194.

In another embodiment, the invention is a ligand comprising an immunoglobulin single variable domain that binds TNFR1, wherein the immunoglobulin single variable domain that binds TNFR1 has a CDR3 sequence that has at least 50% identity to the CDR3 sequences of an anti-TNFR1 dAb disclosed herein, such as TAR2h-131-511, TAR2h-131-193 and TAR2h-131-194.

In another embodiment, the invention is a ligand comprising an immunoglobulin single variable domain that binds TNFR1, wherein the immunoglobulin single variable domain that binds TNFR1 has a CDR1 and a CDR2 sequence that has at least 50% identity to the CDR1 and CDR2 sequences, respectively, of an anti-TNFR1 dAb disclosed herein, such as TAR2h-131-511, TAR2h-131-193 and TAR2h-131-194.

In another embodiment, the invention is a ligand comprising an immunoglobulin single variable domain that binds TNFR1, wherein the immunoglobulin single variable domain that binds TNFR1 has a CDR2 and a CDR3 sequence that has at least 50% identity to the CDR2 and CDR3 sequences, respectively, of an anti-TNFR1 dAb disclosed herein, such as TAR2h-131-511, TAR2h-131-193 and TAR2h-131-194.

In another embodiment, the invention is a ligand comprising an immunoglobulin single variable domain that binds TNFR1, wherein the immunoglobulin single variable domain that binds TNFR1 has a CDR1 and a CDR3 sequence that has at least 50% identity to the CDR1 and CDR3 sequences, respectively, of an anti-TNFR1 dAb disclosed herein, such as TAR2h-131-511, TAR2h-131-193 and TAR2h-131-194.

In another embodiment, the invention is a ligand comprising an immunoglobulin single variable domain that binds TNFR1, wherein the immunoglobulin single variable domain that binds TNFR1 has a CDR1, CDR2, and a CDR3 sequence that has at least 50% identity to the CDR1, CDR2 and CDR3 sequences, respectively, of an anti-TNFR1 dAb disclosed herein, such as TAR2h-131-511, TAR2h-131-193 and TAR2h-131-194.

In some embodiments, the ligand comprising a dAb that binds human TNFR1 and is an antagonist of human TNFR1, wherein said ligand inhibits TNFα-induced inflammation or TNFα-induced inflammatory mediator at a dose [mg/kg] that is no more than ½, ⅓, ¼, ⅕, ⅒, ¹⁄₁₅, ¹⁄₂₀, ¹⁄₂₅, or ¹⁄₃₀ the dose of etanercept (ENBREL, Immunex Corporation) that is required to inhibit said TNFα-induced inflammation or TNFα-induced inflammatory mediator to substantially the same of to the same degree. For example, the ligand can inhibit TNFα-induced cell influx of tissue (e.g., lung), TNFα-induced increase in the production, concentration or level of inflammatory mediators, such as the early acting neutrophil chemoattractants KC and MIP-1, and the later acting chemokine MCP-1 and adhesion molecule E-selectin, at a dose [mg/kg] that is no more than ½, ⅓, ¼, ⅕, ⅒, ¹⁄₁₅, ¹⁄₂₀, ¹⁄₂₅, or ¹⁄₃₀ the dose of etanercept (ENBREL, Immunex Corporation) that is required to achieve substantially the same or the same level of inhibition. Preferably, the level of inhibition is at least about 50%, at least about 60%, at least about 70%, at least about 80%, at least about 90%, or at least about 95%.

The dAb monomer can comprise any suitable immunoglobulin variable domain, and preferably comprises a human variable domain or a variable domain that comprises human framework regions. In certain embodiments, the dAb monomer comprises a universal framework, as described herein.

The universal framework can be a $V_L$ framework (Vλ or Vκ), such as a framework that comprises the framework amino acid sequences encoded by the human germline DPK1, DPK2, DPK3, DPK4, DPK5, DPK6, DPK7, DPK8, DPK9, DPK10, DPK12, DPK13, DPK15, DPK16, DPK18, DPK19, DPK20, DPK21, DPK22, DPK23, DPK24, DPK25, DPK26 or DPK 28 immunoglobulin gene segment. If desired, the $V_L$ framework can further comprises the framework amino acid sequence encoded by the human germline $J_\kappa 1$, $J_\kappa 2$, $J_\kappa 3$, $J_\kappa 4$, or $J_\kappa 5$ immunoglobulin gene segment.

In other embodiments the universal framework can be a $V_H$ framework, such as a framework that comprises the framework amino acid sequences encoded by the human germline DP4, DP7, DP8, DP9, DP10, DP31, DP33, DP38, DP45, DP46, DP47, DP49, DP50, DP51, DP53, DP54, DP65, DP66, DP67, DP68 or DP69 immunoglobulin gene segment. If desired, the $V_H$ framework can further comprises the framework amino acid sequence encoded by the human germline $J_H 1$, $J_H 2$, $J_H 3$, $J_H 4$, $J_H 4b$, $J_H 5$ and $J_H 6$ immunoglobulin gene segment.

In particular embodiments, the dAb monomer comprises the DPK9 $V_L$ framework, or a $V_H$ framework selected from the group consisting of DP47, DP45 and DP38.

In certain embodiments, the dAb monomer comprises one or more framework regions comprising an amino acid sequence that is the same as the amino acid sequence of a corresponding framework region encoded by a human germline antibody gene segment, or the amino acid sequences of one or more of said framework regions collectively comprise up to 5 amino acid differences relative to the amino acid sequence of said corresponding framework region encoded by a human germline antibody gene segment.

In other embodiments, the amino acid sequences of FW1, FW2, FW3 and FW4 of the dAb monomer are the same as the amino acid sequences of corresponding framework regions encoded by a human germline antibody gene segment, or the amino acid sequences of FW1, FW2, FW3 and FW4 collectively contain up to 10 amino acid differences relative to the amino acid sequences of corresponding framework regions encoded by said human germline antibody gene segment.

In other embodiments, the dAb monomer comprises FW1, FW2 and FW3 regions, and the amino acid sequence of said FW1, FW2 and FW3 regions are the same as the amino acid sequences of corresponding framework regions encoded by human germline antibody gene segments.

In some embodiments, the dAb monomer does not comprise a Camelid immunoglobulin variable domain, or one or more framework amino acids that are unique to immunoglobulin variable domains encoded by Camelid germline antibody gene segments.

Nucleic Acid Molecules, Vectors and Host Cells

The invention also provides isolated and/or recombinant nucleic acid molecules encoding ligands as described herein. Nucleic acids referred to herein as "isolated" are nucleic acids which have been separated away from the nucleic acids of the genomic DNA or cellular RNA of their source of origin (e.g., as it exists in cells or in a mixture of nucleic acids such as a library), and include nucleic acids obtained by methods described herein or other suitable methods, including essentially pure nucleic acids, nucleic acids produced by chemical synthesis, by combinations of biological and chemical methods, and recombinant nucleic acids which are isolated (see e.g., Daugherty, B. L. et al., *Nucleic Acids Res.,* 19(9): 2471-2476 (1991); Lewis, A. P. and J. S. Crowe, *Gene,* 101: 297-302 (1991)).

Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes.

In certain embodiments, the isolated and/or recombinant nucleic acid comprises a nucleotide sequence encoding a ligand, as described herein, wherein said ligand comprises an amino acid sequence that has at least about 80%, at least about 85%, at least about 90%, at least about 91%, at least about 92%, at least about 93%, at least about 94%, at least about 95%, at least about 96%, at least about 97%, at least about 98%, or at least about 99% amino acid sequence identity with the amino acid sequence of a dAb that binds TNFR1 disclosed herein.

For example, in some embodiments, the isolated and/or recombinant nucleic acid comprises a nucleotide sequence encoding a ligand that has binding specificity for TNFR1 wherein said ligand comprises an amino acid sequence that has at least about 80%, at least about 85%, at least about 90%, at least about 91%, at least about 92%, at least about 93%, at least about 94%, at least about 95%, at least about 96%, at least about 97%, at least about 98%, or at least about 99% amino acid sequence identity with the amino acid sequence of a dAb selected from the group consisting of TAR2m-15-8 (SEQ ID NO:216), TAR2m-15-12 (SEQ ID NO:217), TAR2 nm-15-2 (SEQ ID NO:218), TAR2m-15-5 (SEQ ID NO:219), TAR2m-15-6 (SEQ ID NO:220), TAR2m-15-9 (SEQ ID NO:221), Tar2h-131-1 (SEQ ID NO:222), Tar2h-131-2 (SEQ ID NO:223), Tar2h-131-3 (SEQ ID NO:224), Tar2h-131-4 (SEQ ID NO:225), Tar2h-131-5 (SEQ ID NO:226), Tar2h-131-6 (SEQ ID NO:227), Tar2h-131-7 (SEQ ID NO:228), Tar2h-131-8 (SEQ ID NO:229), Tar2h-131-9 (SEQ ID NO:230), Tar2h-131-10 (SEQ ID NO:231), Tar2h-131-11 (SEQ ID NO:232), Tar2h-131-12 (SEQ ID NO:233), Tar2h-131-13 (SEQ ID NO:234), Tar2h-131-14 (SEQ ID NO:235), Tar2h-131-15 (SEQ ID NO:236), Tar2h-131-16 (SEQ ID NO:237), Tar2h-131-17 (SEQ ID NO:238), Tar2h-131-18 (SEQ ID NO:239), Tar2h-131-19 (SEQ ID NO:240), Tar2h-131-20 (SEQ ID NO:241), Tar2h-131-21 (SEQ ID NO:242), Tar2h-131-22 (SEQ ID NO:243), Tar2h-131-23 (SEQ ID NO:244), Tar2h-131-24 (SEQ ID NO:245), Tar2h-131-25 (SEQ ID NO:246), Tar2h-131-26 (SEQ ID NO:247), Tar2h131-27 (SEQ ID NO:248), Tar2h131-28 (SEQ ID NO:249), Tar2h131-29 (SEQ ID NO:250), Tar2h131-30 (SEQ ID NO:251), Tar2h131-31 (SEQ ID NO:252), Tar2h131-32 (SEQ ID NO:253), Tar2h131-33 (SEQ ID NO:254), Tar2h131-34 (SEQ ID NO:255), Tar2h131-35 (SEQ ID NO:256), Tar2h131-36 (SEQ ID NO:257), Tar2h131-37 (SEQ ID NO:258), Tar2h131-38 (SEQ ID NO:259), Tar2h131-39 (SEQ ID NO:260), Tar2h131-40 (SEQ ID NO:261), Tar2h131-41 (SEQ ID NO:262), Tar2h131-42 (SEQ ID NO:263), Tar2h131-43 (SEQ ID NO:264), Tar2h131-44 (SEQ ID NO:265), Tar2h131-45 (SEQ ID NO:266), Tar2h131-46 (SEQ ID NO:267), Tar2h131-47 (SEQ ID NO:268), Tar2h131-48 (SEQ ID NO:269), Tar2h131-49 (SEQ ID NO:270), Tar2h-131-50 (SEQ ID NO:271), Tar2h-131-51 (SEQ ID NO:272), Tar2h-131-52 (SEQ ID NO:273), Tar2h-131-53 (SEQ ID NO:274), Tar2h-131-54 (SEQ ID NO:275), Tar2h-131-55 (SEQ ID NO:276), Tar2h-131-56 (SEQ ID NO:277), Tar2h-131-57 (SEQ ID NO:278), Tar2h-131-58 (SEQ ID NO:279), Tar2h-131-59 (SEQ ID NO:280), Tar2h-131-60 (SEQ ID NO:281), Tar2h-131-61 (SEQ ID NO:282), Tar2h-131-62 (SEQ ID NO:283), Tar2h-131-63 (SEQ ID NO:284), Tar2h-131-64 (SEQ ID NO:285), Tar2h-131-65 (SEQ ID NO:286), Tar2h-131-66 (SEQ ID NO:287), Tar2h-131-67 (SEQ ID NO:288), Tar2h-131-68 (SEQ ID NO:289), Tar2h-131-69 (SEQ ID NO:290), Tar2h-131-70 (SEQ ID NO:291), Tar2h-131-71 (SEQ ID NO:292), Tar2h-131-72 (SEQ ID NO:293), Tar2h-131-73 (SEQ ID NO:294), Tar2h-131-74 (SEQ ID NO:295), Tar2h-131-75 (SEQ ID NO:296), Tar2h-131-76 (SEQ ID NO:297), Tar2h-131-77 (SEQ ID NO:298), Tar2h-131-78 (SEQ ID NO:299), Tar2h-131-79 (SEQ ID NO:300), Tar2h-131-80 (SEQ ID NO:301), Tar2h-131-81 (SEQ ID NO:302), Tar2h-131-82 (SEQ ID NO:303), Tar2h-131-83 (SEQ ID NO:304), Tar2h-131-86 (SEQ ID NO:305), Tar2h-131-87 (SEQ ID NO:306), Tar2h-131-88 (SEQ ID NO:307), Tar2h-131-89 (SEQ ID NO:308), Tar2h-131-90 (SEQ ID NO:309), Tar2h-131-91 (SEQ ID NO:310), Tar2h-131-92 (SEQ ID NO:311), Tar2h-131-93 (SEQ ID NO:312), Tar2h-131-94 (SEQ ID NO:313), Tar2h-131-95 (SEQ ID NO:314), Tar2h-131-96 (SEQ ID NO:315), Tar2h-131-97 (SEQ ID NO:316), Tar2h-131-99 (SEQ ID NO:317), Tar2h-131-100 (SEQ ID NO:318), Tar2h-131-101 (SEQ ID NO:319), Tar2h-131-102 (SEQ ID NO:320), Tar2h-131-103 (SEQ ID NO:321), Tar2h-131-104 (SEQ ID NO:322), Tar2h-131-105 (SEQ ID NO:323), Tar2h-131-106 (SEQ ID NO:324), Tar2h-131-107 (SEQ ID NO:325), Tar2h-131-108 (SEQ ID NO:326), Tar2h-131-109 (SEQ ID NO:327), Tar2h-131-110 (SEQ ID NO:328), Tar2h-131-111 (SEQ ID NO:329), Tar2h-131-112 (SEQ ID NO:330), Tar2h-131-113 (SEQ ID NO:331), Tar2h-131-114 (SEQ ID NO:332), Tar2h-131-115 (SEQ ID NO:333), Tar2h-131-116 (SEQ ID NO:334), Tar2h-131-117 (SEQ ID NO:335), Tar2h-131-120 (SEQ ID NO:336), Tar2h-131-121 (SEQ ID NO:337), Tar2h-131-122 (SEQ ID NO:338), Tar2h-131-123 (SEQ ID NO:339), Tar2h-131-124 (SEQ ID NO:340), Tar2h-131-125 (SEQ ID NO:341), Tar2h-131-126 (SEQ ID NO:342), Tar2h-131-127 (SEQ ID NO:343), Tar2h-131-128 (SEQ ID NO:344), Tar2h-131-129 (SEQ ID NO:345), Tar2h-131-130 (SEQ ID NO:346), Tar2h-131-131 (SEQ ID NO:347), Tar2h-131-132 (SEQ ID NO:348), Tar2h-131-136 (SEQ ID NO:349), Tar2h-131-151 (SEQ ID NO:350), Tar2h-131-180 (SEQ ID NO:351), Tar2h-131-181 (SEQ ID NO:352), Tar2h-131-182 (SEQ ID NO:353), Tar2h-131-183 (SEQ ID NO:354), Tar2h-131-184 (SEQ ID NO:355), Tar2h-131-185 (SEQ ID NO:356), Tar2h-131-188 (SEQ ID NO:357), Tar2h-131-189 (SEQ ID NO:358), Tar2h-131-190 (SEQ ID NO:359), Tar2h-131-191 (SEQ ID NO:360), Tar2h-131-192 (SEQ ID NO:361), Tar2h-131-193 (SEQ ID NO:362), Tar2h-131-194 (SEQ ID NO:363), Tar2h-131-195 (SEQ ID NO:364), Tar2h-131-196 (SEQ ID NO:365), Tar2h-131-197 (SEQ ID NO:366), Tar2h-131-198 (SEQ ID NO:367), Tar2h-131-500 (SEQ ID NO:368), Tar2h-131-501 (SEQ ID NO:369), Tar2h-131-502 (SEQ ID NO:370), Tar2h-131-503 (SEQ ID NO:371), Tar2h-131-504 (SEQ ID NO:372), Tar2h-131-505 (SEQ ID NO:373), Tar2h-131-506 (SEQ ID NO:374), Tar2h-131-507 (SEQ ID NO:375), Tar2h-131-508 (SEQ ID NO:376), Tar2h-131-509 (SEQ ID NO:377), Tar2h-131-510 (SEQ ID NO:378), Tar2h-131-511 (SEQ ID NO:379), Tar2h-131-512 (SEQ ID NO:380), Tar2h-131-513 (SEQ ID NO:381), Tar2h-131-514 (SEQ ID NO:382), Tar2h-131-515 (SEQ ID NO:383), Tar2h-131-516 (SEQ ID NO:384), Tar2h-131-517 (SEQ ID NO:385), Tar2h-131-518

(SEQ ID NO:386), Tar2h-131-519 (SEQ ID NO:387), Tar2h-131-520 (SEQ ID NO:388), Tar2h-131-521 (SEQ ID NO:389), Tar2h-131-522 (SEQ ID NO:390), Tar2h-131-523 (SEQ ID NO:391), Tar2h-131-524 (SEQ ID NO:392), Tar2h-131-525 (SEQ ID NO:393), Tar2h-131-526 (SEQ ID NO:394), Tar2h-131-527 (SEQ ID NO:395), Tar2h-131-528 (SEQ ID NO:396), Tar2h-131-529 (SEQ ID NO:397), Tar2h-131-530 (SEQ ID NO:398), Tar2h-131-531 (SEQ ID NO:399), Tar2h-131-532 (SEQ ID NO:400), Tar2h-131-533 (SEQ ID NO:401), TAR2h-131-534 (SEQ ID NO:402), Tar2h-131-535 (SEQ ID NO:403), Tar2h-131-536 (SEQ ID NO:404), Tar2h-131-537 (SEQ ID NO:405), Tar2h-131-538 (SEQ ID NO:406), Tar2h-131-539 (SEQ ID NO:407), Tar2h-131-539 (SEQ ID NO:408), Tar2h-131-539 (SEQ ID NO:409), Tar2h-131-540 (SEQ ID NO:410), Tar2h-131-541 (SEQ ID NO:411), Tar2h-131-542 (SEQ ID NO:412), Tar2h-131-543 (SEQ ID NO:413), Tar2h-131-544 (SEQ ID NO:414), Tar2h-131-545 (SEQ ID NO:415), Tar2h-131-546 (SEQ ID NO:416), Tar2h-131-547 (SEQ ID NO:417), Tar2h-131-548 (SEQ ID NO:418), Tar2h-131-549 (SEQ ID NO:419), Tar2h-131-550 (SEQ ID NO:420), Tar2h-131-551 (SEQ ID NO:421), Tar2h-131-552 (SEQ ID NO:422), Tar2h-131-553 (SEQ ID NO:423), Tar2h-131-554 (SEQ ID NO:424), Tar2h-131-555 (SEQ ID NO:425), Tar2h-131-556 (SEQ ID NO:426), Tar2h-131-557 (SEQ ID NO:427), Tar2h-131-558 (SEQ ID NO:428), Tar2h-131-559 (SEQ ID NO:429), Tar2h-131-560 (SEQ ID NO:430), Tar2h-131-561 (SEQ ID NO:431), Tar2h-131-562 (SEQ ID NO:432), and Tar2h-131-563 (SEQ ID NO:433).

In other embodiments, the isolated and/or recombinant nucleic acid encoding a ligand that has binding specificity for TNER1, as described herein, wherein said nucleic acid comprises a nucleotide sequence has at least about 80%, at least about 85%, at least about 90%, at least about 91%, at least about 92%, at least about 93%, at least about 94%, at least about 95%, at least about 96%, at least about 97%, at least about 98%, or at least about 99% nucleotide sequence identity with a nucleotide sequence encoding an anti-TNFR1 dAb selected from the group consisting of Tar2h-131 (SEQ ID NO:434), Tar2h-131-1(SEQ ID NO:435), Tar2h-131-2 (SEQ ID NO:436), Tar2h-431-3(SEQ ID NO:437, Tar2h-131-4(SEQ ID NO:438), Tar2h-131-5(SEQ ID NO:439), Tar2h-131-6(SEQ ID NO:440), Tar2h-131-7(SEQ ID NO:441), Tar2h-131-8(SEQ ID NO:442), Tar2h-131-9(SEQ ID NO:443), Tar2h-131-10(SEQ ID NO:444), Tar2h-131-11(SEQ ID NO:445), Tar2h-131-12(SEQ ID NO:446), Tar2h-131-13(SEQ ID NO:447), Tar2h-131-14(SEQ ID NO:448), Tar2h-131-15(SEQ ID NO:449), Tar2h-131-16 (SEQ ID NO:450), Tar2h-131-17(SEQ ID NO:451), Tar2h-131-18(SEQ ID NO:452), Tar2h-131-19(SEQ ID NO:453), Tar2h-131-20(SEQ ID NO:454), Tar2h-131-21(SEQ ID NO:455), Tar2h-131-22(SEQ ID NO:456), Tar2h-131-23 (SEQ ID NO:457), Tar2h-131-24(SEQ ID NO:458). Tar2h-131-25(SEQ ID NO:459), Tar2h-131-26(SEQ ID NO:460), Tar2h131-27(SEQ ID NO:461), Tar2h131-28(SEQ ID NO:462), Tar2h131-29(SEQ ID NO:463), Tar2h131-30 (SEQ ID NO:464), Tar2h131-31(SEQ ID NO:465), Tar2h131-32(SEQ ID NO:466), Tar2h131-33(SEQ ID NO:467), Tar2h131-34(SEQ ID NO:468), Tar2h131-35 (SEQ ID NO:469), Tar2h131-36(SEQ ID NO:470), Tar2h131-37(SEQ ID NO:471), Tar2h131-38(SEQ ID NO:472), Tar2h/31-39(SEQ ID NO:473), Tar2h131-40(SEQ ID NO:474), Tar2h131-41(SEQ ID NO:475), Tar2h131-42 (SEQ ID NO:476), Tar2h131-43(SEQ ID NO:477), Tar2h131-44(SEQ ID NO:478), Tar2h131-45(SEQ ID NO:479), Tar2h131-46(SEQ ID NO:480), Tar2h131-47 (SEQ ID NO:481), Tar2h131-48(SEQ ID NO:482), Tar2h131-49(SEQ ID NO:483), Tar2h-131-50(SEQ ID NO:484), Tar2h-131-51(SEQ ID NO:485), Tar2h-131-52 (SEQ ID NO:486), Tar2h-131-53(SEQ ID NO:487), Tar2h-131-54 (SEQ ID NO:488), Tar2h-131-55 (SEQ ID NO:489), Tar2h-131-56 (SEQ ID NO:490), Tar2h-131-57 (SEQ ID NO:491), Tar2h-131-58 (SEQ ID NO:492), Tar2h-131-59 (SEQ ID NO:493), Tar2h-131-60 (SEQ ID NO:494), Tar2h-131-61 (SEQ ID NO:495), Tar2h-131-62 (SEQ ID NO:496), Tar2h-131-63 (SEQ ID NO:497), Tar2h-131-64 (SEQ ID NO:498), Tar2h-131-65 (SEQ ID NO:499), Tar2h-131-66 (SEQ ID NO:500), Tar2h-131-67 (SEQ ID NO:501), Tar2h-131-68 (SEQ ID NO:502), Tar2h-131-69 (SEQ ID NO:503), Tar2h-131-70 (SEQ ID NO:504), Tar2h-131-71 (SEQ ID NO:505), Tar2h-131-72 (SEQ ID NO:506), Tar2h-131-73 (SEQ ID NO:507), Tar2h-131-74 (SEQ ID NO:508), Tar2h-131-75 (SEQ ID NO:509), Tar2h-131-76 (SEQ ID NO:510), Tar2h-131-77 (SEQ ID NO:511), Tar2h-131-78 (SEQ ID NO:512), Tar2h-131-79 (SEQ ID NO:513), Tar2h-131-80 (SEQ ID NO:514), Tar2h-131-81 (SEQ ID NO:515), Tar2h-131-82 (SEQ ID NO:516), Tar2h-131-83(SEQ ID NO:517), Tar2h-131-86 (SEQ ID NO:518), Tar2h-131-87 (SEQ ID NO:519), Tar2h-131-88 (SEQ ID NO:520), Tar2h-131-89 (SEQ ID NO:521), Tar2h-131-90 (SEQ ID NO:522), Tar2h-131-91 (SEQ ID NO:523), Tar2h-131-92 (SEQ ID NO:524), Tar2h-131-93 (SEQ ID NO:525), Tar2h-131-94 (SEQ ID NO:526), Tar2h-131-95 (SEQ ID NO:527), Tar2h-131-96 (SEQ ID NO:528), Tar2h-131-97 (SEQ ID NO:529), Tar2h-131-99 (SEQ ID NO:530), Tar2h-131-100 (SEQ ID NO:531), Tar2h-131-101 (SEQ ID NO:532), Tar2h-131-102 (SEQ ID NO:533), Tar2h-131-103 (SEQ ID NO:534), Tar2h-131-104 (SEQ ID NO:535), Tar2h-131-105 (SEQ ID NO:536), Tar2h-131-106 (SEQ ID NO:537), Tar2h-131-107 (SEQ ID NO:538), Tar2h-131-108 (SEQ ID NO:539), Tar2h-131-109 (SEQ ID NO:540), Tar2h-131-110 (SEQ ID NO:541), Tar2h-131-111 (SEQ ID NO:542), Tar2h-131-112 (SEQ ID NO:543), Tar2h-131-113 (SEQ ID NO:544), Tar2h-131-114 (SEQ ID NO:545), Tar2h-131-115 (SEQ ID NO:546), Tar2h-131-116 (SEQ ID NO:547), Tar2h-131-117 (SEQ ID NO:548), Tar2h-131-120 (SEQ ID NO:549), Tar2h-131-121 (SEQ ID NO:550), Tar2h-131-122 (SEQ ID NO:551), Tar2h-131-123 (SEQ ID NO:552), Tar2h-131-124 (SEQ ID NO:553), Tar2h-131-125 (SEQ ID NO:554), Tar2h-131-126 (SEQ ID NO:555), Tar2h-131-127 (SEQ ID NO:556), Tar2h-131-128 (SEQ ID NO:557), Tar2h-131-129 (SEQ ID NO:558), Tar2h-131-130 (SEQ ID NO:559), Tar2h-131-131 (SEQ ID NO:560), Tar2h-131-132 (SEQ ID NO:561), Tar2h-131-136(SEQ ID NO:562), Tar2h-131-151 (SEQ ID NO:563), Tar2h-131-180 (SEQ ID NO:564), Tar2h-131-181 (SEQ ID NO:565), Tar2h-131-182 (SEQ ID NO:566), Tar2h-131-183 (SEQ ID NO:567), Tar2h-131-184 (SEQ ID NO:568), Tar2h-131-185 (SEQ ID NO:469), Tar2h-131-188 (SEQ 11) NO:570), Tar2h-131-189 (SEQ ID NO:571), Tar2h-131-190 (SEQ ID NO:572), Tar2h-131-191 (SEQ ID NO:573), Tar2h-131-192 (SEQ ID NO:574), Tar2h-131-193 (SEQ ID NO:575), Tar2h-131-194 (SEQ ID NO:576), Tar2h-131-195 (SEQ ID NO:577), Tar2h-131-196 (SEQ ID NO:578), Tar2h-131-197 (SEQ ID NO:579), Tar2h-131-198 (SEQ ID NO:580), Tar2h-131-500 (SEQ ID NO:581), Tar2h-131-501 (SEQ ID NO:582), Tar2h-131-502 (SEQ ID NO:583), Tar2h-131-503 (SEQ ID NO:584), Tar2h-131-504 (SEQ ID NO:585), Tar2h-131-505 (SEQ ID NO:586), Tar2h-131-506 (SEQ ID NO:587), Tar2h-131-507 (SEQ ID NO:488), Tar2h-131-508 (SEQ ID NO:489), Tar2h-131-509 (SEQ ID NO:590), Tar2h-131-510 (SEQ ID NO:591), Tar2h-131-511 (SEQ ID NO:592), Tar2h-131-512 (SEQ ID NO:593), Tar2h-131-513 (SEQ ID NO:594), Tar2h-131-514 (SEQ ID NO:595), Tar2h-131-515(SEQ ID NO:596), Tar2h-131-516(SEQ ID NO:597), Tar2h-131-517 (SEQ ID NO:598), Tar2h-131-518 (SEQ ID NO:599), Tar2h-131-519 (SEQ ID NO:600), Tar2h-131-520 (SEQ ID NO:601), Tar2h-131-521 (SEQ ID NO:602), Tar2h-131-522 (SEQ ID NO:603), Tar2h-131-523 (SEQ ID NO:604), Tar2h-131-524 (SEQ ID NO:605), Tar2h-131-525 (SEQ ID NO:606), Tar2h-131-526 (SEQ ID NO:607), Tar2h-131-527 (SEQ ID NO:608), Tar2h-131-528(SEQ ID NO:609), Tar2h-131-529 (SEQ ID NO:610), Tar2h-131-530 (SEQ ID NO:611), Tar2h-131-531 (SEQ ID NO:612), Tar2h-131-532 (SEQ ID NO:613), Tar2h-131-533 (SEQ ID NO:614), Tar2h-131-534 (SEQ ID NO:615), Tar2h-131-535 (SEQ ID NO:616), Tar2h-131-536 (SEQ ID NO:617), Tar2h-131-537 (SEQ ID NO:618), Tar2h-131-538 (SEQ ID NO:619), Tar2h-131-539 (SEQ ID NO:620), Tar2h-131-540 (SEQ ID NO:621), Tar2h-131-541 (SEQ ID NO:622), Tar2h-131-542 (SEQ ID NO:623), Tar2h-131-543 (SEQ ID NO:624), Tar2h-131-544 (SEQ ID NO:625), Tar2h-131-545 (SEQ ID NO:626), Tar2h-131-546 (SEQ ID NO:627), Tar2h-131-547 (SEQ ID NO:628), Tar2h-131-548 (SEQ ID NO:629), Tar2h-131-549 (SEQ ID NO:630), Tar2h-131-550(SEQ ID NO:631), Tar2h-131-551 (SEQ ID NO:632), Tar2h-131-552 (SEQ ID NO:633), Tar2h-131-553 (SEQ ID NO:634), Tar2h-131-554 (SEQ ID NO:635), Tar2h-131-555 (SEQ ID NO:636), Tar2h-131-556 (SEQ ID NO:637), Tar2h-131-557 (SEQ ID NO:638), Tar2h-131-558 (SEQ ID NO:639), Tar2h-131-559 (SEQ ID NO:640), Tar2h-131-560 (SEQ ID NO:641), Tar2h-131-561 (SEQ ID NO:642), Tar2h-131-562 (SEQ ID NO:643), Tar2m-15-2(SEQ ID NO:645), Tar2m-15-5(SEQ ID NO:646), Tar2m-15-6(SEQ ID NO:647), Tar2m-15-8(SEQ ID NO:648), Tar2m-15-9(SEQ ID NO:649), and Tar2m-15-12(SEQ ID NO:650). Preferably, nucleotide sequence identity is determined over the whole length of the nucleotide sequence that encodes the selected anti-TNFR1 dAb.

The invention also provides a vector comprising a recombinant nucleic acid molecule of the invention. In certain embodiments, the vector is an expression vector comprising one or more expression control elements or sequences that are operably linked to the recombinant nucleic acid of the invention The invention also provides a recombinant host cell comprising a recombinant nucleic acid molecule or vector of the invention. Suitable vectors (e.g., plasmids, phagmids), expression control elements, host cells and methods for producing recombinant host cells of the invention are well-known in the art, and examples are further described herein.

Suitable expression vectors can contain a number of components, for example, an origin of replication, a selectable marker gene, one or more expression control elements, such as a transcription control element (e.g., promoter, enhancer, terminator) and/or one or more translation signals, a signal sequence or leader sequence, and the like. Expression control elements and a signal sequence, if present, can be provided by the vector or other source. For example, the transcriptional and/or translational control sequences of a cloned nucleic acid encoding an antibody chain can be used to direct expression.

A promoter can be provided for expression in a desired host cell. Promoters can be constitutive or inducible. For example, a promoter can be operably linked to a nucleic acid encoding an antibody, antibody chain or portion thereof, such that it directs transcription of the nucleic acid. A variety of suitable promoters for procaryotic (e.g., lac, tac, T3, T7 promoters for *E. coli*) and eucaryotic (e.g., Simian Virus 40 early or late promoter, Rous sarcoma virus long terminal repeat promoter, cytomegalovirus promoter, adenovirus late promoter) hosts are available.

In addition, expression vectors typically comprise a selectable marker for selection of host cells carrying the vector, and, in the case of a replicable expression vector, an origin of replication. Genes encoding products which confer antibiotic or drug resistance are common selectable markers and may be used in procaryotic (e.g., lactamase gene (ampicillin resistance), Tet gene for tetracycline resistance) and eucaryotic cells (e.g., neomycin (G418 or geneticin), gpt (mycophenolic acid), ampicillin, or hygromycin resistance genes). Dihydrofolate reductase marker genes permit selection with methotrexate in a variety of hosts. Genes encoding the gene product of auxotrophic markers of the host (e.g., LEU2, URA3, HIS3) are often used as selectable markers in yeast. Use of viral (e.g., baculovirus) or phage vectors, and vectors which are capable of integrating into the genome of the host cell, such as retroviral vectors, are also contemplated. Suitable expression vectors for expression in mammalian cells and prokaryotic cells (*E. coli*), insect cells (Drosophila Schnieder S2 cells, Sf9) and yeast (*P. methanolica, P. pastoris, S. cerevisiae*) are well-known in the art.

Suitable host cells can be prokaryotic, including bacterial cells such as *E. coli, B. subtilis* and/or other suitable bacteria; eukaryotic cells, such as fungal or yeast cells (e.g., *Pichia pastoris, Aspergillus* sp., *Saccharomyces cerevisiae, Schizosaccharomyces pombe, Neurospora crassa*), or other lower eukaryotic cells, and cells of higher eukaryotes such as those from insects (e.g., *Drosophila* Schnieder S2 cells, SD insect cells (WO 94/26087 (O'Connor)), mammals (e.g., COS cells, such as COS-1 (ATCC Accession No. CRL-1650) and COS-7 (ATCC Accession No. CRL-1651), CHO (e.g., ATCC Accession No. CRL-9096, CHO DG44 (Urlaub, G. and Chasin, L A., *Proc. Natl. Acac. Sci. USA*, 77(7): 4216-4220 (1980))), 293 (ATCC Accession No. CRL-1573), HeLa (ATCC Accession No. CCL-2), CV1 (ATCC Accession No. CCL-70), WOP (Dailey, L., et al., *J. Virol.*, 54:739-749 (1985), 3T3, 293T (Pear, W. S., et al., *Proc. Natl. Acad. Sci. U.S.A.*, 90:8392-8396 (1993)) NS0 cells, SP2/0, HuT 78 cells and the like, or plants (e.g., tobacco). (See, for example, Ausubel, F. M. et al., eds. *Current Protocols in Molecular Biology*, Greene Publishing Associates and John Wiley & Sons Inc. (1993).) In some embodiments, the host cell is an isolated host cell and is not part of a multicellular organism (e.g., plant or animal). In preferred embodiments, the host cell is a non-human host cell.

The invention also provides a method for producing a ligand (e.g., dual-specific ligand, multispecific ligand) of the invention, comprising maintaining a recombinant host cell comprising a recombinant nucleic acid of the invention under conditions suitable for expression of the recombinant nucleic acid, whereby the recombinant nucleic acid is expressed and a ligand is produced. In some embodiments, the method further comprises isolating the ligand.

Ligand Formats

Ligands and dAb monomers can be formatted as mono or multispecific antibodies or antibody fragments or into mono or multispecific non-antibody structures. Suitable formats include, any suitable polypeptide structure in which an antibody variable domain or one or more of the CDRs thereof can be incorporated so as to confer binding specificity for antigen on the structure. A variety of suitable antibody formats are known in the art, such as, IgG-like formats, chimeric antibodies, humanized antibodies, human antibodies, single chain antibodies, bispecific antibodies, antibody heavy chains, antibody light chains, homodimers and heterodimers of antibody heavy chains and/or light chains, antigen-binding fragments of any of the foregoing (e.g., a Fv fragment (e.g., single chain Fv (scFv), a disulfide bonded Fv), a Fab fragment, a Fab' fragment, a F(ab')$_2$ fragment), a single variable domain (e.g., $V_H$, $V_L$, $V_{HH}$), a dAb, and modified versions of any of the foregoing (e.g., modified by the covalent attachment of polyalkylene glycol (e.g., polyethylene glycol, polypropylene glycol, polybutylene glycol) or other suitable polymer). See, PCT/GB03/002804, filed Jun. 30, 2003, which designated the United States, (WO 2004/081026) regarding PEGylated of single variable domains and dAbs, suitable methods for preparing same, increased in vivo half life of the PEGylated single variable domains and dAb monomers and multimers, suitable PEGs, preferred hydrodynamic sizes of PEGs, and preferred hydrodynamic sizes of PEGylated single variable domains and dAb monomers and multimers. The entire teaching of PCT/GB03/002804 (WO 2004/081026), including the portions referred to above, are incorporated herein by reference.

The ligand can be formatted as a dimer, trimer or polymer of the a desired dAb monomers, for example using a suitable linker such as $(Gly_4Ser)_n$, where n=from 1 to 8, e.g., 2, 3, 4, 5, 6 or 7. If desired, ligands, including dAb monomers, dimers and trimers, can be linked to an antibody Fc region, comprising one or both of $C_H2$ and $C_H3$ domains, and optionally a hinge region. For example, vectors encoding ligands linked as a single nucleotide sequence to an Fc region may be used to prepare such polypeptides.

Ligands and dAb monomers can also be combined and/or formatted into non-antibody multi-ligand structures to form multivalent complexes, which bind target molecules with the same antigen, thereby providing superior avidity. For example natural bacterial receptors such as SpA can been used as scaffolds for the grafting of CDRs to generate ligands which bind specifically to one or more epitopes. Details of this procedure are described in U.S. Pat. No. 5,831,012. Other suitable scaffolds include those based on fibronectin and affibodies. Details of suitable procedures are described in WO 98/58965. Other suitable scaffolds include lipocallin and CTLA4, as described in van den Beuken et al., J. Mol. Biol. 310:591-601 (2001), and scaffolds such as those described in WO 00/69907 (Medical Research Council), which are based for example on the ring structure of bacterial GroEL or other chaperone polypeptides. Protein scaffolds may be combined; for example, CDRs may be grafted on to a CTLA4 scaffold and used together with immunoglobulin $V_H$ or $V_L$ domains to form a ligand. Likewise, fibronectin, lipocallin and other scaffolds may be combined A variety of suitable methods for preparing any desired format are known in the art. For example, antibody chains and formats (e.g., IgG-like formats, chimeric antibodies, humanized antibodies, human antibodies, single chain antibodies, bispecific antibodies, antibody heavy chains, antibody light chains, homodimers and heterodimers of antibody heavy chains and/or light chains) can be prepared by expression of suitable expression constructs and/or culture of suitable cells (e.g., hybridomas, heterohybridomas, recombinant host cells containing recombinant constructs encoding the format). Further, formats such as antigen-binding fragments of antibodies or antibody chains (e.g., a Fv fragment (e.g., single chain Fv (scFv), a disulfide bonded Fv), a Fab fragment, a Fab' fragment, a F(ab')$_2$ fragment), can be prepared by expression of suitable expression constructs or by enzymatic digestion of antibodies, for example using papain or pepsin.

The ligand can be formatted as a dual specific ligand or a multispecific ligand, for example as described in WO 03/002609, the entire teachings of which are incorporated herein by reference. The dual specific ligands comprise immunoglobulin single variable domains that have different binding specificities. Such dual specific ligands can comprise combinations of heavy and light chain domains. For example, the dual specific ligand may comprise a $V_H$ domain and a $V_L$ domain, which may be linked together in the form of an scFv (e.g., using a suitable linker such as $Gly_4Ser$), or formatted into a bispecific antibody or antigen-binding fragment thereof (e.g. F(ab')$_2$ fragment). The dual specific ligands do not comprise complementary $V_H/V_L$ pairs which form a conventional two chain antibody antigen-binding site that binds antigen or epitope co-operatively. Instead, the dual format ligands comprise a $V_H/V_L$ complementary pair, wherein the V domains have different binding specificities.

In addition, the dual specific ligands may comprise one or more $C_H$ or $C_L$ domains if desired. A hinge region domain may also be included if desired. Such combinations of domains may, for example, mimic natural antibodies, such as IgG or IgM, or fragments thereof, such as Fv, scFv, Fab or F(ab')$_2$ molecules. Other structures, such as a single arm of an IgG molecule comprising $V_H$, $V_L$, $C_H1$ and $C_L$ domains, are envisaged. Preferably, the dual specific ligand of the invention comprises only two variable domains although several such ligands may be incorporated together into the same protein, for example two such ligands can be incorporated into an IgG or a multimeric immunoglobulin, such as IgM. Alternatively, in another embodiment a plurality of dual specific ligands are combined to form a multimer. For example, two different dual specific ligands are combined to create a tetra-specific molecule. It will be appreciated by one skilled in the art that the light and heavy variable regions of a dual-specific ligand produced according to the method of the present invention may be on the same polypeptide chain, or alternatively, on different polypeptide chains. In the case that the variable regions are on different polypeptide chains, then they may be linked via a linker, generally a flexible linker (such as a polypeptide chain), a chemical linking group, or any other method known in the art.

The multispecific ligand possesses more than one epitope binding specificity. Generally, the multi-specific ligand comprises two or more epitope binding domains, such dAbs or non-antibody protein domain comprising a binding site for an epitope, e.g., an affibody, an SpA domain, an LDL receptor class A domain, an EGF domain, an avimer. Multispecific ligands can be formatted further as described herein.

In some embodiments, the ligand is an IgG-like format. Such formats have the conventional four chain structure of an IgG molecule (2 heavy chains and two light chains), in which one or more of the variable regions ($V_H$ and or $V_L$) have been replaced with a dAb or single variable domain of a desired specificity. Preferably, each of the variable regions (2 $V_H$ regions and 2 $V_L$ regions) is replaced with a dAb or single variable domain. The dAb(s) or single variable domain(s) that are included in an IgG-like format can have the same specificity or different specificities. In some embodiments, the IgG-like format is tetravalent and can have one, two, three or four specificities. For example, the IgG-like format can be monospecific and comprises 4 dAbs that have the same specificity; bispecific and comprises 3 dAbs that have the same specificity and another dAb that has a different specificity; bispecific and comprise two dAbs that have the same specificity and two dAbs that have a common but different specificity; trispecific and comprises first and second dAbs that have the same specificity, a third dAbs with a different specificity and a fourth dAb with a different specificity from the first, second and third dAbs; or tetraspecific and comprise four dAbs that each have a different specificity. Antigen-binding fragments of IgG-like formats (e.g., Fab, F(ab')$_2$, Fab', Fv, scFv) can be prepared. Preferably, the IgG-like formats or antigen-binding fragments thereof do not crosslink TNFR1.

Half-Life Extended Formats

An antagonist of TNFR1 (e.g., ligand, dAb monomer, dimer or multimer, dual specific format, multi-specific format) can be formatted to extend its in vivo serum half life. Increased in vivo half-life is useful in in vivo applications of immunoglobulins, especially antibodies and most especially antibody fragments of small size such as dAbs. Such fragments (Fvs, disulphide bonded Fvs, Fabs, scFvs, dAbs) are rapidly cleared from the body, which can severely limit clinical applications.

An antagonist of TNFR1 can be formatted to have a larger hydrodynamic size, for example, by attachment of a polyalkyleneglycol group (e.g. polyethyleneglycol (PEG) group), serum albumin, transferrin, transferrin receptor or at least the transferrin-binding portion thereof, an antibody Fc region, or by conjugation to an antibody domain. In some embodiments, the antagonist (e.g., ligand, dAb monomer) is PEGylated. Preferably the PEGylated antagonist (e.g., ligand, dAb monomer) binds TNFR1 with substantially the same affinity as the same ligand that is not PEGylated. For example, the ligand can be a PEGylated dAb monomer that binds, wherein the PEGylated dAb monomer binds TNFR1 with an affinity that differs from the affinity of dAb in unPEGylated form by no more than a factor of about 1000, preferably no more than a factor of about 100, more preferably no more than a factor of about 10, or with affinity substantially unchanged affinity relative to the unPEGylated form.

Small antagonists, such as a dAb monomer, can be formatted as a larger antigen-binding fragment of an antibody or as and antibody (e.g., formatted as a Fab, Fab', F(ab)$_2$, F(ab')$_2$, IgG, scFv). The hydrodynaminc size of an antagonist (e.g., ligand, dAb monomer) and its serum half-life can also be increased by conjugating or linking the antagonist to a binding domain (e.g., antibody or antibody fragment) that binds an antigen or epitope that increases half-live in vivo, as described herein. For example, the antagonists (e.g., ligand, dAb monomer) can be conjugated or linked to an anti-serum albumin or anti-neonatal Fc receptor antibody or antibody fragment, eg an anti-SA or anti-neonatal Fc receptor dAb, Fab, Fab' or say, or to an anti-SA affibody or anti-neonatal Fc receptor affibody.

Examples of suitable albumin, albumin fragments or albumin variants for use in a TNFR1-binding ligand according to the invention are described in WO 2005/077042A2, which is incorporated herein by reference M its entirety. Iii particular, the following albumin, albumin fragments or albumin variants can be used in the present invention:

SEQ ID NO:1 (as disclosed in WO 2005/077042A2, this sequence being explicitly incorporated into the present disclosure by reference);

Albumin fragment or variant comprising or consisting of amino acids 1-387 of SEQ ID NO:1 in WO 2005/077042A2;

Albumin, or fragment or variant thereof, comprising an amino acid sequence selected from the group consisting of: (a) amino acids 54 to 61 of SEQ ID NO:1 in WO 2005/077042A2; (b) amino acids 76 to 89 of SEQ ID NO:1 in WO 2005/077042A2; (c) amino acids 92 to 100 of SEQ ID NO:1 in WO 2005/077042A2; (d) amino acids 170 to 176 of SEQ ID NO:1 in WO 2005/077042A2; (e) amino acids 247 to 252 of SEQ ID NO:1 in WO 2005/077042A2; (f) amino acids 266 to 277 of SEQ ID NO:1 in WO 2005/077042A2; (g) amino acids 280 to 288 of SEQ ID NO:1 in WO 2005/077042A2; (h) amino acids 362 to 368 of SEQ ID NO:1 in WO 2005/077042A2; (i) amino acids 439 to 447 of SEQ ID NO:1 in WO 2005/077042A2 (j) amino acids 462 to 475 of SEQ ID NO:1 in WO 2005/077042A2; (k) amino acids 478 to 486 of SEQ ID NO:1 in WO 2005/077042A2; and (l) amino acids 560 to 566 of SEQ ID NO:1 in WO 2005/077042A2.

Figure 3:
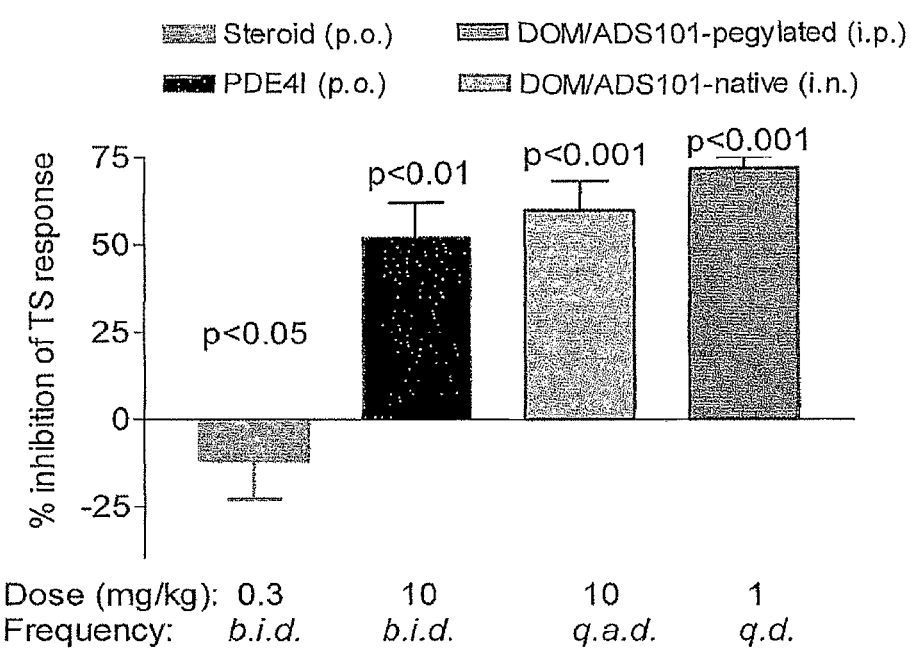
FIG. 3 is a histogram in which the data for certain groups that are shown in FIGS. 1 and 2 are replotted along with the results for a study in which an oral steroid (Dexamethasone) was administered in the model. The histogram shows that local administration of anti-TNFR1 dAb monomer (DOM/ADS 101-native (Dom1 in FIG. 1)) to the lung by intranasal administration (1 mg/kg administered once each day (q.d.)), and systemic administration of PEGylated anti-TNFR1 dAb monomer (DOM/ADS101-pegylated (TNFR1 in FIG. 2)) by intraperitoneal administration (10 mg/kg administered once every two days (q.a.d.)) were more efficacious in the model than phosphodiesterase 4 inhibitor (PDE4I) that was administered at a high dose (10 mg/kg administered orally twice a day (b.i.d.)). The histogram also shows that orally administered steroid (0.3 mg/kg administered orally twice a day) increased the number of cells in BAL, and thus was not efficacious in the model.
Figures 4A, 4B:
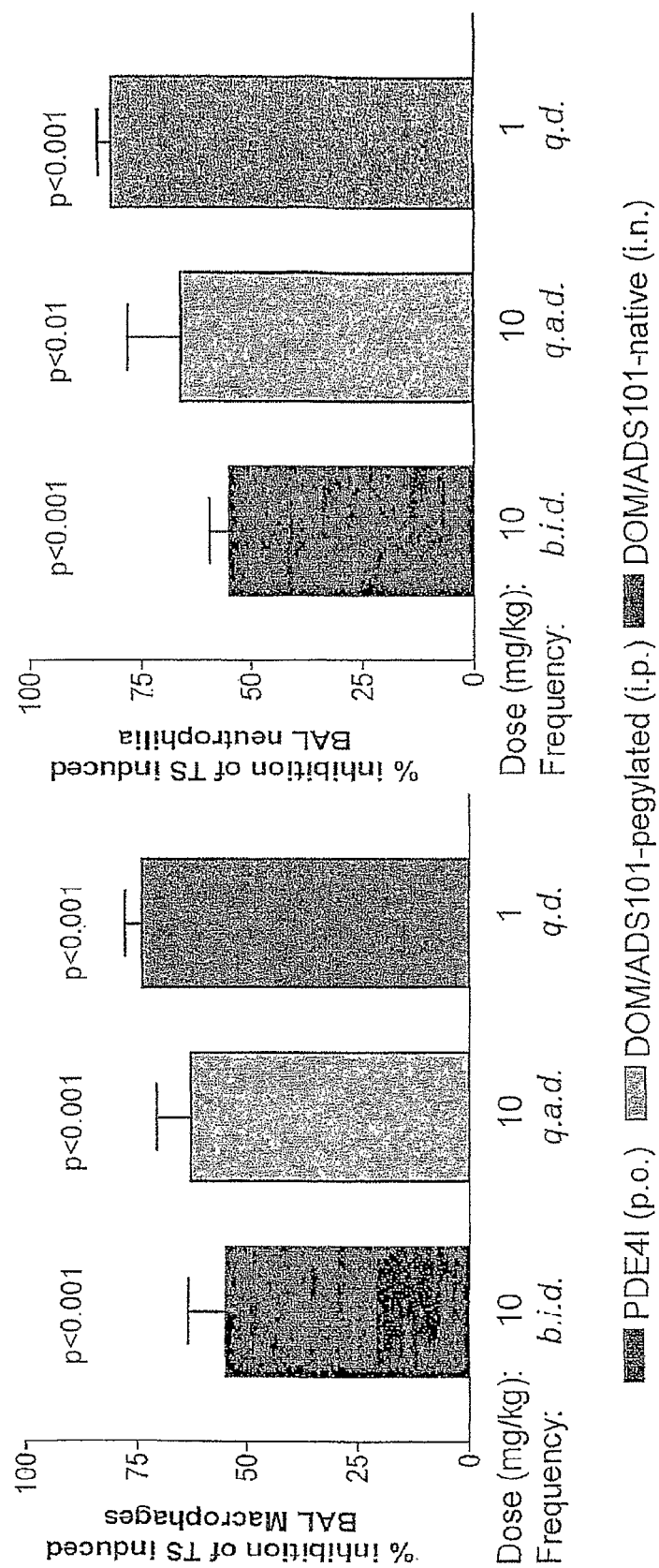
FIGS. 4A and 4B are histograms showing the differential cell counts for macrophages (4A) or neutrophils (4B) in BAL for certain study groups that are shown in FIGS. 1 and 2.
Figure 5:
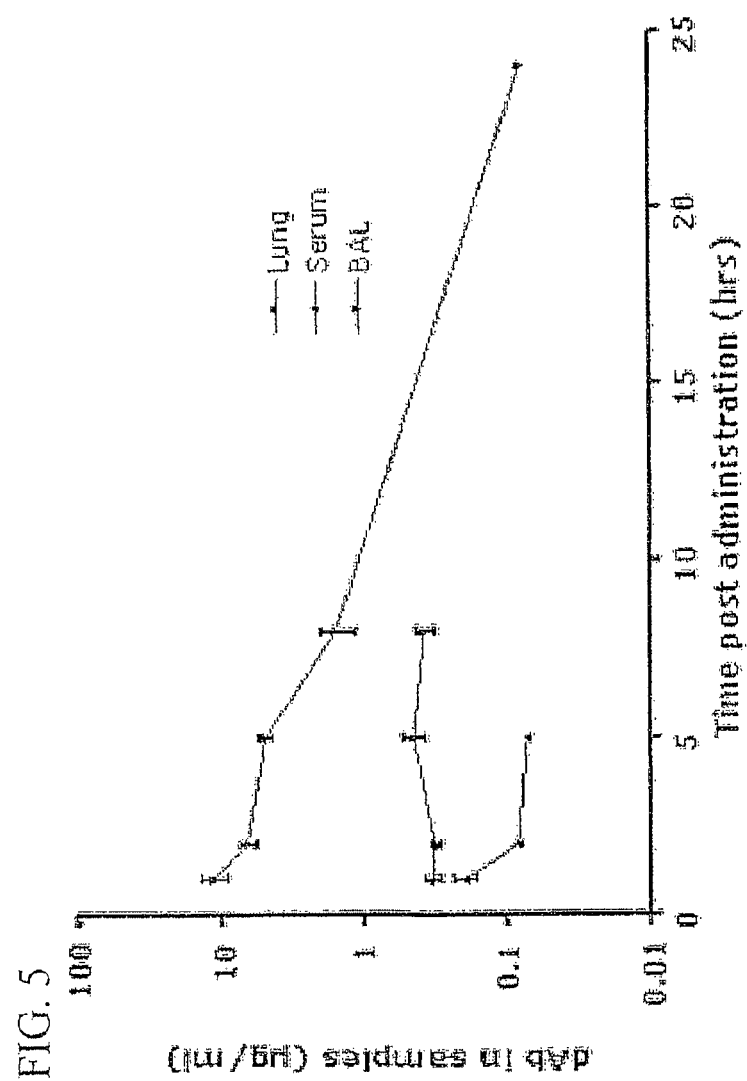
FIG. 5 is a graph showing the results of the pharmacokinetic study of an agent that binds TNFR1 (DOM1m (TAR2 m21-23)) following local administration to pulmonary tissue by intranasal administration (see, Example 3). The graph shows that the levels of DOM1m in lung tissue remained relatively constant for at least 8 hours after administration, while the levels in BAL declined gradually, and the levels in serum rapidly declined and were undetectable after 5 hours. Maximum levels of DOM1m in BAL and serum were detected 1 hour after administration. (about 14 µg/ml in BAL, about 150 ng/ml in serum). The levels in the BAL remained high for a prolonged period of time, and gradually declined over 24 hours (>10-fold decline after 24 hours). The levels in serum rapidly declined, and DOM1m was not detectable in serum after 5 hours. The levels of DOM1 in lung tissue were relatively constant for at least 8 hours after administration, and were undetectable 24 hours after administration.

Further examples of suitable albumin, fragments and analogs for use in a TNFR1-binding ligand according to the invention are described in WO 03/076567A2, which is incorporated herein by reference in its entirety. In particular, the following albumin, fragments or variants can be used in the present invention:

Human serum albumin as described in WO 03/076567A2, eg, in FIG. 3 (this sequence information being explicitly incorporated into the present disclosure by reference);

Human serum albumin (HA) consisting of a single nonglycosylated polypeptide chain of 585 amino acids with a formula molecular weight of 66,500 (See, Meloun, et al., *FEBS Letters* 58:136 (1975); Behrens, et al., *Fed. Proc.* 34:591 (1975); Lawn, et al., *Nucleic Acids Research* 9:6102-6114 (1981); Minghetti, et al., *J. Biol. Chem.* 261:6747 (1986));

A polymorphic variant or analog or fragment of albumin as described in Weitkamp, et al., *Ann. Hum. Genet.* 37:219 (1973);

An albumin fragment or variant as described in EP 322094, eg, HA(1-373, HA(1-388), HA(1-389), HA(1-369), and HA(1-419) and fragments between 1-369 and 1-419;

An albumin fragment or variant as described in EP 399666, eg, HA(1-177) and HA(1-200) and fragments between HA(1-X), where X is any number from 178 to 199.

Where a (one or more) half-life extending moiety (eg, albumin, transferrin and fragments and analogues thereon is used in the TNFR1-binding ligands of the invention, it can be conjugated using any suitable method, such as, by direct fusion to the TNFR1-binding moiety (eg, anti-TNFR1 dAb or antibody fragment), for example by using a single nucleotide construct that encodes a fusion protein, wherein the fusion protein is encoded as a single polypeptide chain with the half-life extending moiety located N- or C-terminally to the TNFR1 binding moiety. Alternatively, conjugation can be achieved by using a peptide linker between moieties, eg, a peptide linker as described in WO 03/076567A2 or WO 2004/003019 (these linker disclosures being incorporated by reference in the present disclosure to provide examples for use in the present invention).

Typically, a polypeptide that enhances serum half-life in vivo is a polypeptide which occurs naturally in vivo and which resists degradation or removal by endogenous mechanisms which remove unwanted material from the organism (e.g., human). For example, a polypeptide that enhances serum half-life in vivo can be selected from proteins from the extracellular matrix, proteins found in blood, proteins found at the blood brain barrier or in neural tissue, proteins localized to the kidney, liver, lung, heart, skin or bone, stress proteins, disease-specific proteins, or proteins involved in Fc transport.

Suitable polypeptides that enhance serum half-life in vivo include, for example, transferrin receptor specific ligand-neuropharmaceutical agent fusion proteins (see U.S. Pat. No. 5,977,307, the teachings of which are incorporated herein by reference), brain capillary endothelial cell receptor, transferrin, transferrin receptor (e.g., soluble transferrin receptor), insulin, insulin-like growth factor 1 (IGF 1) receptor, insulin-like growth factor 2 (IGF 2) receptor, insulin receptor, blood coagulation factor X, α1-antitrypsin and HNF 1α. Suitable polypeptides that enhance serum half-life also include alpha-1 glycoprotein (orosomucoid; AAG), alpha-1 antichymotrypsin (ACT), alpha-1 microglobulin (protein HC; AIM), antithrombin III (AT III), apolipoprotein A-1 (Apo A-1), apolipoprotein B (Apo B), ceruloplasmin (Cp), complement component C3 (C3), complement component C4 (C4), C1 esterase inhibitor (C1 INH), C-reactive protein (CRP), fenitin (FER), heinopexin (HPX), lipoprotein(a) (Lp(a)), mannose-binding protein (MBP), myoglobin (Myo), prealbumin (transthyretin; PAL), retinol-binding protein (RBP), and rheumatoid factor (RF).

Suitable proteins from the extracellular matrix include, for example, collagens, laminins, integrins and fibronectin. Collagens are the major proteins of the extracellular matrix. About 15 types of collagen molecules are currently known, found in different parts of the body, e.g. type I collagen (accounting for 90% of body collagen) found in bone, skin, tendon, ligaments, cornea, internal organs or type II collagen found in cartilage, vertebral disc, notochord, and vitreous humor of the eye.

Suitable proteins from the blood include, for example, plasma proteins (e.g., fibrin, α-2 macroglobulin, serum albumin, fibrinogen (e.g., fibrinogen A, fibrinogen B), serum amyloid protein A, haptoglobin, profilin, ubiquitin, uteroglobulin and β-2-microglobulin), enzymes and enzyme inhibitors (e.g., plasminogen, lysozyme, cystatin C, alpha-1-antitrypsin and pancreatic trypsin inhibitor), proteins of the immune system, such as immunoglobulin proteins (e.g., IgA, IgD, IgE, IgG, IgM, immunoglobulin light chains (kappa/lambda)), transport proteins (e.g., retinol binding protein, α-1 microglobulin), defensins (e.g., beta-defensin 1, neutrophil defensin 1, neutrophil defensin 2 and neutrophil defensin 3) and the like.

Suitable proteins found at the blood brain barrier or in neural tissue include, for example, melanocortin receptor, myelin, ascorbate transporter and the like.

Suitable polypeptides that enhances serum half-life in vivo also include proteins localized to the kidney (e.g., polycystin, type IV collagen, organic anion transporter K1, Heymann's antigen), proteins localized to the liver (e.g., alcohol dehydrogenase, G250), proteins localized to the lung (e.g., secretory component, which binds IgA), proteins localized to the heart (e.g., HSP 27, which is associated with dilated cardiomyopathy), proteins localized to the skin (e.g., keratin), bone specific proteins such as morphogenic proteins (BMPs), which are a subset of the transforming growth factor β superfamily of proteins that demonstrate osteogenic activity (e.g., BMP-2, BMP-4, BMP-5, BMP-6, BMP-7, BMP-8), tumor specific proteins (e.g., trophoblast antigen, herceptin receptor, oestrogen receptor, cathepsins (e.g., cathepsin B, which can be found in liver and spleen)).

Suitable disease-specific proteins include, for example, antigens expressed only on activated T-cells, including LAG-3 (lymphocyte activation gene), osteoprotegerin ligand (OPGL; see *Nature* 402, 304-309 (1999)), OX40 (a member of the TNF receptor family, expressed on activated T cells and specifically up-regulated in human T cell leukemia virus type-I (HTLV-I)-producing cells; see *Immunol.* 165 (1):263-70 (2000)). Suitable disease-specific proteins also include, for example, metalloproteases (associated with arthritis/cancers) including CG6512 *Drosophila*, human paraplegin, human FtsH, human AFG3L2, murine ftsH; and angiogenic growth factors, including acidic fibroblast growth factor (FGF-1), basic fibroblast growth factor (FGF-2), vascular endothelial growth factor/vascular permeability factor (VEGF/VPF), transforming growth factor-α (TGF α), tumor necrosis factor-alpha (TNF-α), angiogenin, interleukin-3 (IL-3), interleukin-8 (IL-8), platelet-derived endothelial growth factor (PD-ECGF), placental growth factor (P1GF), midkine platelet-derived growth factor-BB (PDGF), and fractalkine.

Suitable polypeptides that enhance serum half-life in vivo also include stress proteins such as heat shock proteins (HSPs). HSPs are normally found intracellularly. When they are found extracellularly, it is an indicator that a cell has died and spilled out its contents. This unprogrammed cell death (necrosis) occurs when as a result of trauma, disease or injury, extracellular HSPs trigger a response from the immune system. Binding to extracellular. HSP can result in localizing the compositions of the invention to a disease site.

Suitable proteins involved in Fc transport include, for example, Brambell receptor (also known as FcRB). This Fc receptor has two functions, both of which are potentially useful for delivery. The functions are (1) transport of IgG from mother to child across the placenta (2) protection of IgG from degradation thereby prolonging its serum half-life. It is thought that the receptor recycles IgG from endosomes. (See, Holliger et al, *Nat Biotechnol* 15(7):632-6 (1997).)

Methods for pharmacokinetic analysis and determination of ligand half-life will be familiar to those skilled in the art. Details may be found in Kenneth, A et al: Chemical Stability of Pharmaceuticals: A Handbook for Pharmacists and in Peters et al, Pharmacokinetic analysis: A Practical Approach (1996). Reference is also made to "Pharmacokinetics", M Gibaldi & D Perron, published by Marcel Dekker, 2$^{nd}$ Rev. ex edition (1982), which describes pharmacokinetic parameters such as t alpha and t beta half lives and area under the curve (AUC).

Preparation of Immunoglobulin Based Ligands

Binding agents, antagonists, ligands, dAbs as described herein according to the invention can be prepared according to previously established techniques, used in the field of antibody engineering, for the preparation of say, "phage" antibodies and other engineered antibody molecules. Techniques for the preparation of antibodies are for example described in the following reviews and the references cited therein: Winter & Milstein, (1991) Nature 349:293-299; Plückthun (1992) Immunological Reviews 130:151-188; Wright et al., (1992) Crit. Rev. Immunol. 12:125-168; Holliger, P. & Winter, G. (1993) Curr. Op. Biotechn. 4, 446-449; Carter, et al. (1995) J. Hematother. 4, 463-470; Chester, K. A. & Hawkins, R. E. (1995) Trends Biotechn. 13, 294-300; Hoogenboom, H. R. (1997) Nature Biotechnol. 15, 125-126; Fearon, D. (1997) Nature Biotechnol. 15, 618-619; Plückthun, A. & Pack, P. (1997) Immunotechnology 3, 83-105; Carter, P. & Merchant, A. M. (1997) Curr. Opin. Biotechnol. 8, 449-454; Holliger, P. & Winter, G. (1997) Cancer Immunol. Immunother. 45, 128-130.

Suitable techniques employed for selection of antibody variable domains with a desired specificity employ libraries and selection procedures which are known in the art. Natural libraries (Marks et al. (1991) *J. Mol. Biol.*, 222: 581;

Vaughan et al. (1996) *Nature Biotech.*, 14: 309) which use rearranged V genes harvested from human B cells are well known to those skilled in the art. Synthetic libraries (Hoogenboom & Winter (1992) *J. Mol. Bid.*, 227: 381; Barbas et al. (1992) *Proc. Natl. Acad. Sci. USA*, 89: 4457; Nissim et al. (1994) *EMBO J.*, 13: 692; Griffiths et al. (1994) *EMBO J.*, 13: 3245; be Kruif et al. (1995) *J. Mol. Biol.*, 248: 97) are prepared by cloning immunoglobulin V genes, usually using PCR. Errors in the PCR process can lead to a high degree of randomisation. $V_H$ and/or $V_L$ libraries may be selected against target antigens or epitopes separately, in which case single domain binding is directly selected for, or together.

Library Vector Systems

A variety of selection systems are known in the art which are suitable for use in the present invention. Examples of such systems are described below.

Bacteriophage lambda expression systems may be screened directly as bacteriophage plaques or as colonies of lysogens, both as previously described (Huse et al. (1989) *Science*, 246: 1275; Caton and Koprowski (1990) *Proc. Natl. Acad. Sci. U.S.A.*, 87; Mullinax et al. (1990) *Proc. Natl. Acad. Sci. U.S.A.*, 87: 8095; Persson et al. (1991) *Proc. Natl. Acad. Sci. U.S.A.*, 88: 2432) and are of use in the invention. Whilst such expression systems can be used to screen up to $10^6$ different members of a library, they are not really suited to screening of larger numbers (greater than $10^6$ members). Of particular use in the construction of libraries are selection display systems, which enable a nucleic acid to be linked to the polypeptide it expresses. As used herein, a selection display system is a system that permits the selection, by suitable display means, of the individual members of the library by binding the generic and/or target ligands.

Selection protocols for isolating desired members of large libraries are known in the art, as typified by phage display techniques. Such systems, in which diverse peptide sequences are displayed on the surface of filamentous bacteriophage (Scott and Smith (1990) *Science*, 249: 386), have proven useful for creating libraries of antibody fragments (and the nucleotide sequences that encoding them) for the in vitro selection and amplification of specific antibody fragments that bind a target antigen (McCafferty at al., WO 92/01047). The nucleotide sequences encoding the variable regions are linked to gene fragments which encode leader signals that direct them to the periplasmic space of *E. coli* and as a result the resultant antibody fragments are displayed on the surface of the bacteriophage, typically as fusions to bacteriophage coat proteins (e.g., pill or pVIII). Alternatively, antibody fragments are displayed externally on lambda phage capsids (phagebodies). An advantage of phage-based display systems is that, because they are biological systems, selected library members can be amplified simply by growing the phage containing the selected library member in bacterial cells. Furthermore, since the nucleotide sequence that encode the polypeptide library member is contained on a phage or phagemid vector, sequencing, expression and subsequent genetic manipulation is relatively straightforward.

Methods for the construction of bacteriophage antibody display libraries and lambda phage expression libraries are well known in the art (McCafferty et al. (1990) *Nature*, 348: 552; Kang et al. (1991) *Proc. Natl. Acad. Sci. U.S.A.*, 88: 4363; Clackson et al. (1991) *Nature*, 352: 624; Lowman et al. (1991) *Biochemistry*, 30: 10832; Burton et al. (1991) *Proc. Natl. Acad. Sci. U.S.A.*, 88: 10134; Hoogenboom et al. (1991) *Nucleic Acids Res.*, 19: 4133; Chang et al. (1991) *J. Immunol.*, 147: 3610; Breitling et al. (1991) *Gene*, 104: 147; Marks et al. (1991) supra; Barbas et al. (1992) supra; Hawkins and Winter (1992) *J. Immunol.*, 22: 867; Marks et al., 1992, *J. Biol. Chem.*, 267: 16007; Lerner et al. (1992) *Science*, 258: 1313, incorporated herein by reference).

One particularly advantageous approach has been the use of scFv phage-libraries (Huston et al., 1988, Proc. Natl. Acad. Sci. U.S.A., 85: 5879-5883; Chaudhary et al. (1990) Proc. Natl. Acad. Sci. U.S.A., 87: 1066-1070; McCafferty et al. (1990) supra; Clackson et al. (1991) *Nature*, 352: 624; Marks et al. (1991) *J. Mol. Biol.*, 222: 581; Chiswell et al. (1992) Trends Biotech., 10: 80; Marks et al. (1992) *J. Biol. Chem.*, 267). Various embodiments of scFv libraries displayed on bacteriophage coat proteins have been described. Refinements of phage display approaches are also known, for example as described in WO96/06213 and WO92/01047 (Medical Research. Council et al.) and WO97/08320 (Morphosys), which are incorporated herein by reference.

Other systems for generating libraries of polypeptides involve the use of cell-free enzymatic machinery for the in vitro synthesis of the library members. In one method, RNA molecules are selected by alternate rounds of selection against a target ligand and PCR amplification (Tuerk and Gold (1990) *Science*, 249: 505; Ellington and Szostak (1990) *Nature*, 346: 818). A similar technique may be used to identify DNA sequences which bind a predetermined human transcription factor (Thiesen and Bach (1990) *Nucleic Acids Res.*, 18: 3203; Beaudry and Joyce (1992) *Science*, 257: 635; WO92/05258 and WO92/14843). In a similar way, in vitro translation can be used to synthesise polypeptides as a method for generating large libraries. These methods which generally comprise stabilised polysome complexes, are described further in WO88/08453, WO90/05785, WO90/07003, WO91/02076, WO91/05058, and WO92/02536. Alternative display systems which are not phage-based, such as those disclosed in WO95/22625 and WO95/11922 (Affymax) use the polysomes to display polypeptides for selection.

A still further category of techniques involves the selection of repertoires in artificial compartments, which allow the linkage of a gene with its gene product. For example, a selection system in which nucleic acids encoding desirable gene products may be selected in microcapsules formed by water-in-oil emulsions is described in WO99/02671, WO00/40712 and Tawfik & Griffiths (1998) *Nature Biotechnol* 16(7), 652-6. Genetic elements encoding a gene product having a desired activity are compartmentalised into microcapsules and then transcribed and/or translated to produce their respective gene products (RNA or protein) within the microcapsules. Genetic elements which produce gene product having desired activity are subsequently sorted. This approach selects gene products of interest by detecting the desired activity by a variety of means.

Library Construction

Libraries intended for selection, may be constructed using techniques known in the art, for example as set forth above, or may be purchased from commercial sources. Libraries which are useful in the present invention are described, for example, in WO99/20749. Once a vector system is chosen and one or more nucleic acid sequences encoding polypeptides of interest are cloned into the library vector, one may generate diversity within the cloned molecules by undertaking mutagenesis prior to expression; alternatively, the encoded proteins may be expressed and selected, as described above, before mutagenesis and additional rounds of selection are performed. Mutagenesis of nucleic acid sequences encoding structurally optimised polypeptides is carried out by standard molecular methods. Of particular use is the polymerase chain reaction, or PCR, (Mullis and Faloona (1987) *Methods Enzymol.*, 155: 335, herein incorporated by reference). PCR, which uses multiple cycles of DNA replication catalysed by a thermostable, DNA-dependent DNA polymerase to amplify the target sequence of interest, is well known in the art. The construction of various antibody libraries has been discussed in Winter et al. (1994) Ann. Rev Immunology 12, 433-55, and references cited therein.

PCR is performed using template DNA (at least 1 fg; more usefully, 1-1000 ng) and at least 25 pmol of oligonucleotide primers; it may be advantageous to use a larger amount of primer when the primer pool is heavily heterogeneous, as each sequence is represented by only a small fraction of the molecules of the pool, and amounts become limiting in the later amplification cycles. A typical reaction mixture includes: 2 µl of DNA, 25 pmol of oligonucleotide primer, 2.5 µl of 10×PCR buffer 1 (Perkin-Elmer, Foster City, Calif.), 0.4 µl of 1.25 µM dNTP, 0.15 µl (or 2.5 units) of Taq DNA polymerase (Perkin Elmer, Foster City, Calif.) and deionized water to a total volume of 25 µl. Mineral oil is overlaid and the PCR is performed using a programmable thermal cycler. The length and temperature of each step of a PCR cycle, as well as the number of cycles, is adjusted in accordance to the stringency requirements in effect. Annealing temperature and timing are determined both by the efficiency with which a primer is expected to anneal to a template and the degree of mismatch that is to be tolerated; obviously, when nucleic acid molecules are simultaneously amplified and mutagenised, mismatch is required, at least in the first round of synthesis. The ability to optimise the stringency of primer annealing conditions is well within the knowledge of one of moderate skill in the art. An annealing temperature of between 30° C. and 72° C. is used. Initial denaturation of the template molecules normally occurs at between 92° C. and 99° C. for 4 minutes, followed by 20-40 cycles consisting of denaturation (94-99° C. for 15 seconds to 1 minute), annealing (temperature determined as discussed above; 1-2 minutes), and extension (72° C. for 1-5 minutes, depending on the length of the amplified product). Final extension is generally for 4 minutes at 72° C., and may be followed by an indefinite (0-24 hour) step at 4° C.

Combining Single Variable Domains

Domains useful in the invention, once selected, may be combined by a variety of methods known in the art, including covalent and non-covalent methods. Preferred methods include the use of polypeptide linkers, as described, for example, in connection with scFv molecules (Bird et al., (1988) Science 242:423-426). Discussion of suitable linkers is provided in Bird et al. Science 242, 423-426; Hudson et al, Journal Immunol Methods 231 (1999) 177-189; Hudson et al, Proc Nat Acad Sci USA 85, 5879-5883. Linkers are preferably flexible, allowing the two single domains to interact. One linker example is a $(Gly_4Ser)_n$ linker, where n=1 to 8, eg, 2, 3, 4, 5 or 7. The linkers used in diabodies, which are less flexible, may also be employed (Holliger et al., (1993) PNAS (USA) 90:6444-6448). In one embodiment, the linker employed is not an immunoglobulin hinge region.

Variable domains may be combined using methods other than linkers. For example, the use of disulphide bridges, provided through naturally-occurring or engineered cysteine residues, may be exploited to stabilise $V_H$-$V_H$, $V_L$-$V_L$ or $V_H$-$V_L$ dimers (Reiter at al., (1994) Protein Eng. 7:697-704) or by remodelling the interface between the variable domains to improve the "fit" and thus the stability of interaction (Ridgeway at al., (1996) Protein Eng. 7:617-621; Zhu at al., (1997) Protein Science 6:781-788). Other techniques for joining or stabilising variable domains of immunoglobulins, and in particular antibody $V_H$ domains, may be employed as appropriate.

Characterisation of Ligands

The binding of a ligand (e.g., dAb monomer, dual-specific ligand) to its specific antigen(s) or epitope(s) can be tested by methods which will be familiar to those skilled in the art and include ELISA. In a preferred embodiment of the invention binding is tested using monoclonal phage ELISA. Phage ELISA may be performed according to any suitable procedure: an exemplary protocol is set forth below.

Populations of phage produced at each round of selection can be screened for binding by ELISA to the selected antigen or epitope, to identify "polyclonal" phage antibodies. Phage from single infected bacterial colonies from these populations can then be screened by ELISA to identify "monoclonal" phage antibodies. It is also desirable to screen soluble antibody fragments for binding to antigen or epitope, and this can also be undertaken by ELISA using reagents, for example, against a C- or N-terminal tag (see for example Winter at al. (1994) Ann. Rev. Immunology 12, 433-55 and references cited therein.

The diversity of the selected phage monoclonal antibodies may also be assessed by gel electrophoresis of pCR products (Marks et al. 1991, supra; Nissim et al. 1994 supra), probing (Tomlinson et al., 1992) J. Mol. Biol. 227, 776) or by sequencing of the vector DNA.

Structure of Ligands

In the case that the variable domains are selected from V-gene repertoires selected for instance using phage display technology as herein described, then these variable domains comprise a universal framework region, such that is they may be recognised by a specific generic ligand as herein defined. The use of universal frameworks, generic Uganda and the like is described in WO99/20749.

Where V-gene repertoires are used variation in polypeptide sequence is preferably located within the structural loops of the variable domains. The polypeptide sequences of either variable domain may be altered by DNA shuffling or by mutation in order to enhance the interaction of each variable domain with its complementary pair. DNA shuffling is known in the art and taught, for example, by Stemmer, 1994, *Nature* 370: 389-391 and U.S. Pat. No. 6,297,053, both of which are incorporated herein by reference. Other methods of mutagenesis are well known to those of skill in the art.

In general, nucleic acid molecules and vector constructs required for selection, preparation and formatting ligands may be constructed and manipulated as set forth in standard laboratory manuals, such as Sambrook et al. (1989) *Molecular cloning: A Laboratory Manual*, Cold Spring Harbor, USA.

The manipulation of nucleic acids useful in the present invention is typically carried out in recombinant vectors.

As used herein, vector refers to a discrete element that is used to introduce heterologous DNA into cells for the expression and/or replication thereof. Methods by which to select or construct and, subsequently, use such vectors are well known to one of ordinary skill in the art. Numerous vectors are publicly available, including bacterial plasmids, bacteriophage, artificial chromosomes and episomal vectors. Such vectors may be used for simple cloning and mutagenesis; alternatively gene expression vector is employed. A vector of use according to the invention may be selected to accommodate a polypeptide coding sequence of a desired size, typically from 0.25 kilobase (kb) to 40 kb or more in length A suitable host cell is transformed with the vector after in vitro cloning manipulations. Each vector contains various functional components, which generally include a cloning (or "polylinker") site, an origin of replication and at least one selectable marker gene. If given vector is an expression vector, it additionally possesses one or more of the following: enhancer element, promoter, transcription termination and signal sequences, each positioned in the vicinity of the cloning site, such that they are operatively linked to the gene encoding a ligand according to the invention.

Both cloning and expression vectors generally contain nucleic acid sequences that enable the vector to replicate in one or more selected host cells. Typically in cloning vectors, this sequence is one that enables the vector to replicate independently of the host chromosomal DNA and includes origins of replication or autonomously replicating sequences. Such sequences are well known for a variety of bacteria, yeast and viruses. The origin of replication from the plasmid pBR322 is suitable for most Gram-negative bacteria, the 2 micron plasmid origin is suitable for yeast, and various viral origins (e.g. SV 40, adenovirus) are useful for cloning vectors in mammalian cells. Generally, the origin of replication is not needed for mammalian expression vectors unless these are used in mammalian cells able to replicate high levels of DNA, such as COS cells.

Advantageously, a cloning or expression vector may contain a selection gene also referred to as selectable marker. This gene encodes a protein necessary for the survival or growth of transformed host cells grown in a selective culture medium. Host cells not transformed with the vector containing the selection gene will therefore not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available in the growth media.

Since the replication of vectors encoding a ligand according to the present invention is most conveniently performed in *E. coli*, an *E. coli*-selectable marker, for example, the β-lactamase gene that confers resistance to the antibiotic ampicillin, is of use. These can be obtained from *E. coli* plasmids, such as pBR322 or a pUC plasmid such as pUC18 or pUC19.

Expression vectors usually contain a promoter that is recognised by the host organism and is operably linked to the coding sequence of interest. Such a promoter may be inducible or constitutive. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences.

Promoters suitable for use with prokaryotic hosts include, for example, the β-lactamase and lactose promoter systems, alkaline phosphatase, the tryptophan (trp) promoter system and hybrid promoters such as the tac promoter. Promoters for use in bacterial systems will also generally contain a Shine-Delgarno sequence operably linked to the coding sequence.

The preferred vectors are expression vectors that enables the expression of a nucleotide sequence corresponding to a polypeptide library member. Thus, selection with the first and/or second antigen or epitope can be performed by separate propagation and expression of a single clone expressing the polypeptide library member or by use of any selection display system. As described above, the preferred selection display system is bacteriophage display. Thus, phage or phagemid vectors may be used, eg pIT1 or pIT2. Leader sequences useful in the invention include pelB, stII, ompA, phoA, bla and pelA. One example are phagemid vectors which have an *E. coli*. origin of replication (for double stranded replication) and also a phage origin of replication (for production of single-stranded DNA). The manipulation and expression of such vectors is well known in the art (Hoogenboom and Winter (1992) supra; Nissim et al. (1994) supra). Briefly, the vector contains a β-lactamase gene to confer selectivity on the phagemid and a lac promoter upstream of a expression cassette that consists (N to C terminal) of a pelB leader sequence (which directs the expressed polypeptide to the periplasmic space), a multiple cloning site (for cloning the nucleotide version of the library member), optionally, one or more peptide tag (for detection), optionally, one or more TAG stop codon and the phage protein pIII. Thus, using various suppressor and non-suppressor strains of *E. coli* and with the addition of glucose, iso-propyl thio-β-D-galactoside (IPTG) or a helper phage, such as VCS M13, the vector is able to replicate as a plasmid with no expression, produce large quantities of the polypeptide library member only or produce phage, some of which contain at least one copy of the polypeptide-pIII fusion on their surface.

Construction of vectors encoding ligands according to the invention employs conventional ligation techniques. Isolated vectors or DNA fragments are cleaved, tailored, and religated in the form desired to generate the required vector. If desired, analysis to confirm that the correct sequences are present in the constructed vector can be performed in a known fashion. Suitable methods for constructing expression vectors, preparing in vitro transcripts, introducing DNA into host cells, and performing analyses for assessing expression and function are known to those skilled in the art. The presence of a gene sequence in a sample is detected, or its amplification and/or expression quantified by conventional methods, such as Southern or Northern analysis, Western blotting, dot blotting of DNA, RNA or protein, in situ hybridisation, immunocytochemistry or sequence analysis of nucleic acid or protein molecules. Those skilled in the art will readily envisage how these methods may be modified, if desired.

Skeletons

Skeletons may be based on immunoglobulin molecules or may be non-immunoglobulin in origin as set forth above. Preferred immunoglobulin skeletons as herein defined includes any one or more of those selected from the following: an immunoglobulin molecule comprising at least (i) the CL (kappa or lambda subclass) domain of an antibody; or (ii) the CH1 domain of an antibody heavy chain; an immunoglobulin molecule comprising the CH1 and CH2 domains of an antibody heavy chain; an immunoglobulin molecule comprising the CH1, CH2 and CH3 domains of an antibody heavy chain; or any of the subset (ii) in conjunction with the CL (kappa or lambda subclass) domain of an antibody. A hinge region domain may also be included. Such combinations of domains may, for example, mimic natural antibodies, such as IgG or IgM, or fragments thereof, such as Fv, scFv, Fab or F(ab')$_2$ molecules. Those skilled in the art will be aware that this list is not intended to be exhaustive.

Protein Scaffolds

Each epitope binding domain comprises a protein scaffold and one or more CDRs which are involved in the specific interaction of the domain with one or more epitopes. Advantageously, an epitope binding domain according to the present invention comprises three CDRs. Suitable protein scaffolds include any of those selected from the group consisting of the following: those based on immunoglobulin domains, those based on fibronectin, those based on affibodies, those based on CTLA4, those based on chaperones such as GroEL, those based on lipocallin and those based on the bacterial Fc receptors SpA and SpD. Those skilled in the art will appreciate that this list is not intended to be exhaustive.

Scaffolds for Use in Constructing Ligands
Selection of the Main-Chain Conformation The members of the immunoglobulin superfamily all share a similar fold for their polypeptide chain. For example, although antibodies are highly diverse in terms of their primary sequence, comparison of sequences and crystallographic structures has revealed that, contrary to expectation, five of the six antigen binding loops of antibodies (H1, H2, L1, L2, L3) adopt a limited number of main-chain conformations, or canonical structures (Chothia and Lesk (1987) *J. Mol. Biol.*, 196: 901; Chothia et al. (1989) *Nature*, 342: 877). Analysis of loop lengths and key residues has therefore enabled prediction of the main-chain conformations of H1, H2, L1, L2 and L3 found in the majority of human antibodies (Chothia et al. (1992) *J. Mol. Biol.*, 227: 799; Tomlinson et al. (1995) *EMBO J.*, 14: 4628; Williams et al. (1996) *J. Mol. Biol.*, 264: 220). Although the H3 region is much more diverse in terms of sequence, length and structure (due to the use of D segments), it also forms a limited number of main-chain conformations for short loop lengths which depend on the length and the presence of particular residues, or types of residue, at key positions in the loop and the antibody framework (Martin et al. (1996) *J. Mol. Biol.*, 263: 800; Shirai et al. (1996) *FEBS Letters*, 399: 1).

Libraries of ligands and/or domains can be designed in which certain loop lengths and key residues have been chosen to ensure that the main-chain conformation of the members is known. Advantageously, these are real conformations of immunoglobulin superfamily molecules found in nature, to minimise the chances that they are non-functional, as discussed above. Germline V gene segments serve as one suitable basic framework for constructing antibody or T-cell receptor libraries; other sequences are also of use Variations may occur at a low frequency, such that a small number of functional members may possess an altered main-chain conformation, which does not affect its function.

Canonical structure theory is also of use to assess the number of different main-chain conformations encoded by ligands, to predict the main-chain conformation based on ligand sequences and to choose residues for diversification which do not affect the canonical structure. It is known that, in the human $V_\kappa$ domain, the L1 loop can adopt one of four canonical structures, the L2 loop has a single canonical structure and that 90% of human V, domains adopt one of four or five canonical structures for the L3 loop (Tomlinson et al. (1995) supra); thus, in the V, domain alone, different canonical structures can combine to create a range of different main-chain conformations. Given that the $V_\kappa$ domain encodes a different range of canonical structures for the L1, L2 and L3 loops and that $V_\kappa$ and $V_\lambda$ domains can pair with any $V_H$ domain which can encode several canonical structures for the H1 and H2 loops, the number of canonical structure combinations observed for these five loops is very large. This implies that the generation of diversity in the main-chain conformation may be essential for the production of a wide range of binding specificities. However, by constructing an antibody library based on a single known main-chain conformation it has been found, contrary to expectation, that diversity in the main-chain conformation is not required to generate sufficient diversity to target substantially all antigens. Even more surprisingly, the single main-chain conformation need not be a consensus structure—a single naturally occurring conformation can be used as the basis for an entire library. Thus, in a preferred aspect, the dual-specific ligands of the invention possess a single known main-chain conformation.

The single main-chain conformation that is chosen is preferably commonplace among molecules of the immunoglobulin superfamily type in question. A conformation is commonplace when a significant number of naturally occurring molecules are observed to adopt it. Accordingly, in a preferred aspect of the invention, the natural occurrence of the different main-chain conformations for each binding loop of an immunoglobulin domain are considered separately and then a naturally occurring variable domain is chosen which possesses the desired combination of main-chain conformations for the different loops. If none is available, the nearest equivalent may be chosen. It is preferable that the desired combination of main-chain conformations for the different loops is created by selecting germline gene segments which encode the desired main-chain conformations. It is more preferable, that the selected germline gene segments are frequently expressed in nature, and most preferable that they are the most frequently expressed of all natural germline gene segments.

In designing ligands (e.g., dAbs) or libraries thereof the incidence of the different main-chain conformations for each of the six antigen binding loops may be considered separately. For H1, H2, L1, L2 and L3, a given conformation that is adopted by between 20% and 100% of the antigen binding loops of naturally occurring molecules is chosen. Typically, its observed incidence is above 35% (i.e. between 35% and 100%) and, ideally, above 50% or even above 65%. Since the vast majority of H3 loops do not have canonical structures, it is preferable to select a main-chain conformation which is commonplace among those loops which do display canonical structures. For each of the loops, the conformation which is observed most often in the natural repertoire is therefore selected. In human antibodies, the most popular canonical structures (CS) for each loop are as follows: H1-CS 1 (79% of the expressed repertoire), H2-CS 3 (46%), L1-CS 2 of $V_\kappa$ (39%), L2-CS 1 (100%), L3-CS 1 of $V_\kappa$ (36%) (calculation assumes a κ:λ ratio of 70:30, Hood et al. (1967) *Cold Spring Harbor Symp. Quant. Biol.*, 48: 133). For H3 loops that have canonical structures, a CDR3 length (Kabat et al. (1991) *Sequences of proteins of immunological interest*, U.S. Department of Health and Human Services) of seven residues with a salt-bridge from residue 94 to residue 101 appears to be the most common. There are at least 16 human antibody sequences in the EMBL data library with the required H3 length and key residues to form this conformation and at least two crystallographic structures in the protein data bank which can be used as a basis for antibody modelling (2cgr and 1tet). The most frequently expressed germline gene segments that this combination of canonical structures are the $V_H$ segment 3-23 (DP-47), the $J_H$ segment JH4b, the $V_\kappa$ segment O2/O12 (DPK9) and the $J_\kappa$ segment $J_\kappa 1$. $V_H$ segments DP45 and DP38 are also suitable. These segments can therefore be used in combination as a basis to construct a library with the desired single main-chain conformation.

Alternatively, instead of choosing the single main-chain conformation based on the natural occurrence of the different main-chain conformations for each of the binding loops in isolation, the natural occurrence of combinations of main-chain conformations is used as the basis for choosing the single main-chain conformation. In the case of antibodies, for example, the natural occurrence of canonical structure combinations for any two, three, four, five or for all six of the antigen binding loops can be determined. Here, it is preferable that the chosen conformation is commonplace in naturally occurring antibodies and most preferable that it observed most frequently in the natural repertoire. Thus, in human antibodies, for example, when natural combinations of the five antigen binding loops, H1, H2, L1, L2 and L3, are considered, the most frequent combination of canonical structures is determined and then combined with the most popular conformation for the H3 loop, as a basis for choosing the single main-chain conformation.

Diversification of the Canonical Sequence

Having selected several known main-chain conformations or, preferably a single known main-chain conformation, ligands (e.g., dAbs) or libraries for use in the invention can be constructed by varying the binding site of the molecule in order to generate a repertoire with structural and/or functional diversity. This means that variants are generated such that they possess sufficient diversity in their structure and/or in their function so that they are capable of providing a range of activities.

The desired diversity is typically generated by varying the selected molecule at one or more positions. The positions to be changed can be chosen at random or are preferably selected. The variation can then be achieved either by randomisation, during which the resident amino acid is replaced by any amino acid or analogue thereof, natural or synthetic, producing a very large number of variants or by replacing the resident amino acid with one or more of a defined subset of amino acids, producing a more limited number of variants.

Various methods have been reported for introducing such diversity. Error-prone PCR (Hawkins et al. (1992) *J. Mol. Biol.*, 226: 889), chemical mutagenesis (Deng et al. (1994) *J. Biol. Chem.*, 269: 9533) or bacterial imitator strains (Low et al. (1996) *J. Mol. Biol.*, 260: 359) can be used to introduce random mutations into the genes that encode the molecule. Methods for mutating selected positions are also well known in the art and include the use of mismatched oligonucleotides or degenerate oligonucleotides, with or without the use of PCR. For example, several synthetic antibody libraries have been created by targeting mutations to the antigen binding loops. The H3 region of a human tetanus toxoid-binding Fab has been randomised to create a range of new binding specificities (Barbas et al. (1992) *Proc. Natl. Acad. Sci. USA,* 89: 4457). Random or semi-random H3 and L3 regions have been appended to germline V gene segments to produce large libraries with unmutated framework regions (Hoogenboom & Winter (1992) *J. Mol. Biol.,* 227: 381; Barbas et al. (1992) *Proc. Natl. Acad. Sci. USA,* 89: 4457; Nissim et al. (1994) *EMBO J.,* 13: 692; Griffiths et al. (1994) *EMBO J.,* 13: 3245; De Kruif et al. (1995) *J. Mol. Biol.,* 248: 97). Such diversification has been extended to include some or all of the other antigen binding loops (Crameri et al, (1996) *Nature Med.,* 2: 100; Riechmann et al. (1995) *Bio/Technology,* 13: 475; Morphosys, WO97/08320, supra).

Since loop randomisation has the potential to create approximately more than $10^{15}$ structures for H3 alone and a similarly large number of variants for the other five loops, it is not feasible using current transformation technology or even by using cell free systems to produce a library representing all possible combinations. For example, in one of the largest libraries constructed to date, $6\times10^{10}$ different antibodies, which is only a fraction of the potential diversity for a library of this design, were generated (Griffiths et al. (1994) supra).

Preferably, only the residues which are directly involved in creating or modifying the desired function of the molecule are diversified. For many molecules, the function will be to bind a target and therefore diversity should be concentrated in the target binding site, while avoiding changing residues which are crucial to the overall packing of the molecule or to maintaining the chosen main-chain conformation.

Diversification of the Canonical Sequence as it Applies to Antibody Domains

In the case of antibody based ligands (e.g., dAbs), the binding site for the target is most often the antigen binding site. Thus, preferably only those residues in the antigen binding site are varied. These residues are extremely diverse in the human antibody repertoire and are known to make contacts in high-resolution antibody/antigen complexes. For example, in L2 it is known that positions 50 and 53 are diverse in naturally occurring antibodies and are observed to make contact with the antigen. In contrast, the conventional approach would have been to diversify all the residues in the corresponding Complementarily Determining Region (CDR1) as defined by Kabat et al. (1991, supra), some seven residues compared to the two diversified in the library for use according to the invention. This represents a significant improvement in twins of the functional diversity required to create a range of antigen binding specificities.

In nature, antibody diversity is the result of two processes: somatic recombination of germline V, D and J gene segments to create a naive primary repertoire (so called germline and junctional diversity) and somatic hypermutation of the resulting rearranged V genes. Analysis of human antibody sequences has shown that diversity in the primary repertoire is focused at the centre of the antigen binding site whereas somatic hypermutation spreads diversity to regions at the periphery of the antigen binding site that are highly conserved in the primary repertoire (see Tomlinson et al. (1996) *J. Mol. Biol.,* 256: 813). This complementarity has probably evolved as an efficient strategy for searching sequence space and, although apparently unique to antibodies, it can easily be applied to other polypeptide repertoires. The residues which are varied are a subset of those that form the binding site for the target. Different (including overlapping) subsets of residues in the target binding site are diversified at different stages during selection, if desired.

In the case of an antibody repertoire, an initial 'naive' repertoire can be created where some, but not all, of the residues in the antigen binding site are diversified. As used herein in this context, the term "naive" refers to antibody molecules that have no pre-determined target. These molecules resemble those which are encoded by the immunoglobulin genes of an individual who has not undergone immune diversification, as is the case with fetal and newborn individuals, whose immune systems have not yet been challenged by a wide variety of antigenic stimuli. This repertoire is then selected against a range of antigens or epitopes. If required, further diversity can then be introduced outside the region diversified in the initial repertoire. This matured repertoire can be selected for modified function, specificity or affinity.

Naive repertoires of binding domains for the construction of ligands in which some or all of the residues in the antigen binding site are varied are known in the art. (See, WO 2004/058821, WO 2004/003019, and WO 03/002609). The "primary" library mimics the natural primary repertoire, with diversity restricted to residues at the centre of the antigen binding site that are diverse in the germline V gene segments (germline diversity) or diversified during the recombination process (junctional diversity). Those residues which are diversified include, but are not limited to, H50, H52, H52a, H53, H55, H56, H58, H95, H96, H97, H98, L50, L53, L91, L92, L93, L94 and L96. In the "somatic" library, diversity is restricted to residues that are diversified during the recombination process (junctional diversity) or are highly somatically mutated). Those residues which are diversified include, but are not limited to: H31, H33, H35, H95, H96, H97, H98, L30, L31, L32, L34 and L96. All the residues listed above as suitable for diversification in these libraries are known to make contacts in, one or more antibody-antigen complexes. Since in both libraries, not all of the residues in the antigen binding site are varied, additional diversity is incorporated during selection by varying the remaining residues, if it is desired to do so. It shall be apparent to one skilled in the art that any subset of any of these residues (or additional residues which comprise the antigen binding site) can be used for the initial and/or subsequent diversification of the antigen binding site.

In the construction of libraries for use in the invention, diversification of chosen positions is typically achieved at the nucleic acid level, by altering the coding sequence which specifies the sequence of the polypeptide such that a number of possible amino acids (all 20 or a subset thereof) can be incorporated at that position. Using the IUPAC nomenclature, the most versatile codon is NNK, which encodes all amino acids as well as the TAG stop codon. The NNK codon is preferably used in order to introduce the required diversity. Other codons which achieve the same ends are also of use, including the NNN codon, which leads to the production of the additional stop codons TGA and TAA.

A feature of side-chain diversity in the antigen binding site of human antibodies is a pronounced bias which favours certain amino acid residues. If the amino acid composition of the ten most diverse positions in each of the $V_H$, $V_\kappa$ and $V_\lambda$ regions are summed, more than 76% of the side-chain diversity comes from only seven different residues, these being, serine (24%), tyrosine (14%), asparagine (11%), glycine (9%), alanine (7%), aspartate (6%) and threonine (6%). This bias towards hydrophilic residues and small residues which can provide main-chain flexibility probably reflects the evolution of surfaces which are predisposed to binding a wide range of antigens or epitopes and may help to explain the required promiscuity of antibodies in the primary repertoire.

Since it is preferable to mimic this distribution of amino acids, the distribution of amino acids at the positions to be varied preferably mimics that seen in the antigen binding site of antibodies. Such bias in the substitution of amino acids that permits selection of certain polypeptides (not just antibody polypeptides) against a range of target antigens is easily applied to any polypeptide repertoire. There are various methods for biasing the amino acid distribution at the position to be varied (including the use of tri-nucleotide mutagenesis, see WO97/08320), of which the preferred method, due to ease of synthesis, is the use of conventional degenerate codons. By comparing the amino acid profile encoded by all combinations of degenerate codons (with single, double, triple and quadruple degeneracy in equal ratios at each position) with the natural amino acid use it is possible to calculate the most representative codon. The codons (AGT)(AGC)T, (AGT)(AGC)C and (AGT)(AGC)(CT) that is, DVT, DVC and DVY, respectively using IUPAC nomenclature—are those closest to the desired amino acid profile: they encode 22% serine and 11% tyrosine, asparagine, glycine, alanine, aspartate, threonine and cysteine. Preferably, therefore, libraries are constructed using either the DVT, DVC or DVY codon at each of the diversified positions.

Receptor Binding Assay

Antagonists of TNFR1 that inhibit binding of TNFα to TNFR1 can be identified in a suitable receptor binding assay. Briefly, Maxisorp plates are incubated overnight with 30 mg/ml anti-human Fc mouse monoclonal antibody (Zymed, San Francisco, USA). The wells are washed with phosphate buffered saline (PBS) containing 0.05% Tween-20 and then blocked with 1% BSA in PBS before being incubated with 100 ng/mlTNFR1-Fc fusion protein (R&D Systems, Minneapolis, USA). Antagonists of TNFR1 are mixed with TNF which added to the washed wells at a final concentration of 10 ng/ml. TNF binding is detected with 0.2 mg/ml biotinylated anti-TNF antibody (HyCult biotechnology, Uben, Netherlands) followed by 1 in 500 dilution of horse radish peroxidase labelled streptavidin (Amersham. Biosciences, UK) and then incubation with TMB substrate (KPL, Gaithersburg, USA). The reaction can be stopped by the addition of HCl and the absorbance is read at 450 nm, Antagonists of TNFR1 that inhibit binding of TNFα to TNFR1 lead to a decrease in TNF binding and therefore a decrease in absorbance compared with the TNF only control.

L929 Cytotoxicity Assay

Antagonists of TNFR1 (e.g., ligands, dAb monomers) can be identified by the ability to inhibit TNF-induced cytotoxicity in mouse L929 fibroblasts (Evans, T. (2000) Molecular Biotechnology 15, 243-248). Briefly, L929 cells plated in microtitre plates are incubated overnight with antagonist of TNFR1, 100 pg/ml TNF and 1 mg/ml actinomycin D (Sigma, Poole, UK). Then, cell viability is measured by reading absorbance at 490 nm following an incubation with [3-(4,5-dimethylthiazol-2-yl)-5-(3-carboxymethoxyphenyl)-2-(4-sulfophenyl)-2H-tetrazolium (Promega, Madison, USA). Antagonists of TNFR1 will inhibit cytotoxicity and therefore produce an increase in absorbance compared with TNF only control.

HeLa IL-8 Assay

Antagonists of TNFR1 (e.g., ligands, dAb monomers) can be identified by the ability to inhibit TNF-induced secretion of IL-8 by human HeLa cells (method adapted from that of Akeson, L. et al (1996) Journal of Biological Chemistry 271, 30517-30523, describing the induction of IL-8 by IL-1 in HUVEC; here we look at induction by human TNF alpha and we use HeLa cells instead of the HUVEC cell line). Briefly, HeLa cells can be plated in microtitre plates were incubated overnight with antagonist of TNFR1 and 300 pg/ml TNF. Post incubation, the supernatant is aspirated off the cells and IL-8 concentration is measured using a sandwich ELISA (R&D Systems), or other suitable method. Antagonists of TNFR1 inhibit IL-8 secreation, and less IL-8 is detected in the supernatant compared with the TNF only control.

MRC-5 IL-8 Release Assay

Antagonists of human TNFR1 can be identified using the following MRC-5 cell assay. The assay is based on the induction of IL-8 secretion by TNF in MRC-5 cells and is adapted from the method described in Alceson, L. et al. *Journal of Biological Chemistry* 271:30517-30523 (1996), describing the induction of IL-8 by IL-1 in HUVEC. Briefly, MRC-5 cells are plated in microtitre plates and the plates were incubated overnight with antagonist of TNFR1 and human TNFα (300 pg/ml). Following incubation, the culture supernatant is aspirated and the IL-8 concentration in the supernatant is measured via a sandwich ELISA (R&D Systems), or other suitable method. Antagonists of TNFR1 result in a decrease in IL-8 secretion into the supernatant compared with control wells that are incubated with TNFα only.

EXAMPLES

Example 1

Antagonist of TNFR1 Locally Administered to Pulmonary Tissue is Efficacious in a Subchronic Model of COPD in C57BL/6 Mice In this study, an antagonist of TNFR1 (anti-TNFR1 dAb monomer (TAR2 m21-23)) and an antagonist of TNF (ENBREL® (etanercept; Immunex Corporation)) were administered locally to the lung by intranasal administration 1 hour prior to each air or tobacco smoke (TS) exposure. The effects on TS-induced changes in pulmonary inflammatory indices induced by 11 consecutive daily TS exposures were examined 24 hours following the final exposure. The anti-TNF compound (ENBREL® (etanercept; Immunex Corporation)) was used as a control. An orally administered phosphodiesterase 4 (PDE4) inhibitor (BAY 19-8004; lirimilast) was also administered 1 hour prior to and 6 hours post TS exposure in another group as a reference.

Methods

Test Substance 1: ENBREL® (etanercept; Immunex Corporation)

Test Substance 2: DOM1m (anti-TNFR1 dAb monomer (TAR2 m21-23))

Test Substance 3: BAY 19-8004 (PDE4 inhibitor)

The vehicle for substances 1 and 2 was Sodium citrate pH 6.0, 100 mM NaCl. The vehicle for substance 3 was 0.5% Carboxymethylcellulose (Sigma, Product No. C-4888, Lot No. 87H0036) in water. Dose volume is 5 ml/kg.

Female mice (C57BL/6) full barrier bred and certified free of specific microorganisms on receipt (16-20 g) (Charles River) were housed in groups of up to 5 in individually ventilated, solid bottomed cages (IVC) with Aspen chip bedding. Environments (airflow, temperature and humidity) within the cages were controlled by the IVC system (Techniplast).

Protocols:

No. Groups: 7

Group Size: n=10

Dose Volume: 50 μl per mouse for groups 1 to 4 and 5 ml/kg for groups 1 to 7

Treatment times: One hour prior to TS or air exposure on days 1 to 11 for groups 1 to 4 and 1 hour prior to exposure and 6 hour post exposure for groups 5 to 7

The study protocol is summarized in Table 1.

TABLE 1

| Group No. | TS/Air Exposure | Test Substance | Dose mg/kg | n= | Dosing Route | Dosing Frequency |
|---|---|---|---|---|---|---|
| 1 | Air | Vehicle Na citrate | 0 | 10 | i.n. | 1 hour prior to TS or air exposure on days 1 to 11 for groups 1 to 6. 1 hour prior & 6 h post for groups 7 to 9. |
| 2 | TS | Vehicle Na citrate | 0 | 10 | i.n. | |
| 3 | TS | 1 (Enbrel ®; etanercept, Immunex Corp) | 1.0 | 10 | i.n. | |
| 4 | TS | 2 (DOM1m) | 1.0 | 10 | i.n. | |
| 5 | Air | Vehicle CMC | 0 | 10 | p.o. | |

TABLE 1-continued

| Group No. | TS/Air Exposure | Test Substance | Dose mg/kg | n= | Dosing Route | Dosing Frequency |
|---|---|---|---|---|---|---|
| 6 | TS | Vehicle CMC | 0 | 10 | p.o. | |
| 7 | TS | 3 (BAY 19-8004) | 10 | 10 | p.o. | | i.n., intranasal
p.o., per os (oral administration)

TS Exposure

Mice (maximum 5 per exposure chamber) were exposed to TS generated from cigarettes (Type 1R1, supplied by University of Kentucky). Initial exposure was to 4 cigarettes on clay 1, and exposure was increased to a maximum of 6 cigarettes/day by day 6/7. Exposure thereafter to Day 11 was 6 cigarettes/day. The rate of increase was regulated with regard to the daily observed tolerance of the mice. The control group of mice was exposed to air for an equivalent length of time on each exposure day (air exposure controls).

Health Monitoring:

Animals were weighed prior to the start of the study, on day 6 of the exposure protocol, and at the time of termination. All animals were monitored during and after each test substance administration and TS exposure.

Terminal Procedures:

Animals were sacrificed by anaesthetic overdose (pentobarbitone Na, 100 mg/kg i.p.) as follows: All groups were sacrificed 24 hours after the 11$^{th}$ and final TS exposure. Mice from all treatment groups were treated as follows: Blood samples were taken from the sub-clavian artery, placed in a microcentrifuge tube and allowed to clot overnight at 4° C. The clot was removed and the remaining fluid was centrifuged at 2900 rpm in a microcentrifuge for 6 minutes. The resulting supernatant serum was decanted and stored at −40° C. for possible PK analysis. A bronchoalveolar lavage (BAL) was performed using 0.4 ml of phosphate buffered saline (PBS). Cells recovered from the BAL were quantified by total and differential cell counts. Lungs were removed, snap frozen in liquid nitrogen and stored at −80° C. for possible PK analysis.

Data Analysis

A test for normality was carried out on the data. If the test was positive, then a preliminary analysis was carried out using a one way analysis of variance test (one way ANOVA) followed by a Bonferroni's multiple comparison post test to compare control and treatment groups. If the data was not normally distributed, then a Kauskal-Wallis test followed by Dunn's multiple comparisons test was employed. Data were considered significant when p<0.05.

Results

The control group TS/vehicle had cellular infiltrates in the lung compared to the air/vehicle group (see FIG. 1).

The TS exposed and Test Substance 1 (DOM1, anti-TNFR1 dAb) treated group, showed significantly reduced cell infiltrates in the lung compared to the TS exposed and control treated groups (FIG. 1): 72% inhibition for total cells (p<0.001), 74% for macrophages (p<0.001), 82% for neutrophils (p<0.001), 86% for lymphocytes (p<0.05) and 55% for epithelial cells (p<0.01). An 82% reduction in eosinophils was observed but this change was not significant due to the variability in eosinophil numbers observed in the study as a whole.

The Test Substance 3 (PDE4 inhibitor, BAY 19-8004) treated group, showed significantly reduced cell infiltrates in the lung compared to the control group (FIG. 1): 52% inhibition for total cells (p<0.01), 55% for macrophages (p<0.01), 55% for neutrophils (p<0.001), 61% for lymphocytes ($p<0.001$) and 56% for eosinophils ($p<0.01$). A 46% reduction in epithelial cells was observed but this change was not significant.

No significant reductions in any of the cell populations were observed in the group exposed to TS and treated with Test Substance 1 (ENBREL® (etanercept; Immunex Corporation).

Example 2

Antagonist of TNFR1 Systemically Administered is Efficacious in a Subchronic Model of COPD in C57BL/6 Mice In this study, an antagonist of TNFR1 (Pegylated anti-TNFR1 dAb monomer (TAR2 m21-23 PEGylated to increase hydrodynamic size and in vivo serum half-life)) and an antagonist of TNF (ENBREL® (etanercept; Immunex Corporation)) were administered systemically by intraperitoneal administration every 48 hours beginning 24 hours prior to the initial TS exposure. The effects on TS-induced changes in pulmonary inflammatory indices induced by 11 consecutive daily TS exposures were examined 24 h following the final exposure. The anti-TNF compound (ENBREL® (etanercept; Immunex Corporation)) was used as a control.

Methods

Test Substance 1: ENBREL® (etanercept; Immunex Corporation)

Test Substance 2: PEG DOM1m (anti-TNFR1 dAb monomer (TAR2 m21-23) PEGylated with a 40 kDa polyethyleneglycol to increase hydrodynamic size and lengthen In vivo serum half-life).

The vehicle for both Test Substances was sterile saline, and the dose volume for both Test Substances was 10 ml/kg.

Female mice (C57BL/6) full barrier bred and certified free of specific micro organisms on receipt (16-20 g) (Charles River) were housed in groups of up to 5 in individually ventilated, solid bottomed cages (IVC) with Aspen chip bedding. Environments (airflow, temperature and humidity) within the cages were controlled by the IVC system (Techniplast).

Protocols

No. Groups: 4
Group Size: n=10 for groups 1 to 4
Dose Volume: 10 ml/kg for groups 1 to 4
Treatment times: Every 48 hours starting 24 h prior to the initial TS exposure. Subsequent doses to be administered 1 hour prior to TS exposure The study protocol is summarized in Table 2. TS exposure, health monitoring, terminal procedures, and data analysis were performed as described in Example 1.

TABLE 2

| Group No. | TS/Air Exposure | Test Substance No. | Dose mg/kg | n= | Dosing Route | Dosing Frequency |
|---|---|---|---|---|---|---|
| 1 | Air | Vehicle | 0 | 10 | i.p. | At 48 hour intervals starting 24 h prior to the initial exposure then 1 h prior to alternate exposures |
| 2 | TS | Vehicle | 0 | 10 | i.p. | |
| 3 | TS | 1 (Enbrel ®; etanercept, Immunex Corp) | 10 | 10 | i.p. | |
| 4 | TS | 2 (PEG DOM1m) | 10 | 10 | i.p. | | i.p., intraperitoneal

Results

Figure 2:
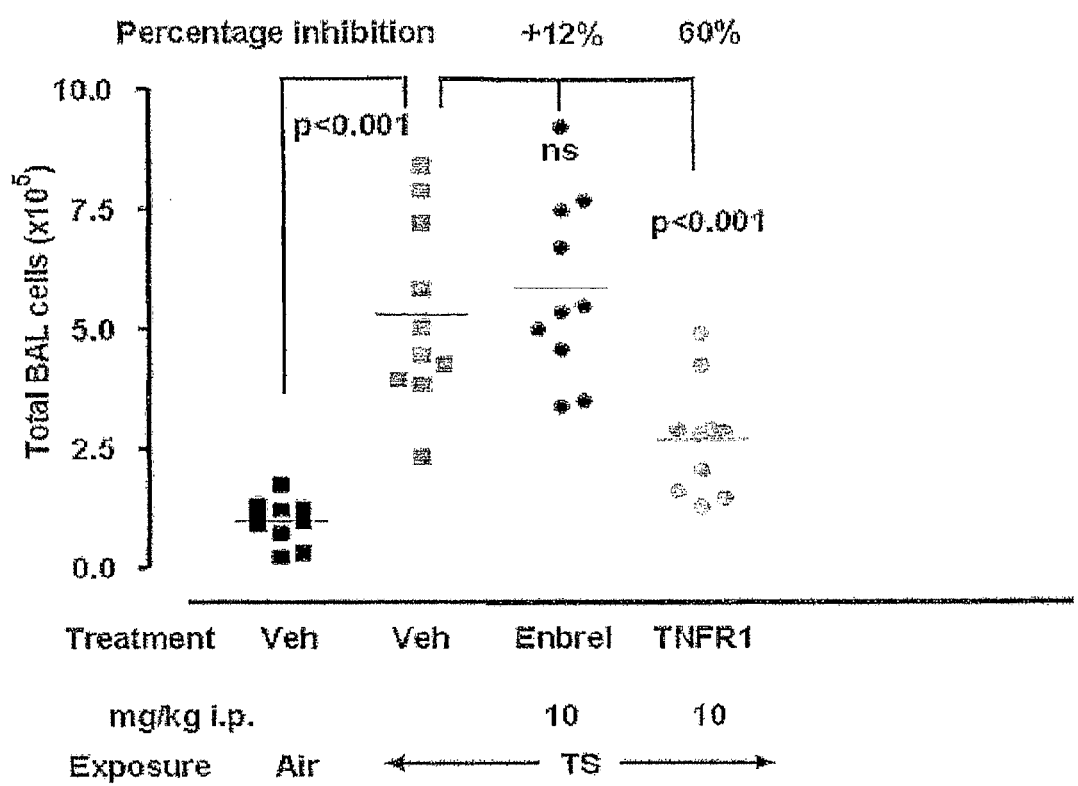
FIG. 2 is a plot showing that an antagonist of TNFR1 has superior efficacy in comparison to a therapeutic agent that targets TNF when administered systemically in a subchronic model of tobacco smoke-induced (TS) chronic obstructive pulmonary disease (COPD) in C57BL/6 mice. The plot shows the number of cells present in BAL of mice at completion of the study described in Example 2. The individual data points for each mouse in the study and the group averages (horizontal lines) are shown. The results show that PEGylated anti-TNFR1 dAb monomer (TNFR1) systemically administered by intraperitoneal administration reduced the number of cells in BAL by 60% compared to the untreated group. The results also show that systemic administration of a therapeutic agent that targets TNF (ENBREL® (etanercept; Immunex Corporation)) resulted in a 12% increase in the number of cells in BAL, although this increase was not statistically significant. TS, tobacco smoke-induced; Veh, vehicle; ns, not statistically significant; i.p. intraperitoneal.

The TS exposed and Test Substance 2 (PEG DOM1m) treated group, showed significantly reduced cell infiltrates in the lung compared to the TS exposed and control treated groups: 60% inhibition for total cells (FIG. 2), 63% for macrophages, 66% for polymorphic nuclear cells, 78% for lymphocytes and 65% for eosinophils. A 40% reduction in epithelial cells was observed but this change was not significant.

No significant reductions in any of the cell populations were observed in group exposed to TS and treated with Test Substance 1 (ENBREL® (etanercept; Immunex Corporation). Treatment with ENBREL® (etanercept; Immunex Corporation) even led to an increase in the number of total and PMN cells in the lung.

Example 3

Pharmacokinetics of Agent that Binds TNFR1 after Local Administration to Pulmonary Tissue In this study, an agent that binds TNFR1 (anti-TNFR1 dAb monomer (TAR2 m21-23)) was administered locally to the lung by intranasal administration and pharmacokinetics of the agent were evaluated.

Methods

DOM1m (anti-TNFR1 dAb monomer (TAR2m21-23)) in 20 mM sodium citrate pH6.0, 100 mM NaCl was used in the study. The diluting agent was sodium citrate pH6.0, 100 mM NaCl.

Protocols

All animals were administered DOM1m by intranasal administration on the same day within 1 to 2 hours of warming the solution.

Female mice (C57BL/6) full barrier bred and certified free of specific microorganisms on receipt (16-20 g) (Charles River) were housed in groups of up to 5 in individually ventilated, solid bottomed cages (IVC) with Aspen chip bedding. Environments (airflow, temperature and humidity) within the cages were controlled by the IVC system (Techniplast).

No. Groups: 5
Group Size: 3
Dose Volume: 50 µl (25 µl/nare)
Sacrifice times: 1 hour, 2 hours, 5 hours, 8 hours and 24 hours after administration The study protocol is summarized in Table 3.

TABLE 3

| Group No. | Compound | Dose (mg/kg) | Concentration of DOM1 in administered solution (mg/ml) | Dosing Route | n= | Sacrifice time (after administration) |
|---|---|---|---|---|---|---|
| 1 | DOM1m | 1 | 0.4 mg/ml | i.n. | 3 | 1 hour |
| 2 | DOM1m | 1 | 0.4 mg/ml | i.n. | 3 | 2 hours |
| 3 | DOM1m | 1 | 0.4 mg/ml | i.n. | 3 | 5 hours |
| 4 | DOM1m | 1 | 0.4 mg/ml | i.n. | 3 | 8 hours |
| 5 | DOM1m | 1 | 0.4 mg/ml | i.n. | 3 | 24 hours | i.n., intranasal

Health Monitoring

Animals were weighed prior to the start of the study. All animals were monitored during and after each compound administration. Animals in the 24 hour group were monitored at regular intervals overnight.

Terminal Procedures

Animals were sacrificed by anaesthetic overdose (pentobarbitone Na, 100 mg/kg i.p.). Blood was taken from the subclavian artery, placed in a microcentrifuge tube and allowed to clot overnight at 4° C. The clot was removed and the remaining fluid centrifuged at 2900 rpm in a microcentrifuge for 6 minutes. The resulting supernatants were decanted, placed in a fresh tube, frozen and stored at −40° C. prior to analysis. Bronchoalveolar lavage (BAL) was collected using 0.4 ml of phosphate buffered saline (PBS) which was instilled and withdrawn 3 times. The BAL was centrifuged at 2700 rpm in a microcentrifuge for 6 minutes and the supernatant was removed and stored at −40° C. prior to analysis. The cell pellet was re-suspended in a suitable volume of PBS and a total cell count made using a haemocytometer. Cytospin slides were prepared to allow differential cell determination. The lungs were excised, snap frozen and stored at −80° C. prior to analysis. Using a mortar and pestle, lungs were pulverized under liquid nitrogen and dissolved in T-PER® Tissue Protein Extraction Reagent (Pierce) and homogenized using 40 strokes with a dounce homogenizer.

ELISA to Detect DOM1m

A 96 well MAXISORP assay plate (Nunc) was coated overnight at 4° C. with 100 μl per well of mTNFR/Fc (R&D systems) at 0.5 μg/ml in PBS. Wells were washed 3 times with 0.05% Tween/PBS and 3 times with PBS. 200 μl per well of 2% BSA in PBS was added to block the plate. Wells were washed and then 100 μl of DOM1m standard or sample was added. Plates were incubated for 1 hour. Wells were washed, and bound DOM1 was detected with chicken anti-VH (1/500) followed by anti-chicken IGY HRP conjugate (1/5000 dilution; Abeam). Plates are developed with 100 μl of SureBlue 1-Component TMB MicroWell Peroxidase (KPL, Gaithersburg, USA) solution which was added to each well, and the plate was left at room temperature until a suitable signal had developed (~5 minutes). The reaction was stopped by the addition of HCl and the absorbance was read at 450 nm.

Results

The level of DOM1m in the BAL was maximum at 1 hour and was about 14 μg/ml (about 3.5 μg in 0.25 ml of BAL fluid). This means that at least 17% (3.5 μg of 20 μg total administered) of the administered material was present in the bronchoalveolar compartment of the lung. More material may be present in the surrounding tissues but this material cannot be recovered. The levels in the BAL were high for a prolonged period of time and showed a gradual decline over 24 hours (>10-fold decline after 24 hours).

The levels of DOM1m in the lung tissue were relatively constant up to 8 hours after administration, and were undetectable 24 hours after administration. At 8 hours after administration the levels in the lung tissue were about 0.35 μg. The percentage of the total administered dose present in the lung tissue at 8 hours was about 2% (Total dose administered was 20 μg). Taken together with the BAL levels, the maximum level of the agent detected in the lung as a whole at the time points examined was at least ~20% of the total dose administered.

The level of DOM1m in the serum was maximum at 1 hour (about 150 ng/ml) and rapidly declined. At 5 hours after administration, the levels in the serum were about 70 ng/ml, which is equivalent to 100 ng/mouse (1.5 ml of blood volume). The percentage of the total administered dose present in the serum 5 hours after administration was about 0.5% (Total dose administered was 20 μg). DOM1m was not detectable in the serum after 5 hours.

Example 4

Cross Reactivity with Cynomolgus TNFR1

A cynomolgus (*Macaca fascicularis*) skin fibroblast cell line was used to test cross-reactivity of anti-human TNFR1 dAbs to cynomolgus TNFR1 in a cell-based TNFR1 assay. Cross-reactivity to cynomolgus TNFR1 is advantageous because pharmacokinetic and toxicology studies can be performed without using a surrogate agent.

Method

Cynomolgus embryo skin fibroblast cells ($5 \times 10^3$ cells per well) were incubated with anti-human TNFR1 dAb for 1 hour at 37° C./5% $CO_2$. 200 pg/ml (final concentration) of human TNF was then added, and the plate was incubated overnight at 37° C./5% $CO_2$.

The human IL-8 DuoSet ELISA, was used to measure the concentration of human IL-8 in the cell culture supernatants. The assay was carried out according to the manufacture's instructions. A 96 well Nunc Maxisorp assay plate was coated with 100 μl detection antibody at 4 μg/ml in PBS. The plate was incubated overnight at 4 C. In between each incubation step the plates were washed three times with 0.05% tween/PBS and three times with PBS using an automated plate washer. 200 μl per well of 1% BSA/PBS was added and the plate was incubated for 1 hour at room temperature. 90 μl of 0.1% BSA, 0.05% Tween-20 in PBS was added to each well and 10 μl cell supernatant, a standard curve was included of IL-8 starting at 5 ng/ml in 0.1% BSA, 0.05% Tween-20 in PBS. 100 μl of detection antibody was added at 20 ng/ml (stock solution diluted 1:180 in 0.1% BSA, 0.05% Tween-20 in PBS) to each well and the plates were incubated for 2 h at room temperature. 100 μl of streptavidin-HRP was added to each well (stock solution diluted 1:200 in 0.1% BSA, 0.05% Tween-20 in PBS). The plates were incubated for 20 mins at room temperature. 100 μl of SureBlue 1-Component TMB MicroWell Peroxidase solution was added to each well and left at room temperature until the blue colour develops. The reaction was stopped by adding 100 μl 1M hydrochloric acid. The absorbance in a plate was read at 450 nm within 30 mins.

Results/Conclusions

Anti-human TNFR1 dAbs in the TAR2h-131 series are able to effectively block TNF induced IL-8 release by cynomolgus fibroblasts. The dAbs TAR2h-131-511 and TAR2h-131-117 had slightly higher potency values in the cynomolgus assay (303 nM and 330 nM, respectively) as compared to potency measured in a human MRC-5 assay (~600 pM). In conclusion TAR2h-131 series dAbs are cross reactive with cynomolgus TNFR1.

Example 5

Effects of a Pulmonary Delivered Anti-TNFR1 dAb on TNFα-induced Pulmonary Inflammation An anti-TNFR1 dAb was administered to the lungs of mice by the intranasal route 1 hour prior to intranasal delivery of TNFα. The effect of pre-dosing the lung with an anti-TNFR1 dAb prior to TNFα administration was investigated by determining the number of neutrophils in the BAL, quantifying the concentration of the inflammatory cytokines KC, MIP-2 and MCP-1 in BAL, and quantifying E-selectin in lung tissue at selected timepoints after TNFα administration.

Methods

The inflammatory stimulus was recombinant murine TNFα in PBS containing 0.1% BSA.

The anti-TNFR1 dAb was TAR2m-21-23 (Batch BH31/01/06-1) in 20 nM citrate buffer pH 6

TNFα (1 μg per mouse) was administered by the intranasal (i.n.) route. The volume administered was 50 μl per mouse (20 μg/ml). The anti-TNFR1 dAbTAR2m-21-23 (1 mg/kg) was also administered by the i.n. route. The volume of dAb administered was 50 μl per mouse (0.4 mg/ml as mice were 20 g).

Female mice (C57/b16) full barrier bred and certified free of specific micro organisms on receipt (16-20 g) (Charles River) were housed in groups of up to 5 in individually ventilated, solid bottomed cages (IVC) with Aspen chip bedding. Environments (airflow, temperature and humidity) within the cages were controlled by the IVC system (Techniplast).

Treatment Groups:
No. Groups: 13
Group Size: n=5-6

Groups of mice were dosed i.n. with either vehicle or dAb at 1 hour prior to TNFα administration. Groups were sacrificed at predetermined times after TNFα administration as listed in Table 4.

TABLE 4

| Group | Anti-TNFR1 | TNFα | Sacrifice time post agonist (hours) | n |
|---|---|---|---|---|
| A | Vehicle | Vehicle | 2-8 | 6 |
| B | Vehicle | 1 μg/mouse | 2 | 5 |
| C | dAb 1 mg/kg | 1 μg/mouse | 2 | 5 |
| D | Vehicle | 1 μg/mouse | 4 | 5 |
| E | dAb 1 mg/kg | 1 μg/mouse | 4 | 5 |
| F | Vehicle | 1 μg/mouse | 6 | 6 |
| G | dAb 1 mg/kg | 1 μg/mouse | 6 | 6 |
| H | Vehicle | 1 μg/mouse | 8 | 6 |
| I | dAb 1 mg/kg | 1 μg/mouse | 8 | 6 |
| J | Vehicle | 1 μg/mouse | 24 | 5 |
| K | dAb 1 mg/kg | 1 μg/mouse | 24 | 5 |
| L | Vehicle | 1 μg/mouse | 48 | 5 |
| M | dAb 1 mg/kg | 1 μg/mouse | 48 | 5 |

Approximately 3 minutes prior to treatment, light anaesthesia was induced by Isofluorane inhalation. Vehicle or the dAb was instilled in a volume of 50 μl/mouse by the i.n. route. Mice were allowed to recover and then returned to the home cage. After 1 hour TNFα (1 μg/mouse) or its vehicle were administered by the same i.n. route. Groups of dAb or vehicle treated mice were sacrificed at 2, 4, 6, 8, 24 and 48 hours post TNFα administration.

Mice were killed by anaesthetic overdose (pentobarbitone Na, 100 mg/kg i.p.). The trachea was cannulated and bronchoalveolar lavage (BAL) conducted using 3 separate 0.4 ml aliquots of PBS. The lavage fluid was kept on ice prior to centrifugation. Hearts and lungs were removed en bloc, the heart was removed and the lungs were snap frozen using liquid nitrogen. The lavage fluid was centrifuged and the supernatant divided into four 250 μl aliquots and stored at −40° C. The cell pellet was re-suspended in 40 μl of PBS, and 10 μl of the cell suspension taken into 90 μl of 'Kimura' or 'Turks' stain for total wet cell counts using a haemocytometer. Cytospin slides were prepared from the cell suspension and stained using 'Wrights Giemsa' stain for differential cell analysis. Cells were differentiated using standard morphometric techniques.

Sample preparation and ELISA: ELISA kits for murine TNFα, KC, MIP-2, MCP-1 and E-selectin were obtained from R&D Systems. Neat BAL supernatant samples were used for determination of the concentration of the cytokines KC, MIP-2 and MCP-1 in BAL. BAL supernatant was diluted 1:100 for determination of the concentration of TNFα in BAL.

Frozen lung was thawed and homogenized in 500 μl of lysis buffer containing 10 mM HEPES pH 7.5, 0.5% triton X-100, 150 mM NaCl, 1 mM EDTA, 0.5 mM AEBSF and a protease inhibitor cocktail (1 μg/ml leupeptin, aprotinin, 10 μg/ml trypsin-chymotrypsin inhibitor and 1 μg/ml pepstatin). Lung homogenate supernatant was diluted for determination of lung tissue E-selectin (1:50) and TNFα. (1:100) concentrations.

BAL and lung homogenate supernatant total protein concentrations were determined using a Quantipro BCA kit (Sigma).

Results

Figure 11A:
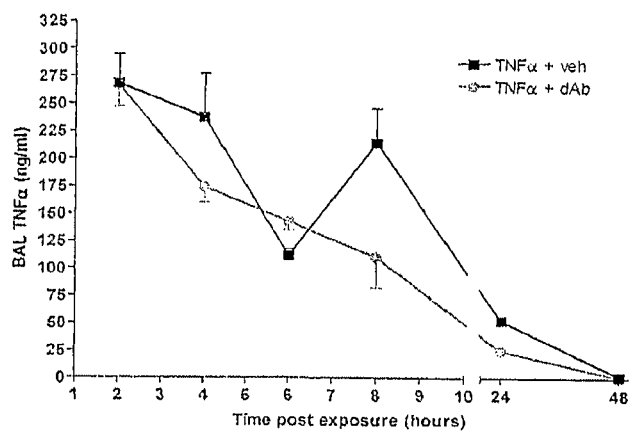
FIGS. 11A and 11B are graphs showing time dependent increases in the TNFα concentration in bronchoalveolar lavage (BAL) (FIG. 11A) or lung tissue (FIG. 11B) following intranasal (i.n.) administration of murine TNFα (1 mg/mouse) one hour after administration (i.n.) of vehicle or anti-TNFR1 dAb (1 mg/kg).
Figure 11B:
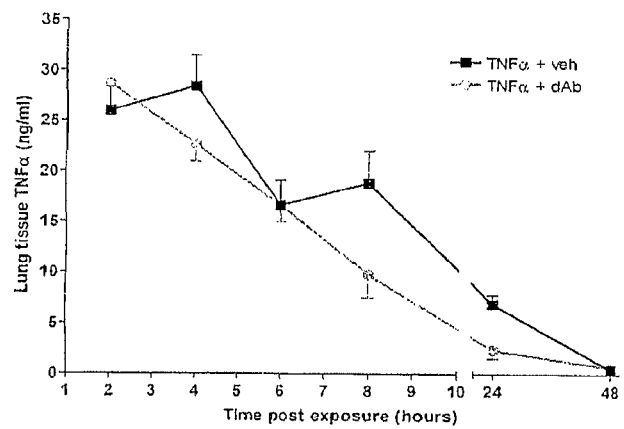

Following intranasal administration of murine TNFα significant levels of BAL and lung tissue TNFα were detected 2 hrs post administration (FIGS. 11A and 11B). Concentrations of TNFα in both BAL and tissue decreased in a time-dependent fashion, and returned to baseline (vehicle treated) levels by 48 hrs. Levels in the BAL were approximately 10 times higher than levels in the lung tissue. These data demonstrate that i.n. administration of TNFα resulted in significant lung delivery of the cytokine. It is possible however, that some of the TNFα detected could be of endogenous origin although the profile of the response does not suggest this.

Figure 12:
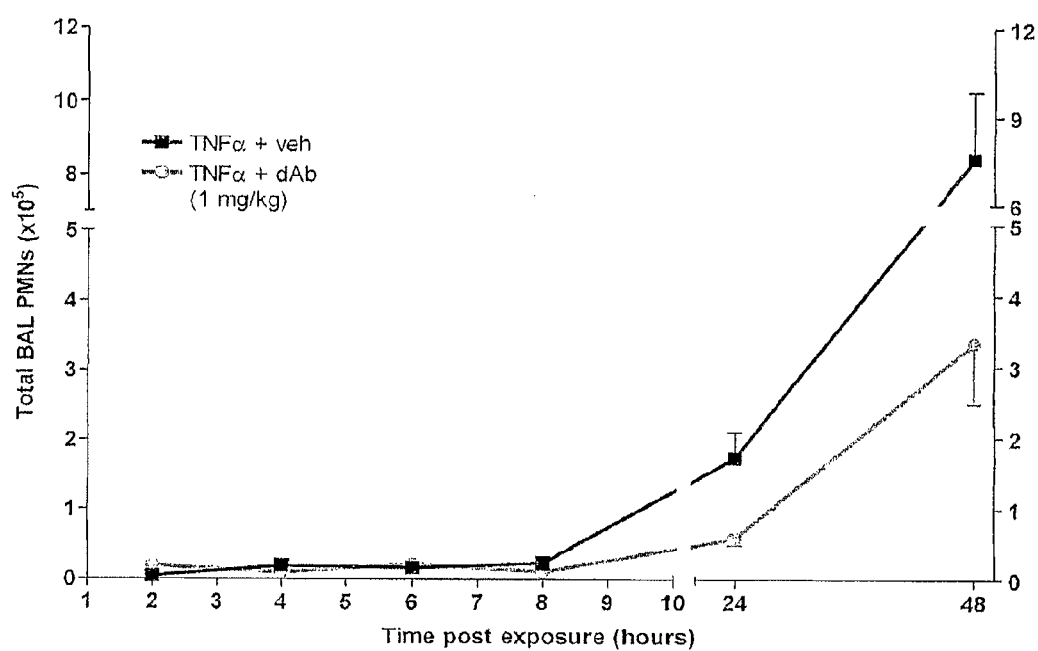
FIG. 12 is a graph showing time dependent increases in BAL neutrophils following i.n. administration of murine TNFα (1 µg/mouse) one hour following pre-administration (i.n.) of vehicle or anti-TNFR1 dAb (1 mg/kg). Pre-administration of anti-TNFR1 dAb partially inhibited the increase in neutrophils induced by TNFα.

A 1 hour pre-dose of 1 mg/kg of the anti-TNFR1 dAb had no obvious effect on BAL and lung tissue TNFα concentration throughout the time points examined. Despite a rapid increase in BAL and lung tissue TNFα concentration following i.n. administration of murine TNFα, BAL neutrophil numbers did not significantly increase above baseline between 1 and 8 hours post TNFα administration. However, at 24 and 48 hrs post TNFα administration, BAL neutrophilia was observed (FIG. 12). The increase in BAL neutrophils at 24 and 48 hrs was partially inhibited by the anti-TNFR1 dAb (26% and 44% inhibition respectively).

Figure 13A:
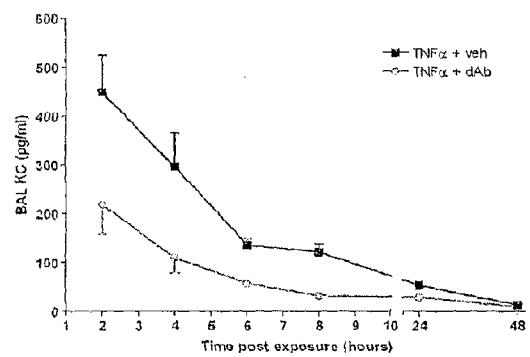
FIGS. 13A-13D are graphs showing time dependent effects of murine TNFα on BAL KC levels (13A), BAL MIP-2 levels (13B), BAL MCP-1 levels (13C), or lung tissue E-selectin levels (13D). Administration of anti-TNFR1 dAb significantly inhibited the increases induced by TNFα.
Figure 13B:
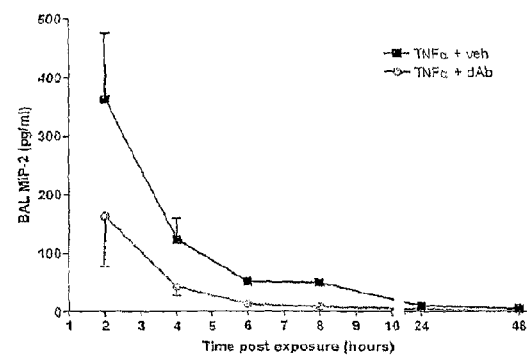

Concentrations of the neutrophil chemoattractants KC and MIP-2 were significantly increased 2 hrs following TNFα administration, and decreased in a time-dependent fashion with both chemokines returning to basal concentrations by 24 hrs (FIGS. 13A and 13B). These increases in BAL KC and MIP-2 were significantly reduced by anti-TNFR1 dAb pre-treatment.

Figure 13C:
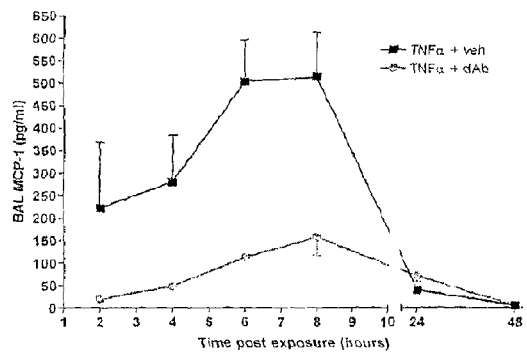
Figure 13D:
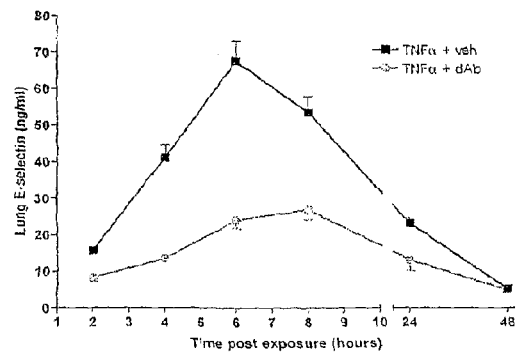

Concentrations of BAL MCP-1 and lung tissue E-selectin were also significantly increased by TNFα, but the peak increase was later than that of BAL KC and MIP-2 (6 hrs rather than 2 hrs). Concentrations of BAL MCP-1 and lung tissue E-selectin returned to basal levels by 48 hrs (FIGS. 13C and 13D). These increases in BAL KC and MIP-2 were significantly reduced by anti-TNFR1 dAb pre-treatment.

Discussion

Intranasal administration of murine TNFα to mice resulted in significant levels of pulmonary TNFα, which induced significant increases in BAL neutrophils, BAL KC, MIP-2 and MCP-1 and lung tissue E-selectin. BAL neutrophils were not increased until about 24 hrs and remained elevated at 48 hrs. Previous data in the literature using rats demonstrated a protracted neutrophil response. The peak increases in BAL KC and MIP-2 were observed at the 2 hr time point, with peak increases in BAL MCP-1 and lung tissue E-selectin at around 6 hrs. Increased levels of each of KC, MIP-2, MCP-1 and E-selecting were detected 6 hrs after administration of TNFα.

Pre-treatment with an anti-TNFR1 dAb (1 mg/kg) 1 hr before administration of murine TNFα inhibited the increases in BAL neutrophils and KC, MIP-2 and MCP-1 and lung tissue E-selectin. These data suggests the TNFR1 receptor mediates the majority of the pulmonary inflammation induced by i.n. TNFα in this model.

Example 6

Effects of Varying Doses of Pulmonary Delivered anti-TNFR1 dAb on TNFα-induced Pulmonary Inflammation Varying doses of an anti-TNFR1 dAb were administered to the lungs of mice by the i.n. route 1 hour prior to intranasal delivery of TNFα. The doses of anti-TNFR1 dAb used were 2.5 mg/kg, 1 mg/kg, 0.3 mg/kg, 0.1 mg/kg, 0.03 mg/kg and 0.01 mg/kg. The effect of pre-dosing with an anti-TNFR1 dAb was investigated by quantifying the concentration of the inflammatory cytokines KC, MIP-2 and MCP-1 in BAL, and quantifying E-selectin in lung tissue.
Methods The inflammatory stimulus and test substance were the same as those described in Example 5. TNFα (1 µg per mouse) was administered by the intranasal (i.n.) route. The volume administered was 50 µl per mouse (20 pig/ml).

The anti-TNFR1 dAb TAR2m-21-23 was administered by the i.n. route at a dose of 2.5 mg/kg, 1 mg/kg, 0.3 mg/kg, 0.1 mg/kg, 0.03 mg/kg or 0.01 mg/kg. The volume of dAb administered was 50 µl per mouse.

Mice were of the same strain and housed as described in Example 5.
Treatment Groups:
Group Size: n=4-7
Groups of mice were dosed i.n. with either vehicle or dAb (2.5, 1, 0.3, 0.1, 0.03 or 0.01 mg/kg) at 1 hour prior to TNFα administration. All groups were sacrificed 6 hrs after TNFα administration.

Mice were dosed using the same procedure as in Example 6. Mice were killed 6 hrs after i.n. administration of TNFα, and BAL cells, BAL supernatant and frozen lung tissue collected as described in Example 6. BAL protein, KC, MIP-2 and MCP-1, lung homogenate supernatant protein and E-selectin were examined and quantified as described in Example 6.
Results As shown in Example 5, intranasal administration of TNFα induced significant concentrations of KC, MIP-2 and MCP-1 in the BAL and E-selectin in the lung tissue 6 hrs after dosing. Pre-treatment (1 hr prior to TNFα) with an anti-TNFR1 dAb inhibited the elevation of these inflammatory mediators in a dose dependent fashion (Table 5) although the potency did vary between mediators.

TABLE 5

Dose dependent inhibition of TNFα-induced increases in BAL KC, MIP-2 and MCP-1 and lung tissue E-selectin concentrations.[1]

| | dAb i.n. dosing (mg/kg) | | | | | |
|---|---|---|---|---|---|---|
| | 2.5 | 1 | 0.3 | 0.1 | 0.03 | 0.01 |
| BAL KC | 66 ± 10 | 82 ± 8 | 71 ± 15 | 70 ± 40 | 77 ± 33 | 7 ± 48 |
| BAL MIP-2 | 89 ± 16 | 91 ± 8 | 77 ± 14 | 74 ± 39 | 61 ± 33 | 14 ± 78 |
| BAL MCP-1 | 64 ± 13 | 60 ± 21 | 60 ± 9 | none | none | none |
| Lung E selectin | 59 ± 18 | 65 ± 10 | 59 ± 18 | 30 ± 30 | none | none |

[1]The table shows percent inhibition (mean ± SD) of TNFα-induced increases in BAL KC, MIP-2 and MCP-1 and lung tissue E-selectin concentrations at dAb doses of 2.5, 1, 0.3, 0.1, 0.03 and 0.01 mg/kg.

The anti-TNFR1 dAb inhibited BAL KC to a similar degree at all doses between 2.5 mg/kg and 0.03 mg/kg, and was inactive at 0.01 mg/kg. Similarly, the anti-TNFR1 dAb inhibited BAL MIP-2 to substantially the same degree at all doses between 2.5 mg/kg and 0.1 mg/kg, with slightly less inhibition at 0.03 mg/kg, and was inactive at 0.01 mg/kg.

The anti-TNFR1 dAb was a less potent inhibitor of BAL MCP-1 as significant inhibition was observed between 2.5 mg/kg and 0.3 mg/kg, but not at lower doses. Lung tissue E-selectin concentrations were inhibited in a similar fashion; significant inhibition was observed between 2.5 mg/kg and 0.3 mg/kg, minimal inhibition at 0.1 mg/kg, and no effect at lower doses.
Discussion Intranasal administration of murine TNFα to mice induced significant increases in BAL neutrophils, BAL KC, MIP-2 and MCP-1, and lung tissue E-selectin. These increases were significantly inhibited in a dose-dependent fashion with an anti-TNFR1 dAb. The anti-TNFR1 dAb had more potent inhibitory activity on BAL KC and MIP-2 compared with BAL MCP-1 and lung tissue E-selectin. This might be because peak increases in BAL KC and MIP-2 were induced relatively quickly following TNFα administration, whereas peak increases in BAL MCP-1 and tissue E-selectin were later.

This study demonstrates that i.n. anti-TNFR1 dAb a dose of 0.3 mg/kg significant inhibited TNFα-induced increases in BAL neutrophils, BAL KC, MIP-2 and MCP-1, and lung tissue E-selectin at six hours post TNFα administration, but that 0.3 mg/kg is not a supra-maximal dose.

Example 8

Duration of Action In Vivo of an Anti-TNFR1 dAb Administered by the Intranasal Route Anti-TNFR1 dAb (TAR2m-21-23) was administered to the lungs of mice by the i.n. route at various times prior to i.n. administration of TNFα. The effect of pre-dosing the lung with anti-TNFR1 dAbs was investigated by quantifying the inflammatory cytokines KC, MIP-2 and MCP-1 in BAL, and quantifying E-selectin in lung tissue, by ELISA. The results are shown in Table 6.
Methods:
Inflammatory stimulus: recombinant murine TNFα
Test Substance 1: TAR2m-21-23 (Batch BH31/01/06-1) (anti-TNFR1 dAb)
Vehicle for rm TNFα: PBS containing 0.1% BSA.
Vehicle for TAR2m-21-23: 20 nM citrate buffer pH 6

Dose of TNFα was 1 pig per mouse by the intranasal (i.n.) route as used in the previous study. Volume administered to the nose was 50 µl per mouse (20 µg/ml). Dose of TAR2m-21-23 was 0.3 mg/kg by i.n. route. Volume administered to the nose was 50 µl per mouse (0.4 mg/ml as mice were 20 g).

Mice used and dAb preparation: Mice were of the same strain and housed as detailed in the previous study protocol.
Protocols:
Treatment Groups:
Group Size: n=4-7
Treatment times:

Groups of mice were dosed i.n. with either vehicle or dAb at 1, 2, 4, or 6 hours prior to TNFα administration. All groups were sacrificed 6 hrs after TNFα administration.

Dosing and Terminal procedures: Mice were dosed as detailed above using the same procedure as the previous study. Mice were killed 6 hrs after i.n. TNFα administration and BAL cells, BAL supernatant and frozen lung tissue were collected as detailed in the previous study.

Sample preparation and ELISA: BAL protein, KC, MIP-2 and MCP-1 and lung homogenate supernatant protein and E-selectin were examined as detailed in the previous experiment.

TABLE 6

Duration of action in vivo of an anti-TNFR1 dAb.[2]

|  | TNF | dAb pre-dose time (hrs) | | | |
|---|---|---|---|---|---|
|  | Veh | (no dAb) | 1 | 2 | 4 | 6 |
| BAL KC | 32 | 145 | 77 | 61 | 46 | 39 |
| BAL MIP-2 | 14 | 54 | 18 | 18 | 13 | 8 |
| BAL MCP-1 | 3 | 418 | 123 | 90 | 218 | 188 |
| Lung E selectin | 3 | 44 | 20 | 23 | 27 | 28 |

[2]The table shows mean BAL KC (pg/ml), MIP-2 (pg/ml) and MCP-1 (pg/ml) and lung tissue E-selectin (ng/ml) concentrations six hours after i.n. administration of TNFα or vehicle. Anti-TNFR1 dAb was administered 1, 2, 4, or 6 hours prior to administration of TNFα.

The results presented in Table 6, show that administration of dAb at 1, 2, 4, or 6 hours prior to administration of TNFα significantly inhibited of BAL KC and MIP-2 induced by TNF at all dAb pre-dose timepoints. Better inhibition was observed at longer pre-dose times. This suggests >1 hr is optimal for dAb binding to the receptor following i.n. dosing. In a similar manner administration of dAb at 1, 2, 4, or 6 hours prior to administration of TNFα also significantly inhibited BAL MCP-1 and lung tissue E-selectin induced by TNF at all dAb pre-dose timepoints. These results show that anti-TNFR1 dAb has a duration of action that is greater than 6 hours.

Example 9

Evaluation of an Anti-TNFR1 dAb that Binds TNFR1 and Inhibits Binding of TNFα to the Receptor Administered by the Intranasal Route on TNFα-induced Pulmonary Inflammation The previous examples show that an anti-TNFR1 dAb ("non-competitive dAb" TAR2m-21-23) which binds TNFR1 but does not inhibit binding of TNFα to TNFR1 significantly inhibited TNFα-induced pulmonary inflammation. This study demonstrates that a dAb that binds TNFR1 and inhibits binding of TNFα to TNFR1 ("competitive dAb" TAR2m-15-12) was also efficacious in inhibiting TNFα-induced pulmonary inflammation.
Methods:
Inflammatory stimulus: recombinant murine TNFα
Test Substance 1: TAR2m-21-23 (Batch BH31/01/06-1) (competitive anti-TNFR1 dAb)
Test Substance 2: TAR2m-15-12 (non-competitive anti-TNFR1 dAb)
Vehicle for rm TNFα: PBS containing 0.1% BSA.
Vehicle for dAbs: 20 nM citrate buffer pH 6
Dose of TNFα was 1 µg per mouse by the intranasal (i.n.) route as used in the previous study. Volume administered to the nose was 50 µl per mouse (20 µg/ml).
Dose of TAR2m-21-23 or TAR2m-15-12 was 0.3, 0.1, and 0.03 mg/kg by i.n. route. Volume administered to the nose was 50 µl per mouse (0.4 mg/ml as mice were 20 g).

Mice used and dAb preparation: Mice were of the same strain and housed as detailed in the previous study protocol. dAb was formulated as previously described.
Protocols:
Treatment Groups:
Group Size: n 4-7
Treatment times:
Groups of mice were dosed i.n. with either vehicle or dAb at 1 hr prior to TNFα administration. All groups were sacrificed 6 hrs after TNFα administration. Dosing and Terminal procedures: Mice were dosed as detailed above using the same procedure as the previous study. Mice were killed 6 hrs after i.n. TNFα administration and BAL cells, BAL supernatant and frozen lung tissue collected as detailed in the previous study.

Sample preparation and ELISA: BAL protein, KC, MIP-2 and MCP-1 and lung homogenate supernatant protein and E-selectin were examined as detailed in the previous experiment.

TABLE 7

Dose dependent effects of a competitive or a non-competitive an anti-TNFR1 dAb on TNFα-induced increases in BAL KC, MIP-2 and MCP-1 and lung tissue E-selectin concentrations.[3]

|  | non-competitive dAb i.n dosing (mg/kg) | | | competitive dAb i.n dosing (mg/kg) | | |
|---|---|---|---|---|---|---|
|  | 0.3 | 0.1 | 0.03 | 0.3 | 0.1 | 0.03 |
| BAL KC | 97 ± 15[1] | 67 ± 22 | 70 ± 16 | 105 ± 20 | 66 ± 9 | 43 ± 22 |
| BAL MIP-2 | 78 ± 8 | 78 ± 14 | 80 ± 14 | 88 ± 11 | 66 ± 18 | 54 ± 16 |
| BAL MCP-1 | 71 ± 11 | 34 ± 19 | 41 ± 8 | 82 ± 26 | 1 ± 60 | 1 ± 41 |
| Lung E selectin | 60 ± 4 | 42 ± 34 | 19 ± 25 | 55 ± 27 | 13 ± 8 | 14 ± 7 |

[3]The table show the percent inhibition (mean ± SD) of TNFα-induced increases in BAL KC, MIP-2 and MCP-1 and lung tissue E-selectin concentrations at dAb doses 0.3, 0.1, and 0.03 mg/kg.

The results present in Table 7 show that similar to previous studies pre-treatment (1 hr prior to TNFα) with a non-competitive anti-TNFR1 dAb (TAR2m-21-23) dose dependently inhibited the elevation of, the inflammatory mediators BAL KC, MIP-2 and MCP-1 and lung tissue E-selectin. In a similar manner a competitive anti-TNFR1 dAb (TAR2m-15-12) also dose dependently inhibited the elevation of the inflammatory mediators BAL KC, MIP-2 BAL and MCP-1 and lung tissue E-selectin.

The TAR2m-15-12 anti-TNFR1 dAb had slightly less efficacy on BAL KC at 0.03 mg/kg, and on BAL MIP-2 at 0.1-0.03 mg/kg compared with TAR2m-21-23. The TAR2m-15-12 anti-TNFR1 dAb was inactive on BAL MCP-1 at 0.1 mg/kg compared with TAR2m-21-23 which showed 34% inhibition on BAL MCP-1. The TAR2m-15-12 anti-TNFR1 dAb had slightly less efficacy on lung tissue E-selectin at 0.1 mg/kg compared with TAR2m-21-23.

The in vitro potency was ~1 nM for TAR2m-21-23 and ~5 nM for TAR2m-15-12. In addition TAR2m-21-23 has greater affinity and slower off-rate than TAR2m-15-12. The difference in efficacy on the inflammatory mediators is likely to be due to reduced affinity and potency. This indicates that there is no obvious difference between a non-competitive dAb (TAR2m-21-23) and a competitive dAb TAR2m-15-12 that inhibits binding of TNFα to TNFR1.

Summary

Table 8 summarizes the results of TS induced studies and TNF induced studies. The TS exposed and PEGylated anti-TNFR1 dAb treated group (10 mg/kg), showed significantly reduced cell infiltrates in the lung compared to the TS exposed and control treated groups: 62% inhibition for total cells. No significant reductions in any of the cell populations were observed in the (10 mg/kg i.p.) TS/ENBREL® (etanercept; Immunex Corporation) treated group. Significantly reduced cell infiltrates were only observed in the TS/ENBREL® (etanercept; Immunex Corporation) treated group when dosing was increased to 30 mg/kg (i.p.). This indicates that >3-fold higher systemic mg/kg dosing of ENBREL® (etanercept; Immunex Corporation) is required compared to PEGylated anti-TNFR1 dAb to achieve significant reductions in cell populations.

In the TNFα-induced model, the anti-TNFR1 dAb treated group (0.3 mg/kg i.n.), show 78% inhibition of TNFα induced MIP-2 levels. A similar level of inhibition in MIP-2 levels (78%) was achieved in the ENBREL® (etanercept; Immunex Corporation) group treated with 10 mg/kg (i.n.). The ENBREL® (etanercept; Immunex Corporation) group treated with 1 mg/kg (i.n.) did not show any significant reductions of cell influx. Together this data indicates that >30 fold higher i.n. mg/kg dosing of ENBREL® (etanercept; Immunex Corporation) is required compared to anti-TNFR1 dAb to achieve efficient inhibition of MIP-2.

TABLE 8

| Molecule | MW, kD | $t^{1/2}_\beta$ | Potency, $ND_{50}$ L929 assay | ROA | Dosing (mg/kg) | Inhibition of cell influx |
|---|---|---|---|---|---|---|
| PEG-TAR2m | 52 | 2-4 d | 1 nM | i.p. | 10 mg/kg | 62% ($p < 0.001$) |
| ENBREL® (etanercept; Immunex Corporation) | 150 | 1 d (estimated) | 5-50 pM | i.p. | 10 mg/kg | −1% (ns) |
| ENBREL® (etanercept; Immunex Corporation) | 150 | 1 d (estimated) | 5-50 pM | i.p. | 30 mg/kg | 37% ($p < 0.01$) |
| Rat anti-TNF mAb | 150 | 2-7 d (estimated) | 6-8 nM (mTNF) | i.p. | 3 mg/kg | 51% ($p < 0.001$) |
| TAR2m monomer | 12 | 4-6 hrs i.n. | 1 nM | i.n. | 1 mg/kg | 53%/72% ($p < 0.05$) |
| ENBREL® (etanercept; Immunex Corporation) | 150 | 1 d (estimated) | 5-50 pM | i.n. | 1 mg/kg | 11% (ns) |

| Molecule | MW, kD | $t^{1/2}_\beta$ | Potency, $ND_{50}$ L929 assay | ROA | Dosing (mg/kg) | Reduction in MIP-2 levels |
|---|---|---|---|---|---|---|
| TAR2m | 12 | 4-6 hrs i.n. | 1 nM | i.n. | 1 mg/kg | 120% |
| ENBREL® (etanercept; Immunex Corporation) | 150 | 1 d (estimated) | 5-50 pM | i.n. | 10 mg/kg | 78% |
| Rat anti-TNF mAb | 150 | 2-7 d (estimated) | 6-8 nM (mTNF) | i.n. | 2.5 mg/kg | 87% |
| TAR2m monomer | 12 | 4-6 hrs i.n. | 1 nM | i.n | 0.3 mg/kg | 78% |
| TAR2m monomer (competitive dAb) | 12 | 4-6 hrs i.n. | 5 nM | i.n. | 0.3 mg/kg | 88% |
| TAR2m monomer | 12 | 4-6 hrs i.n. | 1 nM | i.n. | 0.1 mg/kg | 78% |
| TAR2m monomer (competitive dAb) | 12 | 4-6 hrs i.n. | 5 nM | i.n. | 0.1 mg/kg | 66% |

While this invention has been particularly shown and described with references to preferred embodiments thereof, it will be understood by those skilled in the art that various changes in form and details may be made therein without departing from the scope of the invention encompassed by the appended claims.

The material in the ASCII text filed named "DB00034C1SeqList.txt" created on Jun. 17, 2013 and having a size of 563,179 bytes is incorporated herein by reference in its entirety.

The invention claimed is:

1. A method for treating acute respiratory distress syndrome (ARDS) in a patient comprising the steps of:
   a) identifying a patient with ARDS;
   b) providing a formulation comprising a ligand that comprises a domain antibody comprising a CDR1 amino acid sequence, a CDR2 amino acid sequence and a CDR3 amino acid sequence of the domain antibody having the amino acid sequence shown in SEQ ID NO: 379; and
   c) administering the formulation locally to pulmonary tissue of the patient in an effective amount; whereby ARDS in the patient is treated.

2. A method for treating acute respiratory distress syndrome (ARDS) in a patient comprising the steps of:
   a) identifying a patient with ARDS;
   b) providing a formulation comprising a domain antibody that binds TNFR1, wherein the domain antibody is an antagonist of the TNFR1 and comprises a CDR1 amino acid sequence, a CDR2 amino acid sequence and a CDR3 amino acid sequence of the domain antibody having the amino acid sequence shown in SEQ ID NO: 379; and
   c) administering the formulation locally to pulmonary tissue of the patient in an effective amount; whereby ARDS in the patient is treated.

3. A method for treating acute respiratory distress syndrome (ARDS) in a patient comprising the steps of:
   a) identifying a patient with ARDS;
   b) providing a formulation comprising a domain antibody that comprises a CDR1 amino acid sequence, a CDR2 amino acid sequence and a CDR3 amino acid sequence of the domain antibody having the amino acid sequence shown in SEQ ID NO: 379; and
   c) administering the formulation locally to pulmonary tissue of the patient in an effective amount; whereby ARDS in the patient is treated.

4. A method for treating acute respiratory distress syndrome (ARDS) in a patient comprising the steps of:
   a) identifying a patient with ARDS;
   b) providing a formulation comprising a domain antibody that binds TNFR1, wherein the domain antibody is an antagonist of the TNFR1 and comprises the amino acid sequence shown in SEQ ID NO: 379; and
   c) administering the formulation locally to pulmonary tissue of the patient in an effective amount; whereby ARDS in the patient is treated.

5. A method for treating acute respiratory distress syndrome (ARDS) in a patient comprising the steps of:
   a) identifying a patient with ARDS;
   b) providing a formulation comprising a domain antibody that comprises the amino acid sequence shown in SEQ ID NO: 379; and
   c) administering the formulation locally to pulmonary tissue of the patient in an effective amount; whereby ARDS in the patient is treated.

6. A method for treating acute respiratory distress syndrome (ARDS) in a patient comprising the steps of:
   a) identifying a patient with ARDS;
   b) providing a formulation comprising a ligand that comprises an immunoglobulin single variable domain that binds TNFR1; wherein the amino acid sequence of the immunoglobulin single variable domain comprises CDR1, CDR2 and CDR3 amino acid sequences derived from the amino acid sequence shown in SEQ ID NO: 379; wherein the first three amino proximal residues of CDR1 comprise up to two amino acid substitutions in CDR1 from the amino acid sequence shown in SEQ ID NO: 379; wherein CDR2 has at least about 80% identity to CDR2 of the amino acid sequence shown in SEQ ID NO: 379; and wherein CDR3 is the same as CDR3 of the amino acid sequence shown in SEQ ID NO: 379; and
   c) administering the formulation locally to pulmonary tissue of the patient in an effective amount; whereby ARDS in the patient is treated.

7. A method for treating acute respiratory distress syndrome (ARDS) in a patient comprising the steps of:
   a) identifying a patient with ARDS;
   b) providing a formulation comprising a ligand that comprises a domain antibody that is an antagonist of TNFR1; and
   c) administering the formulation locally to the lung of the patient in an effective amount; whereby ARDS in the patient is treated.

8. A method for treating a respiratory disease selected from the group consisting of cystic fibrosis, acute respiratory distress syndrome (ARDS), acute lung injury (ALI), asthma, hypersensitivity pneumonitis, idiopathic pulmonary fibrosis, interstitial lung disease, bronchiecstasis, environmental lung disease, and mesothelioma in a patient comprising the steps of:
   a) identifying a patient with the respiratory disease;
   b) providing a formulation comprising a ligand that comprises a domain antibody comprising a CDR1 amino acid sequence, a CDR2 amino acid sequence and a CDR3 amino acid sequence of the domain antibody having the amino acid sequence shown in SEQ ID NO: 379; and
   c) administering the formulation locally to pulmonary tissue of the patient in an effective amount; whereby the respiratory disease in the patient is treated.

9. The method of claim 8, wherein the respiratory disease is environmental lung disease.

10. The method of claim 8, wherein the respiratory disease is mesothelioma.

11. The method of claim 8, wherein the respiratory disease is interstitial lung disease, hypersensitivity pneumonitis, or idiopathic pulmonary fibrosis.

12. The method of claim 8, wherein the respiratory disease is cystic fibrosis or bronchiecstasis.

13. The method of claim 8, wherein the respiratory disease is selected from acute lung injury (ALI) and acute respiratory distress syndrome (ARDS).

14. The method of claim 8, wherein the respiratory disease is acute lung injury (ALI).

15. The method of claim 8, wherein the respiratory disease is acute respiratory distress syndrome (ARDS).

16. The method of claim 8, wherein the respiratory disease is asthma.

17. A method for treating a respiratory disease selected from the group consisting of cystic fibrosis, acute respiratory distress syndrome (ARDS), acute lung injury (ALI), asthma, hypersensitivity pneumonitis, idiopathic pulmonary fibrosis, interstitial lung disease, bronchiecstasis, environmental lung disease, and mesothelioma in a patient comprising the steps of:
 a) identifying a patient with the respiratory disease;
 b) providing a formulation comprising a domain antibody that binds TNFR1, wherein the domain antibody is an antagonist of the TNFR1 and comprises a CDR1 amino acid sequence, a CDR2 amino acid sequence and a CDR3 amino acid sequence of the domain antibody having the amino acid sequence shown in SEQ ID NO: 379; and
 c) administering the formulation locally to pulmonary tissue of the patient in an effective amount; whereby the respiratory disease in the patient is treated.

18. The method of claim 17, wherein the respiratory disease is environmental lung disease.

19. The method of claim 17, wherein the respiratory disease is mesothelioma.

20. The method of claim 17, wherein the respiratory disease is interstitial lung disease, hypersensitivity pneumonitis, or idiopathic pulmonary fibrosis.

21. The method of claim 17, wherein the respiratory disease is cystic fibrosis or bronchiecstasis.

22. The method of claim 17, wherein the respiratory disease is selected from acute lung injury (ALI) and acute respiratory distress syndrome (ARDS).

23. The method of claim 17, wherein the respiratory disease is acute lung injury (ALI).

24. The method of claim 17, wherein the respiratory disease is acute respiratory distress syndrome (ARDS).

25. The method of claim 17, wherein the respiratory disease is asthma.

26. A method for treating a respiratory disease selected from the group consisting of cystic fibrosis, acute respiratory distress syndrome (ARDS), acute lung injury (ALI), asthma, hypersensitivity pneumonitis, idiopathic pulmonary fibrosis, interstitial lung disease, bronchiecstasis, environmental lung disease, and mesothelioma in a patient comprising the steps of: a) identifying a patient with the respiratory disease; b) providing a formulation comprising a domain antibody that comprises a CDR1 amino acid sequence, a CDR2 amino acid sequence and a CDR3 amino acid sequence of the domain antibody having the amino acid sequence shown in SEQ ID NO: 379; and c) administering the formulation locally to pulmonary tissue of the patient in an effective amount; whereby the respiratory disease in the patient is treated.

27. The method of claim 26, wherein the respiratory disease is environmental lung disease.

28. The method of claim 26, wherein the respiratory disease is mesothelioma.

29. The method of claim 26, wherein the respiratory disease is interstitial lung disease, hypersensitivity pneumonitis, or idiopathic pulmonary fibrosis.

30. The method of claim 26, wherein the respiratory disease is cystic fibrosis or bronchiecstasis.

31. The method of claim 26, wherein the respiratory disease is selected from acute lung injury (ALI) and acute respiratory distress syndrome (ARDS).

32. The method of claim 26, wherein the respiratory disease is acute lung injury (ALI).

33. The method of claim 26, wherein the respiratory disease is acute respiratory distress syndrome (ARDS).

34. The method of claim 26, wherein the respiratory disease is asthma.

35. A method for treating a respiratory disease selected from the group consisting of cystic fibrosis, acute respiratory distress syndrome (ARDS), acute lung injury (ALI), asthma, hypersensitivity pneumonitis, idiopathic pulmonary fibrosis, interstitial lung disease, bronchiecstasis, environmental lung disease, and mesothelioma in a patient comprising the steps of: a) identifying a patient with the respiratory disease; b) providing a formulation comprising a domain antibody that binds TNFR1, wherein the domain antibody is an antagonist of the TNFR1 and comprises the amino acid sequence shown in SEQ ID NO: 379; and c) administering the formulation locally to pulmonary tissue of the patient in an effective amount; whereby the respiratory disease in the patient is treated.

36. The method of claim 35, wherein the respiratory disease is environmental lung disease.

37. The method of claim 35, wherein the respiratory disease is mesothelioma.

38. The method of claim 35, wherein the respiratory disease is interstitial lung disease, hypersensitivity pneumonitis, or idiopathic pulmonary fibrosis.

39. The method of claim 35, wherein the respiratory disease is cystic fibrosis or bronchiecstasis.

40. The method of claim 35, wherein the respiratory disease is selected from acute lung injury (ALI) and acute respiratory distress syndrome (ARDS).

41. The method of claim 35, wherein the respiratory disease is acute lung injury (ALI).

42. The method of claim 35, wherein the respiratory disease is acute respiratory distress syndrome (ARDS).

43. The method of claim 35, wherein the respiratory disease is asthma.

44. A method for treating a respiratory disease selected from the group consisting of cystic fibrosis, acute respiratory distress syndrome (ARDS), acute lung injury (ALI), asthma, hypersensitivity pneumonitis, idiopathic pulmonary fibrosis, interstitial lung disease, bronchiecstasis, environmental lung disease, and mesothelioma in a patient comprising the steps of: a) identifying a patient with the respiratory disease; b) providing a formulation comprising a domain antibody that comprises the amino acid sequence shown in SEQ ID NO: 379; and c) administering the formulation locally to pulmonary tissue of the patient in an effective amount; whereby the respiratory disease in the patient is treated.

45. The method of claim 44, wherein the respiratory disease is environmental lung disease.

46. The method of claim 44, wherein the respiratory disease is mesothelioma.

47. The method of claim 44, wherein the respiratory disease is interstitial lung disease, hypersensitivity pneumonitis, or idiopathic pulmonary fibrosis.

48. The method of claim 44, wherein the respiratory disease is cystic fibrosis or bronchiecstasis.

49. The method of claim 44, wherein the respiratory disease is selected from acute lung injury (ALI) and acute respiratory distress syndrome (ARDS).

50. The method of claim 44, wherein the respiratory disease is acute lung injury (ALI).

51. The method of claim 44, wherein the respiratory disease is acute respiratory distress syndrome (ARDS).

52. The method of claim 44, wherein the respiratory disease is asthma.

53. A method for treating a respiratory disease selected from the group consisting of cystic fibrosis, acute respiratory distress syndrome (ARDS), acute lung injury (ALI), asthma, hypersensitivity pneumonitis, idiopathic pulmonary fibrosis, interstitial lung disease, bronchiecstasis, environmental lung disease, and mesothelioma in a patient comprising the steps of: a) identifying a patient with the respiratory disease; b) providing a formulation comprising a ligand that comprises an immunoglobulin single variable domain that binds TNFR1; wherein the amino acid sequence of the immunoglobulin single variable domain comprises CDR1, CDR2 and CDR3 amino acid sequences derived from the amino acid sequence shown in SEQ ID NO: 379; wherein the first three amino proximal residues of CDR1 comprise up to two amino acid substitutions in CDR1 from the amino acid sequence shown in SEQ ID NO: 379; wherein CDR2 has at least about 80% identity to CDR2 of the amino acid sequence shown in SEQ ID NO: 379; and wherein CDR3 is the same as CDR3 of the amino acid sequence shown in SEQ ID NO: 379; and c) administering the formulation locally to pulmonary tissue of the patient in an effective amount; whereby the respiratory disease in the patient is treated.

54. The method of claim 53, wherein the respiratory disease is environmental lung disease.

55. The method of claim 53, wherein the respiratory disease is mesothelioma.

56. The method of claim 53, wherein the respiratory disease is interstitial lung disease, hypersensitivity pneumonitis, or idiopathic pulmonary fibrosis.

57. The method of claim 53, wherein the respiratory disease is cystic fibrosis or bronchiecstasis.

58. The method of claim 53, wherein the respiratory disease is selected from acute lung injury (ALI) and acute respiratory distress syndrome (ARDS).

59. The method of claim 53, wherein the respiratory disease is acute lung injury.

60. The method of claim 53, wherein the respiratory disease is acute respiratory distress syndrome (ARDS).

61. The method of claim 53, wherein the respiratory disease is asthma.

62. A method for treating a respiratory disease selected from the group consisting of cystic fibrosis, acute respiratory distress syndrome (ARDS), acute lung injury (ALI), asthma, hypersensitivity pneumonitis, idiopathic pulmonary fibrosis, interstitial lung disease, bronchiecstasis, environmental lung disease, and mesothelioma in a patient comprising the steps of:
  a) identifying a patient with the respiratory disease;
  b) providing a formulation comprising a ligand that comprises a domain antibody that is an antagonist of TNFR1; and
  c) administering the formulation locally to the lung of the patient in an effective amount; whereby the respiratory disease in the patient is decreased.

63. The method of claim 62, wherein the respiratory disease is environmental lung disease.

64. The method of claim 62, wherein the respiratory disease is mesothelioma.

65. The method of claim 62, wherein the respiratory disease is interstitial lung disease, hypersensitivity pneumonitis, or idiopathic pulmonary fibrosis.

66. The method of claim 62, wherein the respiratory disease is cystic fibrosis or bronchiecstasis.

67. The method of claim 62, wherein the respiratory disease is selected from acute lung injury (ALI) and acute respiratory distress syndrome (ARDS).

68. The method of claim 62, wherein the respiratory disease is acute lung injury (ALI).

69. The method of claim 62, wherein the respiratory disease is acute respiratory distress syndrome (ARDS).

70. The method of claim 62, wherein the lung inflammation the respiratory disease is asthma.

* * * * *

SEQUENCE LISTING

<160> NUMBER OF SEQ ID NOS: 650

<210> SEQ ID NO 1
<211> LENGTH: 122
<212> TYPE: PRT
<213> ORGANISM: Homo sapiens

<400> SEQUENCE: 1

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Ala Tyr
            20                  25                  30

Asn Met Gly Trp Val Arg Gln Ala Pro Gly Lys Gly Leu Glu Trp Val
        35                  40                  45

Ser Phe Ile Asp Met Tyr Gly Ala Lys Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Cys Leu Met Asp Cys Ser Gly Asp Ile Phe Asp Tyr Trp
            100                 105                 110

Gly Gln Gly Thr Leu Val Thr Val Ser Ser
            115                 120

<210> SEQ ID NO 2
<211> LENGTH: 116
<212> TYPE: PRT
<213> ORGANISM: Homo sapiens

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Ala Asp
            20                  25                  30

Glu Met Tyr Trp Val Arg Gln Ala Pro Gly Lys Gly Leu Glu Trp Val
        35                  40                  45

Ser Ser Ile Gly Trp Pro Gly Gly Ala Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Gly Arg Asn Phe Asp Tyr Trp Gly Gln Gly Thr Leu Val
            100                 105                 110

Thr Val Ser Ser
        115

<210> SEQ ID NO 3
<211> LENGTH: 122
<212> TYPE: PRT
<213> ORGANISM: Homo sapiens

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Gln Tyr
            20                  25                  30

Asp Met Ser Trp Val Arg Gln Ala Pro Gly Lys Gly Leu Glu Trp Val
        35                  40                  45

Ser Leu Ile Asp Pro Ser Gly Gly His Thr Tyr Tyr Ala Asp Ser Val
    50                  55                  60

Lys Gly Arg Phe Thr Ile Ser Arg Asn Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Val Phe Ser Asp Trp Pro Ala Val Glu Phe Asp Tyr Trp
            100                 105                 110

Gly Gln Gly Thr Leu Val Thr Val Ser Ser
        115                 120

<210> SEQ ID NO 4
<211> LENGTH: 116
<212> TYPE: PRT
<213> ORGANISM: Homo sapiens

<400> SEQUENCE: 4

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Gly Asn Tyr
             20                  25                  30

Asp Met Gln Trp Val Arg Gln Ala Pro Gly Lys Gly Leu Glu Trp Val
         35                  40                  45

Ser Ser Ile Asp Gly Thr Gly Gly Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Gln Glu Thr Asn Ala Phe Asp Tyr Trp Gly Gln Gly Thr Leu Val
            100                 105                 110

Thr Val Ser Ser
        115

<210> SEQ ID NO 5
<211> LENGTH: 124
<212> TYPE: PRT
<213> ORGANISM: Homo sapiens

<400> SEQUENCE: 5

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Gly Gly Tyr
             20                  25                  30

Gln Met Gly Trp Val Arg Gln Ala Pro Gly Lys Gly Leu Glu Trp Val
         35                  40                  45

Ser Phe Ile Asp Phe Thr Gly Ala His Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Lys Leu Ser Asp Asp Leu Thr Leu Pro Glu Arg Phe Pro Phe Asp
            100                 105                 110

Tyr Trp Gly Gln Gly Thr Leu Val Thr Val Ser Ser
            115                 120

<210> SEQ ID NO 6
<211> LENGTH: 123
<212> TYPE: PRT
<213> ORGANISM: Homo sapiens

<400> SEQUENCE: 6

Glu Val Gln Leu Leu Glu Ser Gly Gly Gly Leu Val Gln Pro Gly Gly

-continued

```
                 1               5                   10                  15
              Ser Leu Arg Leu Ser Cys Ala Ala Ser Gly Phe Thr Phe Ala Asp Tyr
                              20                  25                  30

Asn Met Thr Trp Val Arg Gln Ala Pro Gly Lys Gly Leu Glu Trp Val
                              35                  40                  45

Ser Trp Ile Asp Gln Glu Gly Val Phe Thr Tyr Tyr Ala Asp Ser Val
                              50                  55                  60

Lys Gly Arg Phe Thr Ile Ser Arg Asp Asn Ser Lys Asn Thr Leu Tyr
               65                  70                  75                  80

Leu Gln Met Asn Ser Leu Arg Ala Glu Asp Thr Ala Val Tyr Tyr Cys
                              85                  90                  95

Ala Lys Asp Phe Ser Ala Ala Val Met Leu Arg Thr Ser Phe Asp Tyr
                             100                 105                 110

Trp Gly Gln Gly Thr Leu Val Thr Val Ser Ser
                             115                 120
```

<210> SEQ ID NO 7
<211> LENGTH: 116
<212> TYPE: PRT
<213> ORGANISM: Homo sapiens

<400> SEQUENCE: 7

```
              Glu Val Gln Leu Leu Glu Ser Gly Gly Gly Leu Val Gln Pro Gly Gly
                1               5                   10                  15

Ser Leu Arg Leu Ser Cys Ala Val Ser Gly Phe Thr Phe His Asp Tyr
                              20                  25                  30

Gly Met Val Trp Val Arg Gln Ala Pro Gly Lys Gly Leu Glu Trp Val
                              35                  40                  45

Ser Gln Ile Ser Ile Asp Gly Arg Thr Thr Tyr Tyr Ala Asp Ser Val
                              50                  55                  60

Lys Gly Arg Phe Thr Ile Ser Arg Asp Asn Ser Lys Asn Thr Leu Tyr
               65                  70                  75                  80

Leu Gln Met Asn Ser Leu Arg Ala Glu Asp Thr Ala Val Tyr Tyr Cys
                              85                  90                  95

Ala Lys Arg Ile Phe Glu Phe Asp Tyr Trp Gly Gln Gly Thr Leu Val
                             100                 105                 110

Thr Val Ser Ser
                             115
```

<210> SEQ ID NO 8
<211> LENGTH: 117
<212> TYPE: PRT
<213> ORGANISM: Homo sapiens

<400> SEQUENCE: 8

```
              Glu Val Gln Leu Leu Glu Ser Gly Gly Gly Leu Val Gln Pro Gly Gly
                1               5                   10                  15

Ser Leu Arg Leu Ser Cys Ala Ala Ser Gly Phe Thr Phe Ser Ala Tyr
                              20                  25                  30

Asn Met Ser Trp Val Arg Gln Ala Pro Gly Lys Gly Leu Glu Trp Val
                              35                  40                  45

Ser Ala Ile Ser Pro Ser Gly Asn Glu Thr Tyr Tyr Ala Asp Ser Val
                              50                  55                  60

Lys Gly Arg Phe Thr Ile Ser Arg Asp Asn Ser Lys Asn Thr Leu Tyr
               65                  70                  75                  80

Leu Gln Met Asn Ser Leu Arg Ala Glu Asp Thr Ala Val Tyr Tyr Cys
```

-continued

```
                85                  90                  95

Ala Lys Gly Ala Gly Glu Ala Phe Asp Tyr Trp Gly Gln Gly Thr Leu
            100                 105                 110

Val Thr Val Ser Ser
        115

<210> SEQ ID NO 9
<211> LENGTH: 117
<212> TYPE: PRT
<213> ORGANISM: Homo sapiens

<400> SEQUENCE: 9

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Thr Glu Tyr
            20                  25                  30

Asn Met Gly Trp Val Arg Gln Ala Pro Gly Lys Gly Leu Glu Trp Val
        35                  40                  45

Ser Phe Ile Gly His Ser Gly Gln His Thr Tyr Tyr Ala Asp Ser Val
    50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Glu Leu Asn Asn Leu Met Phe Asp Tyr Trp Gly Gln Gly Thr Leu
            100                 105                 110

Val Thr Val Ser Ser
        115

<210> SEQ ID NO 10
<211> LENGTH: 121
<212> TYPE: PRT
<213> ORGANISM: Homo sapiens

<400> SEQUENCE: 10

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Gly Glu Tyr
            20                  25                  30

Asn Met Ala Trp Val Arg Gln Ala Pro Gly Lys Gly Gln Glu Trp Val
        35                  40                  45

Ser Phe Ile Ser Thr Gly Gly His Val Thr Tyr Tyr Ala Asp Ser Val
    50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Lys Phe Ser Val Arg Phe Arg Ser Ser Ile Phe Asp Tyr Trp Gly
            100                 105                 110

Gln Gly Thr Leu Val Thr Val Ser Ser
        115                 120

<210> SEQ ID NO 11
<211> LENGTH: 122
<212> TYPE: PRT
<213> ORGANISM: Homo sapiens

<400> SEQUENCE: 11
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Thr Phe Thr Glu Tyr
            20                  25                  30

Thr Met Gly Trp Val Arg Gln Ala Pro Gly Lys Gly Leu Glu Trp Val
        35                  40                  45

Ser Trp Ile Ala Val Asp Gly Ile His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Asp Trp Thr Ala Thr Asp Phe Ser Ile Phe Asp Tyr Trp
            100                 105                 110

Gly Gln Gly Thr Leu Val Thr Val Ser Ser
            115                 120

<210> SEQ ID NO 12
<211> LENGTH: 122
<212> TYPE: PRT
<213> ORGANISM: Homo sapiens

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Asn Tyr
            20                  25                  30

Thr Met Leu Trp Val Arg Gln Ala Pro Gly Lys Gly Leu Glu Trp Val
        35                  40                  45

Ser Val Ile Ser Ala Glu Gly Arg Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Asn Met Lys Ala Thr Asn Phe Lys Asp Phe Asp Tyr Trp
            100                 105                 110

Gly Gln Gly Thr Leu Val Thr Val Ser Ser
            115                 120

<210> SEQ ID NO 13
<211> LENGTH: 122
<212> TYPE: PRT
<213> ORGANISM: Homo sapiens

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Glu Tyr
            20                  25                  30

Ala Met Leu Trp Val Arg Gln Ala Pro Gly Lys Gly Leu Glu Trp Val
        35                  40                  45

Ser Leu Ile Asp Arg Thr Gly Val Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Asp Tyr Gln Tyr His Leu Tyr Gln Asp Phe Asp Tyr Arg
            100                 105                 110

Gly Gln Gly Thr Leu Val Thr Val Ser Ser
        115                 120

<210> SEQ ID NO 14
<211> LENGTH: 122
<212> TYPE: PRT
<213> ORGANISM: Homo sapiens

<400> SEQUENCE: 14

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ala Thr Tyr
             20                  25                  30

Ser Met Gly Trp Val Arg Gln Ala Pro Gly Lys Gly Leu Glu Trp Val
         35                  40                  45

Ser Met Ile Asp Pro Glu Gly Tyr His Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Glu Thr Asn Arg Pro Leu Thr Tyr Lys Pro Trp Phe Asp Tyr Trp
            100                 105                 110

Gly Gln Gly Thr Leu Val Thr Val Ser Ser
        115                 120

<210> SEQ ID NO 15
<211> LENGTH: 121
<212> TYPE: PRT
<213> ORGANISM: Homo sapiens

<400> SEQUENCE: 15

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Thr Asp Tyr
             20                  25                  30

Asn Met Ala Trp Val Arg Gln Ala Pro Gly Lys Gly Leu Glu Trp Val
         35                  40                  45

Ser Phe Ile Ser Gln Glu Gly His His Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Phe Ser Thr Ile Ala Thr Leu Ser Leu Phe Asp Tyr Trp Gly
            100                 105                 110

Gln Gly Thr Leu Val Thr Val Ser Ser
        115                 120

<210> SEQ ID NO 16
<211> LENGTH: 122
<212> TYPE: PRT
<213> ORGANISM: Homo sapiens

```
<400> SEQUENCE: 16

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala Thr Tyr
            20                  25                  30

Asn Met Gly Trp Val Arg Gln Ala Pro Gly Lys Gly Leu Glu Trp Val
        35                  40                  45

Ser Ser Ile Ala Trp Leu Gly Ser Glu Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys His Cys Lys Ala Glu Cys Thr Gly Asp Leu Phe Asp Tyr Trp
            100                 105                 110

Gly Gln Gly Thr Leu Val Thr Val Ser Ser
        115                 120

<210> SEQ ID NO 17
<211> LENGTH: 122
<212> TYPE: PRT
<213> ORGANISM: Homo sapiens

<400> SEQUENCE: 17

Glu Val Gln Leu Leu Glu Ser Gly Gly Gly Leu Val Gln Pro Gly Gly
 1               5                  10                  15

Ala Leu Arg Leu Ser Cys Ala Ala Ser Gly Phe Thr Phe Gly Ile Tyr
            20                  25                  30

Ser Met Gly Trp Val Arg Gln Ala Pro Gly Lys Gly Leu Glu Trp Val
        35                  40                  45

Ser Ser Ile Ser Gly Val Gly Met Glu Thr Tyr Tyr Ala Asp Ser Val
    50                  55                  60

Lys Gly Arg Phe Thr Ile Ser Arg Asp Asn Ser Glu Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys His Ser Tyr Pro Thr Arg Gly Arg His Leu Phe Asp Tyr Trp
            100                 105                 110

Gly Gln Gly Thr Leu Val Thr Val Ser Ser
        115                 120

<210> SEQ ID NO 18
<211> LENGTH: 120
<212> TYPE: PRT
<213> ORGANISM: Homo sapiens

<400> SEQUENCE: 18

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Lys Leu Gly Gly Gly Pro Asn Phe Asp Tyr Arg Gly Gln
            100                 105                 110

Gly Thr Leu Val Thr Val Ser Ser
            115                 120

<210> SEQ ID NO 19
<211> LENGTH: 120
<212> TYPE: PRT
<213> ORGANISM: Homo sapiens

<400> SEQUENCE: 19

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe His Arg Tyr
             20                  25                  30

Ser Met Gly Trp Val Arg Gln Ala Pro Gly Lys Gly Leu Glu Trp Val
         35                  40                  45

Ser Ala Ile Ser Ser Ser Gly Gly Ile Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Thr Gln Ala Gln Gly Leu Glu Leu Asp Tyr Trp Gly Gln
            100                 105                 110

Gly Thr Leu Val Thr Val Ser Ser
            115                 120

<210> SEQ ID NO 20
<211> LENGTH: 120
<212> TYPE: PRT
<213> ORGANISM: Homo sapiens

<400> SEQUENCE: 20

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Glu Trp Tyr
             20                  25                  30

Trp Met Gly Trp Val Arg Gln Ala Pro Gly Lys Gly Leu Glu Trp Val
         35                  40                  45

Ser Ala Ile Ser Gly Ser Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Asn Leu Arg Ala Glu Asp Thr Ala Val Tyr Tyr Cys
                 85                  90                  95

Ala Lys Val Lys Leu Gly Gly Gly Pro Asn Phe Asp Tyr Arg Gly Gln
            100                 105                 110

Gly Thr Leu Val Thr Val Ser Ser
            115                 120

<210> SEQ ID NO 21
<211> LENGTH: 120
```

```
<212> TYPE: PRT
<213> ORGANISM: Homo sapiens

<400> SEQUENCE: 21

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Lys Leu Gly Gly Gly Pro Asn Phe Asp Tyr Arg Gly Gln
            100                 105                 110

Gly Thr Leu Val Thr Val Ser Ser
            115                 120

<210> SEQ ID NO 22
<211> LENGTH: 120
<212> TYPE: PRT
<213> ORGANISM: Homo sapiens

<400> SEQUENCE: 22

Glu Val Gln Leu Leu Glu Ser Gly Gly Gly Leu Val Gln Pro Gly Gly
 1               5                  10                  15

Ser Leu Arg Leu Thr Cys Ala Ala Ser Gly Phe Thr Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Lys Leu Gly Gly Gly Pro Asn Phe Asp Tyr Trp Gly Gln
            100                 105                 110

Gly Thr Leu Val Thr Val Ser Ser
            115                 120

<210> SEQ ID NO 23
<211> LENGTH: 120
<212> TYPE: PRT
<213> ORGANISM: Homo sapiens

<400> SEQUENCE: 23

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Glu Trp Tyr
            20                  25                  30

Trp Met Gly Trp Ile Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
```

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Lys Leu Gly Gly Gly Pro Asn Phe Asp Tyr Trp Gly Gln
                100                 105                 110

Gly Thr Leu Val Thr Val Ser Ser
            115                 120
```

<210> SEQ ID NO 24
<211> LENGTH: 120
<212> TYPE: PRT
<213> ORGANISM: Homo sapiens

<400> SEQUENCE: 24

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Glu Trp Tyr
                 20                  25                  30

Trp Met Gly Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Lys Leu Gly Gly Gly Pro Asn Phe Asp Tyr Arg Gly Gln
                100                 105                 110

Gly Thr Leu Val Thr Val Ser Ser
            115                 120
```

<210> SEQ ID NO 25
<211> LENGTH: 120
<212> TYPE: PRT
<213> ORGANISM: Homo sapiens

<400> SEQUENCE: 25

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Glu Trp Tyr
                 20                  25                  30

Trp Met Gly Trp Val Arg Gln Ala Pro Gly Lys Gly Pro Glu Trp Val
             35                  40                  45

Ser Ala Ile Ser Gly Ser Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Lys Leu Gly Gly Gly Pro Asn Phe Asp Tyr Arg Gly Gln
                100                 105                 110

Gly Thr Leu Val Thr Val Ser Ser
            115                 120
```

```
<210> SEQ ID NO 26
<211> LENGTH: 120
<212> TYPE: PRT
<213> ORGANISM: Homo sapiens

<400> SEQUENCE: 26

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Lys Asp Thr Ala Val Tyr Tyr Cys
                85                  90                  95

Ala Lys Val Lys Leu Gly Gly Gly Pro Asn Phe Asp Tyr Arg Gly Gln
            100                 105                 110

Gly Thr Leu Val Thr Val Ser Ser
        115                 120

<210> SEQ ID NO 27
<211> LENGTH: 120
<212> TYPE: PRT
<213> ORGANISM: Homo sapiens

<400> SEQUENCE: 27

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Gly Asp Thr Ala Val Tyr Tyr Cys
                85                  90                  95

Ala Lys Val Lys Leu Gly Gly Gly Pro Asn Phe Asp Tyr Arg Gly Gln
            100                 105                 110

Gly Thr Leu Val Thr Val Ser Ser
        115                 120

<210> SEQ ID NO 28
<211> LENGTH: 120
<212> TYPE: PRT
<213> ORGANISM: Homo sapiens

<400> SEQUENCE: 28

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Glu Trp Val
        35                  40                  45
```

```
Ser Ala Ile Ser Gly Ser Gly Gly Arg Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Lys Leu Gly Gly Gly Pro Asn Phe Asp Tyr Trp Gly Gln
            100                 105                 110

Gly Thr Leu Val Thr Val Ser Ser
            115                 120

<210> SEQ ID NO 29
<211> LENGTH: 120
<212> TYPE: PRT
<213> ORGANISM: Homo sapiens

<400> SEQUENCE: 29

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Lys Leu Gly Gly Gly Pro Asn Phe Asp Asp Arg Gly Gln
            100                 105                 110

Gly Thr Leu Val Thr Val Ser Ser
            115                 120

<210> SEQ ID NO 30
<211> LENGTH: 120
<212> TYPE: PRT
<213> ORGANISM: Homo sapiens

<400> SEQUENCE: 30

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Gly Ser Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Lys Leu Gly Gly Gly Pro Asn Phe Asp Tyr Arg Gly Gln
            100                 105                 110

Gly Thr Leu Val Thr Val Ser Ser
            115                 120
```

<210> SEQ ID NO 31
<211> LENGTH: 120
<212> TYPE: PRT
<213> ORGANISM: Homo sapiens

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Trp Tyr
            20                  25                  30

Trp Met Gly Trp Val Arg Gln Ala Pro Gly Lys Gly Leu Glu Trp Ala
        35                  40                  45

Ser Ala Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Lys Leu Gly Gly Gly Pro Asn Phe Asp Tyr Trp Gly Gln
            100                 105                 110

Gly Thr Leu Val Thr Val Ser Ser
        115                 120

<210> SEQ ID NO 32
<211> LENGTH: 120
<212> TYPE: PRT
<213> ORGANISM: Homo sapiens

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Gly Trp Val
        35                  40                  45

Ser Ala Ile Ser Gly Ser Gly Gly Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Lys Leu Gly Gly Gly Pro Asn Phe Asp Tyr Arg Gly Gln
            100                 105                 110

Gly Thr Leu Val Thr Val Ser Ser
        115                 120

<210> SEQ ID NO 33
<211> LENGTH: 120
<212> TYPE: PRT
<213> ORGANISM: Homo sapiens
<220> FEATURE:
<221> NAME/KEY: VARIANT
<222> LOCATION: 20
<223> OTHER INFORMATION: Xaa = Any Amino Acid

<400> SEQUENCE: 33

Glu Val Gln Leu Leu Glu Ser Gly Gly Gly Leu Val Gln Pro Gly Gly
1               5                   10                  15

Ser Leu Arg Xaa Ser Cys Ala Ala Ser Gly Phe Thr Phe Glu Trp Tyr
            20                  25                  30

Trp Met Gly Trp Val Arg Gln Ala Pro Gly Lys Gly Pro Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Lys Leu Gly Gly Gly Pro Asn Phe Asp Tyr Trp Gly Gln
                100                 105                 110

Gly Thr Leu Val Thr Val Ser Ser
            115                 120

<210> SEQ ID NO 34
<211> LENGTH: 120
<212> TYPE: PRT
<213> ORGANISM: Homo sapiens

<400> SEQUENCE: 34

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Lys Leu Gly Gly Gly Pro Asn Phe Asp Tyr Arg Gly Arg
                100                 105                 110

Gly Thr Leu Val Thr Val Ser Ser
            115                 120

<210> SEQ ID NO 35
<211> LENGTH: 120
<212> TYPE: PRT
<213> ORGANISM: Homo sapiens

<400> SEQUENCE: 35

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Trp Tyr
            20                  25                  30

Trp Met Gly Trp Ile Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Lys Asp Thr Ala Val Tyr Tyr Cys
                85                  90                  95

```
Ala Lys Val Lys Leu Gly Gly Gly Pro Asn Phe Asp Tyr Arg Gly Gln
            100                 105                 110

Gly Thr Leu Val Thr Val Ser Ser
        115                 120

<210> SEQ ID NO 36
<211> LENGTH: 120
<212> TYPE: PRT
<213> ORGANISM: Homo sapiens

<400> SEQUENCE: 36

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Glu Trp Tyr
             20                  25                  30

Trp Met Gly Trp Ile Arg Gln Ala Pro Gly Lys Gly Leu Gly Trp Val
         35                  40                  45

Ser Ala Ile Ser Gly Ser Gly Ser Thr Tyr Tyr Ala Asp Ser Val
     50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Lys Leu Gly Gly Gly Pro Asn Phe Asp Tyr Arg Gly Gln
            100                 105                 110

Gly Thr Leu Val Thr Val Ser Ser
        115                 120

<210> SEQ ID NO 37
<211> LENGTH: 120
<212> TYPE: PRT
<213> ORGANISM: Homo sapiens

<400> SEQUENCE: 37

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Gly Trp Tyr
             20                  25                  30

Trp Met Gly Trp Val Arg Gln Ala Pro Gly Lys Gly Leu Glu Trp Ala
         35                  40                  45

Ser Ala Ile Ser Gly Ser Gly Gly Asn Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Lys Leu Gly Gly Gly Pro Asn Phe Asp Tyr Trp Gly Gln
            100                 105                 110

Gly Thr Leu Val Thr Val Ser Ser
        115                 120

<210> SEQ ID NO 38
<211> LENGTH: 120
<212> TYPE: PRT
<213> ORGANISM: Homo sapiens

<400> SEQUENCE: 38
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Gly Trp Val
        35                  40                  45

Ser Ala Ile Ser Gly Ser Gly Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Lys Asp Thr Ala Val Tyr Tyr Cys
            85                  90                  95

Ala Lys Val Lys Leu Gly Gly Gly Pro Asn Phe Asp Tyr Arg Gly Gln
            100                 105                 110

Gly Thr Leu Val Thr Val Ser Ser
            115                 120

<210> SEQ ID NO 39
<211> LENGTH: 120
<212> TYPE: PRT
<213> ORGANISM: Homo sapiens

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Trp Tyr
            20                  25                  30

Trp Met Gly Trp Val Arg Gln Ala Pro Gly Lys Gly Leu Glu Trp Ala
        35                  40                  45

Ser Ala Ile Ser Gly Ser Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Lys Asp Thr Ala Val Tyr Tyr Cys
            85                  90                  95

Ala Lys Val Lys Leu Gly Gly Gly Pro Asn Phe Asp Tyr Trp Gly Gln
            100                 105                 110

Gly Thr Leu Val Thr Val Ser Ser
            115                 120

<210> SEQ ID NO 40
<211> LENGTH: 120
<212> TYPE: PRT
<213> ORGANISM: Homo sapiens

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

-continued

Leu Gln Met Asn Ser Leu Arg Ala Lys Asp Thr Ala Val Tyr Tyr Cys
                85                  90                  95

Ala Lys Val Lys Leu Gly Gly Gly Pro Asn Phe Asp Tyr Arg Gly Gln
            100                 105                 110

Gly Thr Leu Val Thr Val Ser Ser
            115                 120

<210> SEQ ID NO 41
<211> LENGTH: 120
<212> TYPE: PRT
<213> ORGANISM: Homo sapiens

<400> SEQUENCE: 41

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Gly Trp Tyr
             20                  25                  30

Trp Met Gly Trp Val Arg Gln Ala Pro Gly Lys Gly Leu Gly Trp Val
         35                  40                  45

Ser Ala Ile Ser Gly Ser Gly Gly Ser Thr Tyr Tyr Ala Asp Ser Val
     50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Val Lys Leu Gly Gly Gly Pro Asn Phe Asp Tyr Arg Gly Gln
            100                 105                 110

Gly Thr Leu Val Thr Val Ser Ser
            115                 120

<210> SEQ ID NO 42
<211> LENGTH: 120
<212> TYPE: PRT
<213> ORGANISM: Homo sapiens

<400> SEQUENCE: 42

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Glu Trp Tyr
             20                  25                  30

Trp Met Gly Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Ala Ala Val Tyr Tyr Cys
                85                  90                  95

Ala Lys Val Lys Leu Gly Gly Gly Pro Asn Phe Gly Tyr Arg Gly Gln
            100                 105                 110

Gly Thr Leu Val Thr Val Ser Ser
            115                 120

<210> SEQ ID NO 43
<211> LENGTH: 120
<212> TYPE: PRT
<213> ORGANISM: Homo sapiens -continued

<400> SEQUENCE: 43

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys Val Lys Leu Gly Gly Gly Pro Asn Phe Gly Tyr Arg Gly Gln
            100                 105                 110

Gly Thr Leu Val Thr Val Ser Ser
        115                 120

<210> SEQ ID NO 44
<211> LENGTH: 120
<212> TYPE: PRT
<213> ORGANISM: Homo sapiens

<400> SEQUENCE: 44

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Ser Thr Leu Tyr
65                  70                  75                  80

Leu Gln Met Asn Ser Leu Arg Ala Glu Asp Ala Ala Val Tyr Tyr Cys
                85                  90                  95

Ala Lys Val Lys Leu Gly Gly Gly Pro Asn Phe Gly Tyr Arg Gly Gln
            100                 105                 110

Gly Thr Leu Val Thr Val Ser Ser
        115                 120

<210> SEQ ID NO 45
<211> LENGTH: 120
<212> TYPE: PRT
<213> ORGANISM: Homo sapiens

<400> SEQUENCE: 45

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr 65                  70                  75                  80
Leu Gln Met Asn Ser Leu His Ala Glu Asp Ala Ala Val Tyr Tyr Cys
                    85                  90                  95

Ala Lys Val Lys Leu Gly Gly Gly Pro Asn Phe Gly Tyr Arg Gly Gln
                100                 105                 110

Gly Thr Leu Val Thr Val Ser Ser
            115                 120

<210> SEQ ID NO 46
<211> LENGTH: 120
<212> TYPE: PRT
<213> ORGANISM: Homo sapiens

<400> SEQUENCE: 46

Glu Val Gln Leu Leu Glu Ser Gly Gly Gly Leu Val Gln Pro Gly Gly
 1               5                  10                  15

Ser Leu Arg Leu Ser Cys Ala Val Ser Gly Leu Thr Phe Glu Trp Tyr
                20                  25                  30

Trp Met Gly Trp Val Arg Gln Ala Pro Gly Lys Gly Leu Glu Trp Val
             35                  40                  45

Ser Ala Ile Ser Gly Ser Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Ala Ala Val Tyr Tyr Cys
                    85                  90                  95

Ala Lys Val Lys Leu Gly Gly Gly Pro Asn Phe Gly Tyr Arg Gly Gln
                100                 105                 110

Gly Thr Leu Val Thr Val Ser Ser
            115                 120

<210> SEQ ID NO 47
<211> LENGTH: 120
<212> TYPE: PRT
<213> ORGANISM: Homo sapiens

<400> SEQUENCE: 47

Glu Val Gln Leu Leu Gly Ser Gly Gly Gly Leu Val Gln Pro Gly Gly
 1               5                  10                  15

Ser Leu Arg Leu Ser Cys Ala Ala Ser Gly Phe Thr Phe Ala Trp Tyr
                20                  25                  30

Trp Met Gly Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Ala Ala Val Tyr Tyr Cys
                    85                  90                  95

Ala Lys Val Lys Leu Gly Gly Gly Pro Asn Phe Gly Tyr Arg Gly Gln
                100                 105                 110

Gly Thr Leu Val Thr Val Ser Ser
            115                 120

<210> SEQ ID NO 48
<211> LENGTH: 120
<212> TYPE: PRT

<213> ORGANISM: Homo sapiens

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Lys Asp Ala Ala Val Tyr Tyr Cys
                85                  90                  95

Ala Lys Val Lys Leu Gly Gly Pro Asn Phe Gly Tyr Arg Gly Gln
            100                 105                 110

Gly Thr Leu Val Thr Val Ser Ser
            115                 120

<210> SEQ ID NO 49
<211> LENGTH: 120
<212> TYPE: PRT
<213> ORGANISM: Homo sapiens

<400> SEQUENCE: 49

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Pro Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys Val Lys Leu Gly Gly Pro Asn Phe Gly Tyr Arg Gly Gln
            100                 105                 110

Gly Thr Leu Val Thr Val Ser Ser
            115                 120

<210> SEQ ID NO 50
<211> LENGTH: 120
<212> TYPE: PRT
<213> ORGANISM: Homo sapiens

<400> SEQUENCE: 50

Glu Val Gln Leu Leu Glu Ser Gly Gly Gly Phe Val Gln Pro Gly Gly
1               5                   10                  15

Ser Leu Arg Leu Ser Cys Ala Ala Ser Gly Phe Thr Phe Glu Trp Tyr
            20                  25                  30

Trp Met Ser Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Ala Ser Val Tyr Tyr Cys
                 85                  90                  95

Ala Lys Val Lys Leu Gly Gly Pro Asn Phe Gly Tyr Arg Gly Gln
            100                 105                 110

Gly Thr Leu Val Thr Val Ser Ser
            115                 120

<210> SEQ ID NO 51
<211> LENGTH: 120
<212> TYPE: PRT
<213> ORGANISM: Homo sapiens

<400> SEQUENCE: 51

Glu Val Gln Leu Leu Glu Ser Gly Gly Gly Leu Val Gln Pro Gly Gly
 1               5                  10                  15

Ser Leu Arg Leu Pro Cys Ala Ala Ser Gly Phe Thr Phe Glu Trp Tyr
                20                  25                  30

Trp Met Thr Trp Val Arg Gln Ala Pro Gly Lys Gly Leu Glu Trp Val
             35                  40                  45

Ser Ala Ile Ser Gly Ser Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Ala Ala Val Tyr Tyr Cys
                 85                  90                  95

Ala Lys Val Lys Leu Gly Gly Pro Asn Phe Gly Tyr Arg Gly Gln
            100                 105                 110

Gly Thr Leu Val Thr Val Ser Ser
            115                 120

<210> SEQ ID NO 52
<211> LENGTH: 120
<212> TYPE: PRT
<213> ORGANISM: Homo sapiens

<400> SEQUENCE: 52

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Leu Thr Phe Glu Trp Tyr
                20                  25                  30

Trp Met Gly Trp Val Arg Gln Ala Pro Gly Lys Gly Leu Glu Trp Val
             35                  40                  45

Ser Ala Ile Ser Gly Ser Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Ala Ala Val Tyr Tyr Cys
                 85                  90                  95

Ala Lys Val Lys Leu Gly Gly Pro Asn Phe Gly Tyr Arg Gly Gln
            100                 105                 110

Gly Thr Leu Val Thr Val Ser Ser
            115                 120

<210> SEQ ID NO 53
```

<211> LENGTH: 120
<212> TYPE: PRT
<213> ORGANISM: Homo sapiens

<400> SEQUENCE: 53

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Leu | Thr | Phe | Glu | Trp | Tyr |
| | | | 20 | | | | | 25 | | | | | 30 | | |

| Trp | Met | Gly | Trp | Val | Arg | Gln | Ala | Pro | Gly | Lys | Gly | Leu | Glu | Trp | Val |
| | | 35 | | | | | 40 | | | | | 45 | | | |

| Ser | Ala | Val | Ser | Gly | Ser | Gly | Gly | Ser | Thr | Tyr | Tyr | Ala | Asp | Ser | Val |
| | 50 | | | | | 55 | | | | | 60 | | | | |

| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |

| Leu | Gln | Met | Asn | Ser | Leu | Arg | Ala | Glu | Asp | Ala | Ala | Val | Tyr | Tyr | Cys |
| | | | | 85 | | | | | 90 | | | | | 95 | |

| Ala | Lys | Val | Lys | Leu | Gly | Gly | Gly | Pro | Asn | Phe | Gly | Tyr | Arg | Gly | Gln |
| | | | 100 | | | | | 105 | | | | | 110 | | |

| Gly | Thr | Leu | Val | Thr | Val | Ser | Ser |
|---|---|---|---|---|---|---|---|
| | | | 115 | | | | 120 |

<210> SEQ ID NO 54
<211> LENGTH: 120
<212> TYPE: PRT
<213> ORGANISM: Homo sapiens

<400> SEQUENCE: 54

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Leu | Thr | Phe | Glu | Trp | Tyr |
| | | | 20 | | | | | 25 | | | | | 30 | | |

| Trp | Met | Gly | Trp | Val | Arg | Gln | Ala | Pro | Gly | Lys | Gly | Leu | Glu | Trp | Val |
| | | 35 | | | | | 40 | | | | | 45 | | | |

| Ser | Ala | Ile | Ser | Gly | Ser | Gly | Asp | Ser | Thr | Tyr | Tyr | Ala | Asp | Ser | Val |
| | 50 | | | | | 55 | | | | | 60 | | | | |

| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |

| Leu | Gln | Met | Asn | Ser | Leu | Arg | Ala | Glu | Asp | Ala | Ala | Val | Tyr | Tyr | Cys |
| | | | | 85 | | | | | 90 | | | | | 95 | |

| Ala | Lys | Val | Lys | Leu | Gly | Gly | Gly | Pro | Asn | Phe | Gly | Tyr | Arg | Gly | Gln |
| | | | 100 | | | | | 105 | | | | | 110 | | |

| Gly | Thr | Leu | Val | Thr | Val | Ser | Ser |
|---|---|---|---|---|---|---|---|
| | | | 115 | | | | 120 |

<210> SEQ ID NO 55
<211> LENGTH: 120
<212> TYPE: PRT
<213> ORGANISM: Homo sapiens

<400> SEQUENCE: 55

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Glu | Trp | Tyr |
| | | | 20 | | | | | 25 | | | | | 30 | | |

| Trp | Met | Gly | Trp | Val | Arg | Gln | Ala | Pro | Gly | Lys | Gly | Leu | Glu | Trp | Val |
| | | 35 | | | | | 40 | | | | | 45 | | | |

```
Ser Ala Met Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Ala Ala Val Tyr Tyr Cys
                 85                  90                  95

Ala Lys Val Lys Leu Gly Gly Pro Asn Phe Gly Asn Arg Gly Leu
                100                 105                 110

Gly Thr Leu Val Thr Val Ser Ser
             115                 120
```

<210> SEQ ID NO 56
<211> LENGTH: 120
<212> TYPE: PRT
<213> ORGANISM: Homo sapiens

<400> SEQUENCE: 56

```
Glu Val Gln Leu Leu Glu Ser Gly Gly Gly Ser Val Gln Pro Gly Gly
 1                5                  10                  15

Ser Leu Arg Leu Ser Cys Ala Ala Ser Gly Phe Thr Phe Asp Trp Tyr
                 20                  25                  30

Trp Met Gly Trp Val Arg Gln Ala Pro Gly Lys Gly Leu Glu Trp Ala
             35                  40                  45

Ser Ala Ile Ser Gly Ser Gly Gly Ser Thr Tyr Tyr Ala Asp Ser Val
    50                  55                  60

Lys Asp Arg Phe Thr Ile Ser Arg Asp Asn Ser Lys Asn Thr Leu Tyr
 65                  70                  75                  80

Leu Gln Met Asn Ser Leu Arg Ala Glu Asp Ala Ala Val Tyr Tyr Cys
                 85                  90                  95

Ala Lys Val Lys Leu Gly Gly Pro Asp Phe Gly Tyr Arg Gly Gln
                100                 105                 110

Gly Thr Leu Val Thr Val Ser Ser
             115                 120
```

<210> SEQ ID NO 57
<211> LENGTH: 120
<212> TYPE: PRT
<213> ORGANISM: Homo sapiens

<400> SEQUENCE: 57

```
Glu Val Gln Leu Leu Glu Ser Gly Gly Gly Leu Val Gln Pro Gly Gly
 1                5                  10                  15

Ser Leu Arg Leu Ser Cys Ala Ala Ser Gly Phe Thr Phe Glu Trp Tyr
                 20                  25                  30

Trp Met Gly Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Gly Ala Val Tyr Tyr Cys
                 85                  90                  95

Ala Lys Val Lys Leu Gly Gly Glu Leu Asn Phe Gly Tyr Arg Gly Gln
                100                 105                 110

Gly Thr Leu Val Thr Val Ser Ser
             115                 120
```

```
<210> SEQ ID NO 58
<211> LENGTH: 120
<212> TYPE: PRT
<213> ORGANISM: Homo sapiens

<400> SEQUENCE: 58

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys Val Lys Leu Gly Gly Gly Pro Asn Phe Gly Asn Arg Gly Gln
            100                 105                 110

Gly Thr Pro Val Thr Val Ser Ser
            115                 120

<210> SEQ ID NO 59
<211> LENGTH: 120
<212> TYPE: PRT
<213> ORGANISM: Homo sapiens

<400> SEQUENCE: 59

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Ala Ala Val Tyr Tyr Cys
                85                  90                  95

Ala Lys Val Lys Leu Gly Gly Gly Pro Asn Phe Gly Pro Arg Gly Gln
            100                 105                 110

Gly Thr Leu Val Thr Val Ser Ser
            115                 120

<210> SEQ ID NO 60
<211> LENGTH: 120
<212> TYPE: PRT
<213> ORGANISM: Homo sapiens

<400> SEQUENCE: 60

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Glu Trp Val
```

```
                35                  40                  45
Ser Ala Ile Ser Gly Ser Gly Gly Ser Thr Tyr Tyr Ala Asp Ser Val
         50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Ala Ala Val Tyr Tyr Cys
                 85                  90                  95
Ala Lys Val Lys Leu Gly Gly Gly Pro Asn Phe Gly Asn Arg Gly Gln
                100                 105                 110
Gly Thr Leu Val Thr Val Ser Ser
            115                 120

<210> SEQ ID NO 61
<211> LENGTH: 120
<212> TYPE: PRT
<213> ORGANISM: Homo sapiens

<400> SEQUENCE: 61

Glu Val Gln Leu Leu Glu Ser Gly Gly Gly Leu Val Gln Pro Gly Gly
  1               5                  10                  15
Ser Leu Arg Leu Ser Cys Ala Ala Ser Gly Phe Thr Ile Glu Trp Tyr
             20                  25                  30
Trp Met Gly Trp Val Arg Gln Ala Pro Gly Lys Gly Leu Glu Trp Val
         35                  40                  45
Ser Ala Ile Ser Gly Ser Gly Gly Ser Thr Tyr Tyr Ala Asp Ser Val
         50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Ala Ala Val Tyr Tyr Cys
                 85                  90                  95
Ala Lys Val Lys Leu Gly Gly Gly Pro Asn Phe Gly Tyr Arg Gly Gln
                100                 105                 110
Gly Thr Leu Val Thr Val Ser Ser
            115                 120

<210> SEQ ID NO 62
<211> LENGTH: 120
<212> TYPE: PRT
<213> ORGANISM: Homo sapiens

<400> SEQUENCE: 62

Glu Val Gln Leu Leu Glu Ser Gly Gly Gly Leu Val Gln Pro Gly Gly
  1               5                  10                  15
Ser Leu Arg Leu Ser Cys Ala Ala Ser Gly Phe Thr Phe Glu Trp Tyr
             20                  25                  30
Trp Met Gly Trp Val Arg Gln Ala Pro Gly Lys Gly Leu Glu Trp Val
         35                  40                  45
Ser Ala Ile Ser Gly Ser Gly Ser Thr Phe Tyr Ala Asp Ser Val
         50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Ala Ala Val Tyr Tyr Cys
                 85                  90                  95
Ala Lys Val Lys Leu Gly Gly Gly Pro Asn Phe Gly Tyr Arg Gly Gln
                100                 105                 110
Gly Thr Leu Val Thr Val Ser Ser
```

115                 120

<210> SEQ ID NO 63
<211> LENGTH: 120
<212> TYPE: PRT
<213> ORGANISM: Homo sapiens

<400> SEQUENCE: 63

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Glu Trp Val
        35                  40                  45

Thr Ala Ile Ser Gly Ser Gly Gly Ser Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys Val Lys Leu Gly Gly Gly Pro Asn Phe Gly Tyr Arg Gly Gln
            100                 105                 110

Gly Thr Leu Val Thr Val Ser Ser
        115                 120

<210> SEQ ID NO 64
<211> LENGTH: 120
<212> TYPE: PRT
<213> ORGANISM: Homo sapiens

<400> SEQUENCE: 64

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Ser Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Asp Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys Val Lys Leu Gly Gly Gly Pro Asn Phe Gly Tyr Arg Gly Gln
            100                 105                 110

Gly Thr Leu Val Thr Val Ser Ser
        115                 120

<210> SEQ ID NO 65
<211> LENGTH: 120
<212> TYPE: PRT
<213> ORGANISM: Homo sapiens

<400> SEQUENCE: 65

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Pro Phe Glu Trp Tyr
            20                  25                  30

```
Trp Met Gly Trp Val Arg Gln Ala Pro Gly Lys Gly Leu Glu Trp Val
            35                  40                  45

Ser Ala Ile Ser Gly Ser Gly Asp Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Gln Gln Met Asn Ser Leu Arg Ala Glu Asp Ala Ala Val Tyr Tyr Cys
                 85                  90                  95

Ala Lys Val Lys Leu Gly Gly Pro Asn Phe Gly Tyr Arg Gly Gln
                100                 105                 110

Gly Thr Leu Val Thr Val Ser Ser
            115                 120

<210> SEQ ID NO 66
<211> LENGTH: 120
<212> TYPE: PRT
<213> ORGANISM: Homo sapiens

<400> SEQUENCE: 66

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Ser Phe Glu Trp Tyr
                 20                  25                  30

Trp Met Gly Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Ala Ala Val Tyr Tyr Cys
                 85                  90                  95

Ala Lys Val Lys Leu Gly Gly Pro Asn Phe Gly Tyr Arg Gly Gln
                100                 105                 110

Gly Thr Leu Val Thr Val Ser Ser
            115                 120

<210> SEQ ID NO 67
<211> LENGTH: 120
<212> TYPE: PRT
<213> ORGANISM: Homo sapiens

<400> SEQUENCE: 67

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Glu Trp Tyr
                 20                  25                  30

Trp Met Gly Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Ala Ala Val Tyr Tyr Cys
                 85                  90                  95

Ala Lys Val Lys Leu Gly Gly Pro Asn Tyr Gly Tyr Arg Gly Gln
                100                 105                 110
```

```
Gly Thr Leu Val Thr Val Ser Ser
        115                 120

<210> SEQ ID NO 68
<211> LENGTH: 119
<212> TYPE: PRT
<213> ORGANISM: Homo sapiens

<400> SEQUENCE: 68

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Pro Glu Tyr
            20                  25                  30

Gly Met Ala Trp Val Arg Gln Ala Pro Gly Lys Gly Leu Glu Trp Val
        35                  40                  45

Ser Thr Ile Ser His Gly Gly Glu His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gln His Pro Val Ser His Pro Lys Phe Asp Tyr Trp Gly Gln Gly
            100                 105                 110

Thr Leu Val Thr Val Ser Ser
        115

<210> SEQ ID NO 69
<211> LENGTH: 116
<212> TYPE: PRT
<213> ORGANISM: Homo sapiens

<400> SEQUENCE: 69

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asp Ala Tyr
            20                  25                  30

Asn Met Phe Trp Val Arg Gln Ala Pro Gly Lys Gly Leu Glu Trp Val
        35                  40                  45

Ser Ala Ile Ser Pro Ser Gly Arg Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Tyr Pro Asp Phe Asp Tyr Trp Gly Gln Gly Thr Leu Val
            100                 105                 110

Thr Val Ser Ser
        115

<210> SEQ ID NO 70
<211> LENGTH: 119
<212> TYPE: PRT
<213> ORGANISM: Homo sapiens

<400> SEQUENCE: 70

Glu Val Gln Leu Leu Glu Ser Gly Gly Gly Leu Val Gln Pro Gly Gly
 1               5                  10                  15
```

Ser Leu Arg Leu Ser Cys Ala Ala Ser Gly Phe Thr Phe Ser Asp Tyr
            20                  25                  30

Thr Met Gly Trp Val Arg Gln Ala Pro Gly Lys Gly Leu Glu Trp Val
        35                  40                  45

Ser Leu Ile Asp Arg Pro Gly Asn His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Trp Gly Leu Asn Val Glu Asp Phe Asp Tyr Trp Gly Gln Gly
            100                 105                 110

Thr Leu Val Thr Val Ser Ser
            115

<210> SEQ ID NO 71
<211> LENGTH: 120
<212> TYPE: PRT
<213> ORGANISM: Homo sapiens

<400> SEQUENCE: 71

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ile Glu Tyr
            20                  25                  30

Asp Met Gly Trp Val Arg Gln Ala Pro Gly Lys Gly Leu Glu Trp Val
        35                  40                  45

Ser Met Ile Ser Ser Asp Gly Arg Leu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Thr Trp Asp Gly Leu Asn Arg Asn Phe Asp Tyr Trp Gly Gln
            100                 105                 110

Gly Thr Leu Val Thr Val Ser Ser
        115                 120

<210> SEQ ID NO 72
<211> LENGTH: 119
<212> TYPE: PRT
<213> ORGANISM: Homo sapiens

<400> SEQUENCE: 72

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ile Gly Tyr
            20                  25                  30

Asn Met Tyr Trp Val Arg Gln Ala Pro Gly Lys Gly Leu Glu Trp Val
        35                  40                  45

Ser Phe Ile Ser Pro Ser Gly Arg Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

```
Ala Lys Thr Leu Ser Ala Asp Gly Arg Phe Asp Tyr Trp Gly Gln Gly
            100                 105                 110

Thr Leu Val Thr Val Ser Ser
        115
```

<210> SEQ ID NO 73
<211> LENGTH: 120
<212> TYPE: PRT
<213> ORGANISM: Homo sapiens

<400> SEQUENCE: 73

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Gly Ser Tyr
             20                  25                  30

Asp Met Gly Trp Val Arg Gln Ala Pro Gly Lys Gly Leu Glu Trp Val
         35                  40                  45

Ser Phe Ile Asp Val Ser Gly Thr Leu Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Thr Val Glu Leu Asp Gly Leu Asp Phe Asp Tyr Trp Gly Gln
            100                 105                 110

Gly Thr Leu Val Thr Val Ser Ser
            115                 120
```

<210> SEQ ID NO 74
<211> LENGTH: 120
<212> TYPE: PRT
<213> ORGANISM: Homo sapiens

<400> SEQUENCE: 74

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ala Asp Tyr
             20                  25                  30

Asp Met Gly Trp Val Arg Gln Ala Pro Gly Lys Gly Leu Glu Trp Val
         35                  40                  45

Ser Phe Ile Asp Ser Ser Gly Ser Arg Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Thr Ala Glu Ile Val Asn Ser Arg Phe Asp Tyr Trp Gly Gln
            100                 105                 110

Gly Thr Leu Val Thr Val Ser Ser
            115                 120
```

<210> SEQ ID NO 75
<211> LENGTH: 120
<212> TYPE: PRT
<213> ORGANISM: Homo sapiens

<400> SEQUENCE: 75

```
Glu Val Gln Leu Leu Glu Ser Gly Gly Gly Leu Val Gln Pro Gly Gly
```

```
                1               5                      10                      15
        Ser Leu Arg Leu Ser Cys Ala Ala Ser Gly Phe Thr Phe Asp Lys Tyr
                        20                      25                      30

Gln Met Gly Trp Val Arg Gln Ala Pro Gly Lys Gly Leu Glu Trp Val
                        35                      40                      45

Ser Phe Ile Asp Ser Asn Gly His His Thr Tyr Tyr Ala Asp Ser Val
                        50                      55                      60

Lys Gly Arg Phe Thr Ile Ser Arg Asp Asn Ser Lys Asn Thr Leu Tyr
         65                     70                      75                      80

Leu Gln Met Asn Ser Leu Arg Ala Glu Asp Thr Ala Val Tyr Tyr Cys
                        85                      90                      95

Ala Glu Leu Asp Asn Leu Ser Ile Thr Pro Phe Asp Tyr Trp Gly Gln
                        100                     105                     110

Gly Thr Leu Val Thr Val Ser Ser
                        115                     120

<210> SEQ ID NO 76
<211> LENGTH: 120
<212> TYPE: PRT
<213> ORGANISM: Homo sapiens

<400> SEQUENCE: 76

Glu Val Gln Leu Leu Glu Ser Gly Gly Gly Leu Val Gln Pro Gly Gly
         1                      5                       10                      15

Ser Leu Arg Leu Ser Cys Ala Ala Ser Gly Phe Thr Phe Ala Lys Tyr
                        20                      25                      30

Asn Met Tyr Trp Val Arg Gln Ala Pro Gly Lys Gly Leu Glu Trp Val
                        35                      40                      45

Ser Ala Ile Ser Pro Lys Gly Gln His Thr Tyr Tyr Ala Asp Ser Val
                        50                      55                      60

Lys Gly Arg Phe Thr Ile Ser Arg Asp Asn Ser Lys Asn Thr Leu Tyr
         65                     70                      75                      80

Leu Gln Met Asn Ser Leu Arg Ala Glu Asp Thr Ala Val Tyr Tyr Cys
                        85                      90                      95

Ala Glu Gly Met Gly Ser Asp Ala Ile Thr Phe Asp Tyr Trp Gly Gln
                        100                     105                     110

Gly Thr Leu Val Thr Val Ser Ser
                        115                     120

<210> SEQ ID NO 77
<211> LENGTH: 122
<212> TYPE: PRT
<213> ORGANISM: Homo sapiens

<400> SEQUENCE: 77

Glu Val Gln Leu Leu Glu Ser Gly Gly Gly Leu Val Gln Pro Gly Gly
         1                      5                       10                      15

Ser Leu Arg Leu Ser Cys Ala Ala Ser Gly Phe Thr Phe Ser Asp Tyr
                        20                      25                      30

Thr Met Gly Trp Ala Arg Gln Ala Pro Gly Lys Gly Leu Glu Trp Val
                        35                      40                      45

Ser Phe Ile Asp Ser Asp Gly Leu His Thr Tyr Tyr Ala Asp Ser Val
                        50                      55                      60

Lys Gly Arg Phe Thr Ile Ser Arg Asp Asn Ser Lys Asn Thr Leu Tyr
         65                     70                      75                      80

Leu Gln Met Asn Ser Leu Arg Ala Glu Asp Thr Ala Val Tyr Tyr Cys
```

```
                    85                  90                  95

Ala Gln Asn Pro Gln Tyr Ala Tyr Glu Ser Ser Arg Phe Asp Tyr Trp
            100                 105                 110

Gly Gln Gly Thr Leu Val Thr Val Ser Ser
        115                 120

<210> SEQ ID NO 78
<211> LENGTH: 121
<212> TYPE: PRT
<213> ORGANISM: Homo sapiens

<400> SEQUENCE: 78

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Leu Gln Tyr
             20                  25                  30

Pro Met Val Trp Val Arg Gln Ala Pro Gly Lys Gly Leu Glu Trp Val
         35                  40                  45

Ser Ser Ile Leu Ala Pro Gly Gly Pro Thr Tyr Tyr Ala Asp Ser Val
     50                  55                  60

Lys Gly Arg Phe Thr Ile Ser Arg Asp Asn Ser Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys His Pro Thr His Thr Pro His Pro Asn Phe Asp Tyr Trp Gly
            100                 105                 110

Gln Gly Thr Leu Val Thr Val Ser Ser
        115                 120

<210> SEQ ID NO 79
<211> LENGTH: 122
<212> TYPE: PRT
<213> ORGANISM: Homo sapiens

<400> SEQUENCE: 79

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Gly Gly Tyr
             20                  25                  30

Arg Met Ala Trp Val Arg Gln Ala Pro Gly Lys Gly Leu Glu Trp Val
         35                  40                  45

Ser Phe Ile Asp Ser Glu Gly Val Leu Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Leu Cys Ser Ser Asn Cys Asn Met Arg Asn Phe Asp Tyr Trp
            100                 105                 110

Gly Gln Gly Thr Leu Val Thr Val Ser Ser
        115                 120

<210> SEQ ID NO 80
<211> LENGTH: 124
<212> TYPE: PRT
<213> ORGANISM: Homo sapiens

<400> SEQUENCE: 80
```

-continued

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Pro Val Tyr
             20                  25                  30

Asn Met Ala Trp Val Arg Gln Ala Pro Gly Lys Gly Leu Glu Trp Val
         35                  40                  45

Ser Phe Ile Ala Gly Asn Gly Gln Gln Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Phe Ala Ser Lys Val Ser Pro Met Ser Leu Thr Asp Phe Asp
            100                 105                 110

Tyr Trp Gly Gln Gly Thr Leu Val Thr Val Ser Ser
            115                 120
```

<210> SEQ ID NO 81
<211> LENGTH: 124
<212> TYPE: PRT
<213> ORGANISM: Homo sapiens

<400> SEQUENCE: 81

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe His Lys Tyr
             20                  25                  30

Gly Met Ala Trp Val Arg Gln Ala Pro Gly Lys Gly Leu Glu Trp Val
         35                  40                  45

Ser Phe Ile Asp Leu Ala Gly Leu His Thr Tyr Tyr Ala Asp Ser Val
     50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Phe Ala Thr Tyr Ser Ser Gly Asn Glu Glu Gln Pro Phe Asp
            100                 105                 110

Tyr Trp Gly Gln Gly Thr Leu Val Thr Val Ser Ser
            115                 120
```

<210> SEQ ID NO 82
<211> LENGTH: 123
<212> TYPE: PRT
<213> ORGANISM: Homo sapiens

<400> SEQUENCE: 82

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ala Tyr
             20                  25                  30

Asn Met Ala Trp Val Arg Gln Ala Pro Gly Lys Gly Leu Glu Trp Val
         35                  40                  45

Ser Phe Ile Ala Gln Ser Gly Gly His Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80
```

```
Leu Gln Met Asn Ser Leu Arg Ala Glu Asp Thr Ala Val Tyr Tyr Cys
                85                  90                  95

Ala Lys Phe Ser His Pro Asp Glu Glu Gly Thr Gln Met Phe Asp Tyr
            100                 105                 110

Trp Gly Gln Gly Thr Leu Val Thr Val Ser Ser
        115                 120
```

<210> SEQ ID NO 83
<211> LENGTH: 116
<212> TYPE: PRT
<213> ORGANISM: Homo sapiens

<400> SEQUENCE: 83

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Thr Tyr
            20                  25                  30

Asn Met Ser Trp Val Arg Gln Ala Pro Gly Lys Gly Leu Glu Trp Val
        35                  40                  45

Ser Ala Ile Asp Ala Gly Gly Met His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Thr Glu Pro Phe Asp Tyr Trp Gly Gln Gly Thr Leu Val
            100                 105                 110

Thr Val Ser Ser
        115
```

<210> SEQ ID NO 84
<211> LENGTH: 116
<212> TYPE: PRT
<213> ORGANISM: Homo sapiens
<220> FEATURE:
<221> NAME/KEY: VARIANT
<222> LOCATION: 33
<223> OTHER INFORMATION: Xaa = Any Amino Acid

<400> SEQUENCE: 84

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Glu Tyr
            20                  25                  30

Xaa Met Gly Trp Val Arg Gln Ala Pro Gly Lys Gly Leu Glu Trp Val
        35                  40                  45

Ser Leu Ile Ser Pro Arg Gly Ser Lys Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Lys Pro Pro Phe Asp Tyr Trp Gly Gln Gly Thr Leu Val
            100                 105                 110

Thr Val Ser Ser
        115
```

```
<210> SEQ ID NO 85
<211> LENGTH: 116
<212> TYPE: PRT
<213> ORGANISM: Homo sapiens

<400> SEQUENCE: 85

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Glu Asp Tyr
            20                  25                  30

Pro Met Ala Trp Val Arg Gln Ala Pro Gly Lys Gly Leu Glu Trp Val
        35                  40                  45

Ser Phe Ile Gly Leu Lys Gly Ile His Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Asp Leu Asn Asn Phe Asp Tyr Trp Gly Gln Gly Thr Leu Val
            100                 105                 110

Thr Val Ser Ser
        115

<210> SEQ ID NO 86
<211> LENGTH: 119
<212> TYPE: PRT
<213> ORGANISM: Homo sapiens

<400> SEQUENCE: 86

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Gly Asn Gly
            20                  25                  30

Asn Met Val Trp Val Arg Gln Ala Pro Gly Lys Gly Leu Glu Trp Val
        35                  40                  45

Ser His Ile Asp Glu Tyr Gly Thr Asn Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Pro Arg Asn Asp Arg Pro Gly Phe Asp Tyr Trp Gly Gln Gly
            100                 105                 110

Thr Leu Val Thr Val Ser Ser
        115

<210> SEQ ID NO 87
<211> LENGTH: 124
<212> TYPE: PRT
<213> ORGANISM: Homo sapiens

<400> SEQUENCE: 87

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Pro Thr Glu
            20                  25                  30

His Met Tyr Trp Val Arg Gln Ala Pro Gly Lys Gly Leu Glu Trp Val
        35                  40                  45
```

```
Ser Gly Ile Asp Thr Gly Ser His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Leu His Trp Ser Ser Asp Ser Gly Pro Val His Phe Asp
            100                 105                 110

Tyr Trp Gly Gln Gly Thr Leu Val Thr Val Ser Ser
            115                 120

<210> SEQ ID NO 88
<211> LENGTH: 121
<212> TYPE: PRT
<213> ORGANISM: Homo sapiens

<400> SEQUENCE: 88

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Asn Val
            20                  25                  30

Asp Met His Trp Val Arg Gln Ala Pro Gly Lys Gly Leu Glu Trp Val
        35                  40                  45

Ser Ala Ile Ser Ser Ala Gly Gly Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Met Leu Ala Asn Ser Pro Leu Ala Phe Asp Tyr Trp Gly
            100                 105                 110

Gln Gly Thr Leu Val Thr Val Ser Ser
            115                 120

<210> SEQ ID NO 89
<211> LENGTH: 116
<212> TYPE: PRT
<213> ORGANISM: Homo sapiens

<400> SEQUENCE: 89

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Tyr Glu
            20                  25                  30

Pro Met Ala Trp Val Arg Gln Ala Pro Gly Lys Gly Leu Glu Trp Val
        35                  40                  45

Ser Thr Ile Ser His Thr Gly Arg Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Trp Ser Ser Phe Asp Tyr Trp Gly Gln Gly Thr Leu Val
            100                 105                 110

Thr Val Ser Ser
            115
```

<210> SEQ ID NO 90
<211> LENGTH: 119
<212> TYPE: PRT
<213> ORGANISM: Homo sapiens

<400> SEQUENCE: 90

```
Glu Val Gln Leu Leu Glu Ser Gly Gly Gly Leu Val Gln Pro Gly Gly
  1               5                  10                  15
Ser Leu Arg Leu Ser Cys Ala Ala Ser Gly Phe Thr Phe Pro Ser Glu
             20                  25                  30
Lys Met Ala Trp Val Arg Gln Ala Pro Gly Lys Gly Leu Glu Trp Val
         35                  40                  45
Ser Ser Ile Asp Glu Arg Gly Ile Met Thr Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Arg Trp Thr Phe Asn Thr Ala Phe Asp Tyr Trp Gly Gln Gly
            100                 105                 110
Thr Leu Val Thr Val Ser Ser
            115
```

<210> SEQ ID NO 91
<211> LENGTH: 119
<212> TYPE: PRT
<213> ORGANISM: Homo sapiens

<400> SEQUENCE: 91

```
Glu Val Gln Leu Leu Glu Ser Gly Gly Gly Leu Val Gln Pro Gly Gly
  1               5                  10                  15
Ser Leu Arg Leu Ser Cys Ala Ala Ser Gly Phe Thr Phe Ser Arg Glu
             20                  25                  30
Asn Met His Trp Val Arg Gln Ala Pro Gly Lys Gly Leu Glu Trp Val
         35                  40                  45
Ser Gly Ile Gly Pro Arg Gly Met Pro Thr Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Gly Met Asn Ser His Asp Gly Phe Asp Tyr Trp Gly Gln Gly
            100                 105                 110
Thr Leu Val Thr Val Ser Ser
            115
```

<210> SEQ ID NO 92
<211> LENGTH: 119
<212> TYPE: PRT
<213> ORGANISM: Homo sapiens

<400> SEQUENCE: 92

```
Glu Val Gln Leu Leu Glu Ser Gly Gly Gly Leu Val Gln Pro Gly Gly
  1               5                  10                  15
Ser Leu Arg Leu Ser Cys Ala Ala Ser Gly Phe Thr Phe Asn Ala Tyr
             20                  25                  30
```

```
Thr Met Ile Trp Val Arg Gln Ala Pro Gly Lys Gly Leu Glu Trp Val
         35                  40                  45

Ser Tyr Ile Asp Pro His Gly Thr Ile Thr Tyr Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Leu Pro Arg Ala Ala Pro Arg Phe Asp Tyr Trp Gly Gln Gly
             100                 105                 110

Thr Leu Val Thr Val Ser Ser
        115
```

<210> SEQ ID NO 93
<211> LENGTH: 119
<212> TYPE: PRT
<213> ORGANISM: Homo sapiens

<400> SEQUENCE: 93

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asp Ala Ser
             20                  25                  30

Glu Met Asp Trp Val Arg Gln Ala Pro Gly Lys Gly Leu Glu Trp Val
         35                  40                  45

Ser Ala Ile Ser Pro Ser Gly Ser Ala Thr Tyr Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Trp Thr Pro Gly Arg Thr Thr Phe Asp Tyr Trp Gly Gln Gly
             100                 105                 110

Thr Leu Val Thr Val Ser Ser
        115
```

<210> SEQ ID NO 94
<211> LENGTH: 124
<212> TYPE: PRT
<213> ORGANISM: Homo sapiens

<400> SEQUENCE: 94

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Pro Thr Glu
             20                  25                  30

His Met Tyr Trp Val Arg Gln Ala Pro Gly Lys Gly Leu Glu Trp Val
         35                  40                  45

Ser Gly Ile Asp Thr Gly Gly Ser His Thr Tyr Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Leu His Trp Ser Ser Asp Ser Gly Pro Val His Phe Asp
             100                 105                 110
```

```
Tyr Trp Gly Gln Gly Thr Leu Val Thr Val Ser Ser
        115                 120
```

<210> SEQ ID NO 95
<211> LENGTH: 123
<212> TYPE: PRT
<213> ORGANISM: Homo sapiens

<400> SEQUENCE: 95

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Lys Leu Tyr
             20                  25                  30

Asn Met Ala Trp Val Arg Gln Ala Pro Gly Lys Gly Leu Glu Trp Val
         35                  40                  45

Ser Phe Ile Ala Ala Gly Pro Glu Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Leu Gly Asp Ile Ser Ser Ile Pro Gln His Pro Phe Asp Tyr
                100                 105                 110

Trp Gly Gln Gly Thr Leu Val Thr Val Ser Ser
            115                 120
```

<210> SEQ ID NO 96
<211> LENGTH: 119
<212> TYPE: PRT
<213> ORGANISM: Homo sapiens

<400> SEQUENCE: 96

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Gly Asn Val
             20                  25                  30

Asp Met His Trp Val Arg Gln Ala Pro Gly Lys Gly Leu Glu Trp Val
         35                  40                  45

Ser Ala Ile Ser Ser Ala Gly Gly Glu Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Ala Asp Ile Thr Lys Gly Phe Asp Tyr Trp Gly Gln Gly
                100                 105                 110

Thr Leu Val Thr Val Ser Ser
            115
```

<210> SEQ ID NO 97
<211> LENGTH: 121
<212> TYPE: PRT
<213> ORGANISM: Homo sapiens

<400> SEQUENCE: 97

```
Glu Val Arg Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Gly Lys Tyr
```

```
            20                  25                  30
Thr Met Thr Trp Val Arg Gln Ala Pro Gly Lys Gly Leu Glu Trp Val
        35                  40                  45
Ser His Ile Ser Asp Asp Gly Asn Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Val Pro Ile Leu Ala Pro Arg Asn Leu Phe Asp Tyr Trp Gly
            100                 105                 110
Gln Gly Thr Leu Val Thr Val Ser Ser
        115                 120

<210> SEQ ID NO 98
<211> LENGTH: 119
<212> TYPE: PRT
<213> ORGANISM: Homo sapiens

<400> SEQUENCE: 98

Glu Val Gln Leu Leu Glu Ser Gly Gly Gly Leu Ile Gln Pro Gly Gly
1               5                   10                  15
Ser Leu Arg Leu Ser Cys Ala Ala Ser Gly Phe Thr Phe Ala His Glu
            20                  25                  30
Thr Met Val Trp Val Arg Gln Ala Pro Gly Lys Gly Leu Glu Trp Val
        35                  40                  45
Ser His Ile Asp Arg Val Gly Gln Asp Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Leu Pro Lys Arg Gly Pro Trp Phe Asp Tyr Arg Gly Gln Gly
            100                 105                 110
Thr Leu Val Thr Val Ser Ser
        115

<210> SEQ ID NO 99
<211> LENGTH: 119
<212> TYPE: PRT
<213> ORGANISM: Homo sapiens

<400> SEQUENCE: 99

Glu Val Gln Leu Leu Glu Ser Gly Gly Gly Leu Ile Gln Pro Gly Gly
1               5                   10                  15
Ser Leu Arg Leu Ser Cys Ala Ala Ser Gly Phe Thr Phe Ala His Glu
            20                  25                  30
Thr Met Val Trp Val Arg Gln Ala Pro Gly Lys Gly Leu Glu Trp Val
        35                  40                  45
Ser His Ile Asp Arg Val Gly Gln Asp Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Leu Pro Lys Arg Gly Pro Trp Phe Asp Tyr Arg Gly Gln Gly
```

-continued

```
                100                 105                 110
Thr Leu Val Thr Val Ser Ser
        115

<210> SEQ ID NO 100
<211> LENGTH: 121
<212> TYPE: PRT
<213> ORGANISM: Homo sapiens

<400> SEQUENCE: 100

Glu Val Arg Leu Leu Glu Ser Gly Gly Gly Leu Val Gln Pro Gly Gly
1               5                   10                  15

Ser Leu Arg Leu Ser Cys Val Ala Ser Gly Phe Thr Phe Gly Lys Ser
            20                  25                  30

Thr Met Thr Trp Val Arg Gln Ala Pro Gly Lys Gly Leu Glu Trp Val
        35                  40                  45

Ser His Ile Ser Asp Asp Gly Asn Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Pro Ile Leu Ala Pro Arg Asn Leu Phe Asp Tyr Trp Gly
            100                 105                 110

Gln Gly Thr Leu Val Thr Val Ser Ser
            115                 120

<210> SEQ ID NO 101
<211> LENGTH: 121
<212> TYPE: PRT
<213> ORGANISM: Homo sapiens

<400> SEQUENCE: 101

Glu Val Arg Leu Leu Glu Ser Gly Gly Gly Leu Val Gln Pro Gly Gly
1               5                   10                  15

Ser Leu Arg Leu Ser Cys Val Ala Ser Gly Phe Asn Phe Gly Lys Ser
            20                  25                  30

Thr Met Thr Trp Val Arg Gln Ala Pro Gly Lys Gly Leu Glu Trp Val
        35                  40                  45

Ser His Ile Ser Asp Asp Gly Asn Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Pro Ile Leu Ala Pro Arg Asn Leu Phe Asp Tyr Trp Gly
            100                 105                 110

Gln Gly Thr Leu Val Thr Val Ser Ser
            115                 120

<210> SEQ ID NO 102
<211> LENGTH: 121
<212> TYPE: PRT
<213> ORGANISM: Homo sapiens

<400> SEQUENCE: 102

Glu Val Arg Leu Leu Glu Ser Gly Gly Gly Leu Val Gln Pro Gly Gly
1               5                   10                  15
```

-continued

```
Ser Leu Arg Leu Ser Cys Val Ala Ser Gly Phe Thr Phe Gly Lys Gly
            20                  25                  30

Thr Met Thr Trp Val Arg Gln Ala Pro Gly Lys Gly Leu Glu Trp Val
        35                  40                  45

Ser His Ile Ser Asp Asp Gly Asn Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Val Pro Ile Leu Ala Pro Arg Asn Leu Phe Asp Tyr Trp Gly
            100                 105                 110

Gln Gly Thr Leu Val Thr Val Ser Ser
        115                 120

<210> SEQ ID NO 103
<211> LENGTH: 122
<212> TYPE: PRT
<213> ORGANISM: Homo sapiens
<220> FEATURE:
<221> NAME/KEY: VARIANT
<222> LOCATION: 62
<223> OTHER INFORMATION: Xaa = Any Amino Acid

<400> SEQUENCE: 103

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala Arg Tyr
            20                  25                  30

Asn Met Gly Trp Val Arg Gln Ala Pro Gly Lys Gly Leu Glu Trp Val
        35                  40                  45

Ser Leu Ile Asp Pro Ser Gly Gly His Thr Tyr Tyr Ala Xaa Ser Val
    50                  55                  60

Lys Gly Arg Ser Thr Ile Ser Arg Asn Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Gly Lys Pro Val Phe Ser Asp Trp Pro Ala Val Glu Phe Asp Tyr Trp
            100                 105                 110

Gly Gln Gly Thr Leu Val Thr Val Ser Ser
        115                 120

<210> SEQ ID NO 104
<211> LENGTH: 119
<212> TYPE: PRT
<213> ORGANISM: Homo sapiens

<400> SEQUENCE: 104

Glu Val Gln Leu Leu Glu Ser Gly Gly Gly Met Val Gln Pro Gly Gly
 1               5                  10                  15

Ser Leu Arg Leu Ser Cys Ala Ala Pro Gly Phe Thr Phe Glu His Glu
            20                  25                  30

Gly Met Val Trp Val Arg Gln Ala Pro Gly Lys Gly Leu Glu Trp Val
        35                  40                  45

Ser His Ile Gly Glu Asp Gly Gln Ser Thr Tyr Tyr Ala Asp Ser Val
    50                  55                  60

Lys Gly Arg Phe Thr Ile Ser Arg Asp Asn Ser Lys Asn Thr Leu Tyr
```

```
                65                  70                  75                  80
Leu Gln Met Asn Ser Leu Arg Ala Glu Asp Thr Ala Val Tyr Tyr Cys
                85                  90                  95

Ala Ser Ile Pro Lys Ala Gly Pro Ser Phe Asp Tyr Trp Gly Gln Gly
            100                 105                 110

Thr Leu Val Thr Val Ser Ser
        115

<210> SEQ ID NO 105
<211> LENGTH: 122
<212> TYPE: PRT
<213> ORGANISM: Homo sapiens

<400> SEQUENCE: 105

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Ser Thr Phe Asp Gln Tyr
            20                  25                  30

Asp Met Ser Trp Val Arg Arg Ala Pro Gly Lys Gly Leu Glu Trp Val
        35                  40                  45

Ser Leu Ile Asp Pro Ser Gly Gly His Thr Tyr Tyr Ala Asp Ser Val
    50                  55                  60

Lys Gly Arg Phe Thr Ile Ser Arg Asn Asn Thr Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Val Phe Ser Asp Trp Pro Ala Val Glu Phe Asp Tyr Trp
            100                 105                 110

Gly Gln Gly Thr Leu Val Thr Val Ser Ser
        115                 120

<210> SEQ ID NO 106
<211> LENGTH: 121
<212> TYPE: PRT
<213> ORGANISM: Homo sapiens

<400> SEQUENCE: 106

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asp Tyr Gly
            20                  25                  30

Asn Met Phe Trp Val Arg Gln Ala Pro Gly Lys Gly Leu Glu Trp Ile
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Met Thr Thr Asp Ser Pro Pro Gly Phe Asp Tyr Trp Gly
            100                 105                 110

Gln Gly Thr Leu Val Thr Val Ser Ser
        115                 120

<210> SEQ ID NO 107
<211> LENGTH: 122
<212> TYPE: PRT
```

<213> ORGANISM: Homo sapiens

<400> SEQUENCE: 107

```
Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Ala Lys Glu
            20                  25                  30
Thr Met Ser Trp Val Arg Gln Ala Pro Gly Lys Gly Leu Glu Trp Val
        35                  40                  45
Ser Trp Ile Ser Pro His Gly Ala His Thr Phe Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Pro Arg Phe Ser Tyr Tyr Pro Arg Val Ser Phe Asp Tyr Arg
            100                 105                 110
Gly Gln Gly Thr Leu Val Thr Val Ser Ser
        115                 120
```

<210> SEQ ID NO 108
<211> LENGTH: 116
<212> TYPE: PRT
<213> ORGANISM: Homo sapiens

<400> SEQUENCE: 108

```
Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Asp Ala Tyr
            20                  25                  30
Asn Met Phe Trp Phe Arg Gln Ala Pro Gly Lys Gly Pro Glu Trp Val
        35                  40                  45
Ser Ala Ile Gly Pro Ser Gly Arg Glu Thr Tyr Tyr Ala Asp Ser Val
    50                  55                  60
Lys Gly Arg Phe Thr Ile Thr Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Arg Tyr Pro Asp Phe Asp Tyr Trp Gly Gln Gly Thr Leu Val
            100                 105                 110
Thr Val Ser Ser
        115
```

<210> SEQ ID NO 109
<211> LENGTH: 119
<212> TYPE: PRT
<213> ORGANISM: Homo sapiens

<400> SEQUENCE: 109

```
Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Glu His Glu
            20                  25                  30
Gly Met Val Trp Val Arg Gln Ala Pro Gly Lys Gly Leu Glu Trp Val
        35                  40                  45
Ser His Ile Gly Glu Asp Gly Gln Ser Thr Tyr Tyr Ala Asp Ser Val
    50                  55                  60
```

```
Lys Gly Arg Phe Thr Ile Ser Arg Asp Asn Ser Arg Asn Thr Leu Tyr
 65                  70                  75                  80

Leu Gln Met Asn Ser Leu Arg Ala Glu Asp Thr Ala Val Tyr Tyr Cys
                 85                  90                  95

Ala Asn Ile Pro Lys Ala Gly Pro Ser Phe Asp Tyr Trp Gly Gln Gly
            100                 105                 110

Thr Leu Val Thr Val Ser Ser
        115
```

<210> SEQ ID NO 110
<211> LENGTH: 123
<212> TYPE: PRT
<213> ORGANISM: Homo sapiens

<400> SEQUENCE: 110

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Lys Leu Tyr
                 20                  25                  30

Asn Met Ala Trp Val Arg Gln Ala Pro Gly Lys Gly Leu Glu Trp Val
             35                  40                  45

Ser Phe Ile Ala Ala Gly Pro Glu Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Leu Gly Asp Ile Ser Ser Ile Pro Gln His Pro Phe Asp Tyr
            100                 105                 110

Trp Gly Gln Gly Thr Leu Val Thr Val Ser Ser
            115                 120
```

<210> SEQ ID NO 111
<211> LENGTH: 119
<212> TYPE: PRT
<213> ORGANISM: Homo sapiens

<400> SEQUENCE: 111

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Arg Glu
                 20                  25                  30

Asn Met His Trp Val Arg Gln Ala Pro Gly Lys Gly Leu Glu Trp Val
             35                  40                  45

Ser Gly Ile Gly Pro Arg Gly Met Pro Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Met Asn Ser His Asp Gly Phe Asp Tyr Trp Gly Gln Gly
            100                 105                 110

Thr Leu Val Thr Val Ser Ser
        115
```

<210> SEQ ID NO 112

```
<211> LENGTH: 121
<212> TYPE: PRT
<213> ORGANISM: Homo sapiens

<400> SEQUENCE: 112

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asp Ala Ser
            20                  25                  30

Glu Met Asp Trp Val Arg Gln Ala Pro Gly Lys Gly Leu Glu Trp Val
        35                  40                  45

Ser Ala Ile Ser Pro Ser Gly Ser Ala Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Met Leu Ala Asn Ser Pro Leu Ala Phe Asp Tyr Trp Gly
            100                 105                 110

Gln Gly Thr Leu Val Thr Val Ser Ser
        115                 120

<210> SEQ ID NO 113
<211> LENGTH: 123
<212> TYPE: PRT
<213> ORGANISM: Homo sapiens

<400> SEQUENCE: 113

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ala Tyr
            20                  25                  30

Asn Met Ala Trp Val Arg Gln Ala Pro Gly Lys Gly Leu Glu Trp Val
        35                  40                  45

Ser Phe Ile Ala Gln Ser Gly Gly His Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Ser His Pro Asp Glu Gly Thr Gln Met Phe Asp Tyr
            100                 105                 110

Trp Gly Gln Gly Thr Leu Val Thr Val Ser Ser
        115                 120

<210> SEQ ID NO 114
<211> LENGTH: 119
<212> TYPE: PRT
<213> ORGANISM: Homo sapiens

<400> SEQUENCE: 114

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala Asp Tyr
            20                  25                  30

Gln Met Ala Trp Val Arg Gln Ala Pro Gly Lys Gly Leu Glu Trp Val
        35                  40                  45
```

```
Ser Arg Ile Asp Arg Gly Gly Phe Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Pro Ser Trp His Ala Asp Gln Tyr Phe Asp Tyr Trp Gly Gln Gly
            100                 105                 110

Thr Leu Val Thr Val Ser Ser
        115

<210> SEQ ID NO 115
<211> LENGTH: 120
<212> TYPE: PRT
<213> ORGANISM: Homo sapiens

<400> SEQUENCE: 115

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Asp Tyr
            20                  25                  30

Asn Met Met Trp Val Arg Gln Ala Pro Gly Lys Gly Leu Glu Trp Val
        35                  40                  45

Ser Ala Ile Ala Thr Ser Gly Arg Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Thr Phe Gly Gly Asn Gln Asp Phe Asp Tyr Trp Gly Gln
            100                 105                 110

Gly Thr Leu Val Thr Val Ser Ser
        115                 120

<210> SEQ ID NO 116
<211> LENGTH: 120
<212> TYPE: PRT
<213> ORGANISM: Homo sapiens

<400> SEQUENCE: 116

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Lys Tyr
            20                  25                  30

Asn Met Tyr Trp Val Arg Gln Ala Pro Gly Lys Gly Leu Glu Trp Val
        35                  40                  45

Ser Ala Ile Ser Pro Lys Gly Gln His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Gly Met Gly Ser Asp Ala Ile Thr Phe Asp Tyr Trp Gly Gln
            100                 105                 110

Gly Thr Leu Val Thr Val Ser Ser
        115                 120
```

<210> SEQ ID NO 117
<211> LENGTH: 123
<212> TYPE: PRT
<213> ORGANISM: Homo sapiens

<400> SEQUENCE: 117

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Asn Met Ala Trp Val Arg Gln Ala Pro Gly Lys Gly Leu Glu Trp Val
        35                  40                  45

Ser Phe Ile Ala Gln Ser Gly Gly His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Ser His Pro Asp Glu Gly Thr Gln Met Phe Asp Tyr
            100                 105                 110

Trp Gly Gln Gly Thr Leu Val Thr Val Ser Ser
        115                 120

<210> SEQ ID NO 118
<211> LENGTH: 122
<212> TYPE: PRT
<213> ORGANISM: Homo sapiens

<400> SEQUENCE: 118

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Arg Tyr
            20                  25                  30

Asp Met Phe Trp Val Arg Gln Ala Pro Gly Lys Gly Leu Glu Trp Val
        35                  40                  45

Ser Gly Ile Ser Pro Arg Gly Arg Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Met Ile Asn Tyr His Gly Thr Pro Ser Phe Asp Tyr Trp
            100                 105                 110

Gly Gln Gly Thr Leu Val Thr Val Ser Ser
        115                 120

<210> SEQ ID NO 119
<211> LENGTH: 122
<212> TYPE: PRT
<213> ORGANISM: Homo sapiens
<220> FEATURE:
<221> NAME/KEY: VARIANT
<222> LOCATION: 30
<223> OTHER INFORMATION: Xaa = Any Amino Acid

<400> SEQUENCE: 119

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Xaa Asn Tyr
            20                  25                  30

Asn Met Val Trp Val Arg Gln Ala Pro Gly Lys Gly Leu Glu Trp Val
            35                  40                  45

Ser Trp Ile Ser Gly Ala Gly His Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Val Asp Met Ala Gly Lys Leu Asn Val Phe Asp Tyr Trp
                100                 105                 110

Gly Gln Gly Thr Leu Val Thr Val Ser Ser
            115                 120

<210> SEQ ID NO 120
<211> LENGTH: 122
<212> TYPE: PRT
<213> ORGANISM: Homo sapiens

<400> SEQUENCE: 120

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Gln Tyr
            20                  25                  30

Asn Met Tyr Trp Val Arg Gln Ala Pro Gly Lys Gly Leu Glu Trp Val
            35                  40                  45

Ser Phe Ile Ser Pro Ser Gly Gly Glu Thr Tyr Tyr Ala Asp Ser Val
    50                  55                  60

Lys Gly Arg Phe Thr Thr Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Val Asp Met Ala Gly Lys Leu Asn Val Phe Asp Tyr Trp
                100                 105                 110

Gly Gln Gly Thr Leu Val Thr Val Ser Ser
            115                 120

<210> SEQ ID NO 121
<211> LENGTH: 120
<212> TYPE: PRT
<213> ORGANISM: Homo sapiens

<400> SEQUENCE: 121

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Asp Tyr
            20                  25                  30

Gln Met Ala Trp Val Arg Gln Ala Pro Gly Lys Gly Leu Glu Trp Val
            35                  40                  45

Ser Arg Ile Asp Arg Gly Gly Phe His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala Lys Pro Ser Trp His Ala Asp Gln Tyr Phe Asp Tyr Trp Gly Gln
            100                 105                 110
Gly Thr Leu Val Thr Val Ser Ser
        115                 120

<210> SEQ ID NO 122
<211> LENGTH: 120
<212> TYPE: PRT
<213> ORGANISM: Homo sapiens

<400> SEQUENCE: 122

Glu Val Gln Leu Leu Glu Ser Gly Gly Gly Leu Val Gln Pro Gly Gly
  1               5                  10                  15
Ser Leu Arg Leu Thr Cys Ala Ala Ser Gly Phe Thr Phe Asp Asp Val
             20                  25                  30
Asn Met Thr Trp Val Arg Gln Ala Pro Gly Lys Gly Leu Glu Trp Val
         35                  40                  45
Ser Ala Ile Gly Pro Ser Gly Thr Glu Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys His Ser Lys Thr Gly Ser Ala Met Phe Asp Tyr Trp Gly Gln
            100                 105                 110
Gly Thr Leu Val Thr Val Ser Ser
        115                 120

<210> SEQ ID NO 123
<211> LENGTH: 119
<212> TYPE: PRT
<213> ORGANISM: Homo sapiens

<400> SEQUENCE: 123

Glu Val Gln Leu Leu Glu Ser Gly Gly Gly Leu Val Gln Pro Gly Gly
  1               5                  10                  15
Ser Leu Arg Leu Ser Cys Ala Ala Ser Gly Phe Thr Phe Gly Asn Gly
             20                  25                  30
Asn Met Val Trp Val Arg Gln Ala Pro Gly Lys Gly Leu Glu Trp Val
         35                  40                  45
Ser His Ile Asp Glu Tyr Gly Thr Asn Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Pro Arg Asn Asp Arg Pro Gly Phe Asp Tyr Trp Gly Gln Gly
            100                 105                 110
Thr Leu Val Thr Val Ser Ser
        115

<210> SEQ ID NO 124
<211> LENGTH: 119
<212> TYPE: PRT
<213> ORGANISM: Homo sapiens

<400> SEQUENCE: 124

Glu Val Gln Leu Leu Glu Ser Gly Gly Gly Leu Val Gln Pro Gly Gly
```

-continued

```
                1               5                  10                 15
            Ser Leu Arg Leu Ser Cys Ala Ala Ser Gly Phe Thr Phe Ser Arg Glu
                            20                 25                 30

Asn Met His Trp Val Arg Gln Ala Pro Gly Lys Gly Leu Glu Trp Val
                        35                 40                 45

Ser Gly Ile Gly Pro Arg Gly Met Pro Thr Tyr Tyr Ala Asp Ser Val
                    50                 55                 60

Lys Gly Arg Phe Thr Ile Ser Arg Asp Asn Ser Lys Asn Thr Leu Tyr
             65                 70                 75                 80

Leu Gln Met Asn Ser Leu Arg Ala Glu Asp Thr Ala Val Tyr Tyr Cys
                            85                 90                 95

Ala Lys Gly Met Asn Ser His Asp Gly Phe Asp Tyr Trp Gly Gln Gly
                        100                105                110

Thr Leu Val Thr Val Ser Ser
                        115
```

<210> SEQ ID NO 125
<211> LENGTH: 117
<212> TYPE: PRT
<213> ORGANISM: Homo sapiens

<400> SEQUENCE: 125

```
            Glu Val Gln Leu Leu Glu Ser Gly Gly Gly Leu Val Gln Pro Gly Gly
             1               5                  10                 15

Ser Leu Arg Leu Ser Cys Ala Ala Ser Gly Phe Thr Phe Lys Gly Ser
                            20                 25                 30

Asn Met Gly Trp Val Arg Gln Ala Pro Gly Lys Gly Leu Glu Trp Val
                        35                 40                 45

Ser Leu Ile Asp Gly Arg Gly Gln His Thr Tyr Tyr Ala Asp Ser Val
                    50                 55                 60

Lys Gly Arg Phe Thr Ile Ser Arg Asp Asn Ser Lys Asn Thr Leu Tyr
             65                 70                 75                 80

Leu Gln Met Asn Ser Leu Arg Ala Glu Asp Thr Ala Val Tyr Tyr Cys
                            85                 90                 95

Ala Lys Pro Ser Val Arg Glu Phe Asp Tyr Arg Gly Gly Gly Thr Leu
                        100                105                110

Val Thr Val Ser Ser
                        115
```

<210> SEQ ID NO 126
<211> LENGTH: 121
<212> TYPE: PRT
<213> ORGANISM: Homo sapiens

<400> SEQUENCE: 126

```
            Glu Val Gln Leu Leu Glu Ser Gly Gly Gly Leu Val Gln Pro Gly Gly
             1               5                  10                 15

Ser Leu Arg Leu Ser Cys Ala Ala Ser Gly Phe Thr Phe Ser Arg Glu
                            20                 25                 30

Asn Met His Trp Val Arg Gln Ala Pro Gly Lys Gly Leu Glu Trp Val
                        35                 40                 45

Ser Gly Ile Gly Pro Arg Gly Met Pro Thr Tyr Tyr Ala Asp Ser Val
                    50                 55                 60

Lys Gly Arg Phe Thr Ile Ser Arg Asp Asn Ser Lys Asn Thr Leu Tyr
             65                 70                 75                 80

Leu Gln Met Asn Ser Leu Arg Ala Glu Asp Thr Ala Val Tyr Tyr Cys
```

```
                     85                  90                  95
Ala Lys Arg Met Leu Ala Asn Ser Pro Leu Ala Phe Asp Tyr Trp Gly
                100                 105                 110

Gln Gly Thr Leu Val Thr Val Ser Ser
            115                 120

<210> SEQ ID NO 127
<211> LENGTH: 116
<212> TYPE: PRT
<213> ORGANISM: Homo sapiens

<400> SEQUENCE: 127

Glu Val Gln Leu Leu Glu Ser Gly Gly Gly Leu Val Gln Pro Gly Gly
  1               5                  10                  15

Ser Leu Arg Leu Ser Cys Thr Ala Ser Gly Phe Thr Phe Ser Glu Ser
             20                  25                  30

Thr Met Asn Trp Val Arg Gln Ala Pro Gly Lys Gly Leu Glu Trp Val
         35                  40                  45

Ser Val Ile Thr Ala Gln Gly Gly Asp Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro Asp Val Leu Phe Asp Tyr Trp Gly Gln Gly Thr Leu Val
                100                 105                 110

Thr Val Ser Ser
            115

<210> SEQ ID NO 128
<211> LENGTH: 117
<212> TYPE: PRT
<213> ORGANISM: Homo sapiens

<400> SEQUENCE: 128

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Glu Glu Tyr
             20                  25                  30

Asn Met Leu Trp Val Arg Gln Ala Pro Gly Lys Gly Leu Glu Trp Val
         35                  40                  45

Ser Gly Ile Gly Pro Ser Gly Arg Glu Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Ser Ile Thr Leu Phe Asp Tyr Trp Gly Gln Gly Thr Leu
                100                 105                 110

Val Thr Val Ser Ser
            115

<210> SEQ ID NO 129
<211> LENGTH: 124
<212> TYPE: PRT
<213> ORGANISM: Homo sapiens

<400> SEQUENCE: 129
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Asn Met Tyr Trp Val Arg Gln Ala Pro Gly Lys Gly Leu Glu Trp Val
        35                  40                  45

Ser Ala Ile Asp Ala Tyr Gly Thr His Thr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Glu Gly Leu Gln Thr Ser Asp His Gly Glu Arg Ile Ser Phe Asp
        100                 105                 110

Tyr Trp Gly Gln Gly Thr Leu Val Thr Val Ser Ser
        115                 120

<210> SEQ ID NO 130
<211> LENGTH: 122
<212> TYPE: PRT
<213> ORGANISM: Homo sapiens

<400> SEQUENCE: 130

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Gln Tyr
            20                  25                  30

Asp Met Ser Trp Val Arg Gln Ala Pro Gly Lys Gly Leu Glu Trp Val
        35                  40                  45

Ser Leu Ile Asp Pro Ser Gly Gly His Thr Tyr Tyr Ala Asp Ser Val
50                  55                  60

Lys Gly Arg Phe Thr Ile Ser Arg Asn Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Pro Val Phe Ser Asp Trp Pro Ala Val Glu Phe Asp Tyr Trp
        100                 105                 110

Gly Gln Gly Thr Leu Val Thr Val Ser Ser
        115                 120

<210> SEQ ID NO 131
<211> LENGTH: 122
<212> TYPE: PRT
<213> ORGANISM: Homo sapiens

<400> SEQUENCE: 131

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Gln Tyr
            20                  25                  30

Asp Met Ser Trp Val Arg Gln Ala Pro Gly Lys Gly Leu Glu Trp Val
        35                  40                  45

Ser Leu Ile Asp Pro Ser Gly Gly His Thr Tyr Tyr Ala Asp Ser Val
50                  55                  60

Lys Gly Arg Phe Thr Ile Ser Arg Asn Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Lys Pro Val Phe Ser Asp Trp Pro Ala Val Glu Phe Asp Tyr Trp
            100                 105                 110

Gly Gln Gly Thr Leu Val Thr Val Ser Ser
        115                 120
```

<210> SEQ ID NO 132
<211> LENGTH: 120
<212> TYPE: PRT
<213> ORGANISM: Homo sapiens

<400> SEQUENCE: 132

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Arg Tyr
            20                  25                  30

Ser Met Gly Trp Val Arg Gln Ala Pro Gly Lys Gly Leu Glu Trp Val
        35                  40                  45

Ser Met Ile Asp Val Pro Gly Leu His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Ser Asn Ala Phe Asp Tyr Trp Gly Gln
            100                 105                 110

Gly Thr Leu Val Thr Val Ser Ser
        115                 120
```

<210> SEQ ID NO 133
<211> LENGTH: 120
<212> TYPE: PRT
<213> ORGANISM: Homo sapiens
<220> FEATURE:
<221> NAME/KEY: VARIANT
<222> LOCATION: 62, 104
<223> OTHER INFORMATION: Xaa = Any Amino Acid

<400> SEQUENCE: 133

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Xaa Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys Val Lys Leu Gly Gly Xaa Pro Asn Phe Gly Tyr Arg Gly Gln
            100                 105                 110

Gly Thr Leu Val Thr Val Ser Ser
        115                 120
```

```
<210> SEQ ID NO 134
<211> LENGTH: 120
<212> TYPE: PRT
<213> ORGANISM: Homo sapiens

<400> SEQUENCE: 134
```

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Thr | Arg | Tyr |
|---|---|---|---|---|---|---|---|---|---|---|---|---|---|---|---|
| | | 20 | | | | | 25 | | | | | 30 | | | |

| Ser | Met | Gly | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Phe | Ile | Asp | Pro | Pro | Ser | Val | His | Thr | Tyr | Tyr | Ala | Asp | Ser | Val |
|---|---|---|---|---|---|---|---|---|---|---|---|---|---|---|---|
| 50 | | | | | 55 | | | | | 60 | | | | | |

| Lys | Gly | Arg | Phe | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Lys | Ile | Ser | Gln | Phe | Gly | Ser | Asn | Ala | Phe | Asp | Tyr | Trp | Gly | Gln |
|---|---|---|---|---|---|---|---|---|---|---|---|---|---|---|---|
| | | | 100 | | | | | 105 | | | | | 110 | | |

| Gly | Thr | Leu | Val | Thr | Val | Ser | Ser |
|---|---|---|---|---|---|---|---|
| | | 115 | | | | | 120 |

```
<210> SEQ ID NO 135
<211> LENGTH: 120
<212> TYPE: PRT
<213> ORGANISM: Homo sapiens
<220> FEATURE:
<221> NAME/KEY: VARIANT
<222> LOCATION: 62
<223> OTHER INFORMATION: Xaa = Any Amino Acid

<400> SEQUENCE: 135
```

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Thr | Arg | Tyr |
|---|---|---|---|---|---|---|---|---|---|---|---|---|---|---|---|
| | | 20 | | | | | 25 | | | | | 30 | | | |

| Ser | Met | Gly | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Met | Ile | Asp | Val | Gly | Gly | Ser | His | Thr | Tyr | Tyr | Ala | Xaa | Ser | Val |
|---|---|---|---|---|---|---|---|---|---|---|---|---|---|---|---|
| 50 | | | | | 55 | | | | | 60 | | | | | |

| Lys | Gly | Arg | Phe | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Lys | Ile | Ser | Gln | Phe | Gly | Ser | Asn | Ala | Phe | Asp | Tyr | Trp | Gly | Gln |
|---|---|---|---|---|---|---|---|---|---|---|---|---|---|---|---|
| | | | 100 | | | | | 105 | | | | | 110 | | |

| Gly | Thr | Leu | Val | Thr | Val | Ser | Ser |
|---|---|---|---|---|---|---|---|
| | | 115 | | | | | 120 |

```
<210> SEQ ID NO 136
<211> LENGTH: 120
<212> TYPE: PRT
<213> ORGANISM: Homo sapiens
<220> FEATURE:
<221> NAME/KEY: VARIANT
<222> LOCATION: 62
<223> OTHER INFORMATION: Xaa = Any Amino Acid

<400> SEQUENCE: 136
```

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Thr Arg Tyr
            20                  25                  30

Ser Met Gly Trp Val Arg Gln Ala Pro Gly Lys Gly Leu Glu Trp Val
        35                  40                  45

Ser Met Ile Asp Thr Gly Gly Val His Thr Tyr Tyr Ala Xaa Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Ser Asn Ala Phe Asp Tyr Trp Gly Gln
            100                 105                 110

Gly Thr Leu Val Thr Val Ser Ser
            115                 120

<210> SEQ ID NO 137
<211> LENGTH: 120
<212> TYPE: PRT
<213> ORGANISM: Homo sapiens

<400> SEQUENCE: 137

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Thr Arg Tyr
            20                  25                  30

Ser Met Gly Trp Val Arg Gln Ala Pro Gly Lys Gly Leu Glu Trp Val
        35                  40                  45

Ser Met Ile Asp Val Pro Gly Arg His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Ser Asn Ala Phe Asp Tyr Trp Gly Gln
            100                 105                 110

Gly Thr Leu Val Thr Val Ser Ser
            115                 120

<210> SEQ ID NO 138
<211> LENGTH: 120
<212> TYPE: PRT
<213> ORGANISM: Homo sapiens

<400> SEQUENCE: 138

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Thr Arg Tyr
            20                  25                  30

Ser Met Gly Trp Val Arg Gln Ala Pro Gly Lys Gly Leu Glu Trp Val
        35                  40                  45

Ser Met Ile Ala His Ala Gly Pro Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

-continued

Leu Gln Met Asn Ser Leu Arg Ala Glu Asp Thr Ala Val Tyr Tyr Cys
                85                  90                  95

Ala Lys Ile Ser Gln Phe Gly Ser Asn Ala Phe Asp Tyr Trp Gly Gln
            100                 105                 110

Gly Thr Leu Val Thr Val Ser Ser
        115                 120

<210> SEQ ID NO 139
<211> LENGTH: 120
<212> TYPE: PRT
<213> ORGANISM: Homo sapiens

<400> SEQUENCE: 139

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Arg Tyr
            20                  25                  30

Ser Met Gly Trp Val Arg Gln Ala Pro Gly Lys Gly Leu Glu Trp Val
        35                  40                  45

Ser Met Ile Asp Thr Arg Gly Val Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Ser Asn Ala Phe Asp Tyr Trp Gly Gln
            100                 105                 110

Gly Thr Leu Val Thr Val Ser Ser
        115                 120

<210> SEQ ID NO 140
<211> LENGTH: 120
<212> TYPE: PRT
<213> ORGANISM: Homo sapiens

<400> SEQUENCE: 140

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Arg Tyr
            20                  25                  30

Ser Met Gly Trp Val Arg Gln Ala Pro Gly Lys Gly Leu Glu Trp Val
        35                  40                  45

Ser Met Ile Asp Val Pro Gly Asn His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Ser Asn Ala Phe Asp Tyr Trp Gly Gln
            100                 105                 110

Gly Thr Leu Val Thr Val Ser Ser
        115                 120

<210> SEQ ID NO 141
<211> LENGTH: 120
<212> TYPE: PRT
<213> ORGANISM: Homo sapiens -continued

```
<400> SEQUENCE: 141

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Thr Arg Tyr
            20                  25                  30

Ser Met Gly Trp Val Arg Gln Ala Pro Gly Lys Gly Leu Glu Trp Val
        35                  40                  45

Ser Met Ile Asp Val Gly Gly Arg His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Pro Asn Ala Phe Asp Tyr Trp Gly Gln
            100                 105                 110

Gly Thr Leu Val Thr Val Ser Ser
        115                 120

<210> SEQ ID NO 142
<211> LENGTH: 118
<212> TYPE: PRT
<213> ORGANISM: Homo sapiens

<400> SEQUENCE: 142

Glu Val Gln Leu Leu Glu Ser Gly Gly Gly Ser Val Gln Pro Gly Gly
 1               5                  10                  15

Ser Leu Arg Leu Ser Cys Ala Ala Ser Gly Phe Thr Phe Thr Arg Tyr
            20                  25                  30

Ser Met Gly Trp Val Arg Gln Ala Pro Gly Lys Gly Leu Glu Trp Val
        35                  40                  45

Ser Arg Ile Asp Ser Tyr Gly Arg Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Arg Ser Pro Tyr Thr Phe Asp Tyr Trp Gly Gln Gly Thr
            100                 105                 110

Leu Val Thr Val Ser Ser
        115

<210> SEQ ID NO 143
<211> LENGTH: 117
<212> TYPE: PRT
<213> ORGANISM: Homo sapiens

<400> SEQUENCE: 143

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Gly Tyr
            20                  25                  30

Asn Met Gly Trp Val Arg Gln Ala Pro Gly Lys Gly Leu Glu Trp Val
        35                  40                  45

Ser Thr Ile Ser Thr Gln Gly Tyr His Thr Tyr Tyr Ala Asp Ser Val
    50                  55                  60

Lys Gly Arg Phe Thr Ile Ser Arg Asp Asn Ser Lys Asn Thr Leu Tyr
```

```
            65                  70                  75                  80
Leu Gln Met Asn Ser Leu Arg Ala Glu Asp Thr Ala Val Tyr Tyr Cys
                85                  90                  95
Ala Lys Ala Phe Thr Ser Asp Phe Asp Tyr Trp Gly Gln Gly Thr Leu
            100                 105                 110
Val Thr Val Ser Ser
        115

<210> SEQ ID NO 144
<211> LENGTH: 119
<212> TYPE: PRT
<213> ORGANISM: Homo sapiens

<400> SEQUENCE: 144

Glu Val Gln Leu Leu Glu Ser Gly Gly Gly Leu Val Gln Pro Gly Gly
  1               5                  10                  15
Ser Leu Arg Leu Ser Cys Ala Ala Ser Gly Phe Thr Phe Ser Gly Tyr
             20                  25                  30
Asn Met Tyr Trp Val Arg Gln Ala Pro Gly Lys Gly Leu Glu Trp Val
         35                  40                  45
Ser Gly Ile Ser Gly Pro Gly Leu Glu Thr Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                85                  90                  95
Ala Gln Gly Met Ser Lys Thr Ser Thr Phe Asp Tyr Trp Gly Gln Gly
            100                 105                 110
Thr Leu Val Thr Val Ser Ser
        115

<210> SEQ ID NO 145
<211> LENGTH: 117
<212> TYPE: PRT
<213> ORGANISM: Homo sapiens

<400> SEQUENCE: 145

Glu Val Gln Leu Leu Glu Ser Gly Gly Gly Leu Val Gln Pro Gly Gly
  1               5                  10                  15
Ser Leu Arg Leu Ser Cys Ala Ala Ser Gly Phe Thr Phe Thr Glu Tyr
             20                  25                  30
Tyr Met Glu Trp Val Arg Gln Ala Pro Gly Lys Gly Leu Glu Trp Val
         35                  40                  45
Ser Ser Ile Asp Pro Asp Gly Ser Leu Thr Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                85                  90                  95
Ala Lys Tyr Pro Arg Glu Lys Phe Asp Tyr Trp Gly Gln Gly Thr Leu
            100                 105                 110
Val Thr Val Ser Ser
        115

<210> SEQ ID NO 146
<211> LENGTH: 120
<212> TYPE: PRT
```

<213> ORGANISM: Homo sapiens

<400> SEQUENCE: 146

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Lys Tyr
            20                  25                  30

Gln Met Gly Trp Val Arg Gln Ala Pro Gly Lys Gly Leu Glu Trp Val
        35                  40                  45

Ser Phe Ile Asp Ser Asn Gly His His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gln Leu Ser Val Gln Gly Ser Asn Leu Phe Asp Tyr Trp Gly Gln
            100                 105                 110

Gly Thr Leu Val Thr Val Ser Ser
        115                 120

<210> SEQ ID NO 147
<211> LENGTH: 120
<212> TYPE: PRT
<213> ORGANISM: Homo sapiens

<400> SEQUENCE: 147

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val His Tyr
            20                  25                  30

Thr Met Gly Trp Val Arg Gln Ala Pro Gly Lys Gly Leu Glu Trp Val
        35                  40                  45

Ser Trp Ile His Ser Asp Gly Val His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Thr Trp Gly Glu Lys Lys Thr Phe Asp Tyr Trp Gly Gln
            100                 105                 110

Gly Thr Leu Val Thr Val Ser Ser
        115                 120

<210> SEQ ID NO 148
<211> LENGTH: 120
<212> TYPE: PRT
<213> ORGANISM: Homo sapiens

<400> SEQUENCE: 148

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Met Gly Tyr
            20                  25                  30

Asp Met His Trp Val Arg Gln Ala Pro Gly Lys Gly Leu Glu Trp Val
        35                  40                  45

Ser Gly Ile Ser Ala Lys Gly Thr Glu Thr Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Ser Ser Gly Ser Asp Gly Leu Phe Asp Tyr Trp Gly Gln
            100                 105                 110

Gly Thr Leu Val Thr Val Ser Ser
            115                 120

<210> SEQ ID NO 149
<211> LENGTH: 124
<212> TYPE: PRT
<213> ORGANISM: Homo sapiens

<400> SEQUENCE: 149

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Pro Val Tyr
                 20                  25                  30

Asn Met Ala Trp Val Arg Gln Ala Pro Gly Lys Gly Leu Glu Trp Val
             35                  40                  45

Ser Phe Ile Ala Gly Asn Gly Gln Gln Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Phe Ala Ser Lys Val Ser Pro Met Ser Leu Thr Asp Phe Asp
            100                 105                 110

Tyr Trp Gly Gln Gly Thr Leu Val Thr Val Ser Ser
            115                 120

<210> SEQ ID NO 150
<211> LENGTH: 124
<212> TYPE: PRT
<213> ORGANISM: Homo sapiens

<400> SEQUENCE: 150

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Gln Tyr
                 20                  25                  30

Asn Met His Trp Val Arg Gln Ala Pro Gly Lys Gly Leu Glu Trp Val
             35                  40                  45

Ser Gly Ile Ser Ser Gly Gly Met Arg Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Ile Arg Asp Ser Thr Leu Pro Arg Gly Leu Phe Asp
            100                 105                 110

Tyr Trp Gly Gln Gly Thr Leu Val Thr Val Ser Ser
            115                 120

<210> SEQ ID NO 151
```

```
<211> LENGTH: 121
<212> TYPE: PRT
<213> ORGANISM: Homo sapiens

<400> SEQUENCE: 151

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Thr Tyr
            20                  25                  30

Ser Met His Trp Val Arg Gln Ala Pro Gly Lys Gly Leu Glu Trp Val
        35                  40                  45

Ser Ser Ile Ser Leu Pro Gly Ser Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Ser Lys Ser Ser His Arg Gln Ser Phe Asp Tyr Trp Gly
            100                 105                 110

Gln Gly Thr Leu Val Thr Val Ser Ser
        115                 120

<210> SEQ ID NO 152
<211> LENGTH: 122
<212> TYPE: PRT
<213> ORGANISM: Homo sapiens

<400> SEQUENCE: 152

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Gln Tyr
            20                  25                  30

Asp Met His Trp Val Arg Gln Ala Pro Gly Lys Gly Leu Glu Trp Val
        35                  40                  45

Ser Gly Ile Ser Phe Ser Gly Tyr Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Arg Gly Pro Ala Pro Met Arg Ser Leu Phe Asp Tyr Trp
            100                 105                 110

Gly Gln Gly Thr Leu Val Thr Val Ser Ser
        115                 120

<210> SEQ ID NO 153
<211> LENGTH: 120
<212> TYPE: PRT
<213> ORGANISM: Homo sapiens

<400> SEQUENCE: 153

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Asp Tyr
            20                  25                  30

Pro Met Val Trp Val Arg Gln Ala Pro Gly Lys Gly Leu Glu Trp Val
        35                  40                  45
```

```
Ser His Ile Thr Ser Met Gly Glu Ser Thr Tyr Tyr Ala Asp Ser Val
    50                  55                  60

Lys Gly Arg Phe Thr Ile Ser Arg Asp Asn Ser Lys Asn Met Leu Tyr
 65                  70                  75                  80

Leu Gln Met Asn Ser Leu Arg Ala Glu Asp Thr Ala Val Tyr Tyr Cys
                 85                  90                  95

Ala Lys Leu Pro Thr His Phe Pro Ile Arg Phe Asp Tyr Trp Gly Gln
            100                 105                 110

Gly Thr Leu Val Thr Val Ser Ser
            115                 120

<210> SEQ ID NO 154
<211> LENGTH: 116
<212> TYPE: PRT
<213> ORGANISM: Homo sapiens

<400> SEQUENCE: 154

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Lys Gln Tyr
             20                  25                  30

Asn Met Tyr Trp Val Arg Gln Ala Pro Gly Lys Gly Leu Glu Trp Val
         35                  40                  45

Ser Phe Ile Ser Pro Ser Gly Glu Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Ile Lys Pro Phe Asp Tyr Trp Gly Gln Gly Thr Leu Val
            100                 105                 110

Thr Val Ser Ser
            115

<210> SEQ ID NO 155
<211> LENGTH: 120
<212> TYPE: PRT
<213> ORGANISM: Homo sapiens

<400> SEQUENCE: 155

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Met Tyr
             20                  25                  30

Ser Met Ala Trp Val Arg Gln Ala Pro Gly Lys Gly Leu Glu Trp Val
         35                  40                  45

Ser Phe Ile Asp Phe Asp Gly Leu His Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Phe Ser Thr Ser Thr Met Ala Leu Phe Asp Tyr Trp Gly Gln
            100                 105                 110

Gly Thr Leu Val Thr Val Ser Ser
            115                 120
```

```
<210> SEQ ID NO 156
<211> LENGTH: 122
<212> TYPE: PRT
<213> ORGANISM: Homo sapiens

<400> SEQUENCE: 156

Glu Val Gln Leu Leu Glu Ser Gly Gly Gly Leu Val Arg Pro Gly Gly
1               5                   10                  15

Ser Leu Arg Leu Ser Cys Ala Ala Ser Gly Phe Thr Phe Pro Glu Tyr
            20                  25                  30

Asn Met His Trp Val Arg Gln Ala Pro Gly Lys Gly Leu Glu Trp Val
        35                  40                  45

Ser Ala Ile Gly Thr Ala Gly Gly Ser Thr Tyr Tyr Ala Asp Ser Val
    50                  55                  60

Lys Gly Arg Phe Thr Ile Ser Arg Asp Asn Ser Lys Asn Met Leu Tyr
65                  70                  75                  80

Leu Gln Met Asn Ser Leu Arg Ala Glu Asp Thr Ala Val Tyr Tyr Cys
                85                  90                  95

Ala Lys Gly Tyr Arg Pro Arg Thr Gly Ser Met Leu Phe Asp Tyr Trp
            100                 105                 110

Gly Gln Gly Thr Leu Val Thr Val Ser Ser
        115                 120

<210> SEQ ID NO 157
<211> LENGTH: 120
<212> TYPE: PRT
<213> ORGANISM: Homo sapiens

<400> SEQUENCE: 157

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Lys Tyr
            20                  25                  30

Asn Met Tyr Trp Val Arg Gln Ala Pro Gly Lys Gly Leu Glu Trp Val
        35                  40                  45

Ser Ala Ile Ser Pro Lys Gly Gln Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Gly Met Gly Ser Asp Ala Ile Thr Phe Asp Tyr Trp Gly Gln
            100                 105                 110

Gly Thr Leu Val Thr Val Ser Ser
        115                 120

<210> SEQ ID NO 158
<211> LENGTH: 122
<212> TYPE: PRT
<213> ORGANISM: Homo sapiens

<400> SEQUENCE: 158

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Asp Tyr
            20                  25                  30

Asp Met Ala Trp Val Arg Gln Ala Pro Gly Lys Gly Leu Glu Trp Val
```

```
                35                  40                  45
Ser Phe Ile Asp Arg Lys Gly His His Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Thr Thr Asp Ile Gln Arg Leu Asn Ser Ala Phe Asp Tyr Trp
                100                 105                 110

Gly Gln Gly Thr Leu Val Thr Val Ser Ser
                115                 120

<210> SEQ ID NO 159
<211> LENGTH: 119
<212> TYPE: PRT
<213> ORGANISM: Homo sapiens

<400> SEQUENCE: 159

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Gly Asn Gly
                 20                  25                  30

Val Met Ala Trp Val Arg Gln Ala Pro Gly Lys Gly Leu Glu Trp Val
             35                  40                  45

Ser His Ile Asn Glu Asn Gly Gly Ala Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro Ser Ile Glu Ser Pro Ile Phe Asp Tyr Trp Gly Gln Gly
                100                 105                 110

Thr Leu Val Thr Val Ser Ser
                115

<210> SEQ ID NO 160
<211> LENGTH: 119
<212> TYPE: PRT
<213> ORGANISM: Homo sapiens

<400> SEQUENCE: 160

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ala His Glu
                 20                  25                  30

Pro Met Val Trp Val Arg Gln Ala Pro Gly Lys Gly Leu Glu Trp Val
             35                  40                  45

Ser His Ile Asp Arg Val Gly Gln Asp Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Leu Pro Lys Arg Gly Pro Arg Phe Asp Tyr Trp Gly Gln Gly
                100                 105                 110

Thr Leu Val Thr Val Ser Ser
```

-continued

115

<210> SEQ ID NO 161
<211> LENGTH: 121
<212> TYPE: PRT
<213> ORGANISM: Homo sapiens

<400> SEQUENCE: 161

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Glu Ser
            20                  25                  30

Val Met Gly Trp Val Arg Gln Ala Pro Gly Lys Gly Leu Glu Trp Val
        35                  40                  45

Ser Ala Ile Ser Pro Gly Gly Ser Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys Arg Thr Gly Pro Pro Gly Ser Thr Val Phe Asp Tyr Trp Gly
            100                 105                 110

Gln Gly Thr Leu Val Thr Val Ser Ser
            115                 120

<210> SEQ ID NO 162
<211> LENGTH: 116
<212> TYPE: PRT
<213> ORGANISM: Homo sapiens

<400> SEQUENCE: 162

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Asp Glu
            20                  25                  30

Pro Met His Trp Val Arg Gln Ala Pro Gly Lys Gly Leu Glu Trp Val
        35                  40                  45

Ser Gly Ile Gly Lys Glu Gly Gln Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Gly Gly Pro Phe Asp Tyr Trp Gly Gln Gly Thr Leu Val
            100                 105                 110

Thr Val Ser Ser
        115

<210> SEQ ID NO 163
<211> LENGTH: 121
<212> TYPE: PRT
<213> ORGANISM: Homo sapiens

<400> SEQUENCE: 163

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Tyr Gly
            20                  25                  30

```
Asn Met Phe Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Met Thr Thr Asp Ser Pro Pro Gly Phe Asp Tyr Trp Gly
            100                 105                 110

Gln Gly Thr Leu Val Thr Val Ser Ser
        115                 120

<210> SEQ ID NO 164
<211> LENGTH: 122
<212> TYPE: PRT
<213> ORGANISM: Homo sapiens

<400> SEQUENCE: 164

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ala Lys Glu
             20                  25                  30

Thr Met Ser Trp Val Arg Gln Ala Pro Gly Lys Gly Leu Glu Trp Val
        35                  40                  45

Ser Trp Ile Ser Pro His Gly Ala Leu Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro Arg Phe Ser Tyr Tyr Pro Arg Val Ser Phe Asp Tyr Trp
            100                 105                 110

Gly Gln Gly Thr Leu Val Thr Val Ser Ser
        115                 120

<210> SEQ ID NO 165
<211> LENGTH: 119
<212> TYPE: PRT
<213> ORGANISM: Homo sapiens

<400> SEQUENCE: 165

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Gly Asn Gly
             20                  25                  30

Asn Met Val Trp Val Arg Gln Ala Pro Gly Lys Gly Leu Glu Trp Val
        35                  40                  45

Ser His Ile Asp Glu Tyr Gly Thr Asn Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro Arg Asn Asp Arg Pro Gly Phe Asp Tyr Trp Gly Gln Gly
            100                 105                 110
```

Thr Leu Val Thr Val Ser Ser
        115

<210> SEQ ID NO 166
<211> LENGTH: 119
<212> TYPE: PRT
<213> ORGANISM: Homo sapiens
<220> FEATURE:
<221> NAME/KEY: VARIANT
<222> LOCATION: 53
<223> OTHER INFORMATION: Xaa = Any Amino Acid

<400> SEQUENCE: 166

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Gly Asn Gly
            20                  25                  30

Asn Met Val Trp Val Arg Gln Ala Pro Gly Lys Gly Leu Glu Trp Val
        35                  40                  45

Ser His Ile Asp Xaa Tyr Gly Thr Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Gly Asp Thr Ala Val Tyr Tyr Cys
                85                  90                  95

Ala Lys Pro Arg Asn Asp Arg Pro Gly Phe Asp Tyr Trp Gly Gln Gly
            100                 105                 110

Thr Leu Val Thr Val Ser Ser
        115

<210> SEQ ID NO 167
<211> LENGTH: 124
<212> TYPE: PRT
<213> ORGANISM: Homo sapiens

<400> SEQUENCE: 167

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala Gly Gln
            20                  25                  30

Asp Met Arg Trp Val Arg Gln Ala Pro Gly Lys Gly Leu Glu Trp Val
        35                  40                  45

Ser Ser Ile Pro Ser Ser Gly Phe Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Ala Lys Asp Arg Ser Val Ser Met Pro Tyr Phe Asp
            100                 105                 110

Tyr Trp Gly Gln Gly Thr Leu Val Thr Val Ser Ser
        115                 120

<210> SEQ ID NO 168
<211> LENGTH: 120
<212> TYPE: PRT
<213> ORGANISM: Homo sapiens

<400> SEQUENCE: 168

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Met Arg Pro
             20                  25                  30

Asp Met Val Trp Val Arg Gln Ala Pro Gly Lys Gly Leu Glu Trp Val
             35                  40                  45

Ser Thr Ile Lys Asp Trp Gly Asp Gln Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Ala Ala Val Tyr Tyr Cys
                 85                  90                  95

Ala Lys Ala Asp Ser Arg Ala Gln Leu Asp Phe Asp Tyr Trp Gly Gln
             100                 105                 110

Gly Thr Leu Val Thr Val Ser Ser
            115                 120

<210> SEQ ID NO 169
<211> LENGTH: 121
<212> TYPE: PRT
<213> ORGANISM: Homo sapiens

<400> SEQUENCE: 169

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro Tyr Phe Leu Phe Arg Ala Thr Ser Phe Asp Tyr Trp Gly
             100                 105                 110

Gln Gly Thr Leu Val Thr Val Ser Ser
            115                 120

<210> SEQ ID NO 170
<211> LENGTH: 120
<212> TYPE: PRT
<213> ORGANISM: Homo sapiens

<400> SEQUENCE: 170

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe His Asp Asp
             20                  25                  30

Asp Met Val Trp Val Arg Gln Ala Pro Gly Lys Gly Leu Glu Trp Val
             35                  40                  45

Ser Ser Ile Pro Gly Asn Gly Tyr Val Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80
```

```
Leu Gln Met Asn Ser Leu Arg Ala Glu Asp Thr Ala Val Tyr Tyr Cys
                85                  90                  95

Ala Lys Arg Pro Asp Pro Thr Ser Val Phe Phe Asp Tyr Trp Gly Gln
            100                 105                 110

Gly Thr Leu Val Thr Val Ser Ser
        115                 120

<210> SEQ ID NO 171
<211> LENGTH: 116
<212> TYPE: PRT
<213> ORGANISM: Homo sapiens

<400> SEQUENCE: 171

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Asp Asp
            20                  25                  30

Trp Met Thr Trp Val Arg Gln Ala Pro Gly Lys Gly Leu Glu Trp Val
        35                  40                  45

Ser Gly Ile Ala Ala Tyr Gly Ile Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Glu Ser Gly Lys Val Phe Asp Tyr Trp Gly Gln Gly Thr Leu Val
            100                 105                 110

Thr Val Ser Ser
        115

<210> SEQ ID NO 172
<211> LENGTH: 120
<212> TYPE: PRT
<213> ORGANISM: Homo sapiens

<400> SEQUENCE: 172

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Glu Arg
            20                  25                  30

Pro Met Asp Trp Val Arg Gln Ala Pro Gly Lys Gly Leu Glu Trp Val
        35                  40                  45

Ser Leu Ile Gly Ala Asp Gly Leu Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Phe Arg Pro Gly Leu Leu Trp Phe Asp Tyr Trp Gly Gln
            100                 105                 110

Gly Thr Leu Val Thr Val Ser Ser
        115                 120

<210> SEQ ID NO 173
<211> LENGTH: 119
<212> TYPE: PRT
<213> ORGANISM: Homo sapiens
```

<400> SEQUENCE: 173

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Gly Gln
            20                  25                  30

Asp Met Gln Trp Val Arg Gln Ala Pro Gly Lys Gly Leu Glu Trp Val
        35                  40                  45

Ser Gly Ile Asn Ala Asp Gly Met Ala Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Thr Ser Pro Thr Met Arg Ser Phe Asp Tyr Trp Gly Gln Gly
            100                 105                 110

Thr Leu Val Thr Val Ser Ser
            115

<210> SEQ ID NO 174
<211> LENGTH: 118
<212> TYPE: PRT
<213> ORGANISM: Homo sapiens

<400> SEQUENCE: 174

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Glu Glu
            20                  25                  30

Tyr Met Gln Trp Val Arg Gln Ala Pro Gly Lys Gly Leu Glu Trp Val
        35                  40                  45

Ser Leu Ile Pro His Thr Gly Asn Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Leu Ala Asn Ser Leu Leu Phe Asp Tyr Trp Gly Gln Gly Thr
            100                 105                 110

Leu Val Thr Val Ser Ser
            115

<210> SEQ ID NO 175
<211> LENGTH: 120
<212> TYPE: PRT
<213> ORGANISM: Homo sapiens

<400> SEQUENCE: 175

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe His Arg Cys
            20                  25                  30

Lys Met Gly Trp Val Arg Gln Ala Pro Gly Lys Gly Leu Glu Trp Val
        35                  40                  45

Ser Phe Ile Glu Tyr Asp Gly Arg Asp Thr Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu Cys Thr Arg Pro Tyr Gly Met Phe Asp Tyr Trp Gly Gln
            100                 105                 110

Gly Thr Leu Val Thr Val Ser Ser
            115                 120
```

<210> SEQ ID NO 176
<211> LENGTH: 120
<212> TYPE: PRT
<213> ORGANISM: Homo sapiens

<400> SEQUENCE: 176

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Asn Arg Tyr
             20                  25                  30

Ser Met Gly Trp Leu Arg Gln Ala Pro Gly Lys Gly Leu Glu Trp Val
         35                  40                  45

Ser Phe Ile Asp Lys Val Gly His His Thr Trp Tyr Glu Asp Pro Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ile Ser Gln Phe Gly Pro Asn Ala Phe Asp Tyr Trp Gly Gln
            100                 105                 110

Gly Thr Gln Val Thr Val Ser Ser
            115                 120
```

<210> SEQ ID NO 177
<211> LENGTH: 120
<212> TYPE: PRT
<213> ORGANISM: Homo sapiens
<220> FEATURE:
<221> NAME/KEY: VARIANT
<222> LOCATION: 101
<223> OTHER INFORMATION: Xaa = Any Amino Acid

<400> SEQUENCE: 177

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Thr Arg Tyr
             20                  25                  30

Ser Met Gly Trp Val Arg Gln Ala Pro Gly Lys Gly Leu Glu Trp Val
         35                  40                  45

Ser Met Ile Ala His Ala Gly Pro Glu Arg Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ile Ser Xaa Phe Gly Ser Asn Ala Phe Asp Tyr Trp Gly Gln
            100                 105                 110

Gly Thr Leu Val Thr Val Ser Ser
            115                 120
```

```
<210> SEQ ID NO 178
<211> LENGTH: 120
<212> TYPE: PRT
<213> ORGANISM: Homo sapiens

<400> SEQUENCE: 178
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Arg Tyr
            20                  25                  30

Asn Met Gly Trp Val Arg Gln Ala Pro Gly Lys Gly Leu Glu Trp Val
        35                  40                  45

Ser Phe Ile Asp Pro Pro Ser Val His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Ile Ser Gln Phe Gly Ser Asn Ala Phe Asp Tyr Trp Gly Gln
            100                 105                 110

Gly Thr Leu Val Thr Val Ser Ser
        115                 120

```
<210> SEQ ID NO 179
<211> LENGTH: 120
<212> TYPE: PRT
<213> ORGANISM: Homo sapiens
<220> FEATURE:
<221> NAME/KEY: VARIANT
<222> LOCATION: 96
<223> OTHER INFORMATION: Xaa = Any Amino Acid

<400> SEQUENCE: 179
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Arg Tyr
            20                  25                  30

Ser Met Gly Trp Val Arg Gln Ala Pro Gly Lys Gly Leu Glu Trp Val
        35                  40                  45

Ser Phe Ile Asp Pro Pro Ser Val His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Xaa
                85                  90                  95

Ala Glu Ile Ser Gln Phe Gly Ser Asn Ala Phe Asp Tyr Trp Gly Gln
            100                 105                 110

Gly Thr Leu Val Thr Val Ser Ser
        115                 120

```
<210> SEQ ID NO 180
<211> LENGTH: 120
<212> TYPE: PRT
<213> ORGANISM: Homo sapiens

<400> SEQUENCE: 180
```

Glu Val Gln Leu Phe Glu Ser Gly Gly Gly Leu Val Gln Pro Gly Gly
1               5                   10                  15

-continued

Ser Leu Arg Leu Ser Cys Ala Ala Ser Gly Phe Thr Phe Thr Arg Tyr
            20                  25                  30

Ser Met Gly Trp Val Arg Gln Ala Pro Gly Lys Gly Leu Glu Trp Val
            35                  40                  45

Ser Met Ile Ala His Ala Gly Pro Glu Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Ser Asn Ala Leu Asp Tyr Trp Gly Arg
            100                 105                 110

Gly Thr Leu Val Thr Val Ser Ser
            115                 120

<210> SEQ ID NO 181
<211> LENGTH: 122
<212> TYPE: PRT
<213> ORGANISM: Homo sapiens

<400> SEQUENCE: 181

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Arg Tyr
            20                  25                  30

Asn Met Gly Trp Val Arg Gln Ala Pro Gly Lys Gly Leu Glu Trp Val
            35                  40                  45

Ser Leu Ile Asp Pro Ser Gly Gly His Thr Tyr Tyr Ala Asp Ser Val
        50                  55                  60

Lys Gly Arg Phe Thr Ile Ser Arg Asn Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Lys Pro Val Phe Ser Asp Trp Pro Ala Val Glu Phe Asp Tyr Trp
            100                 105                 110

Gly Gln Gly Thr Val Val Thr Val Ser Ser
            115                 120

<210> SEQ ID NO 182
<211> LENGTH: 119
<212> TYPE: PRT
<213> ORGANISM: Homo sapiens

<400> SEQUENCE: 182

Glu Val Gln Leu Leu Glu Ser Gly Gly Gly Met Val Gln Pro Gly Gly
1               5                   10                  15

Ser Leu Arg Leu Ser Cys Ala Ala Ser Gly Phe Thr Phe Glu His Glu
            20                  25                  30

Gly Met Val Trp Val Arg Gln Ala Pro Gly Lys Gly Leu Glu Trp Val
            35                  40                  45

Ser His Ile Gly Glu Asp Gly Gln Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala Asn Ile Pro Lys Ala Gly Pro Ser Phe Asp Tyr Trp Gly Gln Gly
                100                 105                 110

Thr Leu Val Thr Val Ser Ser
        115

<210> SEQ ID NO 183
<211> LENGTH: 119
<212> TYPE: PRT
<213> ORGANISM: Homo sapiens

<400> SEQUENCE: 183

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
         35                  40                  45

Ser Gln Ile Ser Asn Thr Gly Gly His Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Tyr Thr Gly Arg Trp Glu Pro Phe Asp Tyr Trp Gly Gln Gly
                100                 105                 110

Thr Leu Val Thr Val Ser Ser
        115

<210> SEQ ID NO 184
<211> LENGTH: 120
<212> TYPE: PRT
<213> ORGANISM: Homo sapiens

<400> SEQUENCE: 184

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Glu Trp Tyr
             20                  25                  30

Trp Met Gly Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Lys Leu Gly Gly Gly Pro Asn Phe Asp Tyr Trp Gly Gln
                100                 105                 110

Gly Thr Leu Val Thr Val Ser Ser
        115                 120

<210> SEQ ID NO 185
<211> LENGTH: 115
<212> TYPE: PRT
<213> ORGANISM: Homo sapiens

<400> SEQUENCE: 185
```

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asp Leu Tyr
            20                  25                  30

Asn Met Phe Trp Val Arg Gln Ala Pro Gly Lys Gly Leu Glu Trp Val
        35                  40                  45

Ser Phe Ile Ser Gln Thr Gly Arg Leu Thr Trp Tyr Ala Asp Ser Val
    50                  55                  60

Lys Gly Arg Phe Thr Ile Ser Arg Asp Asn Lys Asn Thr Leu Tyr
65                   70                  75                  80

Leu Gln Met Asn Ser Leu Arg Ala Glu Asp Thr Ala Val Tyr Tyr Cys
                85                  90                  95

Ala Lys Thr Leu Glu Asp Phe Asp Tyr Trp Gly Gln Gly Thr Leu Val
            100                 105                 110

Thr Val Ser
        115

<210> SEQ ID NO 186
<211> LENGTH: 118
<212> TYPE: PRT
<213> ORGANISM: Homo sapiens

<400> SEQUENCE: 186

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Pro Val Tyr
            20                  25                  30

Met Met Gly Trp Val Arg Gln Ala Pro Gly Lys Gly Leu Glu Trp Val
        35                  40                  45

Ser Ser Ile Asp Ala Leu Gly Arg Thr Gly Tyr Ala Asp Ser Val
    50                  55                  60

Lys Gly Arg Phe Thr Ile Ser Arg Asp Asn Ser Lys Asn Thr Leu Tyr
65                   70                  75                  80

Leu Gln Met Asn Ser Leu Arg Ala Glu Asp Thr Ala Val Tyr Tyr Cys
                85                  90                  95

Ala Lys Thr Met Ser Asn Lys Thr His Thr Phe Asp Tyr Trp Gly Gln
            100                 105                 110

Gly Thr Leu Val Thr Ser
        115

<210> SEQ ID NO 187
<211> LENGTH: 115
<212> TYPE: PRT
<213> ORGANISM: Homo sapiens
<220> FEATURE:
<221> NAME/KEY: VARIANT
<222> LOCATION: 57
<223> OTHER INFORMATION: Xaa = Any Amino Acid

<400> SEQUENCE: 187

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Ala Tyr
            20                  25                  30

Asn Met Thr Trp Val Arg Gln Ala Pro Gly Lys Gly Leu Glu Trp Val
        35                  40                  45

Ser Ser Ile Asn Thr Phe Gly Asn Xaa Thr Arg Tyr Ala Asp Ser Val
    50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Arg Pro Phe Asp Tyr Trp Gly Gln Gly Thr Leu Val
            100                 105                 110

Thr Val Ser
        115

<210> SEQ ID NO 188
<211> LENGTH: 119
<212> TYPE: PRT
<213> ORGANISM: Homo sapiens
<220> FEATURE:
<221> NAME/KEY: VARIANT
<222> LOCATION: 30
<223> OTHER INFORMATION: Xaa = Any Amino Acid

<400> SEQUENCE: 188

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Xaa Gly Tyr
            20                  25                  30

Arg Met Gly Trp Val Arg Gln Ala Pro Gly Lys Gly Leu Glu Trp Val
            35                  40                  45

Ser Trp Ile Thr Arg Thr Gly Gly Thr Thr Gln Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Ala Lys Leu Val Gly Val Gly Phe Asp Tyr Trp Gly Gln
            100                 105                 110

Gly Thr Leu Val Thr Val Ser
        115

<210> SEQ ID NO 189
<211> LENGTH: 119
<212> TYPE: PRT
<213> ORGANISM: Homo sapiens
<220> FEATURE:
<221> NAME/KEY: VARIANT
<222> LOCATION: 33
<223> OTHER INFORMATION: Xaa = Any Amino Acid

<400> SEQUENCE: 189

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Lys Tyr
            20                  25                  30

Xaa Met Gly Trp Val Arg Gln Ala Pro Gly Lys Gly Leu Glu Trp Val
            35                  40                  45

Ser Gln Ile Gly Ala Lys Gly Gln Ser Thr Asp Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala Lys Lys Lys Arg Gly Glu Asn Tyr Phe Asp Tyr Trp Gly Gln
            100                 105                 110

Gly Thr Leu Val Thr Val Ser
            115

<210> SEQ ID NO 190
<211> LENGTH: 119
<212> TYPE: PRT
<213> ORGANISM: Homo sapiens

<400> SEQUENCE: 190

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Arg Arg Tyr
             20                  25                  30

Ser Met Ser Trp Val Arg Gln Ala Pro Gly Lys Gly Leu Glu Trp Val
         35                  40                  45

Ser Asp Ile Ser Arg Ser Gly Arg Tyr Thr His Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Arg Ile Asp Ser Ser Gln Asn Gly Phe Asp Tyr Trp Gly Gln
            100                 105                 110

Gly Thr Leu Val Thr Val Ser
            115

<210> SEQ ID NO 191
<211> LENGTH: 115
<212> TYPE: PRT
<213> ORGANISM: Homo sapiens
<220> FEATURE:
<221> NAME/KEY: VARIANT
<222> LOCATION: 30
<223> OTHER INFORMATION: Xaa = Any Amino Acid

<400> SEQUENCE: 191

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Xaa Gly Tyr
             20                  25                  30

Lys Met Phe Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gln Lys Glu Asn Phe Asp Tyr Trp Gly Gln Gly Thr Leu Val
            100                 105                 110

Thr Val Ser
        115

<210> SEQ ID NO 192
<211> LENGTH: 119
<212> TYPE: PRT
<213> ORGANISM: Homo sapiens
```

<400> SEQUENCE: 192

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Asp Tyr
            20                  25                  30

Ala Met Trp Trp Val Arg Gln Ala Pro Gly Lys Gly Leu Glu Trp Val
        35                  40                  45

Ser Val Ile Ser Ser Asn Gly Ser Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Val Arg Lys Arg Thr Pro Glu Phe Asp Tyr Trp Gly Gln
            100                 105                 110

Gly Thr Leu Val Thr Val Ser
        115

<210> SEQ ID NO 193
<211> LENGTH: 119
<212> TYPE: PRT
<213> ORGANISM: Homo sapiens

<400> SEQUENCE: 193

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Arg Tyr
            20                  25                  30

Lys Met Gly Trp Val Arg Gln Ala Pro Gly Lys Gly Leu Glu Trp Val
        35                  40                  45

Ser Ala Ile Gly Arg Asn Gly Thr Lys Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Tyr Thr Gly Lys Pro Ala Ala Phe Asp Tyr Trp Gly Gln
            100                 105                 110

Gly Thr Leu Val Thr Val Ser
        115

<210> SEQ ID NO 194
<211> LENGTH: 119
<212> TYPE: PRT
<213> ORGANISM: Homo sapiens
<220> FEATURE:
<221> NAME/KEY: VARIANT
<222> LOCATION: 33
<223> OTHER INFORMATION: Xaa = Any Amino Acid

<400> SEQUENCE: 194

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Lys Tyr
            20                  25                  30

Xaa Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
          50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Met Leu Arg Thr Lys Asn Lys Val Phe Asp Tyr Trp Gly Gln
                100                 105                 110

Gly Thr Leu Val Thr Val Ser
                115

<210> SEQ ID NO 195
<211> LENGTH: 119
<212> TYPE: PRT
<213> ORGANISM: Homo sapiens

<400> SEQUENCE: 195

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Arg Arg Tyr
                20                  25                  30

Lys Met Gly Trp Val Arg Gln Ala Pro Gly Lys Gly Leu Glu Trp Val
                35                  40                  45

Ser Ala Ile Gly Arg Asn Gly Thr Lys Thr Asn Tyr Ala Asp Ser Val
          50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ile Tyr Thr Gly Lys Pro Ala Ala Phe Asp Tyr Trp Gly Gln
                100                 105                 110

Gly Thr Leu Val Thr Val Ser
                115

<210> SEQ ID NO 196
<211> LENGTH: 119
<212> TYPE: PRT
<213> ORGANISM: Homo sapiens
<220> FEATURE:
<221> NAME/KEY: VARIANT
<222> LOCATION: 30
<223> OTHER INFORMATION: Xaa = Any Amino Acid

<400> SEQUENCE: 196

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Xaa Ser Tyr
                20                  25                  30

Arg Met Gly Trp Val Arg Gln Ala Pro Gly Lys Gly Leu Glu Trp Val
                35                  40                  45

Ser Ser Ile Ser Ser Arg Gly Arg His Thr Ser Tyr Ala Asp Ser Val
          50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Arg Val Pro Gly Arg Gly Arg Ser Phe Asp Tyr Trp Gly Gln

Gly Thr Leu Val Thr Val Ser
        115

<210> SEQ ID NO 197
<211> LENGTH: 119
<212> TYPE: PRT
<213> ORGANISM: Homo sapiens

<400> SEQUENCE: 197

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Pro Phe Arg Arg Tyr
            20                  25                  30

Arg Met Arg Trp Val Arg Gln Ala Pro Gly Lys Gly Leu Glu Trp Val
        35                  40                  45

Ser Gly Ile Ser Pro Gly Gly Lys His Thr Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Gly Gly Ala Ser Ser Ala Phe Asp Tyr Trp Gly Gln
            100                 105                 110

Gly Thr Leu Val Thr Val Ser
        115

<210> SEQ ID NO 198
<211> LENGTH: 119
<212> TYPE: PRT
<213> ORGANISM: Homo sapiens
<220> FEATURE:
<221> NAME/KEY: VARIANT
<222> LOCATION: 30
<223> OTHER INFORMATION: Xaa = Any Amino Acid

<400> SEQUENCE: 198

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Xaa Arg Tyr
            20                  25                  30

Gly Met Val Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg His Ser Ser Glu Ala Arg Gln Phe Asp Tyr Trp Gly Gln
            100                 105                 110

Gly Thr Leu Val Thr Val Ser
        115

<210> SEQ ID NO 199
<211> LENGTH: 108
<212> TYPE: PRT
<213> ORGANISM: Homo sapiens

<400> SEQUENCE: 199

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Pro Ile Gly Val Ala
            20                  25                  30

Leu Asn Trp Tyr Gln Gln Lys Pro Gly Lys Ala Pro Lys Leu Leu Ile
        35                  40                  45

Tyr Gly Gly Ser Tyr Leu Gln Ser Gly Val Pro Ser Arg Tyr Ser Gly
50                  55                  60

Ser Gly Ser Gly Thr Asp Phe Thr Leu Thr Ile Ser Ser Leu Gln Pro
65                  70                  75                  80

Gly Asp Phe Ala Thr Tyr Tyr Cys Gln Gln Asp Trp Arg Tyr Pro Gly
                85                  90                  95

Thr Phe Gly Gln Gly Thr Lys Val Glu Ile Lys Arg
            100                 105

<210> SEQ ID NO 200
<211> LENGTH: 108
<212> TYPE: PRT
<213> ORGANISM: Homo sapiens

<400> SEQUENCE: 200

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Ile His Thr Ser
            20                  25                  30

Leu Gln Trp Tyr Gln Gln Lys Pro Gly Lys Ala Pro Lys Leu Leu Ile
        35                  40                  45

Tyr Gly Ser Ser Arg Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn His His Ser Pro Phe
                85                  90                  95

Thr Phe Gly Gln Gly Thr Lys Val Glu Ile Lys Arg
            100                 105

<210> SEQ ID NO 201
<211> LENGTH: 119
<212> TYPE: PRT
<213> ORGANISM: Homo sapiens

<400> SEQUENCE: 201

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Lys Tyr
            20                  25                  30

Asp Met His Trp Val Arg Gln Ala Pro Gly Lys Gly Leu Glu Trp Val
        35                  40                  45

Ser Thr Ile Ser Pro Ser Gly Arg Arg Thr Tyr Tyr Ala Asp Ser Val
50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Asn Leu Asp Gln Val Leu Ser Phe Asp Tyr Trp Gly Gln Gly

Thr Leu Val Thr Val Ser Ser
        115

<210> SEQ ID NO 202
<211> LENGTH: 120
<212> TYPE: PRT
<213> ORGANISM: Homo sapiens

<400> SEQUENCE: 202

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Ser Met Ser Trp Val Arg Gln Ala Pro Gly Lys Gly Leu Glu Trp Val
        35                  40                  45

Ser Gly Ile Asp Asn Gly Gly His Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Ser Ser Gly Leu Pro Phe Pro Phe Asp Tyr Trp Gly Gln
            100                 105                 110

Gly Thr Leu Val Thr Val Ser Ser
        115                 120

<210> SEQ ID NO 203
<211> LENGTH: 120
<212> TYPE: PRT
<213> ORGANISM: Homo sapiens

<400> SEQUENCE: 203

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Arg Tyr
            20                  25                  30

Ser Met Gly Trp Val Arg Gln Ala Pro Gly Lys Gly Leu Glu Trp Val
        35                  40                  45

Ser Arg Ile Asp Ser Tyr Gly Arg Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Ser Asn Ala Phe Asp Tyr Trp Gly Gln
            100                 105                 110

Gly Thr Leu Val Thr Val Ser Ser
        115                 120

<210> SEQ ID NO 204
<211> LENGTH: 108
<212> TYPE: PRT
<213> ORGANISM: Homo sapiens

<400> SEQUENCE: 204

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Tyr Ile His Ser Ser
            20                  25                  30

Leu Gln Trp Tyr Gln Gln Lys Pro Gly Lys Ala Pro Lys Leu Leu Ile
        35                  40                  45

Tyr Ser Ser Ser Arg Leu His Ser Gly Val Pro Pro Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Asn His Phe Arg Pro His
                85                  90                  95

Thr Phe Gly Gln Gly Thr Lys Val Glu Ile Lys Arg
            100                 105
```

<210> SEQ ID NO 205
<211> LENGTH: 120
<212> TYPE: PRT
<213> ORGANISM: Homo sapiens

<400> SEQUENCE: 205

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Asn Arg Tyr
            20                  25                  30

Ser Met Gly Trp Leu Arg Gln Ala Pro Gly Lys Gly Leu Glu Trp Val
        35                  40                  45

Ser Arg Ile Asp Ser Tyr Gly Arg Gly Thr Tyr Tyr Glu Asp Pro Val
 50                  55                  60

Lys Gly Arg Phe Ser Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Ser Asn Ala Phe Asp Tyr Trp Gly Gln
            100                 105                 110

Gly Thr Gln Val Thr Val Ser Ser
        115                 120
```

<210> SEQ ID NO 206
<211> LENGTH: 120
<212> TYPE: PRT
<213> ORGANISM: Homo sapiens

<400> SEQUENCE: 206

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Arg Cys
            20                  25                  30

Ser Met Gly Trp Leu Arg Gln Ala Pro Gly Lys Gly Leu Glu Trp Val
        35                  40                  45

Ser Arg Ile Asp Ser Tyr Gly Arg Gly Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Ile Ser Lys Phe Gly Ser Asn Ala Phe Asp Tyr Trp Gly Gln
            100                 105                 110
```

-continued

Gly Thr Leu Val Thr Val Ser Ser
        115                 120

<210> SEQ ID NO 207
<211> LENGTH: 120
<212> TYPE: PRT
<213> ORGANISM: Homo sapiens

<400> SEQUENCE: 207

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Arg Tyr
            20                  25                  30

Ser Met Gly Trp Leu Arg Gln Ala Pro Gly Lys Gly Leu Glu Trp Val
        35                  40                  45

Ser Arg Ile Asp Ser Tyr Gly Arg Gly Thr Tyr Asp Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Ser Asn Ala Phe Asp Tyr Trp Gly Gln
            100                 105                 110

Gly Thr Leu Val Thr Val Ser Ser
        115                 120

<210> SEQ ID NO 208
<211> LENGTH: 120
<212> TYPE: PRT
<213> ORGANISM: Homo sapiens

<400> SEQUENCE: 208

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Thr Arg Tyr
            20                  25                  30

Ser Met Gly Trp Leu Arg Gln Ala Pro Gly Lys Gly Leu Glu Trp Val
        35                  40                  45

Ser Arg Ile Asp Ser Tyr Gly Arg Gly Thr Tyr Asp Thr Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Ser Asn Ala Phe Asp Tyr Trp Gly Gln
            100                 105                 110

Gly Thr Leu Val Thr Val Ser Ser
        115                 120

<210> SEQ ID NO 209
<211> LENGTH: 120
<212> TYPE: PRT
<213> ORGANISM: Homo sapiens

<400> SEQUENCE: 209

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Thr Arg Tyr
            20                  25                  30

Ser Met Gly Trp Leu Arg Gln Ala Pro Gly Lys Gly Leu Glu Trp Val
        35                  40                  45

Ser Arg Ile Asp Ser Tyr Gly Arg Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Ser Asn Ala Phe Asp Tyr Trp Gly Gln
            100                 105                 110

Gly Thr Leu Val Thr Val Ser Ser
            115                 120

<210> SEQ ID NO 210
<211> LENGTH: 120
<212> TYPE: PRT
<213> ORGANISM: Homo sapiens

<400> SEQUENCE: 210

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Arg Tyr
            20                  25                  30

Ser Met Gly Trp Ile Arg Gln Ala Pro Gly Lys Gly Leu Glu Trp Val
        35                  40                  45

Ser Arg Ile Asp Ser Tyr Gly Arg Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Ser Asn Ala Phe Asp Tyr Trp Gly Gln
            100                 105                 110

Gly Thr Leu Val Thr Val Ser Ser
            115                 120

<210> SEQ ID NO 211
<211> LENGTH: 120
<212> TYPE: PRT
<213> ORGANISM: Homo sapiens

<400> SEQUENCE: 211

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Arg Tyr
            20                  25                  30

Ser Met Gly Trp Val Arg Gln Ala Pro Gly Lys Gly Leu Glu Trp Val
        35                  40                  45

Ser Arg Ile Asp Ser Tyr Gly Arg Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Lys Ile Ser Gln Phe Gly Ser Asn Ala Phe Asp Tyr Trp Gly Gln
            100                 105                 110
Gly Thr Val Val Thr Val Ser Ser
        115                 120

<210> SEQ ID NO 212
<211> LENGTH: 546
<212> TYPE: DNA
<213> ORGANISM: Homo sapiens

<400> SEQUENCE: 212
ctggtccctc acctagggga cagggagaag agagatagtg tgtgtcccca aggaaaatat    60
atccaccctc aaaataattc gatttgctgt accaagtgcc acaaaggaac ctacttgtac   120
aatgactgtc caggcccggg gcaggatacg gactgcaggg agtgtgagag cggctccttc   180
accgcttcag aaaaccacct cagacactgc ctcagctgct ccaaatgccg aaaggaaatg   240
ggtcaggtgg agatctcttc ttgcacagtg gaccgggaca ccgtgtgtgg ctgcaggaag   300
aaccagtacc ggcattattg gagtgaaaac ctttccagt gcttcaattg cagcctctgc   360
ctcaatggga ccgtgcacct ctcctgccag gagaaacaga caccgtgtg cacctgccat   420 gcaggtttct ttctaagaga aaacgagtgt gtctcctgta gtaactgtaa gaaaagcctg   480
gagtgcacga agttgtgcct accccagatt gagaatgtta agggcactga ggactcaggc   540
accaca                                                              546

<210> SEQ ID NO 213
<211> LENGTH: 182
<212> TYPE: PRT
<213> ORGANISM: Homo sapiens

<400> SEQUENCE: 213

Leu Val Pro His Leu Gly Asp Arg Glu Lys Arg Asp Ser Val Cys Pro
  1               5                  10                  15

Gln Gly Lys Tyr Ile His Pro Gln Asn Asn Ser Ile Cys Cys Thr Lys
             20                  25                  30

Cys His Lys Gly Thr Tyr Leu Tyr Asn Asp Cys Pro Gly Pro Gly Gln
         35                  40                  45

Asp Thr Asp Cys Arg Glu Cys Glu Ser Gly Ser Phe Thr Ala Ser Glu
     50                  55                  60

Asn His Leu Arg His Cys Leu Ser Cys Ser Lys Cys Arg Lys Glu Met
 65                  70                  75                  80

Gly Gln Val Glu Ile Ser Ser Cys Thr Val Asp Arg Asp Thr Val Cys
                 85                  90                  95

Gly Cys Arg Lys Asn Gln Tyr Arg His Tyr Trp Ser Glu Asn Leu Phe
            100                 105                 110

Gln Cys Phe Asn Cys Ser Leu Cys Leu Asn Gly Thr Val His Leu Ser
        115                 120                 125

Cys Gln Glu Lys Gln Asn Thr Val Cys Thr Cys His Ala Gly Phe Phe
    130                 135                 140

Leu Arg Glu Asn Glu Cys Val Ser Cys Ser Asn Cys Lys Lys Ser Leu
145                 150                 155                 160

Glu Cys Thr Lys Leu Cys Leu Pro Gln Ile Glu Asn Val Lys Gly Thr
                165                 170                 175

Glu Asp Ser Gly Thr Thr
            180
```

```
<210> SEQ ID NO 214
<211> LENGTH: 549
<212> TYPE: DNA
<213> ORGANISM: Mus musculus

<400> SEQUENCE: 214
ctagtccctt ctcttggtga ccgggagaag agggatagct tgtgtcccca aggaaagtat      60
gtccattcta agaacaattc catctgctgc accaagtgcc acaaggaac ctacttggtg     120 agtgactgtc cgagcccagg gcgggataca gtctgcaggg agtgtgaaaa gggcacccttt    180 acggcttccc agaattacct caggcagtgt ctcagttgca agacatgtcg gaaagaaatg    240
tcccaggtgg agatctctcc ttgccaagct gacaaggaca cggtgtgtgg ctgtaaggag    300
aaccagttcc aacgctacct gagtgagaca cacttccagt gcgtggactg cagcccctgc   360
ttcaacggca ccgtgacaat ccctgtaag gagactcaga caccgtgtg taactgccat     420 gcagggttct ttctgagaga aagtgagtgc gtcccttgca gccactgcaa gaaaaatgag   480
gagtgtatga agttgtgcct acctcctccg cttgcaaatg tcacaaaccc ccaggactca   540
ggtactgcg                                                                 549

<210> SEQ ID NO 215
<211> LENGTH: 183
<212> TYPE: PRT
<213> ORGANISM: Mus musculus

<400> SEQUENCE: 215

Leu Val Pro Ser Leu Gly Asp Arg Glu Lys Arg Asp Ser Leu Cys Pro
  1               5                  10                  15

Gln Gly Lys Tyr Val His Ser Lys Asn Asn Ser Ile Cys Cys Thr Lys
             20                  25                  30

Cys His Lys Gly Thr Tyr Leu Val Ser Asp Cys Pro Ser Pro Gly Arg
         35                  40                  45

Asp Thr Val Cys Arg Glu Cys Glu Lys Gly Thr Phe Thr Ala Ser Gln
     50                  55                  60

Asn Tyr Leu Arg Gln Cys Leu Ser Cys Lys Thr Cys Arg Lys Glu Met
 65                  70                  75                  80

Ser Gln Val Glu Ile Ser Pro Cys Gln Ala Asp Lys Asp Thr Val Cys
                 85                  90                  95

Gly Cys Lys Glu Asn Gln Phe Gln Arg Tyr Leu Ser Glu Thr His Phe
            100                 105                 110

Gln Cys Val Asp Cys Ser Pro Cys Phe Asn Gly Thr Val Thr Ile Pro
        115                 120                 125

Cys Lys Glu Thr Gln Asn Thr Val Cys Asn Cys His Ala Gly Phe Phe
    130                 135                 140

Leu Arg Glu Ser Glu Cys Val Pro Cys Ser His Cys Lys Lys Asn Glu
145                 150                 155                 160

Glu Cys Met Lys Leu Cys Leu Pro Pro Leu Ala Asn Val Thr Asn
                165                 170                 175

Pro Gln Asp Ser Gly Thr Ala
            180

<210> SEQ ID NO 216
<211> LENGTH: 108
<212> TYPE: PRT
<213> ORGANISM: Homo sapiens

<400> SEQUENCE: 216
```

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Tyr Ile His Thr Ser
                20                  25                  30

Val Gln Trp Tyr Gln Gln Lys Pro Gly Lys Ala Pro Lys Leu Leu Ile
             35                  40                  45

Tyr Gly Ser Ser Arg Leu His Ser Gly Val Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn His Tyr Ser Pro Phe
                85                  90                  95

Thr Phe Gly Gln Gly Thr Lys Val Glu Ile Lys Arg
            100                 105
```

<210> SEQ ID NO 217
<211> LENGTH: 108
<212> TYPE: PRT
<213> ORGANISM: Homo sapiens

<400> SEQUENCE: 217

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Tyr Ile His Thr Ser
                20                  25                  30

Val Gln Trp Tyr Gln Gln Lys Pro Gly Lys Ala Pro Lys Leu Leu Ile
             35                  40                  45

Tyr Gly Ser Ser Arg Leu His Ser Gly Val Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn His Tyr Ser Pro Phe
                85                  90                  95

Thr Tyr Gly Gln Gly Thr Lys Val Glu Ile Lys Arg
            100                 105
```

<210> SEQ ID NO 218
<211> LENGTH: 108
<212> TYPE: PRT
<213> ORGANISM: Homo sapiens

<400> SEQUENCE: 218

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Tyr Ile His Thr Ser
                20                  25                  30

Leu Gln Trp Tyr Gln Gln Lys Pro Gly Lys Ala Pro Lys Leu Leu Ile
             35                  40                  45

Tyr Gly Ser Ser Arg Leu His Ser Gly Val Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn His Tyr Ser Pro Phe
                85                  90                  95

Thr Phe Gly Gln Gly Thr Lys Val Glu Ile Lys Arg
            100                 105
```

<210> SEQ ID NO 219
<211> LENGTH: 108
<212> TYPE: PRT
<213> ORGANISM: Homo sapiens

<400> SEQUENCE: 219

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Ile His Thr Ser
            20                  25                  30

Leu Gln Trp Tyr Gln Gln Lys Pro Gly Lys Ala Leu Lys Leu Leu Ile
        35                  40                  45

Tyr Gly Ser Ser Arg Leu Gln Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln Asn His His Ser Pro Phe
                85                  90                  95

Thr Tyr Gly Gln Gly Thr Lys Val Glu Ile Lys Arg
            100                 105

<210> SEQ ID NO 220
<211> LENGTH: 108
<212> TYPE: PRT
<213> ORGANISM: Homo sapiens

<400> SEQUENCE: 220

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Ile His Thr Ser
            20                  25                  30

Leu Gln Trp Tyr Gln Gln Lys Pro Gly Lys Ala Pro Lys Leu Leu Ile
        35                  40                  45

Tyr Gly Ser Ser Arg Leu His Ser Gly Val Pro Ser Arg Phe Ser Gly
50                  55                  60

Ser Gly Ser Gly Thr Asp Phe Thr Leu Thr Ile Arg Ser Leu Gln Pro
65                  70                  75                  80

Glu Asp Leu Ala Thr Tyr Tyr Cys Gln Gln Asn His Tyr Ser Pro Phe
                85                  90                  95

Thr Phe Gly Gln Gly Thr Lys Val Glu Ile Asn Gly
            100                 105

<210> SEQ ID NO 221
<211> LENGTH: 108
<212> TYPE: PRT
<213> ORGANISM: Homo sapiens

<400> SEQUENCE: 221

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Ile His Thr Ser
            20                  25                  30

Leu Gln Trp Tyr Gln Gln Lys Pro Gly Lys Ala Pro Lys Leu Leu Ile
        35                  40                  45

Tyr Gly Ser Ser Arg Leu His Ser Gly Val Pro Ser Arg Phe Ser Gly
50                  55                  60

Ser Gly Ser Gly Thr Asp Phe Thr Leu Thr Ile Ser Ser Leu Gln Pro

```
                65                  70                  75                  80
Glu Asp Phe Ala Thr Tyr Tyr Cys Gln Gln Asn His Tyr Ser Pro Phe
                85                  90                  95

Thr Tyr Gly Gln Gly Thr Lys Val Glu Ile Lys Arg
            100                 105
```

<210> SEQ ID NO 222
<211> LENGTH: 119
<212> TYPE: PRT
<213> ORGANISM: Homo sapiens

<400> SEQUENCE: 222

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Pro Met Val Trp Val Arg Gln Ala Pro Gly Lys Gly Leu Glu Trp Val
            35                  40                  45

Ser His Ile Asp Arg Val Gly Gln Asp Thr Tyr Tyr Ala Asp Ser Val
        50                  55                  60

Lys Gly Arg Phe Ile Ile Ser Arg Asp Asn Ser Lys Asn Thr Leu Tyr
65                  70                  75                  80

Leu Gln Met Tyr Ser Leu Arg Ala Glu Asp Thr Ala Val Tyr Tyr Cys
                85                  90                  95

Ala Ile Leu Pro Lys Arg Gly Pro Arg Phe Asp Tyr Trp Gly Gln Gly
            100                 105                 110

Thr Leu Val Thr Val Ser Ser
            115
```

<210> SEQ ID NO 223
<211> LENGTH: 119
<212> TYPE: PRT
<213> ORGANISM: Homo sapiens

<400> SEQUENCE: 223

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Pro Met Val Trp Val Arg Gln Ala Pro Gly Lys Gly Leu Glu Trp Val
            35                  40                  45

Ser His Ile Asp Arg Val Gly Gln Asp Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Lys Arg Gly Pro Arg Phe Asp Tyr Trp Gly His Gly
            100                 105                 110

Thr Leu Val Thr Val Ser Ser
            115
```

<210> SEQ ID NO 224
<211> LENGTH: 119
<212> TYPE: PRT
<213> ORGANISM: Homo sapiens

<400> SEQUENCE: 224

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Pro Met Val Trp Val Arg Gln Ala Pro Gly Lys Gly Leu Glu Trp Val
                35                  40                  45

Ser His Ile Asp Arg Val Gly Gln Asp Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Leu Pro Lys Arg Gly Pro Arg Phe Asp Tyr Trp Gly Gln Gly
                100                 105                 110

Thr Leu Val Thr Val Ser Ser
            115

<210> SEQ ID NO 225
<211> LENGTH: 119
<212> TYPE: PRT
<213> ORGANISM: Homo sapiens

<400> SEQUENCE: 225

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ala His Glu
            20                  25                  30

Pro Met Val Trp Val Arg Gln Ala Pro Gly Lys Gly Leu Glu Trp Val
                35                  40                  45

Ser His Ile Asp Arg Val Gly Gln Asp Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Lys Arg Gly Pro Arg Phe Asp Tyr Trp Gly Leu Gly
                100                 105                 110

Thr Leu Val Thr Val Ser Ser
            115

<210> SEQ ID NO 226
<211> LENGTH: 119
<212> TYPE: PRT
<213> ORGANISM: Homo sapiens

<400> SEQUENCE: 226

Glu Val Lys Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Pro Met Val Trp Ile Arg Gln Ala Pro Gly Lys Gly Leu Glu Trp Val
                35                  40                  45

Ser His Ile Asp Arg Val Gly Gln Asp Thr Tyr Tyr Ala Asp Ser Val
        50                  55                  60

Lys Gly Arg Tyr Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Arg Leu Pro Lys Arg Gly Pro Arg Phe Asp Tyr Trp Gly Gln Gly
            100                 105                 110

Thr Leu Val Thr Val Ser Ser
        115

<210> SEQ ID NO 227
<211> LENGTH: 119
<212> TYPE: PRT
<213> ORGANISM: Homo sapiens

<400> SEQUENCE: 227

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ala His Glu
             20                  25                  30

Pro Met Val Trp Val Arg Gln Ala Pro Gly Lys Gly Leu Glu Trp Val
         35                  40                  45

Ser His Ile Asp Arg Val Gly Gln Asp Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Leu Pro Lys Arg Gly Pro Arg Phe Asp Tyr Trp Gly Leu Gly
            100                 105                 110

Thr Leu Val Thr Val Ser Ser
        115

<210> SEQ ID NO 228
<211> LENGTH: 119
<212> TYPE: PRT
<213> ORGANISM: Homo sapiens

<400> SEQUENCE: 228

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ala His Glu
             20                  25                  30

Pro Met Val Trp Val Arg Gln Ala Pro Gly Lys Gly Leu Glu Trp Val
         35                  40                  45

Ser His Ile Asp Arg Ala Gly Gln Asp Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Leu Pro Lys Arg Gly Pro Arg Phe Asp Tyr Trp Gly Leu Gly
            100                 105                 110

Thr Leu Val Thr Val Ser Ser
        115

<210> SEQ ID NO 229
<211> LENGTH: 119
<212> TYPE: PRT
<213> ORGANISM: Homo sapiens
```

-continued

```
<400> SEQUENCE: 229

Glu Val Gln Leu Leu Glu Ser Gly Gly Gly Leu Ile Gln Pro Gly Gly
 1               5                  10                  15

Ser Leu Arg Leu Ser Cys Ala Ala Ser Gly Phe Thr Phe Ala His Glu
             20                  25                  30

Thr Met Val Trp Val Arg Gln Ala Pro Gly Lys Gly Leu Glu Trp Val
         35                  40                  45

Ser His Ile Asp Arg Val Gly Gln Asp Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Leu Pro Lys Arg Gly Pro Trp Phe Asp Tyr Arg Gly Gln Gly
            100                 105                 110

Thr Leu Val Thr Val Ser Ser
        115

<210> SEQ ID NO 230
<211> LENGTH: 119
<212> TYPE: PRT
<213> ORGANISM: Homo sapiens

<400> SEQUENCE: 230

Glu Val Gln Leu Leu Glu Ser Gly Gly Gly Leu Val Arg Pro Gly Gly
 1               5                  10                  15

Ser Leu Arg Leu Ser Cys Ala Ala Ser Gly Phe Thr Phe Ala His Glu
             20                  25                  30

Pro Met Val Trp Val Arg Gln Ala Pro Gly Lys Gly Leu Glu Trp Val
         35                  40                  45

Ser His Ile Asp Arg Val Gly Gln Asp Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Leu Pro Lys Arg Gly Pro Arg Phe Asp Tyr Trp Gly Leu Gly
            100                 105                 110

Thr Leu Val Thr Val Ser Ser
        115

<210> SEQ ID NO 231
<211> LENGTH: 119
<212> TYPE: PRT
<213> ORGANISM: Homo sapiens

<400> SEQUENCE: 231

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala His Glu
             20                  25                  30

Pro Met Val Trp Val Arg Gln Ala Pro Gly Lys Gly Leu Glu Trp Val
         35                  40                  45

Ser His Ile Asp Arg Val Gly Gln Asp Thr Tyr Tyr Ala Asp Ser Val
     50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Ile Tyr Tyr Cys
                 85                  90                  95

Ala Arg Leu Pro Lys Arg Gly Pro Arg Phe Asp Tyr Trp Gly Leu Gly
            100                 105                 110

Thr Leu Val Thr Val Ser Ser
            115
```

<210> SEQ ID NO 232
<211> LENGTH: 119
<212> TYPE: PRT
<213> ORGANISM: Homo sapiens

<400> SEQUENCE: 232

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ala His Glu
             20                  25                  30

Pro Met Val Trp Val Arg Gln Ala Pro Gly Lys Gly Leu Glu Trp Val
         35                  40                  45

Ser His Ile Asp Arg Val Gly Gln Asp Pro Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Leu Pro Lys Arg Gly Pro Arg Phe Asp Tyr Trp Gly Gln Gly
            100                 105                 110

Thr Leu Val Thr Val Ser Ser
            115
```

<210> SEQ ID NO 233
<211> LENGTH: 119
<212> TYPE: PRT
<213> ORGANISM: Homo sapiens

<400> SEQUENCE: 233

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ala His Glu
             20                  25                  30

Pro Met Val Trp Ile Arg Gln Ala Pro Gly Lys Gly Leu Glu Trp Val
         35                  40                  45

Ser His Ile Asp Arg Val Gly Gln Asp Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Leu Pro Lys Arg Gly Pro Arg Phe Asp Tyr Trp Gly Gln Gly
            100                 105                 110

Thr Leu Val Thr Val Ser Ser
            115
```

<210> SEQ ID NO 234
<211> LENGTH: 119

<212> TYPE: PRT
<213> ORGANISM: Homo sapiens

<400> SEQUENCE: 234

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Pro Met Val Trp Val Arg Gln Ala Pro Gly Lys Gly Leu Glu Trp Val
        35                  40                  45

Ser His Ile Asp Arg Val Gly Gln Asp Pro Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Leu Pro Lys Arg Gly Pro Arg Phe Asp Tyr Trp Gly Leu Gly
            100                 105                 110

Thr Leu Val Thr Val Ser Ser
        115
```

<210> SEQ ID NO 235
<211> LENGTH: 119
<212> TYPE: PRT
<213> ORGANISM: Homo sapiens

<400> SEQUENCE: 235

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Pro Met Val Trp Val Arg Gln Ala Pro Gly Lys Gly Leu Glu Trp Val
        35                  40                  45

Ser His Ile Asp Arg Val Gly Gln Asp Ala Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Ile Leu Pro Lys Arg Gly Pro Arg Phe Asp Tyr Trp Gly Gln Gly
            100                 105                 110

Thr Leu Val Thr Val Ser Ser
        115
```

<210> SEQ ID NO 236
<211> LENGTH: 119
<212> TYPE: PRT
<213> ORGANISM: Homo sapiens

<400> SEQUENCE: 236

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Pro Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
```

```
            50                  55                  60
Lys Gly Arg Ser Thr Ile Ser Arg Asp Asn Ser Lys Asn Thr Leu Tyr
 65                  70                  75                  80

Leu Gln Met Asn Ser Leu Arg Ala Glu Asp Thr Ala Ile Tyr Tyr Cys
                 85                  90                  95

Ala Arg Leu Pro Lys Arg Gly Pro Arg Phe Asp Tyr Trp Gly Leu Gly
                100                 105                 110

Thr Leu Val Thr Val Ser Ser
            115

<210> SEQ ID NO 237
<211> LENGTH: 119
<212> TYPE: PRT
<213> ORGANISM: Homo sapiens

<400> SEQUENCE: 237

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala His Glu
                 20                  25                  30

Pro Met Val Trp Val Arg Gln Ala Pro Gly Lys Gly Leu Glu Trp Val
             35                  40                  45

Ser His Ile Asp Arg Val Gly Gln Asp Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Ile Tyr Tyr Cys
                 85                  90                  95

Ala Arg Pro Pro Lys Arg Gly Pro Arg Phe Asp Tyr Trp Gly Leu Gly
                100                 105                 110

Thr Leu Val Thr Val Ser Ser
            115

<210> SEQ ID NO 238
<211> LENGTH: 119
<212> TYPE: PRT
<213> ORGANISM: Homo sapiens

<400> SEQUENCE: 238

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala His Glu
                 20                  25                  30

Pro Met Val Trp Val Arg Gln Ala Pro Gly Lys Gly Leu Glu Trp Val
             35                  40                  45

Ser His Ile Asp Arg Val Gly Gln Asp Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Lys Asp Thr Ala Ile Tyr Tyr Cys
                 85                  90                  95

Ala Arg Leu Pro Lys Arg Gly Pro Arg Phe Asp Tyr Trp Gly Leu Gly
                100                 105                 110

Thr Leu Val Thr Val Ser Ser
            115
```

```
<210> SEQ ID NO 239
<211> LENGTH: 119
<212> TYPE: PRT
<213> ORGANISM: Homo sapiens

<400> SEQUENCE: 239

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ala His Glu
             20                  25                  30

Pro Met Val Trp Val Arg Gln Ala Pro Gly Lys Gly Leu Glu Trp Val
         35                  40                  45

Ser His Ile Asp Arg Val Gly Gln Asp Thr Tyr Tyr Ala Asp Ser Ala
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Ile Tyr Tyr Cys
                 85                  90                  95

Ala Arg Leu Pro Lys Arg Gly Pro Arg Phe Asp Tyr Trp Gly Leu Gly
            100                 105                 110

Thr Leu Val Thr Val Ser Ser
        115

<210> SEQ ID NO 240
<211> LENGTH: 119
<212> TYPE: PRT
<213> ORGANISM: Homo sapiens

<400> SEQUENCE: 240

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ala His Glu
             20                  25                  30

Pro Met Val Trp Val Arg Gln Ala Pro Gly Lys Gly Leu Glu Trp Val
         35                  40                  45

Ser His Ile Asp Arg Val Gly Gln Asp Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Pro Gln Met Asn Ser Leu Arg Ala Glu Asp Thr Ala Ile Tyr Tyr Cys
                 85                  90                  95

Ala Arg Leu Pro Lys Arg Gly Pro Arg Phe Asp Tyr Trp Gly Leu Gly
            100                 105                 110

Thr Leu Val Thr Val Ser Ser
        115

<210> SEQ ID NO 241
<211> LENGTH: 119
<212> TYPE: PRT
<213> ORGANISM: Homo sapiens

<400> SEQUENCE: 241

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ala His Glu
             20                  25                  30

Pro Met Val Trp Val Arg Gln Ala Pro Gly Lys Gly Leu Glu Trp Val
         35                  40                  45
```

```
Ser His Ile Asp Arg Val Gly Gln Asp Thr Tyr Tyr Ala Asp Ser Val
    50                  55                  60

Lys Gly Arg Phe Thr Val Ser Arg Asp Asn Ser Lys Asn Thr Leu Tyr
 65                  70                  75                  80

Leu Gln Met Asn Ser Leu Arg Ala Glu Asp Thr Ala Ile Tyr Tyr Cys
                 85                  90                  95

Ala Arg Leu Pro Lys Arg Gly Pro Arg Phe Asp Tyr Trp Gly Leu Gly
            100                 105                 110

Thr Leu Val Thr Val Ser Ser
            115

<210> SEQ ID NO 242
<211> LENGTH: 119
<212> TYPE: PRT
<213> ORGANISM: Homo sapiens

<400> SEQUENCE: 242

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ala His Glu
                 20                  25                  30

Pro Met Val Trp Val Arg Gln Ala Pro Gly Lys Gly Leu Glu Trp Val
             35                  40                  45

Ser His Ile Asp Arg Val Gly Gln Asp Thr Tyr Tyr Ala Asp Ser Val
    50                  55                  60

Lys Gly Arg Phe Ile Ile Ser Arg Asp Asn Ser Lys Asn Thr Leu Tyr
 65                  70                  75                  80

Leu Gln Met Tyr Ser Leu Arg Ala Glu Asp Thr Ala Val Tyr Tyr Cys
                 85                  90                  95

Ala Met Leu Pro Lys Arg Gly Pro Arg Phe Gly Tyr Trp Gly Gln Gly
            100                 105                 110

Thr Leu Val Thr Val Ser Ser
            115

<210> SEQ ID NO 243
<211> LENGTH: 119
<212> TYPE: PRT
<213> ORGANISM: Homo sapiens

<400> SEQUENCE: 243

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ala His Glu
                 20                  25                  30

Pro Met Val Trp Val Arg Gln Ala Pro Gly Lys Gly Leu Glu Trp Val
             35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Cys Ala Glu Asp Thr Ala Ile Tyr Tyr Cys
                 85                  90                  95

Ala Arg Leu Pro Lys Arg Gly Pro Arg Phe Asp Tyr Trp Gly Leu Gly
            100                 105                 110

Thr Leu Val Thr Val Ser Ser
            115
```

<210> SEQ ID NO 244
<211> LENGTH: 119
<212> TYPE: PRT
<213> ORGANISM: Homo sapiens

<400> SEQUENCE: 244

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Leu Pro Lys Arg Gly Pro Trp Phe Asp Tyr Arg Gly Gln Gly
            100                 105                 110

Thr Leu Val Thr Val Ser Ser
        115

<210> SEQ ID NO 245
<211> LENGTH: 119
<212> TYPE: PRT
<213> ORGANISM: Homo sapiens

<400> SEQUENCE: 245

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Lys Arg Gly Pro Trp Phe Asp Tyr Arg Gly Gln Gly
            100                 105                 110

Thr Leu Val Thr Val Ser Ser
        115

<210> SEQ ID NO 246
<211> LENGTH: 119
<212> TYPE: PRT
<213> ORGANISM: Homo sapiens

<400> SEQUENCE: 246

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Gln Leu Pro Lys Arg Gly Pro Trp Phe Asp Tyr Arg Gly Gln Gly
                100                 105                 110

Thr Leu Val Thr Val Ser Ser
        115

<210> SEQ ID NO 247
<211> LENGTH: 119
<212> TYPE: PRT
<213> ORGANISM: Homo sapiens

<400> SEQUENCE: 247

Glu Val Gln Leu Leu Glu Ser Gly Gly Gly Leu Ile Gln Pro Gly Gly
 1               5                   10                  15

Ser Leu Arg Leu Ser Cys Ala Ala Ser Gly Phe Thr Phe Ala His Glu
                 20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Val Glu Asp Thr Ala Val Tyr Tyr Cys
                 85                  90                  95

Ala Ser Leu Pro Lys Arg Gly Pro Trp Phe Asp Tyr Arg Gly Gln Gly
                100                 105                 110

Thr Leu Val Thr Val Ser Ser
        115

<210> SEQ ID NO 248
<211> LENGTH: 119
<212> TYPE: PRT
<213> ORGANISM: Homo sapiens

<400> SEQUENCE: 248

Glu Val Gln Leu Leu Glu Ser Gly Gly Gly Leu Tyr Gln Pro Gly Gly
 1               5                   10                  15

Ser Leu Arg Leu Ser Cys Ala Ala Ser Gly Phe Thr Phe Ala His Glu
                 20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Leu Pro Lys Arg Gly Pro Trp Phe Asp Tyr Arg Gly Gln Gly
                100                 105                 110

-continued

Thr Leu Val Thr Val Ser Ser
        115

<210> SEQ ID NO 249
<211> LENGTH: 119
<212> TYPE: PRT
<213> ORGANISM: Homo sapiens

<400> SEQUENCE: 249

Glu Val Gln Leu Leu Glu Ser Gly Gly Gly Leu Gly Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Pro Lys Arg Gly Pro Trp Phe Asp Tyr Arg Gly Gln Gly
            100                 105                 110

Thr Leu Val Thr Val Ser Ser
        115

<210> SEQ ID NO 250
<211> LENGTH: 119
<212> TYPE: PRT
<213> ORGANISM: Homo sapiens
<220> FEATURE:
<221> NAME/KEY: VARIANT
<222> LOCATION: 12
<223> OTHER INFORMATION: Xaa = Any Amino Acid

<400> SEQUENCE: 250

Glu Gly Gln Leu Leu Glu Ser Gly Gly Gly Leu Xaa Gln Pro Gly Gly
1               5                   10                  15

Ser Leu Leu Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Pro Lys Arg Gly Pro Trp Phe Asp Tyr Arg Gly Gln Gly
            100                 105                 110

Thr Leu Val Thr Val Ser Ser
        115

<210> SEQ ID NO 251
<211> LENGTH: 119
<212> TYPE: PRT
<213> ORGANISM: Homo sapiens

<400> SEQUENCE: 251

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Pro Lys Arg Gly Pro Trp Phe Asp Tyr Arg Gly Gln Gly
            100                 105                 110

Thr Leu Val Thr Val Ser Ser
        115

<210> SEQ ID NO 252
<211> LENGTH: 119
<212> TYPE: PRT
<213> ORGANISM: Homo sapiens

<400> SEQUENCE: 252

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Pro Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Pro Lys Arg Gly Pro Trp Phe Asp Tyr Arg Gly Gln Gly
            100                 105                 110

Thr Leu Val Thr Val Ser Ser
        115

<210> SEQ ID NO 253
<211> LENGTH: 119
<212> TYPE: PRT
<213> ORGANISM: Homo sapiens

<400> SEQUENCE: 253

Glu Gly Gln Leu Leu Glu Ser Gly Gly Gly Leu Ile Gln Pro Gly Gly
1               5                   10                  15

Ser Leu Arg Leu Ser Cys Gly Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Pro Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Pro Lys Arg Gly Pro Trp Phe Asp Tyr Arg Gly Gln Gly
            100                 105                 110

Thr Leu Val Thr Val Ser Ser
        115

<210> SEQ ID NO 254
<211> LENGTH: 119
<212> TYPE: PRT
<213> ORGANISM: Homo sapiens

<400> SEQUENCE: 254

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Asn Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Pro Lys Arg Gly Pro Trp Phe Asp Tyr Arg Gly Gln Gly
            100                 105                 110

Thr Leu Val Thr Val Ser Ser
        115

<210> SEQ ID NO 255
<211> LENGTH: 119
<212> TYPE: PRT
<213> ORGANISM: Homo sapiens

<400> SEQUENCE: 255

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Pro Lys Arg Gly Pro Gly Phe Asp Tyr Arg Gly Gln Gly
            100                 105                 110

Thr Leu Val Thr Val Ser Ser
        115

<210> SEQ ID NO 256
<211> LENGTH: 119
<212> TYPE: PRT
<213> ORGANISM: Homo sapiens

```
<400> SEQUENCE: 256

Glu Val Gln Leu Leu Glu Ser Gly Gly Gly Leu Ile Gln Pro Gly Gly
 1               5                  10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Leu Pro Lys Arg Gly Pro Val Phe Asp Tyr Arg Gly Gln Gly
            100                 105                 110

Thr Leu Val Thr Val Ser Ser
        115

<210> SEQ ID NO 257
<211> LENGTH: 119
<212> TYPE: PRT
<213> ORGANISM: Homo sapiens

<400> SEQUENCE: 257

Glu Val Gln Leu Leu Glu Ser Gly Gly Gly Leu Ile Gln Pro Gly Gly
 1               5                  10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Leu Pro Lys Arg Gly Pro Trp Phe Asp Tyr Tyr Gly Gln Gly
            100                 105                 110

Thr Leu Val Thr Val Ser Ser
        115

<210> SEQ ID NO 258
<211> LENGTH: 119
<212> TYPE: PRT
<213> ORGANISM: Homo sapiens

<400> SEQUENCE: 258

Glu Gly Gln Leu Leu Glu Ser Gly Gly Gly Leu Ile Gln Pro Gly Gly
 1               5                  10                  15

Ser Leu Leu Leu Ser Cys Ala Pro Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
```

Leu Gln Met Asn Ser Leu Arg Ala Glu Asp Thr Ala Val Tyr Tyr Cys
            85                  90                  95

Ala Lys Leu Pro Lys Arg Gly Pro Trp Phe Asp Tyr Lys Gly Gln Gly
                100                 105                 110

Thr Leu Val Thr Val Ser Ser
            115

<210> SEQ ID NO 259
<211> LENGTH: 119
<212> TYPE: PRT
<213> ORGANISM: Homo sapiens

<400> SEQUENCE: 259

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Leu Pro Lys Arg Gly Pro Trp Phe Asp Tyr Val Gly Gln Gly
                100                 105                 110

Thr Leu Val Thr Val Ser Ser
            115

<210> SEQ ID NO 260
<211> LENGTH: 119
<212> TYPE: PRT
<213> ORGANISM: Homo sapiens

<400> SEQUENCE: 260

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Leu Pro Lys Arg Gly Pro Trp Phe Asp Tyr Leu Gly Gln Gly
                100                 105                 110

Thr Leu Val Thr Val Ser Ser
            115

<210> SEQ ID NO 261
<211> LENGTH: 119
<212> TYPE: PRT

<213> ORGANISM: Homo sapiens

<400> SEQUENCE: 261

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala His Glu
            20                  25                  30

Pro Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Pro Lys Arg Gly Pro Arg Phe Asp Tyr Trp Gly Gln Gly
            100                 105                 110

Thr Leu Val Thr Val Ser Ser
        115

<210> SEQ ID NO 262
<211> LENGTH: 119
<212> TYPE: PRT
<213> ORGANISM: Homo sapiens

<400> SEQUENCE: 262

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala His Glu
            20                  25                  30

Pro Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Leu Pro Lys Arg Gly Pro Arg Phe Asp Tyr Trp Gly Gln Gly
            100                 105                 110

Thr Leu Val Thr Val Ser Ser
        115

<210> SEQ ID NO 263
<211> LENGTH: 119
<212> TYPE: PRT
<213> ORGANISM: Homo sapiens

<400> SEQUENCE: 263

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala His Glu
            20                  25                  30

Pro Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Leu Pro Lys Arg Gly Pro Arg Phe Asp Tyr Trp Gly Gln Gly
            100                 105                 110

Thr Leu Val Thr Val Ser Ser
        115

<210> SEQ ID NO 264
<211> LENGTH: 119
<212> TYPE: PRT
<213> ORGANISM: Homo sapiens

<400> SEQUENCE: 264

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ala His Glu
             20                  25                  30

Pro Met Val Trp Val Arg Gln Ala Pro Gly Lys Gly Leu Gly Trp Val
         35                  40                  45

Ser His Ile Asp Arg Val Gly Gln Asp Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Pro Leu Pro Lys Arg Gly Pro Arg Phe Asp Tyr Trp Gly Gln Gly
            100                 105                 110

Thr Leu Val Thr Val Ser Ser
        115

<210> SEQ ID NO 265
<211> LENGTH: 119
<212> TYPE: PRT
<213> ORGANISM: Homo sapiens

<400> SEQUENCE: 265

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ala His Glu
             20                  25                  30

Pro Met Val Trp Val Arg Gln Ala Pro Gly Lys Gly Leu Glu Trp Val
         35                  40                  45

Ser His Ile Asp Arg Val Gly Gln Asp Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Leu Pro Lys Arg Gly Pro Arg Phe Asp Tyr Trp Gly Gln Gly
            100                 105                 110

Thr Leu Val Thr Val Ser Ser
        115

<210> SEQ ID NO 266
```

```
<211> LENGTH: 119
<212> TYPE: PRT
<213> ORGANISM: Homo sapiens

<400> SEQUENCE: 266

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala His Glu
            20                  25                  30

Pro Met Val Trp Ile Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Met Leu Pro Lys Arg Gly Pro Arg Phe Asp Tyr Trp Gly Gln Gly
            100                 105                 110

Thr Leu Val Thr Val Ser Ser
        115

<210> SEQ ID NO 267
<211> LENGTH: 119
<212> TYPE: PRT
<213> ORGANISM: Homo sapiens

<400> SEQUENCE: 267

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala His Glu
            20                  25                  30

Pro Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Arg Phe Asp Tyr Trp Gly Gln Gly
            100                 105                 110

Thr Leu Val Thr Val Ser Ser
        115

<210> SEQ ID NO 268
<211> LENGTH: 119
<212> TYPE: PRT
<213> ORGANISM: Homo sapiens
<220> FEATURE:
<221> NAME/KEY: VARIANT
<222> LOCATION: 32
<223> OTHER INFORMATION: Xaa = Any Amino Acid

<400> SEQUENCE: 268

Glu Val Gln Leu Leu Glu Ser Gly Gly Gly Leu Ile Gln Pro Gly Gly
 1               5                  10                  15

Ser Leu Arg Leu Ser Cys Ala Ala Ser Gly Phe Thr Phe Ala His Xaa
            20                  25                  30
```

```
Thr Met Val Trp Val Arg Gln Ala Pro Gly Lys Gly Leu Glu Trp Val
        35                  40                  45

Ser His Ile Asp Arg Val Gly Gln Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Pro Lys Arg Gly Pro Trp Phe Asp Tyr Arg Gly Gln Gly
                100                 105                 110

Thr Leu Val Thr Val Ser Ser
            115

<210> SEQ ID NO 269
<211> LENGTH: 119
<212> TYPE: PRT
<213> ORGANISM: Homo sapiens
<220> FEATURE:
<221> NAME/KEY: VARIANT
<222> LOCATION: 32
<223> OTHER INFORMATION: Xaa = Any Amino Acid

<400> SEQUENCE: 269

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Xaa
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Pro Lys Arg Gly Pro Trp Phe Asp Tyr Ile Gly Gln Gly
                100                 105                 110

Thr Leu Val Thr Val Ser Ser
            115

<210> SEQ ID NO 270
<211> LENGTH: 119
<212> TYPE: PRT
<213> ORGANISM: Homo sapiens

<400> SEQUENCE: 270

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

-continued

```
                85                  90                  95

Ala Lys Leu Pro Lys Arg Gly Pro Trp Phe Asp Tyr Asn Gly Gln Gly
                100                 105                 110

Thr Leu Val Thr Val Ser Ser
        115

<210> SEQ ID NO 271
<211> LENGTH: 119
<212> TYPE: PRT
<213> ORGANISM: Homo sapiens

<400> SEQUENCE: 271

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
                20                  25                  30

Val Met Val Trp Val Arg Gln Ala Pro Gly Lys Gly Leu Glu Trp Val
            35                  40                  45

Ser His Ile Asp Arg Val Gly Gln Asp Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Pro Lys Arg Gly Pro Trp Phe Asp Tyr Arg Gly Gln Gly
                100                 105                 110

Thr Leu Val Thr Val Ser Ser
        115

<210> SEQ ID NO 272
<211> LENGTH: 119
<212> TYPE: PRT
<213> ORGANISM: Homo sapiens

<400> SEQUENCE: 272

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
                20                  25                  30

Leu Met Val Trp Val Arg Gln Ala Pro Gly Lys Gly Leu Glu Trp Val
            35                  40                  45

Ser His Ile Asp Arg Val Gly Gln Asp Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Pro Lys Arg Gly Pro Trp Phe Asp Tyr Arg Gly Gln Gly
                100                 105                 110

Thr Leu Val Thr Val Ser Ser
        115

<210> SEQ ID NO 273
<211> LENGTH: 119
<212> TYPE: PRT
<213> ORGANISM: Homo sapiens

<400> SEQUENCE: 273
```

```
Glu Val Gln Leu Leu Glu Ser Gly Gly Asn Leu Val Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
            35                  40                  45

Ser His Ile Asp Arg Val Gly Gln Asp Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Pro Lys Arg Gly Pro Trp Phe Asp Tyr Arg Gly Gln Gly
            100                 105                 110

Thr Leu Val Thr Val Ser Ser
            115
```

<210> SEQ ID NO 274
<211> LENGTH: 119
<212> TYPE: PRT
<213> ORGANISM: Homo sapiens

<400> SEQUENCE: 274

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
            35                  40                  45

Ser His Ile Asp Arg Val Gly Gln Asp Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Pro Lys Arg Gly Pro Trp Phe Asp Tyr Arg Gly Gln Gly
            100                 105                 110

Thr Leu Val Thr Val Ser Ser
            115
```

<210> SEQ ID NO 275
<211> LENGTH: 119
<212> TYPE: PRT
<213> ORGANISM: Homo sapiens

<400> SEQUENCE: 275

```
Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Lys
            20                  25                  30

Thr Met Val Trp Val Arg Gln Ala Pro Gly Lys Gly Leu Glu Trp Val
            35                  40                  45

Ser His Ile Asp Arg Val Gly Gln Asp Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80
```

-continued

Leu Gln Met Asn Ser Leu Arg Ala Glu Asp Thr Ala Val Tyr Tyr Cys
                 85                  90                  95

Ala Leu Leu Pro Lys Arg Gly Pro Trp Phe Asp Tyr Arg Gly Gln Gly
            100                 105                 110

Thr Leu Val Thr Val Ser Ser
        115

<210> SEQ ID NO 276
<211> LENGTH: 119
<212> TYPE: PRT
<213> ORGANISM: Homo sapiens

<400> SEQUENCE: 276

Glu Val Gln Leu Leu Glu Ser Gly Gly Gly Leu Ile Gln Pro Gly Gly
 1               5                  10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Arg Leu Pro Lys Arg Gly Pro Trp Phe Asp Tyr Arg Gly Gln Gly
            100                 105                 110

Thr Leu Ala Thr Val Ser Ser
        115

<210> SEQ ID NO 277
<211> LENGTH: 119
<212> TYPE: PRT
<213> ORGANISM: Homo sapiens

<400> SEQUENCE: 277

Glu Val Gln Leu Leu Glu Ser Gly Gly Gly Leu Ile Gln Pro Gly Gly
 1               5                  10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                 85                  90                  95

Ala Val Leu Pro Lys Arg Gly Pro Trp Phe Asp Tyr Arg Gly Gln Gly
            100                 105                 110

Thr Leu Val Thr Val Ser Ser
        115

<210> SEQ ID NO 278
<211> LENGTH: 119
<212> TYPE: PRT
<213> ORGANISM: Homo sapiens

<400> SEQUENCE: 278

```
Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Pro Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Lys Arg Gly Pro Trp Phe Asp Tyr Arg Gly Gln Gly
            100                 105                 110

Thr Leu Val Thr Val Ser Ser
        115
```

<210> SEQ ID NO 279
<211> LENGTH: 119
<212> TYPE: PRT
<213> ORGANISM: Homo sapiens

<400> SEQUENCE: 279

```
Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Asp
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Lys Arg Gly Pro Trp Phe Asp Tyr Gln Gly Gln Gly
            100                 105                 110

Thr Leu Val Thr Val Ser Ser
        115
```

<210> SEQ ID NO 280
<211> LENGTH: 119
<212> TYPE: PRT
<213> ORGANISM: Homo sapiens

<400> SEQUENCE: 280

```
Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Asp
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60
```

```
Lys Asp Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Val Leu Pro Lys Arg Gly Pro Trp Phe Asp Tyr Arg Gly Gln Gly
            100                 105                 110

Thr Leu Val Thr Val Ser Ser
            115

<210> SEQ ID NO 281
<211> LENGTH: 119
<212> TYPE: PRT
<213> ORGANISM: Homo sapiens

<400> SEQUENCE: 281

Glu Val Gln Leu Leu Glu Ser Gly Gly Gly Leu Ile Gln Pro Gly Gly
  1               5                  10                  15

Ser Leu Arg Leu Ser Cys Ala Ala Ser Gly Phe Thr Phe Ala His Glu
                 20                  25                  30

Thr Met Val Trp Val Arg Gln Ala Pro Gly Lys Gly Leu Glu Trp Val
             35                  40                  45

Ser His Ile Asp Arg Val Gly Gln Asp Thr Tyr Tyr Ala Asp Ser Val
     50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Arg Leu Pro Lys Arg Gly Pro Trp Phe Asp Tyr Arg Gly Arg Gly
            100                 105                 110

Thr Leu Val Thr Val Ser Ser
            115

<210> SEQ ID NO 282
<211> LENGTH: 119
<212> TYPE: PRT
<213> ORGANISM: Homo sapiens

<400> SEQUENCE: 282

Glu Val Gln Leu Leu Glu Ser Gly Gly Gly Leu Ile Gln Pro Gly Gly
  1               5                  10                  15

Ser Leu Arg Leu Ser Cys Ala Ala Ser Gly Phe Thr Phe Ala His Glu
                 20                  25                  30

Thr Met Val Trp Val Arg Gln Ala Pro Gly Lys Gly Leu Glu Trp Val
             35                  40                  45

Ser His Ile Asp Arg Val Gly Gln Asp Thr Tyr Tyr Ala Asp Ser Val
     50                  55                  60

Glu Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Val Leu Pro Lys Arg Gly Pro Trp Phe Asp Tyr Arg Gly Gln Gly
            100                 105                 110

Thr Leu Val Thr Val Ser Ser
            115

<210> SEQ ID NO 283
<211> LENGTH: 119
```

<212> TYPE: PRT
<213> ORGANISM: Homo sapiens

<400> SEQUENCE: 283

```
Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Arg Gly Gln Gly
            100                 105                 110

Thr Leu Val Thr Val Ser Ser
            115
```

<210> SEQ ID NO 284
<211> LENGTH: 119
<212> TYPE: PRT
<213> ORGANISM: Homo sapiens

<400> SEQUENCE: 284

```
Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Gln Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Val Leu Pro Lys Arg Gly Pro Trp Phe Asp Tyr Arg Gly Gln Gly
            100                 105                 110

Thr Leu Val Thr Val Ser Ser
            115
```

<210> SEQ ID NO 285
<211> LENGTH: 119
<212> TYPE: PRT
<213> ORGANISM: Homo sapiens

<400> SEQUENCE: 285

```
Glu Val Gln Leu Ser Glu Ser Gly Gly Gly Leu Ile Gln Pro Gly Gly
1               5                   10                  15

Ser Leu Arg Leu Ser Cys Val Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
```

```
                 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Ile Leu Pro Lys Arg Gly Pro Trp Phe Asp Tyr Arg Gly Gln Gly
                100                 105                 110

Thr Leu Val Thr Val Ser Ser
            115

<210> SEQ ID NO 286
<211> LENGTH: 119
<212> TYPE: PRT
<213> ORGANISM: Homo sapiens

<400> SEQUENCE: 286

Glu Val Gln Leu Leu Glu Ser Gly Gly Gly Leu Ile Gln Pro Gly Gly
  1               5                  10                  15

Ser Leu Arg Leu Thr Cys Ala Ala Ser Gly Phe Thr Phe Ala His Glu
                 20                  25                  30

Thr Met Val Trp Val Arg Gln Ala Pro Gly Lys Gly Leu Glu Trp Val
             35                  40                  45

Ser His Ile Asp Arg Val Gly Gln Asp Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Val Leu Pro Lys Arg Gly Pro Trp Phe Asp Tyr Arg Gly Gln Gly
                100                 105                 110

Thr Leu Val Thr Val Ser Ser
            115

<210> SEQ ID NO 287
<211> LENGTH: 119
<212> TYPE: PRT
<213> ORGANISM: Homo sapiens

<400> SEQUENCE: 287

Glu Val Gln Leu Leu Glu Ser Gly Gly Gly Leu Ile Gln Pro Gly Gly
  1               5                  10                  15

Ser Leu Arg Leu Ser Cys Ala Ala Ser Gly Phe Thr Phe Ala His Glu
                 20                  25                  30

Thr Met Val Trp Val Arg Gln Ala Pro Gly Lys Gly Leu Glu Trp Val
             35                  40                  45

Ser His Ile Asp Arg Val Gly Gln Asp Thr Tyr Tyr Ala Asp Ser Val
         50                  55                  60

Lys Gly Arg Phe Thr Ile Ser Arg Asp Asn Ser Met Asn Thr Leu Tyr
 65                  70                  75                  80

Leu Gln Met Asn Ser Leu Arg Ala Glu Asp Thr Ala Val Tyr Tyr Cys
                     85                  90                  95

Ala Leu Leu Pro Lys Arg Gly Pro Trp Phe Asp Tyr Arg Gly Gln Gly
                100                 105                 110

Thr Leu Val Thr Val Ser Ser
            115
```

```
<210> SEQ ID NO 288
<211> LENGTH: 119
<212> TYPE: PRT
<213> ORGANISM: Homo sapiens

<400> SEQUENCE: 288

Glu Val Gln Leu Leu Glu Ser Gly Gly Gly Ser Ile Gln Pro Gly Gly
 1               5                  10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Val Leu Pro Lys Arg Gly Pro Trp Phe Asp Tyr Arg Gly Gln Gly
            100                 105                 110

Thr Leu Val Thr Val Ser Ser
        115

<210> SEQ ID NO 289
<211> LENGTH: 119
<212> TYPE: PRT
<213> ORGANISM: Homo sapiens

<400> SEQUENCE: 289

Glu Val Gln Leu Leu Glu Ser Gly Gly Gly Leu Ile Gln Pro Gly Gly
 1               5                  10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asn Asn Ser Met Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Leu Pro Lys Arg Gly Pro Trp Phe Asp Tyr Arg Gly Gln Gly
            100                 105                 110

Thr Leu Val Thr Val Ser Ser
        115

<210> SEQ ID NO 290
<211> LENGTH: 119
<212> TYPE: PRT
<213> ORGANISM: Homo sapiens

<400> SEQUENCE: 290

Glu Val Gln Leu Leu Glu Ser Gly Gly Gly Leu Ile Gln Pro Gly Gly
 1               5                  10                  15

Ser Leu Arg Leu Ser Cys Ala Ala Ser Gly Phe Thr Phe Ala His Glu
            20                  25                  30

Thr Met Val Trp Val Arg Gln Ala Pro Gly Arg Gly Leu Glu Trp Val
        35                  40                  45
```

Ser His Ile Asp Arg Val Gly Gln Asp Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Val Leu Pro Lys Arg Gly Pro Trp Phe Asp Tyr Arg Gly Gln Gly
            100                 105                 110

Thr Leu Val Thr Val Ser Ser
        115

<210> SEQ ID NO 291
<211> LENGTH: 119
<212> TYPE: PRT
<213> ORGANISM: Homo sapiens

<400> SEQUENCE: 291

Glu Val Gln Leu Leu Glu Ser Gly Gly Gly Leu Ile Gln Pro Gly Gly
 1               5                  10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Pro Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Arg Gly Gln Gly
            100                 105                 110

Thr Leu Val Thr Val Ser Ser
        115

<210> SEQ ID NO 292
<211> LENGTH: 119
<212> TYPE: PRT
<213> ORGANISM: Homo sapiens

<400> SEQUENCE: 292

Glu Val Gln Leu Leu Glu Ser Gly Gly Gly Leu Ile Gln Pro Gly Gly
 1               5                  10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Met Leu Pro Lys Arg Gly Pro Trp Phe Asp Tyr Arg Gly Gln Gly
            100                 105                 110

Thr Leu Val Thr Val Ser Ser
        115

<210> SEQ ID NO 293
<211> LENGTH: 119
<212> TYPE: PRT
<213> ORGANISM: Homo sapiens

<400> SEQUENCE: 293

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Asp
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Thr Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Arg Gly Gln Gly
            100                 105                 110

Thr Leu Val Thr Val Ser Ser
        115

<210> SEQ ID NO 294
<211> LENGTH: 119
<212> TYPE: PRT
<213> ORGANISM: Homo sapiens

<400> SEQUENCE: 294

Glu Val Gln Leu Leu Glu Ser Gly Gly Gly Leu Ile Glu Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ser Ala Val Tyr Tyr Cys
                85                  90                  95

Ala Arg Leu Pro Lys Arg Gly Pro Trp Phe Asp Tyr Arg Gly Gln Gly
            100                 105                 110

Thr Leu Val Thr Val Ser Ser
        115

<210> SEQ ID NO 295
<211> LENGTH: 119
<212> TYPE: PRT
<213> ORGANISM: Homo sapiens

<400> SEQUENCE: 295

Asp Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

```
Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Ala Tyr Tyr Cys
                 85                  90                  95

Ala Val Leu Pro Lys Arg Gly Pro Trp Phe Asp Tyr Arg Gly Gln Gly
             100                 105                 110

Thr Leu Val Thr Val Ser Ser
         115
```

<210> SEQ ID NO 296
<211> LENGTH: 119
<212> TYPE: PRT
<213> ORGANISM: Homo sapiens

<400> SEQUENCE: 296

```
Glu Val Gln Leu Met Glu Ser Gly Gly Gly Leu Ile Gln Pro Gly Gly
 1               5                  10                  15

Ser Leu Arg Leu Ser Cys Ala Ala Ser Gly Phe Thr Phe Ala His Glu
             20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Glu Leu Pro Lys Arg Gly Pro Trp Phe Asp His Arg Gly Gln Gly
             100                 105                 110

Thr Leu Val Thr Val Ser Ser
         115
```

<210> SEQ ID NO 297
<211> LENGTH: 119
<212> TYPE: PRT
<213> ORGANISM: Homo sapiens

<400> SEQUENCE: 297

```
Glu Val Gln Leu Leu Glu Ser Gly Gly Gly Leu Ile Gln Pro Gly Gly
 1               5                  10                  15

Ser Leu Arg Leu Ser Cys Ala Ala Ser Gly Phe Thr Phe Ala His Glu
             20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
 50                  55                  60

Lys Gly Arg Phe Ala Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Met Leu Pro Lys Arg Gly Pro Trp Phe Asp Tyr Arg Gly Gln Gly
             100                 105                 110
```

```
Thr Leu Val Thr Val Ser Ser
        115

<210> SEQ ID NO 298
<211> LENGTH: 119
<212> TYPE: PRT
<213> ORGANISM: Homo sapiens

<400> SEQUENCE: 298

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Arg Gly Gln Gly
            100                 105                 110

Thr Met Val Thr Val Ser Ser
        115

<210> SEQ ID NO 299
<211> LENGTH: 119
<212> TYPE: PRT
<213> ORGANISM: Homo sapiens

<400> SEQUENCE: 299

Glu Val Gln Leu Leu Glu Ser Gly Gly Gly Leu Met Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Leu Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr His Cys
                85                  90                  95

Ala Arg Leu Pro Lys Arg Gly Pro Trp Phe Asp Tyr Arg Gly Gln Gly
            100                 105                 110

Thr Leu Val Thr Val Ser Ser
        115

<210> SEQ ID NO 300
<211> LENGTH: 119
<212> TYPE: PRT
<213> ORGANISM: Homo sapiens

<400> SEQUENCE: 300

Glu Val Gln Leu Leu Glu Ser Gly Gly Gly Leu Ile Gln Pro Gly Gly
1               5                   10                  15

Ser Leu Arg Leu Ser Cys Ala Thr Ser Gly Phe Thr Phe Ala His Glu
```

```
            20                  25                  30
Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Met Gln Met Asn Ser Leu Arg Ala Glu Asp Thr Ala Val Tyr Tyr Cys
                85                  90                  95

Ala Val Leu Pro Lys Arg Gly Pro Trp Phe Asp Tyr Gln Gly Gln Gly
            100                 105                 110

Thr Leu Val Thr Val Ser Ser
            115

<210> SEQ ID NO 301
<211> LENGTH: 119
<212> TYPE: PRT
<213> ORGANISM: Homo sapiens

<400> SEQUENCE: 301

Glu Val Gln Leu Leu Glu Ser Gly Gly Gly Leu Ile Gln Pro Gly Gly
 1               5                  10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Pro Val
 50                  55                  60

Lys Gly Arg Phe Thr Ile Ser Arg Asp Asn Ser Arg Asn Thr Leu Tyr
 65                  70                  75                  80

Leu Gln Met Asn Ser Leu Arg Ser Glu Asp Thr Ala Val Tyr Tyr Cys
                85                  90                  95

Ala Val Leu Pro Lys Arg Gly Pro Trp Phe Asp Tyr Arg Gly Gln Gly
            100                 105                 110

Thr Leu Val Thr Val Ser Ser
            115

<210> SEQ ID NO 302
<211> LENGTH: 119
<212> TYPE: PRT
<213> ORGANISM: Homo sapiens

<400> SEQUENCE: 302

Glu Val Gln Leu Leu Glu Ser Gly Gly Gly Leu Ile Gln Pro Gly Gly
 1               5                  10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Ser Cys
                85                  90                  95

Ala Leu Leu Pro Lys Arg Gly Pro Trp Phe Asp Tyr Arg Gly Gln Gly
```

Thr Leu Val Thr Val Ser Ser
        115

<210> SEQ ID NO 303
<211> LENGTH: 119
<212> TYPE: PRT
<213> ORGANISM: Homo sapiens

<400> SEQUENCE: 303

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Ala Leu Tyr
65                  70                  75                  80

Leu Gln Met Asn Ser Leu Arg Ala Glu Asp Thr Ala Val Tyr Tyr Cys
                85                  90                  95

Ala Val Leu Pro Lys Arg Gly Pro Trp Phe Asp Tyr Arg Gly Gln Gly
            100                 105                 110

Thr Leu Val Thr Val Ser Ser
        115

<210> SEQ ID NO 304
<211> LENGTH: 119
<212> TYPE: PRT
<213> ORGANISM: Homo sapiens

<400> SEQUENCE: 304

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 305
<211> LENGTH: 119
<212> TYPE: PRT
<213> ORGANISM: Homo sapiens

<400> SEQUENCE: 305

Glu Val Gln Leu Leu Glu Ser Gly Gly Gly Leu Ile Gln Pro Gly Gly
1               5                   10                  15

```
Ser Leu Arg Leu Ser Cys Ala Ala Ser Gly Phe Thr Phe Ala His Glu
            20                  25                  30

Thr Met Val Trp Val Arg Glu Ala Pro Gly Lys Gly Leu Glu Trp Val
        35                  40                  45

Ser His Ile Asp Arg Val Gly Gln Asp Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Ile Leu Pro Lys Arg Gly Pro Trp Phe Asp Tyr Arg Gly Gln Gly
                100                 105                 110

Thr Leu Val Thr Val Ser Ser
        115

<210> SEQ ID NO 306
<211> LENGTH: 119
<212> TYPE: PRT
<213> ORGANISM: Homo sapiens

<400> SEQUENCE: 306

Glu Val Gln Leu Leu Glu Ser Gly Gly Gly Leu Ile Gln Pro Gly Gly
 1               5                  10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
 50                  55                  60

Glu Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Val Leu Pro Lys Arg Gly Pro Trp Phe Asp Tyr Arg Gly Gln Gly
                100                 105                 110

Thr Leu Val Thr Val Ser Ser
        115

<210> SEQ ID NO 307
<211> LENGTH: 119
<212> TYPE: PRT
<213> ORGANISM: Homo sapiens

<400> SEQUENCE: 307

Glu Val Gln Leu Leu Glu Ser Gly Gly Gly Leu Ile Gln Pro Gly Gly
 1               5                  10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Pro Val
 50                  55                  60

Lys Gly Arg Phe Thr Ile Ser Arg Asp Asn Ser Arg Asn Thr Leu Tyr
 65                  70                  75                  80

Leu Gln Met Asn Ser Leu Arg Ala Glu Asp Thr Ala Val Tyr Tyr Cys
                85                  90                  95
```

Ala Val Leu Pro Lys Arg Gly Pro Trp Phe Asp Tyr Arg Gly Gln Gly
                100                 105                 110

Thr Leu Val Thr Val Ser Ser
        115

<210> SEQ ID NO 308
<211> LENGTH: 119
<212> TYPE: PRT
<213> ORGANISM: Homo sapiens

<400> SEQUENCE: 308

Glu Val Gln Leu Leu Glu Ser Gly Gly Asp Leu Ile Gln Pro Gly Gly
 1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Val Leu Pro Lys Arg Gly Pro Trp Phe Asp Tyr Arg Gly Gln Gly
                100                 105                 110

Thr Leu Val Thr Val Ser Ser
        115

<210> SEQ ID NO 309
<211> LENGTH: 119
<212> TYPE: PRT
<213> ORGANISM: Homo sapiens

<400> SEQUENCE: 309

Glu Val Gln Leu Leu Glu Ser Gly Gly Gly Ser Ile Gln Pro Gly Gly
 1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Val Leu Pro Lys Arg Gly Pro Trp Phe Asp Tyr Arg Gly Gln Gly
                100                 105                 110

Thr Leu Val Thr Val Ser Ser
        115

<210> SEQ ID NO 310
<211> LENGTH: 119
<212> TYPE: PRT
<213> ORGANISM: Homo sapiens

<400> SEQUENCE: 310

Glu Val Gln Leu Leu Glu Ser Gly Gly Gly Leu Ile Gln Pro Gly Gly
1               5                   10                  15

Ser Leu His Leu Ser Cys Ala Ala Ser Gly Phe Thr Phe Glu His Glu
            20                  25                  30

Thr Met Val Trp Val Arg Gln Ala Pro Gly Lys Gly Leu Glu Trp Val
            35                  40                  45

Ser His Ile Asp Arg Val Gly Gln Asp Pro Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Lys Arg Gly Pro Trp Phe Asp Tyr Arg Gly Gln Gly
            100                 105                 110

Thr Leu Val Thr Val Ser Ser
            115

<210> SEQ ID NO 311
<211> LENGTH: 119
<212> TYPE: PRT
<213> ORGANISM: Homo sapiens

<400> SEQUENCE: 311

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Asp
            20                  25                  30

Thr Met Val Trp Val Arg Gln Ala Pro Gly Lys Gly Leu Glu Trp Val
            35                  40                  45

Ser His Ile Asp Arg Val Gly Gln Asp Thr Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Lys Arg Gly Pro Trp Phe Asp Tyr Arg Gly Gln Gly
            100                 105                 110

Thr Leu Val Thr Val Ser Ser
            115

<210> SEQ ID NO 312
<211> LENGTH: 119
<212> TYPE: PRT
<213> ORGANISM: Homo sapiens

<400> SEQUENCE: 312

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
            35                  40                  45

Ser His Ile Asp Arg Val Gly Gln Asp Pro Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
            85                  90                  95

Ala Arg Leu Pro Lys Arg Gly Pro Trp Phe Asp Tyr Arg Gly Gln Gly
            100                 105                 110

Thr Leu Val Thr Val Ser Ser
            115

<210> SEQ ID NO 313
<211> LENGTH: 119
<212> TYPE: PRT
<213> ORGANISM: Homo sapiens

<400> SEQUENCE: 313

Glu Val Gln Leu Leu Glu Ser Gly Gly Gly Leu Ile Gln Pro Gly Gly
 1               5                  10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Asp Leu Glu Trp Val
            35                  40                  45

Ser His Ile Asp Arg Val Gly Gln Asp Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Val Leu Pro Lys Arg Gly Pro Trp Phe Asp Tyr Arg Gly Gln Gly
            100                 105                 110

Thr Leu Val Thr Val Ser Ser
            115

<210> SEQ ID NO 314
<211> LENGTH: 119
<212> TYPE: PRT
<213> ORGANISM: Homo sapiens

<400> SEQUENCE: 314

Glu Val Gln Leu Leu Glu Ser Gly Gly Gly Leu Ile Gln Pro Gly Gly
 1               5                  10                  15

Ser Leu Arg Leu Ser Cys Ala Ala Ser Gly Phe Thr Phe Ala His Asp
            20                  25                  30

Thr Met Val Trp Val Arg Gln Ala Pro Gly Lys Gly Leu Glu Trp Val
            35                  40                  45

Ser His Ile Asp Arg Val Gly Gln Asp Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Leu Pro Lys Arg Gly Pro Trp Phe Asp Tyr Arg Gly Gln Gly
            100                 105                 110

Thr Leu Val Thr Val Ser Ser
            115

<210> SEQ ID NO 315
<211> LENGTH: 119
<212> TYPE: PRT
<213> ORGANISM: Homo sapiens
```

<400> SEQUENCE: 315

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr His Cys
                85                  90                  95

Ala Val Leu Pro Lys Arg Gly Pro Trp Phe Asp Tyr Arg Gly Gln Gly
            100                 105                 110

Thr Leu Val Thr Val Ser Ser
        115

<210> SEQ ID NO 316
<211> LENGTH: 119
<212> TYPE: PRT
<213> ORGANISM: Homo sapiens

<400> SEQUENCE: 316

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Glu Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Val Leu Pro Lys Arg Gly Pro Trp Phe Asp Tyr Arg Gly Gln Gly
            100                 105                 110

Thr Leu Val Thr Val Ser Ser
        115

<210> SEQ ID NO 317
<211> LENGTH: 119
<212> TYPE: PRT
<213> ORGANISM: Homo sapiens

<400> SEQUENCE: 317

Glu Val Gln Leu Leu Glu Ser Gly Gly Gly Leu Ile His Pro Gly Gly
1               5                   10                  15

Thr Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Pro Tyr Tyr Ala Asp Ser Val
    50                  55                  60

Lys Gly Arg Phe Thr Ile Ser Arg Asp Asn Ser Lys Asn Thr Leu Tyr

```
                    65                  70                  75                  80
Leu Gln Met Asn Ser Leu Arg Ala Glu Asp Thr Ala Val Tyr Tyr Cys
                85                  90                  95

Ala Arg Leu Pro Lys Arg Gly Pro Trp Phe Asp Tyr Arg Gly Gln Gly
                100                 105                 110

Thr Leu Val Thr Val Ser Ser
            115

<210> SEQ ID NO 318
<211> LENGTH: 119
<212> TYPE: PRT
<213> ORGANISM: Homo sapiens

<400> SEQUENCE: 318

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
                20                  25                  30

Thr Met Val Trp Val Arg Gln Ala Pro Gly Lys Gly Leu Glu Trp Val
                35                  40                  45

Ser His Ile Asp Arg Val Gly Gln Asp Pro Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Lys Arg Gly Pro Trp Phe Asp Tyr Arg Gly Gln Gly
                100                 105                 110

Thr Gln Val Thr Val Ser Ser
            115

<210> SEQ ID NO 319
<211> LENGTH: 119
<212> TYPE: PRT
<213> ORGANISM: Homo sapiens

<400> SEQUENCE: 319

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
                20                  25                  30

Thr Met Val Trp Val Arg Gln Ala Pro Gly Lys Gly Leu Glu Trp Val
                35                  40                  45

Ser His Ile Asp Arg Val Gly Gln Asp Thr Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Trp Gly Gln Gly
                100                 105                 110

Thr Leu Val Thr Val Ser Ser
            115

<210> SEQ ID NO 320
<211> LENGTH: 119
<212> TYPE: PRT
```

<213> ORGANISM: Homo sapiens

<400> SEQUENCE: 320

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Val Leu Pro Lys Arg Gly Pro Trp Phe Asp Tyr Trp Gly Gln Gly
            100                 105                 110

Thr Leu Val Thr Val Ser Ser
        115

<210> SEQ ID NO 321
<211> LENGTH: 119
<212> TYPE: PRT
<213> ORGANISM: Homo sapiens

<400> SEQUENCE: 321

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Pro Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 322
<211> LENGTH: 119
<212> TYPE: PRT
<213> ORGANISM: Homo sapiens

<400> SEQUENCE: 322

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Asp Leu Glu Trp Val
        35                  40                  45

Ser His Ile Asp Arg Asp Gly Gln Asp Thr Tyr Tyr Ala Asp Ser Val
    50                  55                  60

```
Lys Gly Arg Phe Ser Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Leu Pro Lys Arg Gly Pro Trp Phe Asp Tyr Arg Gly Gln Gly
            100                 105                 110

Thr Leu Val Thr Val Ser Ser
            115

<210> SEQ ID NO 323
<211> LENGTH: 119
<212> TYPE: PRT
<213> ORGANISM: Homo sapiens

<400> SEQUENCE: 323

Glu Val Gln Leu Leu Glu Ser Gly Gly Gly Leu Ile Gln Pro Gly Gly
  1               5                  10                  15

Ser Leu Arg Leu Ser Cys Ala Ala Ser Gly Phe Thr Phe Ala His Glu
             20                  25                  30

Thr Met Val Trp Val Arg Gln Ala Pro Gly Lys Gly Leu Glu Trp Val
         35                  40                  45

Ser His Ile Asp Arg Val Gly Gln Asp Thr Tyr Tyr Ala Asp Ser Val
     50                  55                  60

Lys Gly Arg Phe Thr Thr Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Leu Pro Lys Arg Gly Pro Trp Phe Asp Tyr Arg Gly Gln Gly
            100                 105                 110

Thr Leu Val Thr Val Ser Ser
            115

<210> SEQ ID NO 324
<211> LENGTH: 119
<212> TYPE: PRT
<213> ORGANISM: Homo sapiens

<400> SEQUENCE: 324

Glu Val Gln Leu Leu Glu Ser Gly Gly Gly Leu Ile Gln Pro Gly Gly
  1               5                  10                  15

Ser Leu Arg Leu Ser Cys Ala Ala Ser Gly Phe Thr Phe Ala His Glu
             20                  25                  30

Thr Met Val Trp Val Arg Gln Ala Pro Gly Lys Gly Leu Glu Trp Val
         35                  40                  45

Ser His Ile Asp Arg Asp Gly Gln Asp Thr Tyr Tyr Ala Asp Ser Val
     50                  55                  60

Met Gly Arg Phe Thr Val Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Ile Pro Lys Arg Gly Pro Trp Phe Asp Tyr Arg Gly Gln Gly
            100                 105                 110

Thr Leu Val Thr Val Ser Ser
            115

<210> SEQ ID NO 325
```

```
<211> LENGTH: 119
<212> TYPE: PRT
<213> ORGANISM: Homo sapiens

<400> SEQUENCE: 325

Glu Val Gln Leu Leu Glu Ser Gly Gly Gly Leu Ile Gln Pro Gly Gly
 1               5                  10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Asp Leu Glu Trp Val
        35                  40                  45

Ser His Ile Asp Arg Val Gly Gln Asp Thr Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Val Leu Pro Lys Arg Gly Pro Trp Phe Asp Tyr Arg Gly Gln Gly
            100                 105                 110

Thr Leu Val Thr Val Ser Ser
        115

<210> SEQ ID NO 326
<211> LENGTH: 119
<212> TYPE: PRT
<213> ORGANISM: Homo sapiens

<400> SEQUENCE: 326

Glu Val Gln Leu Leu Glu Ser Gly Gly Gly Leu Ile Gln Pro Gly Gly
 1               5                  10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Thr Asp Arg Val Gly Gln Asp Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Val Leu Pro Lys Arg Gly Pro Trp Phe Asp Tyr Arg Gly Gln Gly
            100                 105                 110

Thr Leu Val Thr Val Ser Ser
        115

<210> SEQ ID NO 327
<211> LENGTH: 119
<212> TYPE: PRT
<213> ORGANISM: Homo sapiens

<400> SEQUENCE: 327

Glu Val Gln Leu Leu Glu Ser Gly Gly Gly Leu Ile Gln Pro Gly Gly
 1               5                  10                  15

Thr Leu Arg Leu Ser Cys Ala Ala Ser Gly Phe Thr Phe Ala Leu Glu
            20                  25                  30

Thr Met Val Trp Val Arg Gln Ala Pro Gly Lys Gly Leu Glu Trp Val
        35                  40                  45
```

-continued

```
Ser His Ile Asp Arg Val Gly Gln Asp Thr Tyr Tyr Ala Asp Ser Val
 50                  55                  60

Lys Gly Arg Phe Thr Thr Ser Arg Asp Asn Ser Arg Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Leu Pro Lys Arg Gly Pro Trp Phe Asp Tyr Arg Gly Gln Gly
             100                 105                 110

Thr Leu Val Thr Val Ser Ser
            115
```

<210> SEQ ID NO 328
<211> LENGTH: 119
<212> TYPE: PRT
<213> ORGANISM: Homo sapiens

<400> SEQUENCE: 328

```
Glu Val Gln Leu Leu Glu Ser Gly Gly Gly Leu Ile Gln Pro Gly Gly
  1               5                  10                  15

Ser Leu Arg Leu Ser Cys Ala Ala Ser Gly Phe Thr Phe Ala His Glu
                 20                  25                  30

Thr Met Val Trp Val Arg Gln Ala Pro Gly Lys Gly Leu Glu Trp Val
             35                  40                  45

Ser His Ile Asp Arg Val Gly Gln Asp Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Val Ile Pro Lys Arg Gly Pro Trp Phe Asp Tyr Arg Gly Gln Gly
             100                 105                 110

Thr Leu Val Thr Val Ser Ser
            115
```

<210> SEQ ID NO 329
<211> LENGTH: 119
<212> TYPE: PRT
<213> ORGANISM: Homo sapiens

<400> SEQUENCE: 329

```
Glu Val Gln Leu Leu Glu Ser Gly Gly Gly Leu Ile Gln Pro Gly Gly
  1               5                  10                  15

Ser Leu Arg Leu Ser Cys Ala Ala Ser Gly Phe Thr Phe Ala His Glu
                 20                  25                  30

Thr Met Val Trp Val Arg Gln Ala Pro Gly Lys Gly Leu Glu Trp Val
             35                  40                  45

Ser His Ile Asp Arg Val Gly Gln Asp Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Val Leu Pro Lys Arg Gly Pro Trp Phe Asp Tyr Arg Gly Gln Gly
             100                 105                 110

Thr Gln Val Thr Val Ser Ser
            115
```

<210> SEQ ID NO 330
<211> LENGTH: 119
<212> TYPE: PRT
<213> ORGANISM: Homo sapiens

<400> SEQUENCE: 330

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Ile Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Val Leu Pro Lys Arg Gly Pro Trp Phe Asp Tyr Arg Gly Gln Gly
            100                 105                 110

Thr Leu Val Thr Val Ser Ser
        115

<210> SEQ ID NO 331
<211> LENGTH: 119
<212> TYPE: PRT
<213> ORGANISM: Homo sapiens

<400> SEQUENCE: 331

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Asp
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Val Leu Pro Lys Arg Gly Pro Trp Phe Asp Tyr Trp Gly Gln Gly
            100                 105                 110

Thr Leu Val Thr Val Ser Ser
        115

<210> SEQ ID NO 332
<211> LENGTH: 119
<212> TYPE: PRT
<213> ORGANISM: Homo sapiens

<400> SEQUENCE: 332

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Asp
            20                  25                  30

Val Met Val Trp Val Arg Gln Ala Pro Gly Lys Gly Leu Glu Trp Val

```
              35                  40                  45
Ser His Ile Asp Arg Val Gly Gln Asp Thr Tyr Tyr Ala Asp Ser Val
 50                  55                  60

Glu Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Val Leu Pro Lys Arg Gly Pro Trp Phe Asp Tyr Trp Gly Gln Gly
                100                 105                 110

Thr Leu Val Thr Val Ser Ser
            115

<210> SEQ ID NO 333
<211> LENGTH: 119
<212> TYPE: PRT
<213> ORGANISM: Homo sapiens

<400> SEQUENCE: 333

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala His Glu
                 20                  25                  30

Thr Met Val Trp Val Arg Gln Ala Pro Gly Lys Gly Leu Glu Trp Val
             35                  40                  45

Ser His Ile Asp Arg Val Gly Gln Asp Pro Tyr Tyr Thr Asp Ser Val
 50                  55                  60

Glu Asp Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Val Leu Pro Lys Arg Gly Pro Trp Phe Asp Tyr Trp Gly Gln Gly
                100                 105                 110

Thr Leu Val Thr Val Ser Ser
            115

<210> SEQ ID NO 334
<211> LENGTH: 119
<212> TYPE: PRT
<213> ORGANISM: Homo sapiens

<400> SEQUENCE: 334

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala His Glu
                 20                  25                  30

Thr Met Val Trp Val Arg Gln Ala Pro Gly Lys Gly Leu Glu Trp Val
             35                  40                  45

Ser His Ile Asp Arg Val Gly Gln Asp Thr Tyr Tyr Ala Asp Ser Val
 50                  55                  60

Glu Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Leu Leu Pro Lys Arg Gly Pro Trp Phe Asp Tyr Trp Gly Gln Gly
                100                 105                 110

Thr Leu Val Thr Val Ser Ser
```

<210> SEQ ID NO 335
<211> LENGTH: 119
<212> TYPE: PRT
<213> ORGANISM: Homo sapiens

<400> SEQUENCE: 335

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Pro Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Val Leu Pro Lys Arg Gly Pro Trp Phe Asp Tyr Trp Gly Gln Gly
            100                 105                 110

Thr Leu Val Thr Val Ser Ser
        115

<210> SEQ ID NO 336
<211> LENGTH: 119
<212> TYPE: PRT
<213> ORGANISM: Homo sapiens

<400> SEQUENCE: 336

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Asn Lys Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Arg Gly Gln Gly
            100                 105                 110

Thr Leu Val Thr Val Ser Ser
        115

<210> SEQ ID NO 337
<211> LENGTH: 119
<212> TYPE: PRT
<213> ORGANISM: Homo sapiens

<400> SEQUENCE: 337

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Asn Thr Glu
            20                  25                  30

Thr Met Val Trp Val Arg Arg Ala Pro Gly Lys Gly Leu Glu Trp Val
         35                  40                  45

Ser His Ile Asp Arg Val Gly Gln Asp Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Leu Leu Pro Lys Arg Gly Pro Trp Phe Asp Tyr Arg Gly Gln Gly
                100                 105                 110

Thr Leu Val Thr Val Ser Ser
            115

<210> SEQ ID NO 338
<211> LENGTH: 119
<212> TYPE: PRT
<213> ORGANISM: Homo sapiens

<400> SEQUENCE: 338

Glu Val Gln Leu Leu Glu Ser Gly Gly Gly Leu Ile Gln Pro Gly Gly
 1               5                  10                  15

Ser Leu Arg Leu Ser Cys Ala Ala Ser Gly Phe Thr Phe Thr Lys Glu
                 20                  25                  30

Thr Met Val Trp Val Arg Gln Ala Pro Gly Lys Gly Leu Glu Trp Val
         35                  40                  45

Ser His Ile Asp Arg Val Gly Gln Asp Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Leu Leu Pro Lys Arg Gly Pro Trp Phe Asp Tyr Arg Gly Gln Gly
                100                 105                 110

Thr Leu Val Thr Val Ser Ser
            115

<210> SEQ ID NO 339
<211> LENGTH: 119
<212> TYPE: PRT
<213> ORGANISM: Homo sapiens

<400> SEQUENCE: 339

Glu Val Gln Leu Leu Glu Ser Gly Gly Gly Leu Ile Gln Pro Gly Gly
 1               5                  10                  15

Ser Leu Arg Leu Ser Cys Ala Ala Ser Gly Phe Thr Phe Ala His Glu
                 20                  25                  30

Thr Met Val Trp Val Arg Gln Ala Pro Gly Lys Gly Leu Glu Trp Val
         35                  40                  45

Ser His Ile Asp Gly Gly Val Asp Thr Tyr Tyr Ala Asp Pro Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Leu Leu Pro Lys Arg Gly Pro Trp Phe Asp Tyr Arg Gly Gln Gly
                100                 105                 110

```
Thr Leu Val Thr Val Ser Ser
        115

<210> SEQ ID NO 340
<211> LENGTH: 119
<212> TYPE: PRT
<213> ORGANISM: Homo sapiens

<400> SEQUENCE: 340

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Gly Gly Arg Asp Thr Tyr Tyr Ala Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Arg Gly Gln Gly
            100                 105                 110

Thr Leu Val Thr Val Ser Ser
        115

<210> SEQ ID NO 341
<211> LENGTH: 119
<212> TYPE: PRT
<213> ORGANISM: Homo sapiens

<400> SEQUENCE: 341

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Gly Gly Val Asp Thr Tyr Tyr Ala Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Arg Gly Gln Gly
            100                 105                 110

Thr Leu Val Thr Val Ser Ser
        115

<210> SEQ ID NO 342
<211> LENGTH: 119
<212> TYPE: PRT
<213> ORGANISM: Homo sapiens

<400> SEQUENCE: 342

Glu Val Gln Leu Leu Glu Ser Gly Gly Gly Leu Ile Gln Pro Gly Gly
1               5                   10                  15
```

```
Ser Leu Arg Leu Ser Cys Ala Ala Ser Gly Phe Thr Phe Asn Asn Gln
             20                  25                  30

Val Met Val Trp Val Arg Gln Ala Pro Gly Lys Gly Leu Glu Trp Val
         35                  40                  45

Ser His Ile Asp Arg Val Gly Gln Asp Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Leu Leu Pro Lys Arg Gly Pro Trp Phe Asp Tyr Arg Gly Gln Gly
            100                 105                 110

Thr Leu Val Thr Val Ser Ser
            115

<210> SEQ ID NO 343
<211> LENGTH: 119
<212> TYPE: PRT
<213> ORGANISM: Homo sapiens

<400> SEQUENCE: 343

Glu Val Gln Leu Leu Glu Ser Gly Gly Gly Leu Ile Gln Pro Gly Gly
  1               5                  10                  15

Ser Leu Arg Leu Ser Cys Ala Ala Ser Gly Phe Thr Phe Ala His Glu
             20                  25                  30

Thr Met Val Trp Val Arg Gln Ala Pro Gly Lys Gly Leu Glu Trp Val
         35                  40                  45

Ser His Ile Asp Gly Gly Leu Asp Thr Tyr Tyr Ala Asp Pro Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Leu Leu Pro Lys Arg Gly Pro Trp Phe Asp Tyr Arg Gly Gln Gly
            100                 105                 110

Thr Leu Val Thr Val Ser Ser
            115

<210> SEQ ID NO 344
<211> LENGTH: 119
<212> TYPE: PRT
<213> ORGANISM: Homo sapiens

<400> SEQUENCE: 344

Glu Val Gln Leu Leu Glu Ser Gly Gly Gly Leu Ile Gln Pro Gly Gly
  1               5                  10                  15

Ser Leu Arg Leu Ser Cys Ala Ala Ser Gly Phe Thr Phe Ala His Glu
             20                  25                  30

Thr Met Val Trp Val Arg Gln Ala Pro Gly Lys Gly Leu Glu Trp Val
         35                  40                  45

Ser His Ile Asp Ala Val Gly Ser Asp Thr Tyr Tyr Ala Asp Pro Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

Ala Leu Leu Pro Lys Arg Gly Pro Trp Phe Asp Tyr Arg Gly Gln Gly
            100                 105                 110

Thr Leu Val Thr Val Ser Ser
            115

<210> SEQ ID NO 345
<211> LENGTH: 119
<212> TYPE: PRT
<213> ORGANISM: Homo sapiens

<400> SEQUENCE: 345

Glu Val Gln Leu Leu Glu Ser Gly Gly Gly Leu Ile Gln Pro Gly Gly
 1               5                  10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Arg Gly Gln Gly
            100                 105                 110

Thr Leu Val Thr Val Ser Ser
            115

<210> SEQ ID NO 346
<211> LENGTH: 119
<212> TYPE: PRT
<213> ORGANISM: Homo sapiens

<400> SEQUENCE: 346

Glu Val Gln Leu Leu Glu Ser Gly Gly Gly Leu Ile Gln Pro Gly Gly
 1               5                  10                  15

Ser Leu Arg Leu Ser Cys Ala Ala Ser Gly Phe Thr Phe Gly Asn Glu
            20                  25                  30

Val Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Arg Gly Gln Gly
            100                 105                 110

Thr Leu Val Thr Val Ser Gly
            115

<210> SEQ ID NO 347
<211> LENGTH: 119
<212> TYPE: PRT
<213> ORGANISM: Homo sapiens

<400> SEQUENCE: 347

Glu Val Gln Leu Leu Glu Ser Gly Gly Gly Leu Ile Gln Pro Gly Gly

```
            1               5                  10                 15
Ser Leu Arg Leu Ser Cys Ala Ala Ser Gly Phe Thr Phe Asn Asn Gln
                20                  25                 30
Thr Met Val Trp Val Arg Gln Ala Pro Gly Lys Gly Leu Glu Trp Val
        35                  40                 45
Ser His Ile Asp Arg Val Gly Gln Asp Thr Tyr Tyr Ala Asp Ser Val
        50                  55                 60
Lys Gly Arg Phe Thr Ile Ser Arg Asp Asn Ser Lys Asn Thr Leu Tyr
 65                 70                  75                 80
Leu Gln Met Asn Ser Leu Arg Ala Glu Asp Thr Ala Val Tyr Tyr Cys
                85                  90                 95
Ala Leu Leu Pro Lys Arg Gly Pro Trp Phe Asp Tyr Arg Gly Gln Gly
                100                 105                110
Thr Leu Val Thr Val Ser Ser
                115

<210> SEQ ID NO 348
<211> LENGTH: 119
<212> TYPE: PRT
<213> ORGANISM: Homo sapiens

<400> SEQUENCE: 348

Glu Val Gln Leu Leu Glu Ser Gly Gly Gly Leu Ile Gln Pro Gly Gly
 1               5                  10                 15
Ser Leu Arg Leu Ser Cys Ala Ala Ser Gly Phe Thr Phe Asp Asn Thr
                20                  25                 30
Thr Met Val Trp Val Arg Gln Ala Pro Gly Lys Gly Leu Glu Trp Val
        35                  40                 45
Ser His Ile Asp Arg Val Gly Gln Asp Thr Tyr Tyr Ala Asp Ser Val
        50                  55                 60
Lys Gly Arg Phe Thr Ile Ser Arg Asp Asn Ser Lys Asn Thr Leu Tyr
 65                 70                  75                 80
Leu Gln Met Asn Ser Leu Arg Ala Glu Asp Thr Ala Val Tyr Tyr Cys
                85                  90                 95
Ala Leu Leu Pro Lys Arg Gly Pro Trp Phe Asp Tyr Arg Gly Gln Gly
                100                 105                110
Thr Leu Val Thr Val Ser Ser
                115

<210> SEQ ID NO 349
<211> LENGTH: 119
<212> TYPE: PRT
<213> ORGANISM: Homo sapiens

<400> SEQUENCE: 349

Glu Val Gln Leu Leu Glu Ser Gly Gly Gly Leu Val Gln Pro Gly Gly
 1               5                  10                 15
Ser Leu Arg Leu Ser Cys Ala Ala Ser Gly Phe Thr Phe Ala His Glu
                20                  25                 30
Thr Met Val Trp Val Arg Gln Ala Pro Gly Lys Gly Leu Glu Trp Val
        35                  40                 45
Ser His Ile Asp Arg Val Gly Gln Asp Pro Tyr Tyr Ala Asp Ser Val
        50                  55                 60
Glu Gly Arg Phe Thr Ile Ser Arg Asp Asn Ser Lys Asn Thr Leu Tyr
 65                 70                  75                 80
Leu Gln Met Asn Ser Leu Arg Ala Glu Asp Thr Ala Val Tyr Tyr Cys
```

-continued

```
                    85                  90                  95

Ala Leu Leu Pro Lys Arg Gly Pro Trp Phe Asp Tyr Trp Gly Gln Gly
                100                 105                 110

Thr Leu Val Thr Val Ser Ser
        115

<210> SEQ ID NO 350
<211> LENGTH: 119
<212> TYPE: PRT
<213> ORGANISM: Homo sapiens

<400> SEQUENCE: 350

Glu Val Gln Leu Leu Glu Ser Gly Gly Gly Leu Ile Gln Pro Gly Gly
  1               5                  10                  15

Ser Leu Arg Leu Ser Cys Ala Ala Ser Gly Phe Thr Phe Ala His Glu
             20                  25                  30

Thr Met Val Trp Val Arg Gln Ala Pro Gly Lys Gly Leu Glu Trp Val
         35                  40                  45

Ser His Ile Asp Gly Gly Val Asp Thr Tyr Tyr Ala Asp Pro Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Leu Leu Pro Lys Arg Gly Pro Trp Phe Asp Tyr Arg Gly Gln Gly
                100                 105                 110

Thr Leu Val Thr Val Ser Ser
        115

<210> SEQ ID NO 351
<211> LENGTH: 119
<212> TYPE: PRT
<213> ORGANISM: Homo sapiens

<400> SEQUENCE: 351

Glu Val Gln Leu Leu Glu Ser Gly Gly Gly Leu Ile Gln Pro Gly Gly
  1               5                  10                  15

Ser Leu Arg Leu Ser Cys Ala Ala Ser Gly Phe Thr Phe Ala His Glu
             20                  25                  30

Thr Met Val Trp Val Arg Gln Ala Pro Gly Lys Gly Leu Glu Trp Val
         35                  40                  45

Ser His Ile Asp Arg Val Gly Gln Asp Pro Tyr Tyr Ala Asp Ser Val
     50                  55                  60

Glu Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Val Leu Pro Lys Arg Gly Pro Trp Phe Asp Tyr Arg Gly Gln Gly
                100                 105                 110

Thr Leu Val Thr Val Ser Ser
        115

<210> SEQ ID NO 352
<211> LENGTH: 119
<212> TYPE: PRT
<213> ORGANISM: Homo sapiens

<400> SEQUENCE: 352
```

```
Glu Val Gln Leu Leu Glu Ser Gly Gly Gly Leu Ile Gln Pro Gly Gly
  1               5                  10                  15

Ser Leu Arg Leu Ser Cys Ala Ala Ser Gly Phe Thr Phe Ala His Glu
             20                  25                  30

Thr Met Val Trp Val Arg Gln Ala Pro Gly Lys Gly Leu Glu Trp Val
             35                  40                  45

Ser His Ile Asp Arg Val Gly Gln Asp Pro Tyr Tyr Ala Asp Ser Val
         50                  55                  60

Glu Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Leu Leu Pro Lys Arg Gly Pro Trp Phe Asp Tyr Arg Gly Gln Gly
            100                 105                 110

Thr Leu Val Thr Val Ser Ser
            115
```

<210> SEQ ID NO 353
<211> LENGTH: 119
<212> TYPE: PRT
<213> ORGANISM: Homo sapiens

<400> SEQUENCE: 353

```
Glu Val Gln Leu Leu Glu Ser Gly Gly Gly Leu Ile Gln Pro Gly Gly
  1               5                  10                  15

Ser Leu Arg Leu Ser Cys Ala Ala Ser Gly Phe Thr Phe Ala His Glu
             20                  25                  30

Thr Met Val Trp Val Arg Gln Ala Pro Gly Lys Gly Leu Glu Trp Val
             35                  40                  45

Ser His Ile Asp Arg Val Gly Gln Asp Pro Tyr Tyr Ala Asp Ser Val
         50                  55                  60

Glu Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Val Leu Pro Lys Arg Gly Pro Trp Phe Asp Tyr Trp Gly Gln Gly
            100                 105                 110

Thr Leu Val Thr Val Ser Ser
            115
```

<210> SEQ ID NO 354
<211> LENGTH: 119
<212> TYPE: PRT
<213> ORGANISM: Homo sapiens

<400> SEQUENCE: 354

```
Glu Val Gln Leu Leu Glu Ser Gly Gly Gly Leu Ile Gln Pro Gly Gly
  1               5                  10                  15

Ser Leu Arg Leu Ser Cys Ala Ala Ser Gly Phe Thr Phe Ala His Glu
             20                  25                  30

Thr Met Val Trp Val Arg Gln Ala Pro Gly Lys Gly Leu Glu Trp Val
             35                  40                  45

Ser His Ile Asp Arg Val Gly Gln Asp Pro Tyr Tyr Ala Asp Ser Val
         50                  55                  60

Glu Gly Arg Phe Thr Ile Ser Arg Asp Asn Ser Lys Asn Thr Leu Tyr
 65                  70                  75                  80
```

-continued

Leu Gln Met Asn Ser Leu Arg Ala Glu Asp Thr Ala Val Tyr Tyr Cys
                85                  90                  95

Ala Val Leu Pro Lys Arg Gly Pro Trp Phe Asp Tyr Trp Gly Gln Gly
            100                 105                 110

Thr Leu Val Thr Val Ser Ser
        115

<210> SEQ ID NO 355
<211> LENGTH: 119
<212> TYPE: PRT
<213> ORGANISM: Homo sapiens

<400> SEQUENCE: 355

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Pro Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 356
<211> LENGTH: 119
<212> TYPE: PRT
<213> ORGANISM: Homo sapiens

<400> SEQUENCE: 356

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Pro Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Arg Gly Gln Gly
            100                 105                 110

Thr Leu Val Thr Val Ser Ser
        115

<210> SEQ ID NO 357
<211> LENGTH: 119
<212> TYPE: PRT
<213> ORGANISM: Homo sapiens

<400> SEQUENCE: 357

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Gly Gly Val Asp Thr Tyr Tyr Ala Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 358
<211> LENGTH: 119
<212> TYPE: PRT
<213> ORGANISM: Homo sapiens

<400> SEQUENCE: 358

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Gly Gly Val Asp Thr Tyr Tyr Ala Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 359
<211> LENGTH: 119
<212> TYPE: PRT
<213> ORGANISM: Homo sapiens

<400> SEQUENCE: 359

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Gly Gly Val Asp Thr Tyr Tyr Ala Asp Pro Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Val Leu Pro Lys Arg Gly Pro Trp Phe Asp Tyr Arg Gly Gln Gly
            100                 105                 110

Thr Leu Val Thr Val Ser Ser
            115
```

<210> SEQ ID NO 360
<211> LENGTH: 119
<212> TYPE: PRT
<213> ORGANISM: Homo sapiens

<400> SEQUENCE: 360

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
         35                  40                  45

Ser His Ile Asp Gly Gly Gly Val Asp Thr Tyr Tyr Ala Asp Pro Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Val Leu Pro Lys Arg Gly Pro Trp Phe Asp Tyr Arg Gly Gln Gly
            100                 105                 110

Thr Leu Val Thr Val Ser Ser
            115
```

<210> SEQ ID NO 361
<211> LENGTH: 119
<212> TYPE: PRT
<213> ORGANISM: Homo sapiens

<400> SEQUENCE: 361

```
Glu Val Gln Leu Leu Glu Ser Gly Gly Gly Leu Ile Gln Pro Gly Gly
 1               5                  10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
         35                  40                  45

Ser His Ile Asp Gly Gly Gly Val Asp Thr Tyr Tyr Ala Asp Pro Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Val Leu Pro Lys Arg Gly Pro Trp Phe Asp Tyr Trp Gly Gln Gly
            100                 105                 110

Thr Leu Val Thr Val Ser Ser
            115
```

<210> SEQ ID NO 362
<211> LENGTH: 119

<212> TYPE: PRT
<213> ORGANISM: Homo sapiens

<400> SEQUENCE: 362

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Gly Gly Val Asp Thr Tyr Tyr Ala Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Val Leu Pro Lys Arg Gly Pro Trp Phe Asp Tyr Trp Gly Gln Gly
            100                 105                 110

Thr Leu Val Thr Val Ser Ser
            115
```

<210> SEQ ID NO 363
<211> LENGTH: 119
<212> TYPE: PRT
<213> ORGANISM: Homo sapiens

<400> SEQUENCE: 363

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Pro Pro Val Gly Gln Asp Pro Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Val Leu Pro Lys Arg Gly Pro Trp Phe Asp Tyr Trp Gly Gln Gly
            100                 105                 110

Thr Leu Val Thr Val Ser Ser
            115
```

<210> SEQ ID NO 364
<211> LENGTH: 119
<212> TYPE: PRT
<213> ORGANISM: Homo sapiens

<400> SEQUENCE: 364

```
Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Pro Pro Val Gly Gln Asp Pro Phe Tyr Ala Asp Ser Val
```

```
            50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Leu Leu Pro Lys Arg Gly Pro Trp Phe Asp Tyr Trp Gly Gln Gly
                100                 105                 110

Thr Leu Val Thr Val Ser Ser
        115

<210> SEQ ID NO 365
<211> LENGTH: 119
<212> TYPE: PRT
<213> ORGANISM: Homo sapiens

<400> SEQUENCE: 365

Glu Val Gln Leu Leu Glu Ser Gly Gly Gly Leu Ile Gln Pro Gly Gly
  1               5                  10                  15

Ser Leu Arg Leu Ser Cys Ala Ala Ser Gly Phe Thr Phe Ala His Glu
                 20                  25                  30

Thr Met Val Trp Val Arg Gln Ala Pro Gly Lys Gly Leu Glu Trp Val
                 35                  40                  45

Ser His Ile Pro Pro Val Gly Gln Asp Pro Tyr Ala Asp Ser Val
             50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Val Leu Pro Lys Arg Gly Pro Trp Phe Asp Tyr Trp Gly Gln Gly
                100                 105                 110

Thr Leu Val Thr Val Ser Ser
        115

<210> SEQ ID NO 366
<211> LENGTH: 119
<212> TYPE: PRT
<213> ORGANISM: Homo sapiens

<400> SEQUENCE: 366

Glu Val Gln Leu Leu Glu Ser Gly Gly Gly Leu Ile Gln Pro Gly Gly
  1               5                  10                  15

Ser Leu Arg Leu Ser Cys Ala Ala Ser Gly Phe Thr Phe Ala His Glu
                 20                  25                  30

Thr Met Val Trp Val Arg Gln Ala Pro Gly Lys Gly Leu Glu Trp Val
                 35                  40                  45

Ser His Ile Asp Gly Gly Val Asp Thr Tyr Tyr Ala Asp Pro Val
             50                  55                  60

Lys Gly Arg Phe Thr Ile Ser Arg Asp Asn Ser Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Leu Leu Pro Lys Arg Gly Pro Trp Phe Asp Tyr Trp Gly Gln Gly
                100                 105                 110

Thr Leu Val Thr Val Ser Ser
        115
```

<210> SEQ ID NO 367
<211> LENGTH: 119
<212> TYPE: PRT
<213> ORGANISM: Homo sapiens

<400> SEQUENCE: 367

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Pro Pro Val Gly Gln Asp Pro Phe Tyr Ala Asp Ser Val
50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 368
<211> LENGTH: 119
<212> TYPE: PRT
<213> ORGANISM: Homo sapiens

<400> SEQUENCE: 368

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe His Asp Gln
            20                  25                  30

His Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 369
<211> LENGTH: 119
<212> TYPE: PRT
<213> ORGANISM: Homo sapiens

<400> SEQUENCE: 369

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Asn Asn
            20                  25                  30

Ile Met Val Trp Val Arg Gln Ala Pro Gly Lys Gly Leu Glu Trp Val
        35                  40                  45

```
Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Asn Leu Arg Ala Glu Asp Thr Ala Val Tyr Tyr Cys
                 85                  90                  95

Ala Leu Leu Pro Lys Arg Gly Pro Trp Phe Asp Tyr Trp Gly Gln Gly
            100                 105                 110

Thr Leu Val Thr Val Ser Ser
            115

<210> SEQ ID NO 370
<211> LENGTH: 119
<212> TYPE: PRT
<213> ORGANISM: Homo sapiens

<400> SEQUENCE: 370

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Ser Phe Lys Asn Lys
            20                  25                  30

Thr Met Val Trp Val Arg Gln Ala Gln Gly Lys Gly Leu Glu Trp Val
         35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Leu Leu Pro Lys Arg Gly Pro Trp Phe Asp Tyr Trp Gly Gln Gly
            100                 105                 110

Thr Leu Val Thr Val Ser Ser
            115

<210> SEQ ID NO 371
<211> LENGTH: 119
<212> TYPE: PRT
<213> ORGANISM: Homo sapiens

<400> SEQUENCE: 371

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asn Lys His
            20                  25                  30

Thr Met Val Trp Val Arg Gln Ala Pro Gly Lys Gly Leu Glu Trp Val
         35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Leu Leu Pro Lys Arg Gly Pro Trp Phe Asp Tyr Trp Gly Gln Gly
            100                 105                 110

Thr Leu Val Thr Val Ser Ser
            115
```

<210> SEQ ID NO 372
<211> LENGTH: 119
<212> TYPE: PRT
<213> ORGANISM: Homo sapiens

<400> SEQUENCE: 372

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asn Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 373
<211> LENGTH: 119
<212> TYPE: PRT
<213> ORGANISM: Homo sapiens

<400> SEQUENCE: 373

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Gly Arg Gly Gly Thr Tyr Tyr Thr Asp Ser Val
    50                  55                  60

Lys Gly Arg Phe Thr Thr Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 374
<211> LENGTH: 119
<212> TYPE: PRT
<213> ORGANISM: Homo sapiens

<400> SEQUENCE: 374

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

```
Thr Met Val Trp Val Arg Gln Ala Pro Gly Lys Gly Leu Glu Trp Val
        35                  40                  45

Ser His Ile Asp Gln Gln Gly Glu Gly Thr Tyr Tyr Thr Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 375
<211> LENGTH: 119
<212> TYPE: PRT
<213> ORGANISM: Homo sapiens

<400> SEQUENCE: 375

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Gly Gly Gly Gly Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 376
<211> LENGTH: 119
<212> TYPE: PRT
<213> ORGANISM: Homo sapiens

<400> SEQUENCE: 376

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Gly Gly Leu Gly Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Trp Gly Gln Gly
            100                 105                 110
```

Thr Leu Val Thr Val Ser Ser
        115

<210> SEQ ID NO 377
<211> LENGTH: 119
<212> TYPE: PRT
<213> ORGANISM: Homo sapiens

<400> SEQUENCE: 377

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Lys Arg Gly Pro Trp Phe Asp Tyr Trp Gly Gln Gly
            100                 105                 110

Thr Leu Val Thr Val Ser Ser
        115

<210> SEQ ID NO 378
<211> LENGTH: 119
<212> TYPE: PRT
<213> ORGANISM: Homo sapiens

<400> SEQUENCE: 378

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asn Asn Lys
            20                  25                  30

Thr Met Val Trp Val Arg Gln Ala Pro Gly Lys Gly Leu Glu Trp Val
        35                  40                  45

Ser His Ile Asp Gly Arg Gly Glu Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 379
<211> LENGTH: 119
<212> TYPE: PRT
<213> ORGANISM: Homo sapiens

<400> SEQUENCE: 379

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala His Glu

```
                    20                  25                  30

Thr Met Val Trp Val Arg Gln Ala Pro Gly Lys Gly Leu Glu Trp Val
            35                  40                  45

Ser His Ile Pro Pro Val Gly Gln Asp Pro Phe Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Trp Gly Gln Gly
                100                 105                 110

Thr Leu Val Thr Val Ser Ser
            115

<210> SEQ ID NO 380
<211> LENGTH: 119
<212> TYPE: PRT
<213> ORGANISM: Homo sapiens

<400> SEQUENCE: 380

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala His Glu
            20                  25                  30

Thr Met Val Trp Val Arg Gln Ala Pro Gly Arg Gly Leu Glu Trp Val
            35                  40                  45

Ser His Ile Asp Arg Val Gly Gln Asp Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Trp Gly Gln Gly
                100                 105                 110

Thr Leu Val Thr Val Ser Ser
            115

<210> SEQ ID NO 381
<211> LENGTH: 119
<212> TYPE: PRT
<213> ORGANISM: Homo sapiens

<400> SEQUENCE: 381

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
            35                  40                  45

Ser His Ile Asp Arg Val Gly Gln Asp Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Leu Pro Arg Arg Gly Pro Trp Phe Asp Tyr Trp Gly Gln Gly
```

-continued

```
                    100                 105                 110
Thr Leu Val Thr Val Ser Ser
        115

<210> SEQ ID NO 382
<211> LENGTH: 119
<212> TYPE: PRT
<213> ORGANISM: Homo sapiens
<220> FEATURE:
<221> NAME/KEY: VARIANT
<222> LOCATION: 4
<223> OTHER INFORMATION: Xaa = Any Amino Acid

<400> SEQUENCE: 382

Glu Val Gln Xaa Leu Glu Ser Gly Gly Gly Leu Val Gln Pro Gly Gly
  1               5                  10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 383
<211> LENGTH: 119
<212> TYPE: PRT
<213> ORGANISM: Homo sapiens

<400> SEQUENCE: 383

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Ser Asp Asp Gly Asn Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Leu Pro Lys Arg Gly Pro Trp Phe Asp Tyr Trp Gly Gln Gly
            100                 105                 110

Thr Leu Val Thr Val Ser Ser
        115

<210> SEQ ID NO 384
<211> LENGTH: 119
<212> TYPE: PRT
<213> ORGANISM: Homo sapiens
```

-continued

<400> SEQUENCE: 384

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Ala Met Val Trp Val Arg Gln Ala Pro Gly Lys Gly Leu Glu Trp Val
        35                  40                  45

Ser His Ile Asp Gly Gly Glu Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Pro Pro Gly Pro Trp Phe Asp Tyr Trp Gly Gln Gly
            100                 105                 110

Thr Leu Val Thr Val Ser Ser
        115

<210> SEQ ID NO 385
<211> LENGTH: 119
<212> TYPE: PRT
<213> ORGANISM: Homo sapiens

<400> SEQUENCE: 385

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe His Asn Lys
            20                  25                  30

Asp Met Val Trp Val Arg Gln Ala Pro Gly Lys Gly Leu Glu Trp Val
        35                  40                  45

Ser His Ile Asp Gly Gly Glu Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Leu Leu Pro Trp Phe Asp Tyr Trp Gly Gln Gly
            100                 105                 110

Thr Leu Val Thr Val Ser Ser
        115

<210> SEQ ID NO 386
<211> LENGTH: 119
<212> TYPE: PRT
<213> ORGANISM: Homo sapiens

<400> SEQUENCE: 386

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Met Arg
            20                  25                  30

Thr Met Val Trp Val Arg Gln Ala Pro Gly Lys Gly Leu Glu Trp Val
        35                  40                  45

Ser His Ile Asp Gly Gly Glu Ser Thr Tyr Tyr Ala Asp Ser Val
    50                  55                  60

Lys Gly Arg Phe Thr Ile Ser Arg Asp Asn Ser Lys Asn Thr Leu Tyr

```
                65                  70                  75                  80
Leu Gln Met Asn Ser Leu Arg Ala Glu Asp Thr Ala Val Tyr Tyr Cys
                85                  90                  95

Ala Arg Leu Pro Lys Arg Gly Pro Trp Phe Asp Tyr Trp Gly Gln Gly
            100                 105                 110

Thr Leu Val Thr Val Ser Ser
        115

<210> SEQ ID NO 387
<211> LENGTH: 119
<212> TYPE: PRT
<213> ORGANISM: Homo sapiens

<400> SEQUENCE: 387

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ala His Glu
                 20                  25                  30

Thr Met Val Trp Val Arg Gln Ala Pro Gly Lys Gly Leu Glu Trp Val
            35                  40                  45

Ser His Ile Asp Gly Gly Gly Glu Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Leu Pro Lys Arg Gly Pro Trp Phe Asp Tyr Trp Gly Gln Gly
            100                 105                 110

Thr Leu Val Thr Val Ser Ser
        115

<210> SEQ ID NO 388
<211> LENGTH: 119
<212> TYPE: PRT
<213> ORGANISM: Homo sapiens

<400> SEQUENCE: 388

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ala His Glu
                 20                  25                  30

Thr Met Val Trp Val Arg Gln Ala Pro Gly Lys Gly Leu Glu Trp Val
            35                  40                  45

Ser His Ile Asp Gly Gly Gly Leu Val Thr Tyr Tyr Thr Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 389
<211> LENGTH: 119
<212> TYPE: PRT
```

<213> ORGANISM: Homo sapiens

<400> SEQUENCE: 389

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asn Thr
            20                  25                  30

Thr Met Val Trp Val Arg Gln Ala Pro Gly Lys Gly Leu Glu Trp Val
        35                  40                  45

Ser His Ile Asp Gly Val Gly Asp Thr Tyr Tyr Ala Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 390
<211> LENGTH: 119
<212> TYPE: PRT
<213> ORGANISM: Homo sapiens

<400> SEQUENCE: 390

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Asn Lys
            20                  25                  30

Thr Met Val Trp Val Arg Gln Ala Pro Gly Lys Gly Leu Glu Trp Val
        35                  40                  45

Ser His Ile Asp Gly Leu Gly Leu Val Thr Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 391
<211> LENGTH: 119
<212> TYPE: PRT
<213> ORGANISM: Homo sapiens

<400> SEQUENCE: 391

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr Thr
            20                  25                  30

Asn Met Val Trp Val Arg Gln Ala Pro Gly Lys Gly Leu Glu Trp Val
        35                  40                  45

Ser Glu Ile Arg Val Gly Gly Asp Thr Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Leu Leu Pro Lys Arg Gly Pro Trp Phe Asp Tyr Trp Gly Gln Gly
            100                 105                 110

Thr Leu Val Thr Val Ser Ser
            115

<210> SEQ ID NO 392
<211> LENGTH: 119
<212> TYPE: PRT
<213> ORGANISM: Homo sapiens

<400> SEQUENCE: 392

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Lys Asn Lys
                 20                  25                  30

Thr Met Val Trp Val Arg Gln Ala Pro Gly Lys Gly Leu Glu Trp Val
             35                  40                  45

Ser His Ile Asp Gln Glu Gly Glu Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Leu Leu Pro Lys Arg Gly Pro Trp Phe Asp Tyr Arg Gly Gln Gly
            100                 105                 110

Thr Leu Val Thr Val Ser Ser
            115

<210> SEQ ID NO 393
<211> LENGTH: 119
<212> TYPE: PRT
<213> ORGANISM: Homo sapiens

<400> SEQUENCE: 393

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Asn Asn Thr
                 20                  25                  30

Thr Met Val Trp Val Arg Gln Ala Pro Gly Lys Gly Leu Glu Trp Val
             35                  40                  45

Ser His Ile Asp Gly Glu Gly Ser Val Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Leu Leu Pro Lys Arg Gly Pro Trp Phe Asp Tyr Trp Gly Gln Gly
            100                 105                 110

Thr Leu Val Thr Val Ser Ser
            115

<210> SEQ ID NO 394
```

```
<211> LENGTH: 119
<212> TYPE: PRT
<213> ORGANISM: Homo sapiens

<400> SEQUENCE: 394

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Asn Lys
            20                  25                  30

Thr Met Val Trp Val Arg Gln Ala Pro Gly Lys Gly Leu Glu Trp Val
        35                  40                  45

Ser His Ile Asp Ala Thr Gly Thr Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Arg Gly Gln Gly
            100                 105                 110

Thr Leu Val Thr Val Ser Ser
        115

<210> SEQ ID NO 395
<211> LENGTH: 119
<212> TYPE: PRT
<213> ORGANISM: Homo sapiens

<400> SEQUENCE: 395

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Lys Lys
            20                  25                  30

Thr Met Val Trp Val Arg Gln Ala Pro Gly Lys Gly Leu Glu Trp Val
        35                  40                  45

Ser His Ile Asp Gly Lys Gly Gln Ala Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 396
<211> LENGTH: 119
<212> TYPE: PRT
<213> ORGANISM: Homo sapiens
<220> FEATURE:
<221> NAME/KEY: VARIANT
<222> LOCATION: 4
<223> OTHER INFORMATION: Xaa = Any Amino Acid

<400> SEQUENCE: 396

Glu Val Gln Xaa Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30
```

```
Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
 50                  55                  60

Glu Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Leu Leu Pro Lys Arg Gly Pro Trp Phe Asp Tyr Trp Gly Gln Gly
             100                 105                 110

Thr Leu Val Thr Val Ser Ser
        115

<210> SEQ ID NO 397
<211> LENGTH: 119
<212> TYPE: PRT
<213> ORGANISM: Homo sapiens

<400> SEQUENCE: 397

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala His Glu
             20                  25                  30

Thr Met Val Trp Val Arg Gln Ala Pro Gly Lys Gly Leu Glu Trp Val
        35                  40                  45

Ser His Ile Asp Gly Gly Gly Glu Ser Thr Tyr Tyr Ala Asp Ser Val
 50                  55                  60

Glu Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Leu Pro Lys Arg Gly Pro Trp Phe Asp Tyr Trp Gly Gln Gly
             100                 105                 110

Thr Leu Val Thr Val Ser Ser
        115

<210> SEQ ID NO 398
<211> LENGTH: 119
<212> TYPE: PRT
<213> ORGANISM: Homo sapiens

<400> SEQUENCE: 398

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala His Glu
             20                  25                  30

Thr Met Val Trp Val Arg Gln Ala Pro Gly Lys Gly Leu Glu Trp Val
        35                  40                  45

Ser His Ile Asp Gly Gly Gly Glu Ser Thr Tyr Tyr Ala Asp Pro Val
 50                  55                  60

Glu Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Leu Pro Lys Arg Gly Pro Trp Phe Asp Tyr Trp Gly Gln Gly
             100                 105                 110
```

Thr Leu Val Thr Val Ser Ser
        115

<210> SEQ ID NO 399
<211> LENGTH: 119
<212> TYPE: PRT
<213> ORGANISM: Homo sapiens

<400> SEQUENCE: 399

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Asn Lys
            20                  25                  30

Thr Met Val Trp Val Arg Gln Ala Pro Gly Lys Gly Leu Glu Trp Val
        35                  40                  45

Ser His Ile Asp Ala Thr Gly Thr Ile Thr Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Arg Gly Gln Gly
            100                 105                 110

Thr Leu Val Thr Val Ser Ser
        115

<210> SEQ ID NO 400
<211> LENGTH: 119
<212> TYPE: PRT
<213> ORGANISM: Homo sapiens

<400> SEQUENCE: 400

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Lys Lys
            20                  25                  30

Thr Met Val Trp Val Arg Gln Ala Pro Gly Lys Gly Leu Glu Trp Val
        35                  40                  45

Ser His Ile Asp Gly Lys Gly Gln Ala Thr Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 401
<211> LENGTH: 119
<212> TYPE: PRT
<213> ORGANISM: Homo sapiens

<400> SEQUENCE: 401

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Asn Lys Lys
            20                  25                  30

Thr Met Val Trp Val Arg Gln Ala Pro Gly Lys Gly Leu Glu Trp Val
        35                  40                  45

Ser His Ile Asp Gly Lys Gly Gln Asp Pro Phe Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Leu Leu Pro Lys Arg Gly Pro Trp Phe Asp Tyr Trp Gly Gln Gly
            100                 105                 110

Thr Leu Val Thr Val Ser Ser
            115

<210> SEQ ID NO 402
<211> LENGTH: 119
<212> TYPE: PRT
<213> ORGANISM: Homo sapiens

<400> SEQUENCE: 402

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Gly Gly Gly Leu Val Thr Tyr Tyr Thr Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Leu Leu Pro Lys Arg Gly Pro Trp Phe Asp Tyr Trp Gly Gln Gly
            100                 105                 110

Thr Leu Val Thr Val Ser Ser
            115

<210> SEQ ID NO 403
<211> LENGTH: 119
<212> TYPE: PRT
<213> ORGANISM: Homo sapiens

<400> SEQUENCE: 403

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Gly Gly Gly Leu Val Thr Tyr Tyr Thr Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95
```

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 404
<211> LENGTH: 119
<212> TYPE: PRT
<213> ORGANISM: Homo sapiens

<400> SEQUENCE: 404

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Gly Gly Leu Val Thr Tyr Tyr Thr Asp Pro Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 405
<211> LENGTH: 119
<212> TYPE: PRT
<213> ORGANISM: Homo sapiens

<400> SEQUENCE: 405

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Pro Pro Val Gly Gln Asp Pro Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 406
<211> LENGTH: 119
<212> TYPE: PRT
<213> ORGANISM: Homo sapiens

<400> SEQUENCE: 406

Glu Val Gln Leu Leu Glu Ser Gly Gly Gly Leu Val Gln Pro Gly Gly

```
                1               5                   10                  15
Ser Leu Arg Leu Ser Cys Ala Ala Ser Gly Phe Thr Phe Ala His Glu
                20                  25                  30

Thr Met Val Trp Val Arg Gln Ala Pro Gly Lys Gly Leu Glu Trp Val
            35                  40                  45

Ser His Ile Pro Pro Val Gly Gln Asp Pro Phe Tyr Ala Asp Pro Val
            50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Trp Gly Gln Gly
                100                 105                 110

Thr Leu Val Thr Val Ser Ser
            115

<210> SEQ ID NO 407
<211> LENGTH: 119
<212> TYPE: PRT
<213> ORGANISM: Homo sapiens

<400> SEQUENCE: 407

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ala His Glu
                20                  25                  30

Thr Met Val Trp Val Arg Gln Ala Pro Gly Lys Gly Leu Glu Trp Val
            35                  40                  45

Ser His Ile Pro Pro Val Gly Gln Asp Pro Phe Tyr Thr Asp Ser Val
            50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Trp Gly Gln Gly
                100                 105                 110

Thr Leu Val Thr Val Ser Ser
            115

<210> SEQ ID NO 408
<211> LENGTH: 119
<212> TYPE: PRT
<213> ORGANISM: Homo sapiens

<400> SEQUENCE: 408

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ala His Glu
                20                  25                  30

Thr Met Val Trp Val Arg Gln Ala Pro Gly Lys Gly Leu Glu Trp Val
            35                  40                  45

Ser His Ile Pro Pro Val Gly Gln Asp Pro Phe Tyr Thr Asp Ser Val
            50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
```

-continued

```
                85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 409
<211> LENGTH: 119
<212> TYPE: PRT
<213> ORGANISM: Homo sapiens

<400> SEQUENCE: 409

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Pro Pro Val Gly Gln Asp Pro Phe Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 410
<211> LENGTH: 119
<212> TYPE: PRT
<213> ORGANISM: Homo sapiens

<400> SEQUENCE: 410

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Pro Pro Val Gly Gln Asp Pro Phe Tyr Thr Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 411
<211> LENGTH: 119
<212> TYPE: PRT
<213> ORGANISM: Homo sapiens

<400> SEQUENCE: 411
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
                35                  40                  45

Ser His Ile Asp Gly Gly Gly Glu Ser Thr Tyr Tyr Thr Asp Pro Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Lys Arg Gly Pro Trp Phe Asp Tyr Trp Gly Gln Gly
                100                 105                 110

Thr Leu Val Thr Val Ser Ser
        115

<210> SEQ ID NO 412
<211> LENGTH: 119
<212> TYPE: PRT
<213> ORGANISM: Homo sapiens

<400> SEQUENCE: 412

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
                35                  40                  45

Ser His Ile Asp Gly Gly Gly Glu Ser Thr Tyr Tyr Thr Asp Ser Val
        50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Lys Arg Gly Pro Trp Phe Asp Tyr Trp Gly Gln Gly
                100                 105                 110

Thr Leu Val Thr Val Ser Ser
        115

<210> SEQ ID NO 413
<211> LENGTH: 119
<212> TYPE: PRT
<213> ORGANISM: Homo sapiens

<400> SEQUENCE: 413

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
                35                  40                  45

Ser His Ile Asp Gly Gly Gly Glu Ser Thr Tyr Tyr Thr Asp Pro Val
        50                  55                  60

Glu Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                 85                  90                  95

Ala Arg Leu Pro Lys Arg Gly Pro Trp Phe Asp Tyr Trp Gly Gln Gly
            100                 105                 110

Thr Leu Val Thr Val Ser Ser
        115

<210> SEQ ID NO 414
<211> LENGTH: 119
<212> TYPE: PRT
<213> ORGANISM: Homo sapiens

<400> SEQUENCE: 414

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asn Lys Lys
             20                  25                  30

Thr Met Val Trp Val Arg Gln Ala Pro Gly Lys Gly Leu Glu Trp Val
         35                  40                  45

Ser His Ile Asp Gly Lys Gly Gln Ala Thr Tyr Tyr Thr Asp Pro Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 415
<211> LENGTH: 119
<212> TYPE: PRT
<213> ORGANISM: Homo sapiens

<400> SEQUENCE: 415

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asn Lys Lys
             20                  25                  30

Thr Met Val Trp Val Arg Gln Ala Pro Gly Lys Gly Leu Glu Trp Val
         35                  40                  45

Ser His Ile Asp Gly Lys Gly Gln Ala Thr Tyr Tyr Thr Asp Ser Val
     50                  55                  60

Glu Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 416
<211> LENGTH: 119
<212> TYPE: PRT
<213> ORGANISM: Homo sapiens
```

<400> SEQUENCE: 416

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Lys Lys
            20                  25                  30

Thr Met Val Trp Val Arg Gln Ala Pro Gly Lys Gly Leu Glu Trp Val
        35                  40                  45

Ser His Ile Asp Gly Lys Gly Gln Ala Thr Tyr Tyr Thr Asp Pro Val
50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 417
<211> LENGTH: 119
<212> TYPE: PRT
<213> ORGANISM: Homo sapiens

<400> SEQUENCE: 417

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Pro Pro Val Gly Gln Asp Pro Phe Tyr Thr Asp Pro Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 418
<211> LENGTH: 119
<212> TYPE: PRT
<213> ORGANISM: Homo sapiens

<400> SEQUENCE: 418

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Pro Pro Val Gly Gln Asp Pro Phe Tyr Ala Asp Pro Val
50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Leu Leu Pro Lys Arg Gly Pro Trp Phe Asp Tyr Trp Gly Gln Gly
            100                 105                 110

Thr Leu Val Thr Val Ser Ser
            115

<210> SEQ ID NO 419
<211> LENGTH: 119
<212> TYPE: PRT
<213> ORGANISM: Homo sapiens

<400> SEQUENCE: 419

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Lys Lys
            20                  25                  30

Thr Met Val Trp Val Arg Gln Ala Pro Gly Lys Gly Leu Glu Trp Val
        35                  40                  45

Ser His Ile Asp Gly Lys Gly Gln Asp Pro Phe Tyr Thr Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Leu Leu Pro Lys Arg Gly Pro Trp Phe Asp Tyr Trp Gly Gln Gly
            100                 105                 110

Thr Leu Val Thr Val Ser Ser
            115

<210> SEQ ID NO 420
<211> LENGTH: 119
<212> TYPE: PRT
<213> ORGANISM: Homo sapiens

<400> SEQUENCE: 420

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Lys Lys
            20                  25                  30

Thr Met Val Trp Val Arg Gln Ala Pro Gly Lys Gly Leu Glu Trp Val
        35                  40                  45

Ser His Ile Asp Gly Lys Gly Gln Asp Pro Phe Tyr Ala Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Leu Leu Pro Lys Arg Gly Pro Trp Phe Asp Tyr Trp Gly Gln Gly
            100                 105                 110

Thr Leu Val Thr Val Ser Ser
            115

<210> SEQ ID NO 421
<211> LENGTH: 119

-continued

<212> TYPE: PRT
<213> ORGANISM: Homo sapiens

<400> SEQUENCE: 421

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Lys Lys
            20                  25                  30

Thr Met Val Trp Val Arg Gln Ala Pro Gly Lys Gly Leu Glu Trp Val
        35                  40                  45

Ser His Ile Asp Gly Lys Gly Gln Asp Pro Phe Tyr Thr Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser
            115

<210> SEQ ID NO 422
<211> LENGTH: 119
<212> TYPE: PRT
<213> ORGANISM: Homo sapiens

<400> SEQUENCE: 422

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Lys Lys
            20                  25                  30

Thr Met Val Trp Val Arg Gln Ala Pro Gly Lys Gly Leu Glu Trp Val
        35                  40                  45

Ser His Ile Asp Gly Lys Gly Gln Asp Pro Phe Tyr Thr Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser
            115

<210> SEQ ID NO 423
<211> LENGTH: 119
<212> TYPE: PRT
<213> ORGANISM: Homo sapiens

<400> SEQUENCE: 423

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Lys Lys
            20                  25                  30

Thr Met Val Trp Val Arg Gln Ala Pro Gly Lys Gly Leu Glu Trp Val
        35                  40                  45

Ser His Ile Asp Gly Lys Gly Gln Asp Pro Phe Tyr Thr Asp Pro Val

```
                    50                  55                  60
Glu Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Leu Leu Pro Lys Arg Gly Pro Trp Phe Asp Tyr Trp Gly Gln Gly
                100                 105                 110

Thr Leu Val Thr Val Ser Ser
            115

<210> SEQ ID NO 424
<211> LENGTH: 119
<212> TYPE: PRT
<213> ORGANISM: Homo sapiens

<400> SEQUENCE: 424

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ala His Glu
                 20                  25                  30

Thr Met Val Trp Val Arg Gln Ala Pro Gly Lys Gly Leu Glu Trp Val
             35                  40                  45

Ser His Ile Pro Pro Val Gly Gln Asp Pro Tyr Thr Asp Pro Val
         50                  55                  60

Glu Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Leu Leu Pro Lys Arg Gly Pro Trp Phe Asp Tyr Trp Gly Gln Gly
                100                 105                 110

Thr Leu Val Thr Val Ser Ser
            115

<210> SEQ ID NO 425
<211> LENGTH: 119
<212> TYPE: PRT
<213> ORGANISM: Homo sapiens

<400> SEQUENCE: 425

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ala His Glu
                 20                  25                  30

Thr Met Val Trp Val Arg Gln Ala Pro Gly Lys Gly Leu Glu Trp Val
             35                  40                  45

Ser His Ile Asp Gly Gly Glu Ser Pro Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Arg Leu Pro Lys Arg Gly Pro Trp Phe Asp Tyr Trp Gly Gln Gly
                100                 105                 110

Thr Leu Val Thr Val Ser Ser
            115
```

```
<210> SEQ ID NO 426
<211> LENGTH: 119
<212> TYPE: PRT
<213> ORGANISM: Homo sapiens

<400> SEQUENCE: 426

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Pro Pro Val Gly Gln Asp Pro Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 427
<211> LENGTH: 119
<212> TYPE: PRT
<213> ORGANISM: Homo sapiens

<400> SEQUENCE: 427

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Pro Pro Val Gly Gln Asp Pro Phe Tyr Ala Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 428
<211> LENGTH: 119
<212> TYPE: PRT
<213> ORGANISM: Homo sapiens

<400> SEQUENCE: 428

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45
```

Ser His Ile Pro Pro Val Gly Gln Asp Pro Phe Tyr Thr Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Leu Leu Pro Lys Arg Gly Pro Trp Phe Asp Tyr Trp Gly Gln Gly
                100                 105                 110

Thr Leu Val Thr Val Ser Ser
            115

<210> SEQ ID NO 429
<211> LENGTH: 119
<212> TYPE: PRT
<213> ORGANISM: Homo sapiens

<400> SEQUENCE: 429

Glu Val Gln Leu Leu Glu Ser Gly Gly Gly Leu Ile Gln Pro Gly Gly
 1               5                  10                  15

Ser Leu Arg Leu Ser Cys Ala Ala Ser Gly Phe Thr Phe Ala His Glu
                 20                  25                  30

Thr Met Val Trp Val Arg Gln Ala Pro Gly Lys Gly Leu Glu Trp Val
             35                  40                  45

Ser His Ile Pro Pro Val Gly Gln Asp Pro Phe Tyr Thr Asp Ser Val
    50                  55                  60

Glu Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Leu Leu Pro Lys Arg Gly Pro Trp Phe Asp Tyr Trp Gly Gln Gly
                100                 105                 110

Thr Leu Val Thr Val Ser Ser
            115

<210> SEQ ID NO 430
<211> LENGTH: 119
<212> TYPE: PRT
<213> ORGANISM: Homo sapiens

<400> SEQUENCE: 430

Glu Val Gln Leu Leu Glu Ser Gly Gly Gly Leu Ile Gln Pro Gly Gly
 1               5                  10                  15

Ser Leu Arg Leu Ser Cys Ala Ala Ser Gly Phe Thr Phe Ala His Glu
                 20                  25                  30

Thr Met Val Trp Val Arg Gln Ala Pro Gly Lys Gly Leu Glu Trp Val
             35                  40                  45

Ser His Ile Asp Gly Gly Glu Ser Thr Tyr Tyr Ala Asp Ser Val
    50                  55                  60

Glu Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Leu Pro Lys Arg Gly Pro Trp Phe Asp Tyr Trp Gly Gln Gly
                100                 105                 110

Thr Leu Val Thr Val Ser Ser
            115

<210> SEQ ID NO 431
<211> LENGTH: 119
<212> TYPE: PRT
<213> ORGANISM: Homo sapiens

<400> SEQUENCE: 431

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Gly Gly Gly Glu Ser Thr Tyr Tyr Thr Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Lys Arg Gly Pro Trp Phe Asp Tyr Trp Gly Gln Gly
            100                 105                 110

Thr Leu Val Thr Val Ser Ser
        115

<210> SEQ ID NO 432
<211> LENGTH: 119
<212> TYPE: PRT
<213> ORGANISM: Homo sapiens

<400> SEQUENCE: 432

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Gly Gly Gly Glu Ser Thr Tyr Tyr Thr Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Lys Arg Gly Pro Trp Phe Asp Tyr Trp Gly Gln Gly
            100                 105                 110

Thr Leu Val Thr Val Ser Ser
        115

<210> SEQ ID NO 433
<211> LENGTH: 119
<212> TYPE: PRT
<213> ORGANISM: Homo sapiens

<400> SEQUENCE: 433

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

```
Thr Met Val Trp Val Arg Gln Ala Pro Gly Lys Gly Leu Glu Trp Val
         35                  40                  45
Ser His Ile Asp Gly Gly Glu Ser Thr Tyr Tyr Thr Asp Pro Val
     50                  55                  60
Glu Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Leu Pro Lys Arg Gly Pro Trp Phe Asp Tyr Trp Gly Gln Gly
            100                 105                 110
Thr Leu Val Thr Val Ser Ser
        115

<210> SEQ ID NO 434
<211> LENGTH: 357
<212> TYPE: DNA
<213> ORGANISM: Homo sapiens

<400> SEQUENCE: 434
gaggtgcagc tgttggagtc tgggggaggc ttggtacagc ctgggggtc cctgcgtctc    60 tcctgtgcag cctccggatt cacctttgcg catgagccga tggtgtgggt ccgccaggct   120
ccagggaagg gtctagagtg ggtctcacat attgatcgtg ttggtcagga tacatactac   180
gcagactccg tgaagggccg gttcaccatc tcccgcgaca attccaagaa cacgctgtat   240
ctgcaaatga acagcctgcg tgccgaggac accgcggtat attactgtgc gaaacttcct   300 aagaggggc ctaggtttga ctactggggt caggaaccc tggtcaccgt ctcgagc       357

<210> SEQ ID NO 435
<211> LENGTH: 357
<212> TYPE: DNA
<213> ORGANISM: Homo sapiens

<400> SEQUENCE: 435
gaggtgcagc tgttggagtc tgggggaggc ttggtacagc ctgggggtc cctgcgtctc    60 tcctgtgcag cctccggatt cacctttgcg catgagccga tggtgtgggt ccgccaggct   120
ccagggaagg gtctagagtg ggtctcacat attgatcgtg ttggtcagga tacatactac   180
gcagactccg tgaagggccg gttcatcatc tcccgcgaca attccaagaa cacgctgtat   240
ctgcaaatgt acagcctgcg tgccgaggac accgcggtat attactgtgc gatacttcct   300 aagaggggc ctaggtttga ctactggggt caggaaccc tggtcaccgt ctcgagc       357

<210> SEQ ID NO 436
<211> LENGTH: 357
<212> TYPE: DNA
<213> ORGANISM: Homo sapiens

<400> SEQUENCE: 436
gaggtgcagc tgttggagtc tgggggaggc ttggtacagc ctgggggtc cctgcgtctc    60 tcctgtgcag cctccggatt cacctttgcg catgagccga tggtgtgggt ccgccaggct   120
ccagggaagg gtctagagtg ggtctcacat attgatcgtg ttggtcagga tacatactac   180
gcagactccg tgaagggccg gttcaccatc tcccgcgaca attccaagaa cacgctgtat   240
ctacaaatga acagcctgcg tgccgaggac accgcggtat attactgtgc gagacttcct   300 aagaggggc ctaggtttga ctactggggt catggaaccc tggtcaccgt ctcgagc      357
```

```
<210> SEQ ID NO 437
<211> LENGTH: 357
<212> TYPE: DNA
<213> ORGANISM: Homo sapiens

<400> SEQUENCE: 437
gaggtgcagc tgttggagtc tgggggaggc ttggtacagc ctggggggtc cctgcgtctc      60
tcctgtgcag cctccggatt cacctttgcg catgagccga tggtgtgggt ccgccaggct     120
ccagggaagg gtctagagtg ggtctcacat attgatcgtg ttggtcagga tacatactac     180
gcagactccg tgaagggccg gttcaccatc tcccgcgaca attccaagaa cacgctgtat     240
ctgcaaatga acagcctgcg tgccgaggac accgcggtat attactgtgc gatacttcct     300 aagaggggc ctaggtttga ctactgggt cagggaaccc tggtcaccgt ctcgagc         357

<210> SEQ ID NO 438
<211> LENGTH: 357
<212> TYPE: DNA
<213> ORGANISM: Homo sapiens

<400> SEQUENCE: 438
gaggtgcagc tgttggagtc tgggggaggc ttggtacagc ctggggggtc cctgcgtctc      60
tcctgtacag cctccggatt cacttttgcg catgagccga tggtgtgggt ccgccaggct     120
ccagggaagg gtctagagtg ggtctcacat attgatcgtg ttggtcagga tacatactac     180
gcagactccg tgaagggccg gttcaccatc tcccgcgaca attccaagaa cacgctgtat     240
ctgcaaatga acagcctgcg tgccgaggac accgcggtat attactgtgc gagacttcct     300 aagaggggc ctaggtttga ctactgggt ctgggaaccc tggtcaccgt ctcgagc         357

<210> SEQ ID NO 439
<211> LENGTH: 357
<212> TYPE: DNA
<213> ORGANISM: Homo sapiens

<400> SEQUENCE: 439
gaggtgaagc tgttggagtc tgggggaggc ttggtacagc ctggggggtc cctgcgtctc      60
tcctgtgcag cctccggatt cacctttgcg catgagccga tggtgtggat ccgccaggct     120
ccagggaagg gtctagagtg ggtctcacat attgatcgtg ttggtcagga tacatactac     180
gcagactccg tgaagggccg gtacaccatc tcccgcgaca attccaagaa tacgctgtat     240
ctgcaaatga acagcctgcg tgccgaggac accgcggtat attactgtgc gagacttcct     300 aagaggggc ctaggtttga ctactgggt cagggaaccc tggtcaccgt ctcgagc         357

<210> SEQ ID NO 440
<211> LENGTH: 357
<212> TYPE: DNA
<213> ORGANISM: Homo sapiens

<400> SEQUENCE: 440
gaggtgcagc tgttggagtc tgggggaggc ttggtacagc ctggggggtc cctgcgtctc      60
tcctgtgcag cctccggatt cacctttgcg catgagccga tggtgtgggt ccgccaggct     120
ccagggaagg gtctagagtg ggtctcacat attgatcgtg ttggtcagga tacatactac     180
gcagactcgg tgaagggccg gttcaccatc tcccgcgaca attccaagaa cacgctgtat     240
ctgcaaatga acagcctgcg tgccgaggac accgcggtat attactgtgc gagacttcct     300 aagaggggc ctaggtttga ctactgggt ctgggaaccc tggtcaccgt ctcgagc         357
```

<210> SEQ ID NO 441
<211> LENGTH: 357
<212> TYPE: DNA
<213> ORGANISM: Homo sapiens

<400> SEQUENCE: 441

| | | | | | |
|---|---|---|---|---|---|
| gaggtgcagc | tgttggagtc | tgggggaggc | ttggtacagc | ctgggggtc | cctgcgtctc | 60 |
| tcctgtgcag | cctccggatt | cacctttgcg | catgagccga | tggtgtgggt | ccgccaggct | 120 |
| ccagggaagg | gtctagagtg | ggtctcacat | attgatcgtg | ctggtcagga | tacatactac | 180 |
| gcagactccg | tgaagggccg | gttcaccatc | tcccgcgaca | attccaagaa | cacgctgtat | 240 |
| ctgcaaatga | acagcctgcg | tgccgaggac | accgcggtat | attactgtgc | gagacttcct | 300 |
| aagagggggc | ctaggtttga | ctactggggt | ctgggaaccc | tggtcaccgt | atcgagc | 357 |

<210> SEQ ID NO 442
<211> LENGTH: 357
<212> TYPE: DNA
<213> ORGANISM: Homo sapiens

<400> SEQUENCE: 442

| | | | | | |
|---|---|---|---|---|---|
| gaggtgcagc | tgttggagtc | tgggggaggc | ttgatacagc | ctgggggtc | cctgcgtctc | 60 |
| tcctgtgcag | cctccggatt | cacctttgcg | catgagacga | tggtgtgggt | ccgccaggct | 120 |
| ccagggaagg | gtctagagtg | ggtctcacat | attgatcgtg | ttggtcagga | tacatactac | 180 |
| gcagactccg | tgaagggccg | gttcaccatc | tcccgcgaca | attccaagaa | cacgctgtat | 240 |
| ctgcaaatga | acagcctgcg | tgccgaggac | acagcggtat | attactgtgc | gaaacttcct | 300 |
| aagagggggc | cttggtttga | ctaccggggt | cagggaaccc | tggtcaccgt | ctcgagc | 357 |

<210> SEQ ID NO 443
<211> LENGTH: 357
<212> TYPE: DNA
<213> ORGANISM: Homo sapiens

<400> SEQUENCE: 443

| | | | | | |
|---|---|---|---|---|---|
| gaagtgcagc | tgttggagtc | tgggggaggc | ttggtacggc | ctgggggtc | cctgcgtctc | 60 |
| tcctgtgcag | cctccggatt | cacctttgcg | catgagccga | tggtgtgggt | ccgccaggct | 120 |
| ccagggaagg | gtctagagtg | ggtctcacat | attgatcgtg | ttggtcagga | tacatactac | 180 |
| gcagactccg | tgaagggccg | gttcaccatc | tcccgcgaca | attccaagaa | cacgctgtat | 240 |
| ctgcaaatga | acagcctgcg | tgccgaggac | accgcggtat | attactgtgc | gagacttcct | 300 |
| aagagggggc | ctaggtttga | ctactggggt | ctgggaaccc | tggtcaccgt | ctcgagc | 357 |

<210> SEQ ID NO 444
<211> LENGTH: 357
<212> TYPE: DNA
<213> ORGANISM: Homo sapiens

<400> SEQUENCE: 444

| | | | | | |
|---|---|---|---|---|---|
| gaggtgcagc | tgttggagtc | tgggggaggc | ttggtacagc | ctgggggtc | cctgcgtctc | 60 |
| tcctgtgcag | cctccggatt | cacctttgcg | catgagccga | tggtgtgggt | ccgccaggct | 120 |
| ccagggaagg | gtctagagtg | ggtctcacat | attgatcgtg | ttggtcagga | tacatactac | 180 |
| gcagactccg | tgaagggccg | gttcaccatc | tcccgcgaca | attccaagaa | cacgctgtat | 240 |
| ctgcagatga | acagcctgcg | tgccgaggac | accgcgatat | attactgtgc | gagacttcct | 300 |
| aagagggggc | ctaggtttga | ctactggggt | ctgggaaccc | tggtcaccgt | ctcgagc | 357 |

<210> SEQ ID NO 445
<211> LENGTH: 357
<212> TYPE: DNA
<213> ORGANISM: Homo sapiens

<400> SEQUENCE: 445

```
gaggtgcagc tgttggagtc tgggggaggc ttggtacagc ctggggggtc cctgcgtctc      60
tcctgtgcag cctccggatt cacctttgcg catgagccga tggtgtgggt ccgccaggct     120
ccagggaagg gtctagagtg ggtctcacat attgatcgtg ttggtcagga tccatactac     180
gcagactccg tgaagggccg gttcaccatc tcccgcgaca attccaagaa cacgctgtat     240
ctgcaaatga acagcctgcg tgccgaggac accgcggtat attactgtgc gagacttcct     300
aagaggggc ctaggtttga ctactggggt caggaaccc tggtcaccgt ctcgagc          357
```

<210> SEQ ID NO 446
<211> LENGTH: 357
<212> TYPE: DNA
<213> ORGANISM: Homo sapiens

<400> SEQUENCE: 446

```
gaggtgcagc tgttggagtc tgggggaggc ttggtacagc ctggggggtc cctgcgtctc      60
tcctgtgcag cctccggatt cacctttgcg catgagccga tggtgtggat ccgccaggct     120
ccagggaagg gtctagagtg ggtctcacat attgatcgtg ttggtcagga tacatactac     180
gcagactccg tgaagggccg gttcaccatc tcccgcgaca attccaagaa cacgctgtat     240
ctgcaaatga acagcctgcg tgccgaggac accgcggtat attactgtgc gatacttcct     300
aagaggggc ctaggtttga ctactggggt caggaaccc tggtcaccgt ctcgagc          357
```

<210> SEQ ID NO 447
<211> LENGTH: 357
<212> TYPE: DNA
<213> ORGANISM: Homo sapiens

<400> SEQUENCE: 447

```
gaggtgcagc tgttggagtc tgggggaggc ttggtacagc ctggggggtc cctgcgtctc      60
tcctgtgcag cctccggatt cacctttgcg catgagccga tggtgtgggt ccgccaggct     120
ccagggaagg gtctagagtg ggtctcacat attgatcgtg ttggtcaaga tccatactac     180
gcagactccg tgaagggccg gttcaccatc tcccgcgaca attccaagaa cacgctgtat     240
ctgcaaatga acagcctgcg tgccgaggac accgcggtat attactgtgc gagacttcct     300
aagaggggc ctaggtttga ctactggggt ctgggaaccc tggtcaccgt ctcgagc         357
```

<210> SEQ ID NO 448
<211> LENGTH: 357
<212> TYPE: DNA
<213> ORGANISM: Homo sapiens

<400> SEQUENCE: 448

```
gaggtgcagc tgttggagtc tgggggaggc ttggtacagc ctggggggtc cctgcgtctc      60
tcctgtgcag cctccggatt cacctttgcg catgagccga tggtgtgggt ccgccaggct     120
ccagggaagg gtctagagtg ggtctcacat attgatcgtg ttggtcagga tgcatactac     180
gcagactccg tgaagggccg gttcaccatc tcccgcgaca attccaagaa cacgctgtat     240
ctgcaaatga acagcctgcg tgccgaggac accgcggtat attactgtgc gatacttcct     300
``` aagaggggc ctaggtttga ctactgggt cagggaaccc tggtcaccgt ctcgagc      357

<210> SEQ ID NO 449
<211> LENGTH: 357
<212> TYPE: DNA
<213> ORGANISM: Homo sapiens

<400> SEQUENCE: 449
gaggtgcagc tgttggagtc tggggggaggc ttggtacagc ctgggggtc cctgcgtctc      60 tcctgtgcag cctccggatt cacctttgcg catgagccga tggtgtgggt ccgccaggct     120
ccagggaagg gtctagagtg ggtctcacat attgatcgtg ttggtcagga tacatactac     180
gcagactccg tgaagggccg gtccaccatc tcccgcgaca attccaagaa cacgctgtat     240
ctgcagatga acagcctgcg tgccgaggac accgcgatat attactgtgc gagacttcct     300 aagaggggc ctaggtttga ctactgggt ctgggaaccc tggtcaccgt ctcgagc      357

<210> SEQ ID NO 450
<211> LENGTH: 357
<212> TYPE: DNA
<213> ORGANISM: Homo sapiens

<400> SEQUENCE: 450
gaggtgcagc tgttggagtc tggggggaggc ttggtacagc ctgggggtc cctgcgtctc      60 tcctgtgcag cctccggatt cacctttgcg catgagccga tggtgtgggt ccgccaggct     120
ccagggaagg gtctagagtg ggtctcacat attgatcgtg ttggtcagga tacatactac     180
gcagactccg tgaagggccg gttcaccatc tcccgcgaca attccaagaa cacgctgtat     240
ctgcagatga acagcctgcg tgccgaggac accgcgatat attactgtgc gagacctcct     300 aagaggggc ctaggtttga ctactgggt ctgggaaccc tggtcaccgt ctcgagc      357

<210> SEQ ID NO 451
<211> LENGTH: 357
<212> TYPE: DNA
<213> ORGANISM: Homo sapiens

<400> SEQUENCE: 451
gaggtgcagc tgttggagtc tggggggaggc ttggtacagc ctgggggtc cctgcgtctc      60 tcctgtgcag cctccggatt cacctttgcg catgagccga tggtgtgggt ccgccaggct     120
ccagggaagg gtctagagtg ggtctcacat attgatcgtg ttggtcagga tacatactac     180
gcagactccg tgaagggccg gttcaccatc tcccgcgaca attccaagaa cacgctgtat     240
ctgcagatga acagcctgcg tgccaaggac accgcgatat attactgtgc gagacttcct     300 aagaggggc ctaggtttga ctactgggt ctgggaaccc tggtcaccgt ctcgagc      357

<210> SEQ ID NO 452
<211> LENGTH: 357
<212> TYPE: DNA
<213> ORGANISM: Homo sapiens

<400> SEQUENCE: 452
gaggtgcagc tgttggagtc tggggggaggc ttggtacagc ctgggggtc cctgcgtctc      60 tcctgtgcag cctccggatt cacctttgcg catgagccga tggtgtgggt ccgccaggct     120
ccagggaagg gtctagagtg ggtctcacat attgatcgtg ttggtcagga tacatactac     180
gcagactccg cgaagggccg gttcaccatc tcccgcgaca attccaagaa cacgctgtat     240
ctgcagatga acagcctgcg tgccgaggac accgcgatat attactgtgc gagacttcct     300

```
aagaggggc ctaggtttga ctactggggt ctgggaaccc tggtcaccgt ctcgagc      357
```

<210> SEQ ID NO 453
<211> LENGTH: 357
<212> TYPE: DNA
<213> ORGANISM: Homo sapiens

<400> SEQUENCE: 453

```
gaggtgcagc tgttggagtc tgggggaggc ttggtacagc ctgggggtc cctgcgtctc    60
tcctgtgcag cctccggatt cacctttgcg catgagccga tggtgtgggt ccgccaggct  120
ccagggaagg gtctagagtg ggtctcacat attgatcgtg ttggtcagga tacatactac  180
gcagactccg tgaagggccg gttcaccatc tcccgcgaca attccaagaa cacgctgtat  240
ccgcagatga acagcctgcg tgccgaggac accgcgatat attactgtgc gagacttcct  300
aagaggggc ctaggtttga ctactggggt ctgggaaccc tggtcaccgt ctcgagc      357
```

<210> SEQ ID NO 454
<211> LENGTH: 357
<212> TYPE: DNA
<213> ORGANISM: Homo sapiens

<400> SEQUENCE: 454

```
gaggtgcagc tgttggagtc tgggggaggc ttggtacagc ctgggggtc cctgcgtctc    60
tcctgtgcag cctccggatt cacctttgcg catgagccga tggtgtgggt ccgccaggct  120
ccagggaagg gtctagagtg ggtctcacat attgatcgtg ttggtcagga tacatactac  180
gcagactccg tgaagggccg gttcaccgtc tcccgcgaca attccaagaa cacgctgtat  240
ctgcagatga acagcctgcg tgccgaggac accgcgatat attactgtgc gagacttcct  300
aagaggggc ctaggttcga ctactggggt ctgggaaccc tggtcaccgt ctcgagc      357
```

<210> SEQ ID NO 455
<211> LENGTH: 357
<212> TYPE: DNA
<213> ORGANISM: Homo sapiens

<400> SEQUENCE: 455

```
gaggtgcagc tgttggagtc tgggggaggc ttggtacagc ctgggggtc cctgcgtctc    60
tcctgtgcag cctccggatt cacctttgcg catgagccga tggtgtgggt ccgccaggct  120
ccagggaagg gtctagagtg ggtctcacat attgatcgtg ttggtcagga tacatactac  180
gcagactccg tgaagggccg gttcatcatc tcccgcgaca attccaagaa cacgctgtat  240
ctgcaaatgt acagcctgcg tgccgaggac accgcggtat attactgtgc gatgcttcct  300
aagaggggc ctaggtttgg ctactggggt cagggaaccc tggtcaccgt ctcgagc      357
```

<210> SEQ ID NO 456
<211> LENGTH: 357
<212> TYPE: DNA
<213> ORGANISM: Homo sapiens

<400> SEQUENCE: 456

```
gaggtgcagc tgttggagtc tgggggaggc ttggtacagc ctgggggtc cctgcgtctc    60
tcctgtgcag cctccggatt cacctttgcg catgagccga tggtgtgggt ccgccaggct  120
ccagggaagg gtctagagtg ggtctcacat attgatcgtg ttggtcagga tacatactac  180
gcagactccg tgaagggccg gttcaccatc tcccgcgaca attccaagaa cacgctgtat  240
```

```
ctgcagatga acagcctgtg tgccgaggac accgcgatat attactgtgc gagacttcct    300 aagaggggc ctaggtttga ctactgggt ctgggaaccc tggtcaccgt ctcgagc         357

<210> SEQ ID NO 457
<211> LENGTH: 357
<212> TYPE: DNA
<213> ORGANISM: Homo sapiens

<400> SEQUENCE: 457
gaggtgcagc tgttggagtc tgggggaggc ttgatacagc ctgggggtc cctgcgtctc     60 tcctgtgcag cctccggatt caccttgcg catgagacga tggtgtgggt ccgccaggct    120
ccagggaagg gtctagagtg gtctcacat attgatcgtg ttggtcagga tacatactac    180
gcagactccg tgaagggccg gttcaccatc tcccgcgaca attccaagaa cacgctgtat   240
ctgcaaatga acagcctgcg tgccgaggac acagcggtat attactgtgc ggggcttcct   300 aagaggggc cttggtttga ctaccggggt cagggaaccc tggtcaccgt ctcgagc       357

<210> SEQ ID NO 458
<211> LENGTH: 357
<212> TYPE: DNA
<213> ORGANISM: Homo sapiens

<400> SEQUENCE: 458
gaggtgcagc tgttggagtc tgggggaggc ttgatacagc ctgggggtc cctgcgtctc     60 tcctgtgcag cctccggatt caccttgcg catgagacga tggtgtgggt ccgccaggct    120
ccagggaagg gtctagagtg gtctcacat attgatcgtg ttggtcagga tacatactac    180
gcagactccg tgaagggccg gttcaccatc tcccgcgaca attccaagaa cacgctgtat   240
ctgcaaatga acagcctgcg tgccgaggac acagcggtat attactgtgc gcgccttcct   300 aagaggggc cttggtttga ctaccggggt cagggaaccc tggtcaccgt ctcgagc       357

<210> SEQ ID NO 459
<211> LENGTH: 357
<212> TYPE: DNA
<213> ORGANISM: Homo sapiens

<400> SEQUENCE: 459
gaggtgcagc tgttggagtc tgggggaggc ttgatacagc ctgggggtc cctgcgtctc     60 tcctgtgcag cctccggatt caccttgcg catgagacga tggtgtgggt ccgccaggct    120
ccagggaagg gtctagagtg gtctcacat attgatcgtg ttggtcagga tacatactac    180
gcagactccg tgaagggccg gttcaccatc tcccgcgaca attccaagaa cacgctgtat   240
ctgcaaatga acagcctgcg tgccgaggac acagccgtat attactgtgc gcagcttcct   300 aagaggggc cttggtttga ctaccggggt cagggaaccc tggtcaccgt ctcgagc       357

<210> SEQ ID NO 460
<211> LENGTH: 357
<212> TYPE: DNA
<213> ORGANISM: Homo sapiens

<400> SEQUENCE: 460
gaggtgcagc tgttggagtc tgggggaggc ttgatacagc ctgggggtc cctgcgtctc     60 tcctgtgcag cctccggatt caccttgcg catgagacga tggtgtgggt ccgccaggct    120
ccagggaagg gtctagagtg gtctcacat attgatcgtg ttggtcagga tacatactac    180
gcagactccg tgaagggccg gttcaccatc tcccgcgaca attccaagaa cacgctgtat   240
```
ctgcaaatga acagcctgcg tgtcgaggac acagcggtat attactgtgc gtcccttcct      300 aagaggggc cttggtttga ctaccggggt cagggaaccc tggtcaccgt ctcgagc          357

<210> SEQ ID NO 461
<211> LENGTH: 357
<212> TYPE: DNA
<213> ORGANISM: Homo sapiens

<400> SEQUENCE: 461
gaggtgcagc tgttggagtc tgggggaggc ttgtaccagc ctggggggtc cctgcgtctc      60
tcctgtgcag cctccggatt caccttttgcg catgagacga tggtgtgggt ccgccaggct     120
ccagggaagg gtctagagtg ggtctcacat attgatcgtg ttggtcagga tacatactac     180
gcagactccg tgaagggccg gttcaccatc tcccgcgaca attccaagaa cacgctgtat     240
ctgcaaatga acagcctgcg tgccgaggac acagcggtat attactgtgc gaaacttcct     300 aagaggggc cttggtttga ctaccggggt cagggaaccc tggtcaccgt ctcgagc          357

<210> SEQ ID NO 462
<211> LENGTH: 357
<212> TYPE: DNA
<213> ORGANISM: Homo sapiens

<400> SEQUENCE: 462
gaggtgcagc tgttggagtc tgggggaggc ttggggcagc ctggggggtc cctgcgtctc      60
tcctgtgcag cctccggatt caccttttgcg catgagacga tggtgtgggt ccgccaggct     120
ccagggaagg gtctagagtg ggtctcacat attgatcgtg ttggtcagga tacatactac     180
gcagactccg tgaagggccg gttcaccatc tcccgcgaca attccaagaa cacgctgtat     240
ctgcaaatga acagcctgcg tgccgaggac acagcggtat attactgtgc gaaacttcct     300 aagaggggc cttggtttga ctaccggggt cagggaaccc tggtcaccgt ctcgagc          357

<210> SEQ ID NO 463
<211> LENGTH: 357
<212> TYPE: DNA
<213> ORGANISM: Homo sapiens

<400> SEQUENCE: 463
gaggggcagc tgttggagtc tgggggaggc ttggttcaac ctggggggtc cctgcttcta      60
tcctgtgcag cctccggatt caccttttgcg catgagacaa tggtgtgggt ccgccaggct     120
ccagggaagg gtctagagtg ggtctcacat attgatcgtg ttggtcagga tacatactac     180
gcagactccg tgaagggccg gttcaccatc tcccgcgaca attccaagaa cacgctgtat     240
ctgcaaatga acagcctgcg tgccgaggac acagcggtat attactgtgc gaaacttcct     300 aagaggggc cttggtttga ctaccggggt cagggaaccc tggtcaccgt ctcgagc          357

<210> SEQ ID NO 464
<211> LENGTH: 357
<212> TYPE: DNA
<213> ORGANISM: Homo sapiens

<400> SEQUENCE: 464
gaggtgcagc tgttggagtc tgggggaggc ttggttcagc ctggggggtc cctgcgtctc      60
tcctgtgcag cctccggatt caccttttgcg catgaaacga tggtgtgggt ccgccaggct     120
ccagggaagg gtctagagtg ggtctcacat attgatcgtg ttggtcagga tacatactac     180

```
gcagactccg tgaagggccg gttcaccatc tcccgcgaca attccaagaa cacgctgtat    240
ctgcaaatga acagcctgcg tgccgaggac acagcggtat attactgtgc gaaacttcct    300
aagagggggc cttggtttga ctaccggggt cagggaaccc tggtcaccgt ctcgagc       357
```

<210> SEQ ID NO 465
<211> LENGTH: 357
<212> TYPE: DNA
<213> ORGANISM: Homo sapiens

<400> SEQUENCE: 465

```
gaggtgcagc tgttggagtc tggggaggc ttgatacagc ctgggggtc cctgcgtctc      60 tcctgtgcag cctccggatt cacctttgcg catgagacga tggtgtgggt ccgccaggct   120
ccagggaagg gtctagagtg ggtctcacat attgatcgtg ttggtcagga tccctactac   180
gcagactccg tgaagggccg gttcaccatc tcccgcgaca attccaagaa cacgctgtat   240
ctgcaaatga acagcctgcg tgccgaggac acagcggtat attactgtgc gaaacttcct   300
aagagggggc cttggtttga ctaccggggt cagggaaccc tggtcaccgt ctcgagc      357
```

<210> SEQ ID NO 466
<211> LENGTH: 357
<212> TYPE: DNA
<213> ORGANISM: Homo sapiens

<400> SEQUENCE: 466

```
gaggggcagc tgttggagtc tggggaggc ttgatacagc ctgggggtc cctgcgtcta      60 tcctgtggag cctccggatt cacctttgcg catgagacaa tggtgtgggt ccgccaggct   120
ccagggaagg gtctagagtg ggtctcacat attgatcgtg ttggtcagga tccctactac   180
gcagactccg tgaagggccg gttcaccatc tcccgcgaca attccaagaa cacgctgtat   240
ctgcaaatga acagcctgcg tgccgaggac acagcggtat attactgtgc gaaacttcct   300
aagagggggc cttggtttga ctaccggggt cagggaaccc tggtcaccgt ctcgagc      357
```

<210> SEQ ID NO 467
<211> LENGTH: 357
<212> TYPE: DNA
<213> ORGANISM: Homo sapiens

<400> SEQUENCE: 467

```
gaggtgcagc tgttggagtc tggggaggc ttgatacagc ctgggggtc cctgcgtctc      60 tcctgtgcag cctccggatt cacctttgcg catgagacga tggtgtgggt ccgccaggct   120
ccagggaagg gtctagagtg ggtctcacat attgatcgtg ttggtcagga taactactac   180
gcagactccg tgaagggccg gttcaccatc tcccgcgaca attccaagaa cacgctgtat   240
ctgcaaatga acagcctgcg tgccgaggac acagcggtat attactgtgc gaaacttcct   300
aagagggggc cttggtttga ctaccggggt cagggaaccc tggtcaccgt ctcgagc      357
```

<210> SEQ ID NO 468
<211> LENGTH: 357
<212> TYPE: DNA
<213> ORGANISM: Homo sapiens

<400> SEQUENCE: 468

```
gaggtgcagc tgttggagtc tggggaggc ttgatacagc ctgggggtc cctgcgtctc      60 tcctgtgcag cctccggatt cacctttgcg catgagacga tggtgtgggt ccgccaggct   120
ccagggaagg gtctagagtg ggtctcacat attgatcgtg ttggtcagga tacatactac   180
```

```
gcagactccg tgaagggccg gttcaccatc tcccgcgaca attccaagaa cacgctgtat    240
ctgcaaatga acagcctgcg tgccgaggac acagcggtat attactgtgc gaaacttcct    300
aagagggggc ctgggtttga ctaccggggt cagggaaccc tggtcaccgt ctcgagc       357
```

```
<210> SEQ ID NO 469
<211> LENGTH: 357
<212> TYPE: DNA
<213> ORGANISM: Homo sapiens

<400> SEQUENCE: 469
gaggtgcagc tgttggagtc tgggggaggc ttgatacagc ctgggggtc cctgcgtctc     60 tcctgtgcag cctccggatt cacctttgcg catgaaacga tggtgtgggt ccgccaggct    120
ccagggaagg gtctagagtg ggtctcacat attgatcgtg ttggtcagga tacatactac    180
gcagactccg tgaagggccg gttcaccatc tcccgcgaca attccaagaa cacgctgtat    240
ctgcaaatga acagcctgcg tgccgaggac acagcggtat attactgtgc gaaacttcct    300
aagagggggc ctgtgtttga ctaccggggt cagggaaccc tggtcaccgt ctcgagc       357
```

```
<210> SEQ ID NO 470
<211> LENGTH: 357
<212> TYPE: DNA
<213> ORGANISM: Homo sapiens

<400> SEQUENCE: 470
gaggtgcagc tgttggagtc tgggggaggc ttgatacagc ctgggggtc cctgcgtctc     60 tcctgtgcag cctccggatt cacctttgcg catgagacga tggtgtgggt ccgccaggct    120
ccagggaagg gtctagagtg ggtctcacat attgatcgtg ttggtcagga tacatactac    180
gcagactccg tgaagggccg gttcaccatc tcccgcgaca attccaagaa cacgctgtat    240
ctgcaaatga acagcctgcg tgccgaggac acagcggtat attactgtgc gaaacttcct    300
aagagggggc cttggtttga ctactacggt cagggaaccc tggtcaccgt ctcgagc       357
```

```
<210> SEQ ID NO 471
<211> LENGTH: 357
<212> TYPE: DNA
<213> ORGANISM: Homo sapiens

<400> SEQUENCE: 471
gaggggcagc tgttggagtc tgggggaggc ttgatacagc ctgggggtc cctgcttcta     60 tcctgtgcac cctccggatt cacctttgcg catgagacaa tggtgtgggt ccgccaggct    120
ccagggaagg gtctagagtg ggtctcacat attgatcgtg ttggtcagga tacatactac    180
gcagactccg tgaagggccg gttcaccatc tcccgcgaca attccaagaa cacgctgtat    240
ctgcaaatga acagcctgcg tgccgaggac acagcggtat attactgtgc gaaacttcct    300
aagagggggc cttggtttga ctacaagggt cagggaaccc tggtcaccgt ctcgagc       357
```

```
<210> SEQ ID NO 472
<211> LENGTH: 357
<212> TYPE: DNA
<213> ORGANISM: Homo sapiens

<400> SEQUENCE: 472
gaggtgcagc tgttggagtc tgggggaggc ttgatacagc ctgggggtc cctgcgtctc     60 tcctgtgcag cctccggatt cacctttgcg catgagacga tggtgtgggt ccgccaggct    120
```

```
ccagggaagg gtctagagtg ggtctcacat attgatcgtg ttggtcagga tacatactac        180
gcagactccg tgaagggccg gttcaccatc tcccgcgaca attccaagaa cacgctgtat        240
ctgcaaatga acagcctgcg tgccgaggac acagcggtat attactgtgc gaaacttcct        300
aagagggggc cttggtttga ctacgtgggt cagggaaccc tggtcaccgt ctcgagc          357
```

<210> SEQ ID NO 473
<211> LENGTH: 357
<212> TYPE: DNA
<213> ORGANISM: Homo sapiens

<400> SEQUENCE: 473

```
gaggtgcagc tgttggagtc tgggggaggc ttgatacagc ctggggggtc cctgcgtctc        60
tcctgtgcag cctccggatt cacctttgcg catgagacga tggtgtgggt ccgccaggct       120
ccagggaagg gtctagagtg ggtctcacat attgatcgtg ttggtcagga tacatactac       180
gcagactccg tgaagggccg gttcaccatc tcccgcgaca attccaagaa cacgctgtat       240
ctgcaaatga acagcctgcg tgccgaggac acagcggtat attactgtgc gaaacttcct       300
aagagggggc cttggtttga ctacttgggt cagggaaccc tggtcaccgt ctcgagc          357
```

<210> SEQ ID NO 474
<211> LENGTH: 357
<212> TYPE: DNA
<213> ORGANISM: Homo sapiens

<400> SEQUENCE: 474

```
gaggtgcagc tgttggagtc tgggggaggc ttggtacagc ctggggggtc cctgcgtctc        60
tcctgtgcag cctccggatt cacctttgcg catgagccga tggtgtgggt ccgccaggct       120
ccagggaagg gtctagagtg ggtctcacat attgatcgtg ttggtcagga tacatactac       180
gcagactccg tgaagggccg gttcaccatc tcccgcgaca attccaagaa cacgctgtat       240
ctgcaaatga acagcctgcg tgccgaggac accgcggtat attactgtgc gagccttcct       300
aagagggggc ctaggtttga ctactgggt cagggaaccc tggtcaccgt ctcgagc           357
```

<210> SEQ ID NO 475
<211> LENGTH: 357
<212> TYPE: DNA
<213> ORGANISM: Homo sapiens

<400> SEQUENCE: 475

```
gaggtgcagc tgttggagtc tgggggaggc ttggtacagc ctggggggtc cctgcgtctc        60
tcctgtgcag cctccggatt cacctttgcg catgagccga tggtgtgggt ccgccaggct       120
ccagggaagg gtctagagtg ggtctcacat attgatcgtg ttggtcagga tacatactac       180
gcagactccg tgaagggccg gttcaccatc tcccgcgaca attccaagaa cacgctgtat       240
ctgcaaatga acagcctgcg tgccgaggac accgcggtat attactgtgc ggggcttcct       300
aagagggggc ctaggtttga ctactgggt cagggaaccc tggtcaccgt ctcgagc           357
```

<210> SEQ ID NO 476
<211> LENGTH: 357
<212> TYPE: DNA
<213> ORGANISM: Homo sapiens

<400> SEQUENCE: 476

```
gaggtgcagc tgttggagtc tgggggaggc ttggtacagc ctggggggtc cctgcgtctc        60
tcctgtgcag cctccggatt cacctttgcg catgagccga tggtgtgggt ccgccaggct       120
```

```
ccagggaagg gtctagagtg ggtctcacat attgatcgtg ttggtcagga tacatactac      180
gcagactccg tgaagggccg gttcaccatc tcccgcgaca attccaagaa cacgctgtat      240
ctgcaaatga acagcctgcg tgccgaggac accgcggtat attactgtgc gaggcttcct      300 aagaggggc ctaggtttga ctactgggt cagggaaccc tggtcaccgt ctcgagc          357
```

<210> SEQ ID NO 477
<211> LENGTH: 357
<212> TYPE: DNA
<213> ORGANISM: Homo sapiens

<400> SEQUENCE: 477

```
gaggtgcagc tgttggagtc tgggggaggc ttggtacagc ctgggggtc cctgcgtctc       60 tcctgtgcag cctccggatt cacctttgcg catgagccga tggtgtgggt ccgccaggct     120
ccagggaagg gtctagggtg gtctcacat attgatcgtg ttggtcagga tacatactac      180
gcagactccg tgaagggccg gttcaccatc tcccgcgaca attccaagaa cacgctgtat     240
ctgcaaatga acagcctgcg tgccgaggac accgcggtat attactgtgc gccccttcct    300 aagaggggc ctaggtttga ctactgggt cagggaaccc tggtcaccgt ctcgagc         357
```

<210> SEQ ID NO 478
<211> LENGTH: 357
<212> TYPE: DNA
<213> ORGANISM: Homo sapiens

<400> SEQUENCE: 478

```
gaggtgcagc tgttggagtc tgggggaggc ttggtacagc ctgggggtc cctgcgcctc       60 tcctgtgcag cctccggatt cacctttgcg catgagccga tggtgtgggt ccgccaggct     120
ccagggaagg gtctagagtg gtctcacat attgatcgtg ttggtcagga tacatactac      180
gcagactccg tgaagggccg gttcaccatc tcccgcgaca attccaagaa cacgctgtat     240
ctgcaaatga acagcctgcg tgccgaggac accgcggtat attactgtgc gatccttcct    300 aagaggggc ctaggtttga ctactgggt cagggaaccc tggtcaccgt ctcgagc         357
```

<210> SEQ ID NO 479
<211> LENGTH: 357
<212> TYPE: DNA
<213> ORGANISM: Homo sapiens

<400> SEQUENCE: 479

```
gaggtgcagc tgttggagtc tgggggaggc ttggtacagc ctgggggtc cctgcgtctc       60 tcctgtgcag cctccggatt cacctttgcg catgagccga tggtgtggat ccgccaggct     120
ccagggaagg gtctagagtg gtctcacat attgatcgtg ttggtcagga tacatactac      180
gcagactccg tgaagggccg gttcaccatc tcccgcgaca attccaagaa cacgctgtat     240
ctgcaaatga acagcctgcg tgccgaggac accgcggtat attactgtgc gatgcttcct    300 aagaggggc ctaggtttga ctactgggt cagggaaccc tggtcaccgt ctcgagc         357
```

<210> SEQ ID NO 480
<211> LENGTH: 357
<212> TYPE: DNA
<213> ORGANISM: Homo sapiens

<400> SEQUENCE: 480

```
gaggtgcagc tgttggagtc tgggggaggc ttggtacagc ctgggggtc cctgcgtctc       60
```
tcctgtgcag cctccggatt cacctttgcg catgagccga tggtgtgggt ccgccaggct    120
ccagggaagg gtctagagtg ggtctcacat attgatcgtg ttggtcagga tacatactac    180
gcagactccg tgaagggccg gttcaccatc tcccgcgaca attccaagaa cacgctgtat    240
ctgcaaatga acagcctgcg tgccgaggac accgcggtat attactgtgc gctgcttcct    300
aagagggggc ctaggtttga ctactggggt cagggaaccc tggtcaccgt ctcgagc       357

<210> SEQ ID NO 481
<211> LENGTH: 357
<212> TYPE: DNA
<213> ORGANISM: Homo sapiens

<400> SEQUENCE: 481
gaggtgcagc tgttggagtc tgggggaggc ttgatacagc ctgggggtc cctgcgtctc     60 tcctgtgcag cctccggatt cacctttgcg catgagacga tggtgtgggt ccgccaggct   120
ccagggaagg gtctagagtg ggtctcacat attgatcgtg ttggtcagga taagtactac   180
gcagactccg tgaagggccg gttcaccatc tcccgcgaca attccaagaa cacgctgtat   240
ctgcaaatga acagcctgcg tgccgaggac acagcggtat attactgtgc gaaacttcct  300
aagagggggc cttggtttga ctaccggggt cagggaaccc tggtcaccgt ctcgagc     357

<210> SEQ ID NO 482
<211> LENGTH: 357
<212> TYPE: DNA
<213> ORGANISM: Homo sapiens

<400> SEQUENCE: 482
gaggtgcagc tgttggagtc tgggggaggc ttgatacagc ctgggggtc cctgcgtctc     60 tcctgtgcag cctccggatt cacctttgcg catgagacga tggtgtgggt ccgccaggct   120
ccagggaagg gtctagagtg ggtctcacat attgatcgtg ttggtcagga tacatactac   180
gcagactccg tgaagggccg gttcaccatc tcccgcgaca attccaagaa cacgctgtat   240
ctgcaaatga acagcctgcg tgccgaggac acagcggtat attactgtgc gaaacttcct  300
aagagggggc cttggtttga ctacatcggt cagggaaccc tggtcaccgt ctcgagc     357

<210> SEQ ID NO 483
<211> LENGTH: 357
<212> TYPE: DNA
<213> ORGANISM: Homo sapiens

<400> SEQUENCE: 483
gaggtgcagc tgttggagtc tgggggaggc ttgatacagc ctgggggtc cctgcgtctc     60 tcctgtgcag cctccggatt cacctttgcg catgagacga tggtgtgggt ccgccaggct   120
ccagggaagg gtctagagtg ggtctcacat attgatcgtg ttggtcagga tacatactac   180
gcagactccg tgaagggccg gttcaccatc tcccgcgaca attccaagaa cacgctgtat   240
ctgcaaatga acagcctgcg tgccgaggac acagcggtat attactgtgc gaaacttcct  300
aagagggggc cttggtttga ctacaacggt cagggaaccc tggtcaccgt ctcgagc     357

<210> SEQ ID NO 484
<211> LENGTH: 357
<212> TYPE: DNA
<213> ORGANISM: Homo sapiens

<400> SEQUENCE: 484
gaggtgcagc tgttggagtc tgggggaggc ttgatacagc ctgggggtc cctgcgtctc     60

```
tcctgtgcag cctccggatt cacctttgcg catgaggtga tggtgtgggt ccgccaggct    120
ccagggaagg gtctagagtg ggtctcacat attgatcgtg ttggtcagga tacatactac    180
gcagactccg tgaagggccg gttcaccatc tcccgcgaca attccaagaa cacgctgtat    240
ctgcaaatga acagcctgcg tgccgaggac acagcggtat attactgtgc gaaacttcct    300 aagaggggc cttggtttga ctaccggggt cagggaaccc tggtcaccgt ctcgagc        357
```

<210> SEQ ID NO 485
<211> LENGTH: 357
<212> TYPE: DNA
<213> ORGANISM: Homo sapiens

<400> SEQUENCE: 485

```
gaggtgcagc tgttggagtc tgggggaggc ttgatacagc ctgggggtc cctgcgtctc      60 tcctgtgcag cctccggatt cacctttgcg catgagttga tggtgtgggt ccgccaggct    120
ccagggaagg gtctagagtg ggtctcacat attgatcgtg ttggtcagga tacatactac    180
gcagactccg tgaagggccg gttcaccatc tcccgcgaca attccaagaa cacgctgtat    240
ctgcaaatga acagcctgcg tgccgaggac acagcggtat attactgtgc gaaacttcct    300 aagaggggc cttggtttga ctaccggggt cagggaaccc tggtcaccgt ctcgagc        357
```

<210> SEQ ID NO 486
<211> LENGTH: 357
<212> TYPE: DNA
<213> ORGANISM: Homo sapiens

<400> SEQUENCE: 486

```
gaggtgcagc tgttggagtc tgggggaaac ttggtacagc ctgggggtc cctgcgtctc      60 tcctgtgcag cctccggatt cacctttgcg catgagacga tggtgtgggt ccgccaggct    120
ccagggaagg gtctagagtg ggtctcacat attgatcgtg ttggtcagga tacatactac    180
gcagactccg tgaagggccg gttcaccatc tcccgcgaca attccaagaa cacgctgtat    240
ctgcaaatga acagcctgcg tgccgaggac acagcggtat attactgtgc gaaacttcct    300 aagaggggc cttggtttga ctaccggggt cagggaaccc tggtcaccgt ctcgagc        357
```

<210> SEQ ID NO 487
<211> LENGTH: 357
<212> TYPE: DNA
<213> ORGANISM: Homo sapiens

<400> SEQUENCE: 487

```
gaggtgcagc tgttggagtc tgggggaggc ttggtacagc ctgggggtc cctgcgtctc      60 tcctgtgcag cctccggatt cacctttgcg catgagacga tggtgtgggt ccgccaggct    120
ccagggaagg gtctagagtg ggtctcacat attgatcgtg ttggtcagga tacatactac    180
gcagactccg tgaagggccg gttcaccatc tcccgcgaca attccaagaa cacgctgtat    240
ctgcaaatga acagcctgcg tgccgaggac acagcggtat attactgtgc gaaacttcct    300 aagaggggc cttggtttga ctaccggggt cagggaaccc tggtcaccgt ctcgagc        357
```

<210> SEQ ID NO 488
<211> LENGTH: 357
<212> TYPE: DNA
<213> ORGANISM: Homo sapiens

<400> SEQUENCE: 488

```
gaggtgcagc tgttggagtc tgggggaggc ttgatacagc ctgggggtc cctgcgtctc      60 tcctgtgcag cctccggatt cacctttgcg cataagacga tggtgtgggt ccgccaggct    120
ccagggaagg gtctagagtg ggtctcacat attgatcgtg ttggtcagga tacatactac   180
gcagactccg tgaagggccg gttcaccatc tcccgcgaca attccaagaa cacgctgtat   240
ctgcaaatga acagcctgcg tgccgaggac acagcggtat attactgtgc gttgcttcct   300
aagagggggc cttggtttga ctaccggggt cagggaaccc tggtcaccgt ctcgagc      357
```

<210> SEQ ID NO 489
<211> LENGTH: 357
<212> TYPE: DNA
<213> ORGANISM: Homo sapiens

<400> SEQUENCE: 489

```
gaggtgcagc tgttggagtc tgggggaggc ttgatacagc ctgggggtc cctgcgtctc      60 tcctgtgcag cctccggatt cacctttgcg catgagacga tggtgtgggt ccgccaggct    120
ccagggaagg gtctagagtg ggtctcacat attgatcgtg ttggtcagga tacatactac   180 gcagacccccg tgaagggccg gttcaccatc tcccgcgaca attccaagaa cacgctgtat   240
ctgcaaatga acagcctgcg tgccgaggac acagcggtat attactgtgc gcgcctacct   300
aagagggggc cttggtttga ctaccggggt cagggaaccc tggccaccgt ctcgagc      357
```

<210> SEQ ID NO 490
<211> LENGTH: 357
<212> TYPE: DNA
<213> ORGANISM: Homo sapiens

<400> SEQUENCE: 490

```
gaggtgcagc tgttggagtc tgggggaggc ttgatacagc ctgggggtc cctgcgtctc      60 tcctgtgcag cctccggatt cacctttgcg catgagacga tggtgtgggt ccgccaggct    120
ccagggaagg gtctagagtg ggtctcacat attgatcgtg ttggtcagga tacatactac   180
gcagactccg tgaagggccg gttcaccatc tcccgcgaca attccaagaa ctcgctgtat   240
ctgcaaatga acagcctgcg tgccgaggac acagccgtat attactgtgc ggtccttcct   300
aagagggggc cttggtttga ctatcggggt cagggaaccc tggtcaccgt ctcgagc      357
```

<210> SEQ ID NO 491
<211> LENGTH: 357
<212> TYPE: DNA
<213> ORGANISM: Homo sapiens

<400> SEQUENCE: 491

```
gaggtgcagc tgttggagtc tgggggaggc ttgatacagc ctgggggtc cctgcgtctc      60 tcctgtgcag cctccggatt cacctttgcg catgagacga tggtgtgggt ccgccaggct    120
ccagggaagg gtctagagtg ggtctcacat attgatcgtg ttggtcagga tacatactac   180
gcagactccg tgaagggccg gttcaccatc tcccgcgaca atcccaagaa cacgctgtat   240
ctgcaaatga acagcctgcg tgccgaggac acagcggtat attactgtgc gcgccttcct   300
aagagggggc cttggtttga ctaccggggt cagggaaccc tggtcaccgt ctcgagc      357
```

<210> SEQ ID NO 492
<211> LENGTH: 357
<212> TYPE: DNA
<213> ORGANISM: Homo sapiens

<400> SEQUENCE: 492

```
gaggtgcagc tgttggagtc tggggggaggc ttgatacagc ctgggggtc cctgcgtctc    60 tcctgtgcag cctccggatt cacctttgcg catgatacga tggtgtgggt ccgccaggct   120
ccagggaagg gtctagagtg ggtctcacat attgatcgtg ttggtcagga tacatactac   180
gcagactccg tgaagggccg gttcaccatc tcccgcgaca attccaagaa cacgctgtat   240
ctgcaaatga acagcctgcg tgccgaggac acagccgtat attactgtgc gcgccttcct   300
aagagggggc cttggtttga ctaccagggt caggaaccc tggtcaccgt ctcgagc       357
```

<210> SEQ ID NO 493
<211> LENGTH: 357
<212> TYPE: DNA
<213> ORGANISM: Homo sapiens

<400> SEQUENCE: 493

```
gaggtgcagc tgttggagtc tggggggaggc ttgatacagc ctgggggtc cctgcgtctc    60 tcctgtgcag cctccggatt cacctttgcg catgatacga tggtgtgggt ccgccaggct   120
ccagggaagg gtctagagtg ggtctcacat attgatcgtg ttggtcagga tacatactac   180
gcagactccg tgaaggaccg gttcaccatc tcccgcgaca attccaagaa cacgctgtat   240
ctgcaaatga atagcctgcg tgccgaggac acagccgtat attactgtgc ggtgcttcct   300
aagagggggc cttggtttga ctaccggggt caggaaccc tggtcaccgt ctcgagc       357
```

<210> SEQ ID NO 494
<211> LENGTH: 357
<212> TYPE: DNA
<213> ORGANISM: Homo sapiens

<400> SEQUENCE: 494

```
gaggtgcagc tgttggagtc tggggggaggc ttgatacagc ctgggggtc cctgcgtctc    60 tcctgtgcag cctccggatt cacctttgcg catgagacga tggtgtgggt ccgccaggct   120
ccagggaagg gtctagagtg ggtctcacat attgatcgtg ttggtcagga tacatactac   180
gcagactccg tgaagggccg gttcaccatc tcccgcgaca attccaagaa cacgctgttt   240
ctgcaaatga acagcctgcg tgccgaggac acagccgtat attactgtgc gcgccttcct   300
aagagggggc cttggtttga ctaccggggt cggggaaccc tggtcaccgt ctcgagc      357
```

<210> SEQ ID NO 495
<211> LENGTH: 357
<212> TYPE: DNA
<213> ORGANISM: Homo sapiens

<400> SEQUENCE: 495

```
gaggtgcagc tgttggagtc tggggggaggc ttgatacagc ctgggggtc cctgcgtctc    60 tcctgtgcag cctccggatt cacctttgcg catgagacga tggtgtgggt ccgccaggct   120
ccagggaagg gtctagagtg ggtctcacat attgatcgtg ttggtcagga tacatactac   180
gcagactccg tggagggccg gttcaccatc tcccgcgaca attccaagaa cacgctgtat   240
ctgcaaatga acagcctgcg tgccgaggac acagccgtat attactgtgc ggtccttcct   300
aagagggggc cttggtttga ctaccggggt caggaaccc tggtcaccgt ctcgagc       357
```

<210> SEQ ID NO 496
<211> LENGTH: 357
<212> TYPE: DNA
<213> ORGANISM: Homo sapiens

<400> SEQUENCE: 496
gaggtgcagc tgttggagtc tggggggaggc ttgatacagc ctgggggtc cctgcgtctc    60 tcctgtgcag cctccggatt caccttgcg catgagacga tggtgtgggt ccgccaggct   120
ccagggaagg gtctagagtg gtctcacat attgatcgtg ttggtcagga tacatactac   180
gcagactccg tggagggccg gttcaccatc tcccgcgaca attccaagaa cacgctgtat   240
ctgcaaatga acagcctgcg tgccgaggac acagccgtat attactgtgc gctgctccct   300 aagaggggc cttggtttga ctaccggggt cagggaaccc tggtcaccgt ctcgagc     357

<210> SEQ ID NO 497
<211> LENGTH: 357
<212> TYPE: DNA
<213> ORGANISM: Homo sapiens

<400> SEQUENCE: 497
gaggtgcagc tgttagagtc tggggggaggc ttgatacagc ctgggggtc cctgcgtctc    60 tcctgtgcag cctccggatt caccttgcg catgagacga tggtgtgggt ccgccaggct   120
ccagggaagg gtcaagagtg gtctcacat attgatcgtg ttggtcagga tacatactac   180
gcagactccg tgaagggccg gttcaccatc tcccgcgaca attccaagaa ctcgctgtat   240
ctgcaaatga acagcctgcg tgccgaggac acagccgtat attactgtgc ggtccttcct   300 aagaggggc cttggtttga ctaccggggt cagggaaccc tggtcaccgt ctcgagc     357

<210> SEQ ID NO 498
<211> LENGTH: 357
<212> TYPE: DNA
<213> ORGANISM: Homo sapiens

<400> SEQUENCE: 498
gaggtgcagc tgtcggagtc tggggggaggc ttgatacagc ctgggggtc cctgcgtctc    60 tcctgtgtag cctccggatt caccttgcg catgagacga tggtgtgggt ccgccaggct   120
ccagggaagg gtctagagtg gtctcacat attgatcgtg ttggtcagga tacatactac   180
gcagactccg tgaagggccg gttcaccatc tcccgcgaca attccaagaa cacgctgtat   240
ctgcaaatga acagcctgcg tgccgaggac acagccgtat attactgtgc gatccttcct   300 aagaggggc cttggtttga ctaccggggt cagggaaccc tggtcaccgt ctcgagc     357

<210> SEQ ID NO 499
<211> LENGTH: 357
<212> TYPE: DNA
<213> ORGANISM: Homo sapiens

<400> SEQUENCE: 499
gaggtgcagc tgttggagtc tggggggaggc ttgatacagc ctgggggtc cctgcgtctc    60 acctgtgcag cctccggatt caccttgcg catgagacga tggtgtgggt ccgccaggct   120
ccagggaagg gtctagagtg gtctcacat attgatcgtg ttggtcagga tacatactac   180
gcagactccg tgaagggccg gttcaccatc tcccgcgaca attccaagaa cacgctgtat   240
ctgcaaatga acagcctgcg tgccgaggac acagcgtat attactgtgc ggtgcttcct   300 aagaggggc cttggtttga ctaccggggt cagggaaccc tggtcaccgt ctcgagc     357

<210> SEQ ID NO 500
<211> LENGTH: 357
<212> TYPE: DNA
<213> ORGANISM: Homo sapiens

<400> SEQUENCE: 500

```
gaggtgcagc tgttggagtc tgggggaggc ttgatacagc ctgggggtc cctgcgtctc      60
tcctgtgcag cctccggatt cacctttgcg catgagacga tggtgtgggt ccgccaggct    120
ccagggaagg gtctagagtg gtctcacat attgatcgtg ttggtcagga tacatactac    180
gcagactccg tgaagggccg gttcaccatc tcccgcgaca attccatgaa cacgctgtat    240
ctgcaaatga acagcctgcg tgccgaggac acagcggtat attactgtgc gttgcttcct    300
aagagggggc cttggtttga ctaccggggt cagggaaccc tggtcaccgt ctcgagc       357
```

<210> SEQ ID NO 501
<211> LENGTH: 357
<212> TYPE: DNA
<213> ORGANISM: Homo sapiens

<400> SEQUENCE: 501

```
gaggtgcagc tgttggagtc tgggggaggc tcgatacagc caggggggtc cctgcgtctc    60
tcctgtgcag cctccggatt cacctttgcg catgagacga tggtgtgggt ccgccaggct   120
ccagggaagg gtctagagtg gtctcacat attgatcgtg ttggtcagga tacatactac   180
gcagactccg tgaagggccg gttcaccatc tcccgcgaca attccaagaa cacgctgtat   240
ctgcaaatga acagcctgcg tgccgaggac acggcggtat attactgtgc ggtccttcct   300
aagagggggc cttggtttga ctaccggggt cagggaaccc tggtcaccgt ctcgagc      357
```

<210> SEQ ID NO 502
<211> LENGTH: 357
<212> TYPE: DNA
<213> ORGANISM: Homo sapiens

<400> SEQUENCE: 502

```
gaggtgcagc tgttggagtc tgggggaggc ttgatacagc ctgggggtc cctgcgtctc     60
tcctgtgcag cctccggatt cacctttgcg catgagacga tggtgtgggt ccgccaggct   120
ccagggaagg gtctagagtg gtctcacat attgatcgtg ttggtcagga tacatactac   180
gcagactccg tgaagggccg gttcaccatc tcccgcaaca attccatgaa cacgctgtat   240
ctgcaaatga acagcctgcg tgccgaggac acagcggtat attactgtgc gatccttcct   300
aagagggggc cttggtttga ctaccggggt cagggaaccc tggtcaccgt ctcgagc      357
```

<210> SEQ ID NO 503
<211> LENGTH: 357
<212> TYPE: DNA
<213> ORGANISM: Homo sapiens

<400> SEQUENCE: 503

```
gaggtgcagc tgttggagtc tgggggaggc ttgatacagc ctgggggtc cctgcgtctc     60
tcctgcgcag cctccggatt cacctttgcg catgagacga tggtgtgggt ccgccaggct   120
ccagggaggg gtctagagtg gtctcacat attgatcgtg ttggtcagga tacatactac   180
gcagactccg tgaagggccg gttcaccatc tcccgcgaca attccaagaa cacgctgtat   240
ctgcaaatga acagcctgcg tgccgaggac acagccgtat attactgtgc ggtgcttcct   300
aagagggggc cttggtttga ctaccggggt cagggaaccc tggtcaccgt ctcgagc      357
```

<210> SEQ ID NO 504
<211> LENGTH: 357
<212> TYPE: DNA

<213> ORGANISM: Homo sapiens

<400> SEQUENCE: 504

```
gaggtgcagc tgttggagtc tgggggaggc ttgatacagc ctggggggtc cctgcgtctc        60
tcctgtgcag cctccggatt cacctttgcg catgagacga tggtgtgggt ccgccaggct       120
ccagggaagg gtctagagtg ggtctcacat attgatcgtg ttggtcagga tccatactac       180
gcagactccg tgaagggccg gttcaccatc tcccgcgaca attccaagaa cacgctgtat       240
ctgcaaatga acagcctgcg tgccgaggac acagccgtat attactgtgc gctccttcct       300
aagagggggc cttggtttga ctaccggggt cagggaaccc tggtcaccgt ctcgagc          357
```

<210> SEQ ID NO 505
<211> LENGTH: 357
<212> TYPE: DNA
<213> ORGANISM: Homo sapiens

<400> SEQUENCE: 505

```
gaggtgcagc tgttggagtc tgggggaggc ttgatacagc ctggggggtc cctgcgtctc        60
tcctgtgcag cctccggatt cacctttgcg catgagacga tggtgtgggt ccgccaggct       120
ccagggaagg gtctagagtg ggtctcacat attgatcgtg ttggtcagga tacatactac       180
gcagactccg tgaagggccg gttcaccatc tcccgcgaca attccaagaa cacgctgtat       240
ctgcaaatga acagcctgcg tgccgaggac acagccgtat attactgtgc gatgcttcct       300
aagagggggc cttggtttga ctaccggggt cagggaaccc tggtcaccgt ctcgagc          357
```

<210> SEQ ID NO 506
<211> LENGTH: 357
<212> TYPE: DNA
<213> ORGANISM: Homo sapiens

<400> SEQUENCE: 506

```
gaggtgcagc tgttggagtc tgggggaggc ttgatacagc ctggggggtc cctgcgtctc        60
tcctgtgcag cctccggatt cacctttgcg catgatacga tggtgtgggt ccgccaggct       120
ccagggaagg gtctagagtg ggtctctcat attgatcgtg ttggtcagga tacatactac       180
gcagactccg tgaagggccg gttcaccatc tcccgcgaca ataccaagaa cacgctgtat       240
ctgcaaatga acagcctgcg tgccgaggac acagccgtat attactgtgc gctccttcct       300
aagagggggc cttggtttga ctaccggggt cagggaaccc tggtcaccgt ctcgagc          357
```

<210> SEQ ID NO 507
<211> LENGTH: 357
<212> TYPE: DNA
<213> ORGANISM: Homo sapiens

<400> SEQUENCE: 507

```
gaggtgcagc tgttggagtc tgggggaggc ttgatagagc ctggggggtc cctgcgtcta        60
tcctgtgcag cctccggatt cacctttgcg catgagacga tggtgtgggt ccgccaggct       120
ccagggaagg gtctagagtg ggtctcacat attgatcgtg ttggtcagga tacatactac       180
gcagactccg tgaagggccg gttcaccatc tcccgcgaca attccaagaa cacgctgtat       240
ctgcaaatga acagcctgcg tgccgaggac tcagcggtat attactgtgc gcgccttcct       300
aagagggggc catggtttga ctaccggggt cagggaaccc tggtcaccgt ctcgagc          357
```

<210> SEQ ID NO 508
<211> LENGTH: 357

<212> TYPE: DNA
<213> ORGANISM: Homo sapiens

<400> SEQUENCE: 508

```
gatgtgcagc tgctggagtc tgggggaggc ttgatacagc ctgggggtc cctgcgtctc      60
tcctgtgcag cctccggatt cacctttgcg catgagacga tggtgtgggt ccgccaggct    120
ccagggaagg gtctagagtg ggtctcacat attgatcgtg ttggtcagga tacatactac    180
gcagactccg tgaagggccg gttcaccatc tcccgcgaca attccaagaa cacgctgtat    240
ctgcaaatga acagcctgcg tgccgaggac acagcggcat attactgtgc ggtccttcct    300
aagaggggc cttggtttga ctaccggggt caggaaccc tggtcaccgt ctcgagc        357
```

<210> SEQ ID NO 509
<211> LENGTH: 357
<212> TYPE: DNA
<213> ORGANISM: Homo sapiens

<400> SEQUENCE: 509

```
gaggtgcagc tgatggagtc tgggggaggc ttgatacagc ctgggggtc cctgcgtctc      60
tcctgtgcag cctccggatt cacctttgcg catgagacga tggtgtgggt ccgccaggct    120
ccagggaagg gtctagagtg ggtctcacat attgatcgtg ttggtcagga tacatactac    180
gcagactccg tgaagggccg gttcaccatc tcccgcgaca attccaagaa cacgctgtat    240
ctgcaaatga acagcctgcg tgccgaggac acagcggtat attactgtgc ggagcttcct    300
aagaggggc cttggtttga ccaccggggt caggaacac tggtcaccgt ctcgagc        357
```

<210> SEQ ID NO 510
<211> LENGTH: 357
<212> TYPE: DNA
<213> ORGANISM: Homo sapiens

<400> SEQUENCE: 510

```
gaggtgcagc tgctggagtc tgggggaggc ttgatacagc ctgggggtc cctgcgtctc      60
tcctgtgcag cctccggatt cacctttgcg catgagacga tggtgtgggt ccgccaggct    120
ccagggaagg gtctagagtg ggtctcacat attgatcgtg ttggtcagga tacatactac    180
gcagactccg tgaagggccg gttcgccatc tcccgcgaca attccaagaa cacgctgtat    240
ctgcaaatga acagcctgcg tgccgaggac acagccgtat attactgtgc gatgcttcct    300
aagaggggc cttggtttga ctaccggggc caggaaccc tggtcaccgt ctcgagc        357
```

<210> SEQ ID NO 511
<211> LENGTH: 357
<212> TYPE: DNA
<213> ORGANISM: Homo sapiens

<400> SEQUENCE: 511

```
gaggtgcagc tgttggagtc tgggggaggc ttgatacagc ctgggggtc cctgcgtctc      60
tcctgtgcag cctccggatt cacctttgcg catgagacga tggtgtgggt ccgccaggct    120
ccagggaagg gtctagagtg ggtctcacat attgatcgtg ttggtcagga tacatactac    180
acagactccg tgaagggccg gttcaccatc tcccgcgaca attccaagaa cacgctgtat    240
ctgcaaatga acagcctgcg tgccgaggac acagccgtat attactgtgc gttgcttcct    300
aagaggggc cttggtttga ctaccggggt caggaacca tggtcaccgt ctcgagc        357
```

<210> SEQ ID NO 512

<211> LENGTH: 357
<212> TYPE: DNA
<213> ORGANISM: Homo sapiens

<400> SEQUENCE: 512

```
gaggtgcagc tgttggagtc tgggggaggc ttgatgcagc ctgggggtc cctgcgtctc    60
tcctgtgcag cctccggatt cacctttgcg catgagacga tggtgtgggt ccgccaggct   120
ccagggaagg gtctagagtg gtctcacat attgatcttg ttggtcagga tacatactat   180
gcagactccg tgaagggccg gttcaccatc tcccgcgaca attccaagaa cacgctgtat   240
ctacaaatga acagcctgcg tgccgaggac acagcagtat atcactgcgc gcgccttcct   300
aagagggggc cttggtttga ctaccggggt cagggaaccc tggtcaccgt ctcgagc     357
```

<210> SEQ ID NO 513
<211> LENGTH: 357
<212> TYPE: DNA
<213> ORGANISM: Homo sapiens

<400> SEQUENCE: 513

```
gaggtgcaac tgttggagtc tgggggaggc ttgatacagc ctgggggtc cctgcgtctc    60
tcctgtgcaa cctccggatt cacctttgcg catgagacga tggtgtgggt ccgccaggct   120
ccagggaagg gtctagagtg gtctcacat attgatcgtg ttggtcagga tacatactac   180
gcagactccg tgaagggccg gttcaccatc tcccgcgaca attccaagaa cacgctgtat   240
atgcaaatga acagcctgcg tgccgaggac acagcggtat attactgtgc ggtccttcct   300
aagagggggc cttggtttga ctaccagggt cagggaaccc tggtcaccgt ctcgagc     357
```

<210> SEQ ID NO 514
<211> LENGTH: 357
<212> TYPE: DNA
<213> ORGANISM: Homo sapiens

<400> SEQUENCE: 514

```
gaggtgcagc tgttggagtc tgggggaggc ttgatacagc ctgggggtc cctgcgtctc    60
tcctgtgcag cctccgggtt cacctttgcg catgagacga tggtgtgggt ccgccaggct   120
ccagggaagg gtctagagtg gtctcacat attgatcgtg taggtcagga tacatactac   180
gcagacccct tgaagggccg gttcaccatc tcccgcgaca attccaggaa cacgctgtat   240
ctgcaaatga acagcctgcg ttccgaggat acagcggtat attactgtgc ggtccttcct   300
aagagggggc cttggtttga ctaccggggt cagggaaccc tggtcaccgt ctcgagc     357
```

<210> SEQ ID NO 515
<211> LENGTH: 357
<212> TYPE: DNA
<213> ORGANISM: Homo sapiens

<400> SEQUENCE: 515

```
gaggtgcagc tgttggagtc tgggggggc ttgatacagc ctgggggtc cctgcgtctc    60
tcctgtgcag cctccggatt cacctttgcg catgagacga tggtgtgggt ccgccaggct   120
ccagggaagg gtctagagtg gtctcacat attgatcgtg ttggtcagga tacatactac   180
gcagactccg tgaagggccg gttcaccatc tcccgcgaca attccaagaa cacgctgtat   240
ctgcaaatga acagcctgcg tgccgaggac acagccgtat atagctgtgc gttgcttcct   300
aagagggggc cttggtttga ctaccggggt cagggaaccc tggtcaccgt ctcgagc     357
```

<210> SEQ ID NO 516
<211> LENGTH: 357
<212> TYPE: DNA
<213> ORGANISM: Homo sapiens

<400> SEQUENCE: 516

```
gaggtgcagc tgttggagtc tgggggaggc ttgatacagc ctggggggtc cctgcgtctc    60
tcctgtgcag cctccggatt cacctttgcg catgagacga tggtgtgggt ccgccaggct   120
ccagggaagg gtctagagtg gtctcacat attgatcgtg ttggtcagga tacatactac    180
gcagactcag tgaagggccg gttcaccatc tcccgcgaca attccaagaa cgcgctgtat   240
ctgcaaatga acagcctgcg tgccgaggac acagcggtat attactgtgc ggtccttcct   300
aagagggggc cttggtttga ctaccggggt cagggaaccc tggtcaccgt ctcgagc      357
```

<210> SEQ ID NO 517
<211> LENGTH: 357
<212> TYPE: DNA
<213> ORGANISM: Homo sapiens

<400> SEQUENCE: 517

```
gaggtgcagc tgttggagtc tgggggaggc ttggtacagc ctggggggtc cctgcgtctc    60
tcctgtgcag cctccggatt cacctttgcg catgagacga tggtgtgggt ccgccaggct   120
ccagggaagg gtctagagtg gtctcacat attgatcgtg ttggtcagga tacatactac    180
gcagactccg tgaagggccg gttcaccatc tcccgcgaca attccaagaa cacgctgtat   240
ctgcaaatga acagcctgcg tgccgaggac acagcggtat attactgtgc gctgcttcct   300
aagagggggc cttggtttga ctactggggt cagggaaccc tggtcaccgt ctcgagc      357
```

<210> SEQ ID NO 518
<211> LENGTH: 357
<212> TYPE: DNA
<213> ORGANISM: Homo sapiens

<400> SEQUENCE: 518

```
gaggtgcagc tgttggagtc tgggggaggc ttgatacagc ctggggggtc cctgcgtctc    60
tcctgtgcag cctccggatt cacctttgcg catgagacga tggtgtgggt ccgcgaggct   120
ccagggaagg gtctagagtg gtctcacat attgatcgtg ttggtcagga tacatactac    180
gcagactccg tgaagggccg gttcaccatc tcccgcgaca attccaagaa cacgctgtat   240
ctgcaaatga acagcctgcg tgccgaggac acagccgtat attactgtgc gatccttcct   300
aagagggggc cttggtttga ctacaggggt cagggaaccc tggtcaccgt ctcgagc      357
```

<210> SEQ ID NO 519
<211> LENGTH: 357
<212> TYPE: DNA
<213> ORGANISM: Homo sapiens

<400> SEQUENCE: 519

```
gaggtgcagc tgttggagtc tgggggaggc ttgatacagc ctggggggtc cctgcgtctc    60
tcctgtgcag cctccggatt cacctttgcg catgagacga tggtgtgggt ccgccaggct   120
ccagggaagg gtctagagtg gtctcacat attgatcgtg ttggtcagga tacatactac    180
gcagactccg tggagggccg gttcaccatc tcccgcgaca attccaagaa cacgctgtat   240
ctgcaaatga acagcctgcg tgccgaggac acagcggtat attactgtgc ggtgcttcct   300
aagagggggc cttggtttga ctaccggggt cagggaaccc tggtcaccgt ctcgagc      357
```

<210> SEQ ID NO 520
<211> LENGTH: 357
<212> TYPE: DNA
<213> ORGANISM: Homo sapiens

<400> SEQUENCE: 520

```
gaggtgcagc tgttggagtc tgggggaggc ttgatacagc ctggggggtc cctgcgtctc      60
tcctgtgcag cctccggatt cacctttgcg catgagacga tggtgtgggt ccgccaggct     120
ccagggaagg gtctagagtg ggtctcacat attgatcgtg ttggtcagga tacatactac     180
gcagaccccg tgaagggccg gttcaccatc tcccgcgaca attccaggaa cacgctgtat     240
ctgcaaatga acagcctgcg tgccgaggac acagcggtat attactgtgc ggtgcttcct     300
aagaggggc cttggtttga ctaccggggt cagggaaccc tggtcaccgt ctcgagc        357
```

<210> SEQ ID NO 521
<211> LENGTH: 357
<212> TYPE: DNA
<213> ORGANISM: Homo sapiens

<400> SEQUENCE: 521

```
gaggtgcaac ttttggagtc tgggggagac ttgatacagc ctggggggtc cctgcgtctc      60
tcctgtgcag cctccggatt cacctttgcg catgagacga tggtgtgggt ccgccaggct     120
ccagggaagg gtctagagtg ggtctcacat attgatcgtg ttggtcagga tacatactac     180
gcagactccg tgaagggccg gttcaccatc tcccgcgaca attccaagaa cacgctgtat     240
ctgcaaatga acagcctgcg tgccgaggac acagccgtat attactgtgc ggtgcttcct     300
aagaggggc cttggtttga ctaccggggt cagggaaccc tggtcaccgt ctcgagc        357
```

<210> SEQ ID NO 522
<211> LENGTH: 357
<212> TYPE: DNA
<213> ORGANISM: Homo sapiens

<400> SEQUENCE: 522

```
gaggtgcagc tgttggagtc tgggggaggc tcgatacagc ctggggggtc cctgcgtctc      60
tcctgtgcag cctccggatt cacctttgcg catgagacga tggtgtgggt ccgccaggct     120
ccagggaagg gtctagagtg ggtctcacat attgatcgtg ttggtcagga tacatactac     180
gcagactccg ttaagggccg gttcaccatc tcccgcgaca attccaagaa cacgctgtat     240
ctgcaaatga acagcctgcg tgccgaggac acagcggtat attactgtgc ggtgcttcct     300
aagaggggc cttggtttga ctaccggggt cagggaaccc tggtcaccgt ctcgagc        357
```

<210> SEQ ID NO 523
<211> LENGTH: 357
<212> TYPE: DNA
<213> ORGANISM: Homo sapiens

<400> SEQUENCE: 523

```
gaggtgcagc tgttggagtc tgggggaggc ttgatacagc ctggggggtc cctgcatctc      60
tcctgtgcag cctccggatt cacctttgag catgagacga tggtgtgggt ccgtcaggct     120
ccagggaagg gtctagagtg ggtctcacat attgatcgag ttggtcagga tccatactac     180
gcagactccg tgaagggccg gttcaccatc tcccgcgaca attccaagaa cacgctgtat     240
ctgcaaatga acagcctgcg tgccgaggac acagcggtat attactgtgc gcgccttcct     300
aagaggggc cttggtttga ctaccggggt cagggaaccc tggtcaccgt ctcgagc        357
```

<210> SEQ ID NO 524
<211> LENGTH: 357
<212> TYPE: DNA
<213> ORGANISM: Homo sapiens

<400> SEQUENCE: 524
gaggtgcagc tgttggagtc tgggggaggc ttgatacagc ctggggggtc cctgcgtctc    60
tcctgtgcgg cctccggatt cacctttgcg catgatacga tggtgtgggt ccgccaggct   120
ccagggaagg gtctagagtg ggtctcacat attgatcgtg ttggtcagga tacatactac   180
gcagattccg tgaagggccg gttcaccatc tcccgcgaca attccaagaa cacgctgtat   240
ctgcaaatga acagcctgcg tgccgaggac acagcggtat attactgtgc gcgccttcct   300
aagaggggc cttggtttga ctaccggggt caggggaccc tggtcaccgt ctcgagc       357

<210> SEQ ID NO 525
<211> LENGTH: 357
<212> TYPE: DNA
<213> ORGANISM: Homo sapiens

<400> SEQUENCE: 525
gaggtgcagc tgttggagtc tgggggaggc ttgatacagc ctggggggtc cctgcgtctc    60
tcctgtgcag cctccggatt cacctttgcg catgagacga tggtgtgggt ccgccaggct   120
ccagggaagg gtctagagtg ggtctcacat attgatcgtg ttggtcagga tccatactac   180
gcagactccg tgaagggccg gttcaccatc tcccgcgaca attccaagaa cacgctgtat   240
ctgcaaatga acagcctgcg tgccgaggac acagcggtat attactgtgc gcgccttcct   300
aagaggggc cttggtttga ctaccggggt cagggaaccc tggtcaccgt ctcgagc       357

<210> SEQ ID NO 526
<211> LENGTH: 357
<212> TYPE: DNA
<213> ORGANISM: Homo sapiens

<400> SEQUENCE: 526
gaggtgcagc tgttggagtc tgggggaggc ttgatacagc ctggggggtc cctgcgtctc    60
tcctgtgcag cctccggatt cacctttgcg catgagacga tggtgtgggt ccgccaggct   120
ccagggaagg atctagagtg ggtctcacat attgatcgtg ttggtcagga tacatactac   180
gcagactccg tgaagggccg gtttaccatc tcccgcgaca attccaagaa cacgctgtat   240
ctgcaaatga acagcctgcg tgccgaggac acagcggtat attactgtgc ggtgcttcct   300
aagaggggc cttggtttga ctaccggggt cagggaaccc tggtcaccgt ctcgagc       357

<210> SEQ ID NO 527
<211> LENGTH: 357
<212> TYPE: DNA
<213> ORGANISM: Homo sapiens

<400> SEQUENCE: 527
gaggtgcagc tgttggagtc tgggggaggc ttgatacagc ctggggggtc cctgcgtctc    60
tcctgtgcag cctccggatt cacctttgcg catgatacga tggtgtgggt ccgccaggct   120
ccagggaagg gtctagagtg ggtctcacat attgatcgtg ttggtcagga tacgtactac   180
gcagactccg tgaagggccg gttcaccatc tcccgcgaca attccaagaa cacgctgtat   240
ctgcaaatga acagcctgcg tgccgaggac acagcggtat attactgtgc gcgccttcct   300
aagagggggc cttggtttga ctaccggggt cagggaaccc tggtcaccgt ctcgagc     357

<210> SEQ ID NO 528
<211> LENGTH: 357
<212> TYPE: DNA
<213> ORGANISM: Homo sapiens

<400> SEQUENCE: 528
gaggtgcagc tgttggagtc cggggggaggc ttgatacagc ctggggggtc cctgcgtctc     60
tcctgtgcag cctccggatt cacctttgcg catgagacga tggtgtgggt ccgccaggct    120
ccagggaagg gtctagagtg ggtctcacat attgatcgtg ttggtcagga tacatactac    180
gcagactccg tgaagggccg gttcaccatc tcccgcgaca attccaagaa cacgctgtat    240
ctgcaaatga acagcctgcg tgccgaggac acagccgtat accactgtgc ggtgcttcct    300
aagagggggc cttggtttga ctaccgggggt cagggaaccc tggtcaccgt ctcgagc     357

<210> SEQ ID NO 529
<211> LENGTH: 357
<212> TYPE: DNA
<213> ORGANISM: Homo sapiens

<400> SEQUENCE: 529
gaggtgcagc tgttggagtc tggggggaggc ctgatacagc ctggggggtc cctgcgtctc     60
tcctgtgcag cctccggatt cacctttgcg catgagacga tggtgtgggt ccgcgaggct    120
ccagggaagg gtctagagtg ggtctcacat attgatcgtg ttggtcagga tacatactac    180
gcagactccg tgaagggccg gttcaccatc tcccgcgaca attccaagaa cacgctgtat    240
ctgcaaatga acagcctgcg tgccgaggac acagccgtat attactgtgc ggtccttcct    300
aagagggggc cttggtttga ctaccggggt cagggaaccc tggtcaccgt ctcgagc     357

<210> SEQ ID NO 530
<211> LENGTH: 357
<212> TYPE: DNA
<213> ORGANISM: Homo sapiens

<400> SEQUENCE: 530
gaggtgcagc tgttggagtc tggggggaggc ttgatacatc ctgggggggac cctgcgtctc     60
tcctgtgcag cctccggatt cacctttgcg catgagacga tggtgtgggt ccgccaggct    120
ccggggaagg gtctagagtg ggtctcacat attgatcgtg ttggtcagga tccatactat    180
gcagactccg tgaagggccg gttcaccatc tcccgcgaca attccaagaa cacgctgtat    240
ctgcaaatga acagcctgcg tgccgaggac acagcggtat attactgtgc gcgcctccct    300
aagagggggc cttggtttga ctaccggggt cagggaaccc tggtcaccgt ctcgagc     357

<210> SEQ ID NO 531
<211> LENGTH: 357
<212> TYPE: DNA
<213> ORGANISM: Homo sapiens

<400> SEQUENCE: 531
gaggtgcagc tgttggagtc tggggggaggc ttgatacagc ctggggggtc cctgcgtctc     60
tcctgtgcag cctccggatt cacctttgcg catgagacga tggtgtgggt ccgccaggct    120
ccagggaagg gtctagagtg ggtctcacat attgatcgtg ttggtcagga tccatactac    180
gcagactccg tgaagggccg gttcaccatc tcccgcgaca attccaagaa cacgctgtat    240
ctgcaaatga acagcctgcg tgccgaggac acagcggtat attactgtgc gcgccttcct    300

```
aagaggggc cttggtttga ctaccggggt cagggaaccc aggtcaccgt ctcgagc      357
```

<210> SEQ ID NO 532
<211> LENGTH: 357
<212> TYPE: DNA
<213> ORGANISM: Homo sapiens

<400> SEQUENCE: 532

```
gaggtgcagc tgttggagtc tgggggaggc ttggtacagc ctgggggtc cctgcgtctc    60 tcctgtgcag cctccggatt cacctttgcg catgagacga tggtgtgggt ccgccaggct   120
ccagggaagg gtctagagtg ggtctcacat attgatcgtg ttggtcagga tacatactac   180
gcagactccg tgaagggccg gttcaccatc tcccgcgaca attccaagaa cacgctgtat   240
ctgcaaatga acagcctgcg tgccgaggac acagcggtat attactgtgc gctgcttcct   300 aagaggggc cttggtttga ctactgggt cagggaaccc tggtcaccgt ctcgagc        357
```

<210> SEQ ID NO 533
<211> LENGTH: 357
<212> TYPE: DNA
<213> ORGANISM: Homo sapiens

<400> SEQUENCE: 533

```
gaggtgcagc tgttggagtc tgggggaggc ttggtacagc ctgggggtc cctgcgtctc    60 tcctgtgcag cctccggatt cacctttgcg catgagacga tggtgtgggt ccgccaggct   120
ccagggaagg gtctagagtg ggtctcacat attgatcgtg ttggtcagga tacatactac   180
gcagactccg tggagggccg gttcaccatc tcccgcgaca attccaagaa cacgctgtat   240
ctgcaaatga acagcctgcg tgccgaggac acagcggtat attactgtgc ggtccttcct   300 aagaggggc cttggtttga ctactgggt cagggaaccc tggtcaccgt ctcgagc        357
```

<210> SEQ ID NO 534
<211> LENGTH: 357
<212> TYPE: DNA
<213> ORGANISM: Homo sapiens

<400> SEQUENCE: 534

```
gaggtgcagc tgttggagtc tgggggaggc ttggtacagc ctgggggtc cctgcgtctc    60 tcctgtgcag cctccggatt cacctttgcg catgagacga tggtgtgggt ccgccaggct   120
ccagggaagg gtctagagtg ggtctcacat attgatcgtg ttggtcagga tccatactac   180
gcagactccg tgaagggccg gttcaccatc tcccgcgaca attccaagaa cacgctgtat   240
ctgcaaatga acagcctgcg tgccgaggac acagccgtat attactgtgc gctccttcct   300 aagaggggc cttggtttga ctactgggt cagggaaccc tggtcaccgt ctcgagc        357
```

<210> SEQ ID NO 535
<211> LENGTH: 357
<212> TYPE: DNA
<213> ORGANISM: Homo sapiens

<400> SEQUENCE: 535

```
gaggtgcagc tgttggagtc tgggggaggc ttgatacagc ctgggggtc cctgcgtctc    60 tcctgtgcag cctccggatt cacctttgcg catgagacga tggtgtgggt ccgccaggct   120
ccagggaagg atctagagtg ggtatcacat attgatcgtg atggtcagga tacatactac   180
gcagactccg tgaagggccg gttctccatc tcccgcgaca attccaaaaa cacgctgtat   240
```

```
ctgcaaatga acagcctgcg tgccgaggac acagcggtat attactgtgc gcgccttcct      300 aagaggggc cttggtttga ctaccggggt cagggaaccc tggtcaccgt ctcgagc          357
```

<210> SEQ ID NO 536
<211> LENGTH: 357
<212> TYPE: DNA
<213> ORGANISM: Homo sapiens

<400> SEQUENCE: 536

```
gaggtgcagc tgttggagtc tgggggaggc ttgatacagc ctggggggtc cctgcgtctc      60
tcctgtgcag cctccggatt cacctttgcg catgagacga tggtgtgggt ccgccaggct      120
ccagggaagg gtctagagtg ggtctcacat attgatcgtg ttggtcagga tacatactac     180
gcagactccg tgaagggccg gttcaccacc tcccgcgaca attccaagaa cacgctgtat      240
ctgcaaatga acagcctgcg tgccgaggac acagcggtat attactgtgc gcgcctccct     300 aagaggggc cttggtttga ctaccggggt cagggaaccc tggtcaccgt ctcgagt         357
```

<210> SEQ ID NO 537
<211> LENGTH: 357
<212> TYPE: DNA
<213> ORGANISM: Homo sapiens

<400> SEQUENCE: 537

```
gaggtgcagc tgttggagtc tgggggaggc ttgatacagc ctggggggtc cctgcgtctc      60
tcctgtgcag cctccggatt cacctttgcg catgagacga tggtgtgggt ccgccaggct      120
ccagggaagg gtctagagtg ggtctcacat attgatcgtg atggtcagga tacatactac     180
gcagactccg tgatgggccg gttcaccgtc tcccgcgaca attccaagaa cacgctgtat      240
ctgcaaatga acagcctgcg tgccgaggac acagccgtat attactgtgc gatcattcct     300 aagaggggc cttggtttga ctaccggggt cagggaaccc tggtcaccgt ctcgagc         357
```

<210> SEQ ID NO 538
<211> LENGTH: 357
<212> TYPE: DNA
<213> ORGANISM: Homo sapiens

<400> SEQUENCE: 538

```
gaggtgcagc tgttggagtc tgggggaggc ttgatacagc ctggggggtc tctgcgtctc      60
tcctgtgcag cctccggatt cacctttgcg catgagacga tggtgtgggt ccgccaggct      120
ccagggaagg atctagagtg ggtctcacat attgatcgtg ttggtcagga tacatactac     180
gcagactccg tggagggccg gttcaccatc tcccgcgaca attccaagaa cacgctgtat      240
ctgcaaatga acagcctgcg tgccgaggac acagccgtat attactgtgc ggtgcttcct     300 aagaggggc cttggtttga ctaccggggt cagggaaccc tggtcaccgt ctcgagc         357
```

<210> SEQ ID NO 539
<211> LENGTH: 357
<212> TYPE: DNA
<213> ORGANISM: Homo sapiens

<400> SEQUENCE: 539

```
gaggtgcagc tgttggagtc tgggggaggc ttgatacagc ctggggggtc cctgcgtctc      60
tcctgtgcag cctccggatt cacctttgcg catgagacga tggtgtgggt ccgccaggct      120
ccagggaagg gtctagagtg ggtctcacat actgatcgtg ttggtcagga tacatactac     180
gcagactccg tgaagggccg gttcaccatc tcccgcgaca attccaggaa cacgctgtat      240
```

-continued ctgcaaatga acagcctgcg tgccgaggac acagcggtat attactgtgc ggtgcttcct    300 aagaggggc catggtttga ctaccggggt cagggaaccc tggtcaccgt ctcgagc    357

<210> SEQ ID NO 540
<211> LENGTH: 357
<212> TYPE: DNA
<213> ORGANISM: Homo sapiens

<400> SEQUENCE: 540
gaggtgcagc tgttggagtc tgggggaggc ttgatacagc ctggggggac cctgcgtctc    60
tcctgtgcag cctccggatt cacctttgcg cttgagacga tggtgtgggt ccgccaggct    120
ccagggaagg gtctagagtg ggtctcacat attgatcgtg ttggtcagga tacatactac    180
gcagactccg tgaagggccg gttcaccacc tcccgcgaca attccaggaa cacgctgtat    240
ctgcaaatga acagcctgcg tgccgaggac acagcggtat attactgtgc gcgccttcct    300 aagaggggc cttggtttga ctaccggggt cagggaaccc tggtcaccgt ctcgagc    357

<210> SEQ ID NO 541
<211> LENGTH: 357
<212> TYPE: DNA
<213> ORGANISM: Homo sapiens

<400> SEQUENCE: 541
gaggtgcagc tgttggagtc tgggggaggc ttgatacagc ctgggggtc cctgcgtctc    60 tcctgtgcag cctccggatt cacctttgcg catgagacga tggtgtgggt acgccaggct    120
ccagggaagg gtctagagtg ggtctcacat attgatcgtg ttggtcagga tacatactac    180
gcagactccg tgaagggccg gttcaccatc tcccgcgaca attccaagaa cacgctgtat    240
ctgcaaatga acagcctgcg tgccgaggac acagcggtat attactgtgc ggtgattcct    300 aagaggggc cttggtttga ctaccggggt cagggaaccc tggtcaccgt ctcgagc    357

<210> SEQ ID NO 542
<211> LENGTH: 357
<212> TYPE: DNA
<213> ORGANISM: Homo sapiens

<400> SEQUENCE: 542
gaggtgcagc tgttggagtc tgggggaggc ttgatacagc ctgggggtc cctgcgtctc    60 tcctgtgcag cctccggatt cacatttgcg catgagacga tggtgtgggt ccgccaggct    120
ccagggaagg gtctagagtg ggtctcacat attgatcgtg ttggtcagga tacatactac    180
gcagactccg tgaagggccg gttcaccatc tcccgcgaca attccaagaa cacgctgtat    240
ctgcaaatga acagcctgcg tgccgaggac acagcggtat attactgtgc ggtgcttcct    300 aagaggggc cttggtttga ctaccggggt cagggaaccc aggtcaccgt ctcgagc    357

<210> SEQ ID NO 543
<211> LENGTH: 357
<212> TYPE: DNA
<213> ORGANISM: Homo sapiens

<400> SEQUENCE: 543
gaggtgcagc tgttggagtc tgggggaggc ttgatacagc ctgggggtc cctgcgtctc    60 tcctgtgcag cctccggatt cacctttgcg catgagacaa tggtgtgggt ccgccaggct    120
cctgggaagg gtatagagtg ggtctcacat attgatcgtg ttggtcagga tacatactac    180

```
gcagactccg tgaagggccg gttcaccatc tcccgcgaca attccaagaa cacgctgtat        240
ctgcaaatga acagcctgcg tgccgaggac acagcggtat attactgtgc ggtgcttcct        300
aagagggggc cttggtttga ctaccggggt cagggaaccc tggtcaccgt ctcgagc           357

<210> SEQ ID NO 544
<211> LENGTH: 357
<212> TYPE: DNA
<213> ORGANISM: Homo sapiens

<400> SEQUENCE: 544
gaggtgcagc tgttggagtc tgggggaggc ttggtacagc ctgggggctc cctgcgtctc        60
tcctgtgcag cctccggatt caccttttgcg catgatacga tggtgtgggt ccgccaggct       120
ccagggaagg gtctagagtg ggtctcacat attgatcgtg ttggtcagga tacatactac       180
gcagactccg tggagggccg gttcaccatc tcccgcgaca attccaagaa cacgctgtat        240
ctgcaaatga acagcctgcg tgccgaggac acagcggtat attactgtgc ggtccttcct        300
aagagggggc cttggtttga ctactggggt cagggaaccc tggtcaccgt ctcgagc           357

<210> SEQ ID NO 545
<211> LENGTH: 357
<212> TYPE: DNA
<213> ORGANISM: Homo sapiens

<400> SEQUENCE: 545
gaggtgcagc tgttggagtc tgggggaggc ttggtacagc ctgggggctc cctgcgtctc        60
tcctgtgcag cctccggatt caccttttgcg catgatgtga tggtgtgggt ccgccaggct       120
ccagggaagg gtctagagtg ggtctcacat attgatcgtg ttggtcagga tacatactac       180
gcagactccg tggagggccg gttcaccatc tcccgcgaca attccaagaa cacgctgtat        240
ctgcaaatga acagcctgcg tgccgaggac acagcggtat attactgtgc ggtccttcct        300
aagagggggc cttggtttga ctactggggt cagggaaccc tggtcaccgt ctcgagc           357

<210> SEQ ID NO 546
<211> LENGTH: 357
<212> TYPE: DNA
<213> ORGANISM: Homo sapiens

<400> SEQUENCE: 546
gaggtgcagc tgttggagtc tgggggaggc ttggtacagc ctgggggctc cctgcgtctc        60
tcctgtgcag cctccggatt caccttttgcg catgagacga tggtgtgggt ccgccaggct       120
ccagggaagg gtctagagtg ggtctcacat attgatcgtg ttggtcagga tccatactac       180
acagattccg tggaggaccg gttcaccatc tcccgcgaca attccaagaa cacgctgtat        240
ctgcaaatga acagcctgcg tgccgaggac acagcggtat attactgtgc ggtccttcct        300
aagagggggc cttggtttga ctactggggt cagggaaccc tggtcaccgt ctcgagc           357

<210> SEQ ID NO 547
<211> LENGTH: 357
<212> TYPE: DNA
<213> ORGANISM: Homo sapiens

<400> SEQUENCE: 547
gaggtgcagc tgttggagtc tgggggaggc ttggtacagc ctgggggctc cctgcgtctc        60
tcctgtgcag cctccggatt caccttttgcg catgagacga tggtgtgggt ccgccaggct       120
ccagggaagg gtctagagtg ggtctcacat attgatcgtg ttggtcagga tacatactac       180
```

```
gcagactccg tggagggccg gttcaccatc tcccgcgaca attccaagaa cacgctgtat    240
ctgcaaatga acagcctgcg tgccgaggac acagcggtat attactgtgc gttgcttcct    300
aagagggggc cttggtttga ctactggggt cagggaaccc tggtcaccgt ctcgagc       357
```

<210> SEQ ID NO 548
<211> LENGTH: 357
<212> TYPE: DNA
<213> ORGANISM: Homo sapiens

<400> SEQUENCE: 548

```
gaggtgcagc tgttggagtc tgggggaggc ttggtacagc ctgggggtc cctgcgtctc      60 tcctgtgcag cctccggatt cacctttgcg catgagacga tggtgtgggt ccgccaggct    120
ccagggaagg gtctagagtg ggtctcacat attgatcgtg ttggtcagga tccatactac    180
gcagattccg tggagggccg gttcaccatc tcccgcgaca attccaagaa cacgctgtat    240
ctgcaaatga acagcctgcg tgccgaggac acagcggtat attactgtgc ggtccttcct    300
aagagggggc cttggtttga ctactggggt cagggaaccc tggtcaccgt ctcgagc       357
```

<210> SEQ ID NO 549
<211> LENGTH: 357
<212> TYPE: DNA
<213> ORGANISM: Homo sapiens

<400> SEQUENCE: 549

```
gaggtgcagc tgttggagtc tgggggaggc ttgatacagc ctgggggtc cctgcgtctc      60 tcctgtgcag cctccggatt cacctttaac aaggagacca tggtgtgggt ccgccaggct    120
ccagggaagg gtctagagtg ggtctcacat attgatcgtg ttggtcagga tacatactac    180
gcagactccg tgaagggccg gttcaccatc tcccgcgaca attccaagaa cacgctgtat    240
ctgcaaatga acagcctgcg tgccgaggac actgcggtat attactgtgc gctgcttcct    300
aagagggggc cttggtttga ctaccggggt cagggaaccc tggtcaccgt ctcgagc       357
```

<210> SEQ ID NO 550
<211> LENGTH: 357
<212> TYPE: DNA
<213> ORGANISM: Homo sapiens

<400> SEQUENCE: 550

```
gaggtgcagc tgttggagtc tgggggaggc ttgatacagc ctgggggtc cctgcgtctc      60 tcctgtgcag cctccggatt cacctttaac acggagacca tggtgtgggt ccgccgggct    120
ccagggaagg gtctagagtg ggtctcacat attgatcgtg ttggtcagga tacatactac    180
gcagactccg tgaagggccg gttcaccatc tcccgcgaca attccaagaa cacgctgtat    240
ctgcaaatga acagcctgcg tgccgaggac acagcggtat attactgtgc gctgcttcct    300
aagagggggc cttggtttga ctaccggggt cagggaaccc tggtcaccgt ctcgagc       357
```

<210> SEQ ID NO 551
<211> LENGTH: 357
<212> TYPE: DNA
<213> ORGANISM: Homo sapiens

<400> SEQUENCE: 551

```
gaggtgcagc tgttggagtc tgggggaggc ttgatacagc ctgggggtc cctgcgtctc      60 tcctgtgcag cctccggatt cacctttacg aaggagacca tggtgtgggt ccgccaggct    120
```

| | |
|---|---|
| ccagggaagg gtctagagtg ggtctcacat attgatcgtg ttggtcagga tacatactac | 180 |
| gcagactccg tgaagggccg gttcaccatc tcccgtgaca attccaagaa cacgctgtat | 240 |
| ctgcaaatga acagcctgcg tgccgaggac acagcggtat attactgtgc gctgcttcct | 300 |
| aagagggggc cttggtttga ctaccggggt cagggaaccc tggtcaccgt ctcgagc | 357 |

<210> SEQ ID NO 552
<211> LENGTH: 357
<212> TYPE: DNA
<213> ORGANISM: Homo sapiens

<400> SEQUENCE: 552

| | |
|---|---|
| gaggtgcagc tgttggagtc tgggggaggc ttgatacagc ctgggggtc cctgcgtctc | 60 |
| tcctgtgcag cctccggatt caccttttgcg catgagacga tggtgtgggt ccgccaggct | 120 |
| ccagggaagg gtctagagtg ggtctcacat attgatgggg gggggtgga tacatactac | 180 |
| gcagaccccg tgaagggccg gttcaccatc tcccgcgaca attccaagaa cacgctgtat | 240 |
| ctgcaaatga acagcctgcg tgccgaggac acagcggtat attactgtgc gctgcttcct | 300 |
| aagagggggc cttggtttga ctaccggggt cagggaaccc tggtcaccgt ctcgagc | 357 |

<210> SEQ ID NO 553
<211> LENGTH: 357
<212> TYPE: DNA
<213> ORGANISM: Homo sapiens

<400> SEQUENCE: 553

| | |
|---|---|
| gaggtgcagc tgttggagtc tgggggaggc ttgatacagc ctgggggtc cctgcgtctc | 60 |
| tcctgtgcag cctccggatt caccttttgcg catgagacga tggtgtgggt ccgccaggct | 120 |
| ccagggaagg gtctagagtg ggtctcacat attgatgggg ggggcggga tacatactac | 180 |
| gcagaccccg tgaagggccg gttcaccatc tcccgcgaca attccaagaa cacgctgtat | 240 |
| ctgcaaatga acagcctgcg tgccgaggac acagcggtat attactgtgc gctgcttcct | 300 |
| aagagggggc cttggtttga ctaccggggt cagggaaccc tggtcaccgt ctcgagc | 357 |

<210> SEQ ID NO 554
<211> LENGTH: 357
<212> TYPE: DNA
<213> ORGANISM: Homo sapiens

<400> SEQUENCE: 554

| | |
|---|---|
| gaggtgcagc tgttggagtc tgggggaggc ttgatacagc ctgggggtc cctgcgtctc | 60 |
| tcctgtgcag cctccggatt caccttttgcg catgagacga tggtgtgggt ccgccaggct | 120 |
| ccagggaagg gtctagagtg ggtctcacat attgatgggg gggggtgga tacatactac | 180 |
| gcagaccccg tgaagggccg gttcaccatc tcccgcgaca attccaagaa cacgctgtat | 240 |
| ctgcaaatga acagcctgcg tgccgaggac acagcggtat attactgtgc gctgcttcct | 300 |
| aagagggggc cttggtttga ctaccggggt cagggaaccc tggtcaccgt ctcgagc | 357 |

<210> SEQ ID NO 555
<211> LENGTH: 357
<212> TYPE: DNA
<213> ORGANISM: Homo sapiens

<400> SEQUENCE: 555

| | |
|---|---|
| gaggtgcagc tgttggagtc tgggggaggc ttgatacagc ctgggggtc cctgcgtctc | 60 |
| tcctgtgcag cctccggatt cacctttaac aaccaggtca tggtgtgggt ccgccaggct | 120 |

```
ccagggaagg gactagagtg ggtctcacat attgatcgtg ttggtcagga tacatactac      180
gcagactccg tgaagggccg gttcaccatc tcccgcgata attccaagaa cacgctgtat      240
ctgcaaatga acagcctgcg tgccgaggac acagcggtat attactgtgc gctgcttcct      300
aagagggggc cttggtttga ctaccggggt cagggaaccc tggtcaccgt ctcgagc         357
```

<210> SEQ ID NO 556
<211> LENGTH: 357
<212> TYPE: DNA
<213> ORGANISM: Homo sapiens

<400> SEQUENCE: 556

```
gaggtgcagc tgttggagtc tgggggaggc ttgatacagc ctgggggtc cctgcgtctc       60 tcctgtgcag cctccggatt cacctttgcg catgagacga tggtgtgggt ccgccaggct      120
ccagggaagg gtctagagtg ggtctcacat attgatgggg gggggttgga tacatactac      180
gcagaccccg tgaagggccg gttcaccatc tcccgcgaca attccaagaa cacgctgtat      240
ctgcaaatga acagcctgcg tgccgaggac acagcggtat attactgtgc gctgcttcct      300
aagagggggc cttggtttga ctaccggggt cagggaaccc tggtcaccgt ctcgagc         357
```

<210> SEQ ID NO 557
<211> LENGTH: 357
<212> TYPE: DNA
<213> ORGANISM: Homo sapiens

<400> SEQUENCE: 557

```
gaggtgcagc tgttggagtc tgggggaggc ttgatacagc ctgggggtc cctgcgtctc       60 tcctgtgcag cctccggatt cacctttgcg catgagacga tggtgtgggt ccgccaggct      120
ccagggaagg gtctagagtg ggtctcacat attgatgcgg tggggtccga tacatactac      180
gcagaccccg tgaagggccg gttcaccatc tcccgcgaca attccaagaa cacgctgtat      240
ctgcaaatga acagcctgcg tgccgaggac acagcggtat attactgtgc gctgcttcct      300
aagagggggc cttggtttga ctaccggggt cagggaaccc tggtcaccgt ctcgagc         357
```

<210> SEQ ID NO 558
<211> LENGTH: 357
<212> TYPE: DNA
<213> ORGANISM: Homo sapiens

<400> SEQUENCE: 558

```
gaggtgcagc tgttggagtc tgggggaggc ttgatacagc ctgggggtc cctgcgtctc       60 tcctgtgcag cctccggatt cacctttgcg catgagacga tggtgtgggt ccgccaggct      120
ccagggaagg gtctagagtg ggtctcacat attgatcgtg ttggtcagga tacatactac      180
gcagactccg tgaagggccg gttcaccatc tcccgcgaca attccaagaa cacgctgtat      240
ctgcaaatga acagcctgcg tgccgaggac acagcggtat attactgtgc gctgcttcct      300
aagagggggc cttggtttga ctaccggggt cagggaaccc tggtcaccgt ctcgagc         357
```

<210> SEQ ID NO 559
<211> LENGTH: 357
<212> TYPE: DNA
<213> ORGANISM: Homo sapiens

<400> SEQUENCE: 559

```
gaggtgcagc tgttggagtc tgggggaggc ttgatacagc ctgggggtc cctgcgtctc       60
```

| | |
|---|---|
| tcctgtgcag cctccggatt caccttggc aacgaggtca tgtgtgggt ccgccaggct | 120 |
| ccagggaagg gtctagagtg ggtctcacat attgatcgtg ttggtcagga tacatactac | 180 |
| gcagactccg tgaagggccg gttcaccatc tcccgcgaca attccaagaa cacgctgtat | 240 |
| ctgcaaatga acagcctgcg tgccgaggac acagcggtat attactgtgc gctgcttcct | 300 |
| aagagggggc cttggtttga ctaccggggt cagggaaccc tggtcaccgt ctcgggc | 357 |

<210> SEQ ID NO 560
<211> LENGTH: 357
<212> TYPE: DNA
<213> ORGANISM: Homo sapiens

<400> SEQUENCE: 560

| | |
|---|---|
| gaggtgcagc tgttggagtc tgggggaggc ttgatacagc ctggggggtc cctgcgtctc | 60 |
| tcctgtgcag cctccggatt caccttaac aaccagacga tgtgtgggt ccgccaggct | 120 |
| ccagggaagg gtctagagtg ggtctcacat attgatcgtg ttggtcagga tacatactac | 180 |
| gcagactccg tgaagggccg gttcaccatc tcccgcgaca attccaagaa cacgctgtat | 240 |
| ctgcaaatga acagcctgcg tgccgaggac acagcggtat attactgtgc gctgcttcct | 300 |
| aagagggggc cttggtttga ctaccggggt cagggaaccc tggtcaccgt ctcgagc | 357 |

<210> SEQ ID NO 561
<211> LENGTH: 357
<212> TYPE: DNA
<213> ORGANISM: Homo sapiens

<400> SEQUENCE: 561

| | |
|---|---|
| gaggtgcagc tgttggagtc tgggggaggc ttgatacagc ctggggggtc cctgcgtctc | 60 |
| tcctgtgcag cctccggatt caccttgac aacacgacga tgtgtgggt ccgccaggct | 120 |
| ccagggaagg gtctagagtg ggtctcacat attgatcgtg ttggtcagga tacatactac | 180 |
| gcagactccg tgaagggccg gttcaccatc tcccgcgaca attccaagaa cacgctgtat | 240 |
| ctgcaaatga acagcctgcg tgccgaggac acagcggtat attactgtgc gctgcttcct | 300 |
| aagagggggc cttggtttga ctaccggggt cagggaaccc tggtcaccgt ctcgagc | 357 |

<210> SEQ ID NO 562
<211> LENGTH: 357
<212> TYPE: DNA
<213> ORGANISM: Homo sapiens

<400> SEQUENCE: 562

| | |
|---|---|
| gaggtgcagc tgttggagtc tgggggaggc ttggtacagc ctggggggtc cctgcgtctc | 60 |
| tcctgtgcag cctccggatt caccttgcg catgagacga tgtgtgggt ccgccaggct | 120 |
| ccagggaagg gtctagagtg ggtctcacat attgatcgtg ttggtcagga tccatactac | 180 |
| gcagattccg tggagggccg gttcaccatc tcccgcgaca attccaagaa cacgctgtat | 240 |
| ctgcaaatga acagcctgcg tgccgaggac acagcggtat attactgtgc gctccttcct | 300 |
| aagagggggc cttggtttga ctactggggt cagggaaccc tggtcaccgt ctcgagc | 357 |

<210> SEQ ID NO 563
<211> LENGTH: 357
<212> TYPE: DNA
<213> ORGANISM: Homo sapiens

<400> SEQUENCE: 563

| | |
|---|---|
| gaggtgcagc tgttggagtc tgggggaggc ttgatacagc ctggggggtc cctgcgtctc | 60 | tcctgtgcag cctccggatt cacctttgcg catgagacga tggtgtgggt ccgccaggct    120 ccagggaagg gtctagagtg ggtctcacat attgatgggg ggggggtgga tacatactac    180 gcagacccg tgaagggccg gttcaccatc tcccgcgaca attccaagaa cacgctgtat    240 ctgcaaatga acagcctgcg tgccgaggac acagcggtat attactgtgc gctgcttcct    300 aagagggggc cttggtttga ctaccggggt cagggaaccc tggtcaccgt ctctagc    357

<210> SEQ ID NO 564
<211> LENGTH: 357
<212> TYPE: DNA
<213> ORGANISM: Homo sapiens

<400> SEQUENCE: 564
gaggtgcagc tgttggagtc tgggggaggc ttgatacagc ctgggggtc cctgcgtctc    60 tcctgtgcag cctccggatt cacctttgcg catgagacga tggtgtgggt ccgccaggct    120
ccagggaagg gtctagagtg ggtctcacat attgatcgtg ttggtcagga tccatactac    180
gcagattccg tggagggccg gttcaccatc tcccgcgaca attccaagaa cacgctgtat    240
ctgcaaatga acagcctgcg tgccgaggac acagcggtat attactgtgc ggtccttcct    300
aagagggggc cttggtttga ctaccggggt cagggaaccc tggtcaccgt ctcgagc    357

<210> SEQ ID NO 565
<211> LENGTH: 357
<212> TYPE: DNA
<213> ORGANISM: Homo sapiens

<400> SEQUENCE: 565
gaggtgcagc tgttggagtc tgggggaggc ttgatacagc ctgggggtc cctgcgtctc    60 tcctgtgcag cctccggatt cacctttgcg catgagacga tggtgtgggt ccgccaggct    120
ccagggaagg gtctagagtg ggtctcacat attgatcgtg ttggtcagga tccatactac    180
gcagattccg tggagggccg gttcaccatc tcccgcgaca attccaagaa cacgctgtat    240
ctgcaaatga acagcctgcg tgccgaggac acagcggtat attactgtgc gctccttcct    300
aagagggggc cttggtttga ctaccggggt cagggaaccc tggtcaccgt ctcgagc    357

<210> SEQ ID NO 566
<211> LENGTH: 357
<212> TYPE: DNA
<213> ORGANISM: Homo sapiens

<400> SEQUENCE: 566
gaggtgcagc tgttggagtc tgggggaggc ttgatacagc ctgggggtc cctgcgtctc    60 tcctgtgcag cctccggatt cacctttgcg catgagacga tggtgtgggt ccgccaggct    120
ccagggaagg gtctagagtg ggtctcacat attgatcgtg ttggtcagga tccatactac    180
gcagattccg tggagggccg gttcaccatc tcccgcgaca attccaagaa cacgctgtat    240
ctgcaaatga acagcctgcg tgccgaggac acagcggtat attactgtgc ggtccttcct    300
aagagggggc cttggtttga ctactggggt cagggaaccc tggtcaccgt ctcgagc    357

<210> SEQ ID NO 567
<211> LENGTH: 357
<212> TYPE: DNA
<213> ORGANISM: Homo sapiens

<400> SEQUENCE: 567

```
gaggtgcagc tgttggagtc tgggggaggc ttgatacagc ctggggggtc cctgcgtctc      60
tcctgtgcag cctccggatt cacctttgcg catgagacga tggtgtgggt ccgccaggct     120
ccagggaagg gtctagagtg ggtctcacat attgatcgtg ttggtcagga tccatactac     180
gcagattccg tggagggccg gttcaccatc tcccgcgaca attccaagaa cacgctgtat     240
ctgcaaatga acagcctgcg tgccgaggac acagcggtat attactgtgc ggtccttcct     300
aagagggggc cttggtttga ctactggggt cagggaaccc tggtcaccgt ctcgagc        357
```

<210> SEQ ID NO 568
<211> LENGTH: 357
<212> TYPE: DNA
<213> ORGANISM: Homo sapiens

<400> SEQUENCE: 568

```
gaggtgcagc tgttggagtc tgggggaggc ttgatacagc ctggggggtc cctgcgtctc      60
tcctgtgcag cctccggatt cacctttgcg catgagacga tggtgtgggt ccgccaggct     120
ccagggaagg gtctagagtg ggtctcacat attgatcgtg ttggtcagga tccatactac     180
gcagattccg tggagggccg gttcaccatc tcccgcgaca attccaagaa cacgctgtat     240
ctgcaaatga acagcctgcg tgccgaggac acagcggtat attactgtgc gctccttcct     300
aagagggggc cttggtttga ctactggggt cagggaaccc tggtcaccgt ctcgagc        357
```

<210> SEQ ID NO 569
<211> LENGTH: 357
<212> TYPE: DNA
<213> ORGANISM: Homo sapiens

<400> SEQUENCE: 569

```
gaggtgcagc tgttggagtc tgggggaggc ttggtacagc ctggggggtc cctgcgtctc      60
tcctgtgcag cctccggatt cacctttgcg catgagacga tggtgtgggt ccgccaggct     120
ccagggaagg gtctagagtg ggtctcacat attgatcgtg ttggtcagga tccatactac     180
gcagattccg tggagggccg gttcaccatc tcccgcgaca attccaagaa cacgctgtat     240
ctgcaaatga acagcctgcg tgccgaggac acagcggtat attactgtgc gctccttcct     300
aagagggggc cttggtttga ctacagggt cagggaaccc tggtcaccgt ctcgagc         357
```

<210> SEQ ID NO 570
<211> LENGTH: 357
<212> TYPE: DNA
<213> ORGANISM: Homo sapiens

<400> SEQUENCE: 570

```
gaggtgcagc tgttggagtc tgggggaggc ttgatacagc ctggggggtc cctgcgtctc      60
tcctgtgcag cctccggatt cacctttgcg catgagacga tggtgtgggt ccgccaggct     120
ccagggaagg gtctagagtg ggtctcacat attgatgggg gggggtgga tacatactac     180 gcagaccccg tgaagggccg gttcaccatc tcccgcgaca attccaagaa cacgctgtat     240
ctgcaaatga acagcctgcg tgccgaggac acagcggtat attactgtgc gctgcttcct     300
aagagggggc cttggtttga ctactggggt cagggaaccc tggtcaccgt ctcgagc        357
```

<210> SEQ ID NO 571
<211> LENGTH: 357
<212> TYPE: DNA
<213> ORGANISM: Homo sapiens

<400> SEQUENCE: 571

```
gaggtgcagc tgttggagtc tggggggaggc ttggtacagc ctggggggtc cctgcgtctc    60
tcctgtgcag cctccggatt cacctttgcg catgagacga tggtgtgggt ccgccaggct   120
ccagggaagg gtctagagtg ggtctcacat attgatgggg ggggggtgga tacatactac   180
gcagaccccg tgaagggccg gttcaccatc tcccgcgaca attccaagaa cacgctgtat   240
ctgcaaatga acagcctgcg tgccgaggac acagcggtat attactgtgc gctgcttcct   300 aagaggggggc cttggtttga ctactggggt cagggaaccc tggtcaccgt ctctagc     357
```

<210> SEQ ID NO 572
<211> LENGTH: 357
<212> TYPE: DNA
<213> ORGANISM: Homo sapiens

<400> SEQUENCE: 572

```
gaggtgcagc tgttggagtc tggggggaggc ttgatacagc ctggggggtc cctgcgtctc    60
tcctgtgcag cctccggatt cacctttgcg catgagacga tggtgtgggt ccgccaggct   120
ccagggaagg gtctagagtg ggtctcacat attgatgggg ggggggtgga tacatactac   180
gcagaccccg tgaagggccg gttcaccatc tcccgcgaca attccaagaa cacgctgtat   240
ctgcaaatga acagcctgcg tgccgaggac acagcggtat attactgtgc ggtacttcct   300 aagaggggggc cttggtttga ctaccggggt cagggaaccc tggtcaccgt ctctagc     357
```

<210> SEQ ID NO 573
<211> LENGTH: 357
<212> TYPE: DNA
<213> ORGANISM: Homo sapiens

<400> SEQUENCE: 573

```
gaggtgcagc tgttggagtc tggggggaggc ttggtacagc ctggggggtc cctgcgtctc    60
tcctgtgcag cctccggatt cacctttgcg catgagacga tggtgtgggt ccgccaggct   120
ccagggaagg gtctagagtg ggtctcacat attgatgggg ggggggtgga tacatactac   180
gcagaccccg tgaagggccg gttcaccatc tcccgcgaca attccaagaa cacgctgtat   240
ctgcaaatga acagcctgcg tgccgaggac acagcggtat attactgtgc ggtacttcct   300 aagaggggggc cttggtttga ctaccggggt cagggaaccc tggtcaccgt ctctagc     357
```

<210> SEQ ID NO 574
<211> LENGTH: 357
<212> TYPE: DNA
<213> ORGANISM: Homo sapiens

<400> SEQUENCE: 574

```
gaggtgcagc tgttggagtc tggggggaggc ttgatacagc ctggggggtc cctgcgtctc    60
tcctgtgcag cctccggatt cacctttgcg catgagacga tggtgtgggt ccgccaggct   120
ccagggaagg gtctagagtg ggtctcacat attgatgggg ggggggtgga tacatactac   180
gcagaccccg tgaagggccg gttcaccatc tcccgcgaca attccaagaa cacgctgtat   240
ctgcaaatga acagcctgcg tgccgaggac acagcggtat attactgtgc ggtacttcct   300 aagaggggggc cttggtttga ctactggggt cagggaaccc tggtcaccgt ctctagc     357
```

<210> SEQ ID NO 575
<211> LENGTH: 357
<212> TYPE: DNA
<213> ORGANISM: Homo sapiens

<400> SEQUENCE: 575

```
gaggtgcagc tgttggagtc tgggggaggc ttggtacagc ctgggggtc cctgcgtctc      60
tcctgtgcag cctccggatt cacctttgcg catgagacga tggtgtgggt ccgccaggct    120
ccagggaagg gtctagagtg gtctcacat attgatgggg ggggggtgga tacatactac    180
gcagaccccg tgaagggccg gttcaccatc tcccgcgaca attccaagaa cacgctgtat    240
ctgcaaatga acagcctgcg tgccgaggac acagcggtat attactgtgc ggtacttcct    300
aagagggggc cttggtttga ctactgggt cagggaaccc tggtcaccgt ctctagc        357
```

<210> SEQ ID NO 576
<211> LENGTH: 357
<212> TYPE: DNA
<213> ORGANISM: Homo sapiens

<400> SEQUENCE: 576

```
gaggtgcagc tgttggagtc tgggggaggc ttggtacagc ctgggggtc cctgcgtctc      60
tcctgtgcag cctccggatt cacctttgcg catgagacga tggtgtgggt ccgccaggct    120
ccagggaagg gtctagagtg gtctcacat attcccccgg ttggtcagga tcccttctac    180
gcagactccg tgaagggccg gttcaccatc tcccgcgaca attccaagaa cacgctatat    240
ctgcaaatga acagcctgcg tgccgaggac acagcggtat attactgtgc ggtacttcct    300
aagagggggc cttggtttga ctactgggt cagggaaccc tggtcaccgt ctcgagc        357
```

<210> SEQ ID NO 577
<211> LENGTH: 357
<212> TYPE: DNA
<213> ORGANISM: Homo sapiens

<400> SEQUENCE: 577

```
gaggtgcagc tgttggagtc tgggggaggc ttgatacagc ctgggggtc cctgcgtctc      60
tcctgtgcag cctccggatt cacctttgcg catgagacga tggtgtgggt ccgccaggct    120
ccagggaagg gtctagagtg gtctcacat attcccccgg ttggtcagga tcccttctac    180
gcagactccg tgaagggccg gttcaccatc tcccgcgaca attccaagaa cacgctatat    240
ctgcaaatga acagcctgcg tgccgaggac acagcggtat attactgtgc gctgcttcct    300
aagagggggc cttggtttga ctactgggt cagggaaccc tggtcaccgt ctcgagc        357
```

<210> SEQ ID NO 578
<211> LENGTH: 357
<212> TYPE: DNA
<213> ORGANISM: Homo sapiens

<400> SEQUENCE: 578

```
gaggtgcagc tgttggagtc tgggggaggc ttgatacagc ctgggggtc cctgcgtctc      60
tcctgtgcag cctccggatt cacctttgcg catgagacga tggtgtgggt ccgccaggct    120
ccagggaagg gtctagagtg gtctcacat attcccccgg ttggtcagga tcccttctac    180
gcagactccg tgaagggccg gttcaccatc tcccgcgaca attccaagaa cacgctatat    240
ctgcaaatga acagcctgcg tgccgaggac acagcggtat attactgtgc ggtacttcct    300
aagagggggc cttggtttga ctactgggt cagggaaccc tggtcaccgt ctcgagc        357
```

<210> SEQ ID NO 579
<211> LENGTH: 357
<212> TYPE: DNA
<213> ORGANISM: Homo sapiens

<400> SEQUENCE: 579

```
gaggtgcagc tgttggagtc tgggggaggc ttgatacagc ctgggggtc cctgcgtctc    60
tcctgtgcag cctccggatt cacctttgcg catgagacga tggtgtgggt ccgccaggct  120
ccagggaagg gtctagagtg gtctcacat attgatgggg gggggtgga tacatactac   180
gcagaccccg tgaagggccg gttcaccatc tcccgcgaca attccaagaa ctccctgtat  240
ctgcaaatga acagcctgcg tgccgaggac acagcggtat attactgtgc gctgcttcct  300
aagagggggc cttggtttga ctactgggt cagggaaccc tggtcaccgt ctcgagc     357
```

<210> SEQ ID NO 580
<211> LENGTH: 357
<212> TYPE: DNA
<213> ORGANISM: Homo sapiens

<400> SEQUENCE: 580

```
gaggtgcagc tgttggagtc tgggggaggc ttggtacagc ctgggggtc cctgcgtctc    60
tcctgtgcag cctccggatt cacctttgcg catgagacga tggtgtgggt ccgccaggct  120
ccagggaagg gtctagagtg gtctcacat attcccccgg ttggtcagga tcccttctac   180
gcagactccg tgaagggccg gttcaccatc tcccgcgaca attccaagaa ctccctatat  240
ctgcaaatga acagcctgcg tgccgaggac acagcggtat attactgtgc gctgcttcct  300
aagagggggc cttggtttga ctactgggt cagggaaccc tggtcaccgt ctcgagc     357
```

<210> SEQ ID NO 581
<211> LENGTH: 357
<212> TYPE: DNA
<213> ORGANISM: Homo sapiens

<400> SEQUENCE: 581

```
gaggtgcagc tgttggagtc tgggggaggc ttggtacagc ctgggggtc cctgcgtctc    60
tcctgtgcag cctccggatt cacctttcac gaccagcaca tggtgtgggt ccgccaggct  120
ccggggaagg gtctagagtg gtctcacat attgatcgtg ttggtcagga tacatactac   180
gcagactccg tgaagggccg gttcaccatc tcccgcgaca attccaagaa cacgctgtat  240
ctgcaaatga acagcctgcg tgccgaggac acagcggtat attactgtgc gctgcttcct  300
aagagggggc cttggtttga ctactgggt cagggaaccc tggtcaccgt ctcgagc     357
```

<210> SEQ ID NO 582
<211> LENGTH: 357
<212> TYPE: DNA
<213> ORGANISM: Homo sapiens

<400> SEQUENCE: 582

```
gaggtgcagc tgttggagtc tgggggaggc ttggtacagc ctgggggtc cctgcgtctc    60
tcctgtgcag cctccggatt cacctttgcg aacaacatca tggtgtgggt ccgccaggct  120
ccagggaagg gtctagagtg gtctcacat attgatcgtg ttggtcagga tacatactac   180
gcagactccg tgaagggccg gttcaccatc tcccgcgaca attccaagaa cacgctgtat  240
ctgcaaatga acaacctgcg tgccgaggac acagcggtat attactgtgc gctgcttcct  300
aagagggggc cttggtttga ctactgggt cagggaaccc tggtcaccgt ctcgagc     357
```

<210> SEQ ID NO 583
<211> LENGTH: 357
<212> TYPE: DNA

<213> ORGANISM: Homo sapiens

<400> SEQUENCE: 583

| gaggtgcagc tgttggagtc tgggggaggc ctggtacagc ctggggggtc cctgcgtctc | 60 |
| tcctgtgcag cctccggatt ctcctttaag aacaagacga tggtgtgggt ccgccaggct | 120 |
| caggggaagg gtctagagtg ggtctcacat attgatcgtg ttggtcagga tacatactac | 180 |
| gcagactccg tgaagggccg gttcaccatc tcccgcgaca attccaagaa cacgctgtat | 240 |
| ctgcaaatga acagcctgcg tgccgaggac acagcggtat attactgtgc gctgcttcct | 300 |
| aagagggggc cttggtttga ctactgggt cagggaaccc tggtcaccgt ctcgagc | 357 |

<210> SEQ ID NO 584
<211> LENGTH: 357
<212> TYPE: DNA
<213> ORGANISM: Homo sapiens

<400> SEQUENCE: 584

| gaggtgcagc tgttggagtc tgggggaggc ttggtacagc ctggggggtc cctgcgtctc | 60 |
| tcctgtgcag cctccggatt cacctttaac aagcacacga tggtgtgggt ccgccaggct | 120 |
| ccagggaagg gtctagagtg ggtctcacat attgatcgtg ttggtcagga tacatactac | 180 |
| gcagactccg tgaagggccg gttcaccatc tcccgcgaca attccaagaa cacgctgtat | 240 |
| ctgcaaatga acagcctgcg tgccgaggac acagcggtat attactgtgc gttgcttcct | 300 |
| aagagggggc cttggtttga ctactggggt cagggaaccc tggtcaccgt ctcgagt | 357 |

<210> SEQ ID NO 585
<211> LENGTH: 357
<212> TYPE: DNA
<213> ORGANISM: Homo sapiens

<400> SEQUENCE: 585

| gaggtgcagc tgttggagtc tgggggaggc ttggtacagc ctggggggtc cctgcgtctc | 60 |
| tcctgtgcag cctccggatt cacctttaac aacgagacga tggtgtgggt ccgccaggct | 120 |
| ccagggaagg gtctagagtg ggtctcacat attgatcgtg ttggtcagga tacatactac | 180 |
| gcagactccg tgaagggccg gttcaccatc tcccgcgaca attccaagaa cacgctgtat | 240 |
| ctgcaaatga acagcctgcg tgccgaggac acagcggtat attactgtgc gctgcttcct | 300 |
| aagagggggc cttggtttga ctactggggt cagggaaccc tggtcaccgt ctcgagc | 357 |

<210> SEQ ID NO 586
<211> LENGTH: 357
<212> TYPE: DNA
<213> ORGANISM: Homo sapiens

<400> SEQUENCE: 586

| gaggtgcagc tgttggagtc tgggggaggc ttggtacagc ctggggggtc cctgcgtctc | 60 |
| tcctgtgcag cctccggatt caccttttgcg catgagacga tggtgtgggt ccgccaggct | 120 |
| ccagggaagg gactagagtg ggtctcacat attgatggga ggggtggggg gacatactac | 180 |
| acagactccg tgaagggccg gttcaccacc tcccgcgaca attccaagaa cacgctgtat | 240 |
| ctgcaaatga acagcctgcg tgccgaggac acagcggtat attactgtgc gctgcttcct | 300 |
| aagagggggc cttggtttga ctactggggt cagggaaccc tggtcaccgt ctcgagc | 357 |

<210> SEQ ID NO 587
<211> LENGTH: 357

```
<212> TYPE: DNA
<213> ORGANISM: Homo sapiens

<400> SEQUENCE: 587
gaggtgcagc tgttggagtc tgggggaggc ttggtacagc ctgggggtc cctgcgtctc      60 tcctgtgcag cctccggatt cacctttgcg catgagacga tggtgtgggt ccgccaggct     120
ccagggaagg gtctagagtg ggtctcacat attgatcagc agggtgaggg gacatactac    180
acagactccg tgaagggccg gttcaccatc tcccgcgaca attccaagaa cacgctgtat    240
ctgcaaatga acagcctgcg tgccgaggac acagcggtat attactgtgc gctgcttcct    300 aagaggggc cttggtttga ctactggggt caggaaccc tggtcaccgt ctcgagc        357

<210> SEQ ID NO 588
<211> LENGTH: 357
<212> TYPE: DNA
<213> ORGANISM: Homo sapiens

<400> SEQUENCE: 588
gaggtgcagc tgttggagtc tgggggaggc ttggtacagc ctgggggtc cctgcgtctc      60 tcctgtgcag cctccggatt cacctttgcg catgagacga tggtgtgggt ccgccaggcc     120
ccagggaagg gtctagagtg ggtctcacat attgatgggg ggggtggggg gacatactac    180
gcagactccg tgaagggccg gttcaccatc tcccgcgaca attccaagaa cacgctgtat    240
ctgcaaatga acagcctgcg tgccgaggac acagcggtat attactgtgc gctgcttcct    300 aagaggggc cttggtttga ctactggggt caggaaccc tggtcaccgt ctcgagc        357

<210> SEQ ID NO 589
<211> LENGTH: 357
<212> TYPE: DNA
<213> ORGANISM: Homo sapiens

<400> SEQUENCE: 589
gaggtgcagc tgttggagtc tgggggaggc ctggtacagc ctgggggtc cctgcgtctc      60 tcctgtgcag cctccggatt cacctttgcg catgagacga tggtgtgggt ccgccaggct     120
ccagggaagg gtctagagtg ggtctcacat attgatgggg ggggtttggg gacatactac    180
gcagactccg tgaagggccg gttcaccatc tcccgcgaca attccaagaa cacgctgtat    240
ctgcaaatga acagcctgcg tgccgaggac acagcggtat attactgtgc gctgcttcct    300 aagaggggc cttggtttga ctactggggt caggaaccc tggtcaccgt ctcgagc        357

<210> SEQ ID NO 590
<211> LENGTH: 357
<212> TYPE: DNA
<213> ORGANISM: Homo sapiens

<400> SEQUENCE: 590
gaggtgcagc tgttggagtc tggaggaggc ttggtacagc ctgggggtc cctgcgtctc      60 tcctgtgcag cctccggatt cacctttgcg catgagacga tggtgtgggt ccgccaggct     120
ccagggaagg gtctagagtg ggtctcacat attgatcgtg ttggtcagga tacatactac    180
gcagactccg tgaagggccg gttcaccatc tcccgcgaca attccaagaa cacgctgtat    240
ctgcaaatga acagcctgcg tgccgaggac acagcggtat attactgtgc gcgcctacct    300 aagagggcc cttggtttga ctactggggt caggaaccc tggtcaccgt ctcgagc        357

<210> SEQ ID NO 591
```

```
<211> LENGTH: 357
<212> TYPE: DNA
<213> ORGANISM: Homo sapiens

<400> SEQUENCE: 591
gaggtgcagc tgttggagtc tgggggaggc ttggtacagc ctgggggtc cctgcgtctc      60 tcctgtgcag cctccggatt cacctttaac aacaagacca tggtgtgggt ccgccaggct    120
ccagggaagg gtctagagtg ggtctcacat attgatgggc gggtgagcg gacatactac     180 gcagactccg tgaagggccg gttcaccatc tcccgcgaca attccaagaa cacgctgtat    240
ctgcaaatga acagcctgcg tgccgaggac acagcggtat attactgtgc gctgcttcct    300 aagaggggc cttggtttga ctactggggt cagggaaccc tggtcaccgt ctcgagc        357

<210> SEQ ID NO 592
<211> LENGTH: 357
<212> TYPE: DNA
<213> ORGANISM: Homo sapiens

<400> SEQUENCE: 592
gaggtgcagc tgttggagtc tgggggaggc ttggtacagc ctgggggtc cctgcgtctc      60 tcctgtgcag cctccggatt cacctttgcg catgagacga tggtgtgggt ccgccaggct    120
ccagggaagg gtctagagtg ggtctcacat attccccgg ttggtcagga tcccttctac     180
gcagactccg tgaagggccg gttcaccatc tcccgcgaca attccaagaa cacgctatat    240
ctgcaaatga acagcctgcg tgccgaggac acagcggtat attactgtgc gctgcttcct    300 aagaggggc cttggtttga ctactggggt cagggaaccc tggtcaccgt ctcgagc        357

<210> SEQ ID NO 593
<211> LENGTH: 357
<212> TYPE: DNA
<213> ORGANISM: Homo sapiens

<400> SEQUENCE: 593
gaggtgcagc tgttggagtc tgggggaggc ttggtacagc ctgggggatc cctgcgtctc     60
tcctgtgcag cctccggatt cacctttgcg catgagacga tggtgtgggt ccgccaggct    120
ccagggaggg gtctagagtg ggtctcacat attgatcgtg ttggtcagga tacatactac    180
gcagactccg tgaagggccg gttcaccatc tcccgcgaca attccaagaa cacgctgtat    240
ctgcaaatga acagcctgcg tgccgaggac accgcggtat attactgtgc gctgcttcct    300 aagaggggc cttggtttga ctactggggt cagggaaccc tggtcaccgt ctcgagc        357

<210> SEQ ID NO 594
<211> LENGTH: 357
<212> TYPE: DNA
<213> ORGANISM: Homo sapiens

<400> SEQUENCE: 594
gaggtgcagc tgttggagtc tgggggaggc ttggtacagc ctgggggtc cctgcgtctc      60 tcctgtgcag cctccggatt cacctttgcg catgagacga tggtgtgggt ccgccaggct    120
ccagggaagg gtctagagtg ggtctcacat attgatcgtg ttggtcagga tacatactac    180
gcagactccg tgaagggccg gttcaccatc tcccgcgaca attccaagaa cacgctgtat    240
ctgcaaatga acagcctgcg tgccgaggac accgcggtat attactgtgc gcgcctacct    300 aggaggggc cttggtttga ctactggggt cagggaaccc tggtaaccgt ctcgagc        357
```

<210> SEQ ID NO 595
<211> LENGTH: 356
<212> TYPE: DNA
<213> ORGANISM: Homo sapiens

<400> SEQUENCE: 595

```
gaggtgcagc gttggagtct gggggaggct tggtacagcc tgggggtcc ctgcgtctct      60
cctgtgcagc ctccggattc acctttgcgc atgagacgat ggtgtgggtc cgccaggctc     120
cagggaaggg tctagagtgg gtctcacata ttgatcgtgt tggtcaggat acatactacg     180
cagactccgt gagggccgg ttcaccatct cccgcgacaa ttccaagaac acgctgtatc      240
tgcaaatgaa cagcctgcgt gccgaggaca cagcggtata ttactgtgcg ctgcttccta     300
agaggggggcc ttggtttgac tactgggtc agggaaccct ggtcaccgtc tcgagc         356
```

<210> SEQ ID NO 596
<211> LENGTH: 357
<212> TYPE: DNA
<213> ORGANISM: Homo sapiens

<400> SEQUENCE: 596

```
gaggtgcagc tgttggagtc tgggggaggc ttggtacagc ctgggggtc cctgcgtctc      60
tcctgtgcag cctccggatt cacctttgcg catgagacga tggtgtgggt ccgccaggct    120
ccagggaagg gtctagagtg ggtctcacat atttcggatg atggtaattc tacatactac    180
gcagactccg tgaagggccg gttcaccatc tcccgcgaca attccaagaa cacgctgtat    240
ctgcaaatga acagcctgcg tgccgaggac accgcggtat attactgtgc gcggctcccg   300
aagagggggc cttggtttga ctactgggt cagggaaccc tggtcaccgt ctcgagc        357
```

<210> SEQ ID NO 597
<211> LENGTH: 357
<212> TYPE: DNA
<213> ORGANISM: Homo sapiens

<400> SEQUENCE: 597

```
gaggtgcagc tgttggagtc tgggggaggc ttggtacagc ctgggggtc cctgcgtctc      60
tcctgtgcag cctccggatt cacctttgcc catgaggcca tggtgtgggt ccgccaggct    120
ccagggaagg gtctagagtg ggtctcacat attgatgggg gggtgagag cacatactac    180
gcagactccg tgaagggccg gttcaccatc tcccgcgaca attccaagaa cacgctgtat    240
ctgcaaatga acagcctgcg tgccgaggac accgcggtat attactgtgc gcgcctacct   300
ccgccggggc cttggtttga ctactgggt cagggaaccc tggtcaccgt ctcgagc        357
```

<210> SEQ ID NO 598
<211> LENGTH: 357
<212> TYPE: DNA
<213> ORGANISM: Homo sapiens

<400> SEQUENCE: 598

```
gaggtgcagc tgttggagtc tgggggaggc ttggtacagc ctgggggtc cctgcgtctc      60
tcctgtgcag cctccggatt caccttcac aacaaggaca tggtgtgggt ccgccaggct    120
ccagggaagg gtctagagtg ggtctcacat attgatgggg gggtgagag cacatactac    180
gcagactccg tgaagggccg gttcaccatc tcccgcgaca attccaagaa cacgctgtat    240
ctgcaaatga acagcctgcg tgccgaggac accgcggtat attactgtgc gcgcctacct   300
ttgttgttgc cttggtttga ctactgggt cagggaaccc tggtcaccgt ctcgagc        357
```

<210> SEQ ID NO 599
<211> LENGTH: 357
<212> TYPE: DNA
<213> ORGANISM: Homo sapiens

<400> SEQUENCE: 599

```
gaggtgcagc tgttggagtc tgggggaggc ttggtacagc ctggggggtc cctgcgtctc      60
tcctgtgcag cctccggatt cacctttgcc atgaggacga tggtgtgggt ccgccaggct     120
ccagggaagg gtctagagtg gtctcacat attgatgggg gggtgagag cacatactac       180
gcagactccg tgaagggccg gttcaccatc tcccgcgaca attccaagaa cacgctgtat     240
ctgcaaatga acagcctgcg tgccgaggac accgcggtat attactgtgc gcgcctacct    300
aagcgggggc cttggtttga ctactggggt cagggaaccc tggtcaccgt ctcgagc       357
```

<210> SEQ ID NO 600
<211> LENGTH: 357
<212> TYPE: DNA
<213> ORGANISM: Homo sapiens

<400> SEQUENCE: 600

```
gaggtgcagc tgttggagtc tgggggaggc ttggtacagc ctggggggtc cctgcgtctc      60
tcctgtgcag cctccggatt cacctttgcg catgagacga tggtgtgggt ccgccaggct    120
ccagggaagg gtctagagtg gtctcacat attgatgggg gggtgagag cacatactac      180
gcagactccg tgaagggccg gttcaccatc tcccgcgaca attccaagaa cacgctgtat    240
ctgcaaatga acagcctgcg tgccgaggac accgcggtat attactgtgc gcgcctacct   300
aagcgggggc cttggtttga ctactggggt cagggaaccc tggtcaccgt ctcgagc      357
```

<210> SEQ ID NO 601
<211> LENGTH: 357
<212> TYPE: DNA
<213> ORGANISM: Homo sapiens

<400> SEQUENCE: 601

```
gaggtgcagc tgttggagtc tgggggaggc ttggtacagc ctggggggtc cctgcgtctc      60
tcctgtgcag cctccggatt cacctttgcg catgagacga tggtgtgggt ccgccaggct    120
ccagggaagg gtctagagtg gtctcacat attgatgggg ggggttggt gacatactac      180
acagactccg tgaagggccg gttcaccatc tcccgcgaca attccaagaa cacgctgtat    240
ctgcaaatga acagcctgcg tgccgaggac acagcggtat attactgtgc gctgcttcct   300
aagagggggc cttggtttga ctactggggt cagggaaccc tggtcaccgt ctcgagc      357
```

<210> SEQ ID NO 602
<211> LENGTH: 357
<212> TYPE: DNA
<213> ORGANISM: Homo sapiens

<400> SEQUENCE: 602

```
gaggtgcagc tgttggagtc tgggggaggc ttggtacagc ctggggggtc cctgcgtctc      60
tcctgtgcag cctccggatt cacctttaac aacacgacca tggtgtgggt ccgccaggct    120
ccagggaagg gtctagagtg gtctcgcat attgatggcg tgggggggga tacatactac     180
gcagaccccg tgaagggccg gttcaccatc tcccgcgaca attccaagaa cacgctgtat    240
ctgcaaatga acagcctgcg tgccgaggac acagcggtat attactgtgc gctgcttcct   300
aagagggggc cttggtttga ctactggggt cagggaaccc tggtcaccgt ctcgagc      357
```

<210> SEQ ID NO 603
<211> LENGTH: 357
<212> TYPE: DNA
<213> ORGANISM: Homo sapiens

<400> SEQUENCE: 603

```
gaggtgcagc tgttggagtc tgggggaggc ttggtacagc ctggggggtc cctgcgtctc      60
tcctgtgcag cctccggatt cacctttgcg aacaagacca tggtgtgggt ccgccaggct     120
ccagggaagg gtctagagtg ggtctcacat attgatgggt tgggtttagt gacatactac     180
gcagactccg tgaagggccg gttcaccatc tcccgcgaca attccaagaa cacgctgtat     240
ctgcaaatga acagcctgcg tgccgaggac acagcggtat attactgtgc gctgcttcct     300
aagaggggc cttggtttga ctactggggt cagggaaccc tggtcaccgt ctcgagc         357
```

<210> SEQ ID NO 604
<211> LENGTH: 357
<212> TYPE: DNA
<213> ORGANISM: Homo sapiens

<400> SEQUENCE: 604

```
gaggtgcagc tgttggagtc tgggggaggc ttggtacagc ctggggggtc cctgcgtctc      60
tcctgtgcag cctccggatt cacctttaac acgacgaaca tggtgtgggt ccgccaggct     120
ccagggaagg gtctagagtg ggtctcagag attaggttg ggggtgggga tacatactac     180
gcagactccg tgaagggccg gttcaccatc tcccgcgaca attccaagaa cacgctgtat     240
ctgcaaatga acagcctgcg tgccgaggac acagcggtat attactgtgc gctgcttcct     300
aagaggggc cttggtttga ctactggggt cagggaaccc tggtcaccgt ctcaagc         357
```

<210> SEQ ID NO 605
<211> LENGTH: 357
<212> TYPE: DNA
<213> ORGANISM: Homo sapiens

<400> SEQUENCE: 605

```
gaggtgcagc tgttggagtc tgggggaggt ttggtacagc ctggggggtc cctgcgtctc      60
tcctgtgcag cctccggatt cacctttaag aacaagacca tggtgtgggt ccgccaggct     120
ccagggaagg gtctagagtg ggtctcacat attgatcagg agggtgaggg cacatactac     180
gcagactccg tgaagggccg gttcaccatc tcccgcgaca attccaagaa cacgctgtat     240
ctgcaaatga acagcctgcg tgccgaggac acagcggtat attactgtgc gctgcttcct     300
aagaggggc cttggtttga ctaccggggt cagggaaccc tggtcaccgt ctcgagc         357
```

<210> SEQ ID NO 606
<211> LENGTH: 357
<212> TYPE: DNA
<213> ORGANISM: Homo sapiens

<400> SEQUENCE: 606

```
gaggtgcagc tgttggagtc tgggggaggc ttggtacagc ctggggggtc cctgcgtctc      60
tcctgtgcag cctccggatt cacctttaac aacaccacga tggtgtgggt ccgccaggct     120
ccagggaagg gtctagagtg ggtctcacat attgatgggg agggttcggt gacatactac     180
gcagactccg tgaagggccg gttcaccatc tcccgcgaca attccaagaa cacgctgtat     240
ctgcaaatga acagcctgcg tgccgaggac acagcggtat attactgtgc gctgcttcct     300
```

```
aagaggggc cttggtttga ctactgggt cagggaaccc tggtcaccgt ctcgagc      357
```

<210> SEQ ID NO 607
<211> LENGTH: 357
<212> TYPE: DNA
<213> ORGANISM: Homo sapiens

<400> SEQUENCE: 607

```
gaggtgcagc tgttggagtc tgggggaggc ttggtacagc ctgggggtc cctgcgtctc   60
tcctgtgcag cctccggatt cacctttgag aacaagacca tggtgtgggt ccgccaggct  120
ccagggaagg gtctagagtg gtctcacat attgatgcca ccggtaccat cacatactac  180
gcagactccg tgaagggccg gttcaccatc tcccgcgaca attccaagaa cacgctgtat  240
ctgcaaatga acagcctgcg tgccgaggac acagcggtat attactgtgc gctgcttcct  300
aagaggggc cttggtttga ctaccgggt cagggaaccc tggtcaccgt ctcgagc      357
```

<210> SEQ ID NO 608
<211> LENGTH: 357
<212> TYPE: DNA
<213> ORGANISM: Homo sapiens

<400> SEQUENCE: 608

```
gaggtgcagc tgttggagtc tgggggaggc ttggtacagc ctgggggtc cctgcgtctc   60
tcctgtgcag cctccggatt cacctttaac aagaagacca tggtgtgggt ccgccaggct  120
ccagggaagg gtctagagtg gtctcacat attgatggga agggtcaggc gacatactac  180
gcagactccg tgaagggccg gttcaccatc tcccgcgaca attccaagaa cacgctgtat  240
ctgcaaatga acagcctgcg tgccgaggac acagcggtat attactgtgc gctgcttcct  300
aagaggggc cttggtttga ctactgggt caggggaccc tggtcaccgt ctcgagc      357
```

<210> SEQ ID NO 609
<211> LENGTH: 356
<212> TYPE: DNA
<213> ORGANISM: Homo sapiens

<400> SEQUENCE: 609

```
gaggtgcagc gttggagtct gggggaggct tggtacagcc tgggggtcc ctgcgtctct   60
cctgtgcagc ctccggattc acctttgcgc atgagacgat ggtgtgggtc cgccaggctc  120
cagggaaggg tctagagtgg gtctcacata ttgatcgtgt tggtcaggat acatactacg  180
cagactccgt ggagggccgg ttcaccatct cccgcgacaa ttccaagaac acgctgtatc  240
tgcaaatgaa cagcctgcgt gccgaggaca cagcggtata ttactgtgcg ctgcttccta  300
agagggggcc ttggtttgac tactggggtc agggaaccct ggtcaccgtc tcgagc      356
```

<210> SEQ ID NO 610
<211> LENGTH: 357
<212> TYPE: DNA
<213> ORGANISM: Homo sapiens

<400> SEQUENCE: 610

```
gaggtgcagc tgttggagtc tgggggaggc ttggtacagc ctgggggtc cctgcgtctc   60
tcctgtgcag cctccggatt cacctttgcg catgagacga tggtgtgggt ccgccaggct  120
ccagggaagg gtctagagtg gtctcacat attgatgggg gggtgagag cacatactac  180
gcagactccg tggagggccg gttcaccatc tcccgcgaca attccaagaa cacgctgtat  240
ctgcaaatga acagcctgcg tgccgaggac accgcggtat attactgtgc gcgcctacct  300
```

```
aagcggggc cttggtttga ctactggggt cagggaaccc tggtcaccgt ctcgagc      357
```

<210> SEQ ID NO 611
<211> LENGTH: 357
<212> TYPE: DNA
<213> ORGANISM: Homo sapiens

<400> SEQUENCE: 611

```
gaggtgcagc tgttggagtc tgggggaggc ttggtacagc ctgggggtc cctgcgtctc    60
tcctgtgcag cctccggatt cacctttgcg catgagacga tggtgtgggt ccgccaggct  120
ccagggaagg gtctagagtg ggtctcacat attgatgggg gggtgagag cacatactac  180
gcagacccgg tggagggccg gttcaccatc tcccgcgaca attccaagaa cacgctgtat  240
ctgcaaatga acagcctgcg tgccgaggac accgcggtat attactgtgc gcgcctacct  300
aagcggggc cttggtttga ctactggggt cagggaaccc tggtcaccgt ctcgagc     357
```

<210> SEQ ID NO 612
<211> LENGTH: 357
<212> TYPE: DNA
<213> ORGANISM: Homo sapiens

<400> SEQUENCE: 612

```
gaggtgcagc tgttggagtc tgggggaggc ttggtacagc ctgggggtc cctgcgtctc    60
tcctgtgcag cctccggatt cacctttgag aacaagacca tggtgtgggt ccgccaggct  120
ccagggaagg gtctagagtg ggtctcacat attgatgcca ccgtaccat cacatactac  180
gcagactccg tggagggccg gttcaccatc tcccgcgaca attccaagaa cacgctgtat  240
ctgcaaatga acagcctgcg tgccgaggac acagcggtat attactgtgc gctgcttcct  300
aagagggggc cttggtttga ctaccggggt cagggaaccc tggtcaccgt ctcgagc     357
```

<210> SEQ ID NO 613
<211> LENGTH: 357
<212> TYPE: DNA
<213> ORGANISM: Homo sapiens

<400> SEQUENCE: 613

```
gaggtgcagc tgttggagtc tgggggaggc ttggtacagc ctgggggtc cctgcgtctc    60
tcctgtgcag cctccggatt cacctttaac aagaagacca tggtgtgggt ccgccaggct  120
ccagggaagg gtctagagtg ggtctcacat attgatggga agggtcaggc gacatactac  180
gcagactccg tggagggccg gttcaccatc tcccgcgaca attccaagaa cacgctgtat  240
ctgcaaatga acagcctgcg tgccgaggac acagcggtat attactgtgc gctgcttcct  300
aagagggggc cttggtttga ctactggggt caggggaccc tggtcaccgt ctcgagc    357
```

<210> SEQ ID NO 614
<211> LENGTH: 357
<212> TYPE: DNA
<213> ORGANISM: Homo sapiens

<400> SEQUENCE: 614

```
gaggtgcagc tgttggagtc tgggggaggc ttggtacagc ctgggggtc cctgcgtctc    60
tcctgtgcag cctccggatt cacctttaac aagaagacca tggtgtgggt ccgccaggct  120
ccagggaagg gtctagagtg ggtctcacat attgatggga agggtcagga tcccttctac  180
accgactccg tgaagggccg gttcaccatc tcccgcgaca attccaagaa cacgctgtat  240
```

```
ctgcaaatga acagcctgcg tgccgaggac acagcggtat attactgtgc gctgcttcct    300 aagaggggc cttggtttga ctactggggt caggggaccc tggtcaccgt ctcgagc       357
```

<210> SEQ ID NO 615
<211> LENGTH: 357
<212> TYPE: DNA
<213> ORGANISM: Homo sapiens

<400> SEQUENCE: 615

```
gaggtgcagc tgttggagtc tgggggaggc ttggtacagc ctggggggtc cctgcgtctc    60
tcctgtgcag cctccggatt cacctttgcg catgagacga tggtgtgggt ccgccaggct   120
ccagggaagg gtctagagtg ggtctcacat attgatgggg ggggttggt gacatactac    180 accgacccgg tgaagggccg gttcaccatc tcccgcgaca attccaagaa cacgctgtat    240
ctgcaaatga acagcctgcg tgccgaggac acagcggtat attactgtgc gctgcttcct    300 aagaggggc cttggtttga ctactggggt cagggaaccc tggtcaccgt ctcgagc       357
```

<210> SEQ ID NO 616
<211> LENGTH: 357
<212> TYPE: DNA
<213> ORGANISM: Homo sapiens

<400> SEQUENCE: 616

```
gaggtgcagc tgttggagtc tgggggaggc ttggtacagc ctggggggtc cctgcgtctc    60
tcctgtgcag cctccggatt cacctttgcg catgagacga tggtgtgggt ccgccaggct   120
ccagggaagg gtctagagtg ggtctcacat attgatgggg ggggttggt gacatactac    180 accgactccg tggagggccg gttcaccatc tcccgcgaca attccaagaa cacgctgtat    240
ctgcaaatga acagcctgcg tgccgaggac acagcggtat attactgtgc gctgcttcct    300 aagaggggc cttggtttga ctactggggt cagggaaccc tggtcaccgt ctcgagc       357
```

<210> SEQ ID NO 617
<211> LENGTH: 357
<212> TYPE: DNA
<213> ORGANISM: Homo sapiens

<400> SEQUENCE: 617

```
gaggtgcagc tgttggagtc tgggggaggc ttggtacagc ctggggggtc cctgcgtctc    60
tcctgtgcag cctccggatt cacctttgcg catgagacga tggtgtgggt ccgccaggct   120
ccagggaagg gtctagagtg ggtctcacat attgatgggg ggggttggt gacatactac    180 accgacccgg tggagggccg gttcaccatc tcccgcgaca attccaagaa cacgctgtat    240
ctgcaaatga acagcctgcg tgccgaggac acagcggtat attactgtgc gctgcttcct    300 aagaggggc cttggtttga ctactggggt cagggaaccc tggtcaccgt ctcgagc       357
```

<210> SEQ ID NO 618
<211> LENGTH: 357
<212> TYPE: DNA
<213> ORGANISM: Homo sapiens

<400> SEQUENCE: 618

```
gaggtgcagc tgttggagtc tgggggaggc ttggtacagc ctggggggtc cctgcgtctc    60
tcctgtgcag cctccggatt cacctttgcg catgagacga tggtgtgggt ccgccaggct   120
ccagggaagg gtctagagtg ggtctcacat attccccgg ttggtcagga tcccttctac    180
gcagactccg tggagggccg gttcaccatc tcccgcgaca attccaagaa cacgctatat    240
```

```
ctgcaaatga acagcctgcg tgccgaggac acagcggtat attactgtgc gctgcttcct    300 aagaggggc cttggtttga ctactggggt cagggaaccc tggtcaccgt ctcgagc       357
```

<210> SEQ ID NO 619
<211> LENGTH: 357
<212> TYPE: DNA
<213> ORGANISM: Homo sapiens

<400> SEQUENCE: 619

```
gaggtgcagc tgttggagtc tgggggaggc ttggtacagc ctgggggtc cctgcgtctc    60 tcctgtgcag cctccggatt cacctttgcg catgagacga tggtgtgggt ccgccaggct   120
ccagggaagg gtctagagtg ggtctcacat attccccgg ttggtcagga tcccttctac    180
gcagacccgg tgaagggccg gttcaccatc tcccgcgaca attccaagaa cacgctatat   240
ctgcaaatga acagcctgcg tgccgaggac acagcggtat attactgtgc gctgcttcct   300 aagaggggc cttggtttga ctactggggt cagggaaccc tggtcaccgt ctcgagc       357
```

<210> SEQ ID NO 620
<211> LENGTH: 357
<212> TYPE: DNA
<213> ORGANISM: Homo sapiens

<400> SEQUENCE: 620

```
gaggtgcagc tgttggagtc tgggggaggc ttggtacagc ctgggggtc cctgcgtctc    60 tcctgtgcag cctccggatt cacctttgcg catgagacga tggtgtgggt ccgccaggct   120
ccagggaagg gtctagagtg ggtctcacat attccccgg ttggtcagga tcccttctac    180
accgactccg tgaagggccg gttcaccatc tcccgcgaca attccaagaa cacgctatat   240
ctgcaaatga acagcctgcg tgccgaggac acagcggtat attactgtgc gctgcttcct   300 aagaggggc cttggtttga ctactggggt cagggaaccc tggtcaccgt ctcgagc       357
```

<210> SEQ ID NO 621
<211> LENGTH: 357
<212> TYPE: DNA
<213> ORGANISM: Homo sapiens

<400> SEQUENCE: 621

```
gaggtgcagc tgttggagtc tgggggaggc ttggtacagc ctgggggtc cctgcgtctc    60 tcctgtgcag cctccggatt cacctttgcg catgagacga tggtgtgggt ccgccaggct   120
ccagggaagg gtctagagtg ggtctcacat attccccgg ttggtcagga tcccttctac    180
accgactccg tggagggccg gttcaccatc tcccgcgaca attccaagaa cacgctatat   240
ctgcaaatga acagcctgcg tgccgaggac acagcggtat attactgtgc gctgcttcct   300 aagaggggc cttggtttga ctactggggt cagggaaccc tggtcaccgt ctcgagc       357
```

<210> SEQ ID NO 622
<211> LENGTH: 357
<212> TYPE: DNA
<213> ORGANISM: Homo sapiens

<400> SEQUENCE: 622

```
gaggtgcagc tgttggagtc tgggggaggc ttggtacagc ctgggggtc cctgcgtctc    60 tcctgtgcag cctccggatt cacctttgcg catgagacga tggtgtgggt ccgccaggct   120
ccagggaagg gtctagagtg ggtctcacat attgatgggg gggtgagag cacatactac   180
```

```
accgacccgg tgaagggccg gttcaccatc tcccgcgaca attccaagaa cacgctgtat      240
ctgcaaatga acagcctgcg tgccgaggac accgcggtat attactgtgc gcgcctacct      300 aagcggggc cttggtttga ctactgggt cagggaaccc tggtcaccgt ctcgagc           357
```

<210> SEQ ID NO 623
<211> LENGTH: 357
<212> TYPE: DNA
<213> ORGANISM: Homo sapiens

<400> SEQUENCE: 623

```
gaggtgcagc tgttggagtc tggggggaggc ttggtacagc ctgggggggtc cctgcgtctc     60 tcctgtgcag cctccggatt cacctttgcg catgagacga tggtgtgggt ccgccaggct     120
ccagggaagg gtctagagtg ggtctcacat attgatgggg gggtgagag cacatactac     180 accgactccg tggagggccg gttcaccatc tcccgcgaca attccaagaa cacgctgtat     240
ctgcaaatga acagcctgcg tgccgaggac accgcggtat attactgtgc gcgcctacct     300 aagcggggc cttggtttga ctactgggt cagggaaccc tggtcaccgt ctcgagc           357
```

<210> SEQ ID NO 624
<211> LENGTH: 357
<212> TYPE: DNA
<213> ORGANISM: Homo sapiens

<400> SEQUENCE: 624

```
gaggtgcagc tgttggagtc tggggggaggc ttggtacagc ctgggggggtc cctgcgtctc     60 tcctgtgcag cctccggatt cacctttgcg catgagacga tggtgtgggt ccgccaggct     120
ccagggaagg gtctagagtg ggtctcacat attgatgggg gggtgagag cacatactac     180 accgacccgg tggagggccg gttcaccatc tcccgcgaca attccaagaa cacgctgtat     240
ctgcaaatga acagcctgcg tgccgaggac accgcggtat attactgtgc gcgcctacct     300 aagcggggc cttggtttga ctactgggt cagggaaccc tggtcaccgt ctcgagc           357
```

<210> SEQ ID NO 625
<211> LENGTH: 357
<212> TYPE: DNA
<213> ORGANISM: Homo sapiens

<400> SEQUENCE: 625

```
gaggtgcagc tgttggagtc tggggggaggc ttggtacagc ctgggggggtc cctgcgtctc     60 tcctgtgcag cctccggatt cacctttaac aagaagacca tggtgtgggt ccgccaggct     120
ccagggaagg gtctagagtg ggtctcacat attgatggga aggtcaggc gacatactac     180 accgacccgg tgaagggccg gttcaccatc tcccgcgaca attccaagaa cacgctgtat     240
ctgcaaatga acagcctgcg tgccgaggac acagcggtat attactgtgc gctgcttcct     300 aagaggggc cttggtttga ctactgggt caggggaccc tggtcaccgt ctcgagc           357
```

<210> SEQ ID NO 626
<211> LENGTH: 357
<212> TYPE: DNA
<213> ORGANISM: Homo sapiens

<400> SEQUENCE: 626

```
gaggtgcagc tgttggagtc tggggggaggc ttggtacagc ctgggggggtc cctgcgtctc     60 tcctgtgcag cctccggatt cacctttaac aagaagacca tggtgtgggt ccgccaggct     120
ccagggaagg gtctagagtg ggtctcacat attgatggga aggtcaggc gacatactac     180
```

```
accgactccg tggagggccg gttcaccatc tcccgcgaca attccaagaa cacgctgtat    240
ctgcaaatga acagcctgcg tgccgaggac acagcggtat attactgtgc gctgcttcct    300 aagaggggggc cttggtttga ctactggggt caggggaccc tggtcaccgt ctcgagc      357
```

<210> SEQ ID NO 627
<211> LENGTH: 357
<212> TYPE: DNA
<213> ORGANISM: Homo sapiens

<400> SEQUENCE: 627

```
gaggtgcagc tgttggagtc tgggggaggc ttggtacagc ctgggggtc cctgcgtctc     60 tcctgtgcag cctccggatt cacctttaac aagaagacca tggtgtgggt ccgccaggct   120
ccagggaagg gtctagagtg ggtctcacat attgatggga agggtcaggc gacatactac   180
accgacccgg tggagggccg gttcaccatc tcccgcgaca attccaagaa cacgctgtat   240
ctgcaaatga acagcctgcg tgccgaggac acagcggtat attactgtgc gctgcttcct   300 aagaggggggc cttggtttga ctactggggt caggggaccc tggtcaccgt ctcgagc     357
```

<210> SEQ ID NO 628
<211> LENGTH: 357
<212> TYPE: DNA
<213> ORGANISM: Homo sapiens

<400> SEQUENCE: 628

```
gaggtgcagc tgttggagtc tgggggaggc ttggtacagc ctgggggtc cctgcgtctc     60 tcctgtgcag cctccggatt cacctttgcg catgagacga tggtgtgggt ccgccaggct   120
ccagggaagg gtctagagtg ggtctcacat attcccccgg ttggtcagga tcccttctac   180
accgacccgg tgaagggccg gttcaccatc tcccgcgaca attccaagaa cacgctatat   240
ctgcaaatga acagcctgcg tgccgaggac acagcggtat attactgtgc gctgcttcct   300 aagaggggggc cttggtttga ctactggggt cagggaaccc tggtcaccgt ctcgagc     357
```

<210> SEQ ID NO 629
<211> LENGTH: 357
<212> TYPE: DNA
<213> ORGANISM: Homo sapiens

<400> SEQUENCE: 629

```
gaggtgcagc tgttggagtc tgggggaggc ttggtacagc ctgggggtc cctgcgtctc     60 tcctgtgcag cctccggatt cacctttgcg catgagacga tggtgtgggt ccgccaggct   120
ccagggaagg gtctagagtg ggtctcacat attcccccgg ttggtcagga tcccttctac   180 gcagaccccgg tggagggccg gttcaccatc tcccgcgaca attccaagaa cacgctatat   240
ctgcaaatga acagcctgcg tgccgaggac acagcggtat attactgtgc gctgcttcct   300 aagaggggggc cttggtttga ctactggggt cagggaaccc tggtcaccgt ctcgagc     357
```

<210> SEQ ID NO 630
<211> LENGTH: 357
<212> TYPE: DNA
<213> ORGANISM: Homo sapiens

<400> SEQUENCE: 630

```
gaggtgcagc tgttggagtc tgggggaggc ttggtacagc ctgggggtc cctgcgtctc     60 tcctgtgcag cctccggatt cacctttaac aagaagacca tggtgtgggt ccgccaggct   120
```

```
ccagggaagg gtctagagtg ggtctcacat attgatggga agggtcagga tcccttctac    180
accgactccg tggagggccg gttcaccatc tcccgcgaca attccaagaa cacgctgtat    240
ctgcaaatga acagcctgcg tgccgaggac acagcggtat attactgtgc gctgcttcct    300 aagaggggc cttggtttga ctactggggt caggggaccc tggtcaccgt ctcgagc        357
```

<210> SEQ ID NO 631
<211> LENGTH: 357
<212> TYPE: DNA
<213> ORGANISM: Homo sapiens

<400> SEQUENCE: 631

```
gaggtgcagc tgttggagtc tgggggaggc ttggtacagc ctggggggtc cctgcgtctc    60
tcctgtgcag cctccggatt cacctttaac aagaagacca tggtgtgggt ccgccaggct   120
ccagggaagg gtctagagtg ggtctcacat attgatggga agggtcagga tcccttctac   180
gcagacccgg tgaagggccg gttcaccatc tcccgcgaca attccaagaa cacgctgtat   240
ctgcaaatga acagcctgcg tgccgaggac acagcggtat attactgtgc gctgcttcct   300 aagaggggc cttggtttga ctactggggt caggggaccc tggtcaccgt ctcgagc      357
```

<210> SEQ ID NO 632
<211> LENGTH: 357
<212> TYPE: DNA
<213> ORGANISM: Homo sapiens

<400> SEQUENCE: 632

```
gaggtgcagc tgttggagtc tgggggaggc ttggtacagc ctggggggtc cctgcgtctc    60
tcctgtgcag cctccggatt cacctttaac aagaagacca tggtgtgggt ccgccaggct   120
ccagggaagg gtctagagtg ggtctcacat attgatggga agggtcagga tcccttctac   180
accgacccgg tgaagggccg gttcaccatc tcccgcgaca attccaagaa cacgctgtat   240
ctgcaaatga acagcctgcg tgccgaggac acagcggtat attactgtgc gctgcttcct   300 aagaggggc cttggtttga ctactggggt caggggaccc tggtcaccgt ctcgagc      357
```

<210> SEQ ID NO 633
<211> LENGTH: 357
<212> TYPE: DNA
<213> ORGANISM: Homo sapiens

<400> SEQUENCE: 633

```
gaggtgcagc tgttggagtc tgggggaggc ttggtacagc ctggggggtc cctgcgtctc    60
tcctgtgcag cctccggatt cacctttaac aagaagacca tggtgtgggt ccgccaggct   120
ccagggaagg gtctagagtg ggtctcacat attgatggga agggtcagga tcccttctac   180
accgactccg tggagggccg gttcaccatc tcccgcgaca attccaagaa cacgctgtat   240
ctgcaaatga acagcctgcg tgccgaggac acagcggtat attactgtgc gctgcttcct   300 aagaggggc cttggtttga ctactggggt caggggaccc tggtcaccgt ctcgagc      357
```

<210> SEQ ID NO 634
<211> LENGTH: 357
<212> TYPE: DNA
<213> ORGANISM: Homo sapiens

<400> SEQUENCE: 634

```
gaggtgcagc tgttggagtc tgggggaggc ttggtacagc ctggggggtc cctgcgtctc    60
tcctgtgcag cctccggatt cacctttaac aagaagacca tggtgtgggt ccgccaggct   120
```

```
ccagggaagg gtctagagtg ggtctcacat attgatggga agggtcagga tcccttctac      180
accgacccgg tggagggccg gttcaccatc tcccgcgaca attccaagaa cacgctgtat      240
ctgcaaatga acagcctgcg tgccgaggac acagcggtat attactgtgc gctgcttcct      300
aagagggggc cttggtttga ctactggggt caggggaccc tggtcaccgt ctcgagc         357

<210> SEQ ID NO 635
<211> LENGTH: 357
<212> TYPE: DNA
<213> ORGANISM: Homo sapiens

<400> SEQUENCE: 635
gaggtgcagc tgttggagtc tgggggaggc ttggtacagc ctggggggtc cctgcgtctc       60
tcctgtgcag cctccggatt cacctttgcg catgagacga tggtgtgggt ccgccaggct      120
ccagggaagg gtctagagtg ggtctcacat attcccccgg ttggtcagga tcccttctac      180
accgacccgg tggagggccg gttcaccatc tcccgcgaca attccaagaa cacgctatat      240
ctgcaaatga acagcctgcg tgccgaggac acagcggtat attactgtgc gctgcttcct      300
aagagggggc cttggtttga ctactggggt cagggaaccc tggtcaccgt ctcgagc         357

<210> SEQ ID NO 636
<211> LENGTH: 357
<212> TYPE: DNA
<213> ORGANISM: Homo sapiens

<400> SEQUENCE: 636
gaggtgcagc tgttggagtc tgggggaggc ttggtacagc ctggggggtc cctgcgtctc       60
tcctgtgcag cctccggatt cacctttgcg catgagacga tggtgtgggt ccgccaggct      120
ccagggaagg gtctagagtg ggtctcacat attgatgggg gggtgagag cccctactac      180 gcagactccg tgaagggccg gttcaccatc tcccgcgaca attccaagaa cacgctgtat      240
ctgcaaatga acagcctgcg tgccgaggac accgcggtat attactgtgc gcgcctacct      300
aagcgggggc cttggtttga ctactggggt cagggaaccc tggtcaccgt ctcgagc         357

<210> SEQ ID NO 637
<211> LENGTH: 357
<212> TYPE: DNA
<213> ORGANISM: Homo sapiens

<400> SEQUENCE: 637
gaggtgcagc tgttggagtc tgggggaggc ttgatacagc ctggggggtc cctgcgtctc       60
tcctgtgcag cctccggatt cacctttgcg catgagacga tggtgtgggt ccgccaggct      120
ccagggaagg gtctagagtg ggtctcacat attcccccgg ttggtcagga tcccttctac      180
gcagactccg tgaagggccg gttcaccatc tcccgcgaca attccaagaa cacgctatat      240
ctgcaaatga acagcctgcg tgccgaggac acagcggtat attactgtgc gctgcttcct      300
aagagggggc cttggtttga ctactggggt cagggaaccc tggtcaccgt ctcgagc         357

<210> SEQ ID NO 638
<211> LENGTH: 357
<212> TYPE: DNA
<213> ORGANISM: Homo sapiens

<400> SEQUENCE: 638
gaggtgcagc tgttggagtc tgggggaggc ttgatacagc ctggggggtc cctgcgtctc       60
```

```
tcctgtgcag cctccggatt cacctttgcg catgagacga tggtgtgggt ccgccaggct    120
ccagggaagg gtctagagtg ggtctcacat attccccccgg ttggtcagga tcccttctac   180
gcagacccgg tgaagggccg gttcaccatc tcccgcgaca attccaagaa cacgctatat    240
ctgcaaatga acagcctgcg tgccgaggac acagcggtat attactgtgc gctgcttcct    300
aagagggggc cttggtttga ctactggggt cagggaaccc tggtcaccgt ctcgagc      357
```

<210> SEQ ID NO 639
<211> LENGTH: 357
<212> TYPE: DNA
<213> ORGANISM: Homo sapiens

<400> SEQUENCE: 639

```
gaggtgcagc tgttggagtc tgggggaggc ttgatacagc ctgggggtc cctgcgtctc     60 tcctgtgcag cctccggatt caccttttgcg catgagacga tggtgtgggt ccgccaggct   120
ccagggaagg gtctagagtg ggtctcacat attccccccgg ttggtcagga tcccttctac   180
accgactccg tgaagggccg gttcaccatc tcccgcgaca attccaagaa cacgctatat    240
ctgcaaatga acagcctgcg tgccgaggac acagcggtat attactgtgc gctgcttcct    300
aagagggggc cttggtttga ctactggggt cagggaaccc tggtcaccgt ctcgagc      357
```

<210> SEQ ID NO 640
<211> LENGTH: 357
<212> TYPE: DNA
<213> ORGANISM: Homo sapiens

<400> SEQUENCE: 640

```
gaggtgcagc tgttggagtc tgggggaggc ttgatacagc ctgggggtc cctgcgtctc     60 tcctgtgcag cctccggatt caccttttgcg catgagacga tggtgtgggt ccgccaggct   120
ccagggaagg gtctagagtg ggtctcacat attccccccgg ttggtcagga tcccttctac   180
accgactccg tggagggccg gttcaccatc tcccgcgaca attccaagaa cacgctatat    240
ctgcaaatga acagcctgcg tgccgaggac acagcggtat attactgtgc gctgcttcct    300
aagagggggc cttggtttga ctactggggt cagggaaccc tggtcaccgt ctcgagc      357
```

<210> SEQ ID NO 641
<211> LENGTH: 357
<212> TYPE: DNA
<213> ORGANISM: Homo sapiens

<400> SEQUENCE: 641

```
gaggtgcagc tgttggagtc tgggggaggc ttgatacagc ctgggggtc cctgcgtctc     60 tcctgtgcag cctccggatt caccttttgcg catgagacga tggtgtgggt ccgccaggct   120
ccagggaagg gtctagagtg ggtctcacat attgatgggg ggggtgagag cacatactac   180
gcagactccg tggagggccg gttcaccatc tcccgcgaca attccaagaa cacgctgtat   240
ctgcaaatga acagcctgcg tgccgaggac accgcggtat attactgtgc gcgcctacct    300
aagcgggggc cttggtttga ctactggggt cagggaaccc tggtcaccgt ctcgagc      357
```

<210> SEQ ID NO 642
<211> LENGTH: 357
<212> TYPE: DNA
<213> ORGANISM: Homo sapiens

<400> SEQUENCE: 642

```
gaggtgcagc tgttggagtc tgggggaggc ttgatacagc ctgggggtc cctgcgtctc     60
```

```
tcctgtgcag cctccggatt cacctttgcg catgagacga tggtgtgggt ccgccaggct      120
ccagggaagg gtctagagtg ggtctcacat attgatgggg ggggtgagag cacatactac      180
accgacccgg tgaagggccg gttcaccatc tcccgcgaca attccaagaa cacgctgtat      240
ctgcaaatga acagcctgcg tgccgaggac accgcggtat attactgtgc gcgcctacct      300
aagcgggggc cttggtttga ctactggggt cagggaaccc tggtcaccgt ctcgagc         357
```

<210> SEQ ID NO 643
<211> LENGTH: 357
<212> TYPE: DNA
<213> ORGANISM: Homo sapiens

<400> SEQUENCE: 643

```
gaggtgcagc tgttggagtc tggggaggc ttgatacagc ctgggggtc cctgcgtctc       60 tcctgtgcag cctccggatt cacctttgcg catgagacga tggtgtgggt ccgccaggct      120
ccagggaagg gtctagagtg ggtctcacat attgatgggg ggggtgagag cacatactac      180
accgactccg tggagggccg gttcaccatc tcccgcgaca attccaagaa cacgctgtat      240
ctgcaaatga acagcctgcg tgccgaggac accgcggtat attactgtgc gcgcctacct      300
aagcgggggc cttggtttga ctactggggt cagggaaccc tggtcaccgt ctcgagc         357
```

<210> SEQ ID NO 644
<211> LENGTH: 357
<212> TYPE: DNA
<213> ORGANISM: Homo sapiens

<400> SEQUENCE: 644

```
gaggtgcagc tgttggagtc tggggaggc ttgatacagc ctgggggtc cctgcgtctc       60 tcctgtgcag cctccggatt cacctttgcg catgagacga tggtgtgggt ccgccaggct      120
ccagggaagg gtctagagtg ggtctcacat attgatgggg ggggtgagag cacatactac      180
accgacccgg tggagggccg gttcaccatc tcccgcgaca attccaagaa cacgctgtat      240
ctgcaaatga acagcctgcg tgccgaggac accgcggtat attactgtgc gcgcctacct      300
aagcgggggc cttggtttga ctactggggt cagggaaccc tggtcaccgt ctcgagc         357
```

<210> SEQ ID NO 645
<211> LENGTH: 324
<212> TYPE: DNA
<213> ORGANISM: Homo sapiens

<400> SEQUENCE: 645

```
gacatccaga tgacccagtc tccatcctcc ctgtctgcat ctgtaggaga ccgtgtcacc      60
atcacttgcc gggcaagtca gtatattcat acgagtttac agtggtacca gcagaaacca     120
gggaaagccc ctaaactcct gatctatggg tcgtccaggt tgcatagtgg ggtcccatca     180
cgtttcagtg gcagtggatc tgggacagat ttcactctca ccatcagcag tctgcaacct     240
gaagattttg ctacgtacta ctgtcaacag aatcattata gtccttttac gttcggccaa     300
gggaccaagg tggaaatcaa acgg                                             324
```

<210> SEQ ID NO 646
<211> LENGTH: 324
<212> TYPE: DNA
<213> ORGANISM: Homo sapiens

<400> SEQUENCE: 646

```
gacatccaga tgacccagtc tccatcctcc ctgtctgcat ctgtaggaga ccgtgtcacc    60
atcacttgcc gggcaagtca gtatattcat acgagtttac agtggtacca gcagaaacca   120
gggaaagccc ttaagctcct gatctatggg tcgtccaggt tgcaaagtgg ggtcccatca   180
cgtttcagtg gcagtggatc tgggacagat ttcactttca ccatcagcag tctgcaacct   240
gaagattttg ctacgtacta ctgtcaacag aatcatcata gtccctttac gtacggccaa   300
gggaccaagg tggaaatcaa acgg                                          324
```

<210> SEQ ID NO 647
<211> LENGTH: 324
<212> TYPE: DNA
<213> ORGANISM: Homo sapiens

<400> SEQUENCE: 647

```
gacatccaga tgacccagtc tccatcctcc ctgtctgcat ctgtaggaga ccgtgtcacc    60
atcacttgcc gggcaagtca gtatattcat acgagtttac agtggtacca gcagaaacca   120
gggaaagccc ctaaactcct gatctatggg tcgtccaggt tgcatagtgg ggtcccatca   180
cgtttcagtg gcagtggatc tgggacagat ttcactctca ccatcaggag tctgcaacct   240
gaagatcttg ctacgtacta ctgtcaacag aatcattaca gtcctttac gttcggccaa   300 gggaccaagg tggaaatcaa cggg                                          324
```

<210> SEQ ID NO 648
<211> LENGTH: 324
<212> TYPE: DNA
<213> ORGANISM: Homo sapiens

<400> SEQUENCE: 648

```
gacatccaga tgacccagtc tccatcctcc ctgtctgcat ctgtaggaga ccgtgtcacc    60
atcacttgcc gggcaagtca gtatattcat acgagtgtac agtggtacca gcagaaacca   120
gggaaagccc ctaaactcct gatctatggg tcgtccaggt tgcatagtgg ggtcccatca   180
cgtttcagtg gcagtggatc tgggacagat ttcactctca ccatcagcag tctgcaacct   240
gaagattttg ctacgtacta ctgtcaacag aatcattata gtccttttac gttcggccaa   300
gggaccaagg tggaaatcaa acgg                                          324
```

<210> SEQ ID NO 649
<211> LENGTH: 324
<212> TYPE: DNA
<213> ORGANISM: Homo sapiens

<400> SEQUENCE: 649

```
gacatccaga tgacccagtc tccatcctcc ctgtctgcat ctgtaggaga ccgtgtcacc    60
atcacttgcc gggcaagtca gtatattcat acgagtttac aatggtacca gcagaaacca   120
gggaaagccc ctaaactcct gatctatggg tcgtccaggt tgcatagtgg ggtcccatca   180
cgtttcagtg gcagtggatc tgggacagat ttcactctca ccatcagcag tctgcaacct   240
gaagattttg ctacgtacta ctgtcaacag aatcattata gtccttttac gtacggccaa   300
gggaccaagg tggaaatcaa acgg                                          324
```

<210> SEQ ID NO 650
<211> LENGTH: 324
<212> TYPE: DNA
<213> ORGANISM: Homo sapiens

<400> SEQUENCE: 650

```
gacatccaga tgacccagtc tccatcctcc ctgtctgcat ctgtaggaga ccgtgtcacc      60
atcacttgcc gggcaagtca gtatattcat acgagtgtac agtggtacca gcagaaacca     120
gggaaagccc ctaaactcct gatctatggg tcgtccaggt tgcatagtgg ggtcccatca     180
cgtttcagtg gcagtggatc tgggacagat ttcactctca ccatcagcag tctgcaacct     240
gaagattttg ctacgtacta ctgtcaacag aatcattata gtccttttac gtacggccaa     300
gggaccaagg tggaaatcaa acgg                                            324
```

UNITED STATES PATENT AND TRADEMARK OFFICE
CERTIFICATE OF CORRECTION

PATENT NO.       : 9,629,909 B2
APPLICATION NO. : 13/920371
DATED            : April 25, 2017
INVENTOR(S)      : De Wildt et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 761 days.

Signed and Sealed this
Twenty-fifth Day of September, 2018

Andrei Iancu
*Director of the United States Patent and Trademark Office*